US012252467B2

(12) United States Patent
Oniciu

(10) Patent No.: US 12,252,467 B2
(45) **Date of Patent: *Mar. 18, 2025**

(54) FUNCTIONALIZED LONG-CHAIN HYDROCARBON MONO- AND DI-CARBOXYLIC ACIDS AND THEIR USE FOR THE PREVENTION OR TREATMENT OF DISEASE

(71) Applicant: Espervita Therapeutics, Inc., Saline, MI (US)

(72) Inventor: Daniela Carmen Oniciu, Gainesville, FL (US)

(73) Assignee: Espervita Therapeutics, Inc., Saline, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/812,284

(22) Filed: Aug. 22, 2024

(65) Prior Publication Data

US 2024/0417363 A1 Dec. 19, 2024

Related U.S. Application Data

(63) Continuation of application No. 18/204,442, filed on Jun. 1, 2023, which is a continuation of application No. 17/571,107, filed on Jan. 7, 2022, now abandoned, which is a continuation of application No. 17/240,513, filed on Apr. 26, 2021, now Pat. No. 11,267,778, which is a continuation of application No. 16/937,154, filed on Jul. 23, 2020, now Pat. No. 11,098,002.

(60) Provisional application No. 62/901,739, filed on Sep. 17, 2019, provisional application No. 62/878,852, filed on Jul. 26, 2019.

(51) Int. Cl.
*C07C 57/13* (2006.01)
*A61K 45/06* (2006.01)

(52) U.S. Cl.
CPC .............. *C07C 57/13* (2013.01); *A61K 45/06* (2013.01)

(58) Field of Classification Search
CPC ................................ C07C 57/13; A61K 45/06
USPC ........................................................ 514/570
See application file for complete search history.

(56) References Cited

U.S. PATENT DOCUMENTS

| | | | |
|---|---|---|---|
| 4,634,795 | A | 1/1987 | Bar-Tana |
| 4,689,344 | A | 8/1987 | Bar-Tana |
| 4,711,896 | A | 12/1987 | Bar-Tana et al. |
| 5,387,672 | A | 2/1995 | Bucci et al. |
| 5,648,387 | A | 7/1997 | Bisgaier et al. |
| 6,459,003 | B1 | 10/2002 | Dasseux et al. |
| 6,699,910 | B2 | 3/2004 | Dasseux et al. |
| 6,790,953 | B2 | 9/2004 | Dasseux et al. |
| 7,405,226 | B2 | 7/2008 | Dasseux et al. |
| 7,638,531 | B2 | 12/2009 | Mutahi et al. |
| 9,452,964 | B2 | 9/2016 | Dasseux et al. |
| 11,084,773 | B1 | 8/2021 | Oniciu |
| 11,098,002 | B2 | 8/2021 | Oniciu |
| 11,267,778 | B2 | 3/2022 | Oniciu |
| 11,730,712 | B2 | 8/2023 | Oniciu |
| 11,737,995 | B2 | 8/2023 | Oniciu et al. |
| 2003/0236212 | A1 | 12/2003 | Dasseux et al. |
| 2003/0236213 | A1 | 12/2003 | Dasseux et al. |
| 2004/0171688 | A1 | 9/2004 | Bar-Tana |
| 2012/0172337 | A1 | 7/2012 | Dasseux et al. |
| 2014/0378922 | A1 | 12/2014 | Fuchs et al. |
| 2017/0174718 | A1 | 6/2017 | Lewis et al. |
| 2017/0360822 | A1 | 12/2017 | Levy et al. |
| 2019/0291404 | A1 | 9/2019 | Rossignol |
| 2020/0048181 | A1 | 2/2020 | Oniciu et al. |
| 2022/0040285 | A1 | 2/2022 | Weissman et al. |
| 2022/0331348 | A1 | 10/2022 | Sun et al. |
| 2022/0402851 | A1 | 12/2022 | Oniciu |
| 2023/0007838 | A1 | 1/2023 | Oniciu |

(Continued)

FOREIGN PATENT DOCUMENTS

| | | | |
|---|---|---|---|
| CN | 105801405 | A | 7/2016 |
| WO | WO-2012097427 | A1 | 7/2012 |
| WO | WO-2012159107 | A1 | 11/2012 |

(Continued)

OTHER PUBLICATIONS

Co-pending U.S. Appl. No. 18/797,591, inventor Oniciu; Daniela Carmen, filed Aug. 8, 2024.

(Continued)

*Primary Examiner* — Ana Z Muresan
(74) *Attorney, Agent, or Firm* — COOLEY LLP

(57) ABSTRACT

This invention provides compounds of Formulae (IA), (IB), (IC), (ID), (IE), (IF), (IG), (IH), (IJ), (IK), (IL), (II), (III), (IIIA), and (IIIB); pharmaceutically acceptable salts and solvates thereof; and compositions thereof. This invention further provides methods for treating a disease, including but not limited to, liver disease or an abnormal liver condition; cancer (such as hepatocellular carcinoma or cholangiocarcinoma); a malignant or benign tumor of the lung, liver, gall bladder, bile duct or digestive tract; an intra- or extra-hepatic bile duct disease; a disorder of lipoprotein; a lipid-and-metabolic disorder; cirrhosis; fibrosis; a disorder of glucose metabolism; a cardiovascular or related vascular disorder; a disease resulting from steatosis, fibrosis, or cirrhosis; a disease associated with increased inflammation (such as hepatic inflammation or pulmonary inflammation); hepatocyte ballooning; a peroxisome proliferator activated receptor-associated disorder; an ATP citrate lyase disorder; an acetyl-coenzyme A carboxylase disorder; obesity; pancreatitis; or renal disease.

16 Claims, 16 Drawing Sheets

(56) References Cited

U.S. PATENT DOCUMENTS

2024/0092721 A1 3/2024 Oniciu

FOREIGN PATENT DOCUMENTS

WO WO-2016077832 A2 5/2016
WO WO-2021021563 A1 2/2021
WO WO-2022159811 A1 7/2022

OTHER PUBLICATIONS

Author Unknown "Fundamentals of Medical Prevention." Methodological Manual for Students of Advanced Training Cycles of State Professional Educational Institutions. Novosibirsk, 2016, 206 pp. 13-21, 18 pages with English translation.

Author Unknown "Soviet Encyclopedia." Chemical Encyclopedic Dictionary. Moscow, 1983, pp. 130-131; and English translation of relevant portion, 3 pages.

Kharkevitch "Pharmacology/Textbook." 10th edition, 2010; pp. 72-82; 20 pages with English translation.

Kholodov et al. "Clinical Pharmacokinetics" (Klinicheskaya Farmakokinetika), Moscow: Meditsina, 1985, 43 pages with English translation.

Mashkovsky M. D. "Medicaments, Doctor's Manual." vol. 1, 14th Edition. OOO Novaya Volna, Publisher S.B. Divov. Moscow. (2001), 3 pages with English translation.

Mironov et al. "Guidelines for Conducting Preclinical Studies of Drugs. Part One. Grif and K." Tula, Russia. 2012. pp. 640-654, 31 pages with English translation.

Sergeev P.V. "Short Course of Molecular Pharmacology." Moscow. 1975, 2 pages with English translation.

Francque et al. "Pharmacological treatment for non-alcoholic fatty liver disease." Advances in Therapy. Mar. 19, 2019;36:1052-1074.

Notice of Allowance for U.S. Appl. No. 18/204,442, dated Sep. 27, 2024, 8 pages.

Office Action for U.S. Appl. No. 18/392,680, dated Sep. 30, 2024, 11 pages.

O'Neil K. "ATP-Citrate Lyase Inhibition Improves Chronic Kidney Disease Through Multiple Mechanisms," (Master's Thesis). McMaster University, MacSphere (Dissertations and Theses) [online], dated Aug. 2023, Access is Allowed From: Sep. 30, 2024. Retrieved from the Internet URL: http://hdl.handle.net/11375/29119, 82 pages.

Perazella et al. "Renal Cell Carcinoma for the Nephrologist." Kidney International. Sep. 1, 2018;94(3): 471-483.

Al-Salama et al. "Lenvatinib: A Review in Hepatocellular Carcinoma." Drugs 2019; 79:665-674.

Baozhu et al. "Health Coming from a Scientific Way of Life." Yanbian University Press, 2011, pp. 68-72.

Barbaras et al. "Abstract 493: Antiatherosclerotic Activity of a New P2y13 Receptor Agonist (ct1007900) in Animal Models", Arteriosclerosis, Thrombosis, and Vascular Biology, 2012; 32:A493, 5 pages.

Bar-Tana et al. "Inhibition of Lipid Synthesis by ββ'-Tetramethyl-substituted, C14-C22, α,ω-Dicarboxylic Acids in the Rat in Vivo." Journal of Biological Chemistry. Jul. 15, 1985;260(14):8404-8410.

Bastin et al. "Salt Selection and Optimisation Procedures for Pharmaceutical New Chemical Entities." Organic Process Research & Development. Sep. 15, 2000;4(5):427-435.

Bilen et al. "Bempedoic Acid (ETC-1002): An Investigational Inhibitor of ATP Citrate Lyase." Current Atherosclerosis Reports 2016; 18:61.

Broadfield et al. "Salicylate enhances the response of prostate cancer to radiotherapy." The Prostate. Apr. 2019;79(5):489-97.

Bruix et al. "Focus on hepatocellular carcinoma." Cancer Cell. Mar. 1, 2004;5(3):215-9.

Calvisi et al. "Increased lipogenesis, induced by AKT-mTORC1-RPS6 signaling, promotes development of human hepatocellular carcinoma." Gastroenterology. Mar. 1, 2011;140(3):1071-83.

CAS Registry STN Substance Record for 137334-84-0, Nov. 15, 1991, 7 pages.

Chou, T.C. "Drug combination studies and their synergy quantification using the Chou-Talalay method." Cancer research. Jan. 15, 2010;70(2):440-6.

Chou, T.C. "Theoretical Basis, Experimental Design, and Computerized Simulation of Synergism and Antagonism in Drug Combination Studies." Pharmacological Reviews 2006; 58:621-681.

Co-pending U.S. Appl. No. 18/392,680, inventors Oniciu; Daniela Carmen et al., filed Dec. 21, 2023.

Abandoned U.S. Appl. No. 18/398,276, inventor Oniciu; Daniela Carmen, filed Dec. 28, 2023.

Day et al. "Metformin-induced increases in GDF15 are important for suppressing appetite and promoting weight loss." Nature Metabolism. Dec. 2019;1(12):1202-8.

Dzamko et al. "AMPK 31 deletion reduces appetite, preventing obesity and hepatic insulin resistance." Journal of Biological Chemistry. Jan. 1, 2010;285(1):115-22.

Dzamko et al. "AMPK-independent pathways regulate skeletal muscle fatty acid oxidation." The Journal of physiology. Dec. 1, 2008;586(23):5819-31.

El-Serag, H.B. "Current status of sorafenib use for treatment of hepatocellular carcinoma." Gastroenterology & Hepatology. Oct. 2017;13(10):623-625.

Extended European Search Report for EP Application No. 20848591.2, dated Aug. 21, 2023, 5 pages.

Folch et al. "A Simple Method for the Isolation and Purification of Total Lipides from Animal Tissues." Journal of biological chemistry. May 1, 1957;226(1):497-509.

Ford et al. "Metformin and salicylate synergistically activate liver AMPK, inhibit lipogenesis and improve insulin sensitivity." Biochemical Journal. May 15, 2015;468(1):125-32.

Franken et al. "Clonogenic assay of cells in vitro." Nat Protoc. 2006;1:2315-9.

Fullerton et al. "Single phosphorylation sites in Acc1 and Acc2 regulate lipid homeostasis and the insulin-sensitizing effects of metformin." Nature Medicine. Dec. 2013;19(12):1649-54.

Fullerton et al. "The development of a metabolic disease phenotype in CTP:phosphoethanolamine cytidylyltransferase-deficient mice." Journal of Biological Chemistry. Sep. 18, 2009;284(38):25704-13.

Galic et al. "Hematopoietic AMPK 31 reduces mouse adipose tissue macrophage inflammation and insulin resistance in obesity." The Journal of clinical investigation. Dec. 1, 2011;121(12):4903-15.

Gao et al. "Inactivation of ATP citrate lyase by Cucurbitacin B: A bioactive compound from cucumber, inhibits prostate cancer growth." Cancer Letters. Jul. 10, 2014;349(1):15-25.

Gleiter et al. "Synthesis and properties of 4, 4, 9, 9-tetramethyl [12] paracyclophane-5, 6, 7, 8-tetrone." The Journal of Organic Chemistry. Jan. 1992;57(1):252-8.

Granchi C. "ATP citrate lyase (ACLY) inhibitors: An anti-cancer strategy at the crossroads of glucose and lipid metabolism." European Journal of Medicinal Chemistry. Sep. 5, 2018;157:1276-91.

Hatzivassiliou et al. "ATP citrate lyase inhibition can suppress tumor cell growth." Cancer Cell. Oct. 1, 2005;8(4):311-21.

Huang et al. "Isobologram Analysis: A Comprehensive Review of Methodology and Current Research." Frontiers in Pharmacology, Oct. 29, 2019;10: 12 pages.

Icard et al. "ATP citrate lyase: A central metabolic enzyme in cancer." Cancer Letters. Feb. 28, 2020;471: 125-134.

International Preliminary Report on Patentability for PCT/US2022/013504, dated Jul. 20, 2023, 8 pages.

International Preliminary Report on Patentability for PCT/US2020/043274, dated Feb. 10, 2022, 7 Pages.

International Preliminary Report on Patentability for PCT/US2022/013514, dated Jul. 20, 2023, 9 pages.

International Search Report and Written Opinion for PCT/US2020/043274, dated Dec. 22, 2020, 21 pages.

International Search Report and Written Opinion for PCT/US2022/013504, dated on Jun. 30, 2022, 24 pages.

International Search Report and Written Opinion for PCT/US2022/013514, dated Jun. 8, 2022, 16 pages.

Invitation to Pay Additional Fees for Application No. PCT/US2022/013504 dated Apr. 6, 2022, 3 pages.

(56) References Cited

OTHER PUBLICATIONS

Invitation to Pay Additional Fees for Application No. PCT/US2022/013514 dated Mar. 23, 2022, 3 pages.
Kearns et al. "Developmental Pharmacology—Drug Disposition, Action, and Therapy in Infants and Children." New England Journal of Medicine. Sep. 18, 2003;349(12):1157-67.
Khwairakpam et al. "ATP Citrate Lyase (ACLY): A Promising Target for Cancer Prevention and Treatment", Current Drug Targets, 2015; 16:156-63.
Kimura et al. "Immunomodulatory activity of lenvatinib contributes to antitumor activity in the Hepa1-6 hepatocellular carcinoma model." Cancer Science. Dec. 2018;109(12):3993-4002.
Kudo et al. "Lenvatinib versus sorafenib in first-line treatment of patients with unresectable hepatocellular carcinoma: a randomised phase 3 non-inferiority trial." The Lancet. Mar. 24, 2018;391(10126):1163-73.
Kuhajda "Fatty-acid synthase and human cancer: new perspectives on its role in tumor biology." Nutrition. Mar. 1, 2000;16(3):202-8.
Leathers et al. "PIB: A Score to Select Sorafenib Treatment Candidates for Hepatocellular Carcinoma in Resource-Limited Settings." Hepatitis monthly. Oct. 2018;18(10), 5 pages.
Li et al. "2-hydroxy-N-arylbenzenesulfonamides as ATP-citrate lyase inhibitors." Bioorganic & medicinal chemistry letters. Jun. 1, 2007;17(11):3208-11.
Llovet et al. "Sorafenib in advanced hepatocellular carcinoma." New England journal of medicine. Jul. 24, 2008;359(4):378-90.
Luong et al. "Molecular characterization of human acetyl-CoA synthetase, an enzyme regulated by sterol regulatory element-binding proteins." Journal of Biological Chemistry. Aug. 25, 2000;275(34):26458-66.
Meynard et al. "Inflammation regulates TMPRSS6 expression via STAT5." PLoS One 2013;8: e82127, 10 pages.
Migita et al. "ATP citrate lyase: activation and therapeutic implications in non-small cell lung cancer." Cancer research. Oct. 15, 2008;68(20):8547-54.
Mueller et al. "Long Hydrocarbon Chain Ether Diols and Ether Diacids That Favorably Alter Lipid Disorders in Vivo." Journal of medicinal chemistry. Oct. 7, 2004;47(21):5183-97.
Notice of Allowance for U.S. Appl. No. 16/937,154, dated Jun. 24, 2021, 9 pages.
Notice of Allowance for U.S. Appl. No. 17/190,844, dated Jun. 11, 2021, 8 pages.
Notice of Allowance for U.S. Appl. No. 17/240,513, dated Dec. 29, 2021, 9 pages.
Notice of Allowance for U.S. Appl. No. 17/582,728, dated Apr. 19, 2023, 8 pages.
Notice of Allowance for U.S. Appl. No. 17/582,774, dated Feb. 8, 2023, 5 pages.
Office Action for U.S. Appl. No. 16/937,154, dated Jan. 1, 2021, 12 pages.
Office Action for U.S. Appl. No. 16/937,154, dated Jan. 28, 2021, 14 pages.
Office Action for U.S. Appl. No. 16/937,154, dated Mar. 19, 2021, 19 pages.
Office Action for U.S. Appl. No. 17/190,844, dated May 3, 2021, 14 pages.
Office Action for U.S. Appl. No. 17/240,513, dated Sep. 3, 13 pages.
Office Action for U.S. Appl. No. 17/571,107, dated Mar. 3, 2023, 16 pages.
Office Action for U.S. Appl. No. 17/571,107, dated Oct. 5, 2023, 14 pages.
Office Action for U.S. Appl. No. 17/373,110, dated Nov. 25, 2022, 10 pages.
O'Neil K. "ATP-Citrate Lyase Inhibition Improves Chronic Kidney Disease Through Multiple Mechanisms—Abstract." McMaster University, MacSphere (Dissertations and Theses) [online], Nov. 2023. Retrieved from the Internet URL: http://hdl.handle.net/11375/29119, 2 pages.
Oniciu et al. "In vitro Models Concur with Clinical Results to Confirm Pleiatropic Mechanisms of Action for Gemcabene." Thrombosis, and Vascular Biology 2017, Abstract No. 579, poster, 1 page.
Oniciu et al. "Long hydrocarbon chain diols and diacids with central ether or ketone moieties that favorably alter lipid disorders." Pharmazie—An International Journal of Pharmaceutical Sciences. Feb. 1, 2006;61(2):157-65.
Paglialunga et al. "Clinical assessment of hepatic de novo lipogenesis in non-alcoholic fatty liver disease." Lipids in Health and Disease. 2016, 15:159-169.
Pawlik et al. "Phase II trial of sorafenib combined with concurrent transarterial chemoembolization with drug-eluting beads for hepatocellular carcinoma." Journal of Clinical Oncology. Oct. 20, 2011;29(30):3960-7.
Pinkosky et al. "AMP-activated protein kinase and ATP-citrate lyase are two distinct molecular targets for ETC-1002, a novel small molecule regulator of lipid and carbohydrate metabolism." Journal of lipid research. Jan. 1, 2013;54(1):134-51.
Pinto et al. "Thermoanalytical studies of carbamazepine: hydration/dehydration, thermal decomposition, and solid phase transitions." Brazilian Journal of Pharmaceutical Sciences. 2014;50(4): 877-884.
Portolani et al. "Early and late recurrence after liver resection for hepatocellular carcinoma: prognostic and therapeutic implications." Annals of Surgery 2006; 243:229-35.
Pubchem, SID 228534127, Substance Record for SCHEMBL2421674, Available Date: Feb. 12, 2015 [retrieved on Mar. 18, 2022]. Retrieved from the Internet: https://pubchem.ncbi.nlm.nih.gov/substance/228534127. 8 pages.
Pubchem SID 275387334, Substance Record for 102239157; Available Date: Dec. 25, 2015, 5 pages. [retrieved on Mar. 31, 2022]. Retrieved from the Internet: https://pubchem.ncbi.nlm.nih.gov/substance/275387334.
Pubchem SID 319409634, Substance Record for 124924-91-0; Available Date: Nov. 29, 2016 [retrieved on May 12, 2022]. Retrieved from the Internet: https://pubchem.ncbi.nlm.nih.gov/substance/319409634. 6 pages.
PUBCHEM-CID: 7734 Create Date: Mar. 27, 2005, pp. 1-46.
Rose-Kahn et al. "Inhibition of Lipid Synthesis by ββ'-Tetramethyl-substituted, C14-C22, α,ω-Dicarboxylic Acids in Cultured Rat Hepatocytes." Journal of Biological Chemistry. Jul. 15, 1985;260(14):8411-5.
Roumans et al. "Hepatic saturated fatty acid fraction is associated with de novo lipogenesis and hepatic insulin resistance." Nature communications. Apr. 20, 2020;11(1):1891, 11 pages.
Sachithanandan et al. "Liver-Specific Suppressor of Cytokine Signaling-3 Deletion in Mice Enhances Hepatic Insulin Sensitivity and Lipogenesis Resulting in Fatty Liver and Obesity 1." Hepatology. Nov. 2010;52(5):1632-42.
Seglen Po "Hepatocyte suspensions and cultures as tools in experimental carcinogenesis." Journal of Toxicology and Environmental Health, Part A Current Issues. Mar. 1, 1979;5(2-3):551-60.
Spallanzani et al. "Lenvatinib as a therapy for unresectable hepatocellular carcinoma." Expert Review of Anticancer Therapy 2018; 18:1069-1076.
Sur et al. "Inhibition of the key metabolic pathways, glycolysis and lipogenesis, of oral cancer by bitter melon extract." Cell Communication and Signaling. Dec. 2019;17:1-3.
Venook et al. "The incidence and epidemiology of hepatocellular carcinoma: a global and regional perspective." The Oncologist, 2010;15 Suppl 4:5-13.
Xie et al. "Development of the novel ACLY inhibitor 326E as a promising treatment for hypercholesterolemia." Acta Pharmaceutica Sinica B 2023;13(2):739-753.
Yahagi et al. "Co-ordinate activation of lipogenic enzymes in hepatocellular carcinoma." European Journal of Cancer. Jun. 1, 2005;41(9):1316-22.
Yamamoto et al. "Recurrence of hepatocellular carcinoma after surgery." The British Journal of Surgery 1996; 83:1219-22.
Zaidi et al. "ATP citrate lyase knockdown induces growth arrest and apoptosis through different cell- and environment-dependent mechanisms." Molecular cancer therapeutics. Sep. 1, 2012;11(9):1925-35.
Zhao et al. "ATP-Citrate Lyase Controls a Glucose-to-Acetate Metabolic Switch." Cell reports. Oct. 18, 2016;17(4):1037-52.

(56) References Cited

OTHER PUBLICATIONS

Cornec-Le Gall et al. "Autosomal dominant polycystic kidney disease." The Lancet. Mar. 2, 2019;393(10174):919-935.
Djudjaj et al. "Cellular and molecular mechanisms of kidney fibrosis." Molecular aspects of medicine. Feb. 1, 2019;65:16-36.
Lee et al. "Therapeutic targets for treating fibrotic kidney diseases." Translational Research. Apr. 1, 2015;165(4):512-530.
Müller et al. "Management of autosomal-dominant polycystic kidney disease-state-of-the-art." Clinical Kidney Journal. Dec. 17, 2018;11(suppl_1):i2-i13.
Ness et al. "Current recommendations for treating autosomal dominant polycystic kidney disease." JAAPA. Dec. 1, 2016;29(12):24-28.
Nogueira et al. "Pathophysiological mechanisms of renal fibrosis: a review of animal models and therapeutic strategies." In Vivo. Jan. 1, 2017;31(1):1-22.
Notice of Allowance for U.S. Appl. No. 18/204,442, dated Nov. 4, 2024, 8 pages.

FUNCTIONALIZED LONG-CHAIN HYDROCARBON MONO- AND DI-CARBOXYLIC ACIDS AND THEIR USE FOR THE PREVENTION OR TREATMENT OF DISEASE

CROSS-REFERENCE TO RELATED APPLICATIONS

This application is a continuation of U.S. application Ser. No. 18/204,442, filed Jun. 1, 2023, which is a continuation of U.S. application Ser. No. 17/571,107, filed Jan. 7, 2022, now abandoned, which is a continuation of U.S. application Ser. No. 17/240,513, filed Apr. 26, 2021, now U.S. Pat. No. 11,267,778, issued Mar. 8, 2022, which is a continuation of U.S. application Ser. No. 16/937,154, filed Jul. 23, 2020, now U.S. Pat. No. 11,098,002, issued Aug. 24, 2021, which claims the benefit of U.S. Provisional Application No. 62/878,852, filed Jul. 26, 2019, and U.S. Provisional Application No. 62/901,739, filed Sep. 17, 2019, the disclosure of each of which is incorporated by reference herein in its entirety.

FIELD OF THE INVENTION

This invention provides compounds of Formulae (IA), (IB), (IC), (ID), (IE), (IF), (IG), (IH), (IJ), (IK), (IL), (II), (III), (IIIA), and (IIIB), and pharmaceutically acceptable salts and solvates thereof, and compositions thereof. This invention further provides methods for preventing or treating a disease, including but not limited to, liver disease or an abnormal liver condition; cancer (such as hepatocellular carcinoma or cholangiocarcinoma); a malignant or benign tumor of the lung, liver, gall bladder, bile duct or digestive tract; an intra- or extra-hepatic bile duct disease; a disorder of lipoprotein; a lipid-and-metabolic disorder; cirrhosis; fibrosis; a disorder of glucose metabolism; a cardiovascular or related vascular disorder; a disease resulting from steatosis, fibrosis, or cirrhosis; a disease associated with increased inflammation (such as hepatic inflammation or pulmonary inflammation); hepatocyte ballooning; a peroxisome proliferator activated receptor-associated disorder; an ATP citrate lyase disorder; an acetyl-coenzyme A carboxylase disorder; obesity; pancreatitis; or renal disease.

BACKGROUND OF THE INVENTION

Hepatocellular carcinoma (HCC) is one of the most common primary liver malignancies. Patients with chronic liver disease, such as liver cirrhosis and fibrosis, are at increased risk for development of HCC. Thus, patients with chronic liver diseases should be closely monitored for development of HCC. Risk factors for HCC include cirrhosis, non-alcoholic fatty liver disease (NAFLD), nonalcoholic stetohepatitis (NASH), chronic alcohol consumption, hepatitis B, and hepatitis C, type IIb hyperlipidemia, mixed dyslipidemia, obesity, and type 2 diabetes.

Type IIb hyperlipidemia patients have a high risk of developing NAFLD and non-alcoholic steatosis hepatitis (NASH), which can develop due to hepatic triglyceride overproduction and accumulation. Elevated levels of low-density lipoprotein cholesterol (LDL-C) and triglycerides are associated with mixed dyslipidemia, including type IIb hyperlipidemia which is characterized by elevation of apolipoprotein B, very low-density lipoprotein cholesterol (VLDL-C), intermediate density lipoprotein cholesterol (IDL), and small dense low-density lipoprotein (LDL) levels, in addition to elevation in LDL-C and triglyceride levels.

Current treatment options for treatment of type IIb hyperlipidemia are limited. While statins can be effective for lowering LDL-C and reducing inflammation, they are generally not very effective for lowering triglyceride concentrations. Further, high dose statin therapy is often not well tolerated because it can cause muscle pain (myalgia) and increase a patient's risk of serious muscle toxicity, such as rhabdomyolysis. Also, commonly used triglyceride-lowering agents that are administered in combination with statins are often not well-tolerated. When administered with statins, fibrates are known to have drug-drug interactions, resulting in increased statin blood drug levels, myalgia, an increased risk of muscle toxicity and an increased safety risk. Indeed, the interaction of the statin Baychol (cerivastatin) with the fibrate gemfibrozil resulted in severe muscle toxicity and deaths and raised safety concerns that resulted in the removal of Baychol from the U.S. market. Fish oil, which has been used to lower triglyceride levels, needs to be taken multiple times daily and can cause a fish oil aftertaste, burping or regurgitation. Niacin causes flushing, particularly when administered in combination with statins.

Hepatocellular adenomas are benign liver neoplasms whose genetics and pathophysiology are not entirely known. These lesions pose diagnostic and therapeutic challenges and treatments post-exeresis are still challenging. Bile duct adenomas raise the same therapeutic challenges. Digestive system adenomas are sporadic neoplasms, arising from the glandular epithelium of the stomach, small intestine, biliary tract, colon, and rectum.

Gastrointestinal (digestive) cancers are cancers that affect the gastrointestinal tract and other organs that are contained within the digestive system. Gastrointestinal stromal tumor (GIST), is a rare type of sarcoma that forms along the gastrointestinal tract, but mostly starts in the stomach or small intestine. The origins of the digestive cancers were linked strongly to chronic inflammation of the organs that develop through a series of histopathologic stages dependent of the organ affected. For cancers of the gastrointestinal tract or GIST, surgery will likely be recommended to remove the tumor and/or to help maintain normal function. Other treatment options are radiotherapy, chemotherapy, hormone therapy, or targeted therapies.

Thus, there is a need for a safe and effective therapy for treatment or prevention of cancer (such as gastrointestinal cancer, hepatocellular carcinoma or cholangiocarcinoma); a malignant or benign tumor of the lung, liver, gall bladder, bile duct or digestive tract; liver disease or an abnormal liver condition, an intra- or extra-hepatic bile duct disease; a disorder of lipoprotein; a lipid-and-metabolic disorder; cirrhosis; fibrosis; a disorder of glucose metabolism; a cardiovascular or related vascular disorder; a disease resulting from steatosis, fibrosis, or cirrhosis; a disease associated with increased inflammation (such as hepatic inflammation or pulmonary inflammation); hepatocyte ballooning; a peroxisome proliferator activated receptor-associated disorder; an ATP citrate lyase disorder; an acetyl-coenzyme A carboxylase disorder; obesity; pancreatitis; or renal disease.

SUMMARY OF THE INVENTION

The present invention provides compounds of Formulae (IA), (IB), (IC), (ID), (IE), (IF), (IG), (IH), (IJ), (IK), (IL), (II), (III), (IIIA), and (IIIB), and pharmaceutically acceptable salts and solvates thereof (each compound, pharmaceutically acceptable salt and solvate being a "compound of the invention").

The present invention also provides compositions comprising i) an effective amount of a compound of the invention and ii) a pharmaceutically acceptable carrier or vehicle (each composition being a "composition of the invention").

The present invention further provides methods for treating or preventing a disease, comprising administering to a subject in need thereof an effective amount of a compound of the invention, wherein the disease is liver disease or an abnormal liver condition; cancer (such as hepatocellular carcinoma or cholangiocarcinoma); a malignant or benign tumor of the lung, liver, gall bladder, bile duct or digestive tract; an intra- or extra-hepatic bile duct disease; a disorder of lipoprotein; a lipid-and-metabolic disorder; cirrhosis; fibrosis; a disorder of glucose metabolism; a cardiovascular or related vascular disorder; a disease resulting from steatosis, fibrosis, or cirrhosis; a disease associated with increased inflammation (such as hepatic inflammation or pulmonary inflammation); hepatocyte ballooning; a peroxisome proliferator activated receptor-associated disorder; an ATP citrate lyase disorder; an acetyl-coenzyme A carboxylase disorder; obesity; pancreatitis; or renal disease.

The present invention further provides methods for treating or preventing a disease, wherein the disease is cancer, a lipid-and-metabolic disorder, a liver disorder, cirrhosis, fibrosis, a disorder of glucose metabolism, a peroxisome proliferator activated receptor-associated disorder, a malignant or benign tumor of the lung, liver, bile and digestive tract, an ATP citrate lyase disorder, an acetyl-coenzyme A carboxylase disorder, obesity, pancreatitis, renal disease, hepatocyte ballooning, hepatic inflammation, or pulmonary inflammation.

The present invention further provides methods for reducing in a subject's blood plasma or blood serum, the subject's C-reactive protein (CRP) concentration, serum amyloid A (SAA) concentration, alanine aminotransferase (ALT) concentration, aspartate aminotransferase (AST) concentration, alkaline phosphatase (ALP) concentration, gamma-glutamyl transferase (GGT) concentration, serum creatinine concentration, 7α-hydroxy-4-cholesten-3-one (C4) concentration, protein:creatinine ratio, creatine kinase concentration, angiopoietin-like protein 3 concentration, angiopoietin-like protein 4 concentration, angiopoietin-like protein 8 concentration, fibrinogen concentration, total cholesterol concentration, low-density lipoprotein cholesterol concentration, low-density lipoprotein concentration, very low-density lipoprotein cholesterol concentration, very low-density lipoprotein concentration, non-HDL cholesterol concentration, non-HDL concentration, apolipoprotein B concentration, lipoprotein(a) concentration, or serum triglyceride concentration, comprising administering to a subject in need thereof an effective amount of a compound of the invention.

The present invention further provides methods for reducing triglyceride concentration in a subject's liver, comprising administering to a subject in need thereof an effective amount of a compound of the invention.

The present invention further provides methods for elevating in a subject's blood plasma or blood serum a concentration of high-density lipoprotein cholesterol or high-density lipoprotein, comprising administering to a subject in need thereof an effective amount of a compound of the invention.

The present invention further provides methods for treating a disease, comprising administering to a subject in need thereof an effective amount of a compound of the invention, wherein the disease is gastrointestinal disease, irritable bowel syndrome (IBS), inflammatory bowel disease (IBD), or autoimmune disease.

The present invention further provides methods for regressing, reducing the rate of progression, or inhibiting progression, of fibrosis, hepatocyte ballooning or hepatic inflammation, comprising administering to a subject in need thereof an effective amount of a compound of the invention.

The present invention further provides methods for inhibiting, reducing, or delaying advancement of a subject's lipid synthesis, liver steatosis, hepatocyte ballooning or inflammation, liver fibrosis, lung fibrosis, or cirrhosis, comprising administering to a subject in need thereof an effective amount of a compound of the invention.

The present invention further provides methods for reducing a subject's risk of developing or having atherosclerosis, coronary heart disease, peripheral vascular disease, stroke, or restenosis, comprising administering to a subject in need thereof an effective amount of a compound of the invention.

The present invention further provides methods for elevating HDL concentration in a subject's blood serum or plasma, comprising administering to a subject in need thereof an effective amount of a compound of the invention.

The present invention further provides methods for inhibiting NF-kB or stellate cell activation, comprising administering to a subject in need thereof an effective amount of a compound of the invention.

The present invention further provides methods for activating PPAR (peroxisome proliferator-activated receptor), comprising administering to a subject in need thereof an effective amount of a compound of the invention.

The present invention further provides methods for reducing the fat or cholesterol content of livestock meat or poultry eggs, comprising administering to the livestock or poultry an effective amount of a compound of the invention.

The present invention further provides methods for modulating, directly inhibiting or allosterically inhibiting ATP citrate lyase in a subject, comprising administering to a subject in need thereof an effective amount of a compound of the invention.

The present invention further provides methods for modulating, directly inhibiting or allosterically inhibiting acetyl-CoA carboxylase 1 or acetyl-CoA carboxylase 2 in a subject, comprising administering to a subject in need thereof an effective amount of a compound of the invention.

The present invention further provides method for treating or preventing a disease, comprising administering to a subject in need thereof an effective amount of a composition of the invention, wherein the disease is cancer, a lipid-and-metabolic disorder, a liver disorder, cirrhosis, fibrosis, a disorder of glucose metabolism, a peroxisome proliferator activated receptor-associated disorder, a malignant or benign tumor of the lung, liver, bile and digestive tract, an ATP citrate lyase disorder, an acetyl-coenzyme A carboxylase disorder, obesity, pancreatitis, renal disease, hepatocyte ballooning, hepatic inflammation, or pulmonary inflammation.

DETAILED DESCRIPTION OF THE INVENTION

Definitions

Figure 1A:
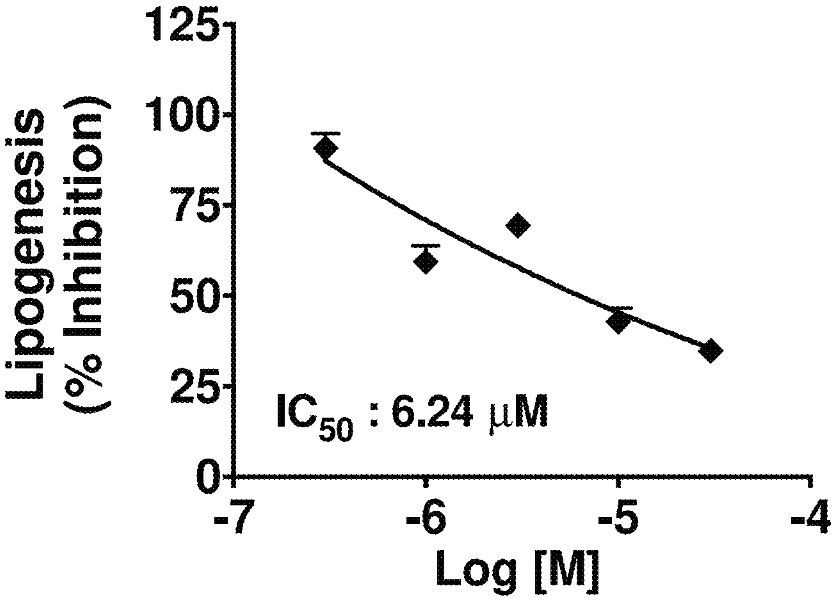
FIGS. 1A-1D show inhibitory effects of Compounds I-32, I-61, I-1, and III-1, respectively, on mouse primary hepatocyte lipogenesis as percent control.
Figure 1B:
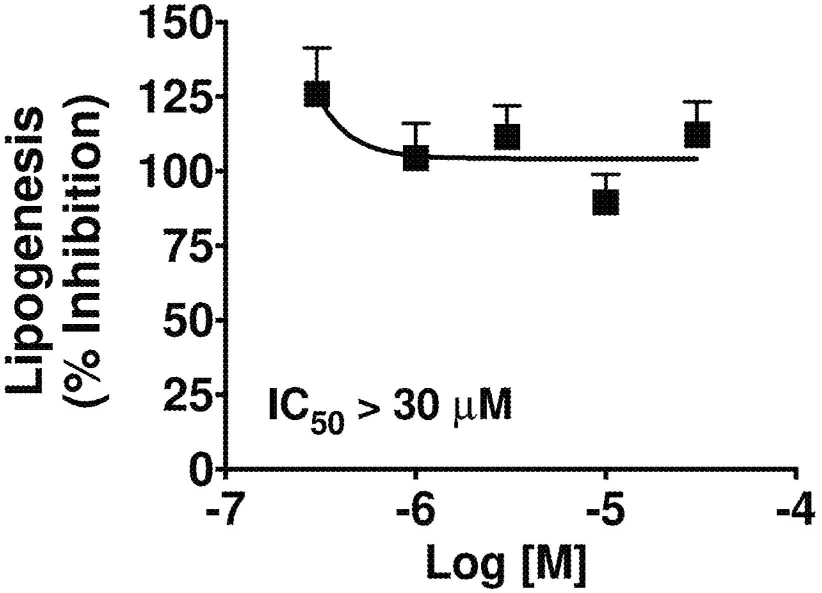
Figure 1C:
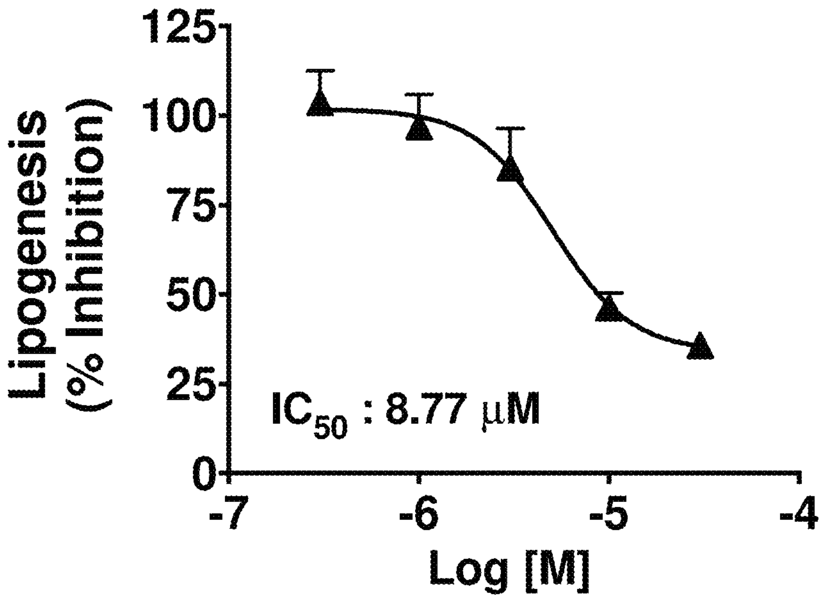
Figure 1D:
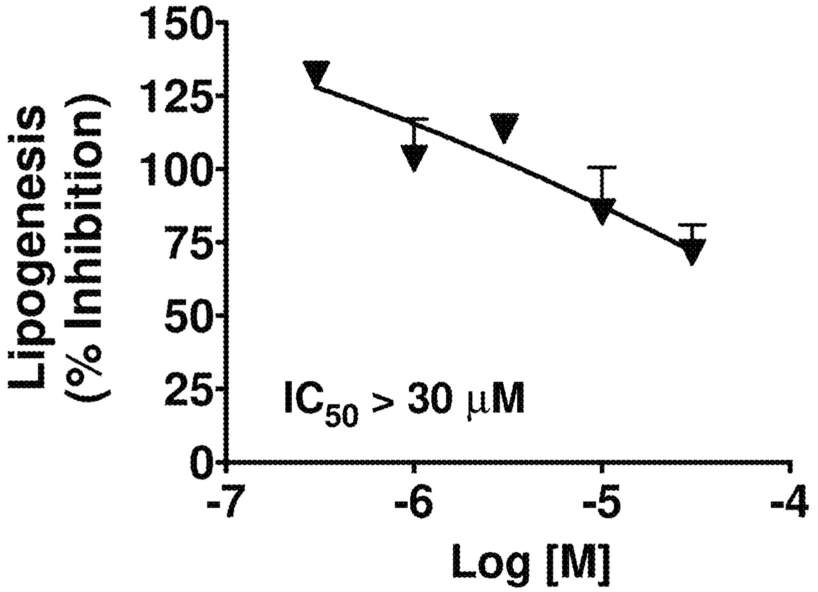
Figure 2A:
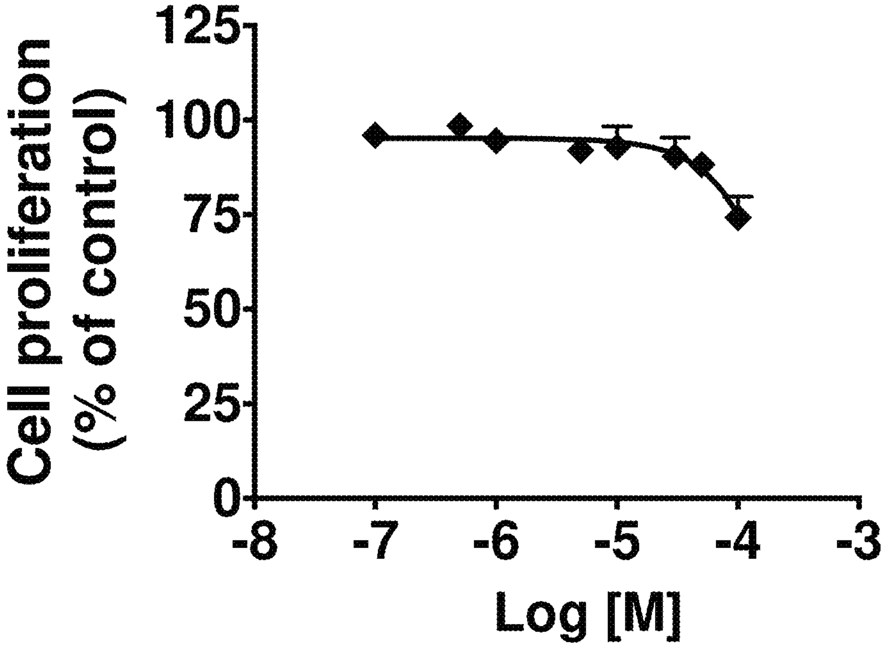
FIGS. 2A-2D show anti-proliferative effects of Compounds I-32, I-61, I-1, and III-1, respectively, on Hepa1-6 cells as a percent of vehicle control.
Figure 2B:
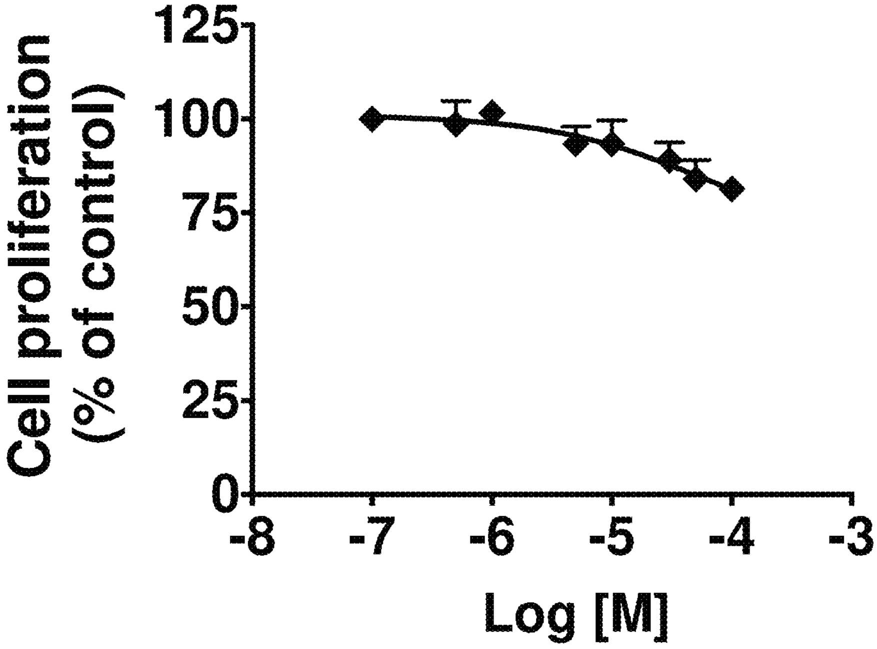
Figure 2C:
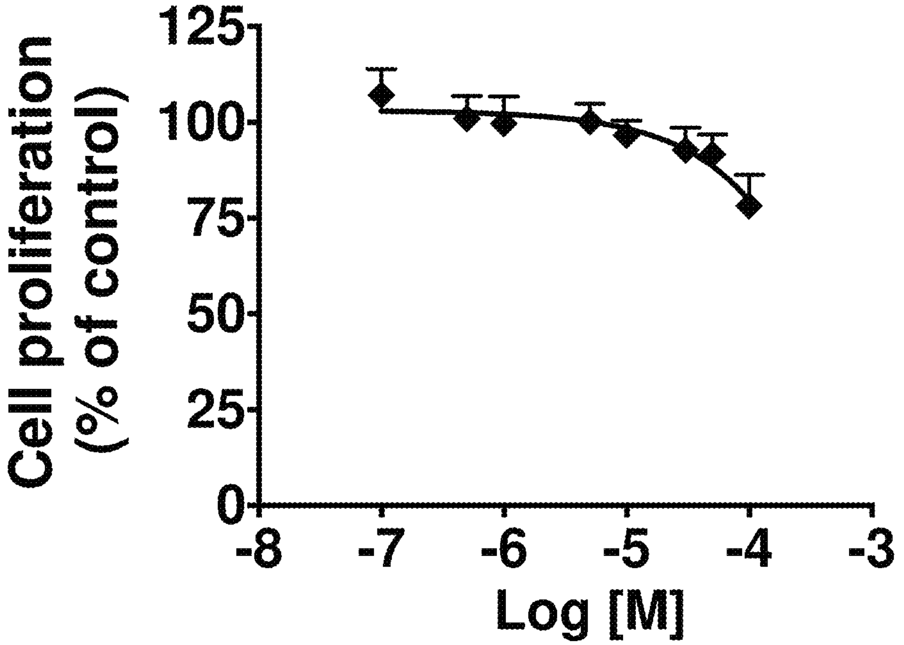
Figure 2D:
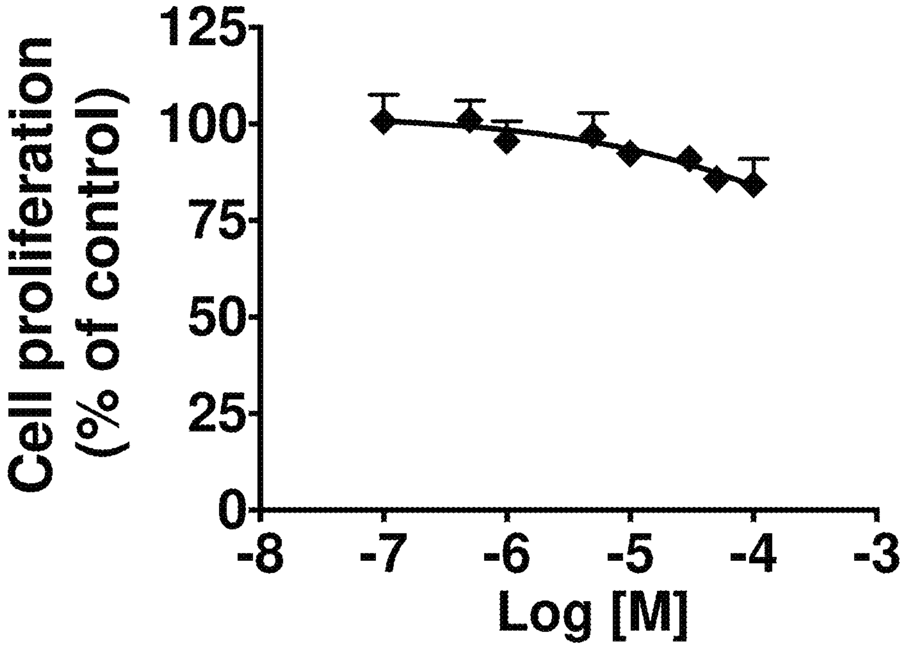
Figure 3A:
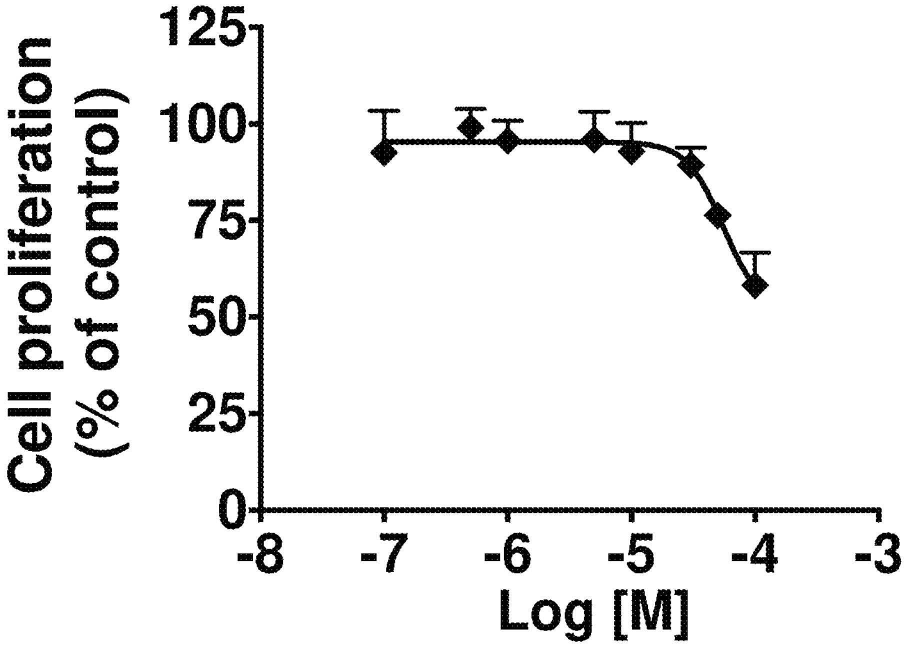
FIGS. 3A-3D show anti-proliferative effects of Compounds I-32, I-61, I-1, and III-1, respectively, on Hep3B cell proliferation as a percent of vehicle control.
Figure 3B:
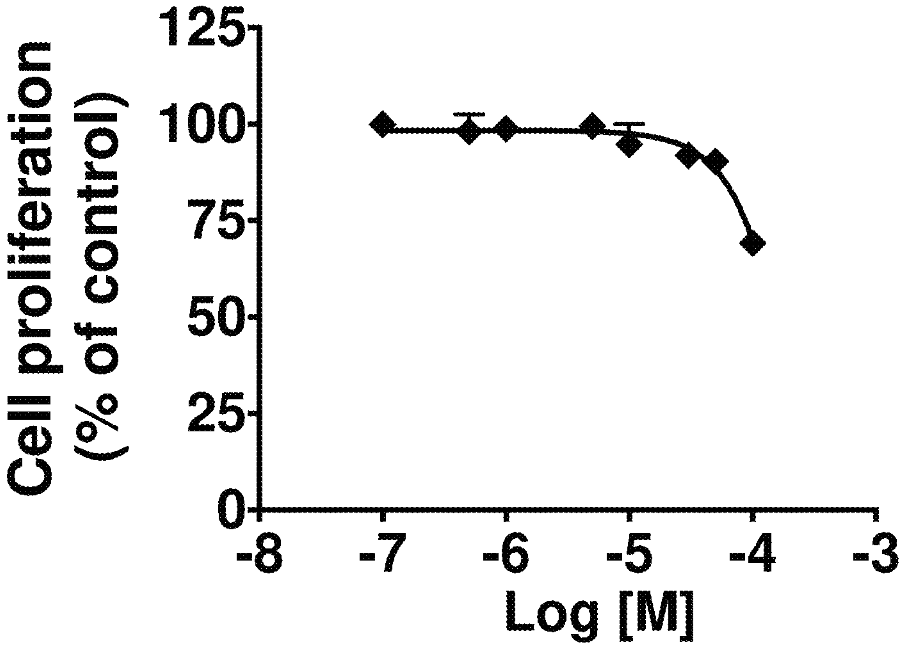
Figure 3C:
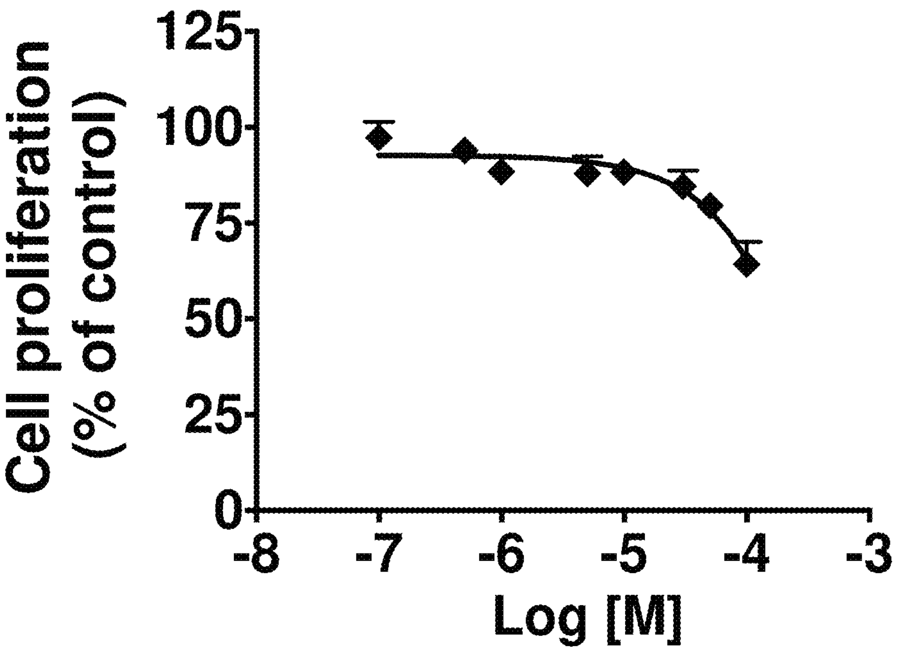
Figure 3D:
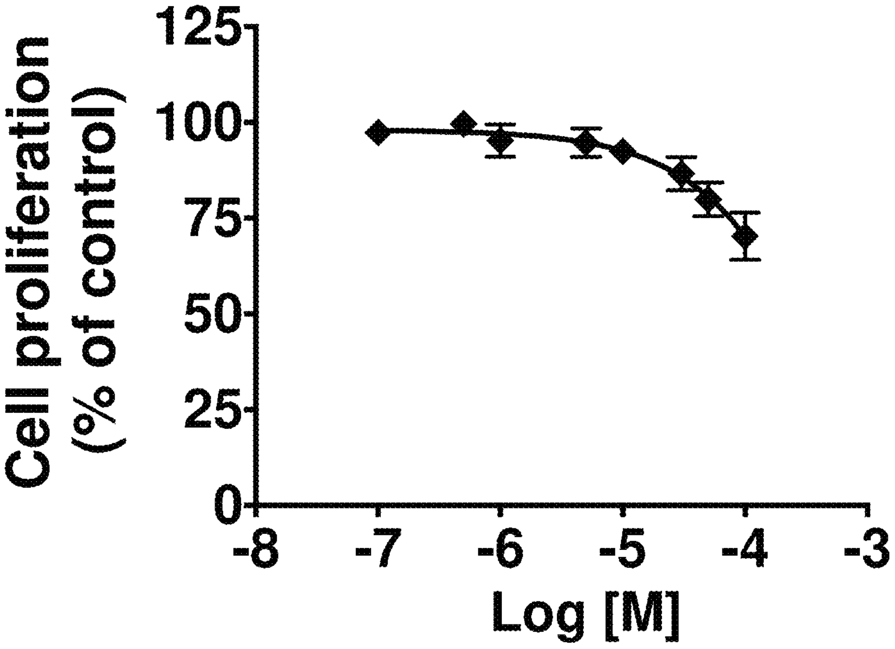
Figure 4A:
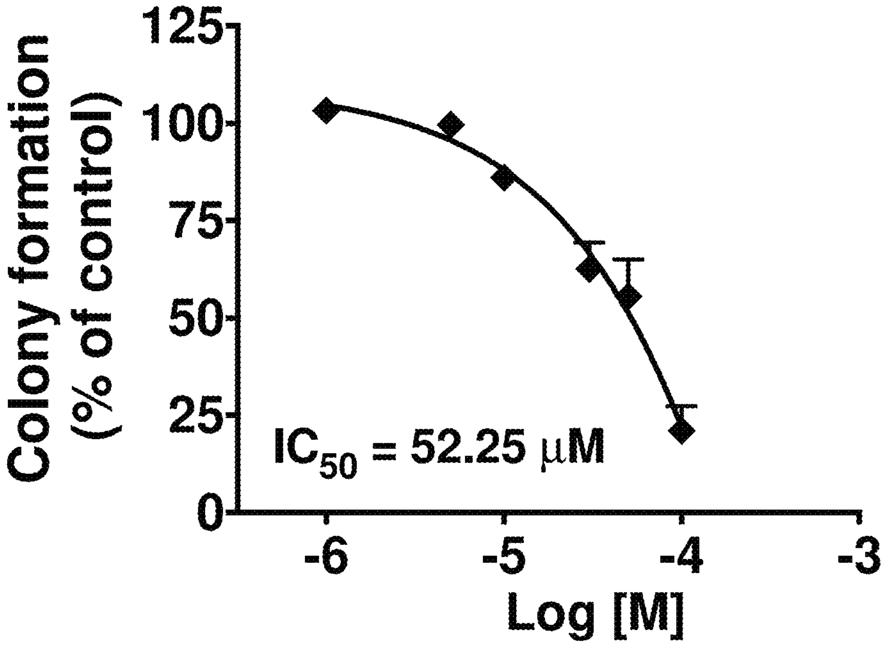
FIGS. 4A-4D show anti-clonogenic effects of Compounds I-32, I-61, I-1, and III-1, respectively, in Hepa1-6 cells as a percent of vehicle control.
Figure 4B:
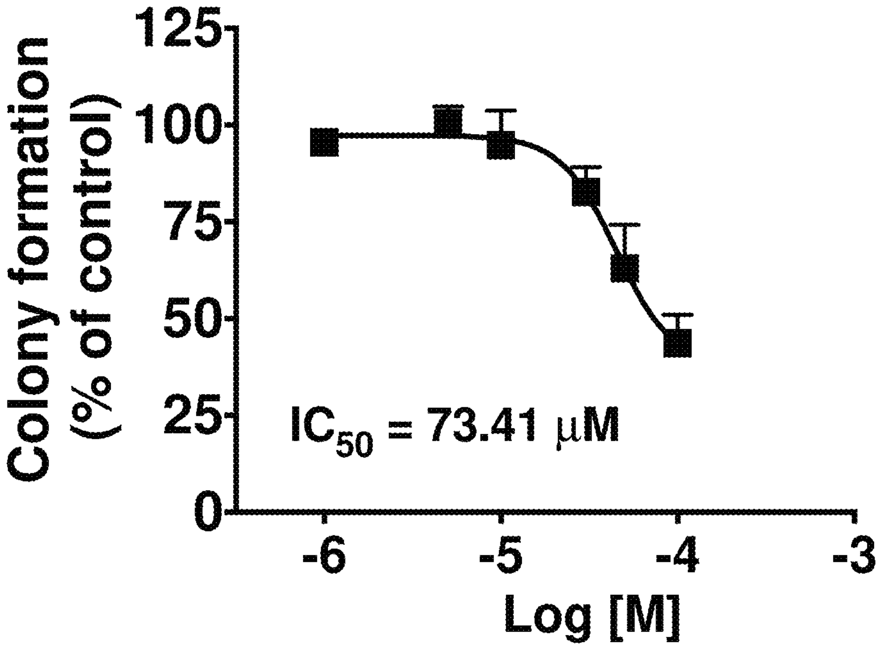
Figure 4C:
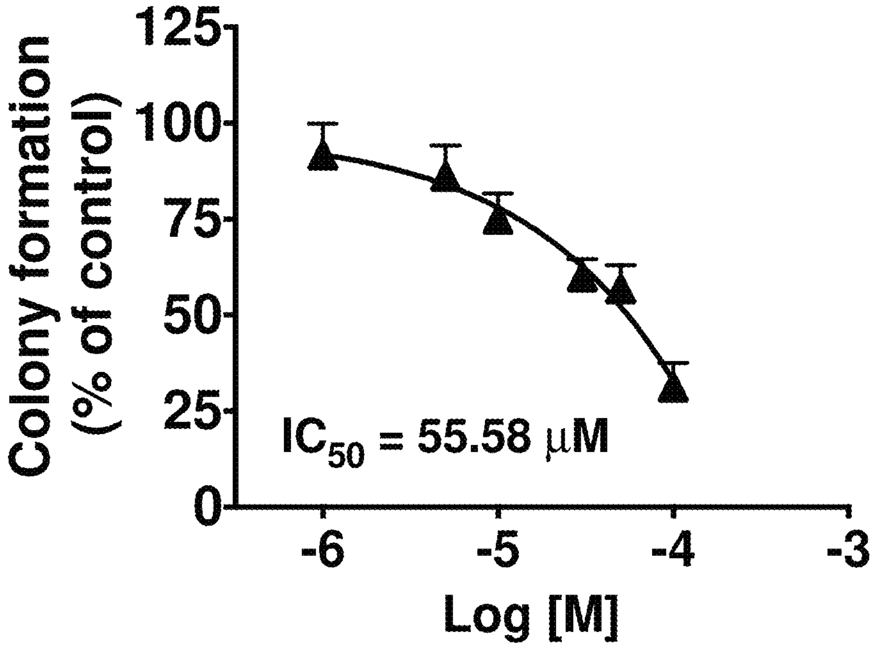
Figure 4D:
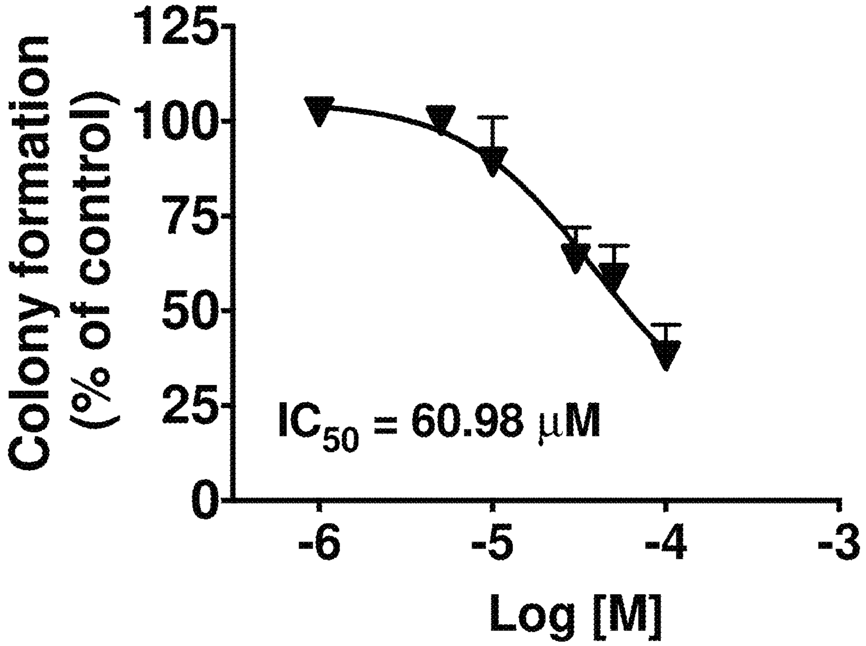
Figure 5A:
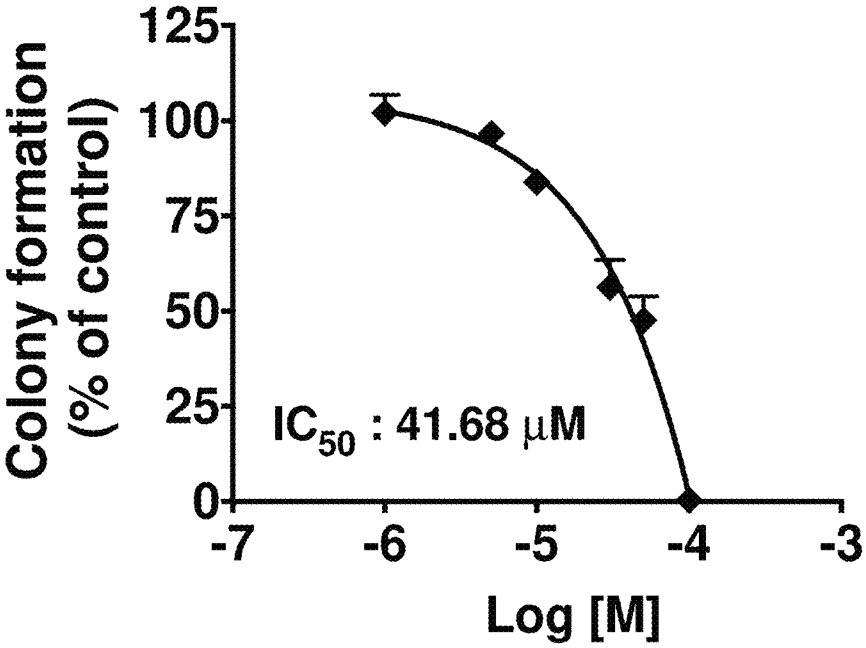
FIGS. 5A-5D show anti-clonogenic effects of Compounds I-32, I-61, I-1, and III-1, respectively, in Hep3B cells as a percent of vehicle control.
Figure 5B:
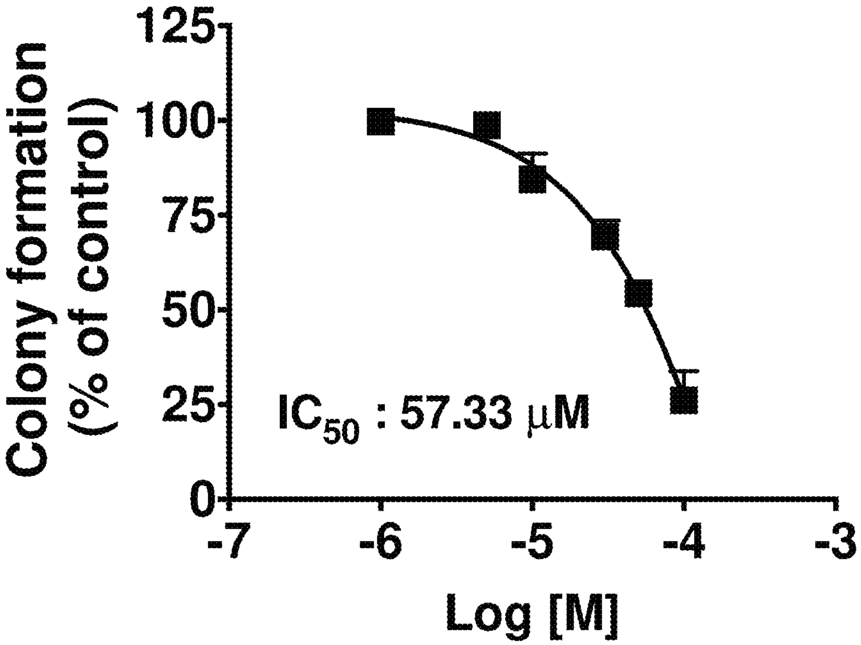
Figure 5C:
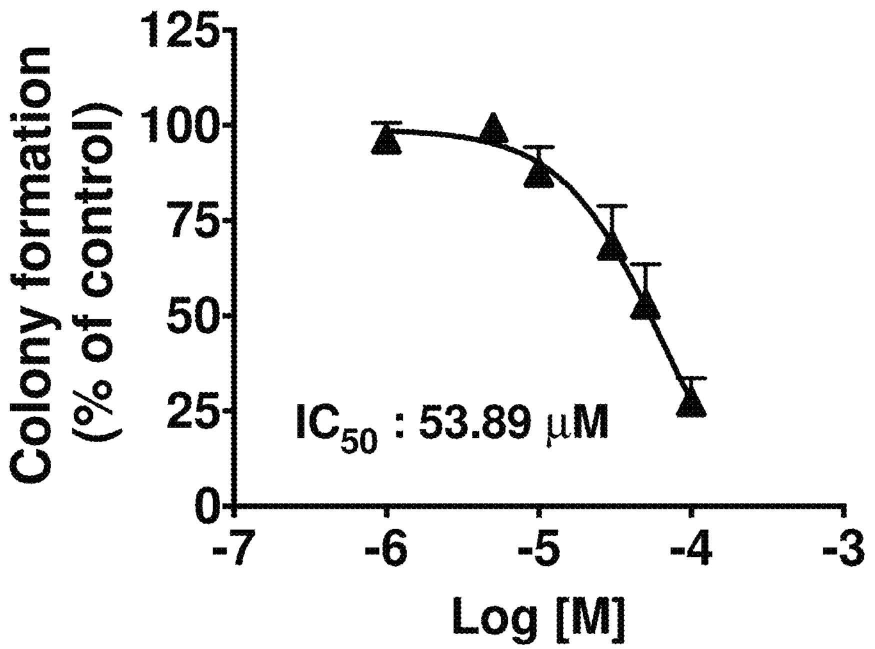
Figure 5D:
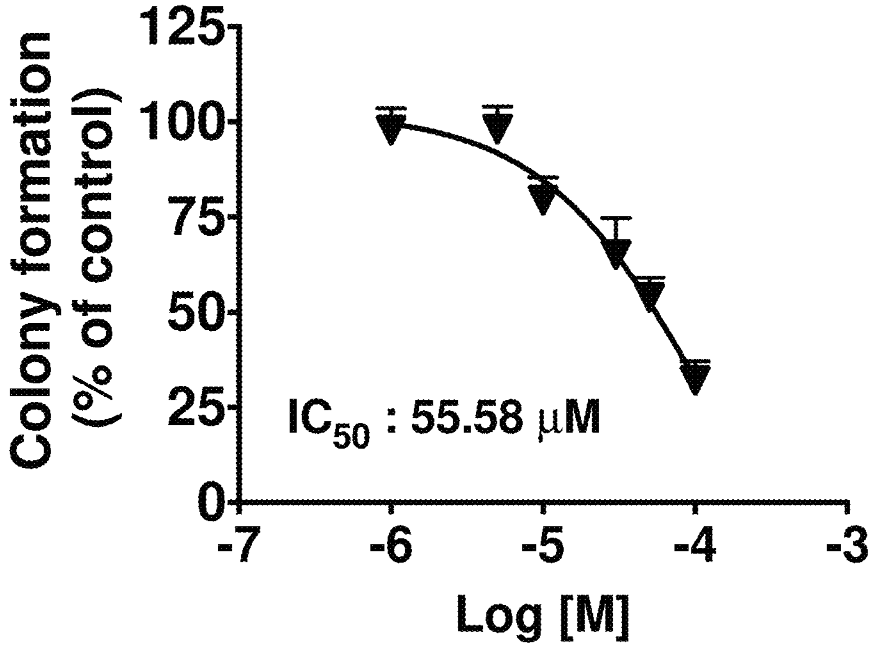

The term "about" when immediately preceding a numerical value means±up to 20% of the numerical value. For example, "about" a numerical value means±up to 20% of the numerical value, in some embodiments, ± up to 19%, ± up to 18%, ± up to 17%, ± up to 16%, ± up to 15%, ± up to 14%, ± up to 13%, ± up to 12%, ± up to 11%, ± up to 10%, ± up to 9%, ± up to 8%, ± up to 7%, ± up to 6%, ± up to 5%, ± up to 4%, ± up to 3%, ± up to 2%, ± up to 1%, ±+up to less than 1%, or any other value or range of values therein.

Throughout the present specification, numerical ranges are provided for certain quantities. These ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "pharmaceutically acceptable salt" includes both an acid and a base addition salt. Pharmaceutically acceptable salts can be obtained by reacting the compound of the invention functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Pharmaceutically acceptable salts can also be obtained by reacting a compound of the invention functioning as an acid, with an inorganic or organic base to form a salt, for example, salts of sodium, potassium, lithium, ammonium, calcium, magnesium, iron, zinc, copper, manganese, aluminum, ammonia, isopropylamine, trimethylamine, etc. Those skilled in the art will further recognize that pharmaceutically acceptable salts can be prepared by reaction of the compounds of the invention with an appropriate inorganic or organic acid or base via any of a number of known methods.

The term "solvate" refers to a solvation complex. Solvates can be formed by solvation (the combination of solvent molecules with molecules or ions of the compounds of the invention), or a solvate can be an aggregate that comprises a solute ion or molecule or a solvent molecules. The solvent can be water, in which case the solvate is a hydrate. Examples of hydrates include, but are not limited to, a hemihydrate, monohydrate, dihydrate, trihydrate, hexahydrate, etc. The solvate can be formed via hydration, including via absorption of moisture. A pharmaceutically acceptable salt can also be a solvate. Where a solvate is obtained via crystallization from a solvent, the solvent can be an alcohol, such as methanol or ethanol; an aldehyde; a ketone, such as acetone; or an ester, such as ethyl acetate.

The compounds of the invention can have one or more asymmetric centers and can thus be enantiomers, racemates, diastereomers, other stereoisomers and mixtures thereof. The compounds of the invention include all such possible isomers (including geometric isomers), as well as their racemic and optically pure forms whether or not they are specifically depicted herein. Optically active (+) and (−), (R)- and (S)-, or (D)- and (L)-isomers can be prepared using chiral synthons or chiral reagents, or resolved using conventional techniques, for example, chromatography and fractional crystallization. Conventional techniques for the preparation or isolation of individual enantiomers include chiral synthesis from a suitable optically pure precursor or resolution of the racemate using, for example, chiral high pressure liquid chromatography (HPLC). When the compounds of the invention comprise an olefinic double bond or another center of geometric asymmetry, and unless specified otherwise, the compounds of the invention include both E and Z geometric isomers. Likewise, the compounds of the invention include all tautomeric forms.

An "effective amount" when used in connection with a compound of the invention means an amount of the compound of the invention that, when administered to a subject is effective to treat or prevent the disease, alone or with another pharmaceutically active agent.

An "effective amount" when used in connection with another pharmaceutically active agent means an amount of the other pharmaceutically active agent that is effective to treat or prevent the disease, alone or in combination with a compound of the invention.

A "subject" is a human or non-human mammal, e.g., a bovine, horse, feline, canine, rodent, or non-human primate. The human can be a male or female, child, adolescent or adult. The female can be premenarcheal or postmenarcheal.

"Mammal" includes a human, domestic animal such as a laboratory animal (e.g., mouse, rat, rabbit, monkey, dog, etc.) and household pet (e.g., cat, dog, swine, cattle, sheep, goat, horse, rabbit), and a non-domestic, wild animal.

All weight percentages (i.e., "% by weight" and "wt. %" and w/w) referenced herein, unless otherwise indicated, are relative to the total weight of the mixture or composition, as the case can be.

The terms below, as used herein, have the following meanings, unless indicated otherwise:

"Halo", "Hal", or "halogen" refers to Br, Cl, F, or I.

"Alkyl" refers to a fully saturated, straight or branched hydrocarbon chain having from one to twelve carbon atoms, and which is attached to an atom by a single bond. Alkyls with a number of carbon atoms ranging from 1 to 12 are included. An alkyl group with 1 to 12 carbon atoms is a $C_1$-$C_{12}$ alkyl, an alkyl group with 1 to 10 carbon atoms is a $C_1$-$C_{10}$ alkyl, an alkyl group with 1 to 6 carbon atoms is a $C_1$-$C_6$ alkyl and an alkyl group with 1 to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise, an alkyl group can be unsubstituted or substituted with a substituent disclosed herein.

"Alkylene" refers to a fully saturated, straight or branched divalent hydrocarbon, and having from one to twelve carbon atoms. Non-limiting examples of $C_1$-$C_{12}$ alkylene include methylene, ethylene, propylene, n-butylene, and the like. Each alkylene terminus is attached to an atom by a single bond. The points of attachment of the alkylene chain can be one or two atoms. Unless stated otherwise, an alkylene chain can be unsubstituted or substituted with a substituent disclosed herein.

"Alkenyl" refers to a straight or branched hydrocarbon chain having from two to twelve carbon atoms, and having one or more carbon-carbon double bonds. Each alkenyl group is attached to an atom by a single bond. Alkenyl groups with a number of carbon atoms ranging from 2 to 12 are included. An alkenyl group with 2 to 12 carbon atoms is a $C_2$-$C_{12}$ alkenyl, an alkenyl group with 2 to 10 carbon atoms is a $C_2$-$C_{10}$ alkenyl, an alkenyl group with 2 to 6 carbon atoms is a $C_2$-$C_6$ alkenyl and an alkenyl group with 2 to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise, an alkyl group can be unsubstituted or substituted with a substituent disclosed herein.

"Alkenylene" refers to a straight or branched divalent hydrocarbon chain radical, having from two to twelve carbon atoms, and having one or more carbon-carbon double bonds. Non-limiting examples of $C_2$-$C_{12}$ alkenylene include ethenylene, propenylene, butenylene, and the like. Each terminus of the alkenylene chain is attached to an atom by a single bond. The points of attachment of the alkenylene chain can be through one two atoms. Unless stated otherwise, an alkenylene chain can be unsubstituted or substituted with a substituent disclosed herein.

"Alkynyl" refers to a straight or branched hydrocarbon chain radical having from two to twelve carbon atoms, and having one or more carbon-carbon triple bonds. Each alkynyl group is attached to an atom by a single bond. Alkynyl groups with a number of carbon atoms ranging from 2 to 12 are included. An alkynyl group having 2 to 12 carbon atoms is a $C_2$-$C_{12}$ alkynyl, an alkynyl group with 2 to 10 carbon atoms is a $C_2$-$C_{10}$ alkynyl, an alkynyl group with 2 to 6 carbon atoms is a $C_2$-$C_6$ alkynyl and an alkynyl group with 2 to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise, an alkyl group can be unsubstituted or substituted with a substituent disclosed herein.

"Alkynylene" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propynylene, butynylene, and the like. Each terminus of the alkynylene chain is attached to an atom through a single bond. The points of attachment of the alkynylene chain can be through one or two atoms. Unless stated otherwise, an alkynylene chain can be unsubstituted or substituted with a substituent disclosed herein.

"Alkoxy" refers to a radical of the formula —$OR_a$ where $R_a$ is an alkyl, alkenyl or alknyl radical as defined herein. Unless stated otherwise, an alkoxy group can be unsubstituted or substituted with a substituent disclosed herein.

"Aryl" refers to a hydrocarbon ring system radical comprising hydrogen, 6 to 18 carbon atoms and at least one aromatic ring. The aryl radical can be a monocyclic, bicyclic, tricyclic or tetracyclic ring system, which can include fused or bridged ring systems. Aryl radicals include, but are not limited to, aceanthrylenyl, acenaphthylenyl, acephenanthrylenyl, anthracenyl, azulenyl, chrysenyl, fluoranthenyl, fluorenyl, as-indacenyl, s-indacenyl, indanyl, indenyl, naphthalenyl, phenalenyl, phenanthrenyl, phenyl, pleiadenyl, pyrenyl, and triphenylenyl. Unless stated otherwise, the aryl can be unsubstituted or substituted with a substituent disclosed herein.

"Arylene" refers to a divalent aryl group, wherein the aryl is as defined herein. Unless stated otherwise, an arylene group can be unsubstituted or substituted with a substituent disclosed herein.

"Arylalkyl" refers to a radical of the formula —$R_b$—$R_c$ where $R_b$ is an alkylene group as defined herein and $R_c$ is an aryl radical as defined herein, for example, benzyl, diphenylmethyl and the like. Unless stated otherwise, an arylalkyl group can be unsubstituted or substituted with a substituent disclosed herein. "Arylalkenyl" refers to a radical of the formula —$R_b$—$R_c$ where $R_b$ is an alkenylene group as defined herein and $R_c$ is an aryl radical as defined herein. Unless stated otherwise, an arylalkenyl group can be unsubstituted or substituted with a substituent disclosed herein.

"Arylalkynyl" refers to a radical of the formula —$R_b$—$R_c$ where $R_b$ is an alkynylene group as defined herein and $R_c$ is an aryl radical as defined herein. Unless stated otherwise, an arylalkynyl group can be unsubstituted or substituted with a substituent disclosed herein.

"Cycloalkyl" refers to a non-aromatic monocyclic or polycyclic fully saturated hydrocarbon radical consisting of carbon and hydrogen atoms, which can include fused or bridged ring systems, having from three to twenty carbon atoms, preferably having from three to ten carbon atoms, and which is attached to an atom by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless stated otherwise, a cycloalkyl group can be unsubstituted or substituted with a substituent disclosed herein.

"Aryloxy" refers to a radical of the formula —O(aryl), wherein the aryl radical is as defined herein. Aryloxy includes, but are is not limited to, phenoxy (—O(phenyl)). Unless stated otherwise, an aryloxy group can be unsubstituted or substituted with a substituent disclosed herein.

"Cycloalkenyl" refers to a non-aromatic monocyclic or polycyclic hydrocarbon radical consisting of carbon and hydrogen atoms and having one or more carbon-carbon double bonds. Cycloalkenyl can include fused or bridged ring systems, having from three to twenty carbon atoms, in some embodiments having from three to ten carbon atoms. A cycloalkenyl group is attached to an atom by a single bond. Monocyclic cycloalkenyl radicals include, for example, cyclopentenyl, cyclohexenyl, cycloheptenyl, cycloctenyl, and the like. Polycyclic cycloalkenyl radicals include, for example, bicyclo[2.2.1]hept-2-enyl and the like. Unless stated otherwise, a cycloalkenyl group can be unsubstituted or substituted with a substituent disclosed herein.

"Cycloalkynyl" refers to a non-aromatic monocyclic or polycyclic hydrocarbon radical consisting solely of carbon and hydrogen atoms, having one or more carbon-carbon triple bonds, which can include fused or bridged ring systems, having from five to twenty carbon atoms, in some embodiments having from five to ten carbon atoms, and which is attached to the rest of the molecule by a single bond. Monocyclic cycloalkynyl radicals include, for example, cycloheptynyl, cyclooctynyl, and the like. Unless stated otherwise, a cycloalkynyl group can be unsubstituted or substituted with a substituent disclosed herein.

"Cycloalkylalkyl" refers to a radical of the formula —$R_b$—$R_d$ where $R_b$ is an alkylene group as defined herein and $R_d$ is a cycloalkyl radical as defined herein. Unless stated otherwise, a cycloalkylalkyl group can be unsubstituted or substituted with a substituent disclosed herein. "Cycloalkylalkenyl" refers to a radical of the formula —$R_b$—$R_d$ where $R_b$ is an alkenylene group as defined herein and $R_d$ is a cycloalkyl radical as defined herein. Unless stated otherwise, a cycloalkylalkenyl group can be unsubstituted or substituted with a substituent disclosed herein. "Cycloalkylalkynyl" refers to a radical of the formula —$R_b$—$R_d$ where $R_b$ is an alkynylene group as defined herein and $R_d$ is a cycloalkyl radical as defined herein. Unless stated otherwise, a cycloalkylalkynyl group can be unsubstituted or substituted with a substituent disclosed herein.

"Cycloalkenylalkyl" refers to a radical of the formula —$R_b$—$R_d$ where $R_b$ is an alkylene group as defined herein and $R_d$ is a cycloalkenyl radical as defined herein. Unless stated otherwise, a cycloalkenylalkyl group can be unsubstituted or substituted with a substituent disclosed herein. "Cycloalkenylalkenyl" refers to a radical of the formula —$R_b$—$R_d$ where $R_b$ is an alkenylene group as defined herein and $R_d$ is a cycloalkyl radical as defined herein. Unless stated otherwise, a cycloalkenylalkenyl group can be unsubstituted or substituted with a substituent disclosed herein. "Cycloalkenylalkynyl" refers to a radical of the formula —$R_b$—$R_d$ where $R_b$ is an alkynylene group as defined herein and $R_d$ is a cycloalkyl radical as defined herein. Unless stated otherwise, a cycloalkenylalkynyl group can be unsubstituted or substituted with a substituent disclosed herein.

"Cycloalkynylalkyl" refers to a radical of the formula —$R_b$—$R_d$ where $R_b$ is an alkylene group as defined herein and $R_d$ is a cycloalkynyl radical as defined herein. Unless stated otherwise, a cycloalkynylalkyl group can be unsubstituted or substituted with a substituent disclosed herein. "Cycloalkynylalkenyl" refers to a radical of the formula —$R_b$—$R_d$ where $R_b$ is an alkenylene group as defined herein and $R_d$ is a cycloalkyl radical as defined herein. Unless stated otherwise, a cycloalkynylalkenyl group can be unsubstituted or substituted with a substituent disclosed herein. "Cycloalkynylalkynyl" refers to a radical of the formula —$R_b$—$R_d$ where $R_b$ is an alkynylene group as defined herein and $R_d$ is a cycloalkyl radical as defined herein. Unless stated otherwise, a cycloalkynylalkynyl group can be unsubstituted or substituted with a substituent disclosed herein.

"Carbocyclyl," "carbocyclic ring" or "carbocycle" refers to a ring structure, wherein the atoms which form the ring are each carbon. The carbocyclyl, carbocyclic ring or carbocycle can comprise from 3 to 20 carbon atoms in the ring. The carbocyclyl, carbocyclic ring or carbocycle includes aryl, cycloalkyl, cycloalkenyl and cycloalkynyl as defined herein. The carbocyclyl, carbocyclic ring or carbocycle can be a monocyclic, bicyclic, tricyclic or tetracyclic ring system, which can include fused, bridged, and spiral ring systems. Unless stated otherwise, a carbocyclyl group, carbocyclic ring or carbocycle can be unsubstituted or substituted with a substituent disclosed herein.

"Haloalkyl" refers to an alkyl radical, as defined herein, that is substituted by one or more halo radicals, as defined herein, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise, a haloalkyl group can be unsubstituted or substituted with a substituent disclosed herein.

"Haloalkenyl" refers to an alkenyl radical, as defined herein, that is substituted by one or more halo radicals, as defined herein, e.g., 1-fluoropropenyl, 1,1-difluorobutenyl, and the like. Unless stated otherwise, a haloalkenyl group can be unsubstituted or substituted with a substituent disclosed herein.

"Haloalkynyl" refers to an alkynyl radical, as defined herein, that is substituted by one or more halo radicals, as defined herein, e.g., 1-fluoropropynyl, 1-fluorobutynyl, and the like. Unless stated otherwise, a haloalkenyl group can be unsubstituted or substituted with a substituent disclosed herein.

"Heterocyclyl" refers to a 3- to 20-membered non-aromatic, partially unsaturated, or aromatic ring radical which includes two to twelve carbon atoms and from one to six nitrogen, oxygen or sulfur heteroatoms. Heterocycly include heteroaryls as defined herein. Unless stated otherwise, the heterocyclyl radical can be a monocyclic, bicyclic, tricyclic or tetracyclic ring system, which can include fused, bridged, and spiral ring systems; and the nitrogen, carbon or sulfur atoms in the heterocyclyl radical can be optionally oxidized; the nitrogen atom can be optionally quaternized; and the heterocyclyl radical can be partially or fully saturated. Examples of heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise, a heterocyclyl group can be unsubstituted or substituted with a substituent disclosed herein.

"Heterocyclylalkyl" refers to a radical of the formula $—R_b—R_e$ where $R_b$ is an alkylene group as defined herein and $R_e$ is a heterocyclyl radical as defined herein. Unless stated otherwise, a heterocyclylalkyl group can be unsubstituted or substituted with a substituent disclosed herein.

"Heterocyclylalkenyl" refers to a radical of the formula $—R_b—R_e$ where $R_b$ is an alkenylene group as defined herein and $R_e$ is a heterocyclyl radical as defined herein. Unless stated otherwise, a heterocyclylalkenyl group can be unsubstituted or substituted with a substituent disclosed herein.

"Heterocyclylalkynyl" refers to a radical of the formula $—R_b—R_e$ where $R_b$ is an alkynylene group as defined herein and $R_e$ is a heterocyclyl radical as defined herein. Unless stated otherwise, a heterocyclylalkynyl group can be unsubstituted or substituted with a substituent disclosed herein.

"N-heterocyclyl" refers to a heterocyclyl radical as defined herein including at least one nitrogen and where the point of attachment of the heterocyclyl radical of an atom of a compound of the invention is through a nitrogen atom in the heterocyclyl radical. Unless stated otherwise, an N-heterocyclyl group can be unsubstituted or substituted with a substituent disclosed herein.

"Heteroaryl" refers to a 5- to 20-membered ring system radical including hydrogen atoms, one to thirteen carbon atoms, one to six nitrogen, oxygen or sulfur heteroatoms, and at least one aromatic ring. The heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples of heteroaryl include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophene), benzotriazolyl, benzo[4,6]imidazo[1,2-a]pyridinyl, carbazolyl, cinnolinyl, dibenzofuranyl, dibenzothiophene, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thienyl). Unless stated otherwise, a heteroaryl group can be unsubstituted or substituted.

"N-heteroaryl" refers to a heteroaryl radical as defined herein having at least one nitrogen atom and where the point of attachment of the heteroaryl radical to an atom of the compound of the invention is through a nitrogen atom in the heteroaryl radical. Unless stated otherwise, an N-heteroaryl group can be unsubstituted or substituted with a substituent disclosed herein.

"Heteroarylalkyl" refers to a radical of the formula $—R_b—R_f$ where $R_b$ is an alkylene chain as defined herein and $R_f$ is a heteroaryl radical as defined herein. Unless stated otherwise, a heteroarylalkyl group can be unsubstituted or substituted with a substituent disclosed herein.

"Heteroarylalkenyl" refers to a radical of the formula $—R_b—R_f$ where $R_b$ is an alkenylene chain as defined herein and $R_f$ is a heteroaryl radical as defined herein. Unless stated otherwise, a heteroarylalkenyl group can be unsubstituted or substituted with a substituent disclosed herein.

"Heteroarylalkynyl" refers to a radical of the formula $—R_b—R_f$ where $R_b$ is an alkynylene chain as defined herein and $R_f$ is a heteroaryl radical as defined herein. Unless stated otherwise, a heteroarylalkynyl group can be unsubstituted or substituted with a substituent disclosed herein.

"Ring" refers to a cyclic group which can be saturated or include one or more double or triple bonds. A ring can be monocyclic, bicyclic, tricyclic, or tetracyclic. Unless stated otherwise, a ring can be unsubstituted or substituted with a substituent disclosed herein.

"Thioalkyl" refers to a radical of the formula $—SR_a$ where $R_a$ is an alkyl, alkenyl, or alkynyl radical as defined herein. Unless stated otherwise, a thioalkyl group can be unsubstituted or substituted with a substituent disclosed herein.

A group or radical disclosed herein can be substituted with one or more of the following substitutents: a halogen atom such as F, Cl, Br, and I; a hydroxyl, alkoxy, or ester; thiol, thioalkyl, sulfone, sulfonyl, or sulfoxide; amine, amide, alkylamine, dialkylamine, arylamine, alkylarylamine, diarylamine, N-oxide, imide, and enamine; trialkylsilyl, dialkylarylsilyl, alkyldiarylsilyl, and triarylsilyl; and other groups, optionally including one or more heteroatoms.

A group or radical disclosed herein can be alternatively or additionally substituted with one or more of the following substituents: oxo, carbonyl, carboxyl, or an ester group; or an imine, oxime, hydrazone, and nitrile.

Examples of other substituents include, but are not limited to:

an amino, cyano, hydroxyl, imino, nitro, oxo, thioxo, halo, alkyl, alkenyl, alkynyl, alkoxy, alkylamino, thioalkyl, aryl, arylalkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and heteroarylalkyl group, $—NR_gR_h$, $—NR_gC(=O)R_h$, $—NR_gC(=O)NR_gR_h$, $—NR_gC(=O)OR_h$, $—NR_gSO_2R_h$, $—OC(=O)NR_gR_h$, $—OR_g$, $—SR_g$, $—SOR_g$, $—SO_2R_g$, $—OSO_2R_g$, $—SO_2OR_g$, $=NSO_2R_g$, $—SO_2NR_gR_h$, $—C(=O)R_g$, $—C(=O)OR_g$, $—C(=O)NR_gR_h$, $—CH_2SO_2R_g$ and $—CH_2SO_2NR_gR_h$, wherein $R_g$ and $R_h$ are the same or different and independently hydrogen, alkyl, alkenyl, alkynyl, alkoxy, alkylamino, thioalkyl, aryl, arylalkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl or heteroarylalkyl, wherein each of the foregoing substituents is unsubstituted or substituted with one or more substituents disclosed herein.

As used herein, the symbol

“ 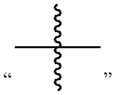 ”

(a “point of attachment bond”) denotes a bond that is a point of attachment between two chemical entities, one of which is depicted as being attached to the point of attachment bond and the other of which is not depicted as being attached to the point of attachment bond. For example, “ 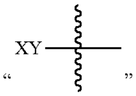 ”

indicates that the chemical entity “XY” is bonded to another chemical entity via the point of attachment bond.

The Compounds of the Invention

Compounds of Formula (IA)

In some embodiments, the compound of the invention is a compound of Formula (IA):

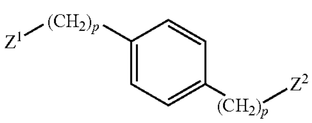

(IA)

or a pharmaceutically acceptable salt or solvate thereof, wherein:

each p is independently 1, 2, 3, 4, 5, 6, or 7;

$Z^1$ and $Z^2$ are independently —$C(R^{1A})(R^{2A})$—$(CH_2)_d$—$X^A$ or —W—$(CH_2)_d$—$C(R^3)(R^4)$—Y—;

each d is independently 0, 1, 2, 3, 4, 5, 6, 7, 8, or 9;

each $R^{1A}$ and $R^{2A}$ is independently H, —$C_1$-$C_6$ alkyl, —$C_2$-$C_6$ alkenyl, —$C_2$-$C_6$ alkynyl, phenyl or benzyl, or each carbon atom together with the $R^{1A}$ and $R^{2A}$ attached to the carbon atom independently form a —$C_3$-$C_7$ cycloalkyl group;

each $R^3$ and $R^4$ is independently H, —$C_1$-$C_6$ alkyl, —$C_2$-$C_6$ alkenyl, —$C_2$-$C_6$ alkynyl, —$O(C_1$-$C_6$ alkyl), phenyl, benzyl, Cl, Br, CN, $NO_2$, or $CF_3$, or each carbon atom together with the $R^3$ and $R^4$ attached to the carbon atom independently form a —$C_3$-$C_7$ cycloalkyl group;

each $X^A$ is independently H, —OH, —$SO_3H$,

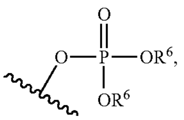 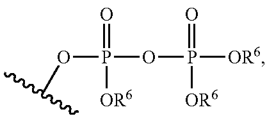

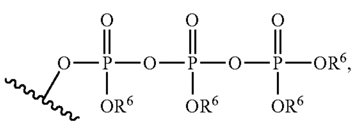 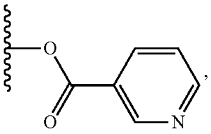,

-continued

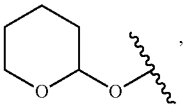, 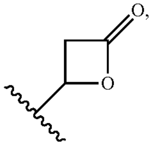 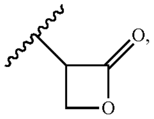

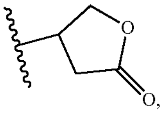 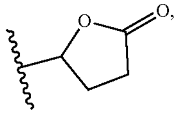 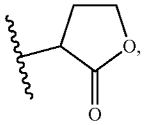

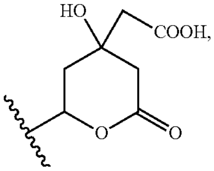 , 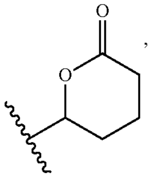 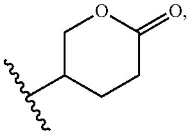

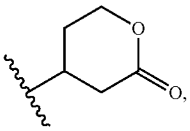 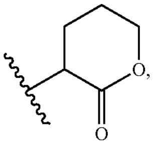 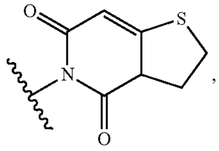,

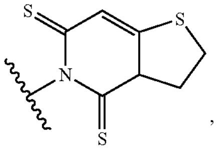, 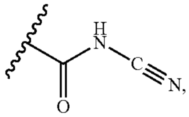

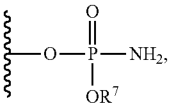 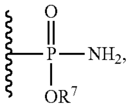 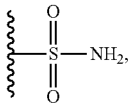 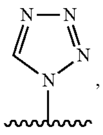,

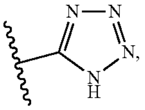 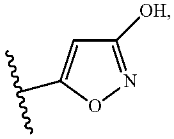 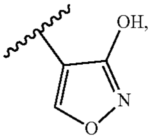

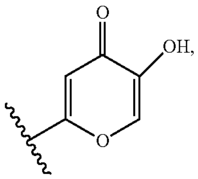 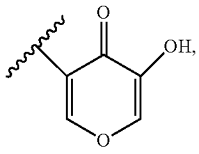

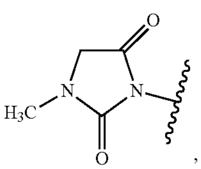, 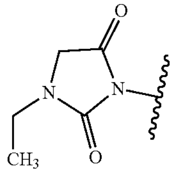, 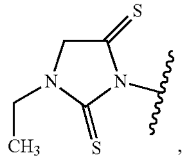,

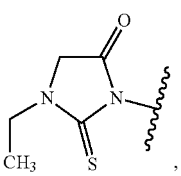, or 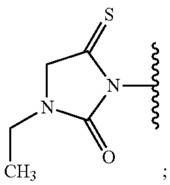;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups;

each $R^7$ is independently H, —$C_1$-$C_6$ alkyl, —$C_2$-$C_6$ alkenyl, or —$C_2$-$C_6$ alkynyl;

each W is independently —O—, —NH—, —N(OH)—, —N(→O)—, —S—, —S(═O)—, —S(O)$_2$—, or —Se—;

each Y is independently —OH, —COOH, —COOR$^5$, —SO$_3$H,

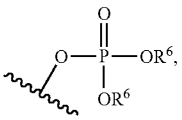 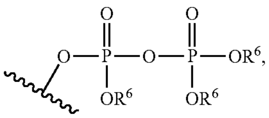

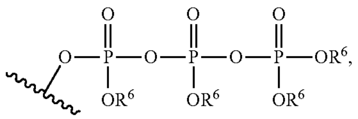 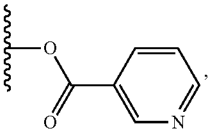 ,

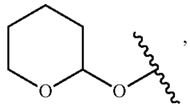 , 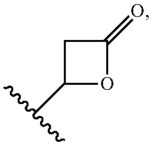 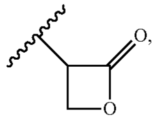

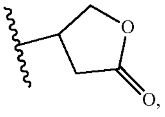

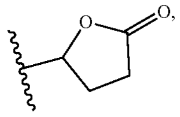 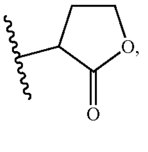

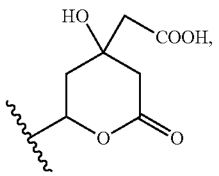 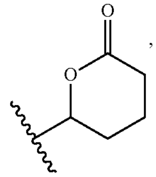 , 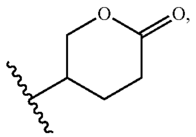

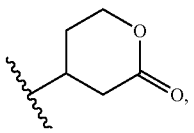 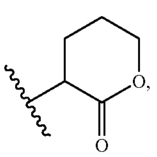 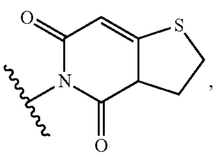 ,

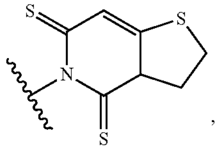 , 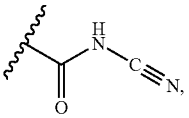

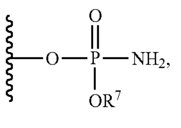 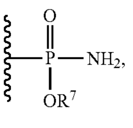 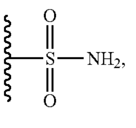 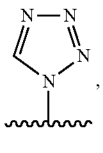 ,

-continued

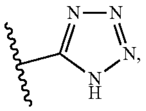 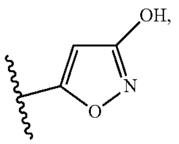 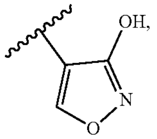

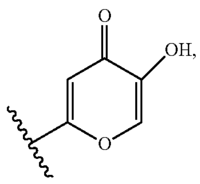 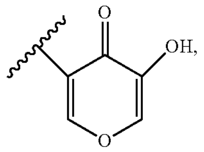

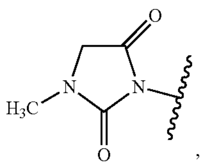 , 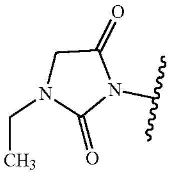 , 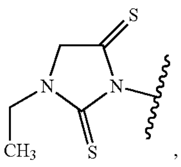 ,

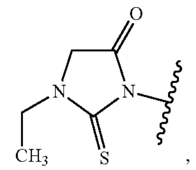 , or 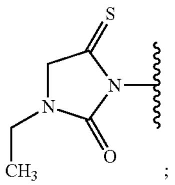 ;

each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups.

In some embodiments of the compounds of Formula (IA), $Z^1$ and $Z^2$ are independently —C($R^{1A}$)($R^{2A}$)—($CH_2$)$_d$—$X^A$.

In some embodiments of the compounds of Formula (IA), each $R^{1A}$ and $R^{2A}$ is independently —$C_1$-$C_6$ alkyl, —$C_2$-$C_6$ alkenyl, or —$C_2$-$C_6$ alkynyl. In some embodiments, each $R^{1A}$ and $R^{2A}$ is independently —$C_1$-$C_3$ alkyl, —$C_2$-$C_3$ alkenyl, or —$C_2$-$C_3$ alkynyl. In some embodiments, each $R^{1A}$ and $R^{2A}$ is independently H or —$C_1$-$C_6$ alkyl. In some embodiments, $R^{1A}$ and $R^{2A}$ are methyl.

In some embodiments of the compounds of Formula (IA), each p is 2, 3, 4, or 5.

In some embodiments of the compounds of Formula (IA), each d is 0, 1, 2, or 3. In some embodiments, d is 0 or 1.

In some embodiments, the compound of the invention is a compound of Formula (IA):

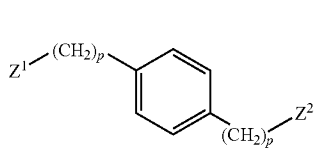

(IA)

or a pharmaceutically acceptable salt or solvate thereof, wherein:

each p is independently 4, 5, 6, or 7;

$Z^1$ and $Z^2$ are independently —C($R^1$)($R^2$)—($CH_2$)$_c$—X or —W—($CH_2$)$_c$—C($R^3$)($R^4$)—Y;

each c is independently 0, 1, 2, or 3;

each $R^1$ and $R^2$ is independently —$C_1$-$C_6$ alkyl, —$C_2$-$C_6$ alkenyl, —$C_2$-$C_6$ alkynyl, phenyl or benzyl, or each carbon atom together with the $R^1$ and $R^2$ attached to the carbon atom independently form a —$C_3$-$C_7$ cycloalkyl group;

each $R^3$ and $R^4$ is independently H, —$C_1$-$C_6$ alkyl, —$C_2$-$C_6$ alkenyl, —$C_2$-$C_6$ alkynyl, —O($C_1$-$C_6$ alkyl), phenyl, benzyl, Cl, Br, CN, $NO_2$, or $CF_3$, or each carbon atom together with the $R^3$ and $R^4$ attached to the carbon atom independently form a —$C_3$-$C_7$ cycloalkyl group;

each X and Y is independently —OH, —COOH, —$COOR^5$, —$SO_3H$,

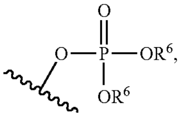
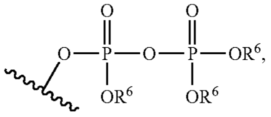
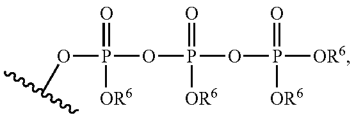
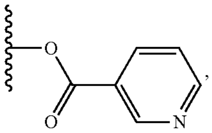,
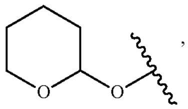,
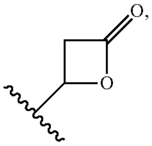
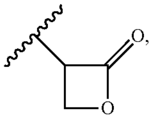
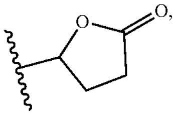
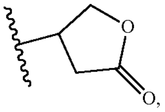
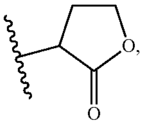
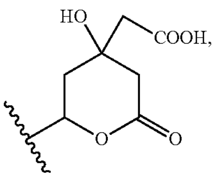
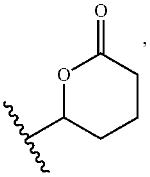,
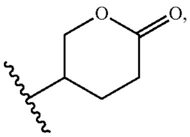
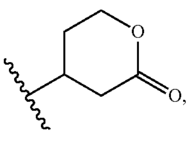
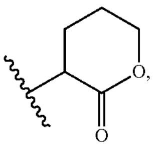
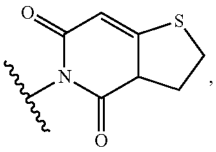, -continued

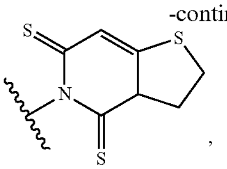,
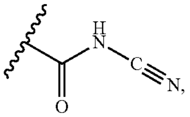
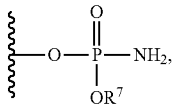
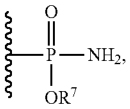
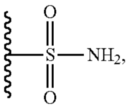
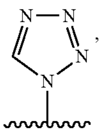,
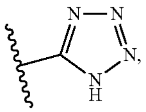
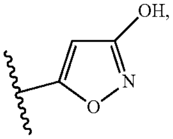
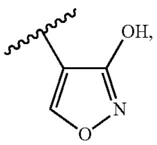
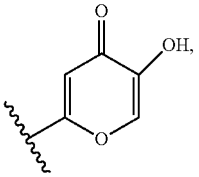
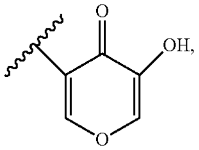
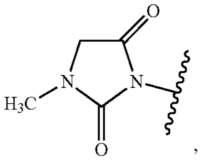,
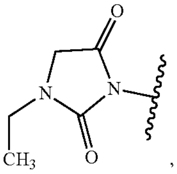,
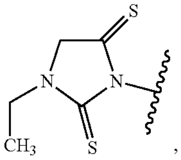,
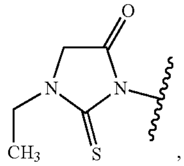,
or
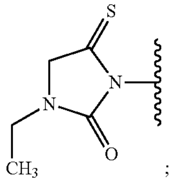;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups;

each $R^7$ is independently H, —$C_1$-$C_6$ alkyl, —$C_2$-$C_6$ alkenyl, or —$C_2$-$C_6$ alkynyl;

each W is independently —O—, —NH—, —N(OH)—, —N(→O)—, —S—, —S(=O)—, —$S(O)_2$—, or —Se—; and each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups.

In some embodiments, the compound of Formula (IA) has any one of the structures shown in Table A-1, or a pharmaceutically acceptable salt or solvate thereof.

TABLE A-1

| Compound No. | Structure and Name |
| --- | --- |
| I-1 | 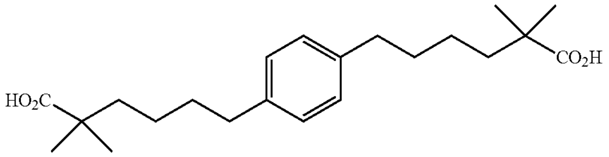 [SMILES: CC(C)(CCCCc1ccc(CCCCC(C)(C)C(=O)O)cc1)C(=O)O] 6-[4-(5-Carboxy-5-methyl-hexyl)-phenyl]-2,2-dimethylhexanoic acid |
| I-2 | 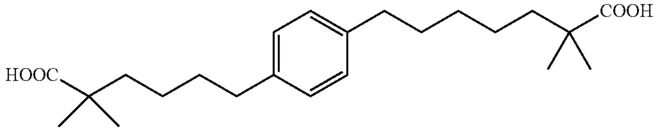 [SMILES: CC(C)(CCCCCc1ccc(CCCCC(C)(C)C(=O)O)cc1)C(=O)O] 7-(4-(5-Carboxy-5-methylhexyl)phenyl)-2,2-dimethylheptanoic acid |
| I-3 | 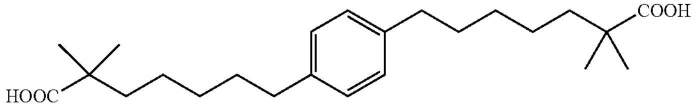 [SMILES: CC(C)(CCCCCc1ccc(CCCCCC(C)(C)C(=O)O)cc1)C(=O)O] 7,7'-(1,4-Phenylene)bis(2,2-dimethylheptanoic acid) |
| I-4 | 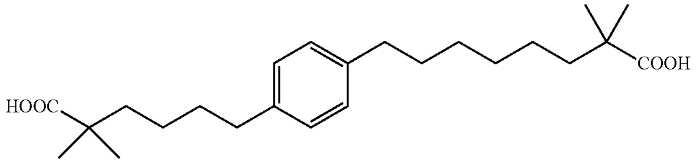 [SMILES: CC(C)(CCCCCCc1ccc(CCCCC(C)(C)C(=O)O)cc1)C(=O)O] 8-(4-(5-Carboxy-5-methylhexyl)phenyl)-2,2-dimethyloctanoic acid |
| I-5 | 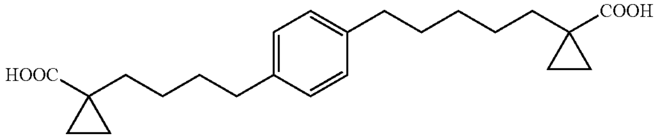 [SMILES: O=C(O)C1(CCCCCc2ccc(CCCCC3(C(=O)O)CC3)cc2)CC1] 1-(5-(4-(4-(1-carboxycyclopropyl)butyl)phenyl)pentyl)cyclopropane-1-carboxylic acid |
| I-6 | 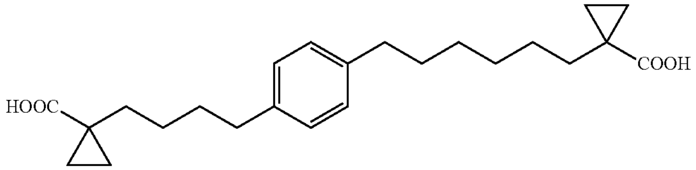 [SMILES: O=C(O)C1(CCCCCCc2ccc(CCCCC3(C(=O)O)CC3)cc2)CC1] 1-(6-(4-(4-(1-carboxycyclopropyl)butyl)phenyl)hexyl)cyclopropane-1-carboxylic acid |
| I-7 | 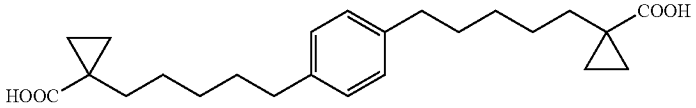 [SMILES: O=C(O)C1(CCCCCc2ccc(CCCCCC3(C(=O)O)CC3)cc2)CC1] 1,1'-(1,4-phenylenebis(pentane-5,1-diyl))bis(cyclopropane-1-carboxylic acid) |
| I-8 | 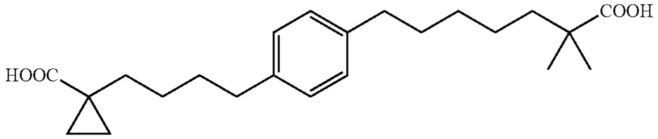 [SMILES: CC(C)(CCCCCc1ccc(CCCCC2(C(=O)O)CC2)cc1)C(=O)O] 1-(4-(4-(6-carboxy-6-methylheptyl)phenyl)butyl)cyclopropane-1- |

TABLE A-1-continued

| Compound No. | Structure and Name |
|---|---|
| | carboxylic acid |
| I-9 | 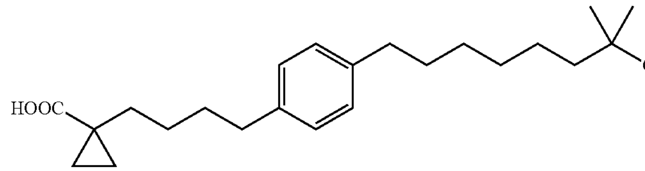<br>1-(4-(4-(7-carboxy-7-methyloctyl)phenyl)butyl)cyclopropane-1-carboxylic acid |
| I-10 | 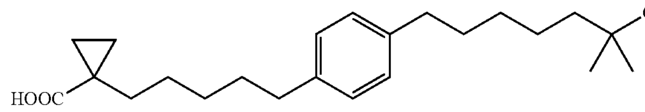<br>1-(5-(4-(6-carboxy-6-methylheptyl)phenyl)pentyl)cyclopropane-1-carboxylic acid |

Compounds of Formula (IB)

In some embodiments, the compound of the invention is a compound of Formula (IB):

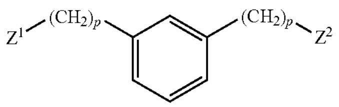

(IB)

or a pharmaceutically acceptable salt or solvate thereof, wherein:

each p is independently 1, 2, 3, 4, 5, 6, or 7;

each $Z^1$ and $Z^2$ is independently $-C(R^1)(R^2)-(CH_2)_c-X$ or $-W-(CH_2)_c-C(R^3)(R^4)-Y$;

each c is independently 0, 1, 2, or 3;

each $R^1$ and $R^2$ is independently $-C_1-C_6$ alkyl, $-C_2-C_6$ alkenyl, $-C_2-C_6$ alkynyl, phenyl or benzyl, or each carbon atom together with the $R^1$ and $R^2$ attached to the carbon atom independently form a $-C_3-C_7$ cycloalkyl group;

each $R^3$ and $R^4$ is independently H, $-C_1-C_6$ alkyl, $-C_2-C_6$ alkenyl, $-C_2-C_6$ alkynyl, $-O(C_1-C_6$ alkyl), phenyl, benzyl, Cl, Br, CN, $NO_2$, or $CF_3$, or each carbon atom together with the $R^3$ and $R^4$ attached to the carbon atom independently form a $-C_3-C_7$ cycloalkyl group;

each X and Y is independently —OH, —COOH, $-COOR^5$, $-SO_3H$,

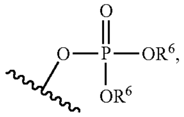 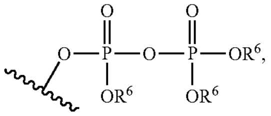

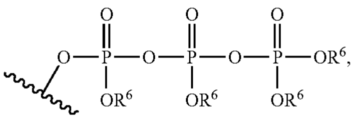 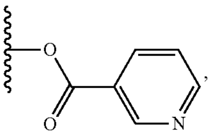,

-continued

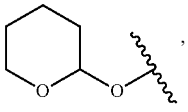, 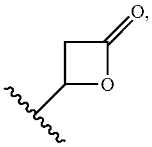 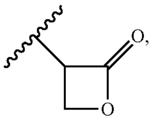

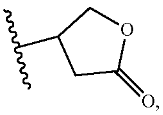 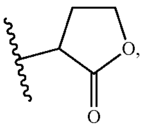

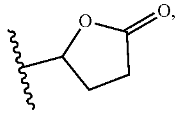

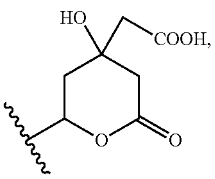 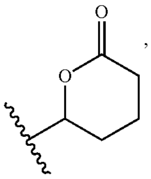, 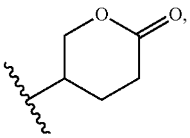

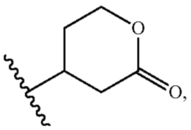 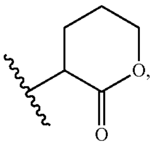 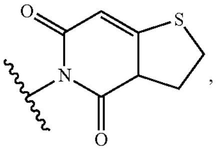,

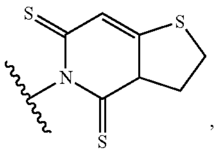, 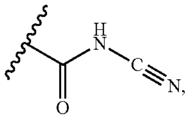

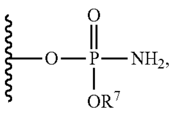 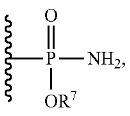 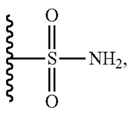

-continued

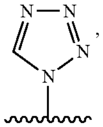

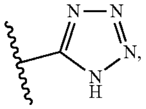

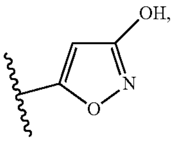

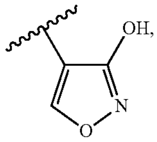

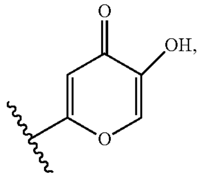

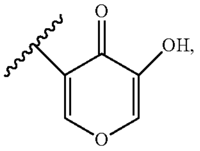

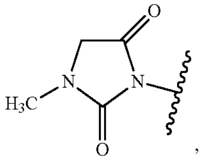

,

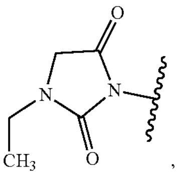

,

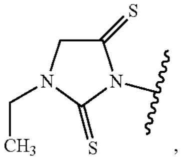

,

-continued

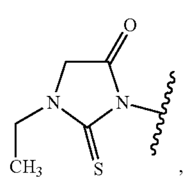

, or

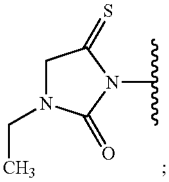

;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups;

each $R^7$ is independently H, —$C_1$-$C_6$ alkyl, —$C_2$-$C_6$ alkenyl, or —$C_2$-$C_6$ alkynyl;

each W is independently —O—, —NH—, —N(OH)—, —N(→O)—, —S—, —S(═O)—, —$S(O)_2$—, or —Se—; and each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups.

In some embodiments, the compound of Formula (IB) has any one of the structures shown in Table A-2, or a pharmaceutically acceptable salt or solvate thereof.

TABLE A-2

| Compound No. | Structure and Name |
| --- | --- |
| I-31 | 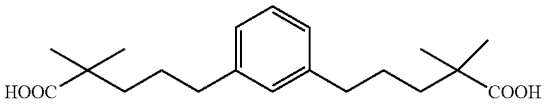 [SMILES: CC(C)(CCCc1cccc(CCCC(C)(C)C(=O)O)c1)C(=O)O] 5-[3-(4-Carboxy-4-methylpentyl)phenyl]-2,2-dimethylpentanoic acid |
| I-32 | 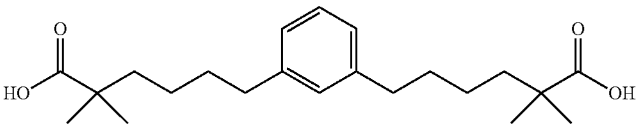 [SMILES: CC(C)(CCCCc1cccc(CCCCC(C)(C)C(=O)O)c1)C(=O)O] 6-[3-(5-Carboxy-5-methylhexyl)-phenyl]-2,2-dimethylhexanoic acid |
| I-33 | 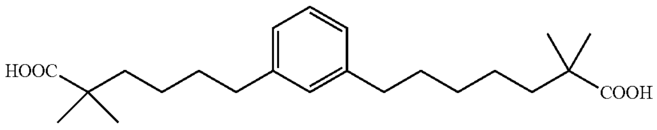 [SMILES: CC(C)(CCCCCc1cccc(CCCCC(C)(C)C(=O)O)c1)C(=O)O] 7-(3-(5-Carboxy-5-methylhexyl)phenyl)-2,2-dimethylheptanoic acid |
| I-34 | 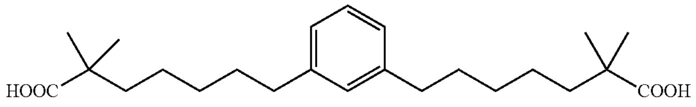 [SMILES: CC(C)(CCCCCc1cccc(CCCCCC(C)(C)C(=O)O)c1)C(=O)O] 7,7'-(1,3-Phenylene)bis(2,2-dimethylheptanoic acid) |
| I-35 | 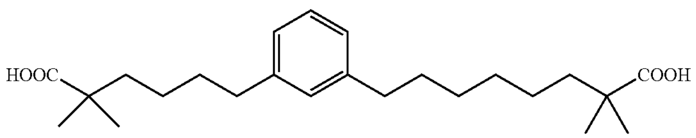 [SMILES: CC(C)(CCCCCCc1cccc(CCCCC(C)(C)C(=O)O)c1)C(=O)O] 8-(3-(5-Carboxy-5-methylhexyl)phenyl)-2,2-dimethyloctanoic acid |

TABLE A-2-continued

| Compound No. | Structure and Name |
| --- | --- |
| I-36 | 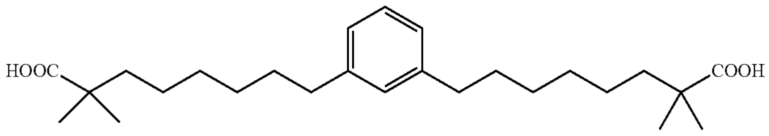 [SMILES: CC(C)(CCCCCCc1cccc(CCCCCCC(C)(C)C(=O)O)c1)C(=O)O] 8,8'-(1,3-Phenylene)bis(2,2-dimethyloctanoic acid) |
| I-37 | 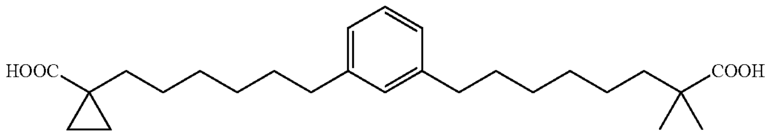 [SMILES: CC(C)(CCCCCCc1cccc(CCCCCCC2(C(=O)O)CC2)c1)C(=O)O] 1-(6-(3-(7-carboxy-7-methyloctyl)phenyl)hexyl)cyclopropane-1-carboxylic acid |
| I-38 | 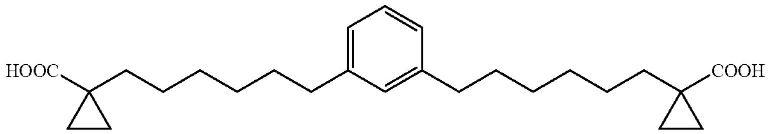 [SMILES: O=C(O)C1(CCCCCCc2cccc(CCCCCCC3(C(=O)O)CC3)c2)CC1] 1,1'-(1,3-phenylenebis(hexane-6,1-diyl))bis(cyclopropane-1-carboxylic acid) |
| I-39 | 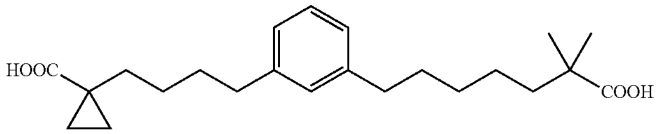 [SMILES: CC(C)(CCCCCc1cccc(CCCCC2(C(=O)O)CC2)c1)C(=O)O] 1-(4-(3-(6-carboxy-6-methylheptyl)phenyl)butyl)cyclopropane-1-carboxylic acid |
| I-40 | 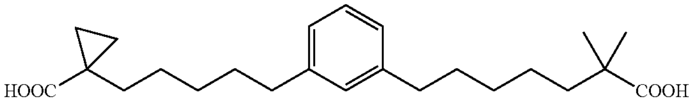 [SMILES: CC(C)(CCCCCc1cccc(CCCCCC2(C(=O)O)CC2)c1)C(=O)O] 1-(5-(3-(6-carboxy-6-methylheptyl)phenyl)pentyl)cyclopropane-1-carboxylic acid |
| I-41 | 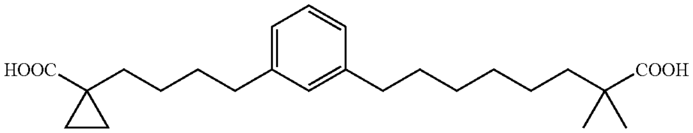 [SMILES: CC(C)(CCCCCCc1cccc(CCCCC2(C(=O)O)CC2)c1)C(=O)O] 1-(4-(3-(7-carboxy-7-methyloctyl)phenyl)butyl)cyclopropane-1-carboxylic acid |
| I-42 | 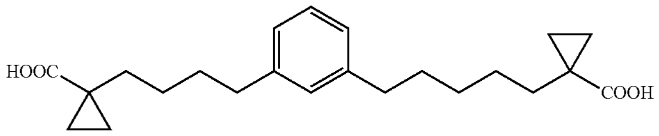 [SMILES: O=C(O)C1(CCCCCc2cccc(CCCCC3(C(=O)O)CC3)c2)CC1] 1-(5-(3-(4-(1-carboxycyclopropyl)butyl)phenyl)pentyl)cyclopropane-1-carboxylic acid |
| I-43 | 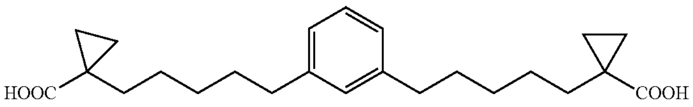 [SMILES: O=C(O)C1(CCCCCc2cccc(CCCCCC3(C(=O)O)CC3)c2)CC1] 1,1'-(1,3-phenylenebis(pentane-5,1-diyl))bis(cyclopropane-1-carboxylic acid) |

TABLE A-2-continued

| Compound No. | Structure and Name |
|---|---|
| I-44 | 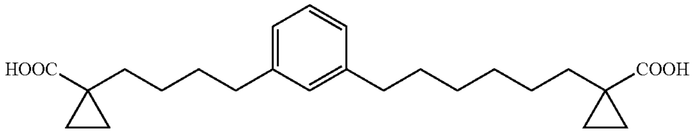 [SMILES: O=C(O)C1(CCCCCCc2cccc(CCCCC3(C(=O)O)CC3)c2)CC1]<br>1-(6-(3-(4-(1-carboxycyclopropyl)butyl)phenyl)hexyl)cyclopropane-1-carboxylic acid |

Compounds of Formula (IC)

In some embodiments, the compound of the invention is a compound of Formula (IC):

(IC)

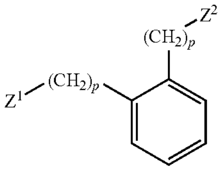

or a pharmaceutically acceptable salt or solvate thereof, wherein:

each p is independently 1, 2, 3, 4, 5, 6, or 7;

each $Z^1$ and $Z^2$ is independently $-C(R^1)(R^2)-(CH_2)_c-X$ or $-W-(CH_2)_c-C(R^3)(R^4)-Y$;

each c is independently 0, 1, 2, or 3;

each $R^1$ and $R^2$ is independently $-C_1$-$C_6$ alkyl, $-C_2$-$C_6$ alkenyl, $-C_2$-$C_6$ alkynyl, phenyl or benzyl, or each carbon atom together with the $R^1$ and $R^2$ attached to the carbon atom independently form a $-C_3$-$C_7$ cycloalkyl group;

each $R^3$ and $R^4$ is independently H, $-C_1$-$C_6$ alkyl, $-C_2$-$C_6$ alkenyl, $-C_2$-$C_6$ alkynyl, $-O(C_1$-$C_6$ alkyl), phenyl, benzyl, Cl, Br, CN, $NO_2$, or $CF_3$, or each carbon atom together with the $R^3$ and $R^4$ attached to the carbon atom independently form a $-C_3$-$C_7$ cycloalkyl group;

each X and Y is independently —OH, —COOH, $-COOR^5$, $-SO_3H$,

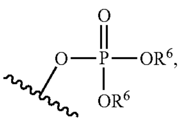 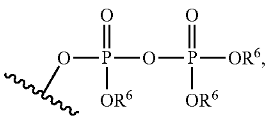

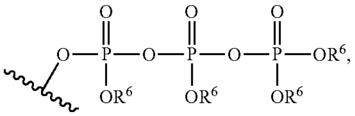 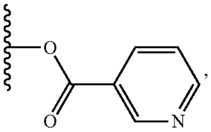,

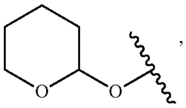, 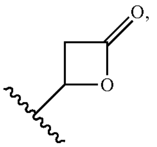 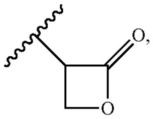

-continued

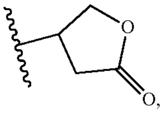 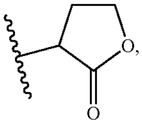

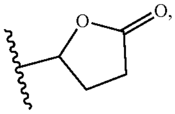

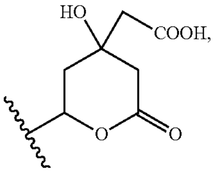 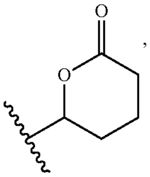, 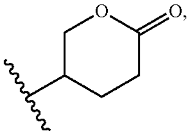

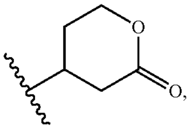 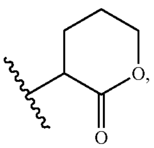 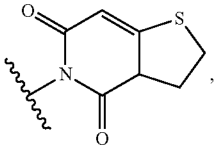,

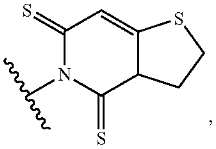, 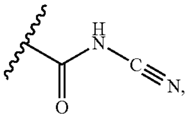

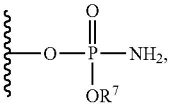 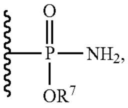 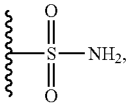 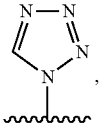,

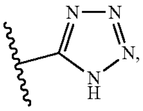 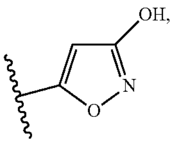 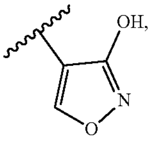

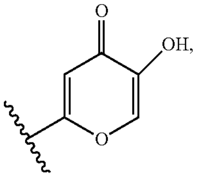 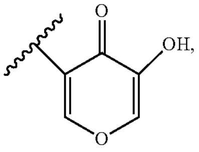

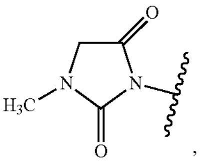, 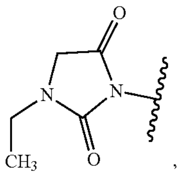, 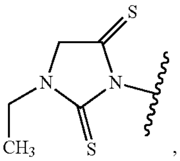,

-continued

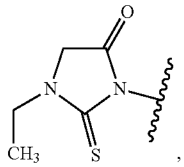

, or

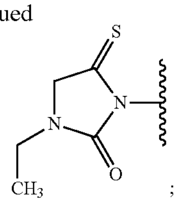

;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups;

each $R^7$ is independently H, —$C_1$-$C_6$ alkyl, —$C_2$-$C_6$ alkenyl, or —$C_2$-$C_6$ alkynyl;

each W is independently —O—, —NH—, —N(OH)—, —N(→O)—, —S—, —S(═O)—, —S(O)$_2$—, or —Se—; and each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups.

In some embodiments of the compounds of Formula (IA), (IB), or (IC), $Z^1$ and $Z^2$ are each independently —C($R^1$)($R^2$)—($CH_2$)$_c$—X. In some embodiments, one or both of $Z^1$ and $Z^2$ is —W—($CH_2$)$_c$—C($R^3$)($R^4$)—Y.

In some embodiments of the compounds of Formula (IA), (IB), or (IC), X is —COOH or —COOR$^5$.

In some embodiments of the compounds of Formula (IA), (IB), or (IC), each $R^1$ and $R^2$ is independently —$C_1$-$C_6$ alkyl, —$C_2$-$C_6$ alkenyl, or —$C_2$-$C_6$ alkynyl. In some embodiments, each $R^1$ and $R^2$ is independently —$C_1$-$C_3$ alkyl, —$C_2$-$C_3$ alkenyl, or —$C_2$-$C_3$ alkynyl. In some embodiments, $R^1$ and $R^2$ are methyl.

In some embodiments of the compounds of Formula (IA), (IB), or (IC), $Z^1$ and $Z^2$ are each independently —C($R^1$)($R^2$)—($CH_2$)$_c$—X, X is —COOH or —COOR$^5$, and $R^1$ and $R^2$ are methyl.

In some embodiments of the compounds of Formula (IA), (IB), or (IC), c is 0 or 1.

In some embodiments of the compounds of Formula (IA), (IB), or (IC), $Z^1$ and $Z^2$ are each —C($R^1$)($R^2$)—($CH_2$)$_c$—X.

In some embodiments, $Z^1$ and $Z^2$ are each —C($R^1$)($R^2$)—($CH_2$)$_c$—X and X is each —COOH.

In some embodiments of the compounds of Formula (IA), (IB), or (IC), each carbon atom together with the $R^1$ and $R^2$ attached to the carbon atom independently form a —$C_3$-$C_7$ cycloalkyl group. In some embodiments, each carbon atom together with the $R^1$ and $R^2$ attached to the carbon atom independently form a cyclopropyl ring.

In some embodiments of the compounds of Formula (IA), (IB), or (IC), $Z^1$ and $Z^2$ are each —C($R^1$)($R^2$)—($CH_2$)$_c$—X and at least one $R^1$ and one $R^2$ together with the carbon atom to which they are attached form a —$C_3$-$C_7$ cycloalkyl group. In some embodiments, $Z^1$ and $Z^2$ are each —C($R^1$)($R^2$)—($CH_2$)$_c$—X and at least one $R^1$ and one $R^2$ together with the carbon atom to which they are attached form a cyclopropyl ring.

In some embodiments of the compounds of Formula (IA), (IB), or (IC), $R^3$ and $R^4$ is independently H, —$C_1$-$C_6$ alkyl, —$C_2$-$C_6$ alkenyl, or —$C_2$-$C_6$ alkynyl.

In some embodiments of the compounds of Formula (IA), (IB), or (IC), Y is —COOH or —COOR$^5$.

In some embodiments of the compounds of Formula (IA), (IB), or (IC), $R^5$ is —$C_1$-$C_6$ alkyl, —$C_2$-$C_6$ alkenyl, or —$C_2$-$C_6$ alkynyl. In some embodiments, $R^5$ is —$C_1$-$C_3$ alkyl, —$C_2$-$C_3$ alkenyl, or —$C_2$-$C_3$ alkynyl.

In some embodiments of the compounds of Formula (IA), (IB), or (IC), p is 3, 4, 5, 6, or 7. In some embodiments, p is 4, 5, 6, or 7.

In some embodiments of the compounds of Formula (IA), (IB), or (IC), one or both of $Z^1$ and $Z^2$ is —W—($CH_2$)$_c$—C($R^3$)($R^4$)—Y, and $R^3$ and $R^4$ is independently H, —$C_1$-$C_6$ alkyl, —$C_2$-$C_6$ alkenyl, or —$C_2$-$C_6$ alkynyl. In some embodiments, one or both of $Z^1$ and $Z^2$ is —W—($CH_2$)$_c$—C($R^3$)($R^4$)—Y, and Y is —COOH or —COOR$^5$. In some embodiments, one or both of $Z^1$ and $Z^2$ is —W—($CH_2$)$_c$—C($R^3$)($R^4$)—Y, Y is —COOH or —COOR$^5$, and $R^5$ is —$C_1$-$C_6$ alkyl, —$C_2$-$C_6$ alkenyl, or —$C_2$-$C_6$ alkynyl. In some embodiments, one or both of $Z^1$ and $Z^2$ is —W—(CH)$_d$ C($R^3$)($R^4$)—Y, Y is —COOH or —COOR$^5$, and $R^5$ is —$C_1$-$C_3$ alkyl, —$C_2$-$C_3$ alkenyl, or —$C_2$-$C_3$ alkynyl.

In some embodiments, the compound of Formula (IC) has of any one of the structures shown in Table A-3, or a pharmaceutically acceptable salt or solvate thereof.

TABLE A-3

| Compound No. | Structure and Name |
|---|---|
| I-61 | 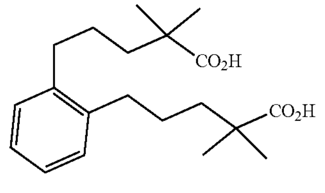 [SMILES: CC(C)(CCCc1ccccc1CCCC(C)(C)C(=O)O)C(=O)O] 5-[2-(4-Carboxy-4-methylpentyl)-phenyl]-2,2-dimethylpentanoic acid |

TABLE A-3-continued
| Compound No. | Structure and Name |
| --- | --- |
| I-62 | 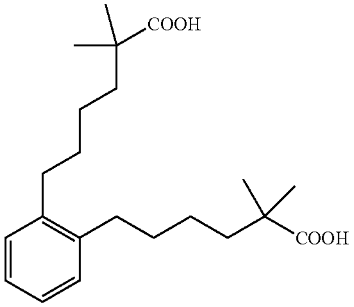 [SMILES: CC(C)(CCCCc1ccccc1CCCCC(C)(C)C(=O)O)C(=O)O] 6,6'-(1,2-Phenylene)bis(2,2-dimethylpentanoic acid |
| I-63 | 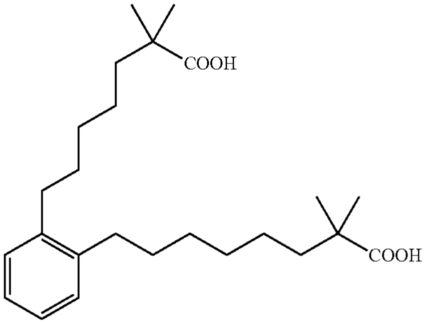 [SMILES: CC(C)(CCCCCCc1ccccc1CCCCCC(C)(C)C(=O)O)C(=O)O] 8-(2-(6-Carboxy-6-methylheptyl)phenyl)-2,2-dimethyloctanoic acid |
| I-64 | 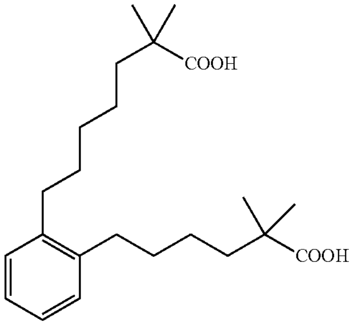 [SMILES: CC(C)(CCCCCc1ccccc1CCCCC(C)(C)C(=O)O)C(=O)O] 7-(2-(5-Carboxy-5-methylhexyl)phenyl)-2,2-dimethylheptanoic acid |
| I-65 | 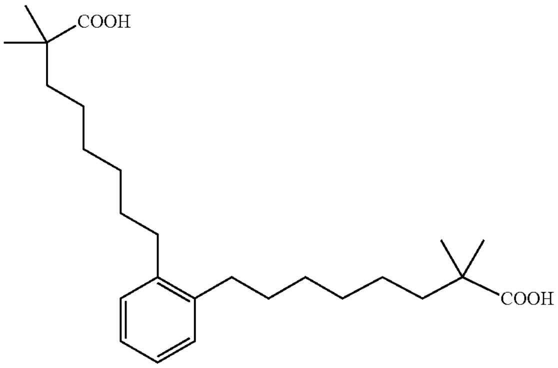 [SMILES: CC(C)(CCCCCCc1ccccc1CCCCCCC(C)(C)C(=O)O)C(=O)O] 8,8'-(1,2-Phenylene)bis(2,2-dimethyloctanoic acid) |

TABLE A-3-continued
| Compound No. | Structure and Name |
|---|---|
| I-66 | 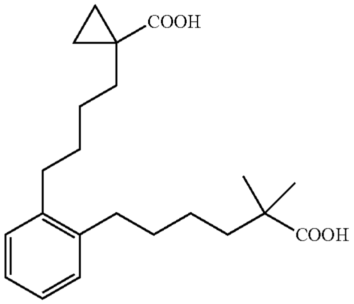 [SMILES: CC(C)(CCCCc1ccccc1CCCCC1(C(=O)O)CC1)C(=O)O]<br>1(4-(2-(5-carboxy-5-methylhexyl)phenyl)butyl) cyclopropane-1-carboxylic acid |
| I-67 | 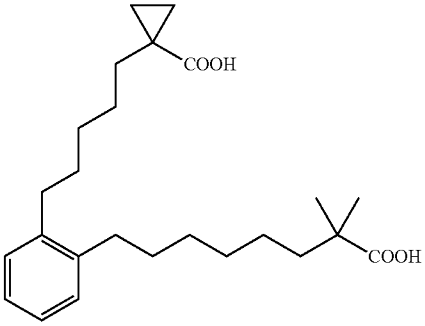 [SMILES: CC(C)(CCCCCCc1ccccc1CCCCCC1(C(=O)O)CC1)C(=O)O]<br>1-(5-(2-(7-methyloctyl)phenyl)pentyl)cyclopropane-1-carboxylic acid |
| I-68 | 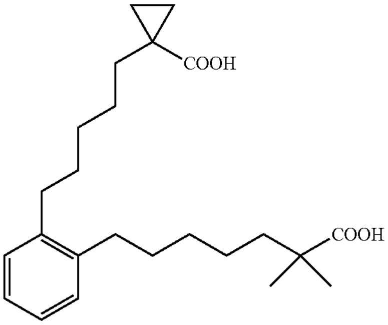 [SMILES: CC(C)(CCCCCc1ccccc1CCCCCC1(C(=O)O)CC1)C(=O)O]<br>1-(5-(2-(6-carboxy-6-methylheptyl)phenyl)pentyl) cyclopropane-1-carboxylic acid |
| I-69 | 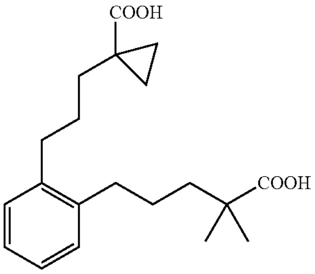 [SMILES: CC(C)(CCCc1ccccc1CCCC1(C(=O)O)CC1)C(=O)O]<br>1(3-(2-(4-carboxy-4-methylpentyl)phenyl)propyl)cyclopropane-1-carboxylic acid |

TABLE A-3-continued
| Compound No. | Structure and Name |
|---|---|
| I-70 | 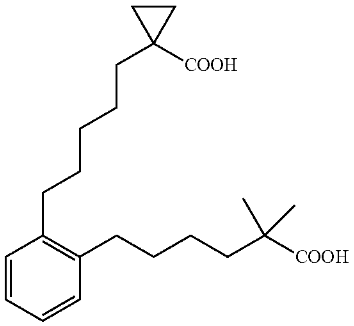 [SMILES: CC(C)(CCCCc1ccccc1CCCCCC1(C(=O)O)CC1)C(=O)O]<br>1-(5-(2-(5-carboxy-5-methylhexyl)phenyl)pentyl)cyclopropane-1-carboxylic acid |
| I-71 | 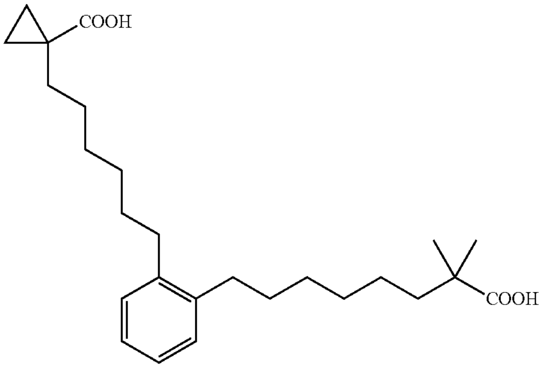 [SMILES: CC(C)(CCCCCCc1ccccc1CCCCCCC1(C(=O)O)CC1)C(=O)O]<br>1-(6-(2--(7-carboxy-7-methyloctyl)phenyl)hexyl)cyclopropane-1-carboxylic acid |
| I-72 | 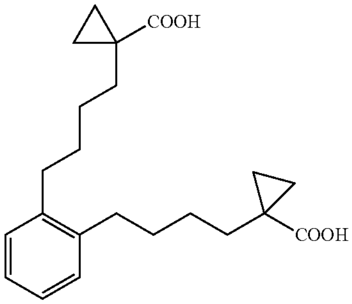 [SMILES: O=C(O)C1(CCCCc2ccccc2CCCCC2(C(=O)O)CC2)CC1]<br>1-1'-(1,2-phenylenebis(butane-4,1-diyl)bis(cyclopropane-1-carboxylic acid) |
| I-73 | 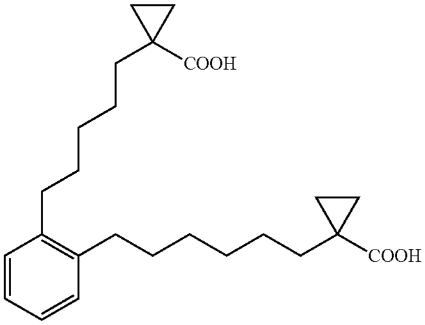 [SMILES: O=C(O)C1(CCCCCCc2ccccc2CCCCCC2(C(=O)O)CC2)CC1]<br>1-(5-(2-(6-(1-carboxycyclopropyl)hecyl)phenyl)pentyl) cyclopropane-1-carboxylic acid |

TABLE A-3-continued
| Compound No. | Structure and Name |
|---|---|
| I-74 | 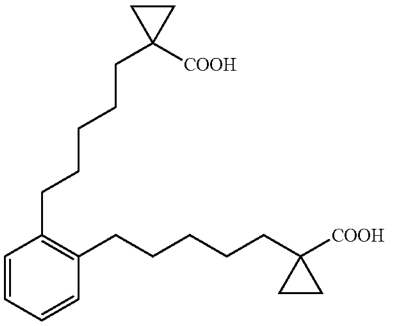 [SMILES: O=C(O)C1(CCCCCc2ccccc2CCCCCC2(C(=O)O)CC2)CC1] 1,1'-(1,2-phenylenebis(pentane-5,1-diyl))bis(cyclopropane-1-carboxylic acid) |
| I-75 | 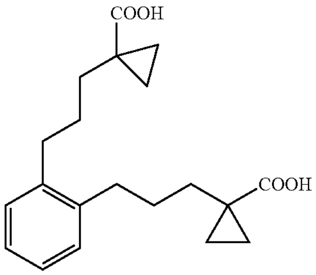 [SMILES: O=C(O)C1(CCCc2ccccc2CCCC2(C(=O)O)CC2)CC1] 1,1'-(1,2-phenylenebis(propane-3,1-diyl))bis(cyclopropane-1-carboxylic acid |
| I-76 | 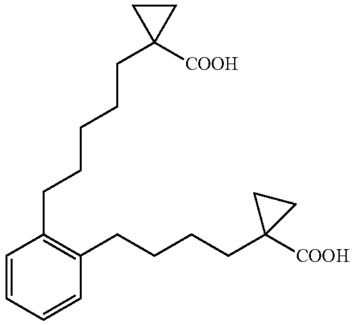 [SMILES: O=C(O)C1(CCCCCc2ccccc2CCCCC2(C(=O)O)CC2)CC1] 1-(5-(2-(4-(1-carboxycyclopropyl)butyl)phenyl)pentyl) cyclopropane-1-carboxylic acid |
| I-77 | 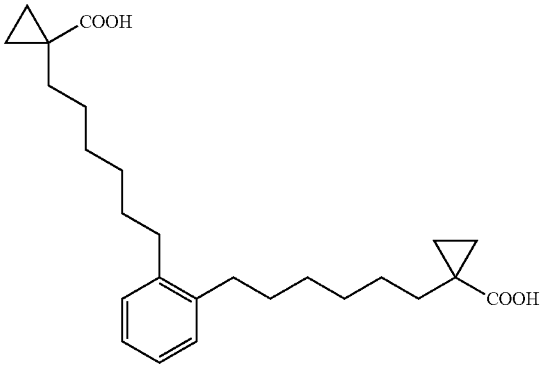 1,1'-(1,2-phenylenebis(hexane-6,1-diyl))bis(cyclopropane-1-carboxylic acid) |

Compounds of Formula (ID)

In some embodiments, the compound of the invention is a compound of Formula (ID):

(ID)

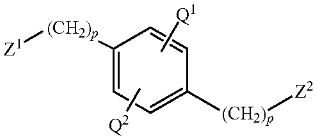

or a pharmaceutically acceptable salt or solvate thereof, wherein:

each p is independently 1, 2, 3, 4, 5, 6, or 7;

$Z^1$ and $Z^2$ are independently $—C(R^{1A})(R^{2A})—(CH_2)_d—X^A$ or $—W—(CH_2)_d—C(R^3)(R^4)—Y$;

each d is independently 0, 1, 2, 3, 4, 5, 6, 7, 8, or 9;

each $R^{1A}$ and $R^{2A}$ is independently H, $—C_1$-$C_6$ alkyl, $—C_2$-$C_6$ alkenyl, $—C_2$-$C_6$ alkynyl, phenyl or benzyl, or each carbon atom together with the $R^{1A}$ and $R^{2A}$ attached to the carbon atom independently form a $—C_3$-$C_7$ cycloalkyl group;

each $R^3$ and $R^4$ is independently H, $—C_1$-$C_6$ alkyl, $—C_2$-$C_6$ alkenyl, $—C_2$-$C_6$ alkynyl, $—O(C_1$-$C_6$ alkyl), phenyl, benzyl, Cl, Br, CN, $NO_2$, or $CF_3$, or each carbon atom together with the $R^3$ and $R^4$ attached to the carbon atom independently form a $—C_3$-$C_7$ cycloalkyl group;

$Q^1$ and $Q^2$ are independently H, OH, $—C_1$-$C_6$ alkyl, $—O(C_1$-$C_6$ alkyl), phenoxy, aryloxy, benzyl, —S-aryl, $—SR^{1A}$, $—NR^{1A}R^{2A}$, F, Cl, Br, I, $—CF_3$, $—COR^{1A}$, heteroaryl, heterocyclyl, or —V—OH, or each carbon atom together with the $Q^1$ and $Q^2$ attached to the carbon atom independently form a heterocyclyl or a carbocyclyl group;

V is $(CH_2)_t$ or arylene;

t is 0, 1, 2, 3, or 4;

each $X^A$ is independently H, —OH, $—SO_3H$,

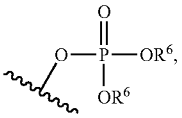 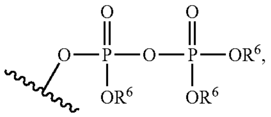

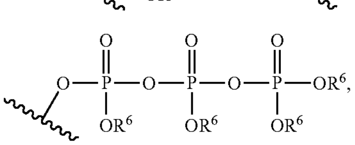 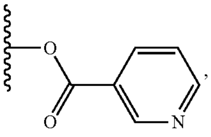 ,

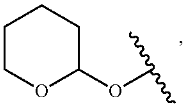 , 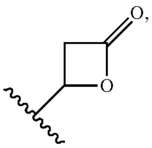 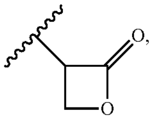

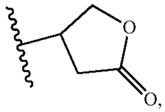 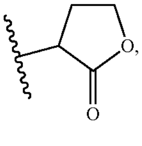 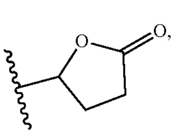

-continued

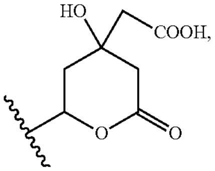 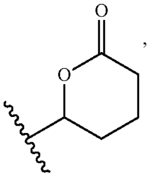 , 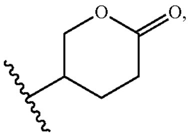

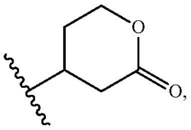 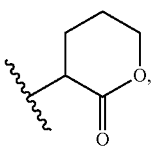 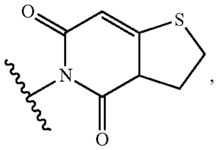 ,

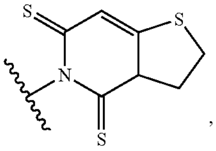 , 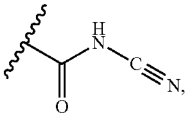

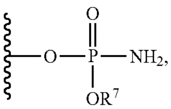 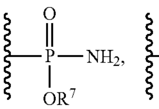 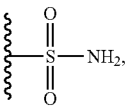 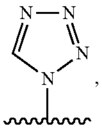 ,

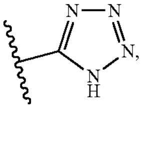 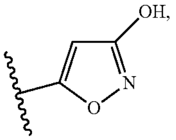 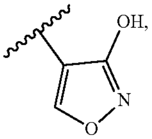

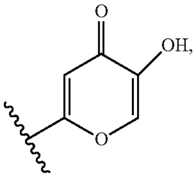 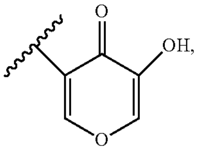

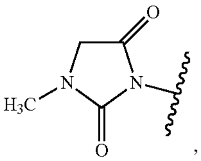 , 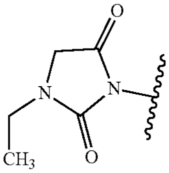 , 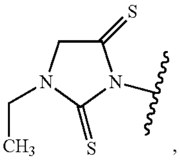 ,

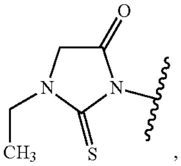 , or 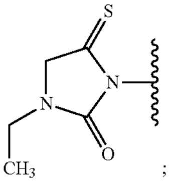 ;

each $R^6$ is independently H, $—C_1$-$C_6$ alkyl, $—C_2$-$C_6$ alkenyl, or $—C_2$-$C_6$ alkynyl, wherein the $—C_1$-$C_6$ alkyl, $—C_2$-$C_6$ alkenyl, or $—C_2$-$C_6$ alkynyl is unsubstituted or substituted with one or two halogen, —OH, $—O(C_1$-$C_6$ alkyl), or phenyl groups;

each $R^7$ is independently H, $—C_1$-$C_6$ alkyl, $—C_2$-$C_6$ alkenyl, or $—C_2$-$C_6$ alkynyl;

each W is independently —O—, —NH—, —N(OH)—, —N(→O)—, —S—, —S(═O)—, $—S(O)_2—$, or —Se—;

each Y is independently —OH, —COOH, $—COOR^5$, $—SO_3H$,

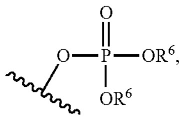, 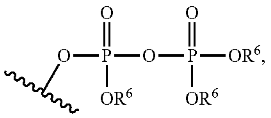,

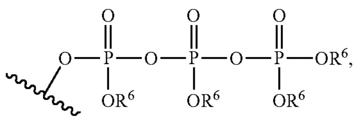, 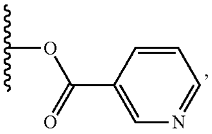,

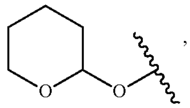, 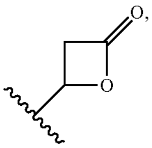, 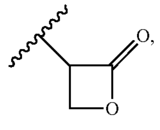,

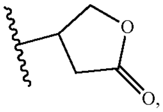, 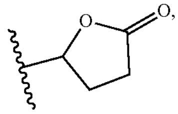, 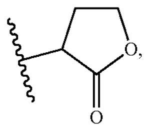,

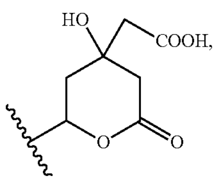, 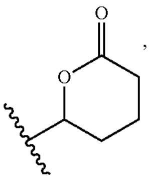, 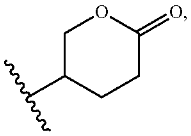,

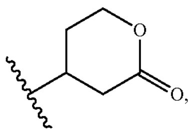, 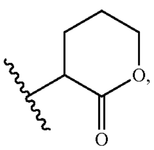, 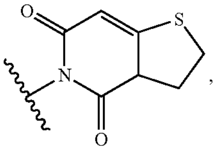,

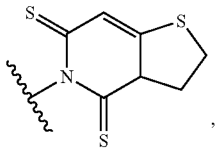, 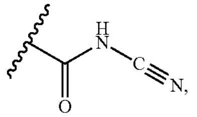,

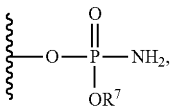, 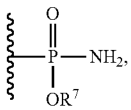, 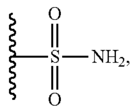, 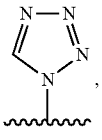,

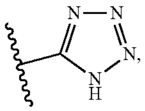, 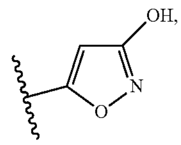, 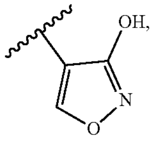,

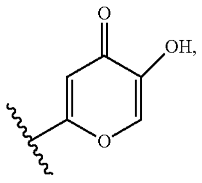, 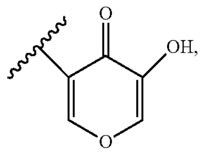,

-continued

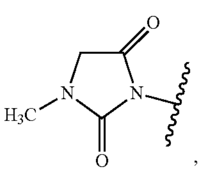, 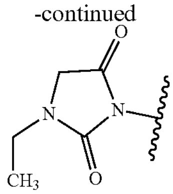, 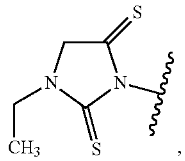,

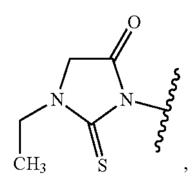, or 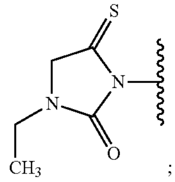;

each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups.

In some embodiments of the compounds of Formula (ID), $Z^1$ and $Z^2$ are independently —C($R^{1A}$)($R^{2A}$)—$(CH_2)_d$—$X^A$.

In some embodiments of the compounds of Formula (ID), each $R^{1A}$ and $R^{2A}$ is independently —$C_1$-$C_6$ alkyl, —$C_2$-$C_6$ alkenyl, or —$C_2$-$C_6$ alkynyl. In some embodiments, each $R^{1A}$ and $R^{2A}$ is independently —$C_1$-$C_3$ alkyl, —$C_2$-$C_3$ alkenyl, or —$C_2$-$C_3$ alkynyl. In some embodiments, each $R^{1A}$ and $R^{2A}$ is independently H or —$C_1$-$C_6$ alkyl. In some embodiments, $R^{1A}$ and $R^{2A}$ are methyl.

In some embodiments of the compounds of Formula (ID), each p is 2, 3, 4, or 5.

In some embodiments of the compounds of Formula (ID), each d is 0, 1, 2, or 3. In some embodiments, d is 0 or 1.

In some embodiments, the compound of the invention is a compound of Formula (ID).

(ID)

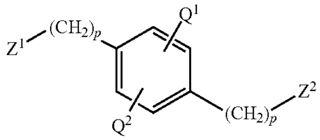

or a pharmaceutically acceptable salt or solvate thereof, wherein:

each p is independently 4, 5, 6, or 7;

$Z^1$ and $Z^2$ are independently —C($R^1$)($R^2$)—$(CH_2)_c$—X or —W—$(CH_2)_c$—C($R^3$)($R^4$)—Y;

each c is independently 0, 1, 2, or 3;

each $R^1$ and $R^2$ is independently —$C_1$-$C_6$ alkyl, —$C_2$-$C_6$ alkenyl, —$C_2$-$C_6$ alkynyl, phenyl or benzyl, or each carbon atom together with the $R^1$ and $R^2$ attached to the carbon atom independently form a —$C_3$-$C_7$ cycloalkyl group;

each $R^3$ and $R^4$ is independently H, —$C_1$-$C_6$ alkyl, —$C_2$-$C_6$ alkenyl, —$C_2$-$C_6$ alkynyl, —O($C_1$-$C_6$ alkyl), phenyl, benzyl, Cl, Br, CN, $NO_2$, or $CF_3$, or each carbon atom together with the $R^3$ and $R^4$ attached to the carbon atom independently form a —$C_3$-$C_7$ cycloalkyl group;

$Q^1$ and $Q^2$ are independently H, OH, —$C_1$-$C_6$ alkyl, —O($C_1$-$C_6$ alkyl), phenoxy, aryloxy, benzyl, —S-aryl, —$SR^{1A}$, —$NR^{1A}R^{2A}$, F, Cl, Br, I, —$CF_3$, —$COR^{1A}$, heteroaryl, heterocyclyl, or —V—OH, or each carbon atom together with the $Q^1$ and $Q^2$ attached to the carbon atom independently form a heterocyclyl or a carbocyclyl group;

each $R^{1A}$ and $R^{2A}$ is independently H, —$C_1$-$C_6$ alkyl, —$C_2$-$C_6$ alkenyl, —$C_2$-$C_6$ alkynyl, phenyl or benzyl;

V is $(CH_2)_t$ or arylene;

t is 0, 1, 2, 3, or 4;

each X and Y is independently —OH, —COOH, —$COOR^5$, —$SO_3H$,

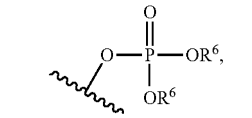
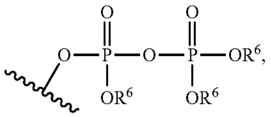
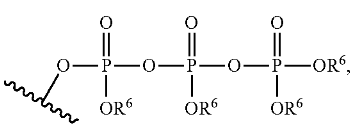
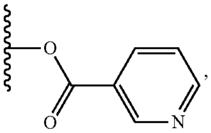
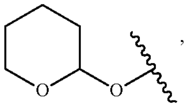
,
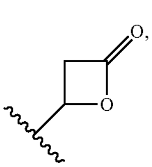
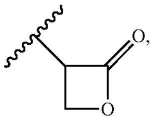
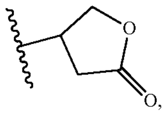
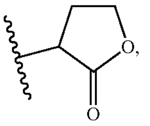
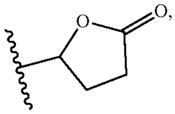
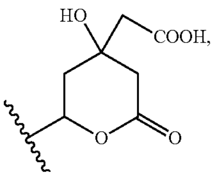
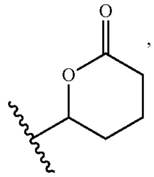
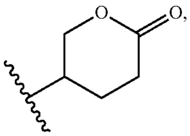
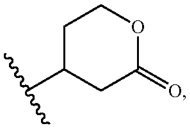
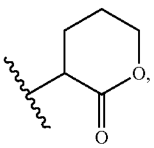
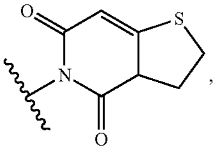
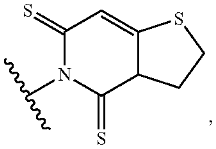
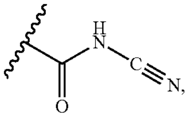
,
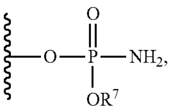
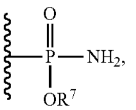
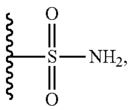
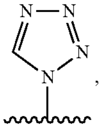
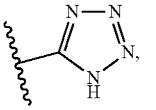
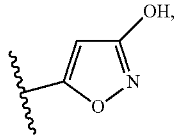
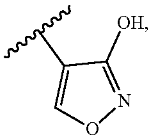

-continued

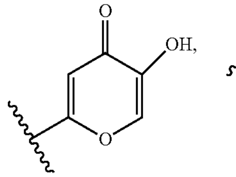
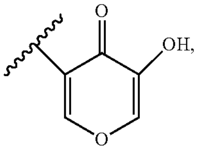
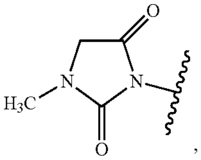
,
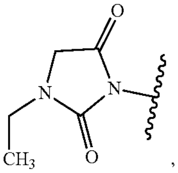
,
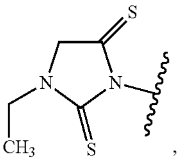
,
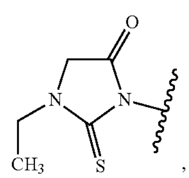
, or
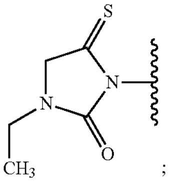
;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups;

each $R^7$ is independently H, —$C_1$-$C_6$ alkyl, —$C_2$-$C_6$ alkenyl, or —$C_2$-$C_6$ alkynyl;

each W is independently —O—, —NH—, —N(OH)—, —N(→O)—, —S—, —S(═O)—, —$S(O)_2$—, or —Se—; and each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups.

In some embodiments, the compound of Formula (ID) has the structure shown in Table A-1, or a pharmaceutically acceptable salt or solvate thereof. In some embodiments, the compound of Formula (ID) has the structure shown in Table A-5 which are mono- or di-substituted with —OH or methyl groups on the phenyl, or a pharmaceutically acceptable salt or solvate thereof.

Compounds of Formula (IG)

In some embodiments, the compound of the invention is a compound of Formula (IG):

(IG)

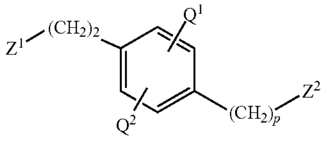

or a pharmaceutically acceptable salt or solvate thereof, wherein:

each p is independently 1, 2, 3, 4, 5, 6, or 7;

$Z^1$ and $Z^2$ are independently —$C(R^1)(R^2)$—$(CH_2)_c$—X or —W—$(CH_2)_c$—$C(R^3)(R^4)$—Y;

each c is independently 0, 1, 2, or 3;

each $R^1$ and $R^2$ is independently —$C_1$-$C_6$ alkyl, —$C_2$-$C_6$ alkenyl, —$C_2$-$C_6$ alkynyl, phenyl or benzyl, or each carbon atom together with the $R^1$ and $R^2$ attached to the carbon atom independently form a —$C_3$-$C_7$ cycloalkyl group;

each $R^3$ and $R^4$ is independently H, $—C_1$-$C_6$ alkyl, $—C_2$-$C_6$ alkenyl, $—C_2$-$C_6$ alkynyl, $—O(C_1$-$C_6$ alkyl), phenyl, benzyl, Cl, Br, CN, $NO_2$, or $CF_3$, or each carbon atom together with the $R^3$ and $R^4$ attached to the carbon atom independently form a $—C_3$-$C_7$ cycloalkyl group;

$Q^1$ and $Q^2$ are independently H, OH, $—C_1$-$C_6$ alkyl, $—O(C_1$-$C_6$ alkyl), phenoxy, aryloxy, benzyl, —S-aryl, $—SR^{1A}$, $—NR^{1A}R^{2A}$, F, Cl, Br, I, $—CF_3$, $—COR^{1A}$, heteroaryl, heterocyclyl, or —V—OH, or each carbon atom together with the $Q^1$ and $Q^2$ attached to the carbon atom independently form a heterocyclyl or a carbocyclyl group;

each $R^{1A}$ and $R^{2A}$ is independently H, $—C_1$-$C_6$ alkyl, $—C_2$-$C_6$ alkenyl, $—C_2$-$C_6$ alkynyl, phenyl or benzyl;

V is $(CH_2)_t$ or arylene;

t is 0, 1, 2, 3, or 4;

each X and Y is independently —OH, —COOH, $—COOR^5$, $—SO_3H$,

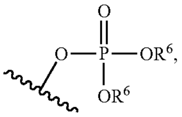
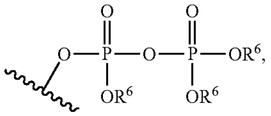
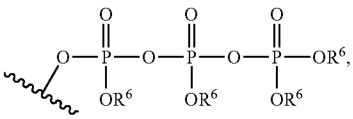
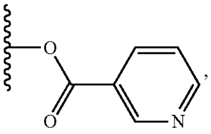
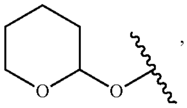
,
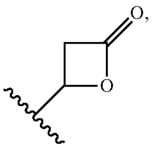
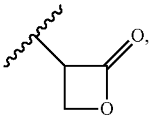
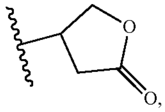
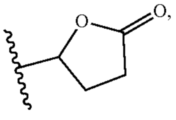
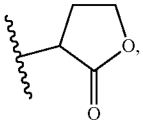
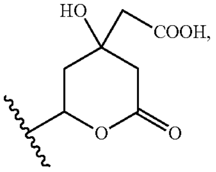
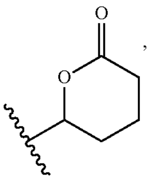
,
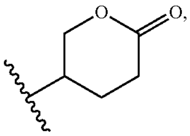
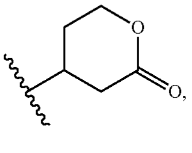
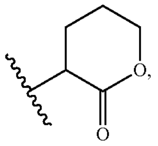
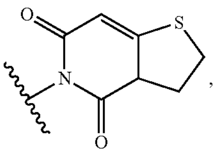
,
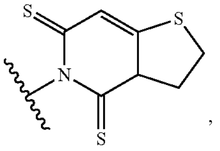
,
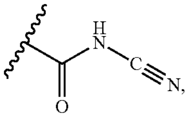

-continued

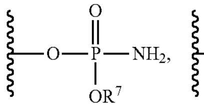
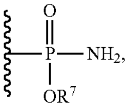
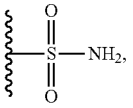
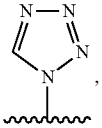
,
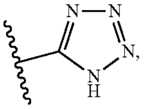
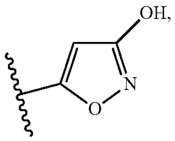
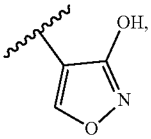
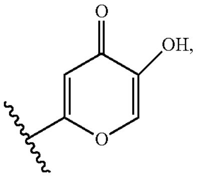
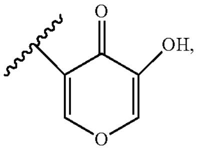

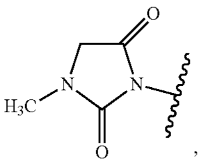
,
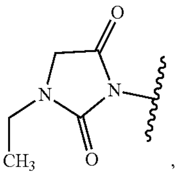
,
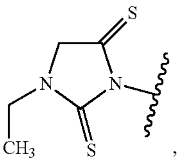
,
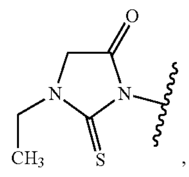
, or
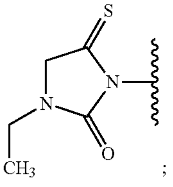
;

each $R^6$ is independently H, $—C_1$-$C_6$ alkyl, $—C_2$-$C_6$ alkenyl, or $—C_2$-$C_6$ alkynyl, wherein the $—C_1$-$C_6$ alkyl, $—C_2$-$C_6$ alkenyl, or $—C_2$-$C_6$ alkynyl is unsubstituted or substituted with one or two halogen, —OH, $—O(C_1$-$C_6$ alkyl), or phenyl groups;

each $R^7$ is independently H, $—C_1$-$C_6$ alkyl, $—C_2$-$C_6$ alkenyl, or $—C_2$-$C_6$ alkynyl;

each W is independently —O—, —NH—, —N(OH)—, —N(→O)—, —S—, —S(═O)—, $—S(O)_2—$, or —Se—; and each $R^5$ is independently $—C_1$-$C_6$ alkyl, $—C_2$-$C_6$ alkenyl, $—C_2$-$C_6$ alkynyl, phenyl, or benzyl, each being unsubstituted or substituted with one or more halogen, —OH, $—O(C_1$-$C_6$ alkyl), or phenyl groups.

In some embodiments, the compound of Formula (IG), $Q^1$ and $Q^2$ are each H.

In some embodiments, the compound of Formula (IG), p is 2, 3, 4, 5, 6, or 7. In some embodiments, the compound of Formula (IG), p is 2.

In some embodiments, the compound of Formula (IG) has the structure shown in Table A-4, or a pharmaceutically acceptable salt or solvate thereof.

TABLE A-4

| Compound No. | Structure and Name |
|---|---|
| I-78 | 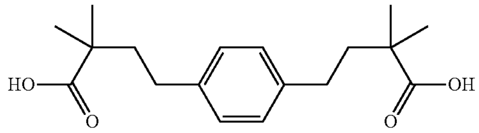 [SMILES: CC(C)(CCc1ccc(CCC(C)(C)C(=O)O)cc1)C(=O)O] 4,4'-(1,4-Phenylene)bis(2,2-dimethylbutanoic acid) |

Compounds of Formula (IE)

In some embodiments, the compound of the invention is a compound of Formula (IE):

(IE)

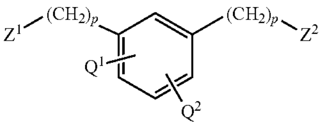

or a pharmaceutically acceptable salt or solvate thereof, wherein:

each p is independently 1, 2, 3, 4, 5, 6, or 7;

each $Z^1$ and $Z^2$ is independently $-C(R^1)(R^2)-(CH_2)_c-X$ or $-W-(CH_2)_c-C(R^3)(R^4)-Y$;

each c is independently 0, 1, 2, or 3;

each $R^1$ and $R^2$ is independently $-C_1$-$C_6$ alkyl, $-C_2$-$C_6$ alkenyl, $-C_2$-$C_6$ alkynyl, phenyl or benzyl, or each carbon atom together with the $R^1$ and $R^2$ attached to the carbon atom independently form a $-C_3$-$C_7$ cycloalkyl group;

each $R^3$ and $R^4$ is independently H, $-C_1$-$C_6$ alkyl, $-C_2$-$C_6$ alkenyl, $-C_2$-$C_6$ alkynyl, $-O(C_1$-$C_6$ alkyl), phenyl, benzyl, Cl, Br, CN, $NO_2$, or $CF_3$, or each carbon atom together with the $R^3$ and $R^4$ attached to the carbon atom independently form a $-C_3$-$C_7$ cycloalkyl group;

$Q^1$ and $Q^2$ are independently H, OH, $-C_1$-$C_6$ alkyl, $-O(C_1$-$C_6$ alkyl), phenoxy, aryloxy, benzyl, —S-aryl, $-SR^{1A}$, $-NR^{1A}R^{2A}$, F, Cl, Br, I, $-CF_3$, $-COR^{1A}$, heteroaryl, heterocyclyl, or —V—OH, or each carbon atom together with the $Q^1$ and $Q^2$ attached to the carbon atom independently form a heterocyclyl or a carbocyclyl group;

each $R^{1A}$ and $R^{2A}$ is independently H, $-C_1$-$C_6$ alkyl, $-C_2$-$C_6$ alkenyl, $-C_2$-$C_6$ alkynyl, phenyl or benzyl;

V is $(CH_2)_t$ or arylene;

t is 0, 1, 2, 3, or 4;

each X and Y is independently —OH, —COOH, $-COOR^5$, $-SO_3H$,

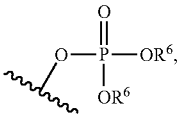 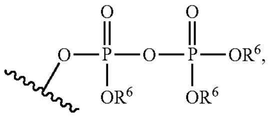

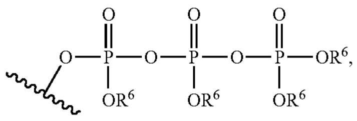 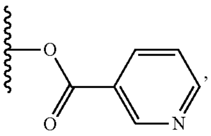

-continued

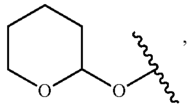 , 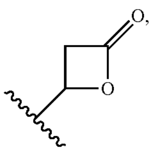 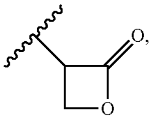

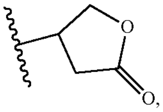 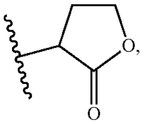

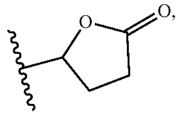

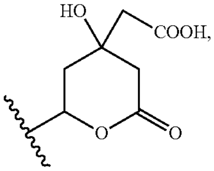 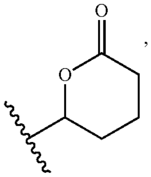 , 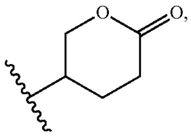

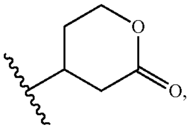 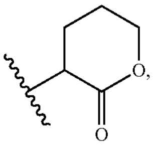 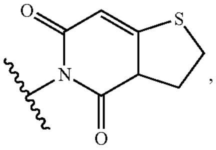

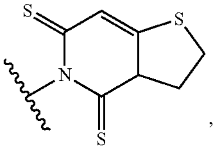 , 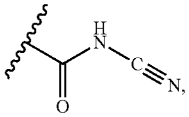

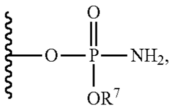 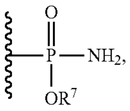 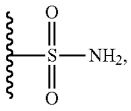

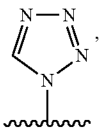 , 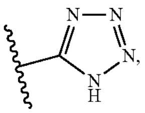 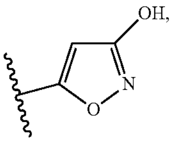

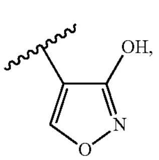 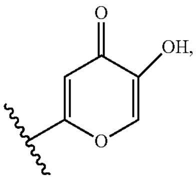 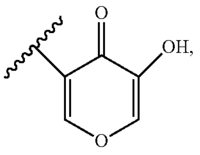

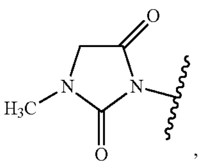 , 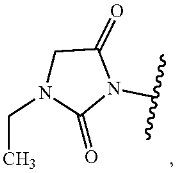 , 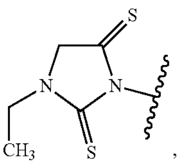 ,

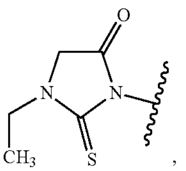 , or 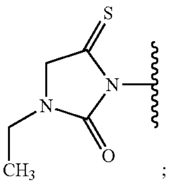 ;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups;

each $R^7$ is independently H, —$C_1$-$C_6$ alkyl, —$C_2$-$C_6$ alkenyl, or —$C_2$-$C_6$ alkynyl;

each W is independently —O—, —NH—, —N(OH)—, —N(→O)—, —S—, —S(═O)—, —$S(O)_2$—, or —Se—; and each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups.

In some embodiments, the compound of Formula (IE) has the structure shown in Table A-2, or a pharmaceutically acceptable salt or solvate thereof. In some embodiments, the compound of Formula (IE) has the structure shown in Table A-6 which are mono- or di-substituted with —OH or methyl groups on the phenyl, or a pharmaceutically acceptable salt or solvate thereof.

Compounds of Formula (IF)

In some embodiments, the compound of the invention is a compound of Formula (IF):

(IF)

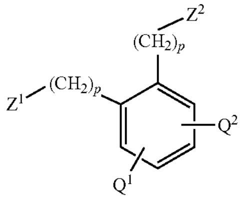

or a pharmaceutically acceptable salt or solvate thereof, wherein:

each p is independently 1, 2, 3, 4, 5, 6, or 7;

each $Z^1$ and $Z^2$ is independently —$C(R^1)(R^2)$—$(CH_2)_c$—X or —W—$(CH_2)_c$—$C(R^3)(R^4)$—Y;

each c is independently 0, 1, 2, or 3;

each $R^1$ and $R^2$ is independently —$C_1$-$C_6$ alkyl, —$C_2$-$C_6$ alkenyl, —$C_2$-$C_6$ alkynyl, phenyl or benzyl, or each carbon atom together with the $R^1$ and $R^2$ attached to the carbon atom independently form a —$C_3$-$C_7$ cycloalkyl group;

each $R^3$ and $R^4$ is independently H, —$C_1$-$C_6$ alkyl, —$C_2$-$C_6$ alkenyl, —$C_2$-$C_6$ alkynyl, —O($C_1$-$C_6$ alkyl), phenyl, benzyl, Cl, Br, CN, $NO_2$, or $CF_3$, or each carbon atom together with the $R^3$ and $R^4$ attached to the carbon atom independently form a —$C_3$-$C_7$ cycloalkyl group;

$Q^1$ and $Q^2$ are independently H, OH, —$C_1$-$C_6$ alkyl, —O($C_1$-$C_6$ alkyl), phenoxy, aryloxy, benzyl, —S-aryl, —$SR^{1A}$, —$NR^{1A}R^{2A}$, F, Cl, Br, I, —$CF_3$, —$COR^{1A}$, heteroaryl, heterocyclyl, or —V—OH, or each carbon atom together with the $Q^1$ and $Q^2$ attached to the carbon atom independently form a heterocyclyl or a carbocyclyl group;

each $R^{1A}$ and $R^{2A}$ is independently H, —$C_1$-$C_6$ alkyl, —$C_2$-$C_6$ alkenyl, —$C_2$-$C_6$ alkynyl, phenyl or benzyl;

V is $(CH_2)_t$ or arylene;

t is 0, 1, 2, 3, or 4;

each X and Y is independently —OH, —COOH, —$COOR^5$, —$SO_3H$,

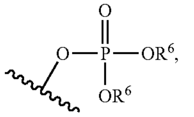
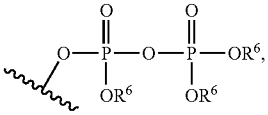
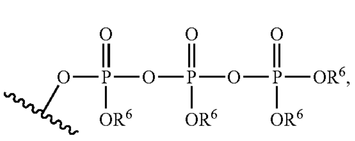
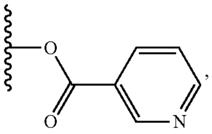,
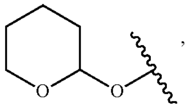,
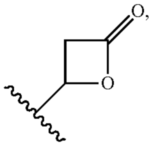
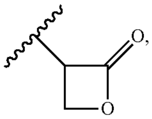
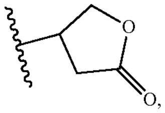
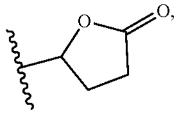
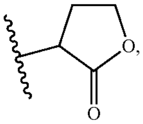
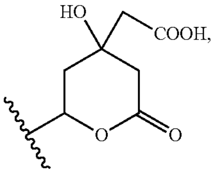
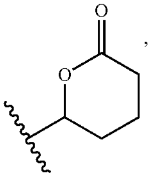,
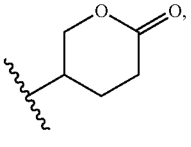
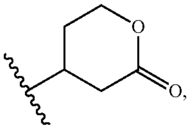
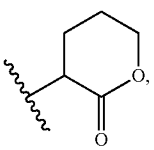
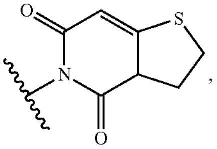,
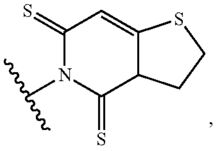,
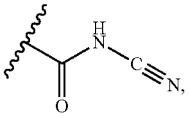
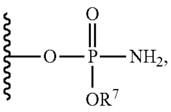
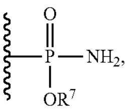
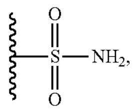
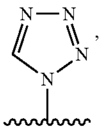,
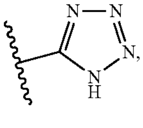
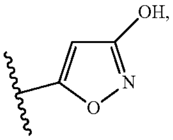
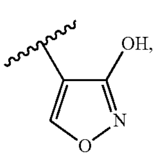
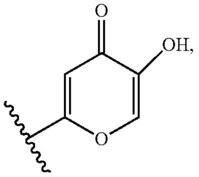
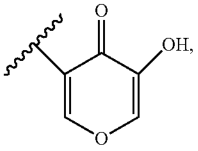

-continued

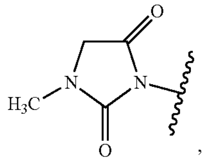 , 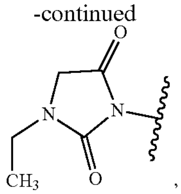 , 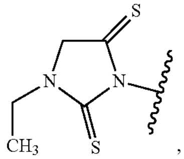 ,

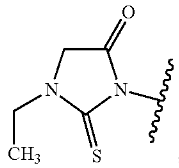 , or 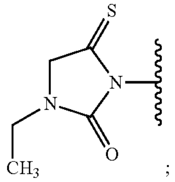 ;

each $R^6$ is independently H, $-C_1$-$C_6$ alkyl, $-C_2$-$C_6$ alkenyl, or $-C_2$-$C_6$ alkynyl, wherein the $-C_1$-$C_6$ alkyl, $-C_2$-$C_6$ alkenyl, or $-C_2$-$C_6$ alkynyl is unsubstituted or substituted with one or two halogen, —OH, $-O(C_1$-$C_6$ alkyl), or phenyl groups;

each $R^7$ is independently H, $-C_1$-$C_6$ alkyl, $-C_2$-$C_6$ alkenyl, or $-C_2$-$C_6$ alkynyl;

each W is independently —O—, —NH—, —N(OH)—, —N(→O)—, —S—, —S(═O)—, $-S(O)_2-$, or —Se—; and each $R^5$ is independently $-C_1$-$C_6$ alkyl, $-C_2$-$C_6$ alkenyl, $-C_2$-$C_6$ alkynyl, phenyl, or benzyl, each being unsubstituted or substituted with one or more halogen, —OH, $-O(C_1$-$C_6$ alkyl), or phenyl groups.

In some embodiments, the compound of Formula (IF) has the structure shown in Table A-3, or a pharmaceutically acceptable salt or solvate thereof. In some embodiments, the compound of Formula (IE) has the structure shown in Table A-7 which are mono- or di-substituted with —OH or methyl groups on the phenyl, or a pharmaceutically acceptable salt or solvate thereof.

Compounds of Formulas (IH) and (IJ)-(IL)

In some embodiments, the compound of the invention is a compound of Formula (IH):

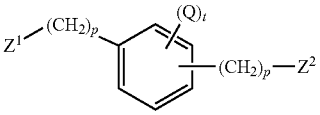

(IH)

or a pharmaceutically acceptable salt or solvate thereof, wherein:

each p is independently 1, 2, 3, 4, 5, 6, or 7;

each $Z^1$ and $Z^2$ is independently $-C(R^1)(R^2)-(CH_2)_c-X$ or $-W-(CH_2)_c-C(R^3)(R^4)-Y$;

each c is independently 0, 1, 2, or 3;

each $R^1$ and $R^2$ is independently $-C_1$-$C_6$ alkyl, $-C_2$-$C_6$ alkenyl, $-C_2$-$C_6$ alkynyl, phenyl or benzyl, or each carbon atom together with the $R^1$ and $R^2$ attached to the carbon atom independently form a $-C_3$-$C_7$ cycloalkyl group;

each $R^3$ and $R^4$ is independently H, $-C_1$-$C_6$ alkyl, $-C_2$-$C_6$ alkenyl, $-C_2$-$C_6$ alkynyl, $-O(C_1$-$C_6$ alkyl), phenyl, benzyl, Cl, Br, CN, $NO_2$, or $CF_3$, or each carbon atom together with the $R^3$ and $R^4$ attached to the carbon atom independently form a $-C_3$-$C_7$ cycloalkyl group;

Q is independently —OH, methyl, or methoxy;

t is 1, 2, 3, or 4;

each X and Y is independently —OH, —COOH, $-COOR^5$, $-SO_3H$,

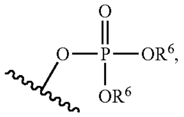 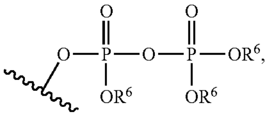

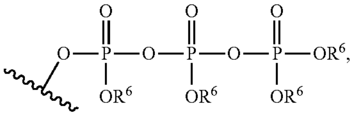 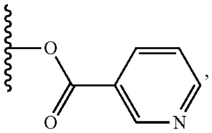 ,

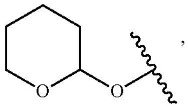 , 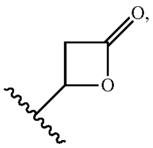 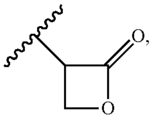

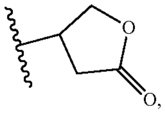 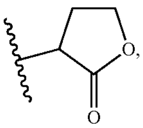 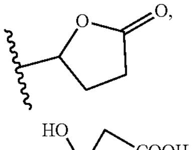

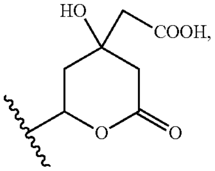 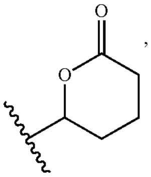 , 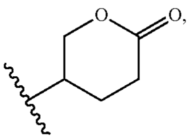

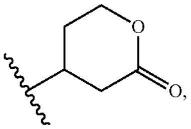 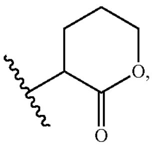 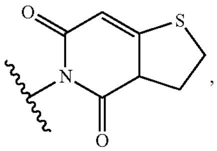 ,

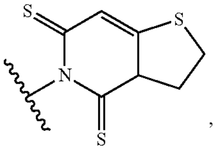 , 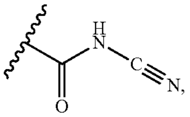

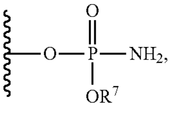 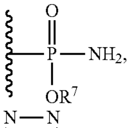 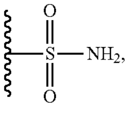

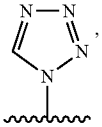 , 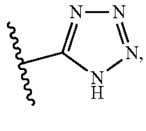 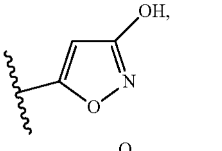

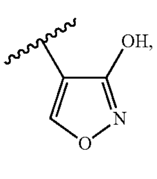 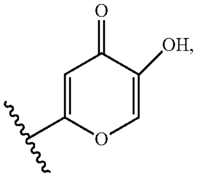 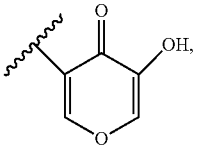

-continued

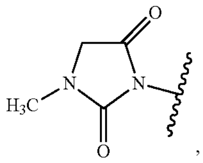, 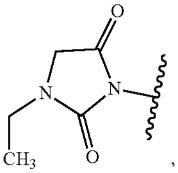, 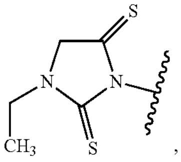,

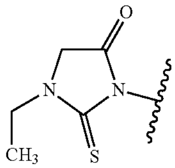, or 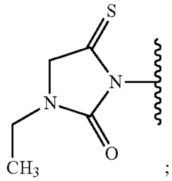;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups;

each $R^7$ is independently H, —$C_1$-$C_6$ alkyl, —$C_2$-$C_6$ alkenyl, or —$C_2$-$C_6$ alkynyl;

each W is independently —O—, —NH—, —N(OH)—, —N(→O)—, —S—, —S(═O)—, —S(O)$_2$—, or —Se—; and each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups.

In some embodiments of formula (IH), the compound has the structure of formula (IJ), (IK), or (IL), or a pharmaceutically acceptable salt thereof:

(IJ)

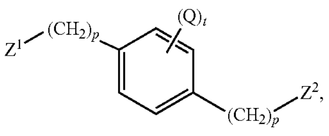

(IK)

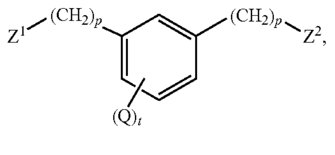

(IL)

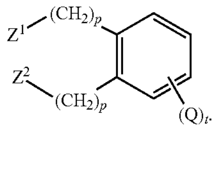

In some embodiments of the compounds of Formula (ID), (IE), (IF), (IG), (IH), (IJ), (IK), or (IL) $Z^1$ and $Z^2$ are each independently —C($R^1$)($R^2$)—($CH_2$)$_c$—X. In some embodiments of the compounds of Formula (ID), (IE), (IF), (IG), (IH), (IJ), (IK), or (IL), one or both of $Z^1$ and $Z^2$ is —W—($CH_2$)$_c$—C($R^3$)($R^4$)—Y.

In some embodiments of the compounds of Formula (ID), (IE), (IF), (IG), (IH), (IJ), (IK), or (IL), X is —COOH or —COOR$^5$.

In some embodiments of the compounds of Formula (ID), (IE), (IF), (IG), (IH), (IJ), (IK), or (IL), each $R^1$ and $R^2$ is independently —$C_1$-$C_6$ alkyl, —$C_2$-$C_6$ alkenyl, or —$C_2$-$C_6$ alkynyl. In some embodiments of the compounds of Formula (ID), (IE), (IF), (IG), (IH), (IJ), (IK), or (IL), each $R^1$ and $R^2$ is independently —$C_1$-$C_3$ alkyl, —$C_2$-$C_3$ alkenyl, or —$C_2$-$C_3$ alkynyl. In some embodiments of the compounds of Formula (ID), (IE), (IF), (IG), (IH), (IJ), (IK), or (IL), $R^1$ and $R^2$ are methyl.

In some embodiments of the compounds of Formula (ID), (IE), (IF), (IG), (IH), (IJ), (IK), or (IL), $Z^1$ and $Z^2$ are each independently —C($R^1$)($R^2$)—($CH_2$)$_c$—X, X is —COOH or —COOR$^5$, and $R^1$ and $R^2$ are methyl.

In some embodiments of the compounds of Formula (ID), (IE), (IF), (IG), (IH), (IJ), (IK), or (IL), c is 0 or 1.

In some embodiments of the compounds of Formula (ID), (IE), (IF), (IG), (IH), (IJ), (IK), or (IL), $Z^1$ and $Z^2$ are each —C($R^1$)($R^2$)—($CH_2$)$_c$—X. In some embodiments of the compounds of Formula (ID), (IE), (IF), (IG), (IH), (IJ), (IK), or (IL), $Z^1$ and $Z^2$ are each —C($R^1$)($R^2$)—($CH_2$)$_c$—X and X is each —COOH.

In some embodiments of the compounds of Formula (ID), (IE), (IF), (IG), (IH), (IJ), (IK), or (IL), each carbon atom together with the $R^1$ and $R^2$ attached to the carbon atom independently form a —$C_3$-$C_7$ cycloalkyl group. In some embodiments of the compounds of Formula (ID), (IE), (IF), (IG), (IH), (IJ), (IK), or (IL) each carbon atom together with the $R^1$ and $R^2$ attached to the carbon atom independently form a cyclopropyl ring.

In some embodiments of the compounds of Formula (ID), (IE), (IF), (IG), (IH), (IJ), (IK), or (IL), $Z^1$ and $Z^2$ are each —C($R^1$)($R^2$)—($CH_2$)$_c$—X and at least one $R^1$ and one $R^2$ together with the carbon atom to which they are attached form a —$C_3$-$C_7$ cycloalkyl group. In some embodiments of the compounds of Formula (ID), (IE), (IF), (IG), (IH), (IJ), (IK), or (IL), $Z^1$ and $Z^2$ are each —C($R^1$)($R^2$)—($CH_2$)$_c$—X and at least one $R^1$ and one $R^2$ together with the carbon atom to which they are attached form a cyclopropyl ring.

In some embodiments of the compounds of Formula (ID), (IE), (IF), (IG), (IH), (IJ), (IK), or (IL), $R^3$ and $R^4$ is independently H, —$C_1$-$C_6$ alkyl, —$C_2$-$C_6$ alkenyl, or —$C_2$-$C_6$ alkynyl.

In some embodiments of the compounds of Formula (ID), (IE), (IF), (IG), (IH), (IJ), (IK), or (IL), Y is —COOH or —COOR$^5$.

In some embodiments of the compounds of Formula (ID), (IE), (IF), (IG), (IH), (IJ), (IK), or (IL), $R^5$ is —$C_1$-$C_6$ alkyl, —$C_2$-$C_6$ alkenyl, or —$C_2$-$C_6$ alkynyl. In some embodiments of the compounds of Formula (ID), (IE), (IF), (IG), (IH), (IJ), (IK), or (IL), $R^5$ is —$C_1$-$C_3$ alkyl, —$C_2$-$C_3$ alkenyl, or —$C_2$-$C_3$ alkynyl.

In some embodiments of the compounds of Formula (ID), (IE), (IF), (IG), (IH), (IJ), (IK), or (IL), p is 3, 4, 5, 6, or 7. In some embodiments, p is 4, 5, 6, or 7.

In some embodiments of the compounds of Formula (ID), (IE), (IF), (IG), (IH), (IJ), (IK), or (IL), one or both of $Z^1$ and $Z^2$ is —W—($CH_2$)$_c$—C($R^3$)($R^4$)—Y, and $R^3$ and $R^4$ is independently H, —$C_1$-$C_6$ alkyl, —$C_2$-$C_6$ alkenyl, or —$C_2$-$C_6$ alkynyl. In some embodiments of the compounds of Formula (ID), (IE), (IF), (IG), (IH), (IJ), (IK), or (IL), one or both of $Z^1$ and $Z^2$ is —W—($CH_2$)$_c$—C($R^3$)($R^4$)—Y, and Y is —COOH or —COOR$^5$. In some embodiments of the compounds of Formula (ID), (IE), (IF), (IG), (IH), (IJ), (IK), or (IL), one or both of $Z^1$ and $Z^2$ is —W—($CH_2$)$_c$—C($R^3$)($R^4$)—Y, Y is —COOH or —COOR$^5$, and $R^5$ is —$C_1$-$C_6$ alkyl, —$C_2$-$C_6$ alkenyl, or —$C_2$-$C_6$ alkynyl. In some embodiments of the compounds of Formula (ID), (IE), (IF), (IG), (IH), (IJ), (IK), or (IL), one or both of $Z^1$ and $Z^2$ is —W—$(CH_2)_c$—$C(R^3)(R^4)$—Y, Y is —COOH or —$COOR^5$, and $R^5$ is —$C_1$-$C_3$ alkyl, —$C_2$-$C_3$ alkenyl, or —$C_2$-$C_3$ alkynyl.

In some embodiments of the compound of Formula (IH), (IJ), (IK), or (IL), Q is independently methyl or —OH.

In some embodiments of the compound of Formula (IH), (IJ), (IK), or (IL), t is 1. In some embodiments, t is 2. In some embodiments, t is 3.

In some embodiments, the compound of Formula (IH), (IJ), (IK), or (IL) has any one of the structures shown in Table A-5, Table A-6, or Table A-7, or a pharmaceutically acceptable salt or solvate thereof.

TABLE A-5

| Structure |
| --- |
| 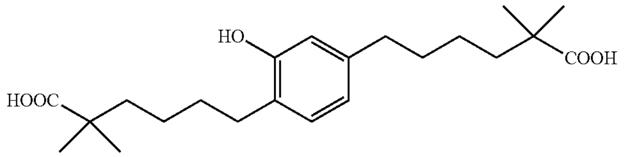 [SMILES: CC(C)(CCCCc1ccc(CCCCC(C)(C)C(=O)O)c(O)c1)C(=O)O] |
| 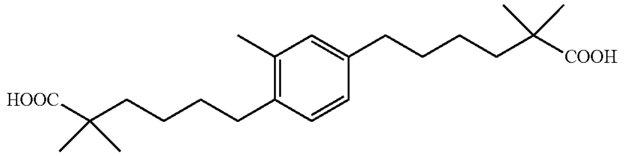 [SMILES: Cc1cc(CCCCC(C)(C)C(=O)O)ccc1CCCCC(C)(C)C(=O)O] |
| 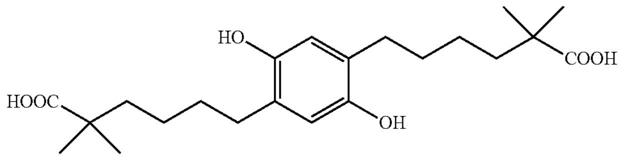 [SMILES: CC(C)(CCCCc1cc(O)c(CCCCC(C)(C)C(=O)O)cc1O)C(=O)O] |
| 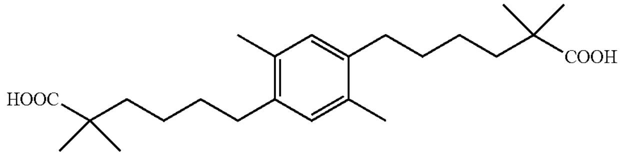 [SMILES: Cc1cc(CCCCC(C)(C)C(=O)O)c(C)cc1CCCCC(C)(C)C(=O)O] |
| 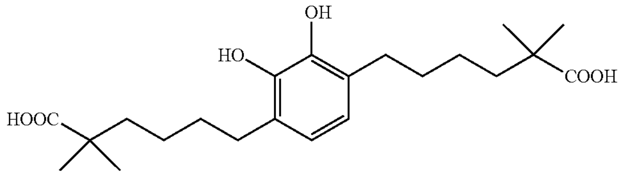 [SMILES: CC(C)(CCCCc1ccc(CCCCC(C)(C)C(=O)O)c(O)c1O)C(=O)O] |
| 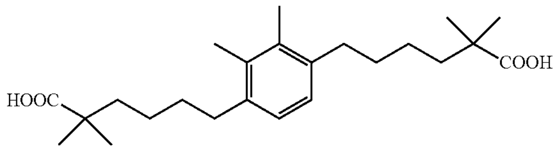 [SMILES: Cc1c(CCCCC(C)(C)C(=O)O)ccc(CCCCC(C)(C)C(=O)O)c1C] |
| 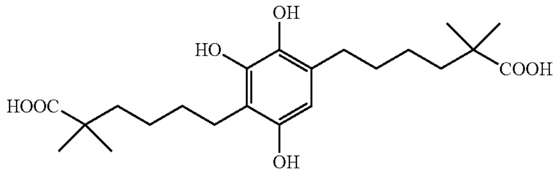 [SMILES: CC(C)(CCCCc1cc(O)c(CCCCC(C)(C)C(=O)O)c(O)c1O)C(=O)O] |
| 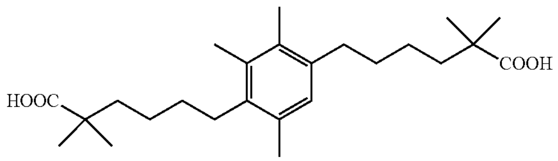 [SMILES: Cc1cc(CCCCC(C)(C)C(=O)O)c(C)c(C)c1CCCCC(C)(C)C(=O)O] |

TABLE A-5-continued
| Structure |
| --- |
| 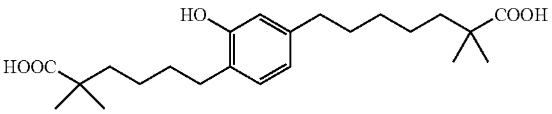 [SMILES: CC(C)(CCCCCc1ccc(CCCCC(C)(C)C(=O)O)c(O)c1)C(=O)O] |
| 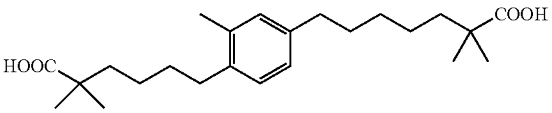 [SMILES: Cc1cc(CCCCCC(C)(C)C(=O)O)ccc1CCCCC(C)(C)C(=O)O] |
| 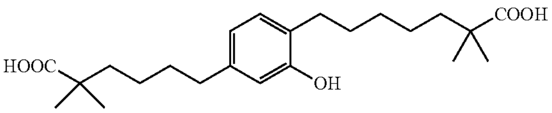 [SMILES: CC(C)(CCCCCc1ccc(CCCCC(C)(C)C(=O)O)cc1O)C(=O)O] |
| 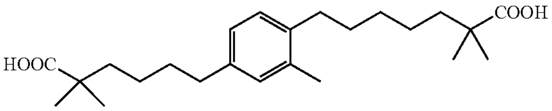 [SMILES: Cc1cc(CCCCC(C)(C)C(=O)O)ccc1CCCCCC(C)(C)C(=O)O] |
| 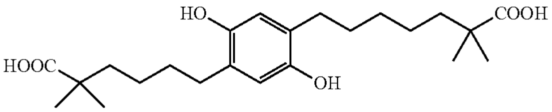 [SMILES: CC(C)(CCCCCc1cc(O)c(CCCCC(C)(C)C(=O)O)cc1O)C(=O)O] |
| 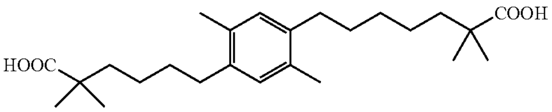 [SMILES: Cc1cc(CCCCC(C)(C)C(=O)O)c(C)cc1CCCCCC(C)(C)C(=O)O] |
| 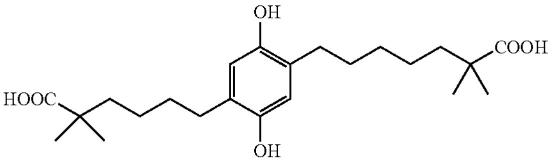 [SMILES: CC(C)(CCCCCc1cc(O)c(CCCCC(C)(C)C(=O)O)cc1O)C(=O)O] |
| 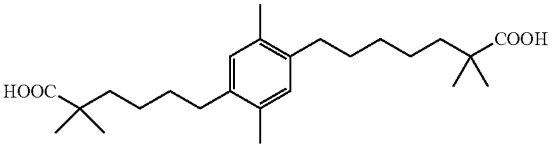 [SMILES: Cc1cc(CCCCC(C)(C)C(=O)O)c(C)cc1CCCCCC(C)(C)C(=O)O] |
| 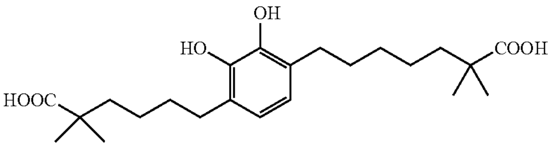 [SMILES: CC(C)(CCCCCc1ccc(CCCCC(C)(C)C(=O)O)c(O)c1O)C(=O)O] |
| 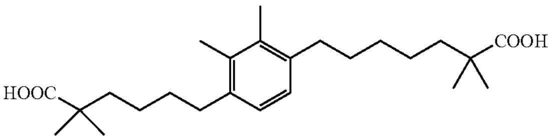 [SMILES: Cc1c(CCCCCC(C)(C)C(=O)O)ccc(CCCCC(C)(C)C(=O)O)c1C] |
| 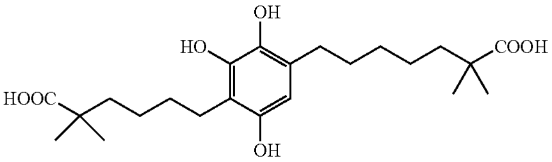 [SMILES: CC(C)(CCCCCc1cc(O)c(CCCCC(C)(C)C(=O)O)c(O)c1O)C(=O)O] |

TABLE A-5-continued
| Structure |
| --- |
| 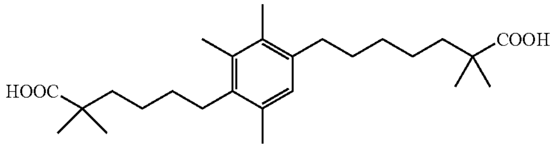 [SMILES: Cc1cc(CCCCCC(C)(C)C(=O)O)c(C)c(C)c1CCCCC(C)(C)C(=O)O] |
| 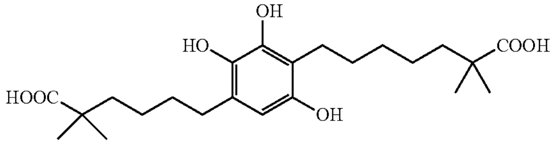 [SMILES: CC(C)(CCCCCc1c(O)cc(CCCCC(C)(C)C(=O)O)c(O)c1O)C(=O)O] |
| 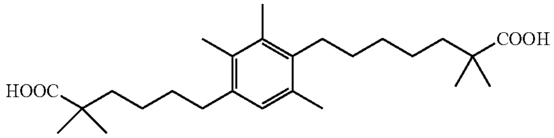 [SMILES: Cc1cc(CCCCC(C)(C)C(=O)O)c(C)c(C)c1CCCCCC(C)(C)C(=O)O] |
| 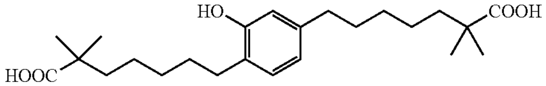 [SMILES: CC(C)(CCCCCc1ccc(CCCCCC(C)(C)C(=O)O)c(O)c1)C(=O)O] |
| 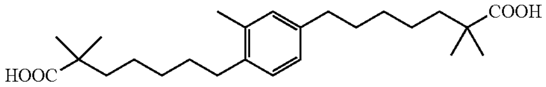 |
| 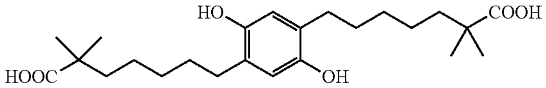 [SMILES: CC(C)(CCCCCc1cc(O)c(CCCCCC(C)(C)C(=O)O)cc1O)C(=O)O] |
| 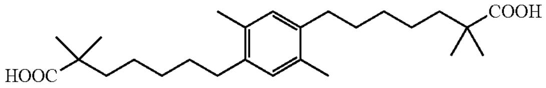 [SMILES: Cc1cc(CCCCCC(C)(C)C(=O)O)c(C)cc1CCCCCC(C)(C)C(=O)O] |
| 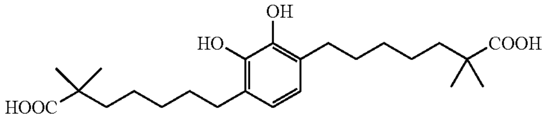 [SMILES: CC(C)(CCCCCc1ccc(CCCCCC(C)(C)C(=O)O)c(O)c1O)C(=O)O] |
| 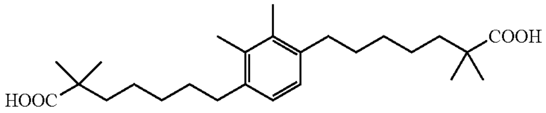 [SMILES: Cc1c(CCCCCC(C)(C)C(=O)O)ccc(CCCCCC(C)(C)C(=O)O)c1C] |
| 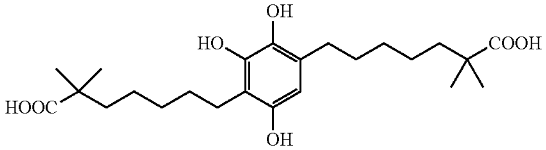 [SMILES: CC(C)(CCCCCc1cc(O)c(CCCCCC(C)(C)C(=O)O)c(O)c1O)C(=O)O] |
| 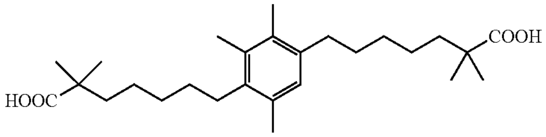 [SMILES: Cc1cc(CCCCCC(C)(C)C(=O)O)c(C)c(C)c1CCCCCC(C)(C)C(=O)O] |
| 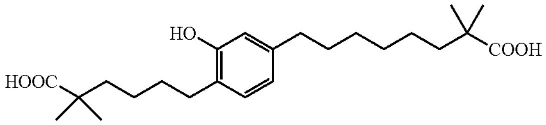 [SMILES: CC(C)(CCCCCCc1ccc(CCCCC(C)(C)C(=O)O)c(O)c1)C(=O)O] |

TABLE A-5-continued
| Structure |
| --- |
| 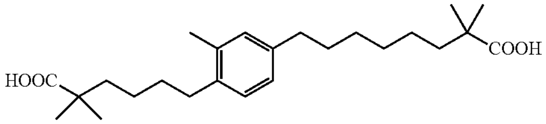 [SMILES: Cc1cc(CCCCCCC(C)(C)C(=O)O)ccc1CCCCC(C)(C)C(=O)O] |
| 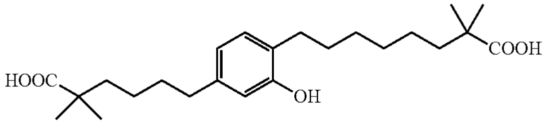 [SMILES: CC(C)(CCCCCCc1ccc(CCCCC(C)(C)C(=O)O)cc1O)C(=O)O] |
| 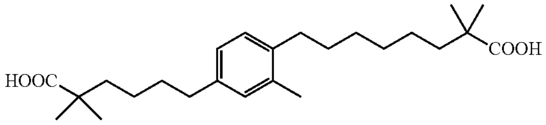 [SMILES: Cc1cc(CCCCC(C)(C)C(=O)O)ccc1CCCCCCC(C)(C)C(=O)O] |
| 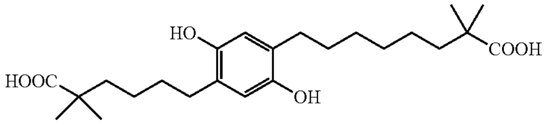 [SMILES: CC(C)(CCCCCCc1cc(O)c(CCCCC(C)(C)C(=O)O)cc1O)C(=O)O] |
| 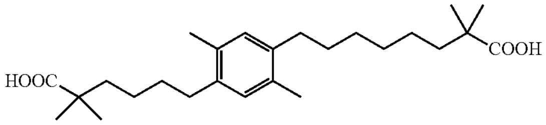 [SMILES: Cc1cc(CCCCC(C)(C)C(=O)O)c(C)cc1CCCCCCC(C)(C)C(=O)O] |
| 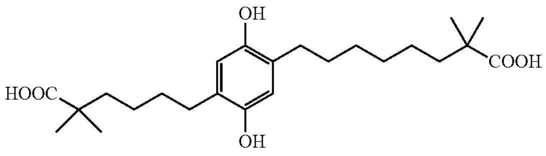 [SMILES: CC(C)(CCCCCCc1cc(O)c(CCCCC(C)(C)C(=O)O)cc1O)C(=O)O] |
| 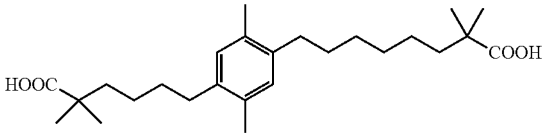 [SMILES: Cc1cc(CCCCC(C)(C)C(=O)O)c(C)cc1CCCCCCC(C)(C)C(=O)O] |
| 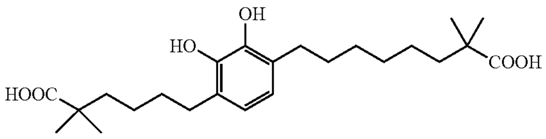 [SMILES: CC(C)(CCCCCCc1ccc(CCCCC(C)(C)C(=O)O)c(O)c1O)C(=O)O] |
| 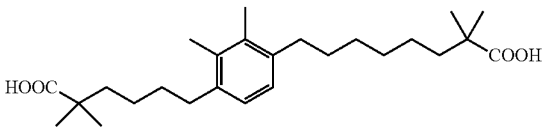 [SMILES: Cc1c(CCCCCCC(C)(C)C(=O)O)ccc(CCCCC(C)(C)C(=O)O)c1C] |
| 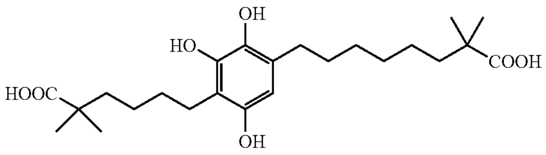 [SMILES: CC(C)(CCCCCCc1cc(O)c(CCCCC(C)(C)C(=O)O)c(O)c1O)C(=O)O] |

TABLE A-5-continued
| Structure |
| --- |
| 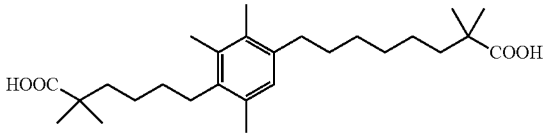 [SMILES: Cc1cc(CCCCCCC(C)(C)C(=O)O)c(C)c(C)c1CCCCC(C)(C)C(=O)O] |
| 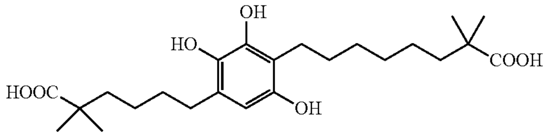 [SMILES: CC(C)(CCCCCCc1c(O)cc(CCCCC(C)(C)C(=O)O)c(O)c1O)C(=O)O] |
| 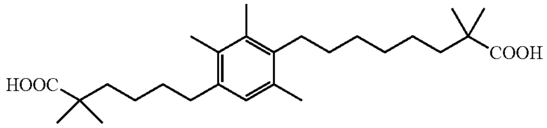 [SMILES: Cc1cc(CCCCC(C)(C)C(=O)O)c(C)c(C)c1CCCCCCC(C)(C)C(=O)O] |
| 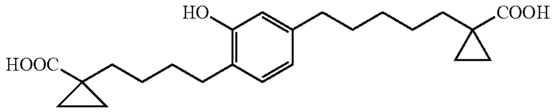 [SMILES: O=C(O)C1(CCCCCc2ccc(CCCCC3(C(=O)O)CC3)c(O)c2)CC1] |
| 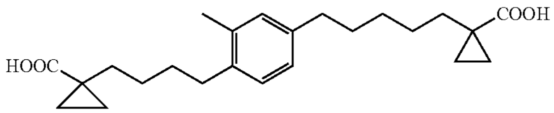 [SMILES: Cc1cc(CCCCCC2(C(=O)O)CC2)ccc1CCCCC1(C(=O)O)CC1] |
| 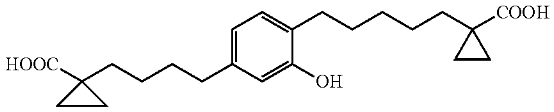 [SMILES: O=C(O)C1(CCCCCc2ccc(CCCCC3(C(=O)O)CC3)cc2O)CC1] |
| 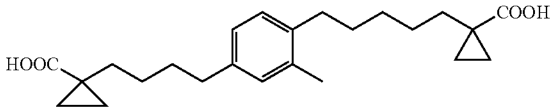 [SMILES: Cc1cc(CCCCC2(C(=O)O)CC2)ccc1CCCCCC1(C(=O)O)CC1] |
| 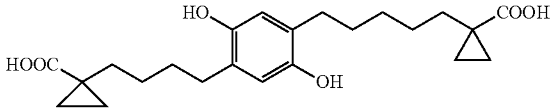 [SMILES: O=C(O)C1(CCCCCc2cc(O)c(CCCCC3(C(=O)O)CC3)cc2O)CC1] |
| 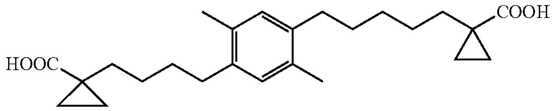 [SMILES: Cc1cc(CCCCC2(C(=O)O)CC2)c(C)cc1CCCCCC1(C(=O)O)CC1] |
| 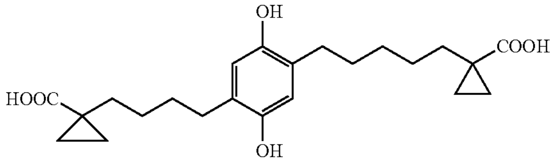 [SMILES: O=C(O)C1(CCCCCc2cc(O)c(CCCCC3(C(=O)O)CC3)cc2O)CC1] |
| 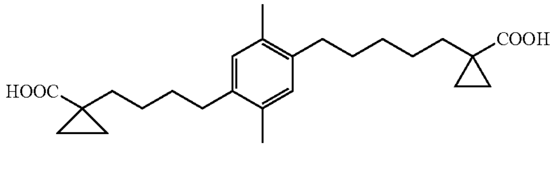 [SMILES: Cc1cc(CCCCC2(C(=O)O)CC2)c(C)cc1CCCCCC1(C(=O)O)CC1] |

TABLE A-5-continued
| Structure |
| --- |
| 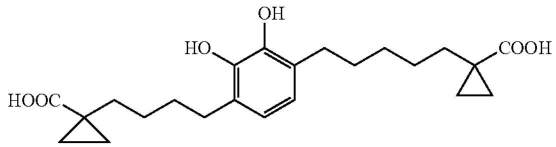 [SMILES: O=C(O)C1(CCCCCc2ccc(CCCCC3(C(=O)O)CC3)c(O)c2O)CC1] |
| 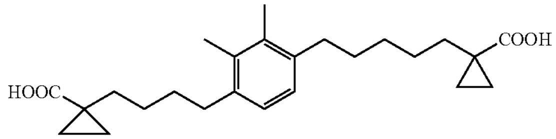 [SMILES: Cc1c(CCCCCC2(C(=O)O)CC2)ccc(CCCCC2(C(=O)O)CC2)c1C] |
| 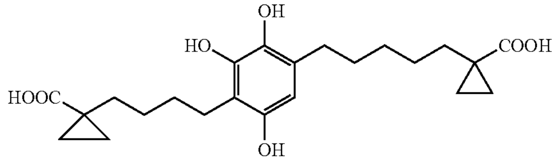 [SMILES: O=C(O)C1(CCCCCc2cc(O)c(CCCCC3(C(=O)O)CC3)c(O)c2O)CC1] |
| 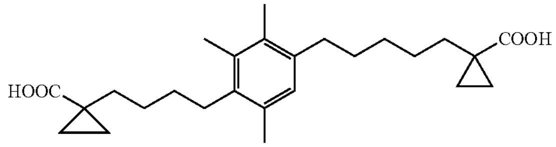 [SMILES: Cc1cc(CCCCCC2(C(=O)O)CC2)c(C)c(C)c1CCCCC1(C(=O)O)CC1] |
| 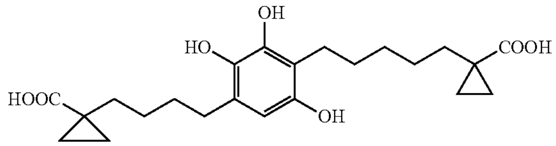 [SMILES: O=C(O)C1(CCCCCc2c(O)cc(CCCCC3(C(=O)O)CC3)c(O)c2O)CC1] |
| 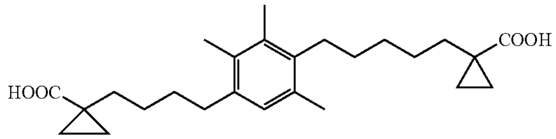 [SMILES: Cc1cc(CCCCC2(C(=O)O)CC2)c(C)c(C)c1CCCCCC1(C(=O)O)CC1] |
| 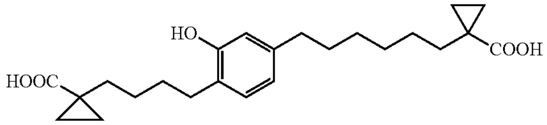 [SMILES: O=C(O)C1(CCCCCCc2ccc(CCCCC3(C(=O)O)CC3)c(O)c2)CC1] |
| 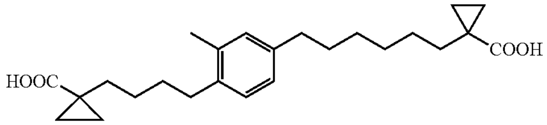 [SMILES: Cc1cc(CCCCCCC2(C(=O)O)CC2)ccc1CCCCC1(C(=O)O)CC1] |
| 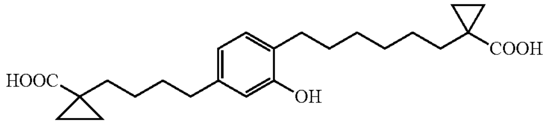 [SMILES: O=C(O)C1(CCCCCCc2ccc(CCCCC3(C(=O)O)CC3)cc2O)CC1] |
| 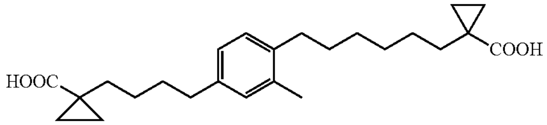 [SMILES: Cc1cc(CCCCC2(C(=O)O)CC2)ccc1CCCCCCC1(C(=O)O)CC1] |

TABLE A-5-continued
| Structure |
| --- |
| 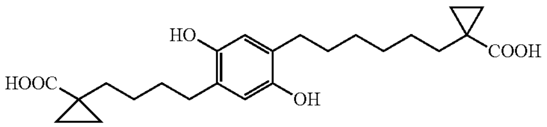 [SMILES: O=C(O)C1(CCCCCCc2cc(O)c(CCCCC3(C(=O)O)CC3)cc2O)CC1] |
| 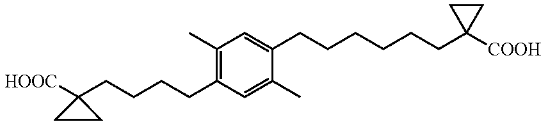 [SMILES: Cc1cc(CCCCC2(C(=O)O)CC2)c(C)cc1CCCCCCC1(C(=O)O)CC1] |
| 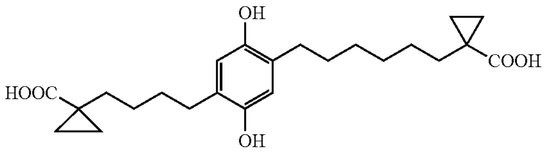 [SMILES: O=C(O)C1(CCCCCCc2cc(O)c(CCCCC3(C(=O)O)CC3)cc2O)CC1] |
| 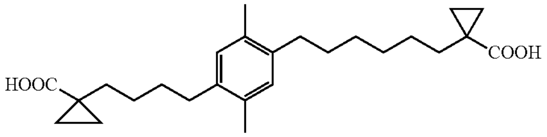 |
| 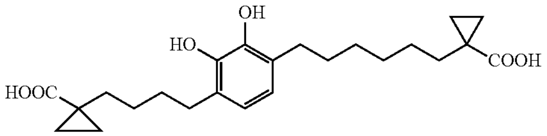 [SMILES: O=C(O)C1(CCCCCCc2ccc(CCCCC3(C(=O)O)CC3)c(O)c2O)CC1] |
| 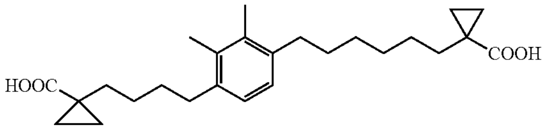 [SMILES: Cc1c(CCCCCCC2(C(=O)O)CC2)ccc(CCCCC2(C(=O)O)CC2)c1C] |
| 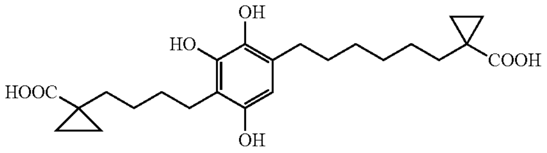 [SMILES: O=C(O)C1(CCCCCCc2cc(O)c(CCCCC3(C(=O)O)CC3)c(O)c2O)CC1] |
| 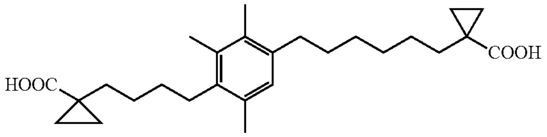 [SMILES: Cc1cc(CCCCCCC2(C(=O)O)CC2)c(C)c(C)c1CCCCC1(C(=O)O)CC1] |
| 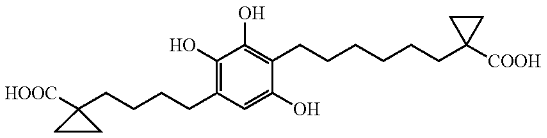 [SMILES: O=C(O)C1(CCCCCCc2c(O)cc(CCCCC3(C(=O)O)CC3)c(O)c2O)CC1] |
| 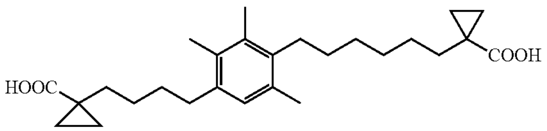 [SMILES: Cc1cc(CCCCC2(C(=O)O)CC2)c(C)c(C)c1CCCCCCC1(C(=O)O)CC1] |
| 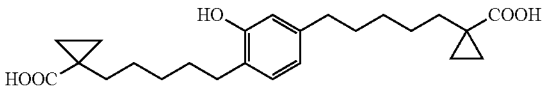 [SMILES: O=C(O)C1(CCCCCc2ccc(CCCCCC3(C(=O)O)CC3)c(O)c2)CC1] |

TABLE A-5-continued
| Structure |
| --- |
| 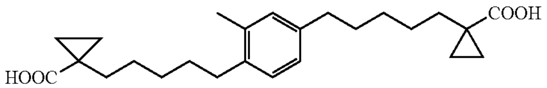 [SMILES: Cc1cc(CCCCCC2(C(=O)O)CC2)ccc1CCCCCC1(C(=O)O)CC1] |
| 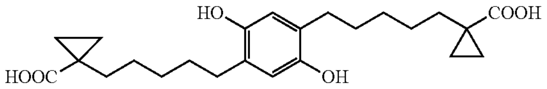 [SMILES: O=C(O)C1(CCCCCc2cc(O)c(CCCCCC3(C(=O)O)CC3)cc2O)CC1] |
| 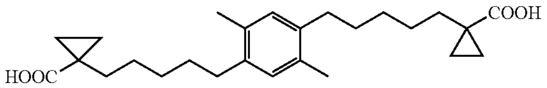 [SMILES: Cc1cc(CCCCCC2(C(=O)O)CC2)c(C)cc1CCCCCC1(C(=O)O)CC1] |
| 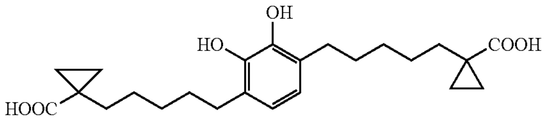 [SMILES: O=C(O)C1(CCCCCc2ccc(CCCCCC3(C(=O)O)CC3)c(O)c2O)CC1] |
| 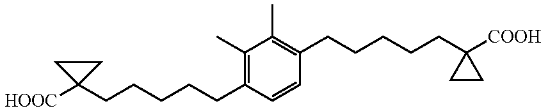 [SMILES: Cc1c(CCCCCC2(C(=O)O)CC2)ccc(CCCCCC2(C(=O)O)CC2)c1C] |
| 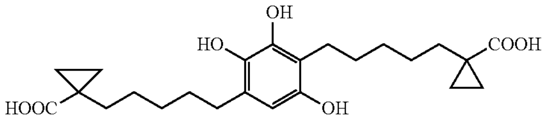 [SMILES: O=C(O)C1(CCCCCc2cc(O)c(CCCCCC3(C(=O)O)CC3)c(O)c2O)CC1] |
| 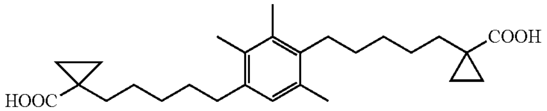 [SMILES: Cc1cc(CCCCCC2(C(=O)O)CC2)c(C)c(C)c1CCCCCC1(C(=O)O)CC1] |
| 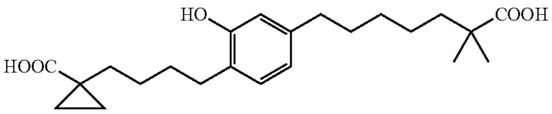 [SMILES: CC(C)(CCCCCc1ccc(CCCCC2(C(=O)O)CC2)c(O)c1)C(=O)O] |
| 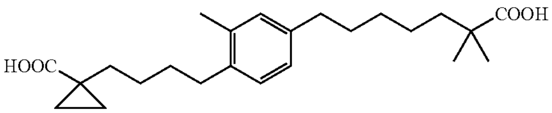 [SMILES: Cc1cc(CCCCCC(C)(C)C(=O)O)ccc1CCCCC1(C(=O)O)CC1] |
| 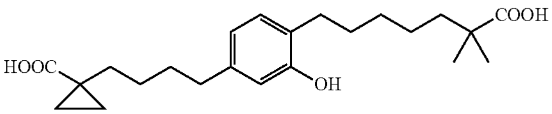 [SMILES: CC(C)(CCCCCc1ccc(CCCCC2(C(=O)O)CC2)cc1O)C(=O)O] |
| 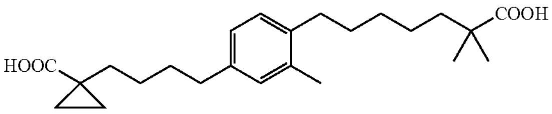 [SMILES: Cc1cc(CCCCC2(C(=O)O)CC2)ccc1CCCCCC(C)(C)C(=O)O] |
| 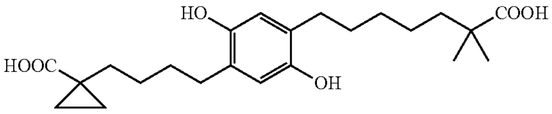 [SMILES: CC(C)(CCCCCc1cc(O)c(CCCCC2(C(=O)O)CC2)cc1O)C(=O)O] |
| 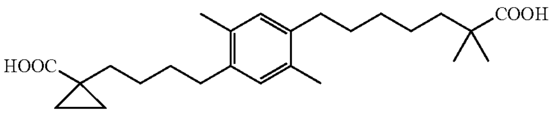 [SMILES: Cc1cc(CCCCC2(C(=O)O)CC2)c(C)cc1CCCCCC(C)(C)C(=O)O] |

TABLE A-5-continued
| Structure |
| --- |
| 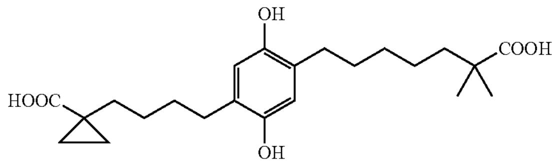 [SMILES: CC(C)(CCCCCc1cc(O)c(CCCCC2(C(=O)O)CC2)cc1O)C(=O)O] |
| 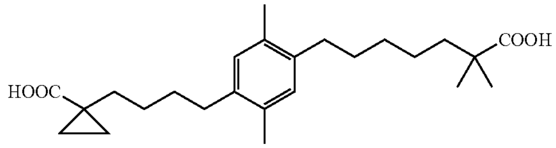 [SMILES: Cc1cc(CCCCC2(C(=O)O)CC2)c(C)cc1CCCCCC(C)(C)C(=O)O] |
| 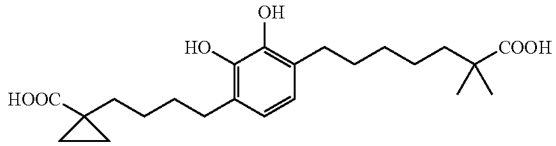 [SMILES: CC(C)(CCCCCc1ccc(CCCCC2(C(=O)O)CC2)c(O)c1O)C(=O)O] |
| 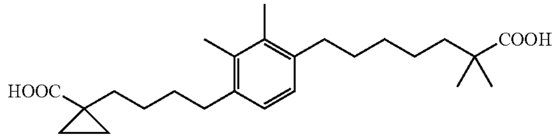 [SMILES: Cc1c(CCCCCC(C)(C)C(=O)O)ccc(CCCCC2(C(=O)O)CC2)c1C] |
| 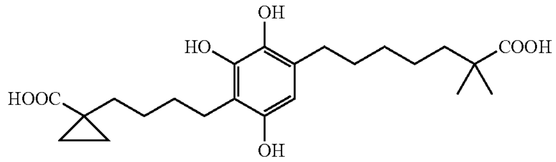 [SMILES: CC(C)(CCCCCc1cc(O)c(CCCCC2(C(=O)O)CC2)c(O)c1O)C(=O)O] |
| 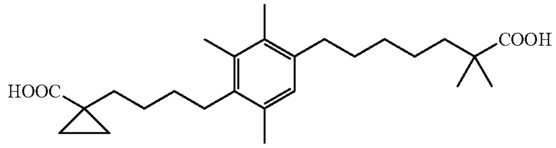 [SMILES: Cc1cc(CCCCCC(C)(C)C(=O)O)c(C)c(C)c1CCCCC1(C(=O)O)CC1] |
| 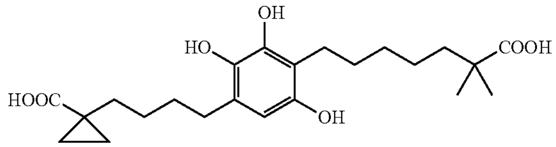 [SMILES: CC(C)(CCCCCc1c(O)cc(CCCCC2(C(=O)O)CC2)c(O)c1O)C(=O)O] |
| 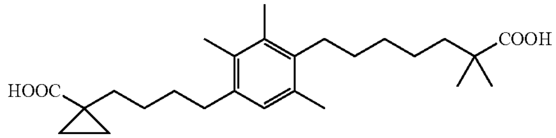 [SMILES: Cc1cc(CCCCC2(C(=O)O)CC2)c(C)c(C)c1CCCCCC(C)(C)C(=O)O] |
| 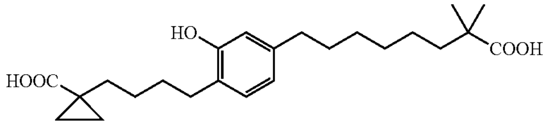 [SMILES: CC(C)(CCCCCCc1ccc(CCCCC2(C(=O)O)CC2)c(O)c1)C(=O)O] |
| 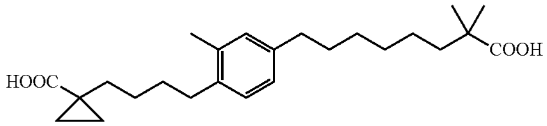 [SMILES: Cc1cc(CCCCCCC(C)(C)C(=O)O)ccc1CCCCC1(C(=O)O)CC1] |

TABLE A-5-continued
| Structure |
| --- |
| 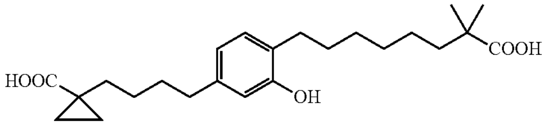 [SMILES: CC(C)(CCCCCCc1ccc(CCCCC2(C(=O)O)CC2)cc1O)C(=O)O] |
| 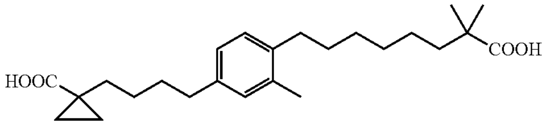 [SMILES: Cc1cc(CCCCC2(C(=O)O)CC2)ccc1CCCCCCC(C)(C)C(=O)O] |
| 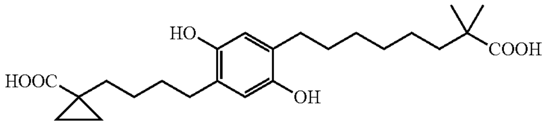 [SMILES: CC(C)(CCCCCCc1cc(O)c(CCCCC2(C(=O)O)CC2)cc1O)C(=O)O] |
| 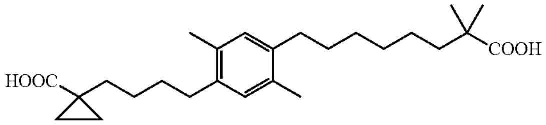 |
| 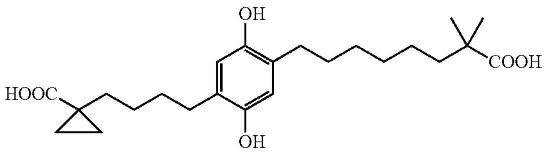 [SMILES: CC(C)(CCCCCCc1cc(O)c(CCCCC2(C(=O)O)CC2)cc1O)C(=O)O] |
| 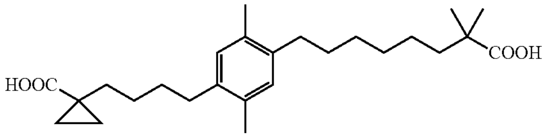 [SMILES: Cc1cc(CCCCC2(C(=O)O)CC2)c(C)cc1CCCCCCC(C)(C)C(=O)O] |
| 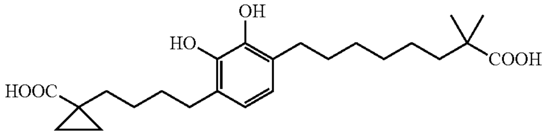 [SMILES: CC(C)(CCCCCCc1ccc(CCCCC2(C(=O)O)CC2)c(O)c1O)C(=O)O] |
| 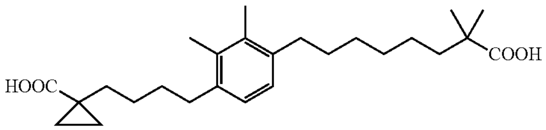 [SMILES: Cc1c(CCCCCCC(C)(C)C(=O)O)ccc(CCCCC2(C(=O)O)CC2)c1C] |
| 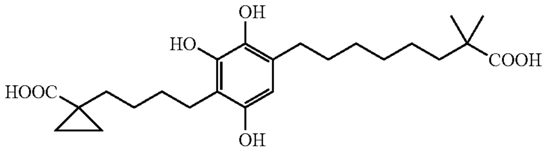 [SMILES: CC(C)(CCCCCCc1cc(O)c(CCCCC2(C(=O)O)CC2)c(O)c1O)C(=O)O] |
| 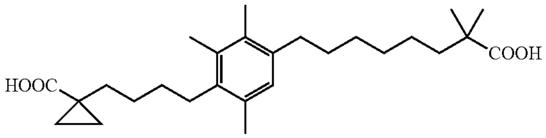 [SMILES: Cc1cc(CCCCCCC(C)(C)C(=O)O)c(C)c(C)c1CCCCC1(C(=O)O)CC1] |
| 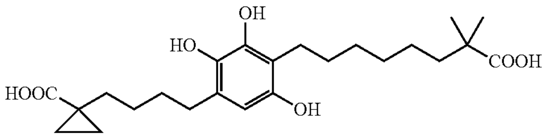 [SMILES: CC(C)(CCCCCCc1c(O)cc(CCCCC2(C(=O)O)CC2)c(O)c1O)C(=O)O] |

TABLE A-5-continued
| Structure |
| --- |
| 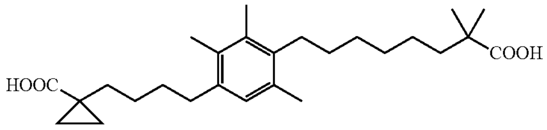 [SMILES: Cc1cc(CCCCC2(C(=O)O)CC2)c(C)c(C)c1CCCCCCC(C)(C)C(=O)O] |
| 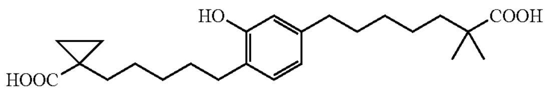 [SMILES: CC(C)(CCCCCc1ccc(CCCCCC2(C(=O)O)CC2)c(O)c1)C(=O)O] |
| 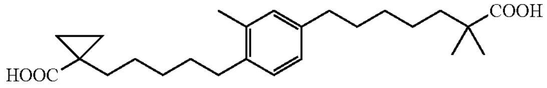 [SMILES: Cc1cc(CCCCCC(C)(C)C(=O)O)ccc1CCCCCC1(C(=O)O)CC1] |
| 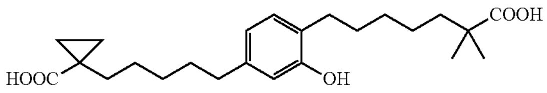 |
| 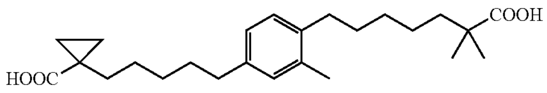 [SMILES: Cc1cc(CCCCCC2(C(=O)O)CC2)ccc1CCCCCC(C)(C)C(=O)O] |
| 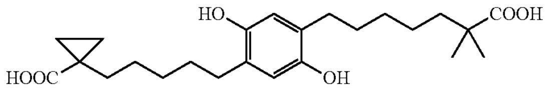 [SMILES: CC(C)(CCCCCc1cc(O)c(CCCCCC2(C(=O)O)CC2)cc1O)C(=O)O] |
| 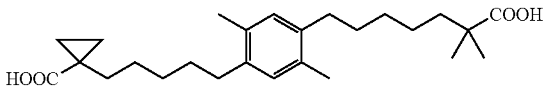 [SMILES: Cc1cc(CCCCCC2(C(=O)O)CC2)c(C)cc1CCCCCC(C)(C)C(=O)O] |
| 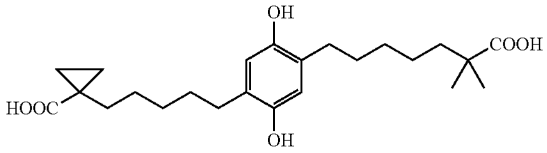 [SMILES: CC(C)(CCCCCc1cc(O)c(CCCCCC2(C(=O)O)CC2)cc1O)C(=O)O] |
| 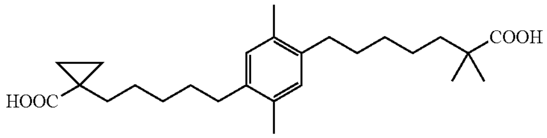 [SMILES: Cc1cc(CCCCCC2(C(=O)O)CC2)c(C)cc1CCCCCC(C)(C)C(=O)O] |
| 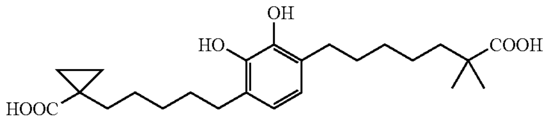 |
| 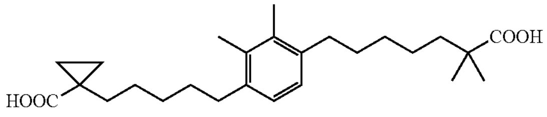 [SMILES: Cc1c(CCCCCC(C)(C)C(=O)O)ccc(CCCCCC2(C(=O)O)CC2)c1C] |
| 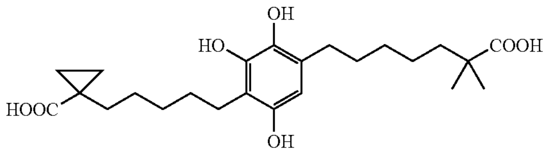 [SMILES: CC(C)(CCCCCc1cc(O)c(CCCCCC2(C(=O)O)CC2)c(O)c1O)C(=O)O] |

TABLE A-5-continued
| Structure |
| --- |
| 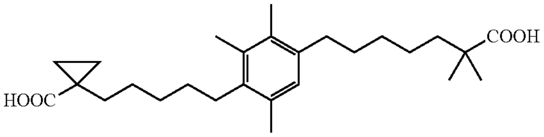 |
| 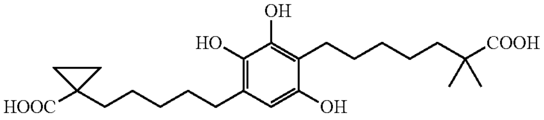 [SMILES: CC(C)(CCCCCc1c(O)cc(CCCCCC2(C(=O)O)CC2)c(O)c1O)C(=O)O] |
| 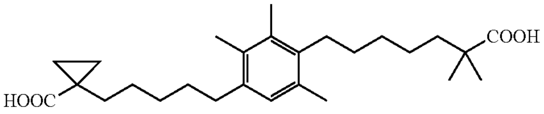 [SMILES: Cc1cc(CCCCCC2(C(=O)O)CC2)c(C)c(C)c1CCCCCC(C)(C)C(=O)O] |
TABLE A-6
| Structure |
| --- |
| 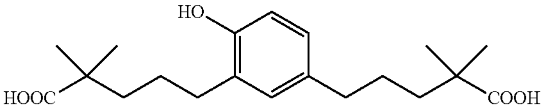 [SMILES: CC(C)(CCCc1ccc(O)c(CCCC(C)(C)C(=O)O)c1)C(=O)O] |
| 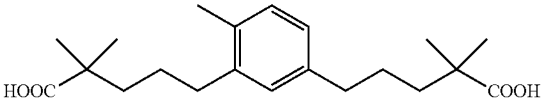 [SMILES: Cc1ccc(CCCC(C)(C)C(=O)O)cc1CCCC(C)(C)C(=O)O] |
| 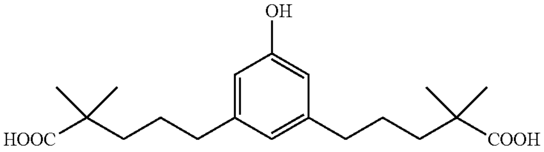 [SMILES: CC(C)(CCCc1cc(O)cc(CCCC(C)(C)C(=O)O)c1)C(=O)O] |
| 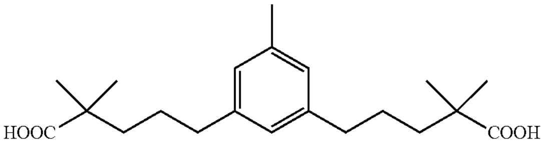 [SMILES: Cc1cc(CCCC(C)(C)C(=O)O)cc(CCCC(C)(C)C(=O)O)c1] |
| 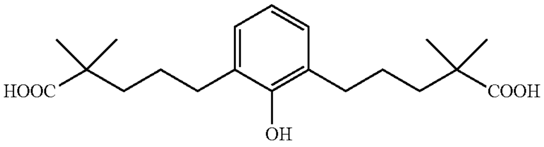 [SMILES: CC(C)(CCCc1cccc(CCCC(C)(C)C(=O)O)c1O)C(=O)O] |
| 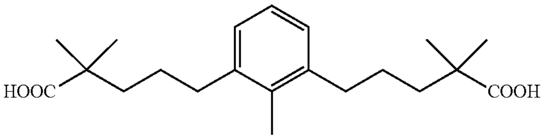 [SMILES: Cc1c(CCCC(C)(C)C(=O)O)cccc1CCCC(C)(C)C(=O)O] |
| 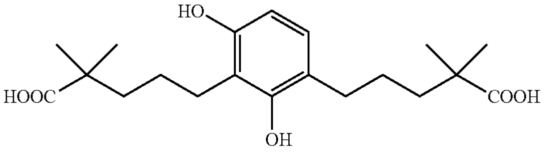 [SMILES: CC(C)(CCCc1ccc(O)c(CCCC(C)(C)C(=O)O)c1O)C(=O)O] |

TABLE A-6-continued
| Structure |
| --- |
| 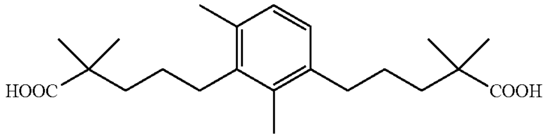 [SMILES: Cc1ccc(CCCC(C)(C)C(=O)O)c(C)c1CCCC(C)(C)C(=O)O] |
| 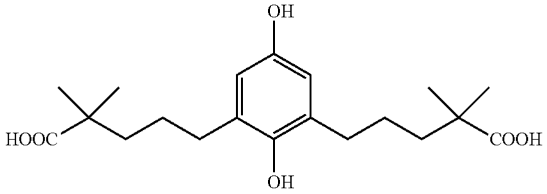 [SMILES: CC(C)(CCCc1cc(O)cc(CCCC(C)(C)C(=O)O)c1O)C(=O)O] |
| 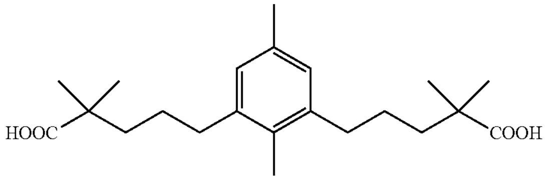 [SMILES: Cc1cc(CCCC(C)(C)C(=O)O)c(C)c(CCCC(C)(C)C(=O)O)c1] |
| 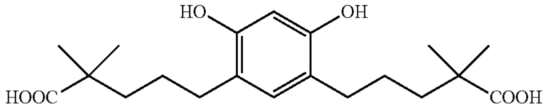 [SMILES: CC(C)(CCCc1cc(CCCC(C)(C)C(=O)O)c(O)cc1O)C(=O)O] |
| 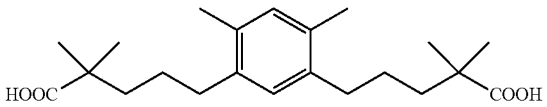 [SMILES: Cc1cc(C)c(CCCC(C)(C)C(=O)O)cc1CCCC(C)(C)C(=O)O] |
| 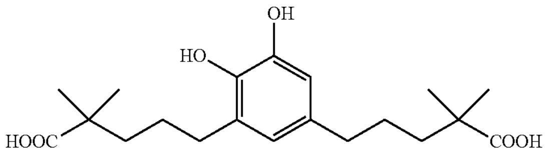 [SMILES: CC(C)(CCCc1cc(O)c(O)c(CCCC(C)(C)C(=O)O)c1)C(=O)O] |
| 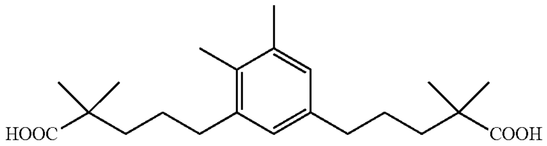 [SMILES: Cc1cc(CCCC(C)(C)C(=O)O)cc(CCCC(C)(C)C(=O)O)c1C] |
| 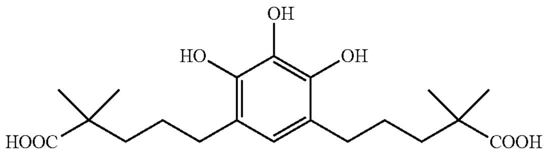 [SMILES: CC(C)(CCCc1cc(CCCC(C)(C)C(=O)O)c(O)c(O)c1O)C(=O)O] |
| 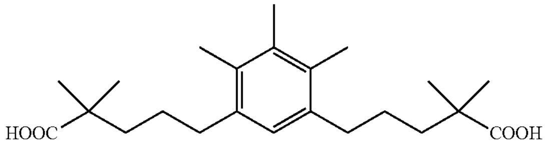 [SMILES: Cc1c(CCCC(C)(C)C(=O)O)cc(CCCC(C)(C)C(=O)O)c(C)c1C] |

TABLE A-6-continued
| Structure |
| --- |
| 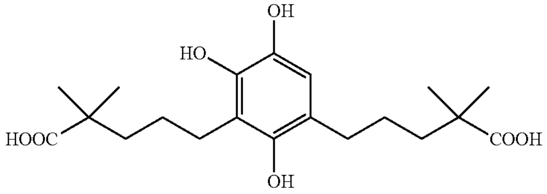 [SMILES: CC(C)(CCCc1cc(O)c(O)c(CCCC(C)(C)C(=O)O)c1O)C(=O)O] |
| 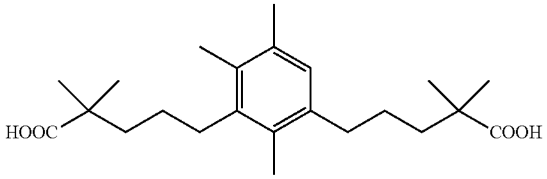 [SMILES: Cc1cc(CCCC(C)(C)C(=O)O)c(C)c(CCCC(C)(C)C(=O)O)c1C] |
| 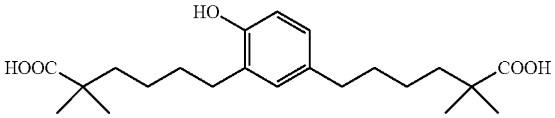 [SMILES: CC(C)(CCCCc1ccc(O)c(CCCCC(C)(C)C(=O)O)c1)C(=O)O] |
| 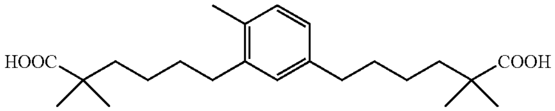 [SMILES: Cc1ccc(CCCCC(C)(C)C(=O)O)cc1CCCCC(C)(C)C(=O)O] |
| 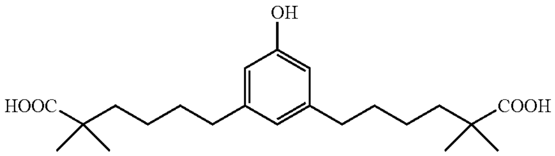 [SMILES: CC(C)(CCCCc1cc(O)cc(CCCCC(C)(C)C(=O)O)c1)C(=O)O] |
| 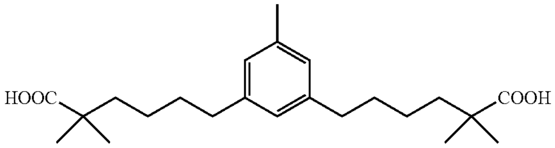 [SMILES: Cc1cc(CCCCC(C)(C)C(=O)O)cc(CCCCC(C)(C)C(=O)O)c1] |
| 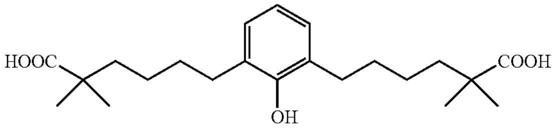 [SMILES: CC(C)(CCCCc1cccc(CCCCC(C)(C)C(=O)O)c1O)C(=O)O] |
| 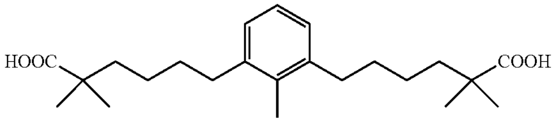 [SMILES: Cc1c(CCCCC(C)(C)C(=O)O)cccc1CCCCC(C)(C)C(=O)O] |
| 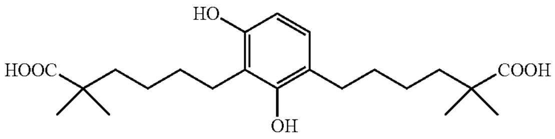 [SMILES: CC(C)(CCCCc1ccc(O)c(CCCCC(C)(C)C(=O)O)c1O)C(=O)O] |
| 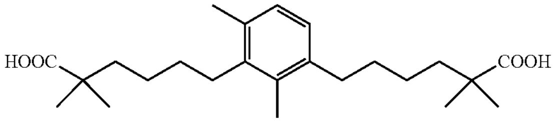 [SMILES: Cc1ccc(CCCCC(C)(C)C(=O)O)c(C)c1CCCCC(C)(C)C(=O)O] |

TABLE A-6-continued
| Structure |
| --- |
| 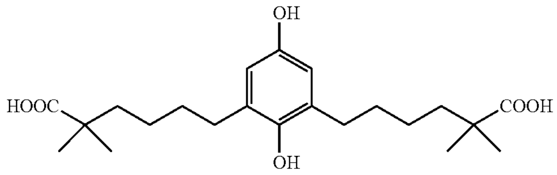 [SMILES: CC(C)(CCCCc1cc(O)cc(CCCCC(C)(C)C(=O)O)c1O)C(=O)O] |
| 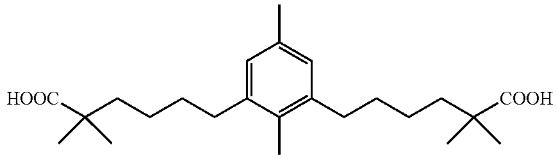 [SMILES: Cc1cc(CCCCC(C)(C)C(=O)O)c(C)c(CCCCC(C)(C)C(=O)O)c1] |
| 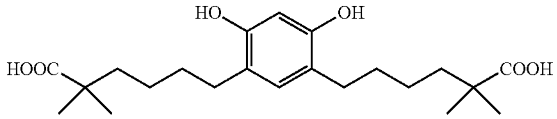 [SMILES: CC(C)(CCCCc1cc(CCCCC(C)(C)C(=O)O)c(O)cc1O)C(=O)O] |
| 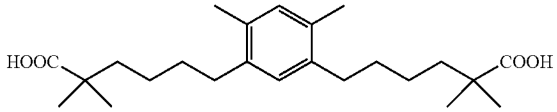 [SMILES: Cc1cc(C)c(CCCCC(C)(C)C(=O)O)cc1CCCCC(C)(C)C(=O)O] |
| 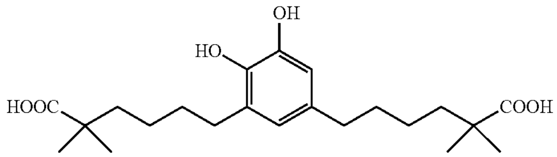 [SMILES: CC(C)(CCCCc1cc(O)c(O)c(CCCCC(C)(C)C(=O)O)c1)C(=O)O] |
| 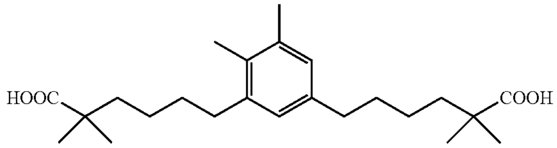 [SMILES: Cc1cc(CCCCC(C)(C)C(=O)O)cc(CCCCC(C)(C)C(=O)O)c1C] |
| 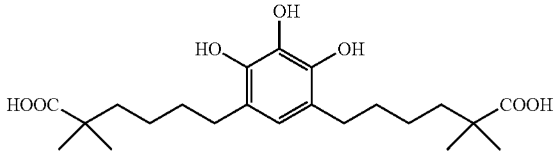 [SMILES: CC(C)(CCCCc1cc(CCCCC(C)(C)C(=O)O)c(O)c(O)c1O)C(=O)O] |
| 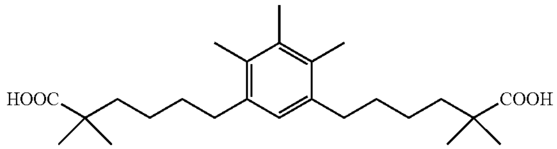 [SMILES: Cc1c(CCCCC(C)(C)C(=O)O)cc(CCCCC(C)(C)C(=O)O)c(C)c1C] |
| 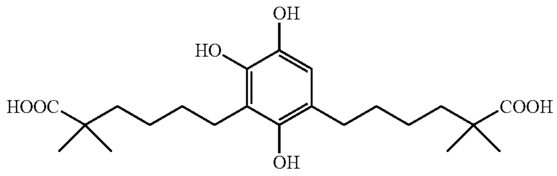 [SMILES: CC(C)(CCCCc1cc(O)c(O)c(CCCCC(C)(C)C(=O)O)c1O)C(=O)O] |

TABLE A-6-continued
| Structure |
|---|
| 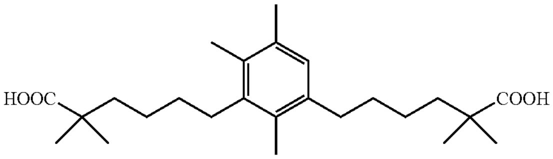 [SMILES: Cc1cc(CCCCC(C)(C)C(=O)O)c(C)c(CCCCC(C)(C)C(=O)O)c1C] |
| 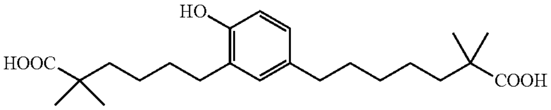 [SMILES: CC(C)(CCCCCc1ccc(O)c(CCCCC(C)(C)C(=O)O)c1)C(=O)O] |
| 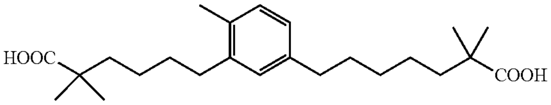 [SMILES: Cc1ccc(CCCCCC(C)(C)C(=O)O)cc1CCCCC(C)(C)C(=O)O] |
| 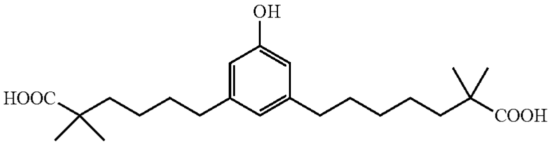 [SMILES: CC(C)(CCCCCc1cc(O)cc(CCCCC(C)(C)C(=O)O)c1)C(=O)O] |
| 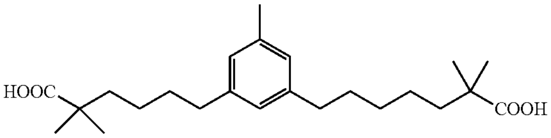 [SMILES: Cc1cc(CCCCCC(C)(C)C(=O)O)cc(CCCCC(C)(C)C(=O)O)c1] |
| 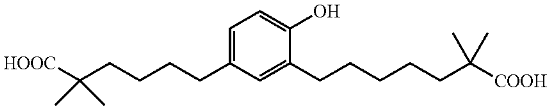 [SMILES: CC(C)(CCCCCc1cc(CCCCC(C)(C)C(=O)O)ccc1O)C(=O)O] |
| 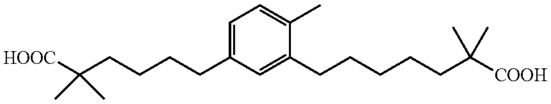 [SMILES: Cc1ccc(CCCCC(C)(C)C(=O)O)cc1CCCCCC(C)(C)C(=O)O] |
| 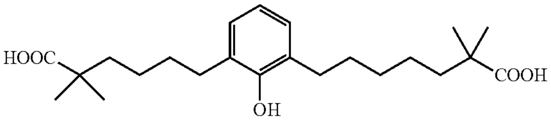 [SMILES: CC(C)(CCCCCc1cccc(CCCCC(C)(C)C(=O)O)c1O)C(=O)O] |
| 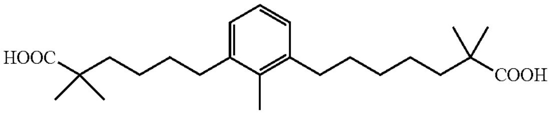 [SMILES: Cc1c(CCCCCC(C)(C)C(=O)O)cccc1CCCCC(C)(C)C(=O)O] |
| 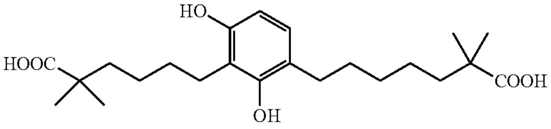 [SMILES: CC(C)(CCCCCc1ccc(O)c(CCCCC(C)(C)C(=O)O)c1O)C(=O)O] |
| 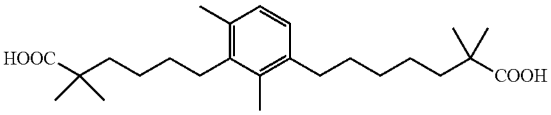 [SMILES: Cc1ccc(CCCCCC(C)(C)C(=O)O)c(C)c1CCCCC(C)(C)C(=O)O] |

TABLE A-6-continued
| Structure |
| --- |
| 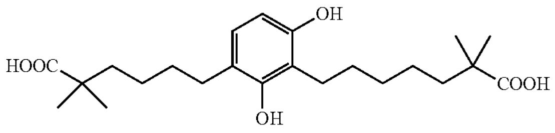 [SMILES: CC(C)(CCCCCc1c(O)ccc(CCCCC(C)(C)C(=O)O)c1O)C(=O)O] |
| 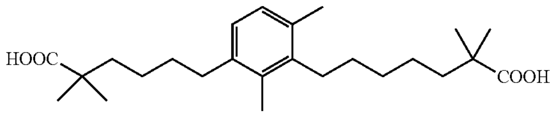 [SMILES: Cc1ccc(CCCCC(C)(C)C(=O)O)c(C)c1CCCCCC(C)(C)C(=O)O] |
| 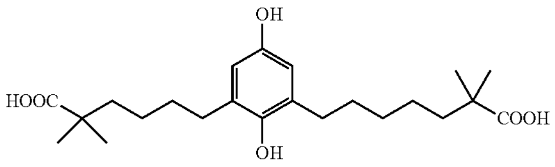 [SMILES: CC(C)(CCCCCc1cc(O)cc(CCCCC(C)(C)C(=O)O)c1O)C(=O)O] |
| 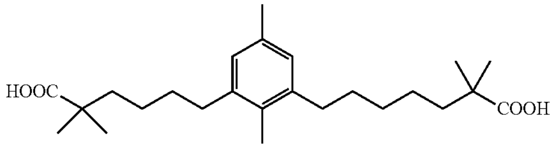 [SMILES: Cc1cc(CCCCCC(C)(C)C(=O)O)c(C)c(CCCCC(C)(C)C(=O)O)c1] |
| 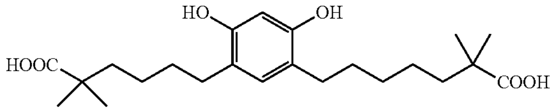 [SMILES: CC(C)(CCCCCc1cc(CCCCC(C)(C)C(=O)O)c(O)cc1O)C(=O)O] |
| 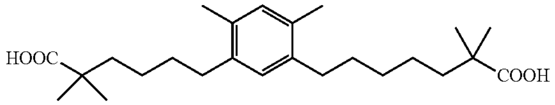 [SMILES: Cc1cc(C)c(CCCCC(C)(C)C(=O)O)cc1CCCCCC(C)(C)C(=O)O] |
| 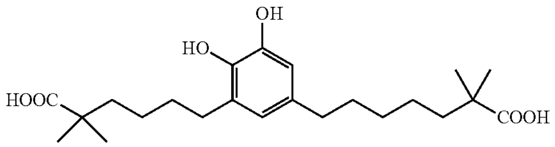 [SMILES: CC(C)(CCCCCc1cc(O)c(O)c(CCCCC(C)(C)C(=O)O)c1)C(=O)O] |
| 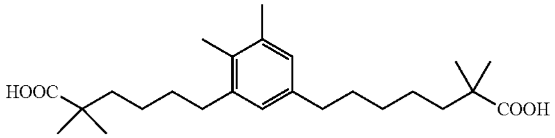 [SMILES: Cc1cc(CCCCCC(C)(C)C(=O)O)cc(CCCCC(C)(C)C(=O)O)c1C] |
| 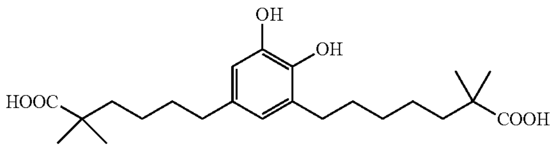 [SMILES: CC(C)(CCCCCc1cc(CCCCC(C)(C)C(=O)O)cc(O)c1O)C(=O)O] |
| 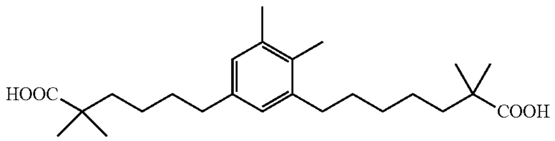 [SMILES: Cc1cc(CCCCC(C)(C)C(=O)O)cc(CCCCCC(C)(C)C(=O)O)c1C] |

TABLE A-6-continued
| Structure |
| --- |
| 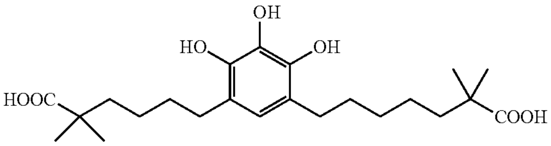 [SMILES: CC(C)(CCCCCc1cc(CCCCC(C)(C)C(=O)O)c(O)c(O)c1O)C(=O)O] |
| 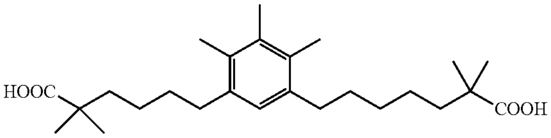 [SMILES: Cc1c(CCCCCC(C)(C)C(=O)O)cc(CCCCC(C)(C)C(=O)O)c(C)c1C] |
| 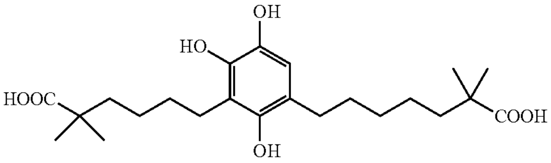 [SMILES: CC(C)(CCCCCc1cc(O)c(O)c(CCCCC(C)(C)C(=O)O)c1O)C(=O)O] |
| 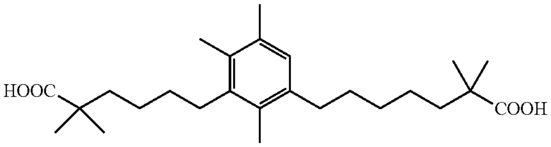 [SMILES: Cc1cc(CCCCCC(C)(C)C(=O)O)c(C)c(CCCCC(C)(C)C(=O)O)c1C] |
| 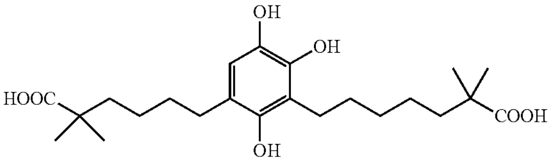 [SMILES: CC(C)(CCCCCc1c(O)c(O)cc(CCCCC(C)(C)C(=O)O)c1O)C(=O)O] |
| 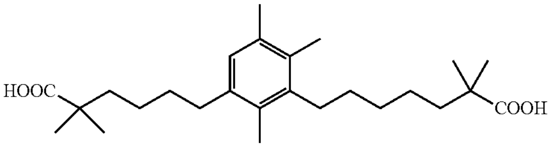 [SMILES: Cc1cc(CCCCC(C)(C)C(=O)O)c(C)c(CCCCCC(C)(C)C(=O)O)c1C] |
| 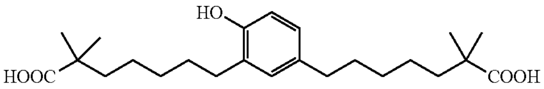 [SMILES: CC(C)(CCCCCc1ccc(O)c(CCCCCC(C)(C)C(=O)O)c1)C(=O)O] |
| 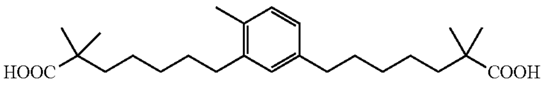 [SMILES: Cc1ccc(CCCCCC(C)(C)C(=O)O)cc1CCCCCC(C)(C)C(=O)O] |
| 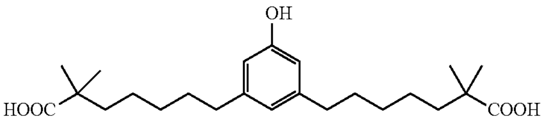 [SMILES: CC(C)(CCCCCc1cc(O)cc(CCCCCC(C)(C)C(=O)O)c1)C(=O)O] |
| 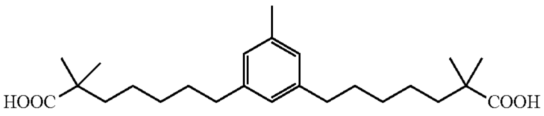 [SMILES: Cc1cc(CCCCCC(C)(C)C(=O)O)cc(CCCCCC(C)(C)C(=O)O)c1] |
| 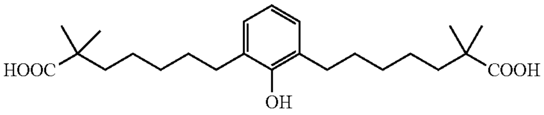 [SMILES: CC(C)(CCCCCc1cccc(CCCCCC(C)(C)C(=O)O)c1O)C(=O)O] |

TABLE A-6-continued
| Structure |
| --- |
| 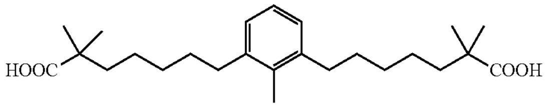 [SMILES: Cc1c(CCCCCC(C)(C)C(=O)O)cccc1CCCCCC(C)(C)C(=O)O] |
| 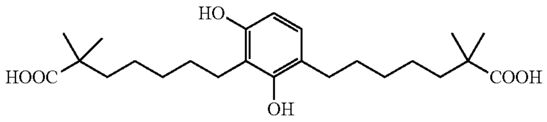 [SMILES: CC(C)(CCCCCc1ccc(O)c(CCCCCC(C)(C)C(=O)O)c1O)C(=O)O] |
| 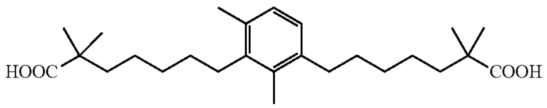 [SMILES: Cc1ccc(CCCCCC(C)(C)C(=O)O)c(C)c1CCCCCC(C)(C)C(=O)O] |
| 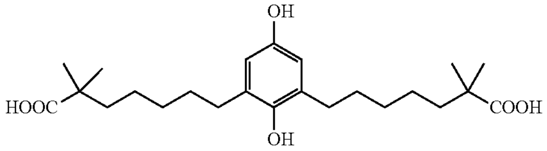 [SMILES: CC(C)(CCCCCc1cc(O)cc(CCCCCC(C)(C)C(=O)O)c1O)C(=O)O] |
| 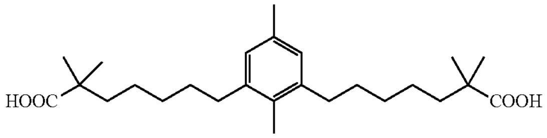 [SMILES: Cc1cc(CCCCCC(C)(C)C(=O)O)c(C)c(CCCCCC(C)(C)C(=O)O)c1] |
| 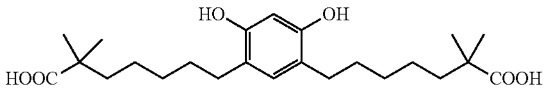 [SMILES: CC(C)(CCCCCc1cc(CCCCCC(C)(C)C(=O)O)c(O)cc1O)C(=O)O] |
| 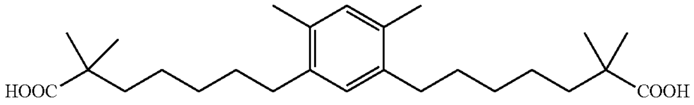 [SMILES: Cc1cc(C)c(CCCCCC(C)(C)C(=O)O)cc1CCCCCC(C)(C)C(=O)O] |
| 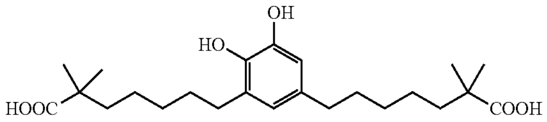 [SMILES: CC(C)(CCCCCc1cc(O)c(O)c(CCCCCC(C)(C)C(=O)O)c1)C(=O)O] |
| 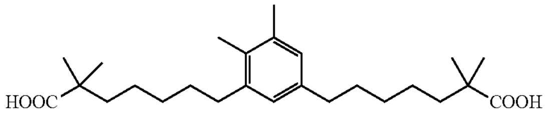 [SMILES: Cc1cc(CCCCCC(C)(C)C(=O)O)cc(CCCCCC(C)(C)C(=O)O)c1C] |
| 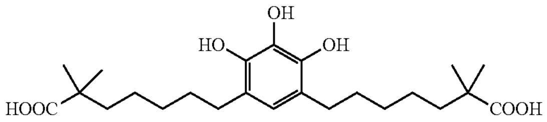 [SMILES: CC(C)(CCCCCc1cc(CCCCCC(C)(C)C(=O)O)c(O)c(O)c1O)C(=O)O] |
| 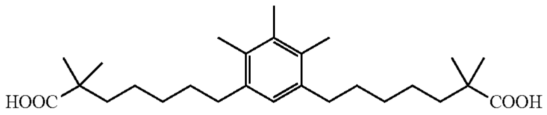 [SMILES: Cc1c(CCCCCC(C)(C)C(=O)O)cc(CCCCCC(C)(C)C(=O)O)c(C)c1C] |
| 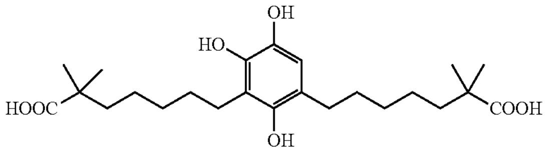 [SMILES: CC(C)(CCCCCc1cc(O)c(O)c(CCCCCC(C)(C)C(=O)O)c1O)C(=O)O] |

TABLE A-6-continued
| Structure |
| --- |
| 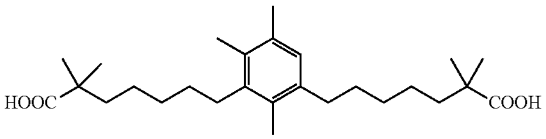 [SMILES: Cc1cc(CCCCCC(C)(C)C(=O)O)c(C)c(CCCCCC(C)(C)C(=O)O)c1C] |
| 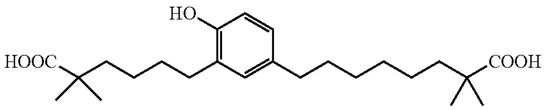 [SMILES: CC(C)(CCCCCCc1ccc(O)c(CCCCC(C)(C)C(=O)O)c1)C(=O)O] |
| 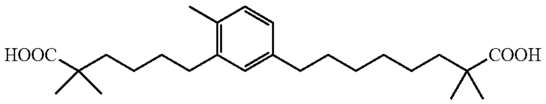 [SMILES: Cc1ccc(CCCCCCC(C)(C)C(=O)O)cc1CCCCC(C)(C)C(=O)O] |
| 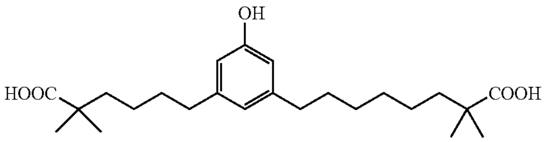 [SMILES: CC(C)(CCCCCCc1cc(O)cc(CCCCC(C)(C)C(=O)O)c1)C(=O)O] |
| 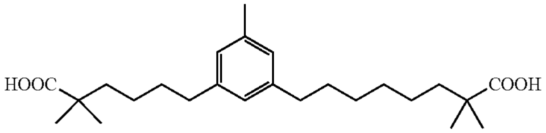 [SMILES: Cc1cc(CCCCCCC(C)(C)C(=O)O)cc(CCCCC(C)(C)C(=O)O)c1] |
| 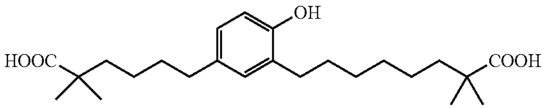 [SMILES: CC(C)(CCCCCCc1cc(CCCCC(C)(C)C(=O)O)ccc1O)C(=O)O] |
| 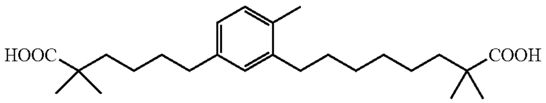 [SMILES: Cc1ccc(CCCCC(C)(C)C(=O)O)cc1CCCCCCC(C)(C)C(=O)O] |
| 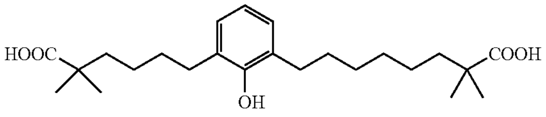 [SMILES: CC(C)(CCCCCCc1cccc(CCCCC(C)(C)C(=O)O)c1O)C(=O)O] |
| 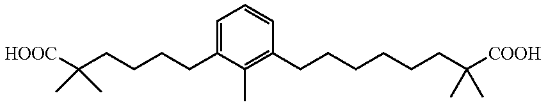 [SMILES: Cc1c(CCCCCCC(C)(C)C(=O)O)cccc1CCCCC(C)(C)C(=O)O] |
| 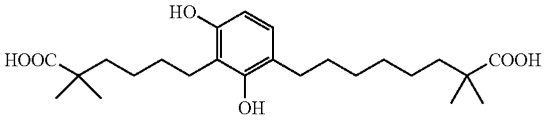 [SMILES: CC(C)(CCCCCCc1ccc(O)c(CCCCC(C)(C)C(=O)O)c1O)C(=O)O] |
| 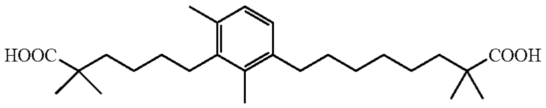 [SMILES: Cc1ccc(CCCCCCC(C)(C)C(=O)O)c(C)c1CCCCC(C)(C)C(=O)O] |
| 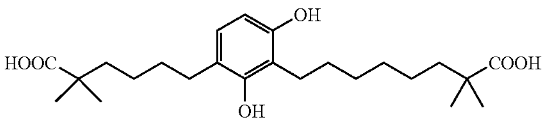 [SMILES: CC(C)(CCCCCCc1c(O)ccc(CCCCC(C)(C)C(=O)O)c1O)C(=O)O] |

TABLE A-6-continued
| Structure |
| --- |
| 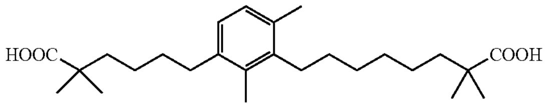 [SMILES: Cc1ccc(CCCCC(C)(C)C(=O)O)c(C)c1CCCCCCC(C)(C)C(=O)O] |
| 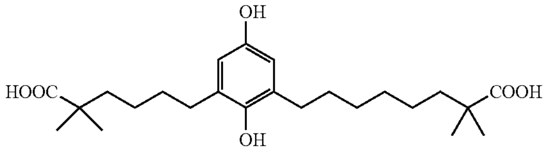 [SMILES: CC(C)(CCCCCCc1cc(O)cc(CCCCC(C)(C)C(=O)O)c1O)C(=O)O] |
| 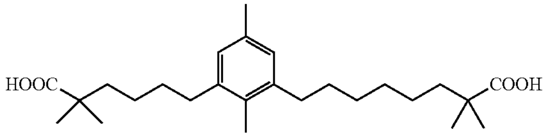 [SMILES: Cc1cc(CCCCCCC(C)(C)C(=O)O)c(C)c(CCCCC(C)(C)C(=O)O)c1] |
| 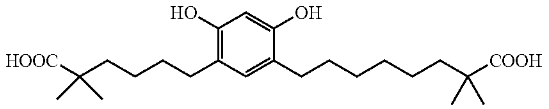 [SMILES: CC(C)(CCCCCCc1cc(CCCCC(C)(C)C(=O)O)c(O)cc1O)C(=O)O] |
| 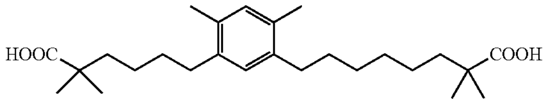 [SMILES: Cc1cc(C)c(CCCCC(C)(C)C(=O)O)cc1CCCCCCC(C)(C)C(=O)O] |
| 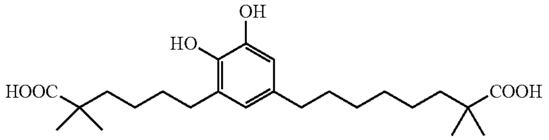 [SMILES: CC(C)(CCCCCCc1cc(O)c(O)c(CCCCC(C)(C)C(=O)O)c1)C(=O)O] |
| 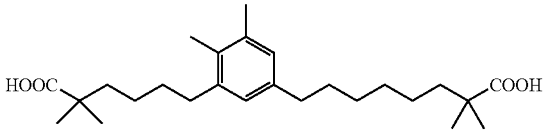 [SMILES: Cc1cc(CCCCCCC(C)(C)C(=O)O)cc(CCCCC(C)(C)C(=O)O)c1C] |
| 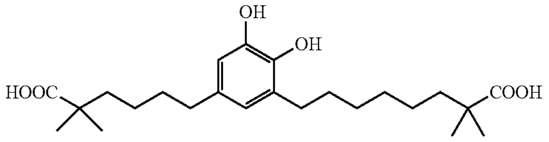 [SMILES: CC(C)(CCCCCCc1cc(CCCCC(C)(C)C(=O)O)cc(O)c1O)C(=O)O] |
| 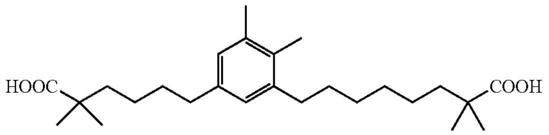 [SMILES: Cc1cc(CCCCC(C)(C)C(=O)O)cc(CCCCCCC(C)(C)C(=O)O)c1C] |
| 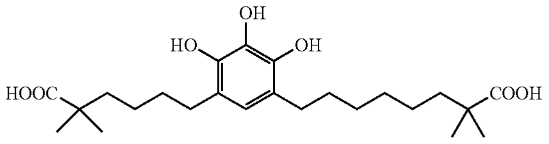 [SMILES: CC(C)(CCCCCCc1cc(CCCCC(C)(C)C(=O)O)c(O)c(O)c1O)C(=O)O] |
| 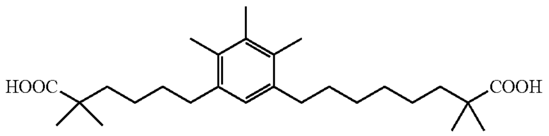 [SMILES: Cc1c(CCCCCCC(C)(C)C(=O)O)cc(CCCCC(C)(C)C(=O)O)c(C)c1C] |

TABLE A-6-continued
| Structure |
| --- |
| 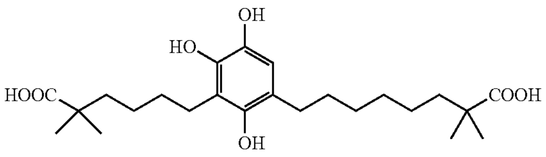 [SMILES: CC(C)(CCCCCCc1cc(O)c(O)c(CCCCC(C)(C)C(=O)O)c1O)C(=O)O] |
| 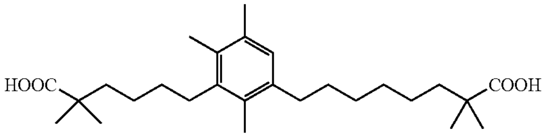 [SMILES: Cc1cc(CCCCCCC(C)(C)C(=O)O)c(C)c(CCCCC(C)(C)C(=O)O)c1C] |
| 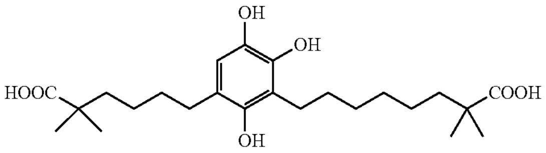 [SMILES: CC(C)(CCCCCCc1c(O)c(O)cc(CCCCC(C)(C)C(=O)O)c1O)C(=O)O] |
| 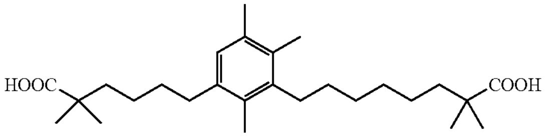 [SMILES: Cc1cc(CCCCC(C)(C)C(=O)O)c(C)c(CCCCCCC(C)(C)C(=O)O)c1C] |
| 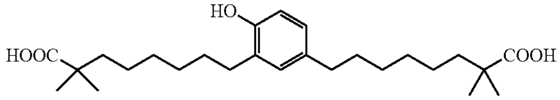 [SMILES: CC(C)(CCCCCCc1ccc(O)c(CCCCCCC(C)(C)C(=O)O)c1)C(=O)O] |
| 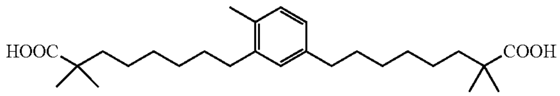 [SMILES: Cc1ccc(CCCCCCC(C)(C)C(=O)O)cc1CCCCCCC(C)(C)C(=O)O] |
| 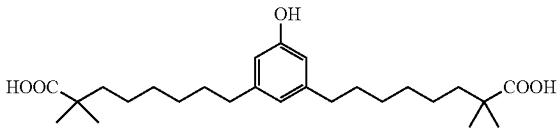 [SMILES: CC(C)(CCCCCCc1cc(O)cc(CCCCCCC(C)(C)C(=O)O)c1)C(=O)O] |
| 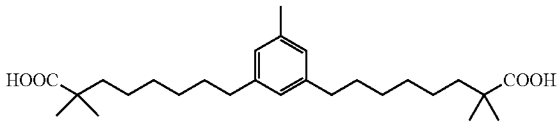 [SMILES: Cc1cc(CCCCCCC(C)(C)C(=O)O)cc(CCCCCCC(C)(C)C(=O)O)c1] |
| 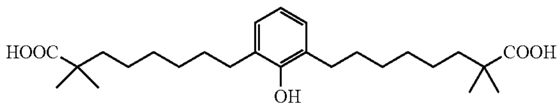 [SMILES: CC(C)(CCCCCCc1cccc(CCCCCCC(C)(C)C(=O)O)c1O)C(=O)O] |
| 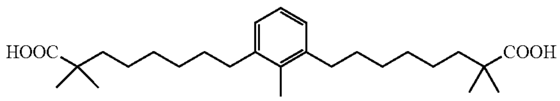 [SMILES: Cc1c(CCCCCCC(C)(C)C(=O)O)cccc1CCCCCCC(C)(C)C(=O)O] |
| 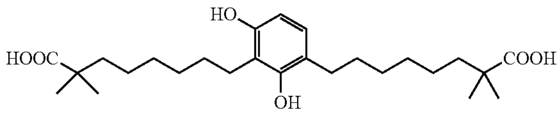 [SMILES: CC(C)(CCCCCCc1ccc(O)c(CCCCCCC(C)(C)C(=O)O)c1O)C(=O)O] |
| 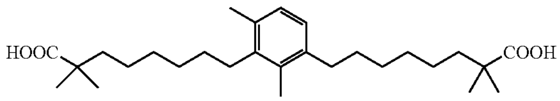 [SMILES: Cc1ccc(CCCCCCC(C)(C)C(=O)O)c(C)c1CCCCCCC(C)(C)C(=O)O] |

TABLE A-6-continued
| Structure |
|---|
| 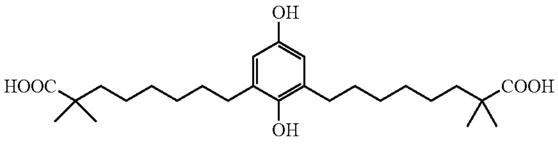 [SMILES: CC(C)(CCCCCCc1cc(O)cc(CCCCCCC(C)(C)C(=O)O)c1O)C(=O)O] |
| 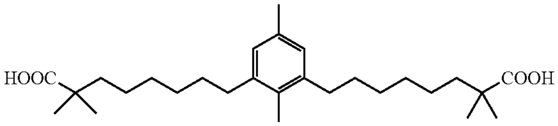 [SMILES: Cc1cc(CCCCCCC(C)(C)C(=O)O)c(C)c(CCCCCCC(C)(C)C(=O)O)c1] |
| 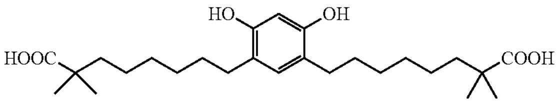 [SMILES: CC(C)(CCCCCCc1cc(CCCCCCC(C)(C)C(=O)O)c(O)cc1O)C(=O)O] |
| 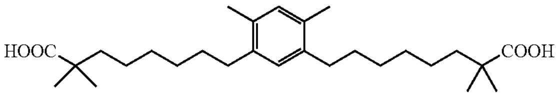 [SMILES: Cc1cc(C)c(CCCCCCC(C)(C)C(=O)O)cc1CCCCCCC(C)(C)C(=O)O] |
| 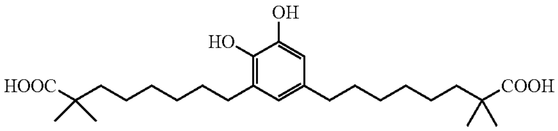 [SMILES: CC(C)(CCCCCCc1cc(O)c(O)c(CCCCCCC(C)(C)C(=O)O)c1)C(=O)O] |
| 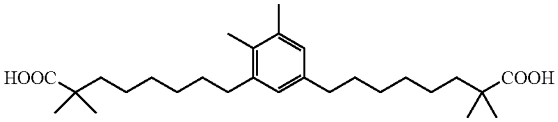 [SMILES: Cc1cc(CCCCCCC(C)(C)C(=O)O)cc(CCCCCCC(C)(C)C(=O)O)c1C] |
| 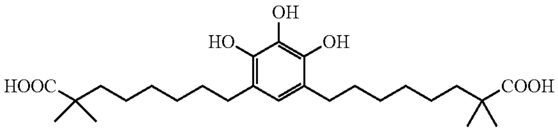 [SMILES: CC(C)(CCCCCCc1cc(CCCCCCC(C)(C)C(=O)O)c(O)c(O)c1O)C(=O)O] |
| 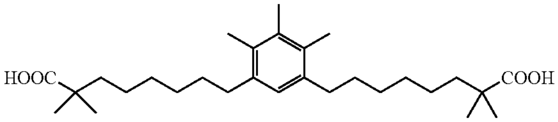 [SMILES: Cc1c(CCCCCCC(C)(C)C(=O)O)cc(CCCCCCC(C)(C)C(=O)O)c(C)c1C] |
| 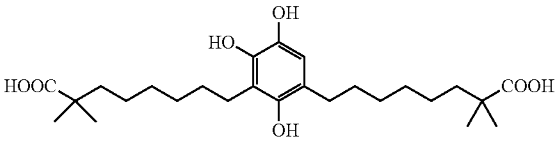 [SMILES: CC(C)(CCCCCCc1cc(O)c(O)c(CCCCCCC(C)(C)C(=O)O)c1O)C(=O)O] |
| 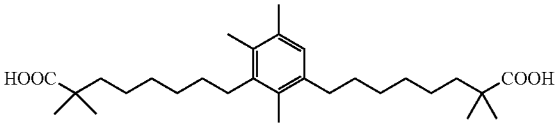 [SMILES: Cc1cc(CCCCCCC(C)(C)C(=O)O)c(C)c(CCCCCCC(C)(C)C(=O)O)c1C] |
| 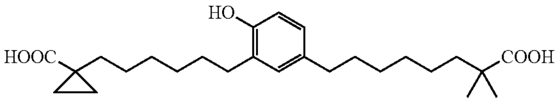 [SMILES: CC(C)(CCCCCCc1ccc(O)c(CCCCCCC2(C(=O)O)CC2)c1)C(=O)O] |
| 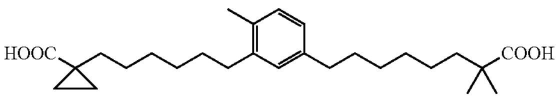 [SMILES: Cc1ccc(CCCCCCC(C)(C)C(=O)O)cc1CCCCCCC1(C(=O)O)CC1] |

TABLE A-6-continued
| Structure |
| --- |
| 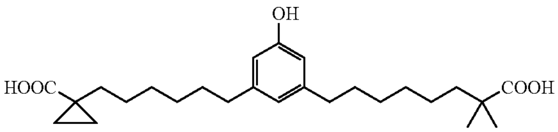 [SMILES: CC(C)(CCCCCCc1cc(O)cc(CCCCCCC2(C(=O)O)CC2)c1)C(=O)O] |
| 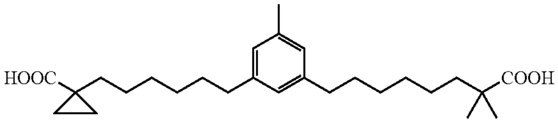 [SMILES: Cc1cc(CCCCCCC(C)(C)C(=O)O)cc(CCCCCCC2(C(=O)O)CC2)c1] |
| 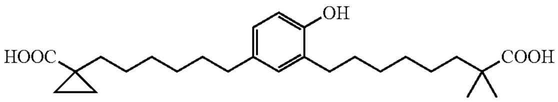 [SMILES: CC(C)(CCCCCCc1cc(CCCCCCC2(C(=O)O)CC2)ccc1O)C(=O)O] |
| 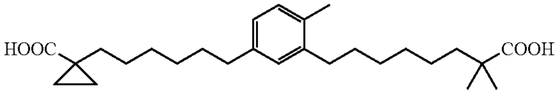 |
| 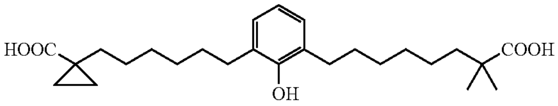 [SMILES: CC(C)(CCCCCCc1cccc(CCCCCCC2(C(=O)O)CC2)c1O)C(=O)O] |
| 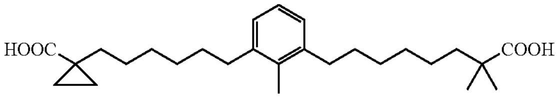 [SMILES: Cc1c(CCCCCCC(C)(C)C(=O)O)cccc1CCCCCCC1(C(=O)O)CC1] |
| 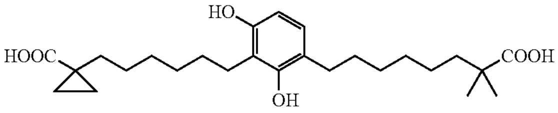 [SMILES: CC(C)(CCCCCCc1ccc(O)c(CCCCCCC2(C(=O)O)CC2)c1O)C(=O)O] |
| 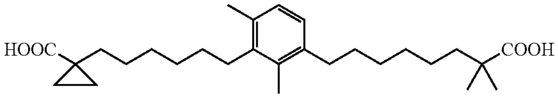 [SMILES: Cc1ccc(CCCCCCC(C)(C)C(=O)O)c(C)c1CCCCCCC1(C(=O)O)CC1] |
| 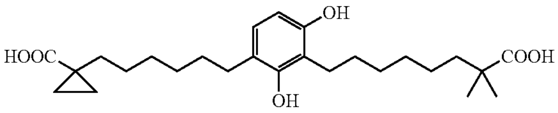 [SMILES: CC(C)(CCCCCCc1c(O)ccc(CCCCCCC2(C(=O)O)CC2)c1O)C(=O)O] |
| 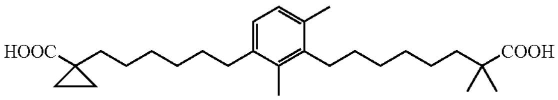 |
| 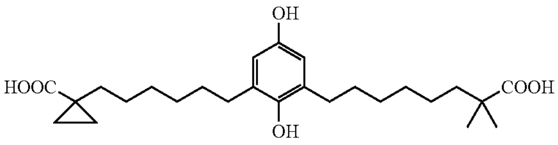 |
| 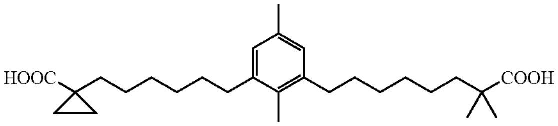 [SMILES: Cc1cc(CCCCCCC(C)(C)C(=O)O)c(C)c(CCCCCCC2(C(=O)O)CC2)c1] |

TABLE A-6-continued
| Structure |
| --- |
| 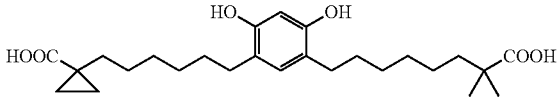 [SMILES: CC(C)(CCCCCCc1cc(CCCCCCC2(C(=O)O)CC2)c(O)cc1O)C(=O)O] |
| 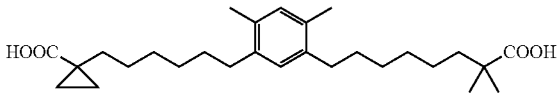 [SMILES: Cc1cc(C)c(CCCCCCC2(C(=O)O)CC2)cc1CCCCCCC(C)(C)C(=O)O] |
| 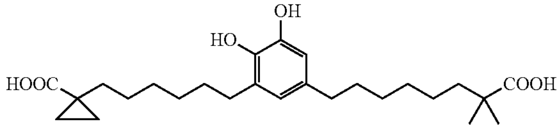 [SMILES: CC(C)(CCCCCCc1cc(O)c(O)c(CCCCCCC2(C(=O)O)CC2)c1)C(=O)O] |
| 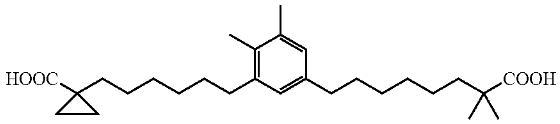 [SMILES: Cc1cc(CCCCCCC(C)(C)C(=O)O)cc(CCCCCCC2(C(=O)O)CC2)c1C] |
| 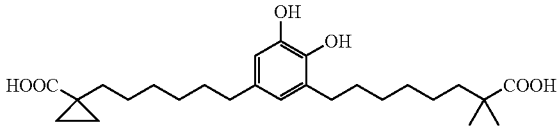 [SMILES: CC(C)(CCCCCCc1cc(CCCCCCC2(C(=O)O)CC2)cc(O)c1O)C(=O)O] |
| 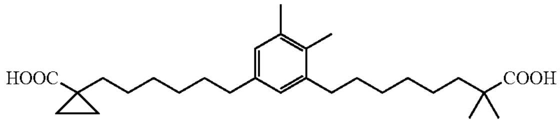 |
| 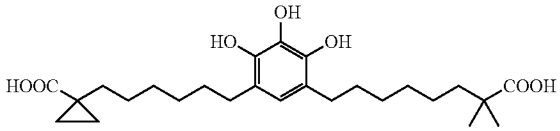 [SMILES: CC(C)(CCCCCCc1cc(CCCCCCC2(C(=O)O)CC2)c(O)c(O)c1O)C(=O)O] |
| 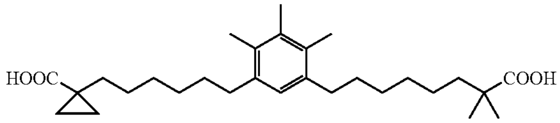 [SMILES: Cc1c(CCCCCCC(C)(C)C(=O)O)cc(CCCCCCC2(C(=O)O)CC2)c(C)c1C] |
| 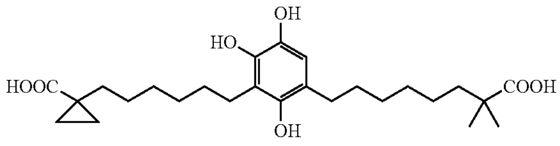 [SMILES: CC(C)(CCCCCCc1cc(O)c(O)c(CCCCCCC2(C(=O)O)CC2)c1O)C(=O)O] |
| 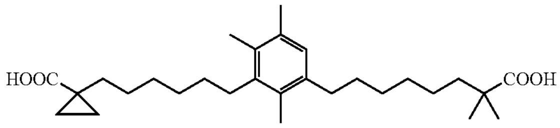 [SMILES: Cc1cc(CCCCCCC(C)(C)C(=O)O)c(C)c(CCCCCCC2(C(=O)O)CC2)c1C] |
| 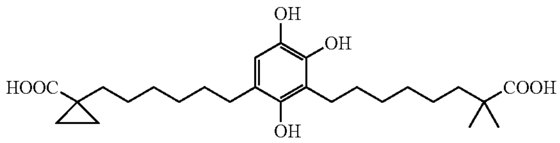 [SMILES: CC(C)(CCCCCCc1c(O)c(O)cc(CCCCCCC2(C(=O)O)CC2)c1O)C(=O)O] |

TABLE A-6-continued
| Structure |
|---|
| 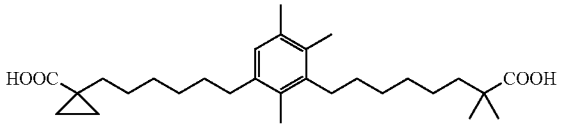 [SMILES: Cc1cc(CCCCCCC2(C(=O)O)CC2)c(C)c(CCCCCCC(C)(C)C(=O)O)c1C] |
| 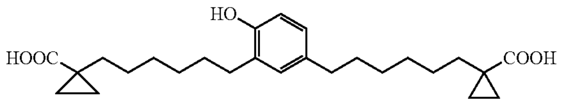 [SMILES: O=C(O)C1(CCCCCCc2ccc(O)c(CCCCCCC3(C(=O)O)CC3)c2)CC1] |
| 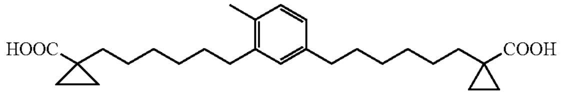 [SMILES: Cc1ccc(CCCCCCC2(C(=O)O)CC2)cc1CCCCCCC1(C(=O)O)CC1] |
| 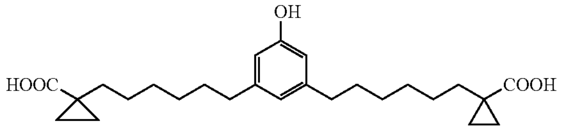 [SMILES: O=C(O)C1(CCCCCCc2cc(O)cc(CCCCCCC3(C(=O)O)CC3)c2)CC1] |
| 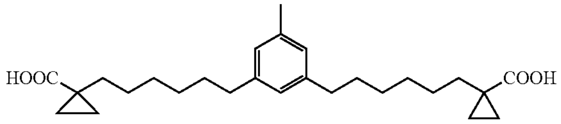 [SMILES: Cc1cc(CCCCCCC2(C(=O)O)CC2)cc(CCCCCCC2(C(=O)O)CC2)c1] |
| 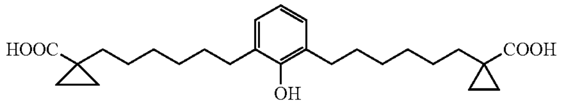 [SMILES: O=C(O)C1(CCCCCCc2cccc(CCCCCCC3(C(=O)O)CC3)c2O)CC1] |
| 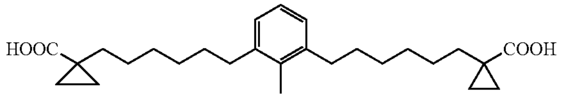 |
| 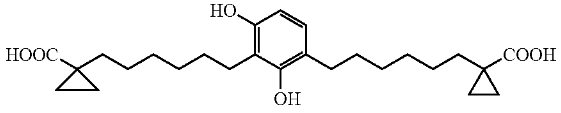 [SMILES: O=C(O)C1(CCCCCCc2ccc(O)c(CCCCCCC3(C(=O)O)CC3)c2O)CC1] |
| 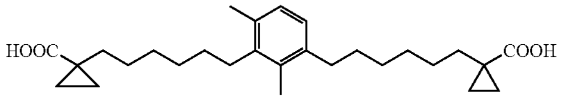 [SMILES: Cc1ccc(CCCCCCC2(C(=O)O)CC2)c(C)c1CCCCCCC1(C(=O)O)CC1] |
| 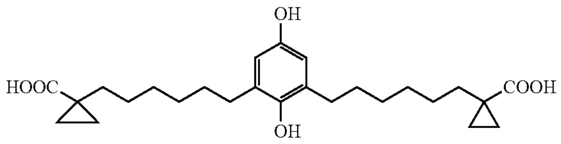 [SMILES: O=C(O)C1(CCCCCCc2cc(O)cc(CCCCCCC3(C(=O)O)CC3)c2O)CC1] |
| 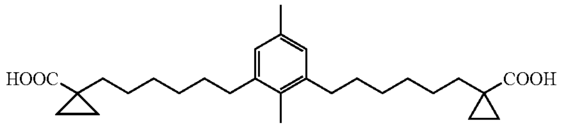 |
| 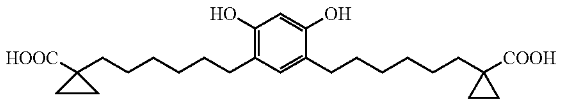 [SMILES: O=C(O)C1(CCCCCCc2cc(CCCCCCC3(C(=O)O)CC3)c(O)cc2O)CC1] |

TABLE A-6-continued
| Structure |
| --- |
| 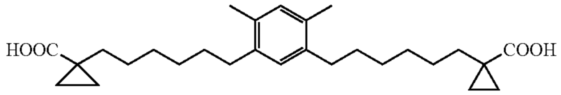 [SMILES: Cc1cc(C)c(CCCCCCC2(C(=O)O)CC2)cc1CCCCCCC1(C(=O)O)CC1] |
| 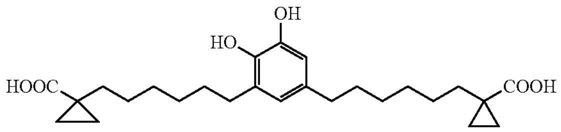 [SMILES: O=C(O)C1(CCCCCCc2cc(O)c(O)c(CCCCCCC3(C(=O)O)CC3)c2)CC1] |
| 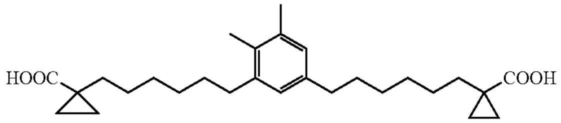 [SMILES: Cc1cc(CCCCCCC2(C(=O)O)CC2)cc(CCCCCCC2(C(=O)O)CC2)c1C] |
| 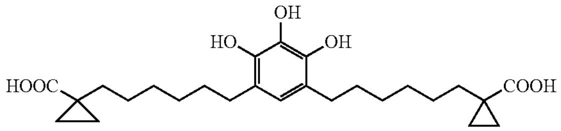 [SMILES: O=C(O)C1(CCCCCCc2cc(CCCCCCC3(C(=O)O)CC3)c(O)c(O)c2O)CC1] |
| 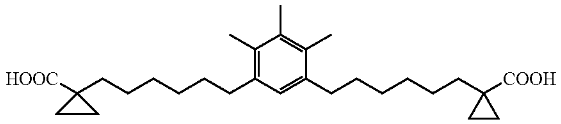 [SMILES: Cc1c(CCCCCCC2(C(=O)O)CC2)cc(CCCCCCC2(C(=O)O)CC2)c(C)c1C] |
| 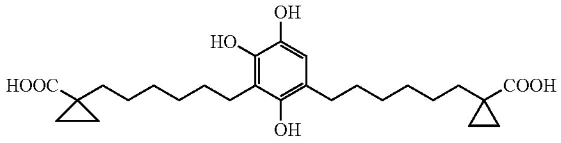 [SMILES: O=C(O)C1(CCCCCCc2cc(O)c(O)c(CCCCCCC3(C(=O)O)CC3)c2O)CC1] |
| 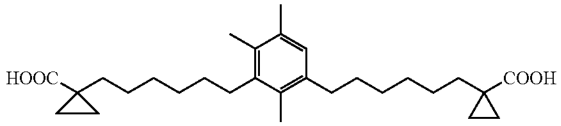 [SMILES: Cc1cc(CCCCCCC2(C(=O)O)CC2)c(C)c(CCCCCCC2(C(=O)O)CC2)c1C] |
| 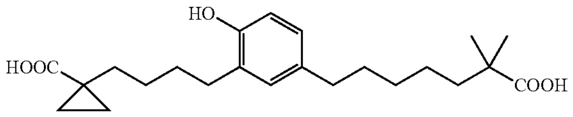 [SMILES: CC(C)(CCCCCc1ccc(O)c(CCCCC2(C(=O)O)CC2)c1)C(=O)O] |
| 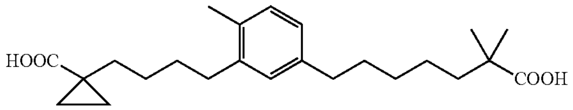 [SMILES: Cc1ccc(CCCCCC(C)(C)C(=O)O)cc1CCCCC1(C(=O)O)CC1] |
| 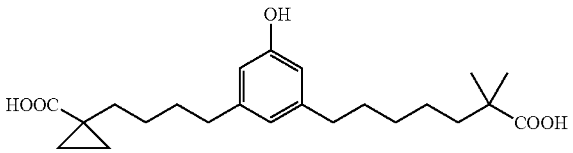 [SMILES: CC(C)(CCCCCc1cc(O)cc(CCCCC2(C(=O)O)CC2)c1)C(=O)O] |
| 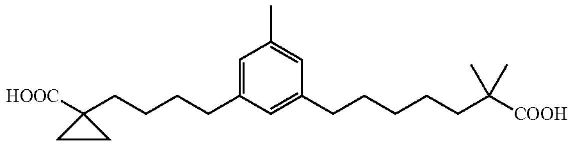 [SMILES: Cc1cc(CCCCCC(C)(C)C(=O)O)cc(CCCCC2(C(=O)O)CC2)c1] |

TABLE A-6-continued
| Structure |
|---|
| 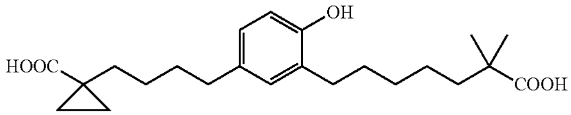 [SMILES: CC(C)(CCCCCc1cc(CCCCC2(C(=O)O)CC2)ccc1O)C(=O)O] |
| 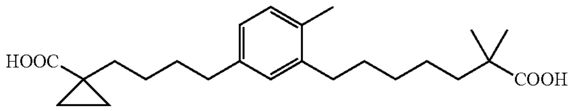 [SMILES: Cc1ccc(CCCCC2(C(=O)O)CC2)cc1CCCCCC(C)(C)C(=O)O] |
| 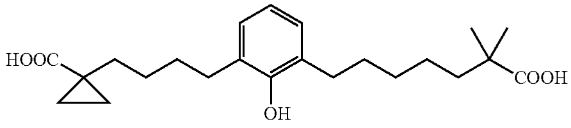 [SMILES: CC(C)(CCCCCc1cccc(CCCCC2(C(=O)O)CC2)c1O)C(=O)O] |
| 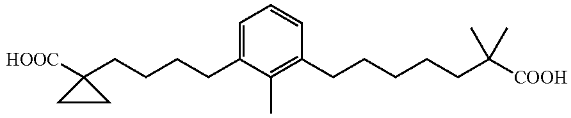 |
| 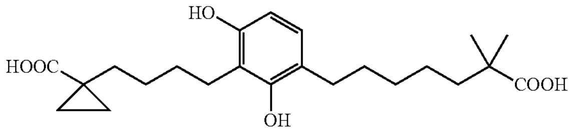 [SMILES: CC(C)(CCCCCc1ccc(O)c(CCCCC2(C(=O)O)CC2)c1O)C(=O)O] |
| 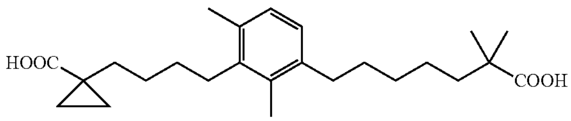 [SMILES: Cc1ccc(CCCCCC(C)(C)C(=O)O)c(C)c1CCCCC1(C(=O)O)CC1] |
| 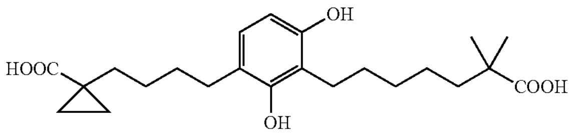 [SMILES: CC(C)(CCCCCc1c(O)ccc(CCCCC2(C(=O)O)CC2)c1O)C(=O)O] |
| 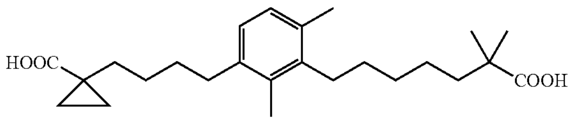 [SMILES: Cc1ccc(CCCCC2(C(=O)O)CC2)c(C)c1CCCCCC(C)(C)C(=O)O] |
| 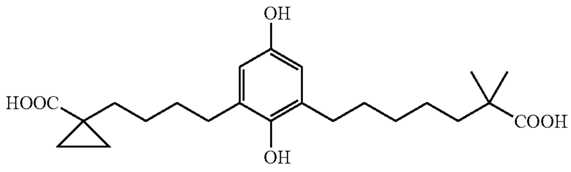 [SMILES: CC(C)(CCCCCc1cc(O)cc(CCCCC2(C(=O)O)CC2)c1O)C(=O)O] |
| 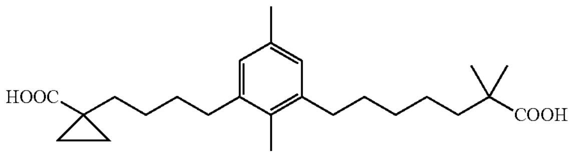 [SMILES: Cc1cc(CCCCCC(C)(C)C(=O)O)c(C)c(CCCCC2(C(=O)O)CC2)c1] |
| 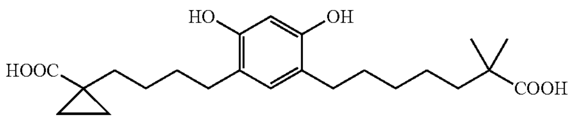 [SMILES: CC(C)(CCCCCc1cc(CCCCC2(C(=O)O)CC2)c(O)cc1O)C(=O)O] |

TABLE A-6-continued
| Structure |
| --- |
| 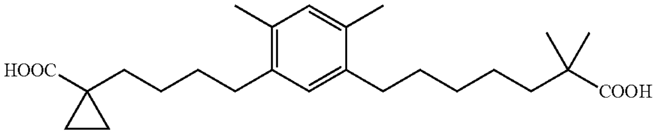 [SMILES: Cc1cc(C)c(CCCCC2(C(=O)O)CC2)cc1CCCCCC(C)(C)C(=O)O] |
| 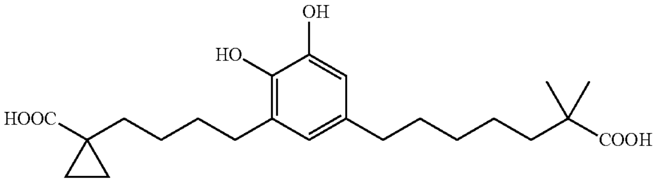 [SMILES: CC(C)(CCCCCc1cc(O)c(O)c(CCCCC2(C(=O)O)CC2)c1)C(=O)O] |
| 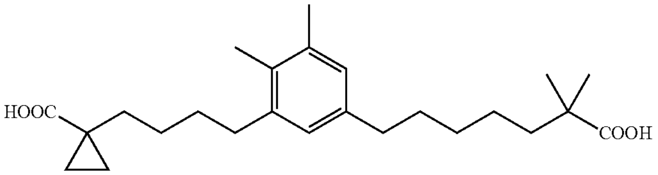 [SMILES: Cc1cc(CCCCCC(C)(C)C(=O)O)cc(CCCCC2(C(=O)O)CC2)c1C] |
| 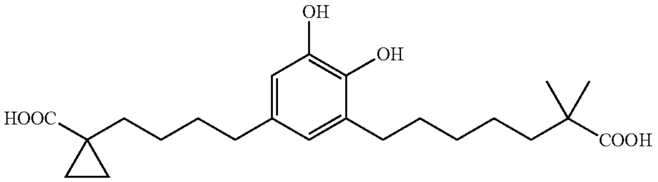 [SMILES: CC(C)(CCCCCc1cc(CCCCC2(C(=O)O)CC2)cc(O)c1O)C(=O)O] |
| 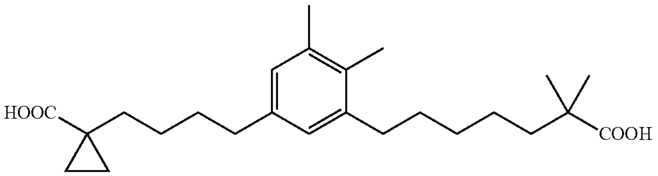 [SMILES: Cc1cc(CCCCC2(C(=O)O)CC2)cc(CCCCCC(C)(C)C(=O)O)c1C] |
| 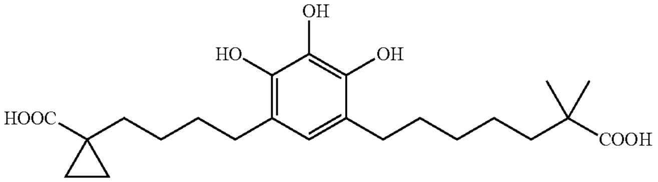 [SMILES: CC(C)(CCCCCc1cc(CCCCC2(C(=O)O)CC2)c(O)c(O)c1O)C(=O)O] |
| 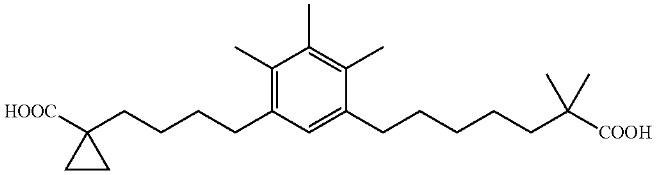 [SMILES: Cc1c(CCCCCC(C)(C)C(=O)O)cc(CCCCC2(C(=O)O)CC2)c(C)c1C] |
| 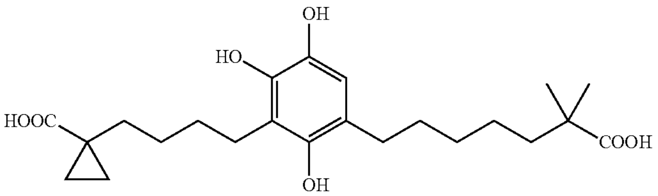 [SMILES: CC(C)(CCCCCc1cc(O)c(O)c(CCCCC2(C(=O)O)CC2)c1O)C(=O)O] |

TABLE A-6-continued
| Structure |
|---|
| 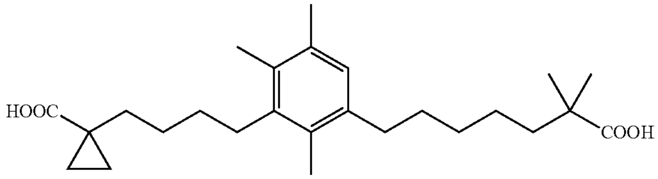 [SMILES: Cc1cc(CCCCCC(C)(C)C(=O)O)c(C)c(CCCCC2(C(=O)O)CC2)c1C] |
| 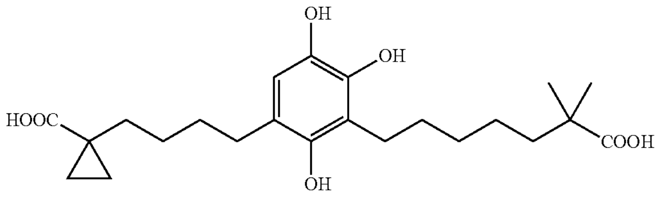 [SMILES: CC(C)(CCCCCc1c(O)c(O)cc(CCCCC2(C(=O)O)CC2)c1O)C(=O)O] |
| 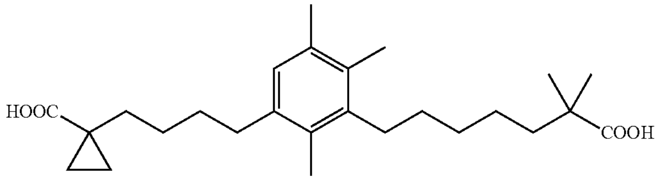 [SMILES: Cc1cc(CCCCC2(C(=O)O)CC2)c(C)c(CCCCCC(C)(C)C(=O)O)c1C] |
| 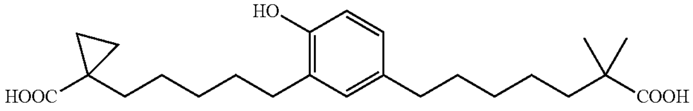 [SMILES: CC(C)(CCCCCc1ccc(O)c(CCCCCC2(C(=O)O)CC2)c1)C(=O)O] |
| 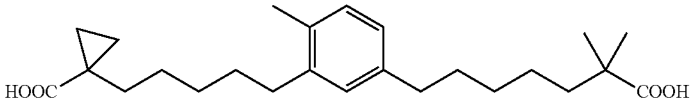 [SMILES: Cc1ccc(CCCCCC(C)(C)C(=O)O)cc1CCCCCC1(C(=O)O)CC1] |
| 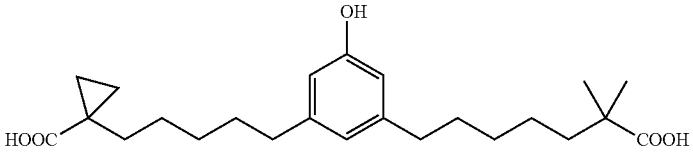 [SMILES: CC(C)(CCCCCc1cc(O)cc(CCCCCC2(C(=O)O)CC2)c1)C(=O)O] |
| 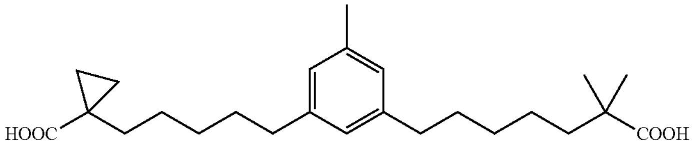 [SMILES: Cc1cc(CCCCCC(C)(C)C(=O)O)cc(CCCCCC2(C(=O)O)CC2)c1] |
| 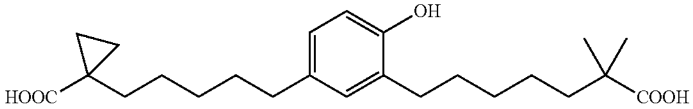 [SMILES: CC(C)(CCCCCc1cc(CCCCCC2(C(=O)O)CC2)ccc1O)C(=O)O] |
| 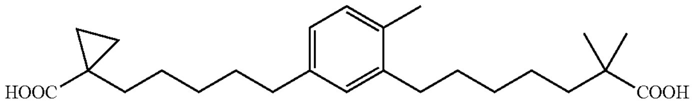 [SMILES: Cc1ccc(CCCCCC2(C(=O)O)CC2)cc1CCCCCC(C)(C)C(=O)O] |
| 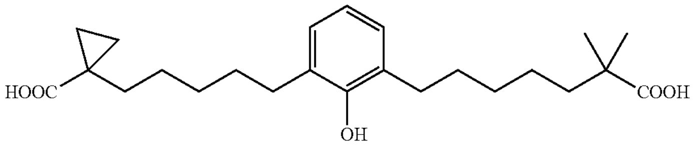 [SMILES: CC(C)(CCCCCc1cccc(CCCCCC2(C(=O)O)CC2)c1O)C(=O)O] |

TABLE A-6-continued
| Structure |
| --- |
| 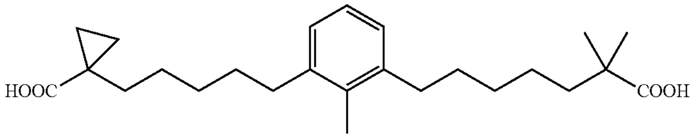 [SMILES: Cc1c(CCCCCC(C)(C)C(=O)O)cccc1CCCCCC1(C(=O)O)CC1] |
| 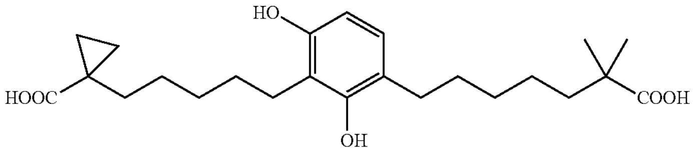 [SMILES: CC(C)(CCCCCc1ccc(O)c(CCCCCC2(C(=O)O)CC2)c1O)C(=O)O] |
| 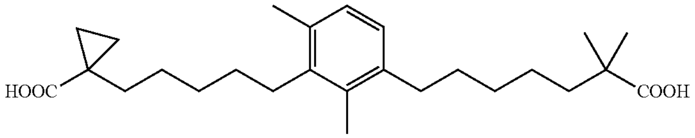 [SMILES: Cc1ccc(CCCCCC(C)(C)C(=O)O)c(C)c1CCCCCC1(C(=O)O)CC1] |
| 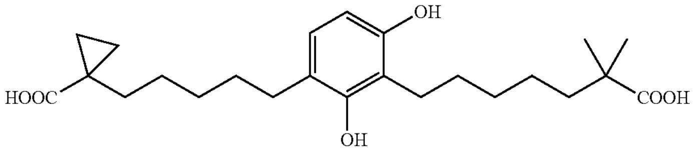 [SMILES: CC(C)(CCCCCc1c(O)ccc(CCCCCC2(C(=O)O)CC2)c1O)C(=O)O] |
| 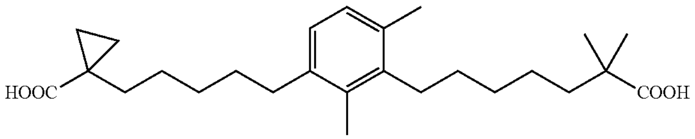 [SMILES: Cc1ccc(CCCCCC2(C(=O)O)CC2)c(C)c1CCCCCC(C)(C)C(=O)O] |
| 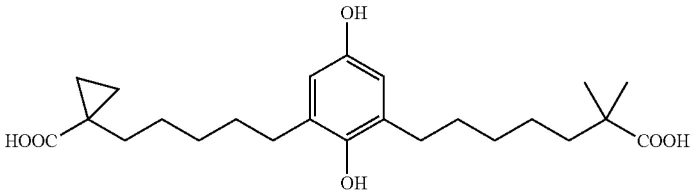 [SMILES: CC(C)(CCCCCc1cc(O)cc(CCCCCC2(C(=O)O)CC2)c1O)C(=O)O] |
| 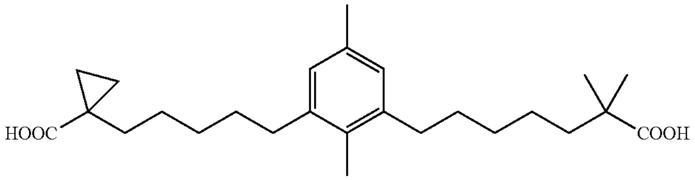 [SMILES: Cc1cc(CCCCCC(C)(C)C(=O)O)c(C)c(CCCCCC2(C(=O)O)CC2)c1] |
| 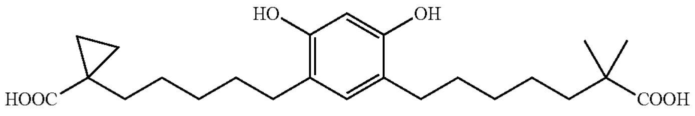 [SMILES: CC(C)(CCCCCc1cc(CCCCCC2(C(=O)O)CC2)c(O)cc1O)C(=O)O] |
| 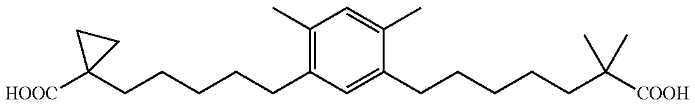 [SMILES: Cc1cc(C)c(CCCCCC2(C(=O)O)CC2)cc1CCCCCC(C)(C)C(=O)O] |
| 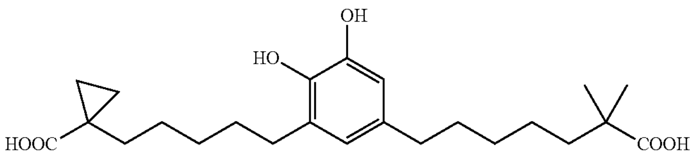 [SMILES: CC(C)(CCCCCc1cc(O)c(O)c(CCCCCC2(C(=O)O)CC2)c1)C(=O)O] |

TABLE A-6-continued
| Structure |
| --- |
| 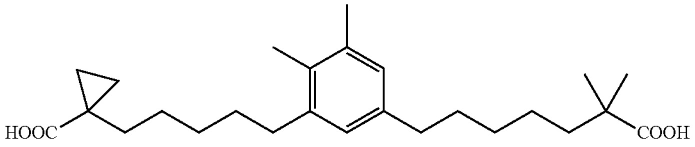 [SMILES: Cc1cc(CCCCCC(C)(C)C(=O)O)cc(CCCCCC2(C(=O)O)CC2)c1C] |
| 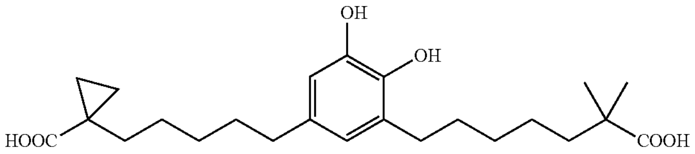 [SMILES: CC(C)(CCCCCc1cc(CCCCCC2(C(=O)O)CC2)cc(O)c1O)C(=O)O] |
| 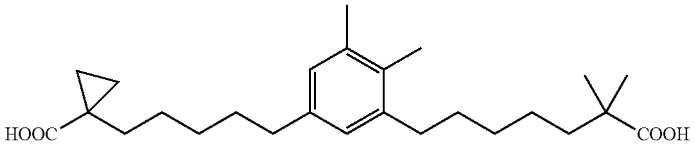 [SMILES: Cc1cc(CCCCCC2(C(=O)O)CC2)cc(CCCCCC(C)(C)C(=O)O)c1C] |
| 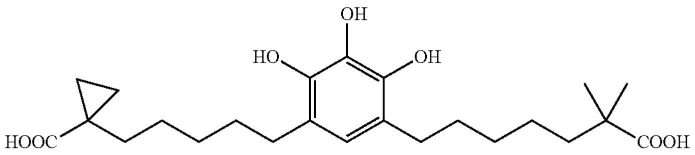 [SMILES: CC(C)(CCCCCc1cc(CCCCCC2(C(=O)O)CC2)c(O)c(O)c1O)C(=O)O] |
| 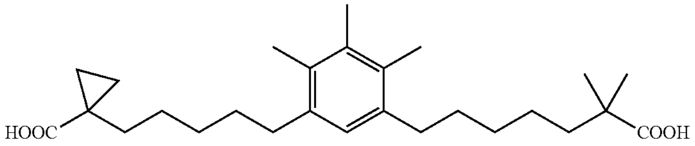 [SMILES: Cc1c(CCCCCC(C)(C)C(=O)O)cc(CCCCCC2(C(=O)O)CC2)c(C)c1C] |
| 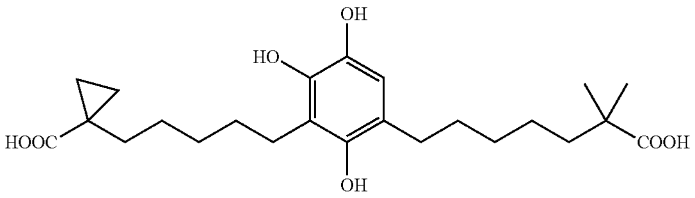 [SMILES: CC(C)(CCCCCc1cc(O)c(O)c(CCCCCC2(C(=O)O)CC2)c1O)C(=O)O] |
| 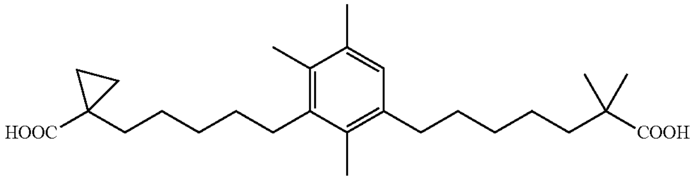 [SMILES: Cc1cc(CCCCCC(C)(C)C(=O)O)c(C)c(CCCCCC2(C(=O)O)CC2)c1C] |
| 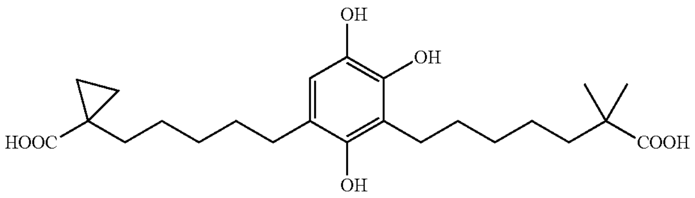 [SMILES: CC(C)(CCCCCc1c(O)c(O)cc(CCCCCC2(C(=O)O)CC2)c1O)C(=O)O] |
| 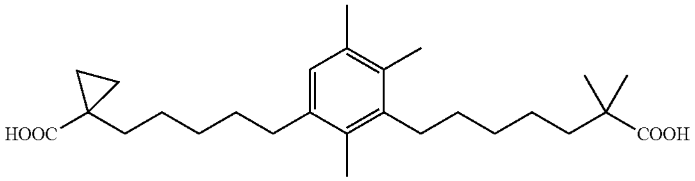 [SMILES: Cc1cc(CCCCCC2(C(=O)O)CC2)c(C)c(CCCCCC(C)(C)C(=O)O)c1C] |

TABLE A-6-continued
| Structure |
| --- |
| 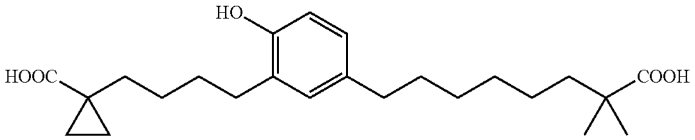 [SMILES: CC(C)(CCCCCCc1ccc(O)c(CCCCC2(C(=O)O)CC2)c1)C(=O)O] |
| 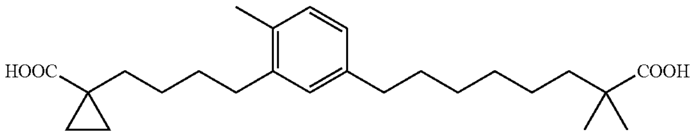 [SMILES: Cc1ccc(CCCCCCC(C)(C)C(=O)O)cc1CCCCC1(C(=O)O)CC1] |
| 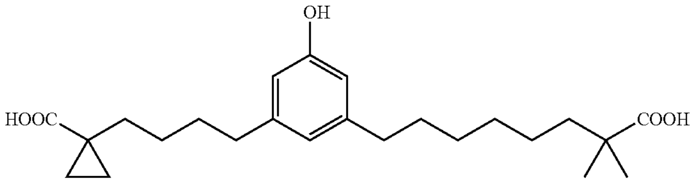 [SMILES: CC(C)(CCCCCCc1cc(O)cc(CCCCC2(C(=O)O)CC2)c1)C(=O)O] |
| 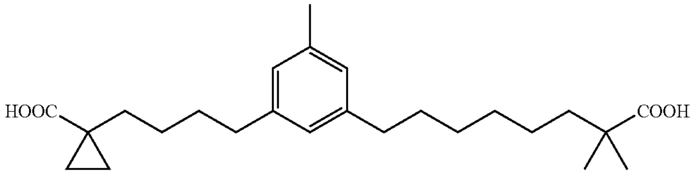 [SMILES: Cc1cc(CCCCCCC(C)(C)C(=O)O)cc(CCCCC2(C(=O)O)CC2)c1] |
| 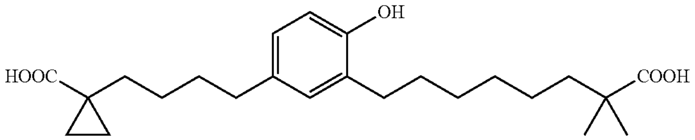 [SMILES: CC(C)(CCCCCCc1cc(CCCCC2(C(=O)O)CC2)ccc1O)C(=O)O] |
| 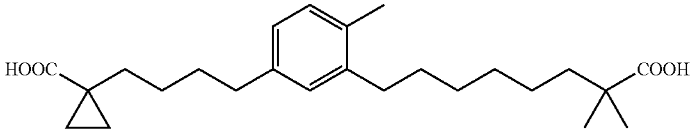 [SMILES: Cc1ccc(CCCCC2(C(=O)O)CC2)cc1CCCCCCC(C)(C)C(=O)O] |
| 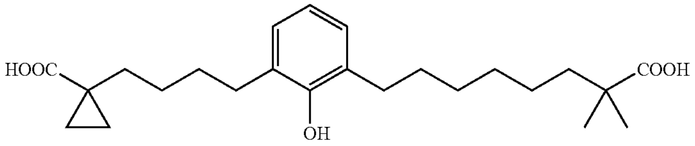 [SMILES: CC(C)(CCCCCCc1cccc(CCCCC2(C(=O)O)CC2)c1O)C(=O)O] |
| 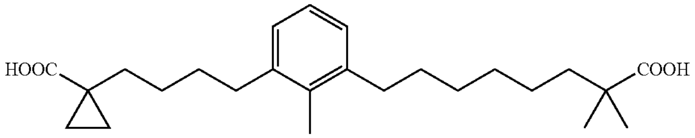 [SMILES: Cc1c(CCCCCCC(C)(C)C(=O)O)cccc1CCCCC1(C(=O)O)CC1] |
| 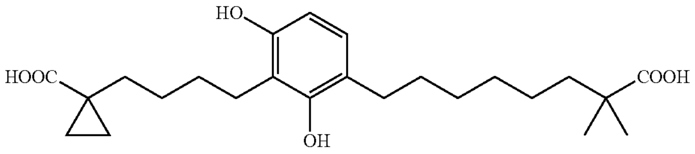 [SMILES: CC(C)(CCCCCCc1ccc(O)c(CCCCC2(C(=O)O)CC2)c1O)C(=O)O] |
| 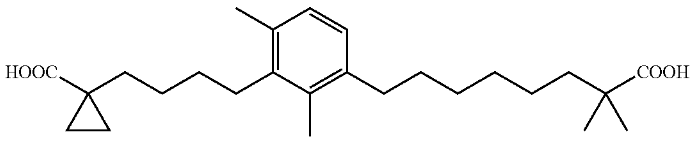 [SMILES: Cc1ccc(CCCCCCC(C)(C)C(=O)O)c(C)c1CCCCC1(C(=O)O)CC1] |

TABLE A-6-continued
| Structure |
| --- |
| 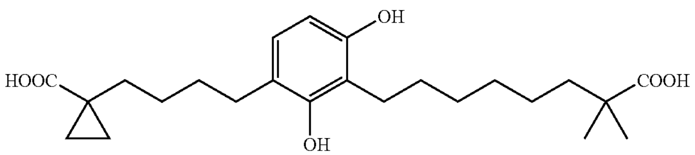 [SMILES: CC(C)(CCCCCCc1c(O)ccc(CCCCC2(C(=O)O)CC2)c1O)C(=O)O] |
| 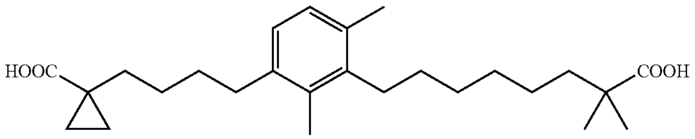 [SMILES: Cc1ccc(CCCCC2(C(=O)O)CC2)c(C)c1CCCCCCC(C)(C)C(=O)O] |
| 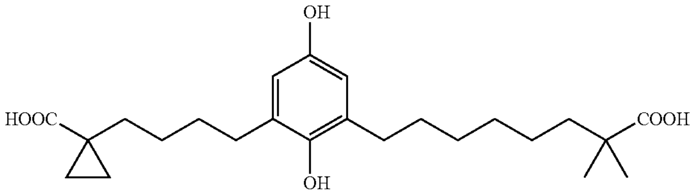 [SMILES: CC(C)(CCCCCCc1cc(O)cc(CCCCC2(C(=O)O)CC2)c1O)C(=O)O] |
| 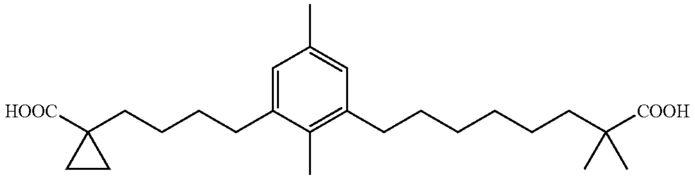 [SMILES: Cc1cc(CCCCCCC(C)(C)C(=O)O)c(C)c(CCCCC2(C(=O)O)CC2)c1] |
| 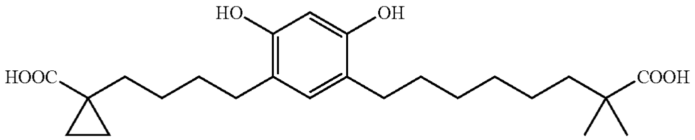 [SMILES: CC(C)(CCCCCCc1cc(CCCCC2(C(=O)O)CC2)c(O)cc1O)C(=O)O] |
| 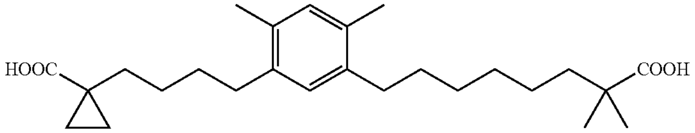 [SMILES: Cc1cc(C)c(CCCCC2(C(=O)O)CC2)cc1CCCCCCC(C)(C)C(=O)O] |
| 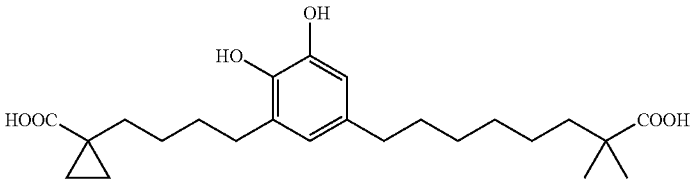 [SMILES: CC(C)(CCCCCCc1cc(O)c(O)c(CCCCC2(C(=O)O)CC2)c1)C(=O)O] |
| 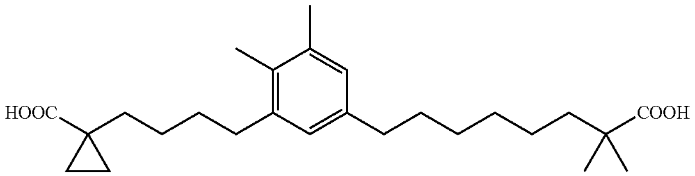 [SMILES: Cc1cc(CCCCCCC(C)(C)C(=O)O)cc(CCCCC2(C(=O)O)CC2)c1C] |
| 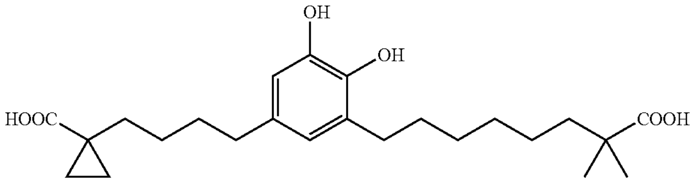 [SMILES: CC(C)(CCCCCCc1cc(CCCCC2(C(=O)O)CC2)cc(O)c1O)C(=O)O] |

TABLE A-6-continued
| Structure |
| --- |
| 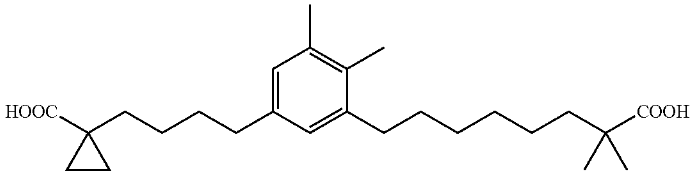 [SMILES: Cc1cc(CCCCC2(C(=O)O)CC2)cc(CCCCCCC(C)(C)C(=O)O)c1C] |
| 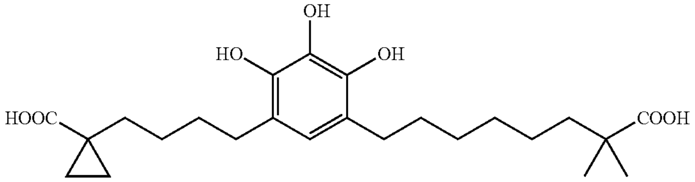 [SMILES: CC(C)(CCCCCCc1cc(CCCCC2(C(=O)O)CC2)c(O)c(O)c1O)C(=O)O] |
| 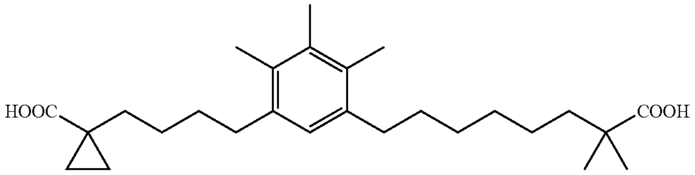 [SMILES: Cc1c(CCCCCCC(C)(C)C(=O)O)cc(CCCCC2(C(=O)O)CC2)c(C)c1C] |
| 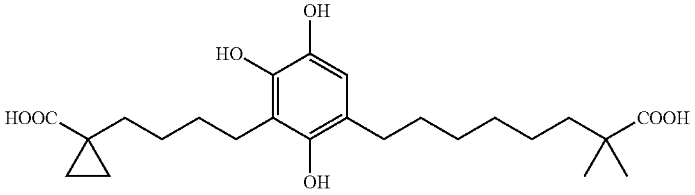 [SMILES: CC(C)(CCCCCCc1cc(O)c(O)c(CCCCC2(C(=O)O)CC2)c1O)C(=O)O] |
| 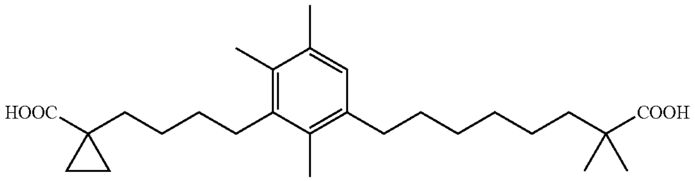 [SMILES: Cc1cc(CCCCCCC(C)(C)C(=O)O)c(C)c(CCCCC2(C(=O)O)CC2)c1C] |
| 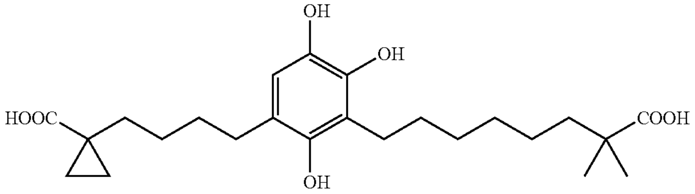 [SMILES: CC(C)(CCCCCCc1c(O)c(O)cc(CCCCC2(C(=O)O)CC2)c1O)C(=O)O] |
| 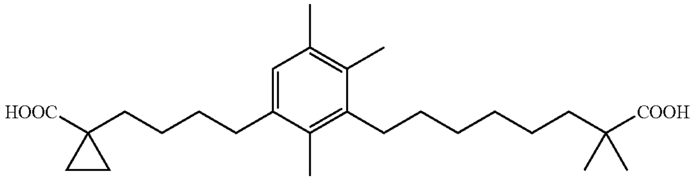 [SMILES: Cc1cc(CCCCC2(C(=O)O)CC2)c(C)c(CCCCCCC(C)(C)C(=O)O)c1C] |
| 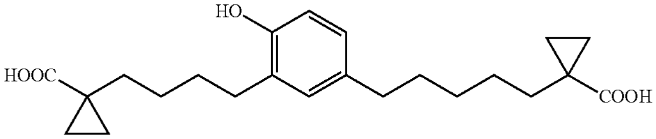 [SMILES: O=C(O)C1(CCCCCc2ccc(O)c(CCCCC3(C(=O)O)CC3)c2)CC1] |

TABLE A-6-continued
| Structure |
| --- |
| 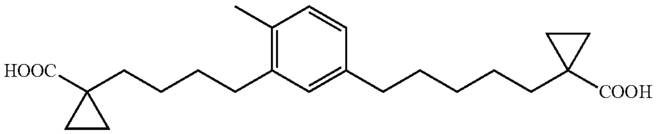 [SMILES: Cc1ccc(CCCCCC2(C(=O)O)CC2)cc1CCCCC1(C(=O)O)CC1] |
| 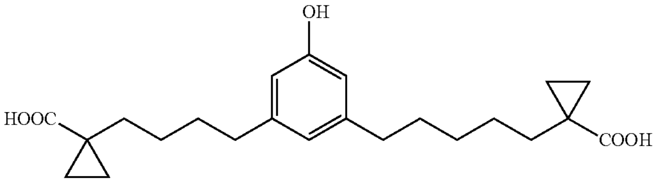 [SMILES: O=C(O)C1(CCCCCc2cc(O)cc(CCCCC3(C(=O)O)CC3)c2)CC1] |
| 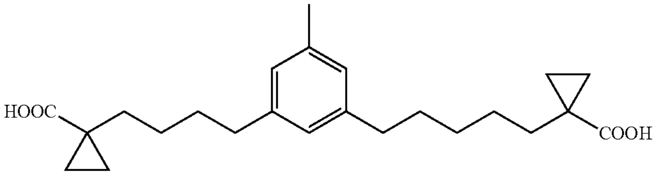 [SMILES: Cc1cc(CCCCCC2(C(=O)O)CC2)cc(CCCCC2(C(=O)O)CC2)c1] |
| 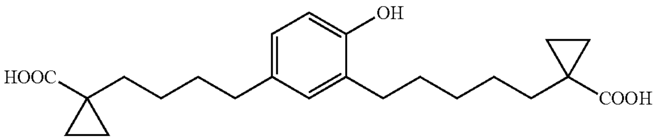 [SMILES: O=C(O)C1(CCCCCc2cc(CCCCC3(C(=O)O)CC3)ccc2O)CC1] |
| 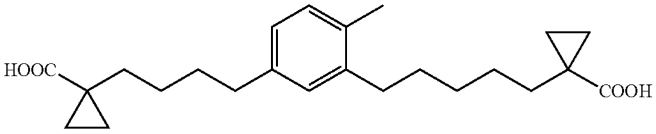 [SMILES: Cc1ccc(CCCCC2(C(=O)O)CC2)cc1CCCCCC1(C(=O)O)CC1] |
| 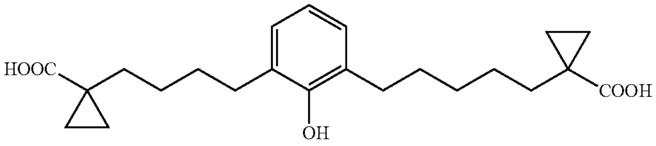 [SMILES: O=C(O)C1(CCCCCc2cccc(CCCCC3(C(=O)O)CC3)c2O)CC1] |
| 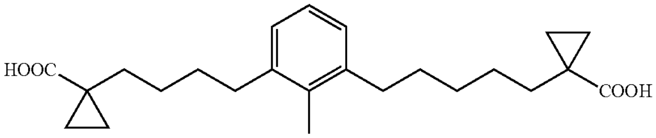 [SMILES: Cc1c(CCCCCC2(C(=O)O)CC2)cccc1CCCCC1(C(=O)O)CC1] |
| 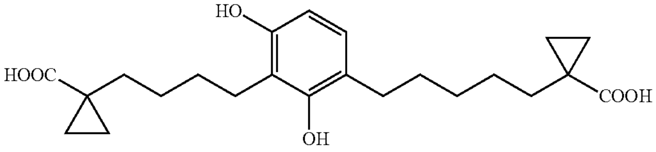 [SMILES: O=C(O)C1(CCCCCc2ccc(O)c(CCCCC3(C(=O)O)CC3)c2O)CC1] |
| 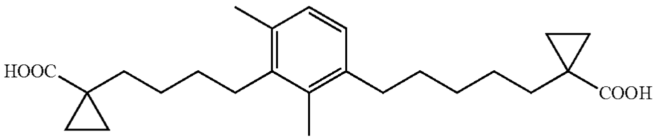 [SMILES: Cc1ccc(CCCCCC2(C(=O)O)CC2)c(C)c1CCCCC1(C(=O)O)CC1] |
| 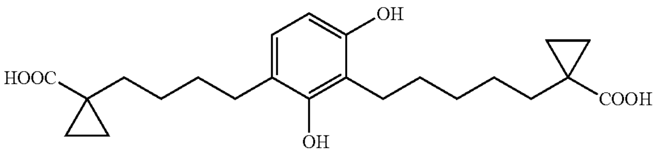 [SMILES: O=C(O)C1(CCCCCc2c(O)ccc(CCCCC3(C(=O)O)CC3)c2O)CC1] |

TABLE A-6-continued
| Structure |
|---|
| 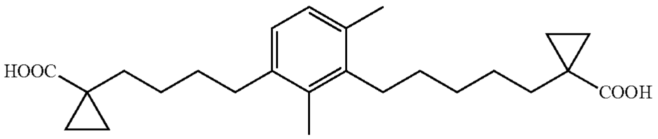 [SMILES: Cc1ccc(CCCCC2(C(=O)O)CC2)c(C)c1CCCCCC1(C(=O)O)CC1] |
| 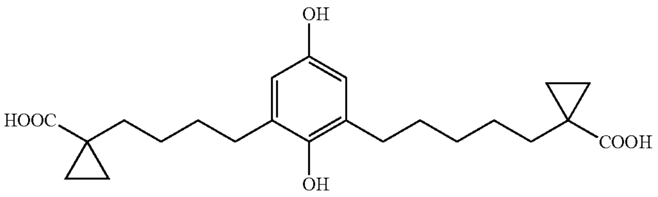 [SMILES: O=C(O)C1(CCCCCc2cc(O)cc(CCCCC3(C(=O)O)CC3)c2O)CC1] |
| 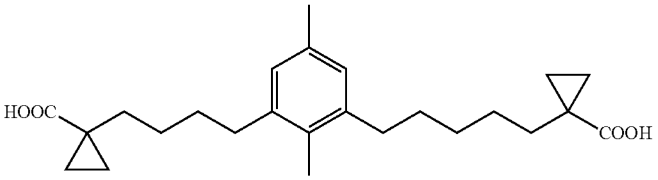 [SMILES: Cc1cc(CCCCCC2(C(=O)O)CC2)c(C)c(CCCCC2(C(=O)O)CC2)c1] |
| 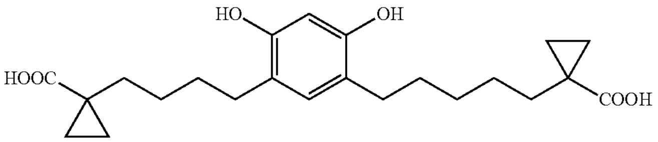 [SMILES: O=C(O)C1(CCCCCc2cc(CCCCC3(C(=O)O)CC3)c(O)cc2O)CC1] |
| 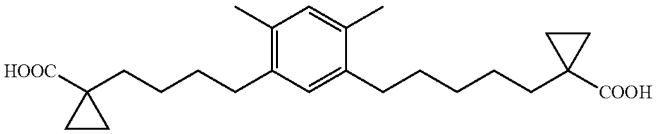 [SMILES: Cc1cc(C)c(CCCCC2(C(=O)O)CC2)cc1CCCCCC1(C(=O)O)CC1] |
| 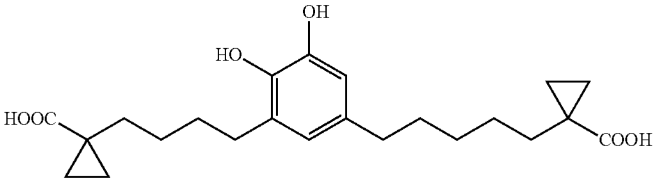 [SMILES: O=C(O)C1(CCCCCc2cc(O)c(O)c(CCCCC3(C(=O)O)CC3)c2)CC1] |
| 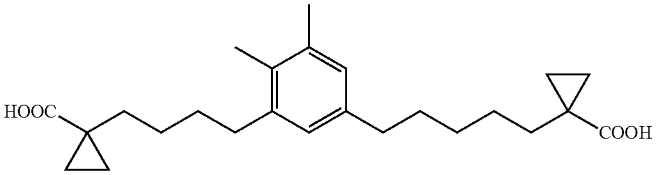 [SMILES: Cc1cc(CCCCCC2(C(=O)O)CC2)cc(CCCCC2(C(=O)O)CC2)c1C] |
| 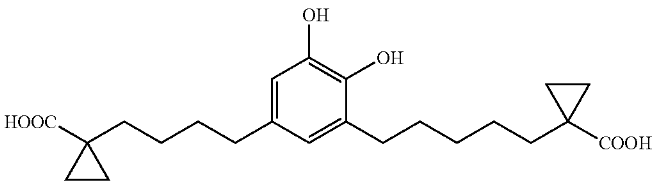 [SMILES: O=C(O)C1(CCCCCc2cc(CCCCC3(C(=O)O)CC3)cc(O)c2O)CC1] |

TABLE A-6-continued
| Structure |
| --- |
| 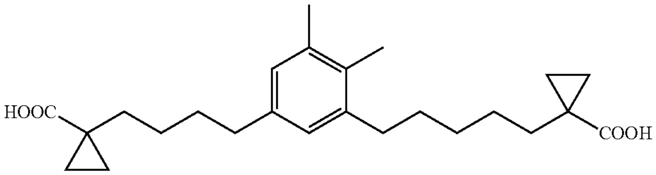 [SMILES: Cc1cc(CCCCC2(C(=O)O)CC2)cc(CCCCCC2(C(=O)O)CC2)c1C] |
| 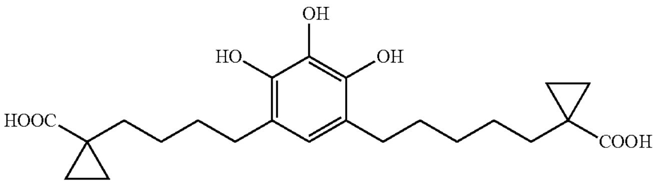 [SMILES: O=C(O)C1(CCCCCc2cc(CCCCC3(C(=O)O)CC3)c(O)c(O)c2O)CC1] |
| 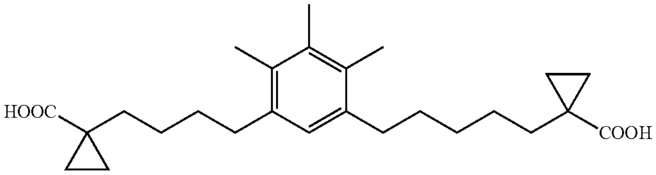 [SMILES: Cc1c(CCCCCC2(C(=O)O)CC2)cc(CCCCC2(C(=O)O)CC2)c(C)c1C] |
| 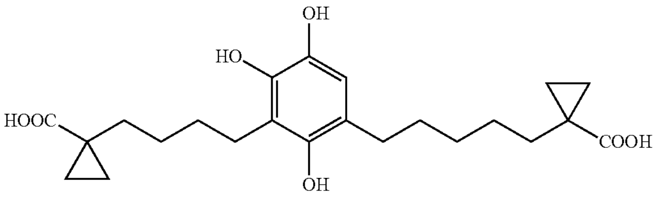 [SMILES: O=C(O)C1(CCCCCc2cc(O)c(O)c(CCCCC3(C(=O)O)CC3)c2O)CC1] |
| 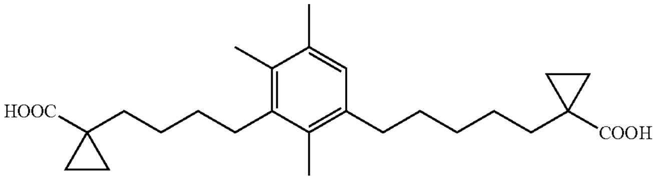 [SMILES: Cc1cc(CCCCCC2(C(=O)O)CC2)c(C)c(CCCCC2(C(=O)O)CC2)c1C] |
| 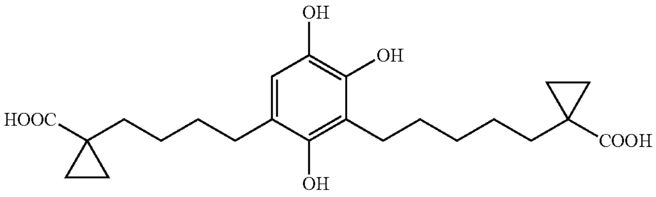 [SMILES: O=C(O)C1(CCCCCc2c(O)c(O)cc(CCCCC3(C(=O)O)CC3)c2O)CC1] |
| 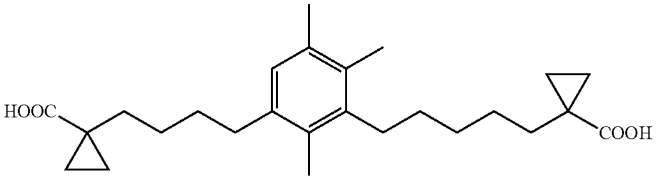 [SMILES: Cc1cc(CCCCC2(C(=O)O)CC2)c(C)c(CCCCCC2(C(=O)O)CC2)c1C] |
| 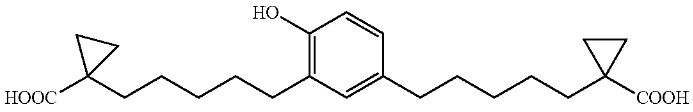 [SMILES: O=C(O)C1(CCCCCc2ccc(O)c(CCCCCC3(C(=O)O)CC3)c2)CC1] |
| 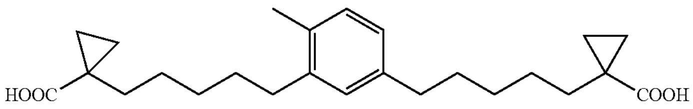 [SMILES: Cc1ccc(CCCCCC2(C(=O)O)CC2)cc1CCCCCC1(C(=O)O)CC1] |

TABLE A-6-continued
| Structure |
| --- |
| 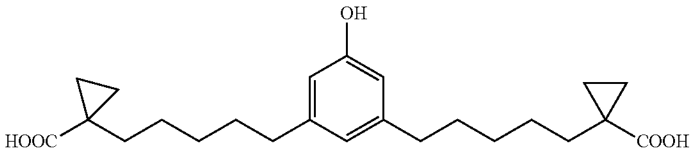 [SMILES: O=C(O)C1(CCCCCc2cc(O)cc(CCCCCC3(C(=O)O)CC3)c2)CC1] |
| 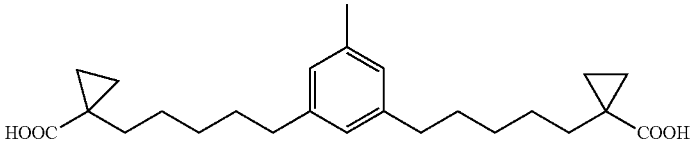 [SMILES: Cc1cc(CCCCCC2(C(=O)O)CC2)cc(CCCCCC2(C(=O)O)CC2)c1] |
| 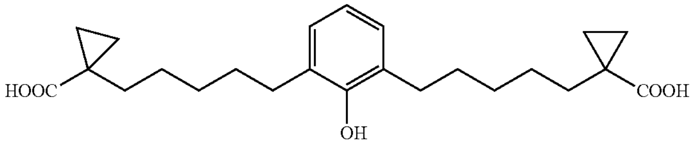 [SMILES: O=C(O)C1(CCCCCc2cccc(CCCCCC3(C(=O)O)CC3)c2O)CC1] |
| 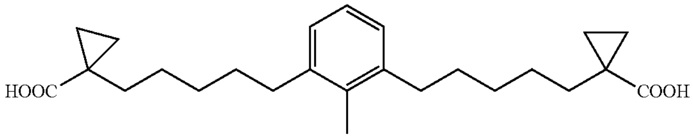 [SMILES: Cc1c(CCCCCC2(C(=O)O)CC2)cccc1CCCCCC1(C(=O)O)CC1] |
| 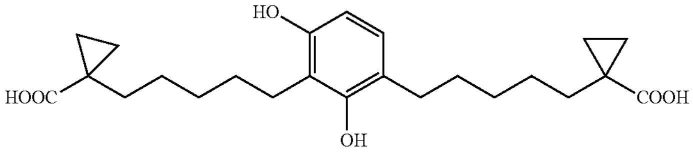 [SMILES: O=C(O)C1(CCCCCc2ccc(O)c(CCCCCC3(C(=O)O)CC3)c2O)CC1] |
| 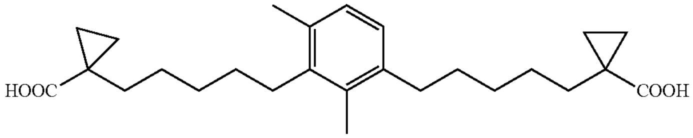 [SMILES: Cc1ccc(CCCCCC2(C(=O)O)CC2)c(C)c1CCCCCC1(C(=O)O)CC1] |
| 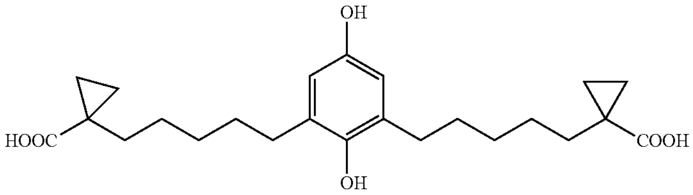 [SMILES: O=C(O)C1(CCCCCc2cc(O)cc(CCCCCC3(C(=O)O)CC3)c2O)CC1] |
| 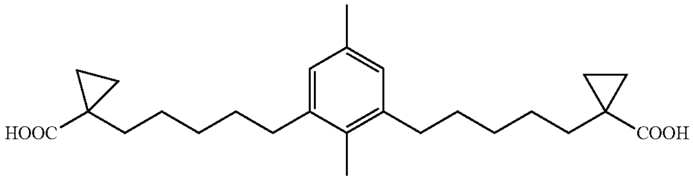 [SMILES: Cc1cc(CCCCCC2(C(=O)O)CC2)c(C)c(CCCCCC2(C(=O)O)CC2)c1] |
| 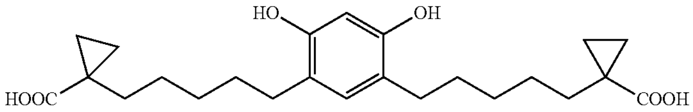 [SMILES: O=C(O)C1(CCCCCc2cc(CCCCCC3(C(=O)O)CC3)c(O)cc2O)CC1] |
| 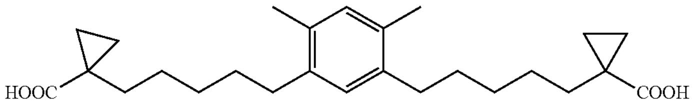 [SMILES: Cc1cc(C)c(CCCCCC2(C(=O)O)CC2)cc1CCCCCC1(C(=O)O)CC1] |

TABLE A-6-continued
| Structure |
| --- |
| 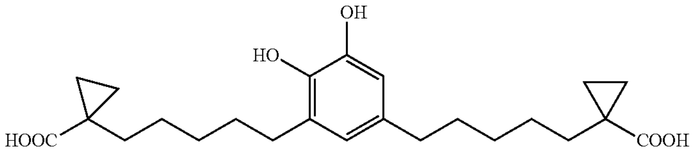 [SMILES: O=C(O)C1(CCCCCc2cc(O)c(O)c(CCCCCC3(C(=O)O)CC3)c2)CC1] |
| 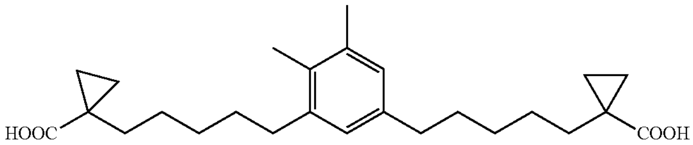 |
| 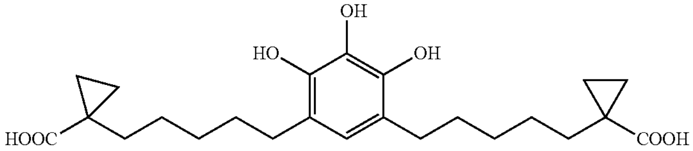 [SMILES: O=C(O)C1(CCCCCc2cc(CCCCCC3(C(=O)O)CC3)c(O)c(O)c2O)CC1] |
| 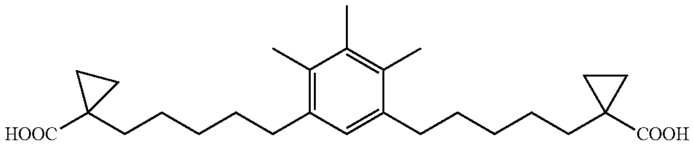 [SMILES: Cc1c(CCCCCC2(C(=O)O)CC2)cc(CCCCCC2(C(=O)O)CC2)c(C)c1C] |
| 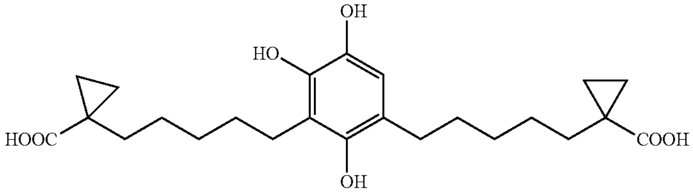 [SMILES: O=C(O)C1(CCCCCc2cc(O)c(O)c(CCCCCC3(C(=O)O)CC3)c2O)CC1] |
| 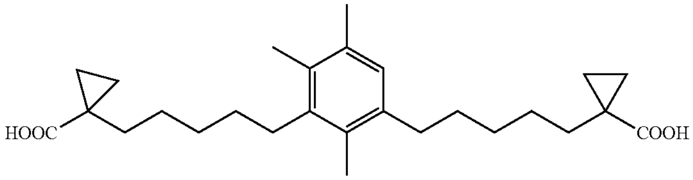 [SMILES: Cc1cc(CCCCCC2(C(=O)O)CC2)c(C)c(CCCCCC2(C(=O)O)CC2)c1C] |
| 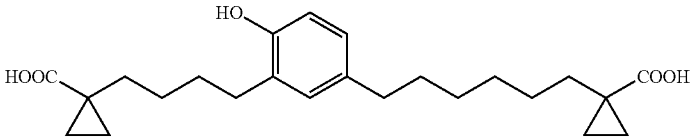 [SMILES: O=C(O)C1(CCCCCCc2ccc(O)c(CCCCC3(C(=O)O)CC3)c2)CC1] |
| 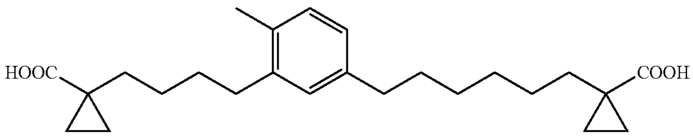 [SMILES: Cc1ccc(CCCCCCC2(C(=O)O)CC2)cc1CCCCC1(C(=O)O)CC1] |
| 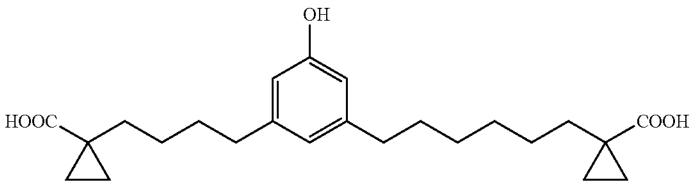 [SMILES: O=C(O)C1(CCCCCCc2cc(O)cc(CCCCC3(C(=O)O)CC3)c2)CC1] |

TABLE A-6-continued
| Structure |
| --- |
| 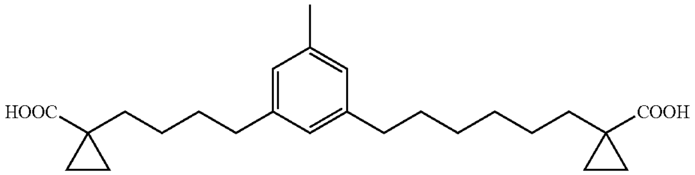 [SMILES: Cc1cc(CCCCCCC2(C(=O)O)CC2)cc(CCCCC2(C(=O)O)CC2)c1] |
| 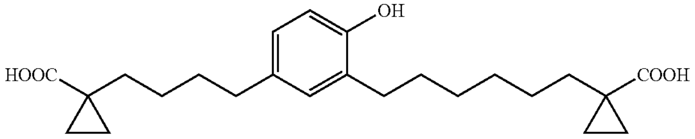 [SMILES: O=C(O)C1(CCCCCCc2cc(CCCCC3(C(=O)O)CC3)ccc2O)CC1] |
| 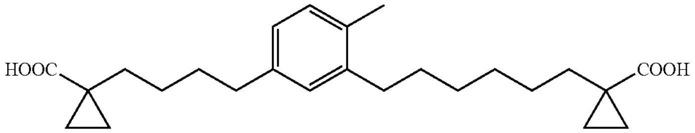 [SMILES: Cc1ccc(CCCCC2(C(=O)O)CC2)cc1CCCCCCC1(C(=O)O)CC1] |
| 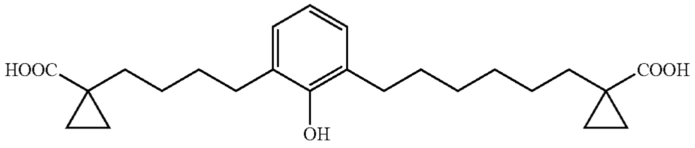 [SMILES: O=C(O)C1(CCCCCCc2cccc(CCCCC3(C(=O)O)CC3)c2O)CC1] |
| 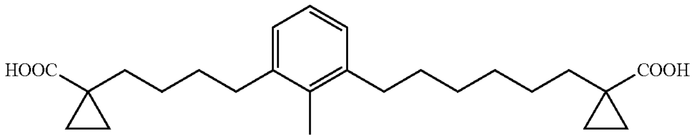 [SMILES: Cc1c(CCCCCCC2(C(=O)O)CC2)cccc1CCCCC1(C(=O)O)CC1] |
| 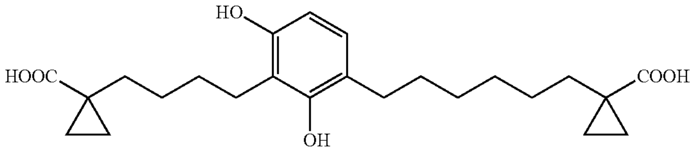 [SMILES: O=C(O)C1(CCCCCCc2ccc(O)c(CCCCC3(C(=O)O)CC3)c2O)CC1] |
| 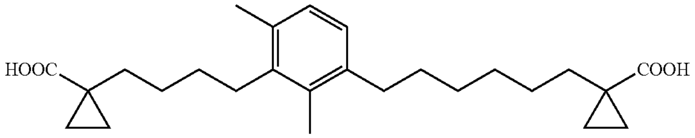 [SMILES: Cc1ccc(CCCCCCC2(C(=O)O)CC2)c(C)c1CCCCC1(C(=O)O)CC1] |
| 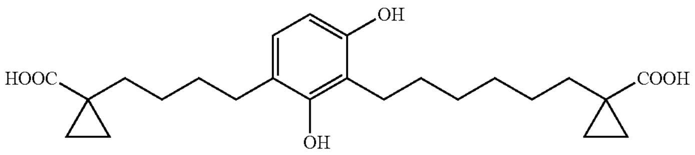 [SMILES: O=C(O)C1(CCCCCCc2c(O)ccc(CCCCC3(C(=O)O)CC3)c2O)CC1] |
| 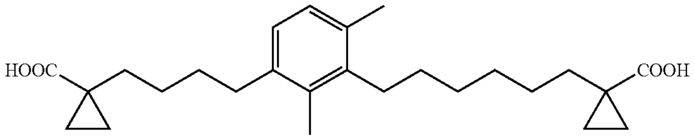 [SMILES: Cc1ccc(CCCCC2(C(=O)O)CC2)c(C)c1CCCCCCC1(C(=O)O)CC1] |

TABLE A-6-continued
| Structure |
| --- |
| 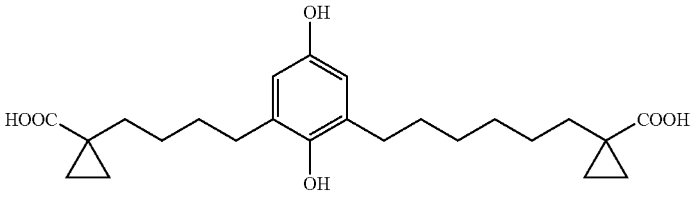 [SMILES: O=C(O)C1(CCCCCCc2cc(O)cc(CCCCC3(C(=O)O)CC3)c2O)CC1] |
| 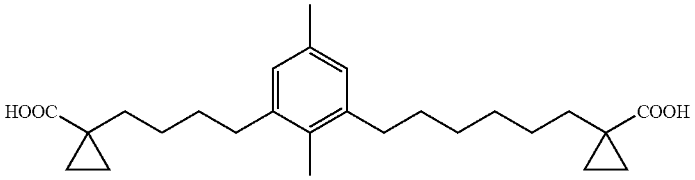 [SMILES: Cc1cc(CCCCCCC2(C(=O)O)CC2)c(C)c(CCCCC2(C(=O)O)CC2)c1] |
| 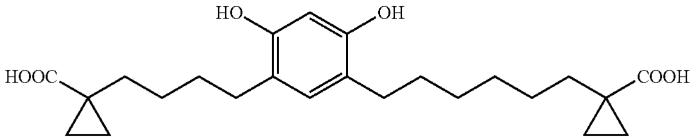 [SMILES: O=C(O)C1(CCCCCCc2cc(CCCCC3(C(=O)O)CC3)c(O)cc2O)CC1] |
| 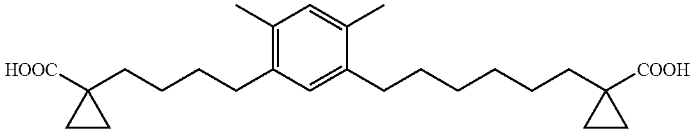 [SMILES: Cc1cc(C)c(CCCCC2(C(=O)O)CC2)cc1CCCCCCC1(C(=O)O)CC1] |
| 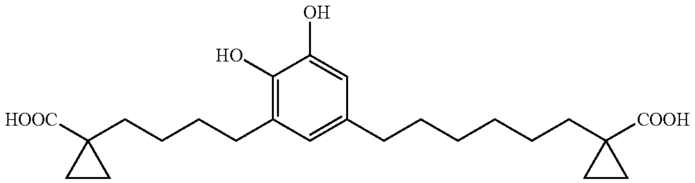 [SMILES: O=C(O)C1(CCCCCCc2cc(O)c(O)c(CCCCC3(C(=O)O)CC3)c2)CC1] |
| 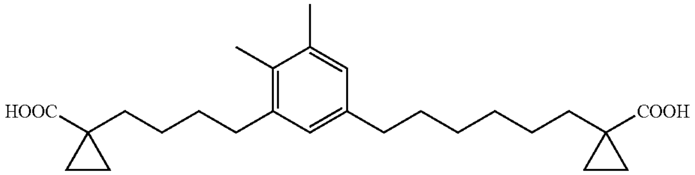 [SMILES: Cc1cc(CCCCCCC2(C(=O)O)CC2)cc(CCCCC2(C(=O)O)CC2)c1C] |
| 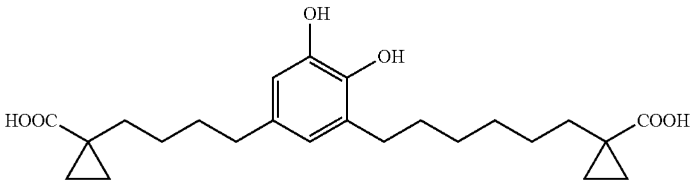 [SMILES: O=C(O)C1(CCCCCCc2cc(CCCCC3(C(=O)O)CC3)cc(O)c2O)CC1] |
| 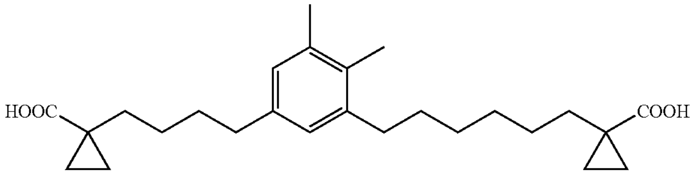 [SMILES: Cc1cc(CCCCC2(C(=O)O)CC2)cc(CCCCCCC2(C(=O)O)CC2)c1C] |

TABLE A-6-continued
| Structure |
| --- |
| 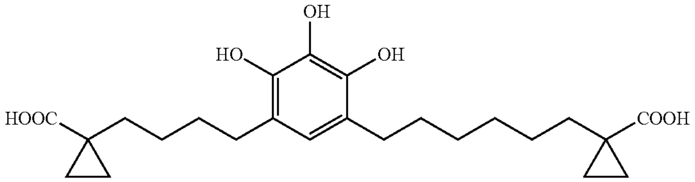 [SMILES: O=C(O)C1(CCCCCCc2cc(CCCCC3(C(=O)O)CC3)c(O)c(O)c2O)CC1] |
| 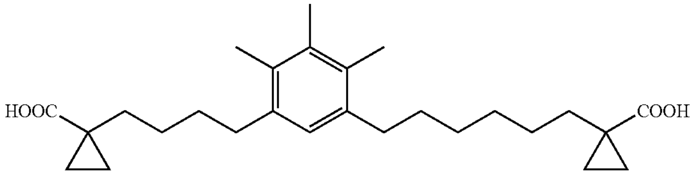 [SMILES: Cc1c(CCCCCCC2(C(=O)O)CC2)cc(CCCCC2(C(=O)O)CC2)c(C)c1C] |
| 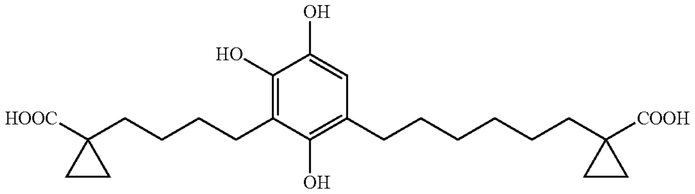 [SMILES: O=C(O)C1(CCCCCCc2cc(O)c(O)c(CCCCC3(C(=O)O)CC3)c2O)CC1] |
| 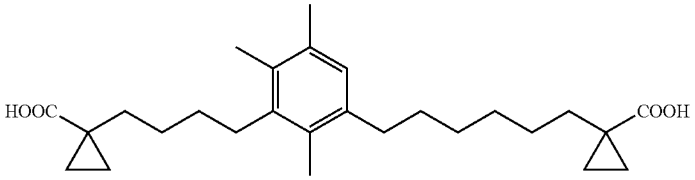 [SMILES: Cc1cc(CCCCCCC2(C(=O)O)CC2)c(C)c(CCCCC2(C(=O)O)CC2)c1C] |
| 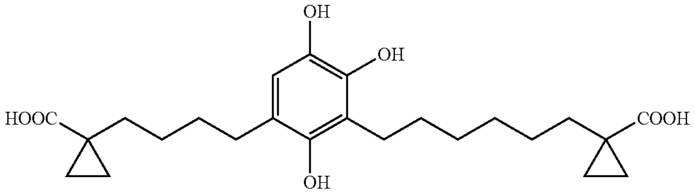 [SMILES: O=C(O)C1(CCCCCCc2c(O)c(O)cc(CCCCC3(C(=O)O)CC3)c2O)CC1] |
| 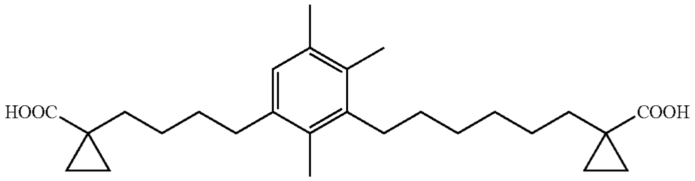 [SMILES: Cc1cc(CCCCC2(C(=O)O)CC2)c(C)c(CCCCCCC2(C(=O)O)CC2)c1C] |
TABLE A-7
| Structure | Structure |
| --- | --- |
| 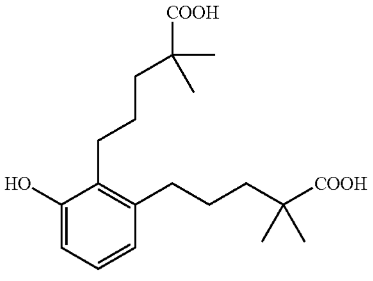 [SMILES: CC(C)(CCCc1cccc(O)c1CCCC(C)(C)C(=O)O)C(=O)O] | 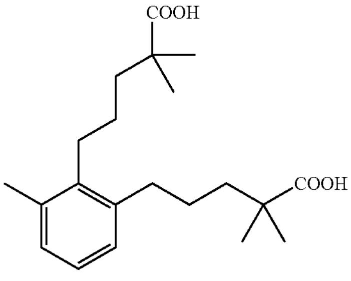 [SMILES: Cc1cccc(CCCC(C)(C)C(=O)O)c1CCCC(C)(C)C(=O)O] |

TABLE A-7-continued
| Structure | Structure |
| --- | --- |
| 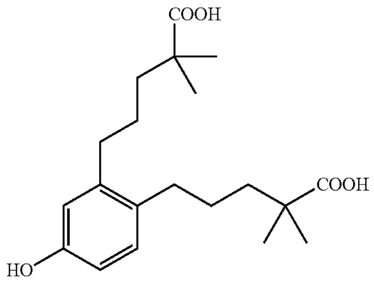 [SMILES: CC(C)(CCCc1ccc(O)cc1CCCC(C)(C)C(=O)O)C(=O)O] | 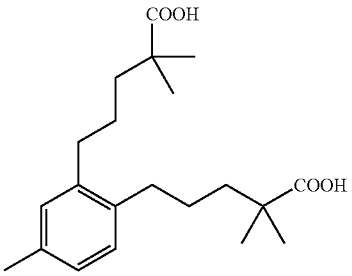 [SMILES: Cc1ccc(CCCC(C)(C)C(=O)O)c(CCCC(C)(C)C(=O)O)c1] |
| 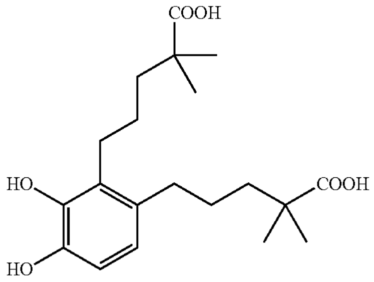 [SMILES: CC(C)(CCCc1ccc(O)c(O)c1CCCC(C)(C)C(=O)O)C(=O)O] | 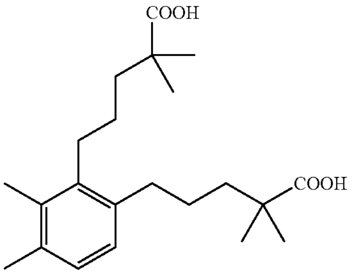 [SMILES: Cc1ccc(CCCC(C)(C)C(=O)O)c(CCCC(C)(C)C(=O)O)c1C] |
| 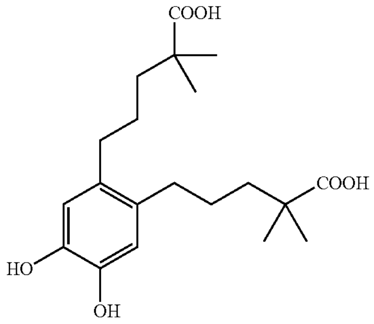 [SMILES: CC(C)(CCCc1cc(O)c(O)cc1CCCC(C)(C)C(=O)O)C(=O)O] | 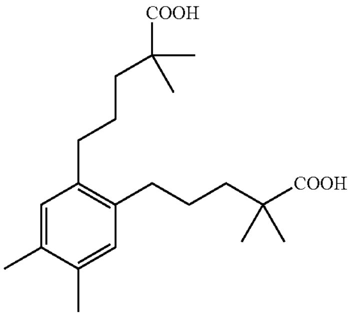 [SMILES: Cc1cc(CCCC(C)(C)C(=O)O)c(CCCC(C)(C)C(=O)O)cc1C] |
| 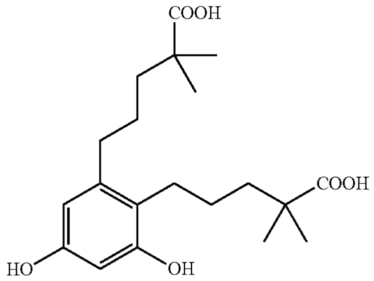 [SMILES: CC(C)(CCCc1cc(O)cc(O)c1CCCC(C)(C)C(=O)O)C(=O)O] | 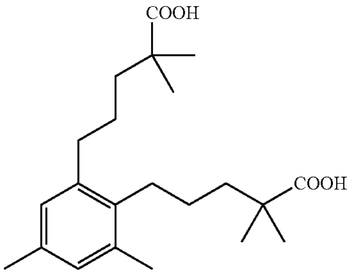 [SMILES: Cc1cc(C)c(CCCC(C)(C)C(=O)O)c(CCCC(C)(C)C(=O)O)c1] |
| 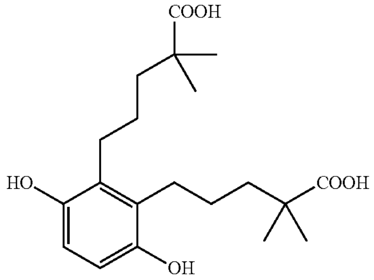 [SMILES: CC(C)(CCCc1c(O)ccc(O)c1CCCC(C)(C)C(=O)O)C(=O)O] | 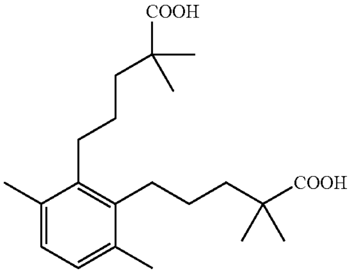 [SMILES: Cc1ccc(C)c(CCCC(C)(C)C(=O)O)c1CCCC(C)(C)C(=O)O] |

TABLE A-7-continued
| Structure | Structure |
| --- | --- |
| 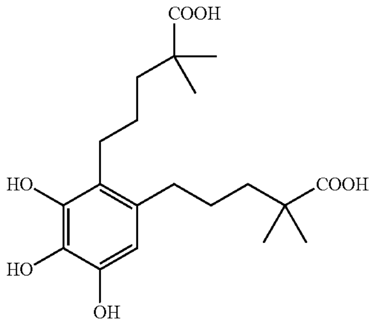 [SMILES: CC(C)(CCCc1cc(O)c(O)c(O)c1CCCC(C)(C)C(=O)O)C(=O)O] | 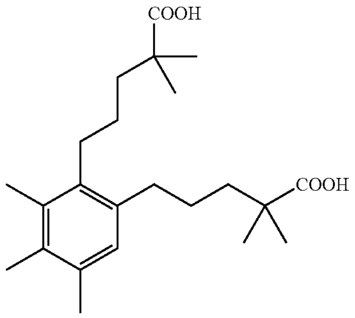 [SMILES: Cc1cc(CCCC(C)(C)C(=O)O)c(CCCC(C)(C)C(=O)O)c(C)c1C] |
| 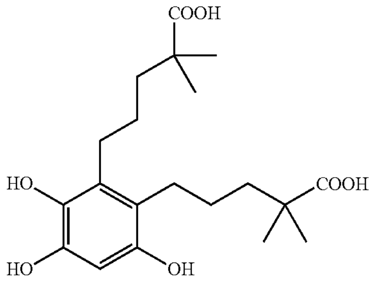 [SMILES: CC(C)(CCCc1c(O)cc(O)c(O)c1CCCC(C)(C)C(=O)O)C(=O)O] | 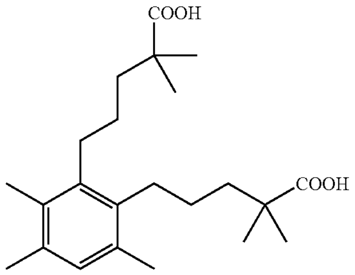 [SMILES: Cc1cc(C)c(CCCC(C)(C)C(=O)O)c(CCCC(C)(C)C(=O)O)c1C] |
| 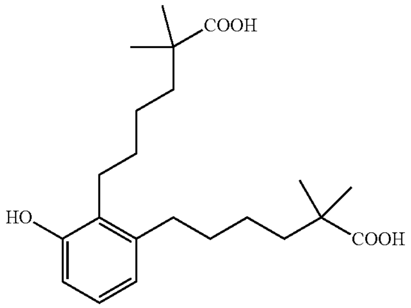 [SMILES: CC(C)(CCCCc1cccc(O)c1CCCCC(C)(C)C(=O)O)C(=O)O] | 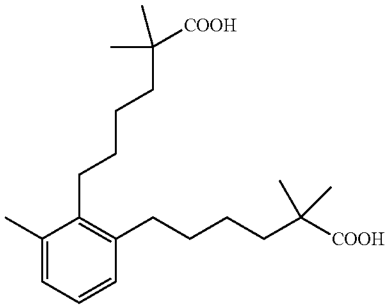 [SMILES: Cc1cccc(CCCCC(C)(C)C(=O)O)c1CCCCC(C)(C)C(=O)O] |
| 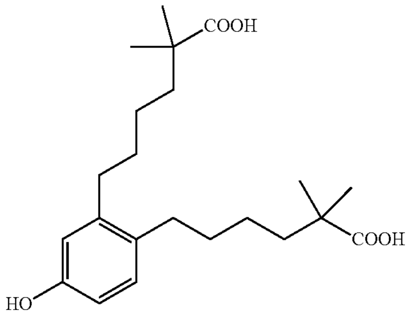 [SMILES: CC(C)(CCCCc1ccc(O)cc1CCCCC(C)(C)C(=O)O)C(=O)O] | 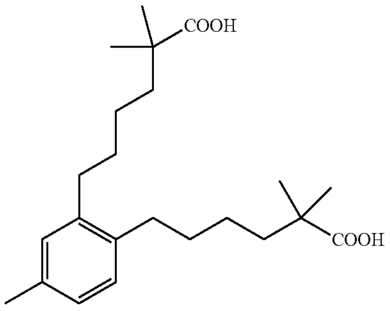 [SMILES: Cc1ccc(CCCCC(C)(C)C(=O)O)c(CCCCC(C)(C)C(=O)O)c1] |
| 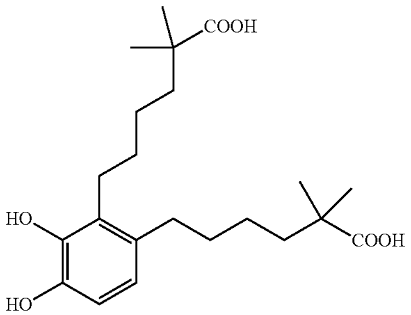 [SMILES: CC(C)(CCCCc1ccc(O)c(O)c1CCCCC(C)(C)C(=O)O)C(=O)O] | 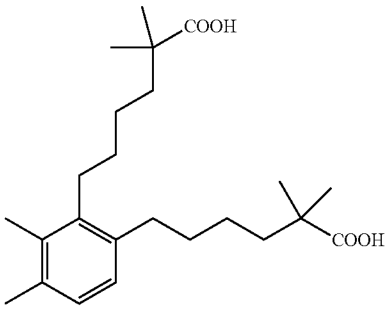 [SMILES: Cc1ccc(CCCCC(C)(C)C(=O)O)c(CCCCC(C)(C)C(=O)O)c1C] |

TABLE A-7-continued
| Structure | Structure |
| --- | --- |
| 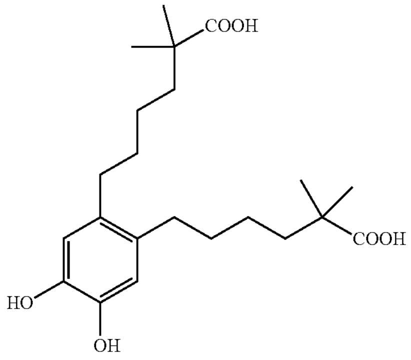 [SMILES: CC(C)(CCCCc1cc(O)c(O)cc1CCCCC(C)(C)C(=O)O)C(=O)O] | 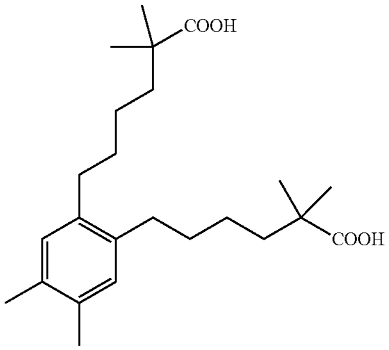 [SMILES: Cc1cc(CCCCC(C)(C)C(=O)O)c(CCCCC(C)(C)C(=O)O)cc1C] |
| 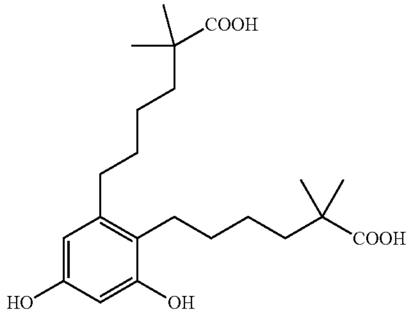 [SMILES: CC(C)(CCCCc1cc(O)cc(O)c1CCCCC(C)(C)C(=O)O)C(=O)O] | 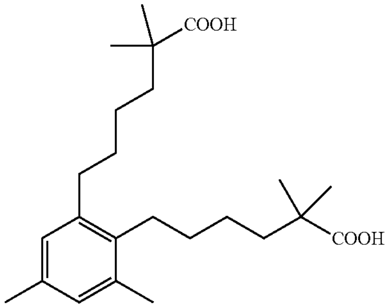 [SMILES: Cc1cc(C)c(CCCCC(C)(C)C(=O)O)c(CCCCC(C)(C)C(=O)O)c1] |
| 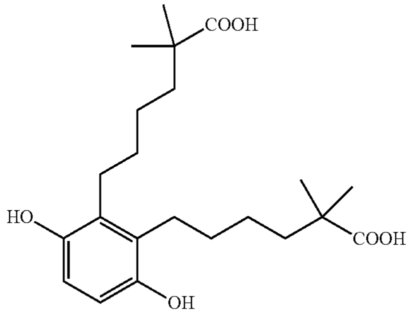 [SMILES: CC(C)(CCCCc1c(O)ccc(O)c1CCCCC(C)(C)C(=O)O)C(=O)O] | 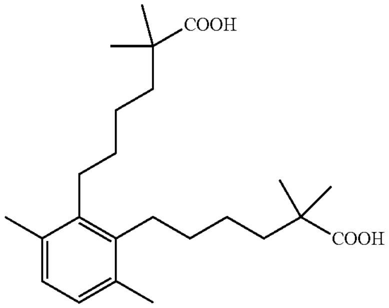 [SMILES: Cc1ccc(C)c(CCCCC(C)(C)C(=O)O)c1CCCCC(C)(C)C(=O)O] |
| 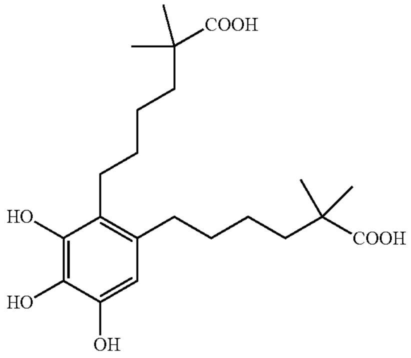 [SMILES: CC(C)(CCCCc1cc(O)c(O)c(O)c1CCCCC(C)(C)C(=O)O)C(=O)O] | 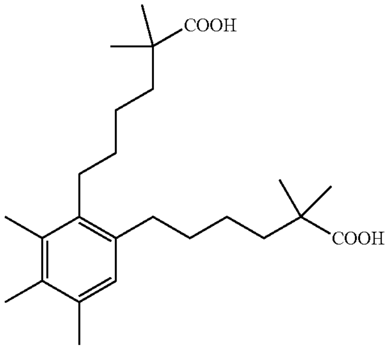 [SMILES: Cc1cc(CCCCC(C)(C)C(=O)O)c(CCCCC(C)(C)C(=O)O)c(C)c1C] |

TABLE A-7-continued
| Structure | Structure |
| --- | --- |
| 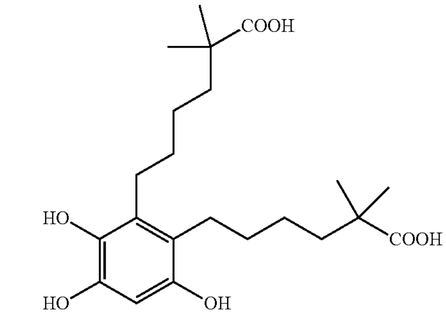 [SMILES: CC(C)(CCCCc1c(O)cc(O)c(O)c1CCCCC(C)(C)C(=O)O)C(=O)O] | 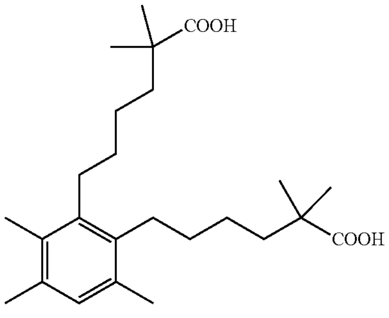 [SMILES: Cc1cc(C)c(CCCCC(C)(C)C(=O)O)c(CCCCC(C)(C)C(=O)O)c1C] |
| 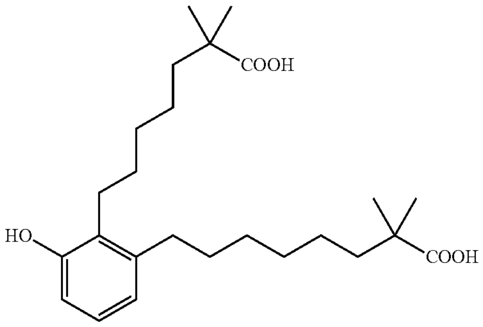 [SMILES: CC(C)(CCCCCCc1cccc(O)c1CCCCCC(C)(C)C(=O)O)C(=O)O] | 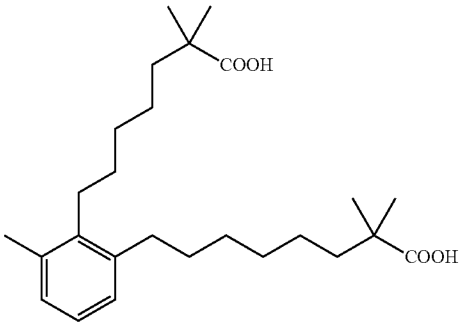 [SMILES: Cc1cccc(CCCCCCC(C)(C)C(=O)O)c1CCCCCC(C)(C)C(=O)O] |
| 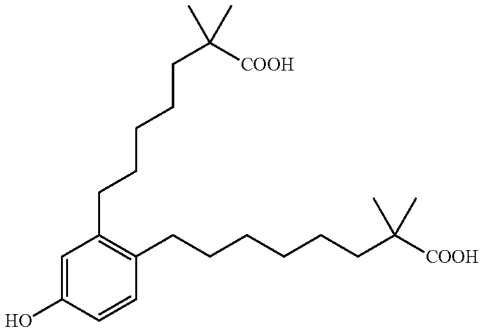 [SMILES: CC(C)(CCCCCCc1ccc(O)cc1CCCCCC(C)(C)C(=O)O)C(=O)O] | 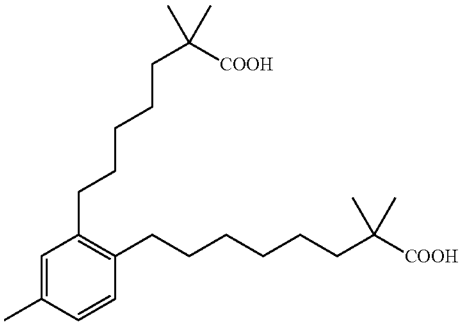 [SMILES: Cc1ccc(CCCCCCC(C)(C)C(=O)O)c(CCCCCC(C)(C)C(=O)O)c1] |
| 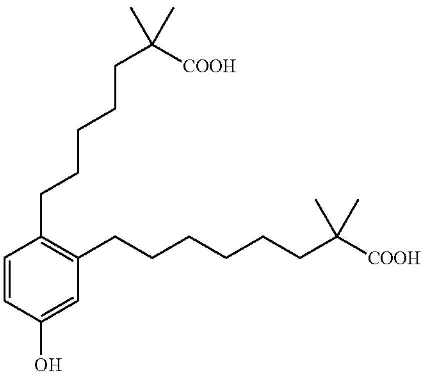 [SMILES: CC(C)(CCCCCCc1cc(O)ccc1CCCCCC(C)(C)C(=O)O)C(=O)O] | 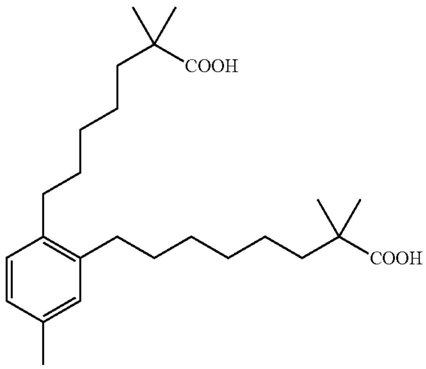 [SMILES: Cc1ccc(CCCCCC(C)(C)C(=O)O)c(CCCCCCC(C)(C)C(=O)O)c1] |

TABLE A-7-continued
| Structure | Structure |
| --- | --- |
| 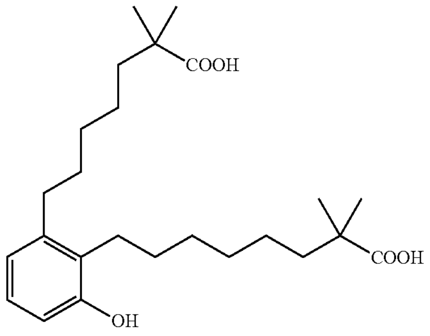 [SMILES: CC(C)(CCCCCCc1c(O)cccc1CCCCCC(C)(C)C(=O)O)C(=O)O] | 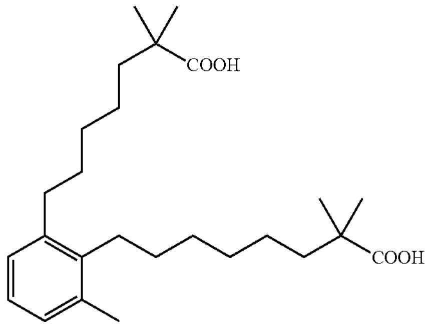 [SMILES: Cc1cccc(CCCCCC(C)(C)C(=O)O)c1CCCCCCC(C)(C)C(=O)O] |
| 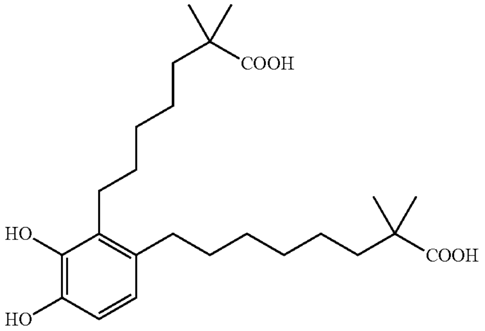 [SMILES: CC(C)(CCCCCCc1ccc(O)c(O)c1CCCCCC(C)(C)C(=O)O)C(=O)O] | 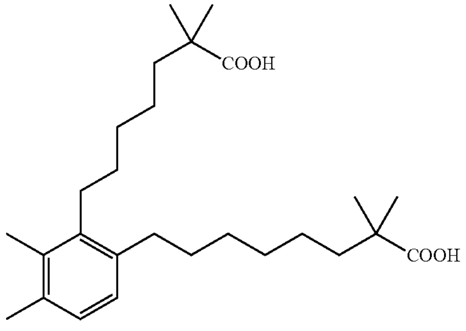 [SMILES: Cc1ccc(CCCCCCC(C)(C)C(=O)O)c(CCCCCC(C)(C)C(=O)O)c1C] |
| 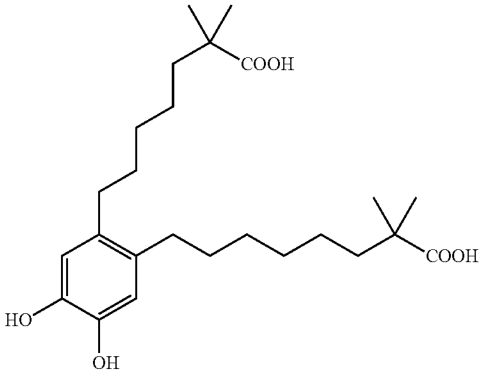 [SMILES: CC(C)(CCCCCCc1cc(O)c(O)cc1CCCCCC(C)(C)C(=O)O)C(=O)O] | 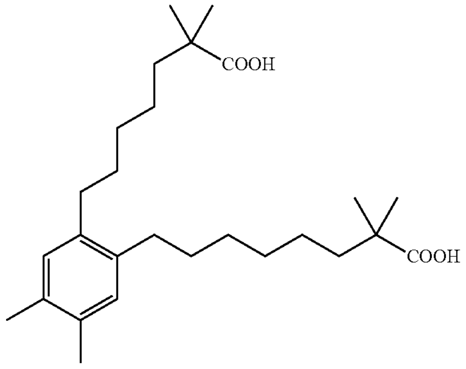 [SMILES: Cc1cc(CCCCCCC(C)(C)C(=O)O)c(CCCCCC(C)(C)C(=O)O)cc1C] |
| 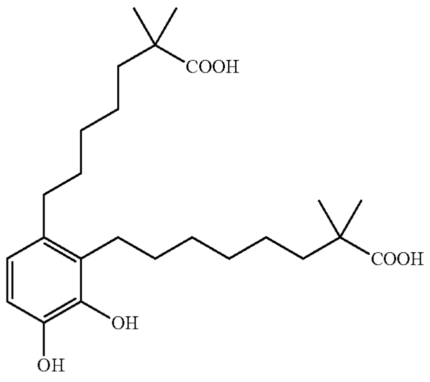 [SMILES: CC(C)(CCCCCCc1c(CCCCCC(C)(C)C(=O)O)ccc(O)c1O)C(=O)O] | 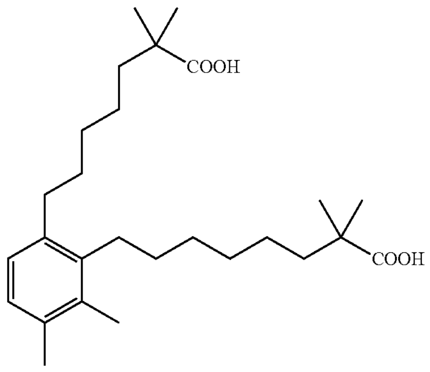 [SMILES: Cc1ccc(CCCCCC(C)(C)C(=O)O)c(CCCCCCC(C)(C)C(=O)O)c1C] |

TABLE A-7-continued
| Structure | Structure |
| --- | --- |
| 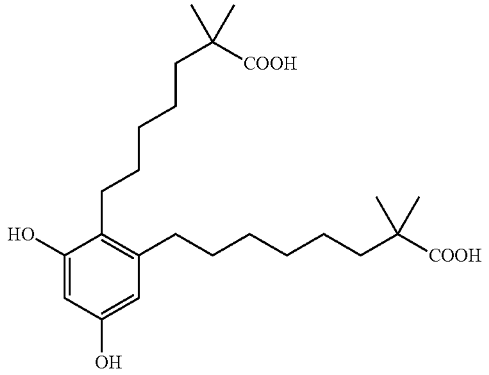 [SMILES: CC(C)(CCCCCCc1cc(O)cc(O)c1CCCCCC(C)(C)C(=O)O)C(=O)O] | 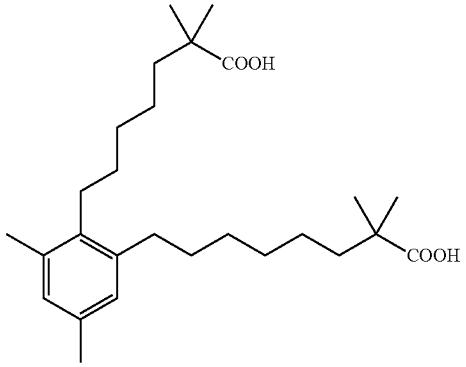 [SMILES: Cc1cc(C)c(CCCCCC(C)(C)C(=O)O)c(CCCCCCC(C)(C)C(=O)O)c1] |
| 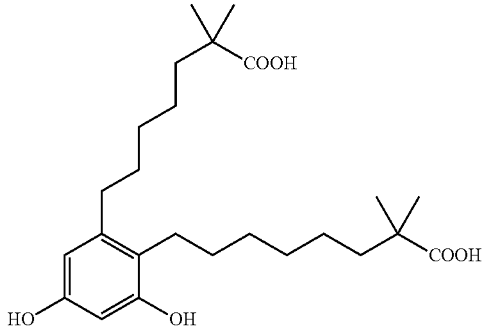 [SMILES: CC(C)(CCCCCCc1c(O)cc(O)cc1CCCCCC(C)(C)C(=O)O)C(=O)O] | 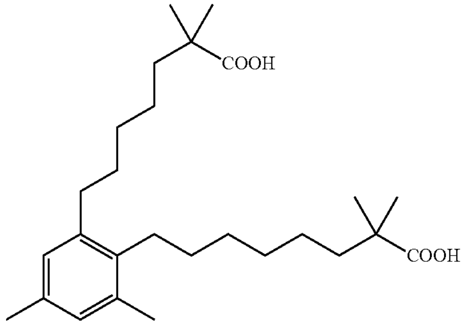 [SMILES: Cc1cc(C)c(CCCCCCC(C)(C)C(=O)O)c(CCCCCC(C)(C)C(=O)O)c1] |
| 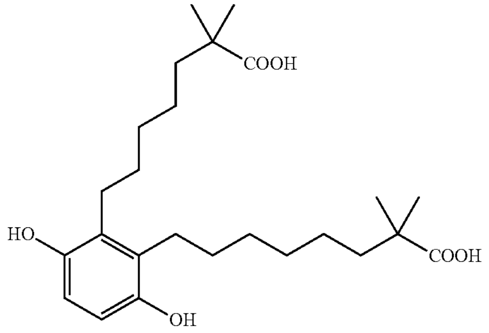 [SMILES: CC(C)(CCCCCCc1c(O)ccc(O)c1CCCCCC(C)(C)C(=O)O)C(=O)O] | 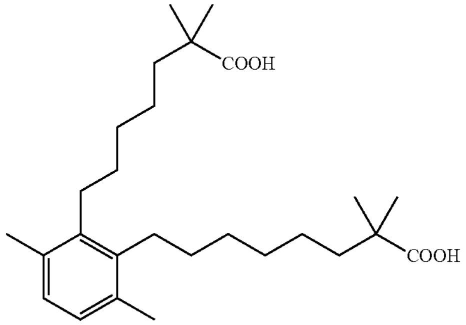 [SMILES: Cc1ccc(C)c(CCCCCC(C)(C)C(=O)O)c1CCCCCCC(C)(C)C(=O)O] |
| 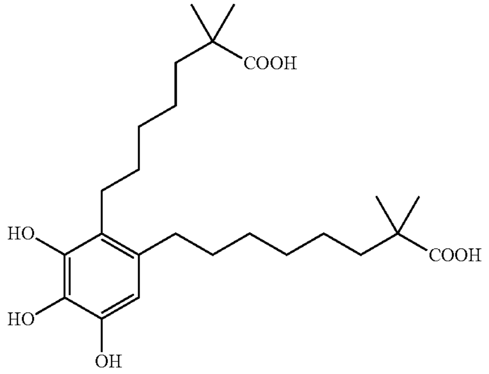 [SMILES: CC(C)(CCCCCCc1cc(O)c(O)c(O)c1CCCCCC(C)(C)C(=O)O)C(=O)O] | 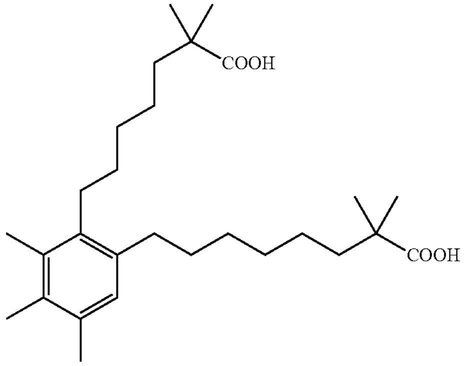 [SMILES: Cc1cc(CCCCCCC(C)(C)C(=O)O)c(CCCCCC(C)(C)C(=O)O)c(C)c1C] |

TABLE A-7-continued
| Structure | Structure |
| --- | --- |
| 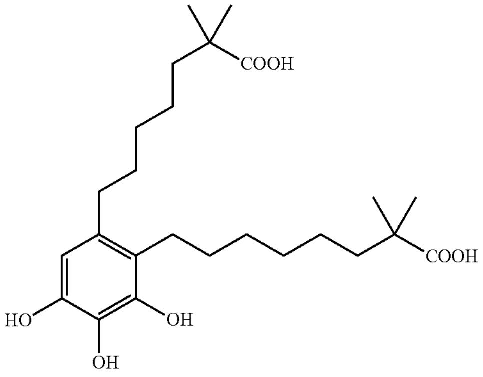 [SMILES: CC(C)(CCCCCCc1c(CCCCCC(C)(C)C(=O)O)cc(O)c(O)c1O)C(=O)O] | 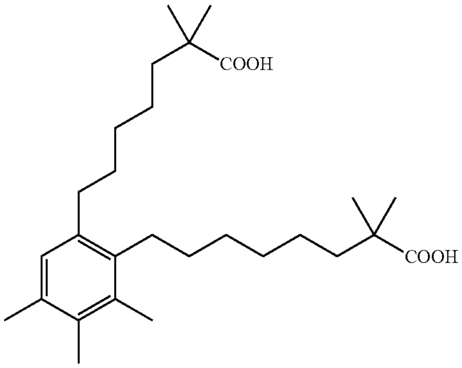 [SMILES: Cc1cc(CCCCCC(C)(C)C(=O)O)c(CCCCCCC(C)(C)C(=O)O)c(C)c1C] |
| 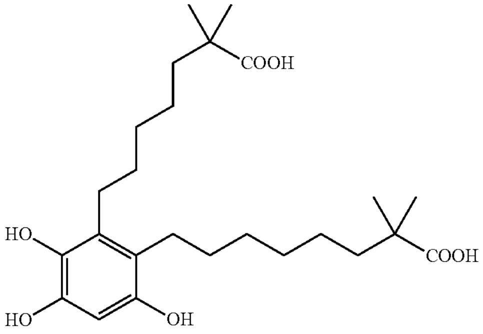 [SMILES: CC(C)(CCCCCCc1c(O)cc(O)c(O)c1CCCCCC(C)(C)C(=O)O)C(=O)O] | 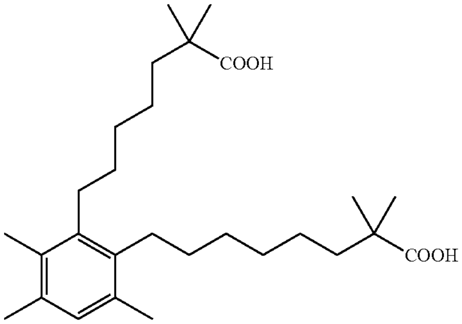 [SMILES: Cc1cc(C)c(CCCCCCC(C)(C)C(=O)O)c(CCCCCC(C)(C)C(=O)O)c1C] |
| 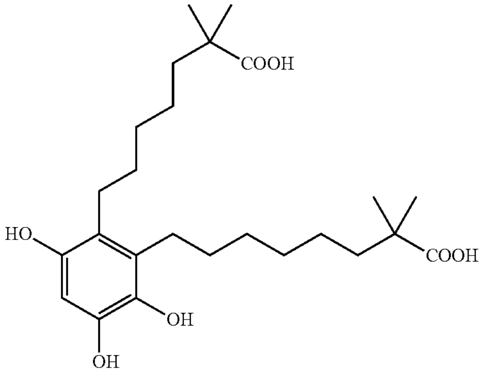 [SMILES: CC(C)(CCCCCCc1c(O)c(O)cc(O)c1CCCCCC(C)(C)C(=O)O)C(=O)O] | 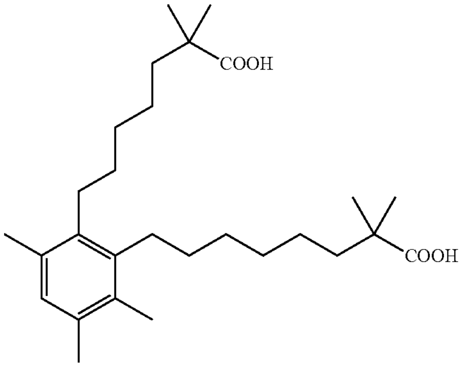 [SMILES: Cc1cc(C)c(CCCCCC(C)(C)C(=O)O)c(CCCCCCC(C)(C)C(=O)O)c1C] |
| 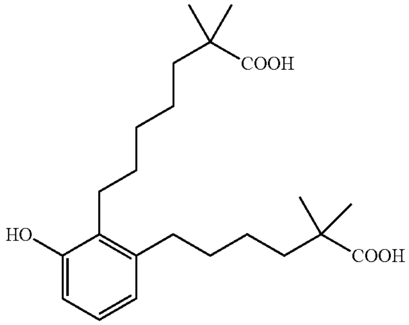 [SMILES: CC(C)(CCCCCc1c(O)cccc1CCCCC(C)(C)C(=O)O)C(=O)O] | 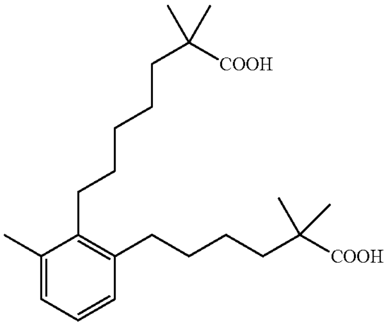 [SMILES: Cc1cccc(CCCCC(C)(C)C(=O)O)c1CCCCCC(C)(C)C(=O)O] |

TABLE A-7-continued
| Structure | Structure |
| --- | --- |
| 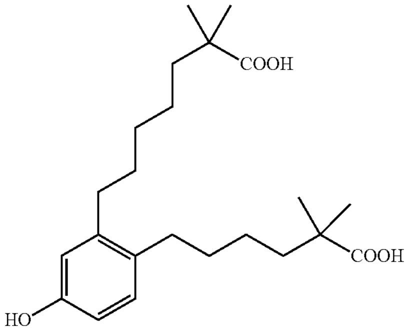 [SMILES: CC(C)(CCCCCc1cc(O)ccc1CCCCC(C)(C)C(=O)O)C(=O)O] | 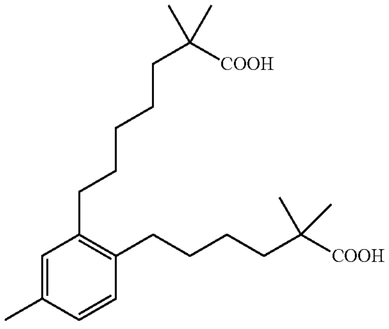 [SMILES: Cc1ccc(CCCCC(C)(C)C(=O)O)c(CCCCCC(C)(C)C(=O)O)c1] |
| 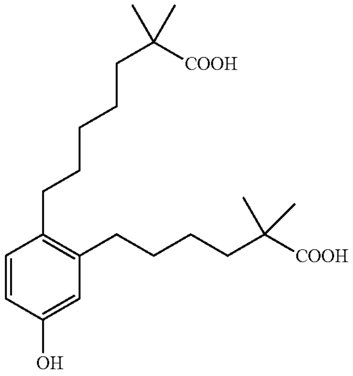 [SMILES: CC(C)(CCCCCc1ccc(O)cc1CCCCC(C)(C)C(=O)O)C(=O)O] | 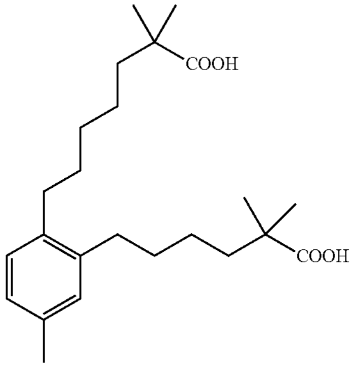 [SMILES: Cc1ccc(CCCCCC(C)(C)C(=O)O)c(CCCCC(C)(C)C(=O)O)c1] |
| 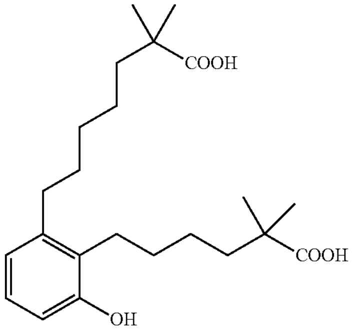 [SMILES: CC(C)(CCCCCc1cccc(O)c1CCCCC(C)(C)C(=O)O)C(=O)O] | 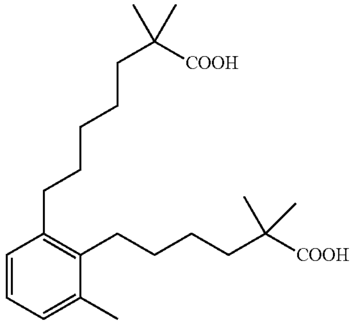 [SMILES: Cc1cccc(CCCCCC(C)(C)C(=O)O)c1CCCCC(C)(C)C(=O)O] |
| 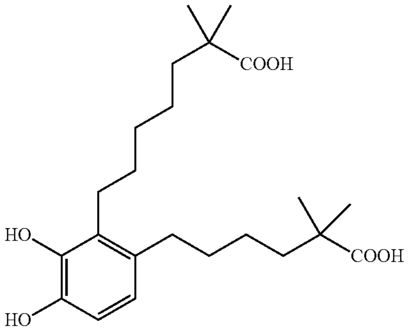 [SMILES: CC(C)(CCCCCc1c(CCCCC(C)(C)C(=O)O)ccc(O)c1O)C(=O)O] | 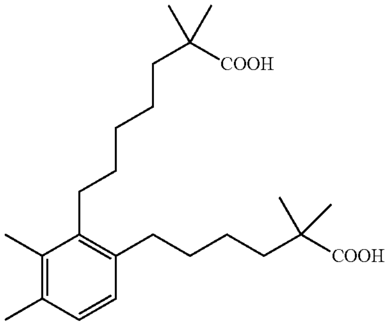 [SMILES: Cc1ccc(CCCCC(C)(C)C(=O)O)c(CCCCCC(C)(C)C(=O)O)c1C] |

TABLE A-7-continued
| Structure | Structure |
| --- | --- |
| 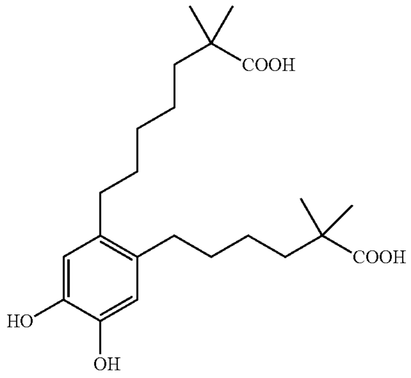 [SMILES: CC(C)(CCCCCc1cc(O)c(O)cc1CCCCC(C)(C)C(=O)O)C(=O)O] | 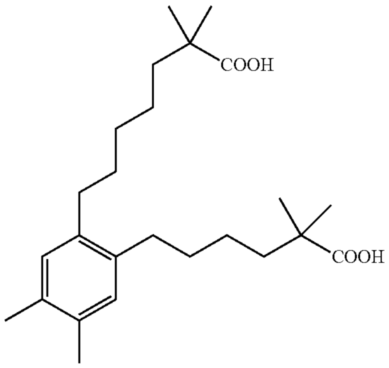 [SMILES: Cc1cc(CCCCCC(C)(C)C(=O)O)c(CCCCC(C)(C)C(=O)O)cc1C] |
| 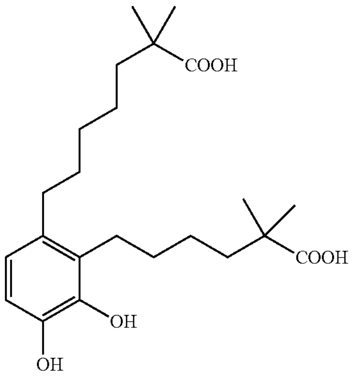 [SMILES: CC(C)(CCCCCc1ccc(O)c(O)c1CCCCC(C)(C)C(=O)O)C(=O)O] | 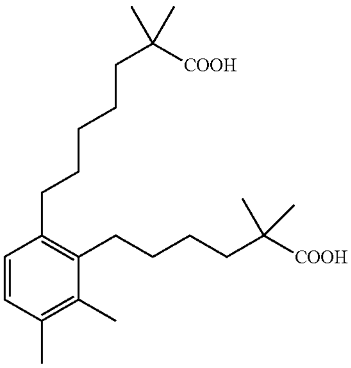 [SMILES: Cc1ccc(CCCCCC(C)(C)C(=O)O)c(CCCCC(C)(C)C(=O)O)c1C] |
| 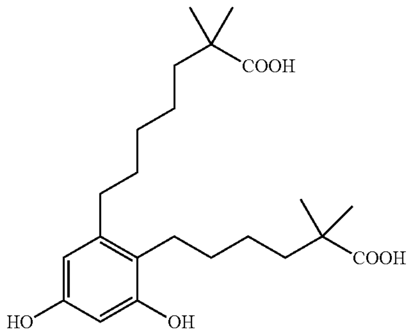 [SMILES: CC(C)(CCCCCc1cc(O)cc(O)c1CCCCC(C)(C)C(=O)O)C(=O)O] | 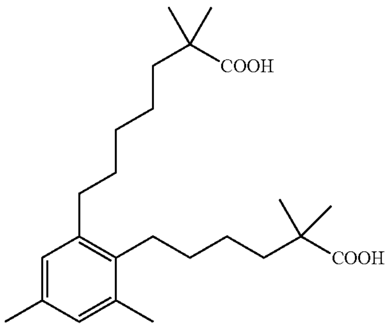 [SMILES: Cc1cc(C)c(CCCCC(C)(C)C(=O)O)c(CCCCCC(C)(C)C(=O)O)c1] |
| 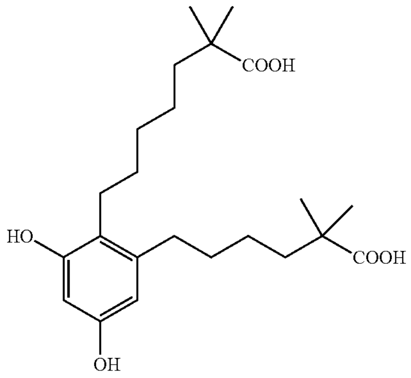 [SMILES: CC(C)(CCCCCc1c(O)cc(O)cc1CCCCC(C)(C)C(=O)O)C(=O)O] | 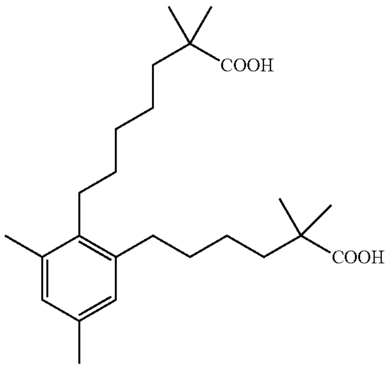 [SMILES: Cc1cc(C)c(CCCCCC(C)(C)C(=O)O)c(CCCCC(C)(C)C(=O)O)c1] |

TABLE A-7-continued
| Structure | Structure |
| --- | --- |
| 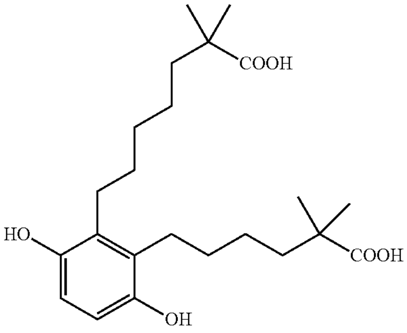 [SMILES: CC(C)(CCCCCc1c(O)ccc(O)c1CCCCC(C)(C)C(=O)O)C(=O)O] | 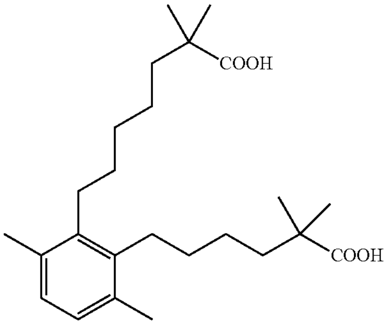 [SMILES: Cc1ccc(C)c(CCCCC(C)(C)C(=O)O)c1CCCCCC(C)(C)C(=O)O] |
| 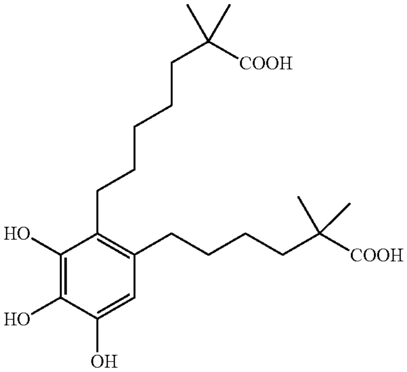 [SMILES: CC(C)(CCCCCc1c(CCCCC(C)(C)C(=O)O)cc(O)c(O)c1O)C(=O)O] | 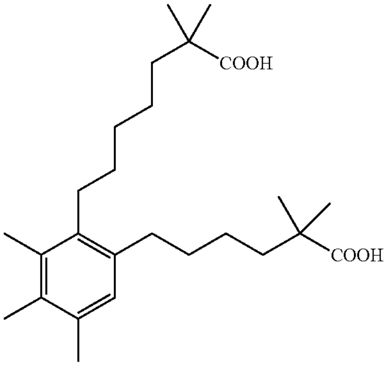 [SMILES: Cc1cc(CCCCC(C)(C)C(=O)O)c(CCCCCC(C)(C)C(=O)O)c(C)c1C] |
| 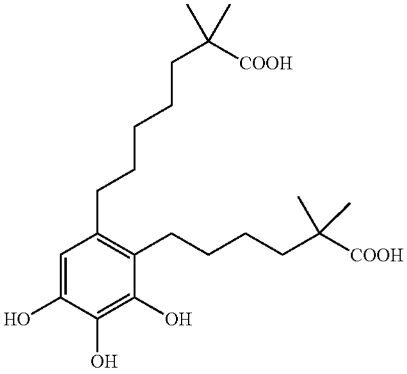 [SMILES: CC(C)(CCCCCc1cc(O)c(O)c(O)c1CCCCC(C)(C)C(=O)O)C(=O)O] | 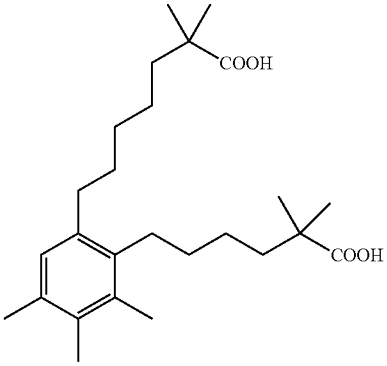 [SMILES: Cc1cc(CCCCCC(C)(C)C(=O)O)c(CCCCC(C)(C)C(=O)O)c(C)c1C] |
| 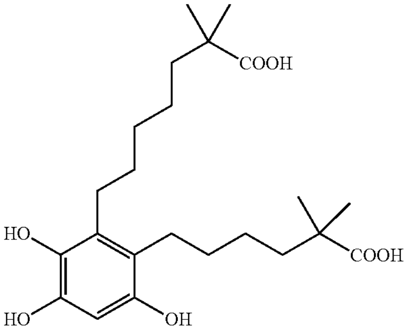 [SMILES: CC(C)(CCCCCc1c(O)c(O)cc(O)c1CCCCC(C)(C)C(=O)O)C(=O)O] | 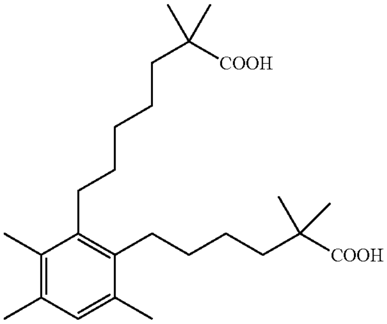 [SMILES: Cc1cc(C)c(CCCCC(C)(C)C(=O)O)c(CCCCCC(C)(C)C(=O)O)c1C] |

TABLE A-7-continued
| Structure | Structure |
| --- | --- |
| 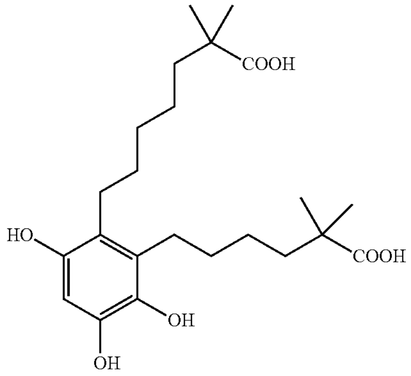 [SMILES: CC(C)(CCCCCc1c(O)cc(O)c(O)c1CCCCC(C)(C)C(=O)O)C(=O)O] | 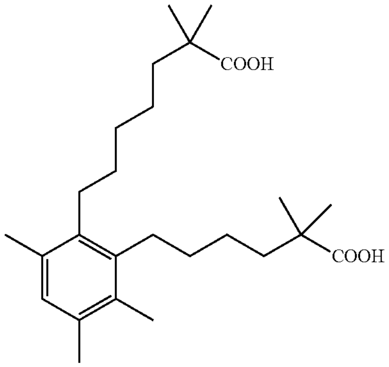 [SMILES: Cc1cc(C)c(CCCCCC(C)(C)C(=O)O)c(CCCCC(C)(C)C(=O)O)c1C] |
| 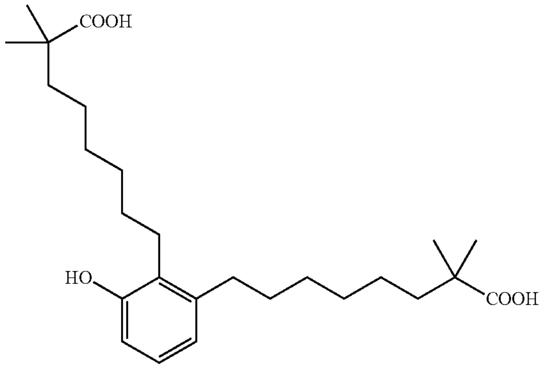 [SMILES: CC(C)(CCCCCCc1cccc(O)c1CCCCCCC(C)(C)C(=O)O)C(=O)O] | 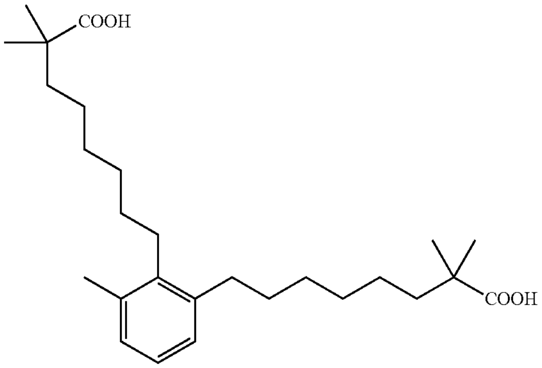 [SMILES: Cc1cccc(CCCCCCC(C)(C)C(=O)O)c1CCCCCCC(C)(C)C(=O)O] |
| 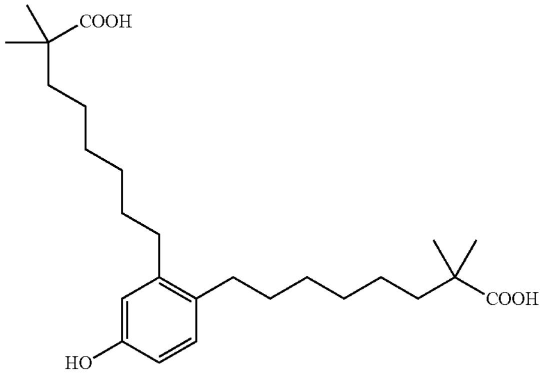 [SMILES: CC(C)(CCCCCCc1ccc(O)cc1CCCCCCC(C)(C)C(=O)O)C(=O)O] | 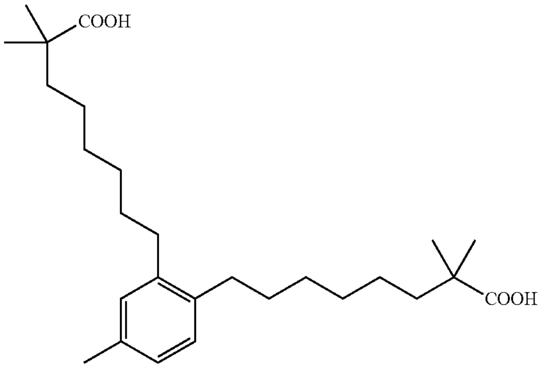 [SMILES: Cc1ccc(CCCCCCC(C)(C)C(=O)O)c(CCCCCCC(C)(C)C(=O)O)c1] |
| 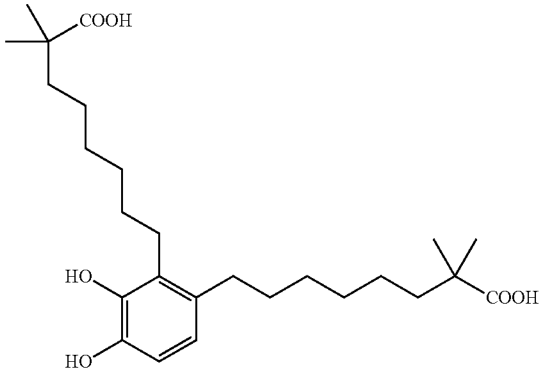 [SMILES: CC(C)(CCCCCCc1ccc(O)c(O)c1CCCCCCC(C)(C)C(=O)O)C(=O)O] | 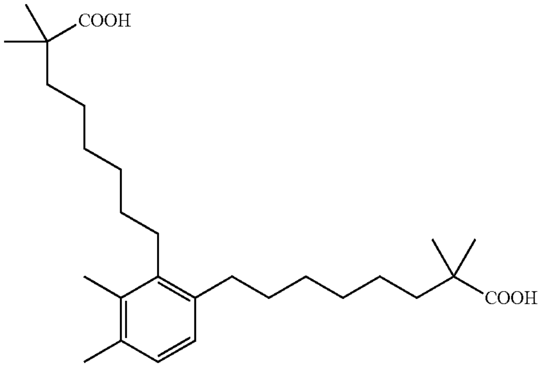 [SMILES: Cc1ccc(CCCCCCC(C)(C)C(=O)O)c(CCCCCCC(C)(C)C(=O)O)c1C] |

TABLE A-7-continued
| Structure | Structure |
| --- | --- |
| 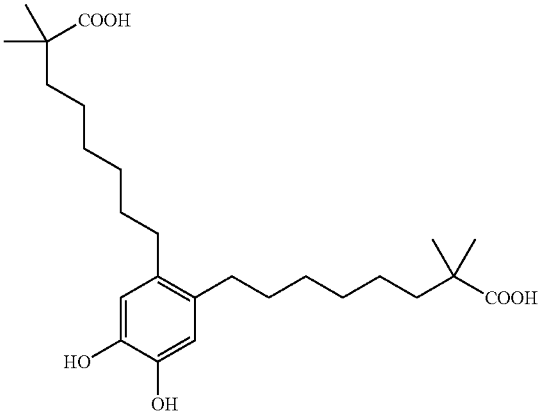 [SMILES: CC(C)(CCCCCCc1cc(O)c(O)cc1CCCCCCC(C)(C)C(=O)O)C(=O)O] | 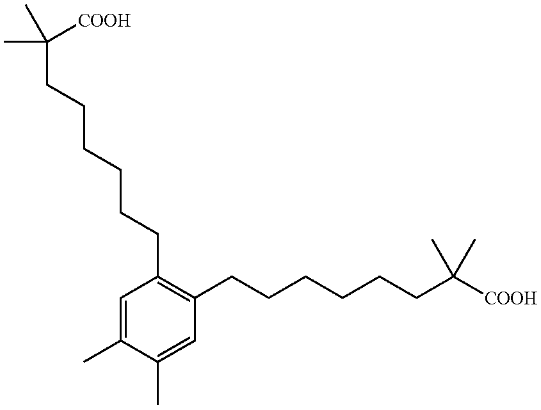 [SMILES: Cc1cc(CCCCCCC(C)(C)C(=O)O)c(CCCCCCC(C)(C)C(=O)O)cc1C] |
| 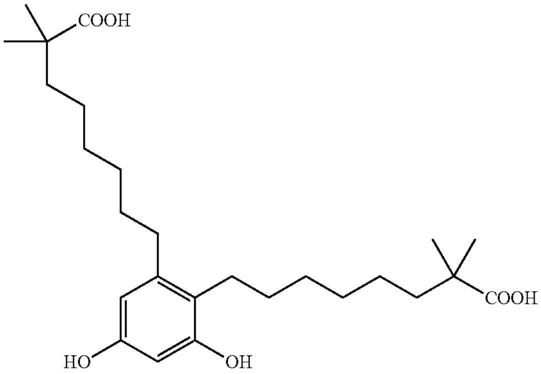 [SMILES: CC(C)(CCCCCCc1cc(O)cc(O)c1CCCCCCC(C)(C)C(=O)O)C(=O)O] | 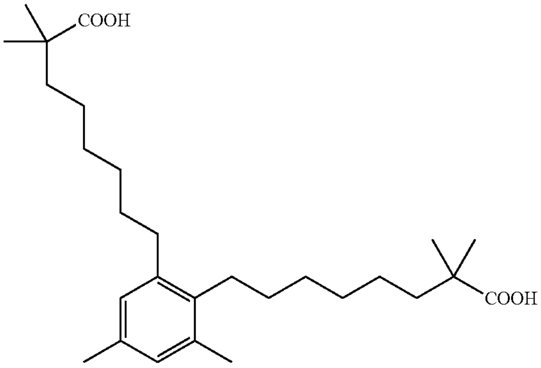 [SMILES: Cc1cc(C)c(CCCCCCC(C)(C)C(=O)O)c(CCCCCCC(C)(C)C(=O)O)c1] |
| 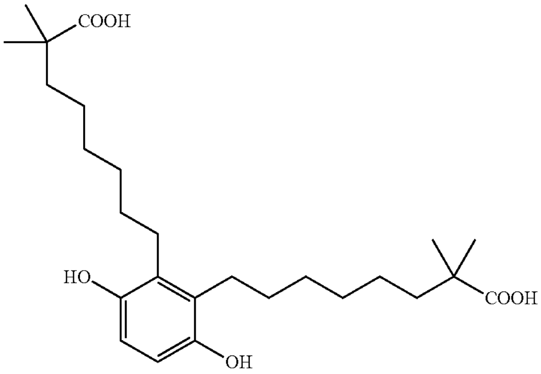 [SMILES: CC(C)(CCCCCCc1c(O)ccc(O)c1CCCCCCC(C)(C)C(=O)O)C(=O)O] | 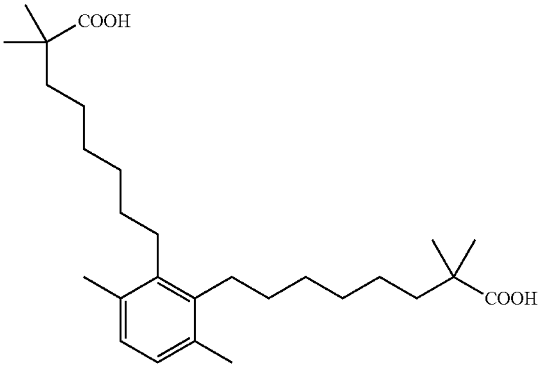 [SMILES: Cc1ccc(C)c(CCCCCCC(C)(C)C(=O)O)c1CCCCCCC(C)(C)C(=O)O] |
| 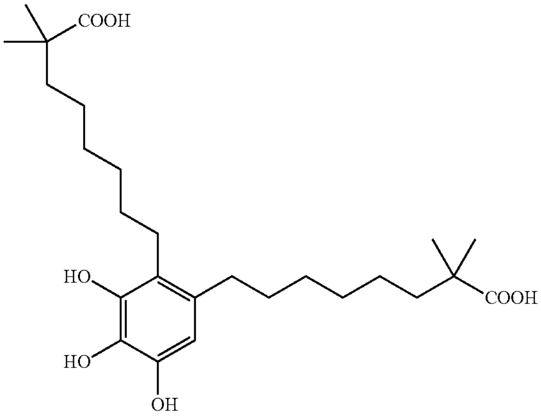 [SMILES: CC(C)(CCCCCCc1cc(O)c(O)c(O)c1CCCCCCC(C)(C)C(=O)O)C(=O)O] | 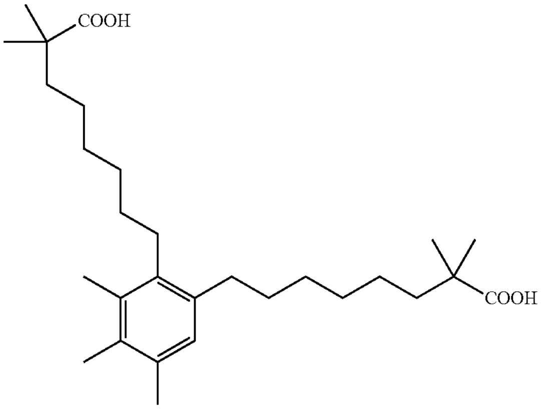 [SMILES: Cc1cc(CCCCCCC(C)(C)C(=O)O)c(CCCCCCC(C)(C)C(=O)O)c(C)c1C] |

TABLE A-7-continued
| Structure | Structure |
| --- | --- |
| 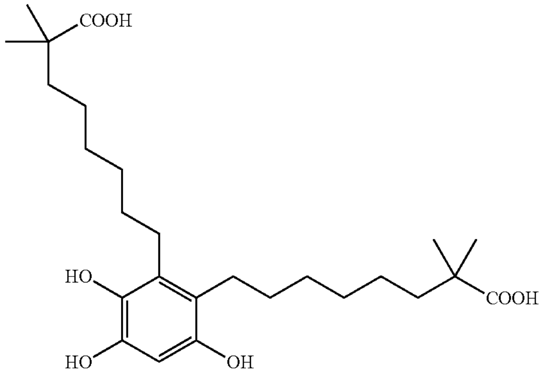 [SMILES: CC(C)(CCCCCCc1c(O)cc(O)c(O)c1CCCCCCC(C)(C)C(=O)O)C(=O)O] | 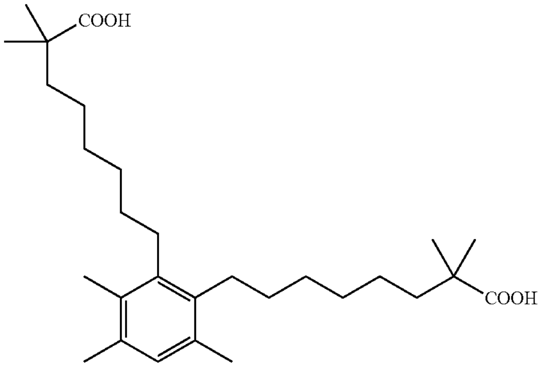 [SMILES: Cc1cc(C)c(CCCCCCC(C)(C)C(=O)O)c(CCCCCCC(C)(C)C(=O)O)c1C] |
| 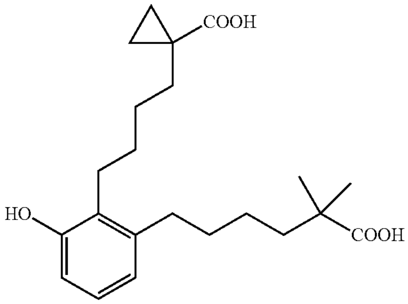 [SMILES: CC(C)(CCCCc1cccc(O)c1CCCCC1(C(=O)O)CC1)C(=O)O] | 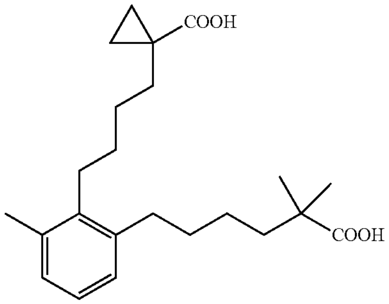 [SMILES: Cc1cccc(CCCCC(C)(C)C(=O)O)c1CCCCC1(C(=O)O)CC1] |
| 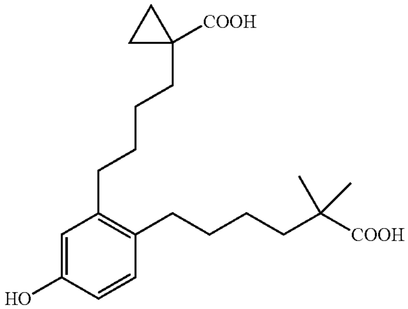 [SMILES: CC(C)(CCCCc1ccc(O)cc1CCCCC1(C(=O)O)CC1)C(=O)O] | 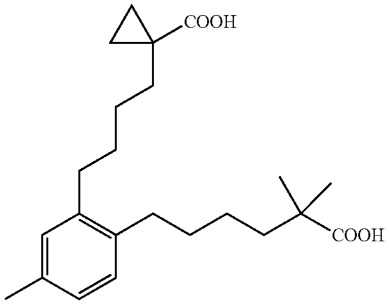 [SMILES: Cc1ccc(CCCCC(C)(C)C(=O)O)c(CCCCC2(C(=O)O)CC2)c1] |
| 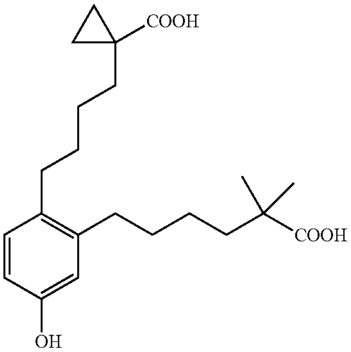 [SMILES: CC(C)(CCCCc1cc(O)ccc1CCCCC1(C(=O)O)CC1)C(=O)O] | 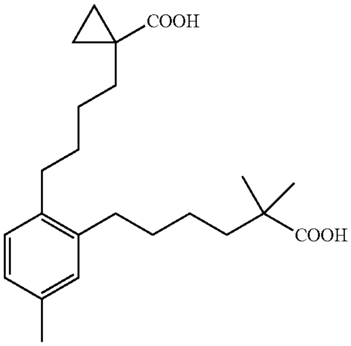 [SMILES: Cc1ccc(CCCCC2(C(=O)O)CC2)c(CCCCC(C)(C)C(=O)O)c1] |

TABLE A-7-continued
| Structure | Structure |
| --- | --- |
| 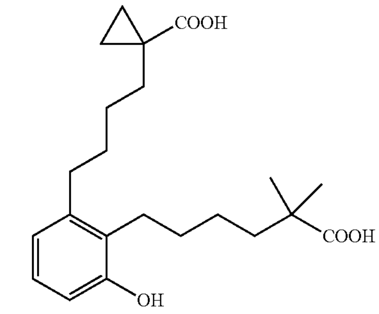 [SMILES: CC(C)(CCCCc1c(O)cccc1CCCCC1(C(=O)O)CC1)C(=O)O] | 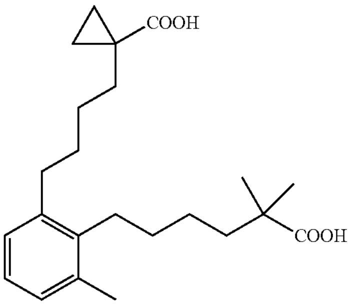 [SMILES: Cc1cccc(CCCCC2(C(=O)O)CC2)c1CCCCC(C)(C)C(=O)O] |
| 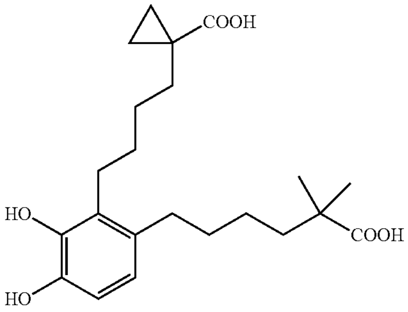 [SMILES: CC(C)(CCCCc1ccc(O)c(O)c1CCCCC1(C(=O)O)CC1)C(=O)O] | 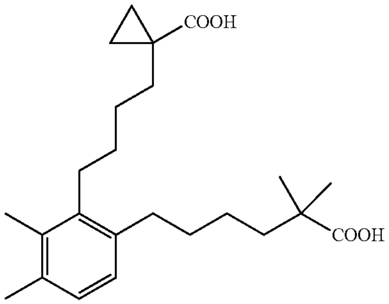 [SMILES: Cc1ccc(CCCCC(C)(C)C(=O)O)c(CCCCC2(C(=O)O)CC2)c1C] |
| 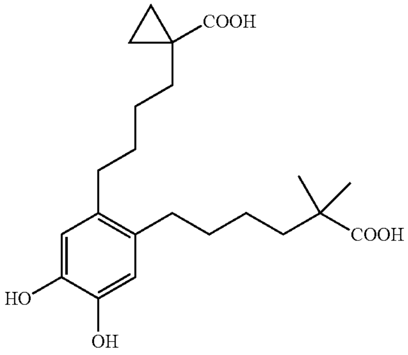 [SMILES: CC(C)(CCCCc1cc(O)c(O)cc1CCCCC1(C(=O)O)CC1)C(=O)O] | 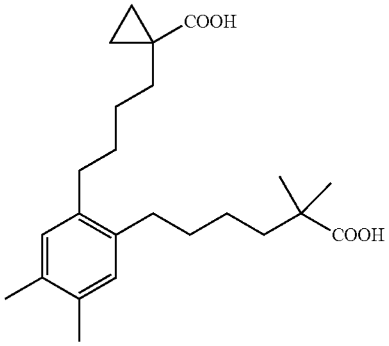 [SMILES: Cc1cc(CCCCC(C)(C)C(=O)O)c(CCCCC2(C(=O)O)CC2)cc1C] |
| 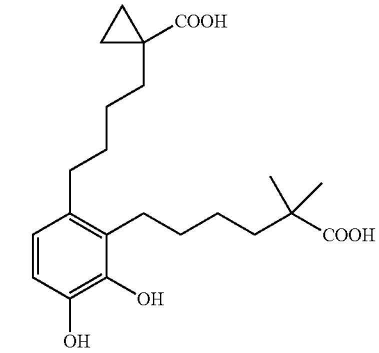 [SMILES: CC(C)(CCCCc1c(CCCCC2(C(=O)O)CC2)ccc(O)c1O)C(=O)O] | 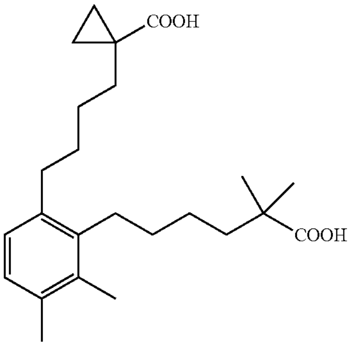 [SMILES: Cc1ccc(CCCCC2(C(=O)O)CC2)c(CCCCC(C)(C)C(=O)O)c1C] |

TABLE A-7-continued
| Structure | Structure |
| --- | --- |
| 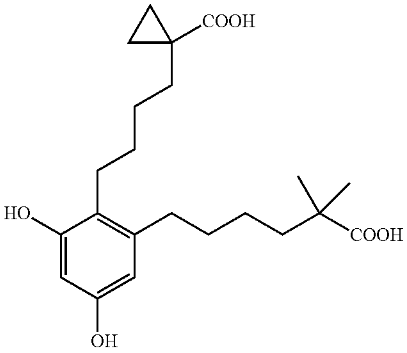 [SMILES: CC(C)(CCCCc1cc(O)cc(O)c1CCCCC1(C(=O)O)CC1)C(=O)O] | 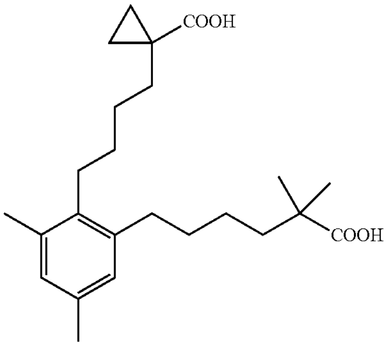 [SMILES: Cc1cc(C)c(CCCCC2(C(=O)O)CC2)c(CCCCC(C)(C)C(=O)O)c1] |
| 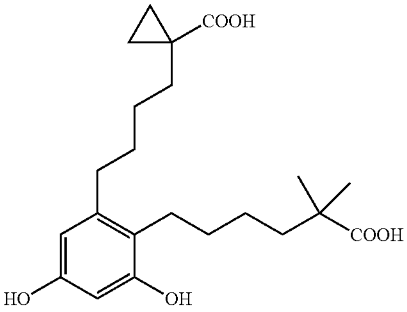 [SMILES: CC(C)(CCCCc1c(O)cc(O)cc1CCCCC1(C(=O)O)CC1)C(=O)O] | 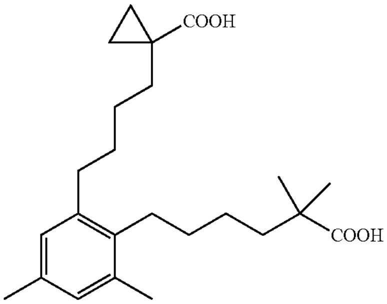 [SMILES: Cc1cc(C)c(CCCCC(C)(C)C(=O)O)c(CCCCC2(C(=O)O)CC2)c1] |
| 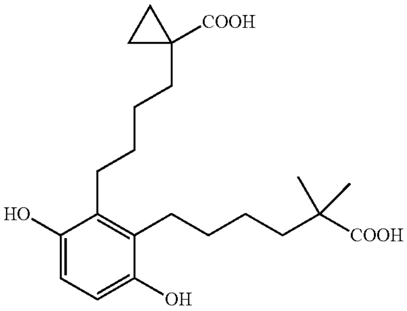 [SMILES: CC(C)(CCCCc1c(O)ccc(O)c1CCCCC1(C(=O)O)CC1)C(=O)O] | 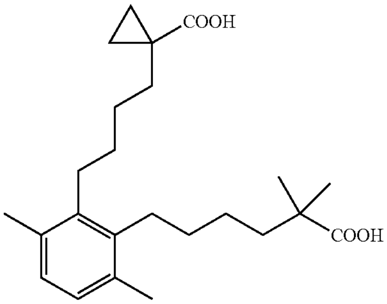 [SMILES: Cc1ccc(C)c(CCCCC2(C(=O)O)CC2)c1CCCCC(C)(C)C(=O)O] |
| 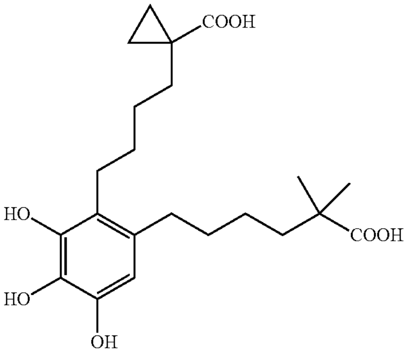 [SMILES: CC(C)(CCCCc1cc(O)c(O)c(O)c1CCCCC1(C(=O)O)CC1)C(=O)O] | 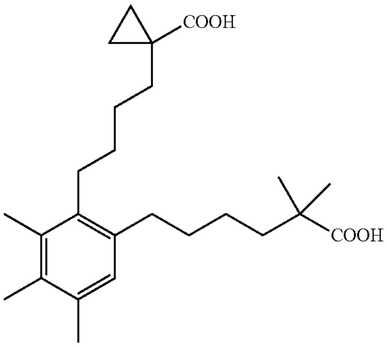 [SMILES: Cc1cc(CCCCC(C)(C)C(=O)O)c(CCCCC2(C(=O)O)CC2)c(C)c1C] |

TABLE A-7-continued
| Structure | Structure |
| --- | --- |
| 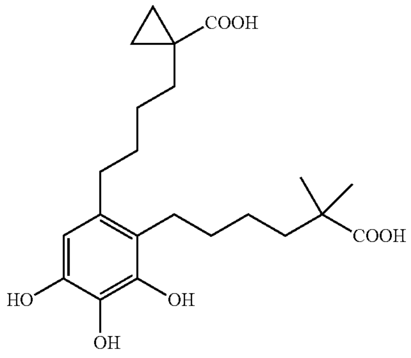 [SMILES: CC(C)(CCCCc1c(CCCCC2(C(=O)O)CC2)cc(O)c(O)c1O)C(=O)O] | 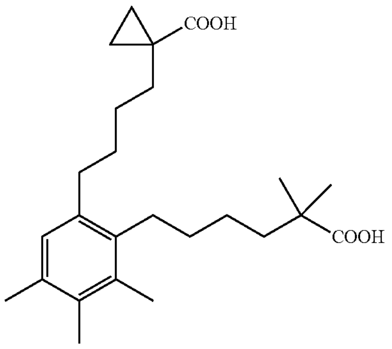 [SMILES: Cc1cc(CCCCC2(C(=O)O)CC2)c(CCCCC(C)(C)C(=O)O)c(C)c1C] |
| 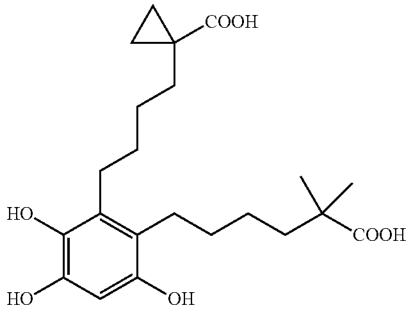 [SMILES: CC(C)(CCCCc1c(O)cc(O)c(O)c1CCCCC1(C(=O)O)CC1)C(=O)O] | 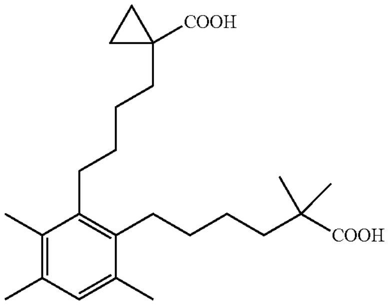 [SMILES: Cc1cc(C)c(CCCCC(C)(C)C(=O)O)c(CCCCC2(C(=O)O)CC2)c1C] |
| 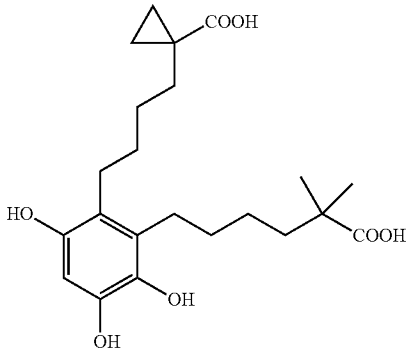 [SMILES: CC(C)(CCCCc1c(O)c(O)cc(O)c1CCCCC1(C(=O)O)CC1)C(=O)O] | 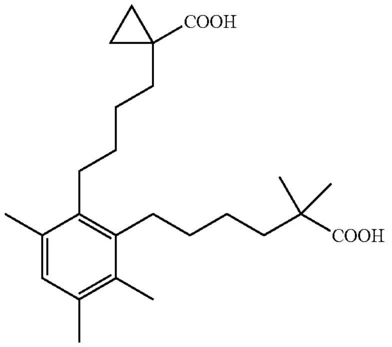 [SMILES: Cc1cc(C)c(CCCCC2(C(=O)O)CC2)c(CCCCC(C)(C)C(=O)O)c1C] |
| 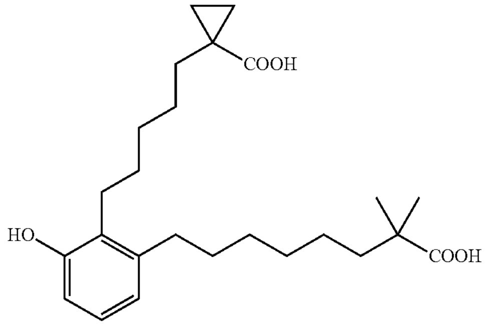 [SMILES: CC(C)(CCCCCCc1cccc(O)c1CCCCCC1(C(=O)O)CC1)C(=O)O] | 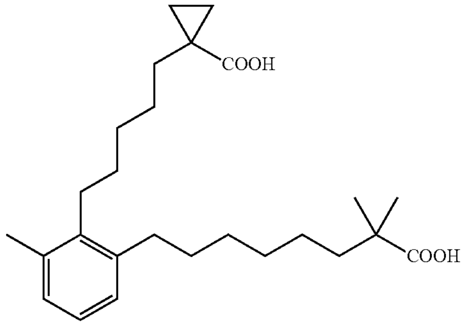 [SMILES: Cc1cccc(CCCCCCC(C)(C)C(=O)O)c1CCCCCC1(C(=O)O)CC1] |

TABLE A-7-continued
| Structure | Structure |
| --- | --- |
| 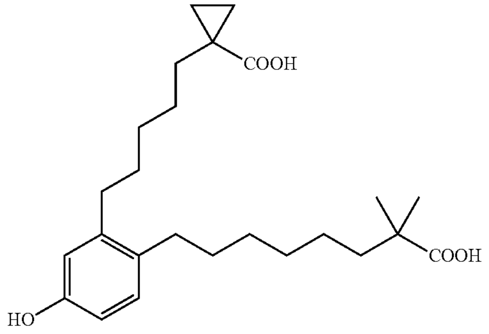 [SMILES: CC(C)(CCCCCCc1ccc(O)cc1CCCCCC1(C(=O)O)CC1)C(=O)O] | 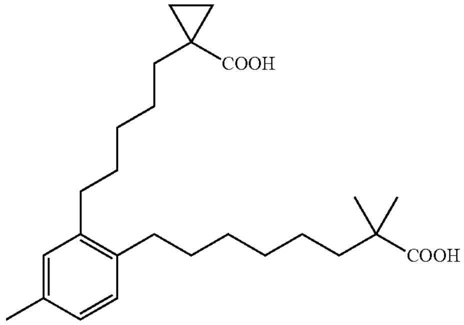 [SMILES: Cc1ccc(CCCCCCC(C)(C)C(=O)O)c(CCCCCC2(C(=O)O)CC2)c1] |
| 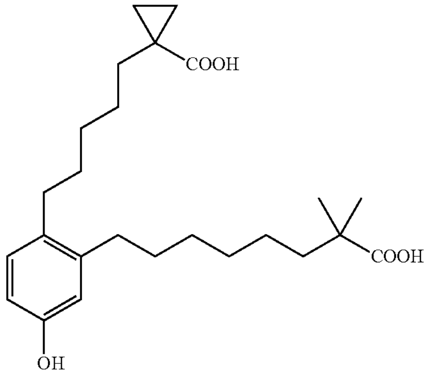 [SMILES: CC(C)(CCCCCCc1cc(O)ccc1CCCCCC1(C(=O)O)CC1)C(=O)O] | 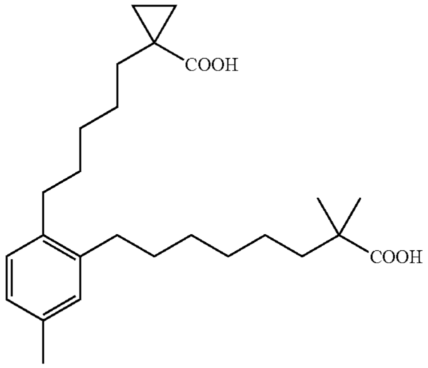 [SMILES: Cc1ccc(CCCCCC2(C(=O)O)CC2)c(CCCCCCC(C)(C)C(=O)O)c1] |
| 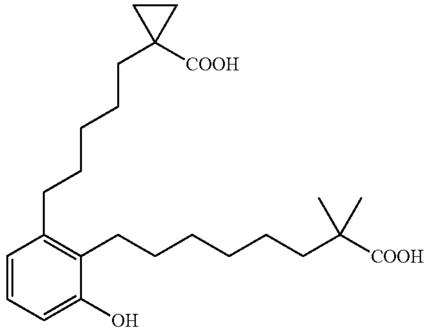 [SMILES: CC(C)(CCCCCCc1c(O)cccc1CCCCCC1(C(=O)O)CC1)C(=O)O] | 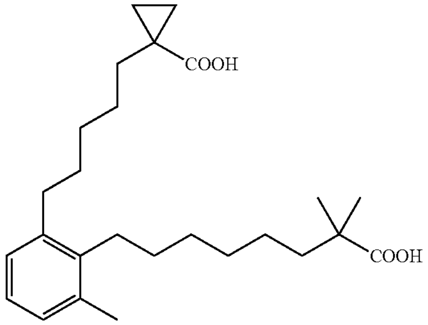 [SMILES: Cc1cccc(CCCCCC2(C(=O)O)CC2)c1CCCCCCC(C)(C)C(=O)O] |
| 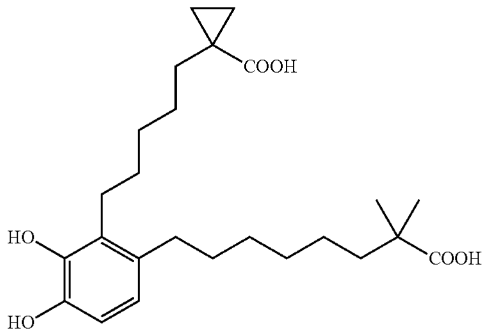 [SMILES: CC(C)(CCCCCCc1ccc(O)c(O)c1CCCCCC1(C(=O)O)CC1)C(=O)O] | 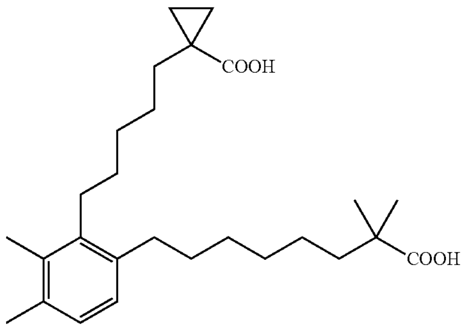 [SMILES: Cc1ccc(CCCCCCC(C)(C)C(=O)O)c(CCCCCC2(C(=O)O)CC2)c1C] |

TABLE A-7-continued
| Structure | Structure |
| --- | --- |
| 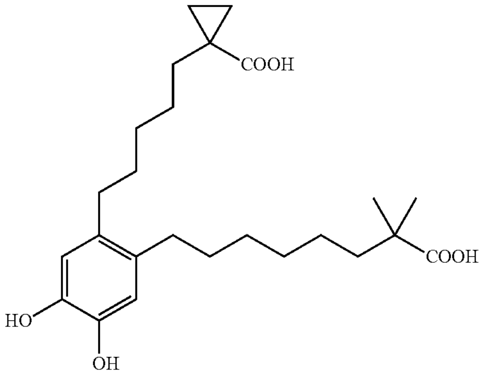 [SMILES: CC(C)(CCCCCCc1cc(O)c(O)cc1CCCCCC1(C(=O)O)CC1)C(=O)O] | 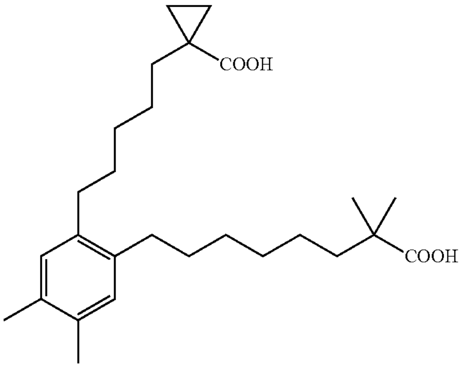 [SMILES: Cc1cc(CCCCCCC(C)(C)C(=O)O)c(CCCCCC2(C(=O)O)CC2)cc1C] |
| 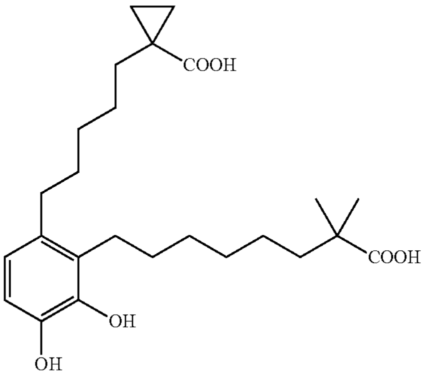 [SMILES: CC(C)(CCCCCCc1c(CCCCCC2(C(=O)O)CC2)ccc(O)c1O)C(=O)O] | 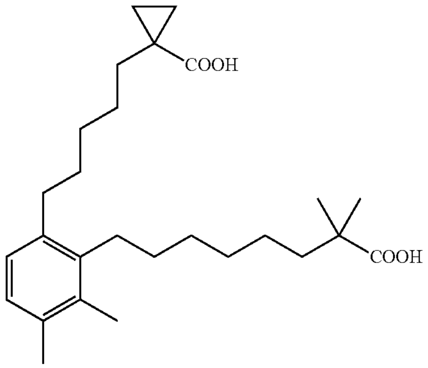 [SMILES: Cc1ccc(CCCCCC2(C(=O)O)CC2)c(CCCCCCC(C)(C)C(=O)O)c1C] |
| 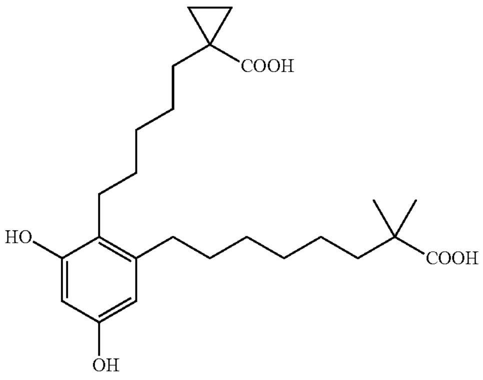 [SMILES: CC(C)(CCCCCCc1cc(O)cc(O)c1CCCCCC1(C(=O)O)CC1)C(=O)O] | 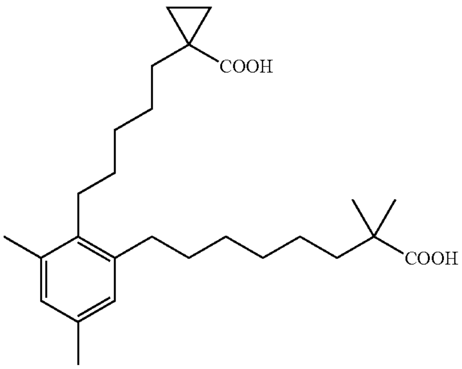 [SMILES: Cc1cc(C)c(CCCCCC2(C(=O)O)CC2)c(CCCCCCC(C)(C)C(=O)O)c1] |
| 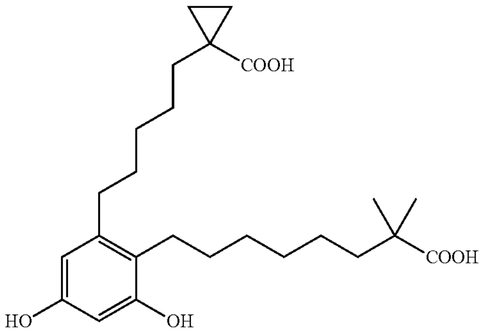 [SMILES: CC(C)(CCCCCCc1c(O)cc(O)cc1CCCCCC1(C(=O)O)CC1)C(=O)O] | 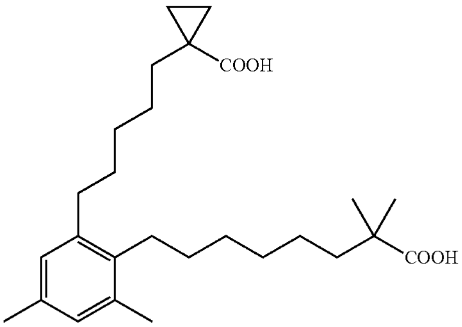 [SMILES: Cc1cc(C)c(CCCCCCC(C)(C)C(=O)O)c(CCCCCC2(C(=O)O)CC2)c1] |

TABLE A-7-continued
| Structure | Structure |
|---|---|
| 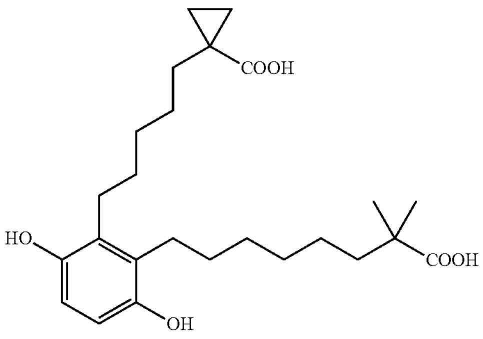 [SMILES: CC(C)(CCCCCCc1c(O)ccc(O)c1CCCCCC1(C(=O)O)CC1)C(=O)O] | 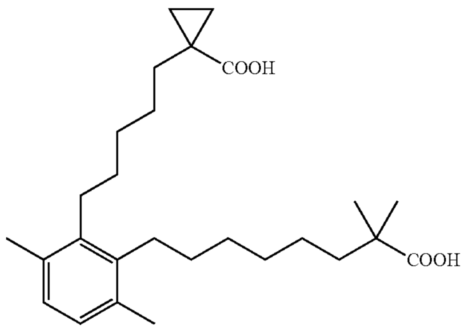 [SMILES: Cc1ccc(C)c(CCCCCC2(C(=O)O)CC2)c1CCCCCCC(C)(C)C(=O)O] |
| 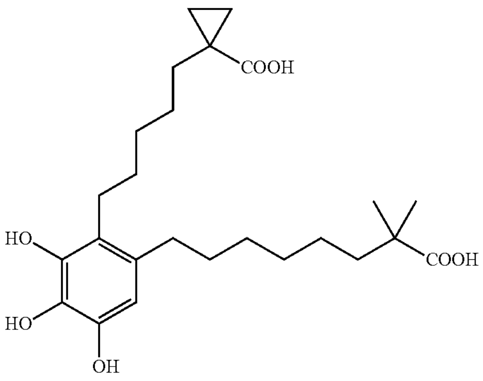 [SMILES: CC(C)(CCCCCCc1cc(O)c(O)c(O)c1CCCCCC1(C(=O)O)CC1)C(=O)O] | 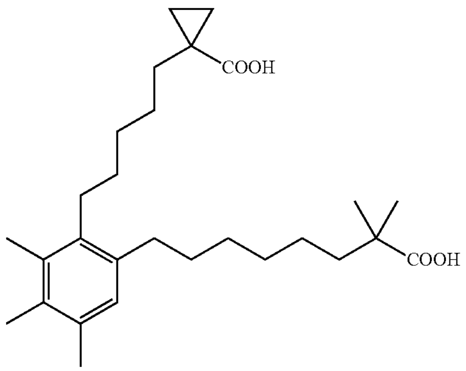 [SMILES: Cc1cc(CCCCCCC(C)(C)C(=O)O)c(CCCCCC2(C(=O)O)CC2)c(C)c1C] |
| 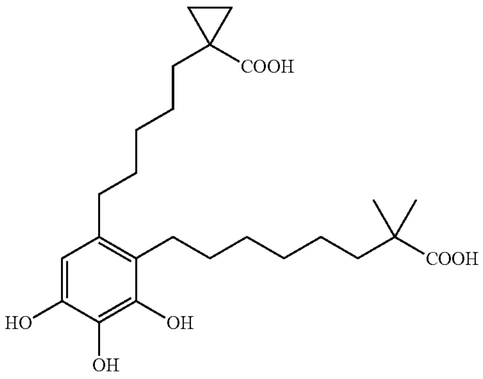 [SMILES: CC(C)(CCCCCCc1c(CCCCCC2(C(=O)O)CC2)cc(O)c(O)c1O)C(=O)O] | 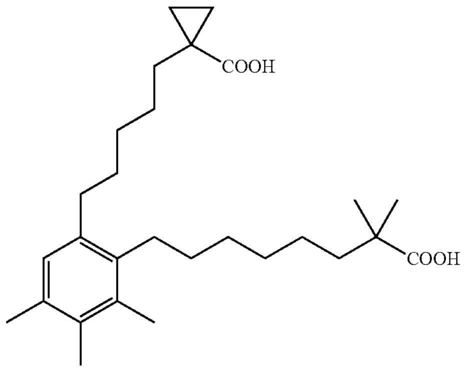 [SMILES: Cc1cc(CCCCCC2(C(=O)O)CC2)c(CCCCCCC(C)(C)C(=O)O)c(C)c1C] |
| 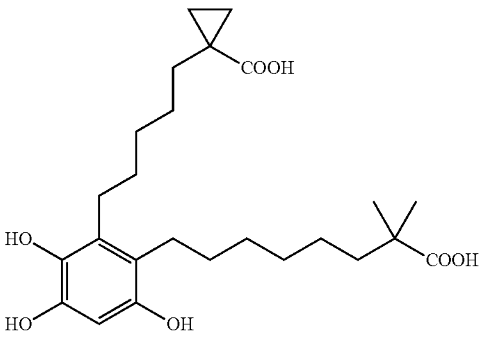 [SMILES: CC(C)(CCCCCCc1c(O)cc(O)c(O)c1CCCCCC1(C(=O)O)CC1)C(=O)O] | 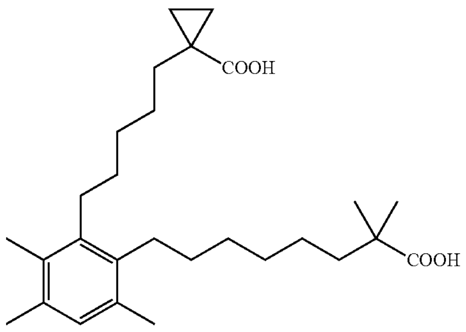 [SMILES: Cc1cc(C)c(CCCCCCC(C)(C)C(=O)O)c(CCCCCC2(C(=O)O)CC2)c1C] |

TABLE A-7-continued
| Structure | Structure |
| --- | --- |
| 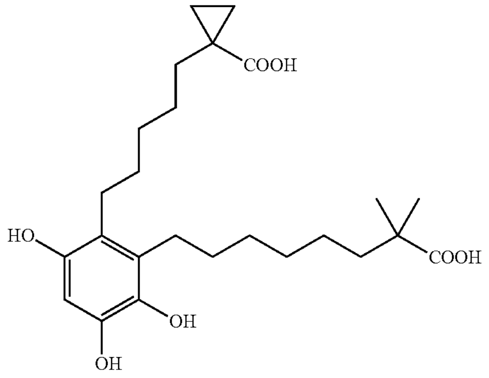 [SMILES: CC(C)(CCCCCCc1c(O)c(O)cc(O)c1CCCCCC1(C(=O)O)CC1)C(=O)O] | 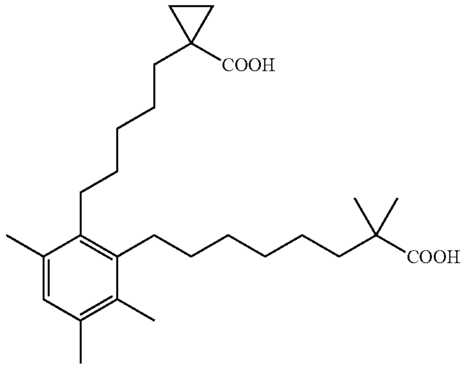 [SMILES: Cc1cc(C)c(CCCCCC2(C(=O)O)CC2)c(CCCCCCC(C)(C)C(=O)O)c1C] |
| 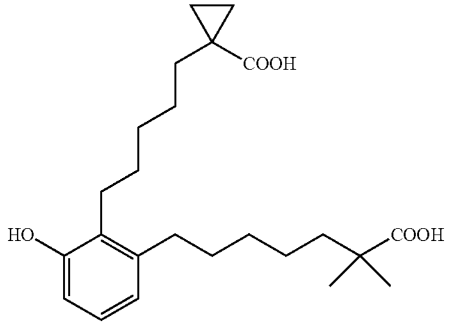 [SMILES: CC(C)(CCCCCc1cccc(O)c1CCCCCC1(C(=O)O)CC1)C(=O)O] | 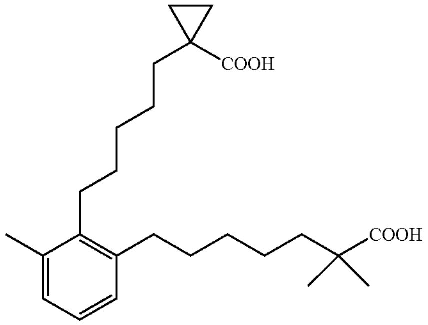 [SMILES: Cc1cccc(CCCCCC(C)(C)C(=O)O)c1CCCCCC1(C(=O)O)CC1] |
| 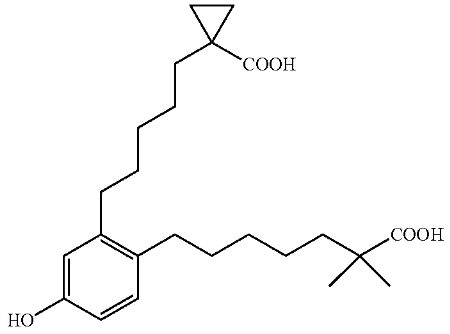 [SMILES: CC(C)(CCCCCc1ccc(O)cc1CCCCCC1(C(=O)O)CC1)C(=O)O] | 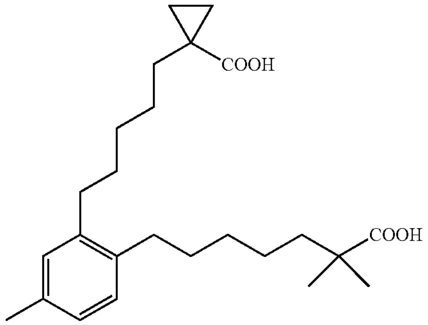 [SMILES: Cc1ccc(CCCCCC(C)(C)C(=O)O)c(CCCCCC2(C(=O)O)CC2)c1] |
| 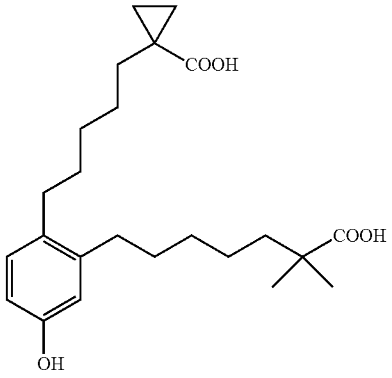 [SMILES: CC(C)(CCCCCc1cc(O)ccc1CCCCCC1(C(=O)O)CC1)C(=O)O] | 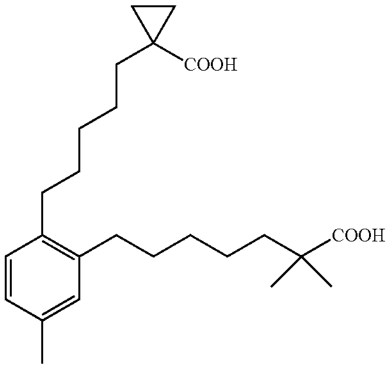 [SMILES: Cc1ccc(CCCCCC2(C(=O)O)CC2)c(CCCCCC(C)(C)C(=O)O)c1] |

TABLE A-7-continued
| Structure | Structure |
| --- | --- |
| 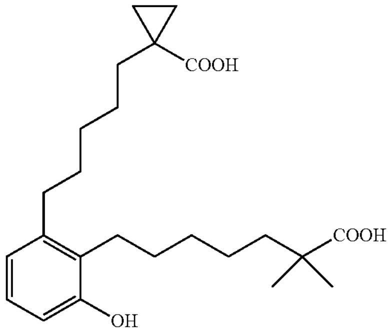 [SMILES: CC(C)(CCCCCc1c(O)cccc1CCCCCC1(C(=O)O)CC1)C(=O)O] | 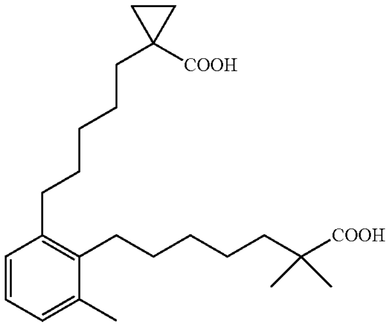 [SMILES: Cc1cccc(CCCCCC2(C(=O)O)CC2)c1CCCCCC(C)(C)C(=O)O] |
| 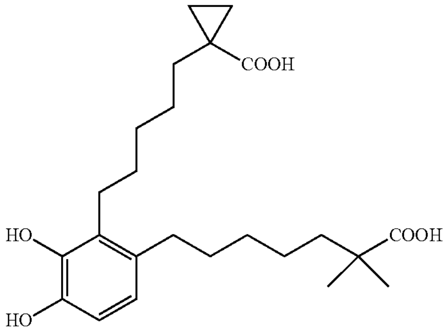 [SMILES: CC(C)(CCCCCc1ccc(O)c(O)c1CCCCCC1(C(=O)O)CC1)C(=O)O] | 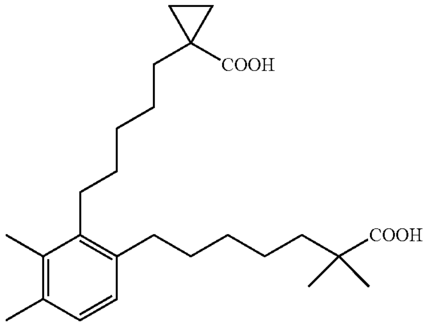 [SMILES: Cc1ccc(CCCCCC(C)(C)C(=O)O)c(CCCCCC2(C(=O)O)CC2)c1C] |
| 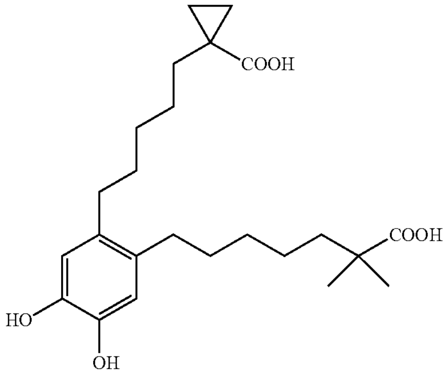 [SMILES: CC(C)(CCCCCc1cc(O)c(O)cc1CCCCCC1(C(=O)O)CC1)C(=O)O] | 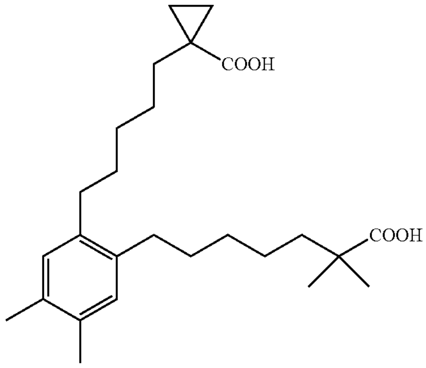 [SMILES: Cc1cc(CCCCCC(C)(C)C(=O)O)c(CCCCCC2(C(=O)O)CC2)cc1C] |
| 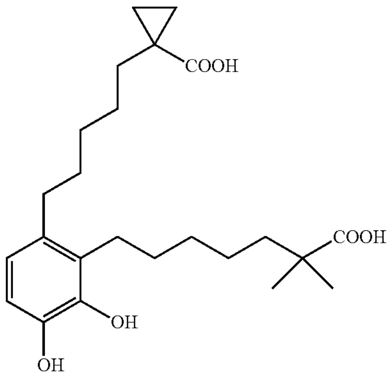 [SMILES: CC(C)(CCCCCc1c(CCCCCC2(C(=O)O)CC2)ccc(O)c1O)C(=O)O] | 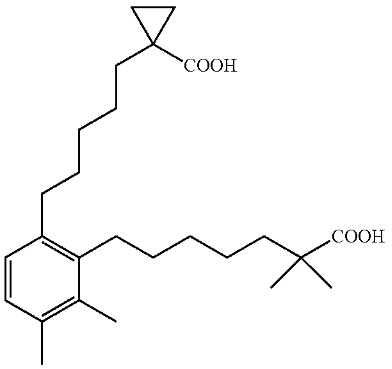 [SMILES: Cc1ccc(CCCCCC2(C(=O)O)CC2)c(CCCCCC(C)(C)C(=O)O)c1C] |

TABLE A-7-continued
| Structure | Structure |
| --- | --- |
| 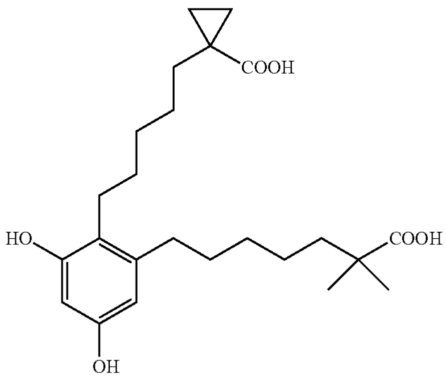 [SMILES: CC(C)(CCCCCc1cc(O)cc(O)c1CCCCCC1(C(=O)O)CC1)C(=O)O] | 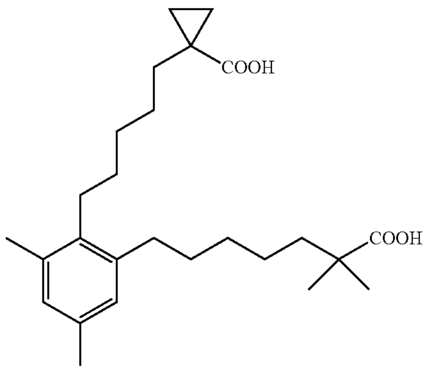 [SMILES: Cc1cc(C)c(CCCCCC2(C(=O)O)CC2)c(CCCCCC(C)(C)C(=O)O)c1] |
| 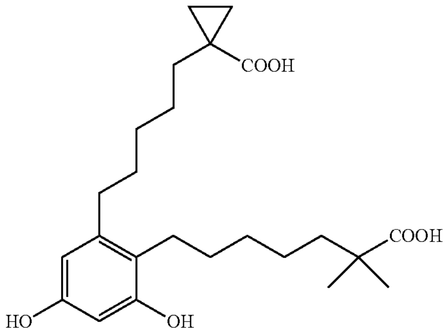 [SMILES: CC(C)(CCCCCc1c(O)cc(O)cc1CCCCCC1(C(=O)O)CC1)C(=O)O] | 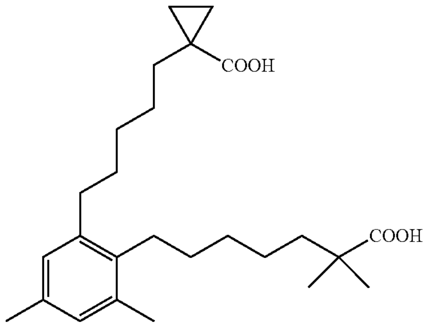 [SMILES: Cc1cc(C)c(CCCCCC(C)(C)C(=O)O)c(CCCCCC2(C(=O)O)CC2)c1] |
| 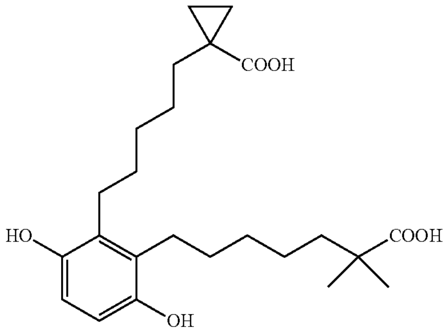 [SMILES: CC(C)(CCCCCc1c(O)ccc(O)c1CCCCCC1(C(=O)O)CC1)C(=O)O] | 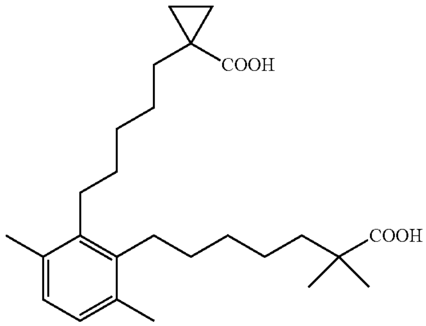 [SMILES: Cc1ccc(C)c(CCCCCC2(C(=O)O)CC2)c1CCCCCC(C)(C)C(=O)O] |
| 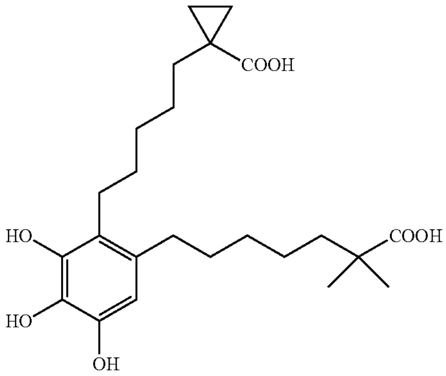 [SMILES: CC(C)(CCCCCc1cc(O)c(O)c(O)c1CCCCCC1(C(=O)O)CC1)C(=O)O] | 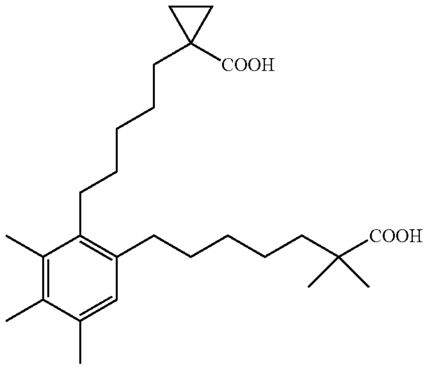 [SMILES: Cc1cc(CCCCCC(C)(C)C(=O)O)c(CCCCCC2(C(=O)O)CC2)c(C)c1C] |

TABLE A-7-continued
| Structure | Structure |
|---|---|
| 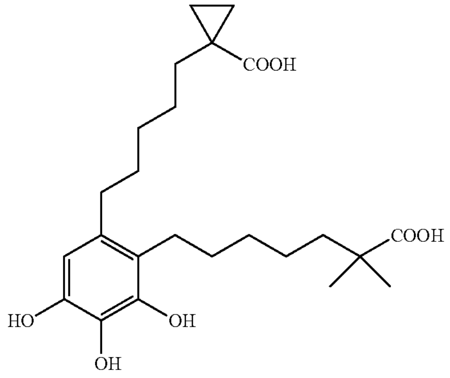 [SMILES: CC(C)(CCCCCc1c(CCCCCC2(C(=O)O)CC2)cc(O)c(O)c1O)C(=O)O] | 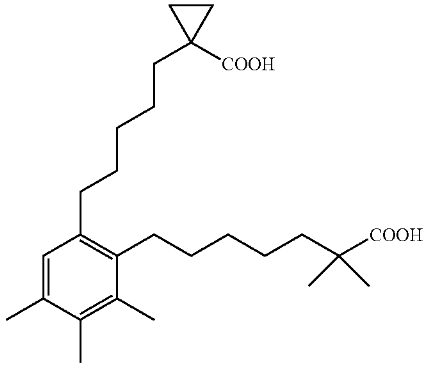 [SMILES: Cc1cc(CCCCCC2(C(=O)O)CC2)c(CCCCCC(C)(C)C(=O)O)c(C)c1C] |
| 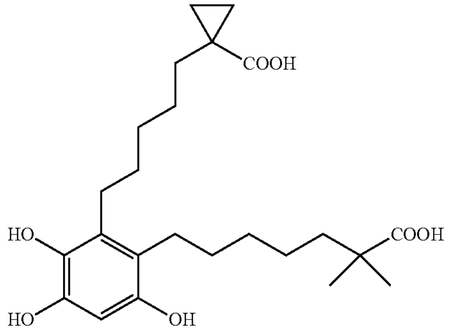 [SMILES: CC(C)(CCCCCc1c(O)cc(O)c(O)c1CCCCCC1(C(=O)O)CC1)C(=O)O] | 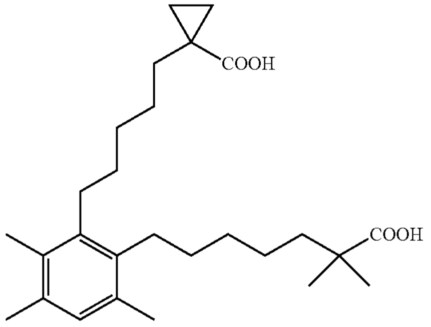 [SMILES: Cc1cc(C)c(CCCCCC(C)(C)C(=O)O)c(CCCCCC2(C(=O)O)CC2)c1C] |
| 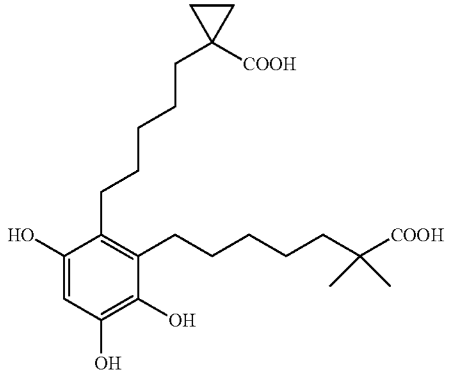 [SMILES: CC(C)(CCCCCc1c(O)c(O)cc(O)c1CCCCCC1(C(=O)O)CC1)C(=O)O] | 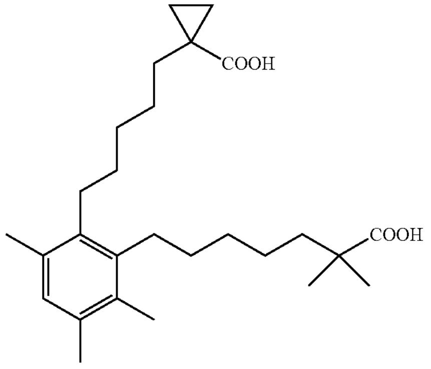 [SMILES: Cc1cc(C)c(CCCCCC2(C(=O)O)CC2)c(CCCCCC(C)(C)C(=O)O)c1C] |
| 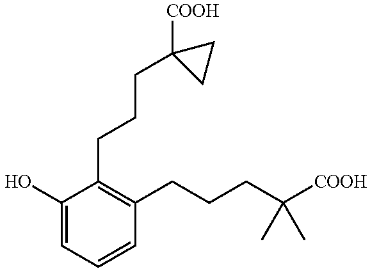 [SMILES: CC(C)(CCCc1cccc(O)c1CCCC1(C(=O)O)CC1)C(=O)O] | 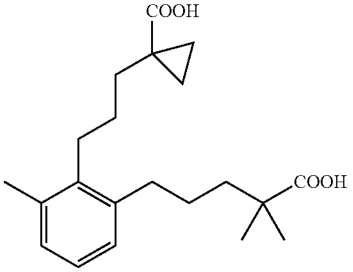 [SMILES: Cc1cccc(CCCC(C)(C)C(=O)O)c1CCCC1(C(=O)O)CC1] |

TABLE A-7-continued
| Structure | Structure |
| --- | --- |
| 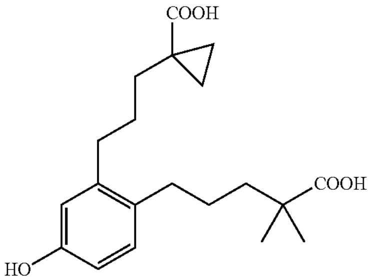 [SMILES: CC(C)(CCCc1ccc(O)cc1CCCC1(C(=O)O)CC1)C(=O)O] | 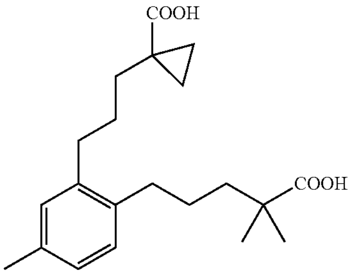 [SMILES: Cc1ccc(CCCC(C)(C)C(=O)O)c(CCCC2(C(=O)O)CC2)c1] |
| 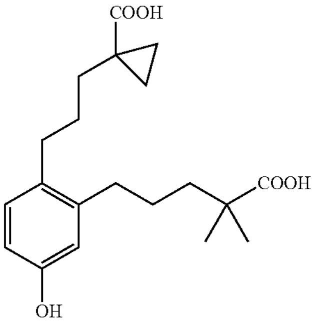 [SMILES: CC(C)(CCCc1cc(O)ccc1CCCC1(C(=O)O)CC1)C(=O)O] | 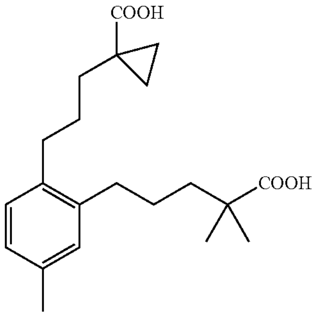 [SMILES: Cc1ccc(CCCC2(C(=O)O)CC2)c(CCCC(C)(C)C(=O)O)c1] |
| 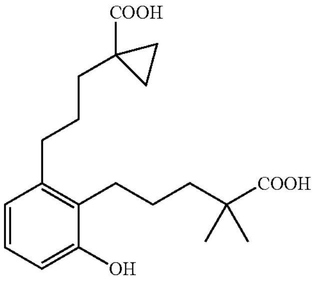 [SMILES: CC(C)(CCCc1c(O)cccc1CCCC1(C(=O)O)CC1)C(=O)O] | 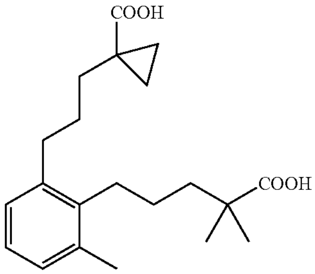 [SMILES: Cc1cccc(CCCC2(C(=O)O)CC2)c1CCCC(C)(C)C(=O)O] |
| 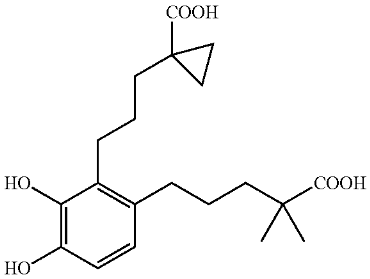 [SMILES: CC(C)(CCCc1ccc(O)c(O)c1CCCC1(C(=O)O)CC1)C(=O)O] | 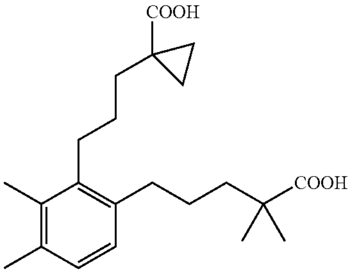 [SMILES: Cc1ccc(CCCC(C)(C)C(=O)O)c(CCCC2(C(=O)O)CC2)c1C] |
| 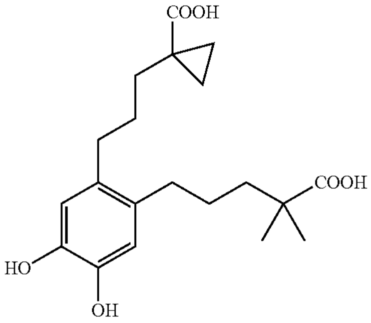 [SMILES: CC(C)(CCCc1cc(O)c(O)cc1CCCC1(C(=O)O)CC1)C(=O)O] | 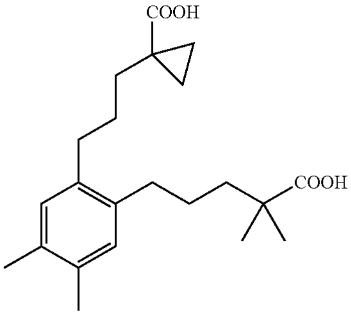 [SMILES: Cc1cc(CCCC(C)(C)C(=O)O)c(CCCC2(C(=O)O)CC2)cc1C] |

TABLE A-7-continued
| Structure | Structure |
| --- | --- |
| 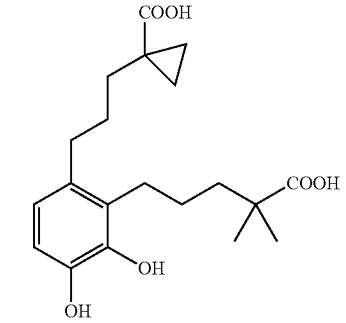 [SMILES: CC(C)(CCCc1c(CCCC2(C(=O)O)CC2)ccc(O)c1O)C(=O)O] | 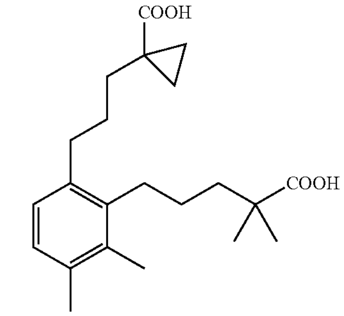 [SMILES: Cc1ccc(CCCC2(C(=O)O)CC2)c(CCCC(C)(C)C(=O)O)c1C] |
| 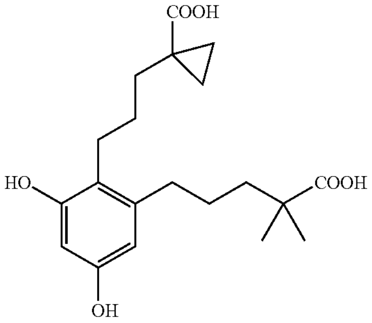 [SMILES: CC(C)(CCCc1cc(O)cc(O)c1CCCC1(C(=O)O)CC1)C(=O)O] | 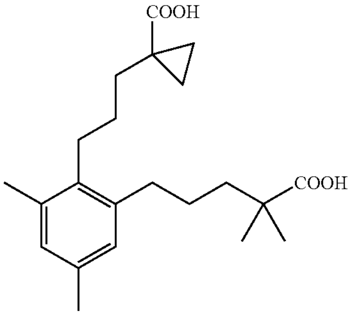 [SMILES: Cc1cc(C)c(CCCC2(C(=O)O)CC2)c(CCCC(C)(C)C(=O)O)c1] |
| 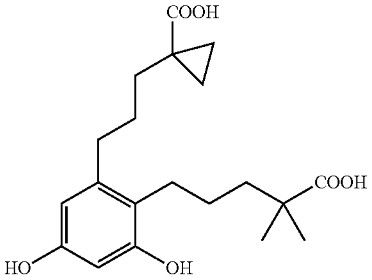 [SMILES: CC(C)(CCCc1c(O)cc(O)cc1CCCC1(C(=O)O)CC1)C(=O)O] | 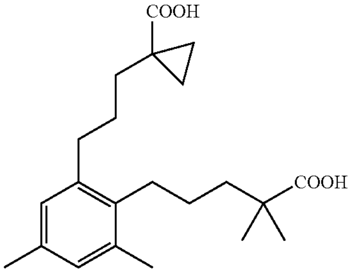 [SMILES: Cc1cc(C)c(CCCC(C)(C)C(=O)O)c(CCCC2(C(=O)O)CC2)c1] |
| 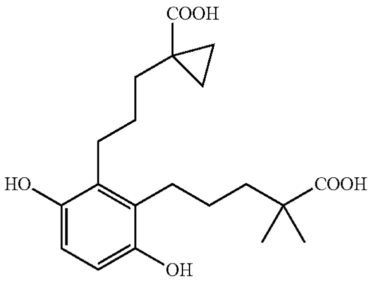 [SMILES: CC(C)(CCCc1c(O)ccc(O)c1CCCC1(C(=O)O)CC1)C(=O)O] | 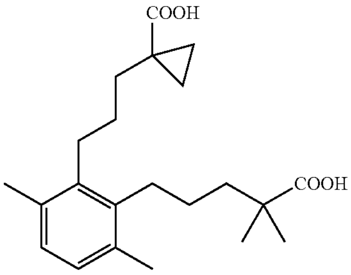 [SMILES: Cc1ccc(C)c(CCCC2(C(=O)O)CC2)c1CCCC(C)(C)C(=O)O] |
| 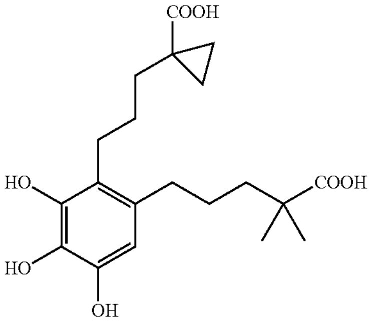 [SMILES: CC(C)(CCCc1cc(O)c(O)c(O)c1CCCC1(C(=O)O)CC1)C(=O)O] | 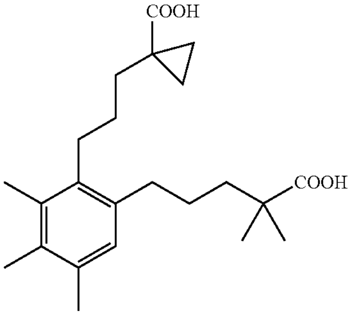 [SMILES: Cc1cc(CCCC(C)(C)C(=O)O)c(CCCC2(C(=O)O)CC2)c(C)c1C] |

TABLE A-7-continued
| Structure | Structure |
| --- | --- |
| 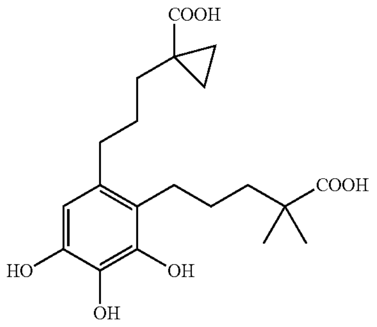 [SMILES: CC(C)(CCCc1c(CCCC2(C(=O)O)CC2)cc(O)c(O)c1O)C(=O)O] | 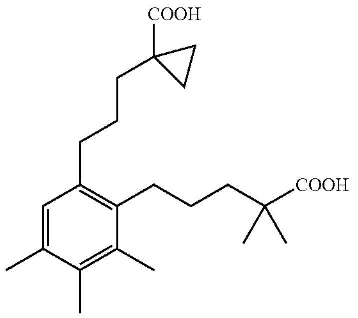 [SMILES: Cc1cc(CCCC2(C(=O)O)CC2)c(CCCC(C)(C)C(=O)O)c(C)c1C] |
| 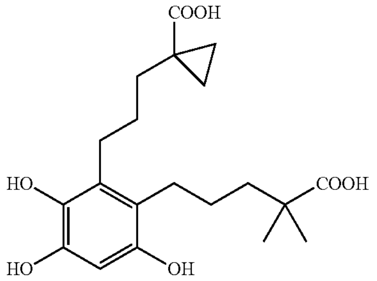 [SMILES: CC(C)(CCCc1c(O)cc(O)c(O)c1CCCC1(C(=O)O)CC1)C(=O)O] | 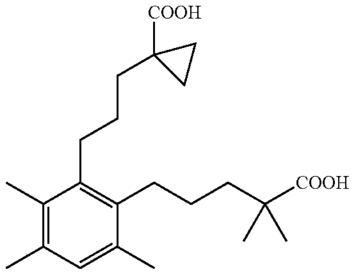 [SMILES: Cc1cc(C)c(CCCC(C)(C)C(=O)O)c(CCCC2(C(=O)O)CC2)c1C] |
| 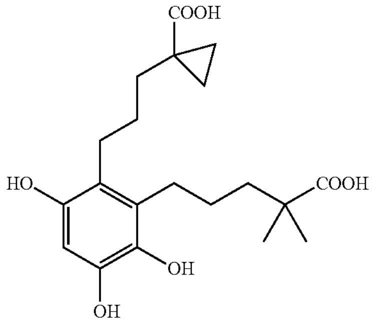 [SMILES: CC(C)(CCCc1c(O)c(O)cc(O)c1CCCC1(C(=O)O)CC1)C(=O)O] | 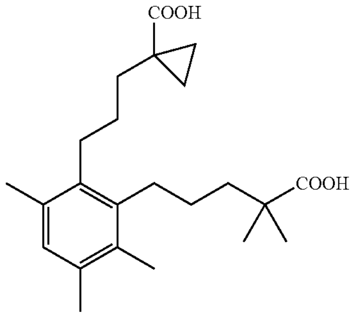 [SMILES: Cc1cc(C)c(CCCC2(C(=O)O)CC2)c(CCCC(C)(C)C(=O)O)c1C] |
| 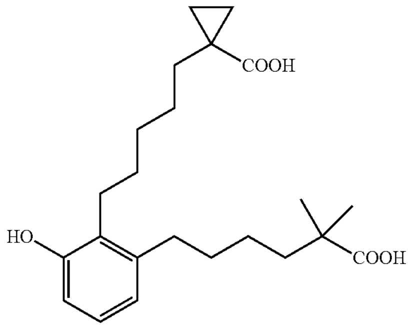 [SMILES: CC(C)(CCCCc1cccc(O)c1CCCCCC1(C(=O)O)CC1)C(=O)O] | 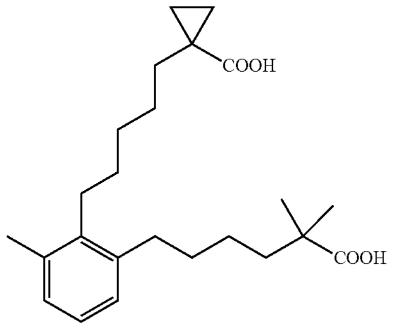 [SMILES: Cc1cccc(CCCCC(C)(C)C(=O)O)c1CCCCCC1(C(=O)O)CC1] |
| 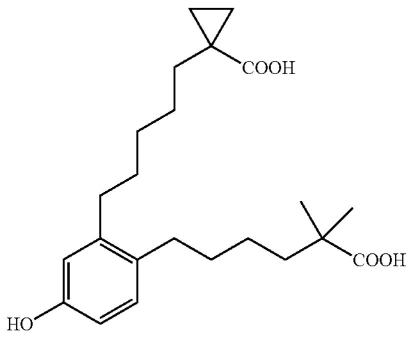 [SMILES: CC(C)(CCCCc1ccc(O)cc1CCCCCC1(C(=O)O)CC1)C(=O)O] | 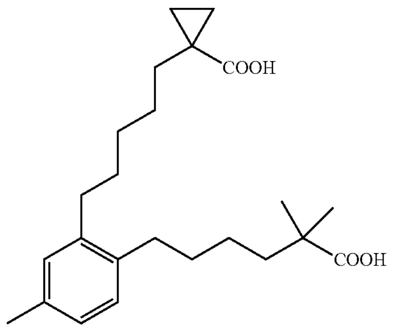 [SMILES: Cc1ccc(CCCCC(C)(C)C(=O)O)c(CCCCCC2(C(=O)O)CC2)c1] |

TABLE A-7-continued
| Structure | Structure |
| --- | --- |
| 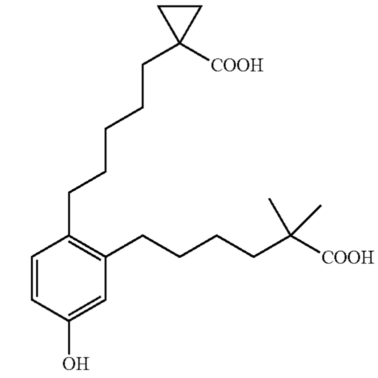 [SMILES: CC(C)(CCCCc1cc(O)ccc1CCCCCC1(C(=O)O)CC1)C(=O)O] | 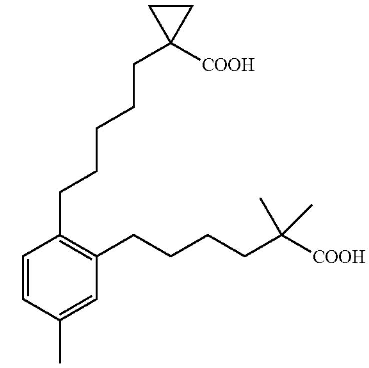 [SMILES: Cc1ccc(CCCCCC2(C(=O)O)CC2)c(CCCCC(C)(C)C(=O)O)c1] |
| 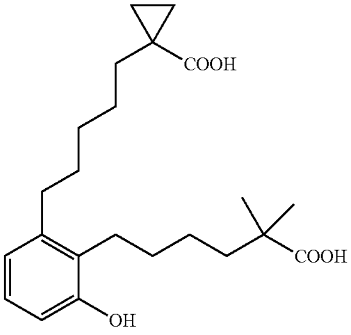 [SMILES: CC(C)(CCCCc1c(O)cccc1CCCCCC1(C(=O)O)CC1)C(=O)O] | 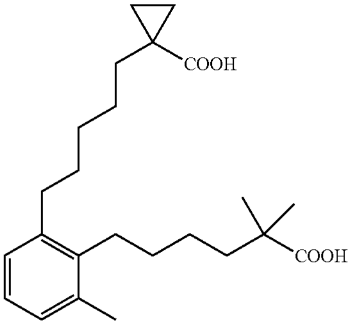 [SMILES: Cc1cccc(CCCCCC2(C(=O)O)CC2)c1CCCCC(C)(C)C(=O)O] |
| 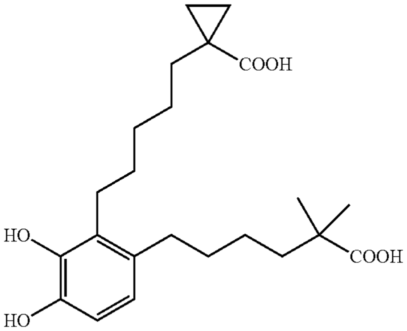 [SMILES: CC(C)(CCCCc1ccc(O)c(O)c1CCCCCC1(C(=O)O)CC1)C(=O)O] | 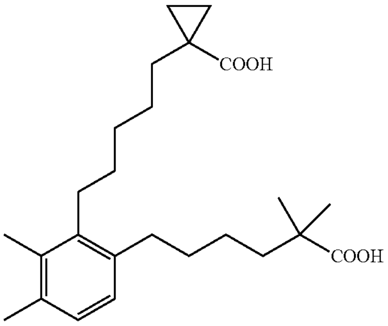 [SMILES: Cc1ccc(CCCCC(C)(C)C(=O)O)c(CCCCCC2(C(=O)O)CC2)c1C] |
| 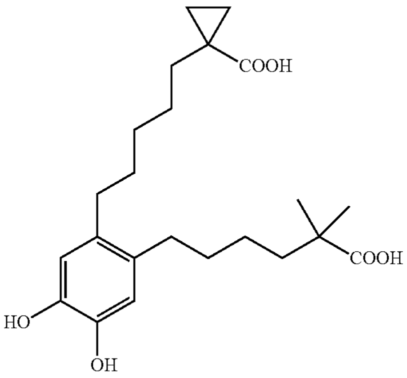 [SMILES: CC(C)(CCCCc1cc(O)c(O)cc1CCCCCC1(C(=O)O)CC1)C(=O)O] | 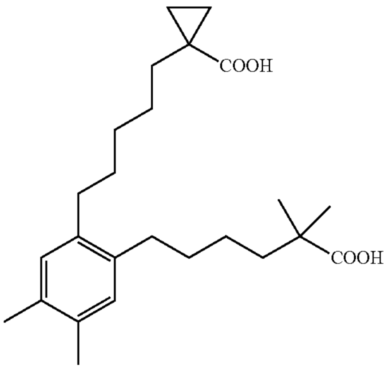 [SMILES: Cc1cc(CCCCCC2(C(=O)O)CC2)c(CCCCC(C)(C)C(=O)O)cc1C] |

TABLE A-7-continued
| Structure | Structure |
|---|---|
| 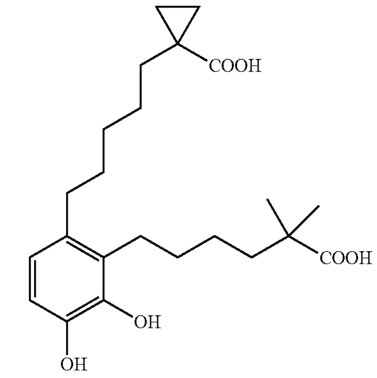 [SMILES: CC(C)(CCCCc1c(CCCCCC2(C(=O)O)CC2)ccc(O)c1O)C(=O)O] | 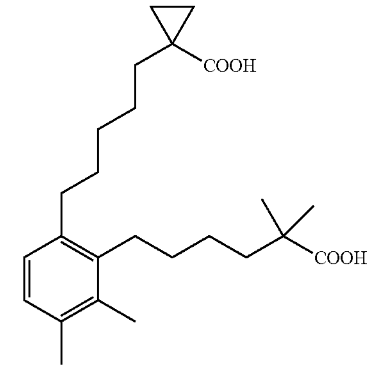 [SMILES: Cc1ccc(CCCCCC2(C(=O)O)CC2)c(CCCCC(C)(C)C(=O)O)c1C] |
| 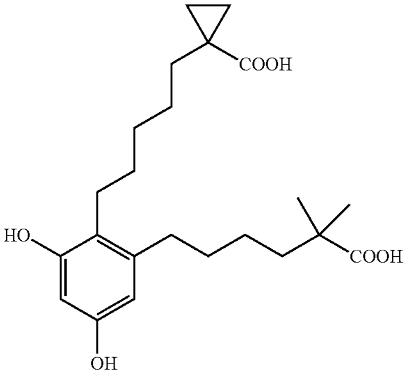 [SMILES: CC(C)(CCCCc1cc(O)cc(O)c1CCCCCC1(C(=O)O)CC1)C(=O)O] | 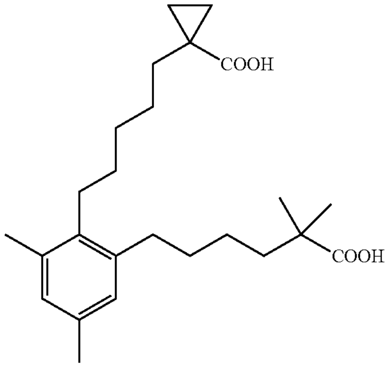 [SMILES: Cc1cc(C)c(CCCCCC2(C(=O)O)CC2)c(CCCCC(C)(C)C(=O)O)c1] |
| 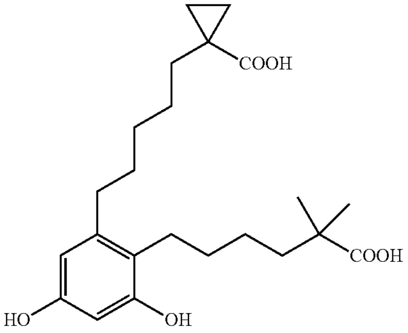 [SMILES: CC(C)(CCCCc1c(O)cc(O)cc1CCCCCC1(C(=O)O)CC1)C(=O)O] | 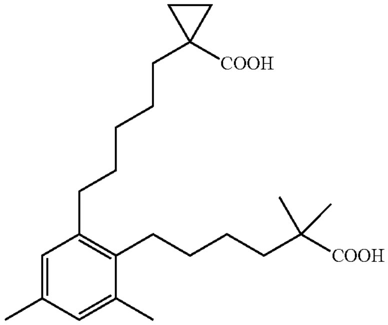 [SMILES: Cc1cc(C)c(CCCCC(C)(C)C(=O)O)c(CCCCCC2(C(=O)O)CC2)c1] |
| 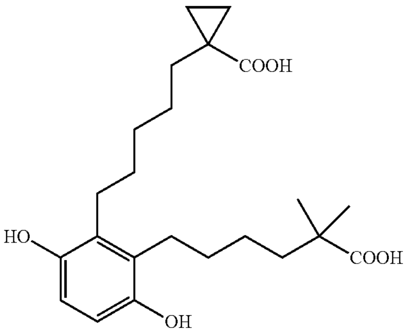 [SMILES: CC(C)(CCCCc1c(O)ccc(O)c1CCCCCC1(C(=O)O)CC1)C(=O)O] | 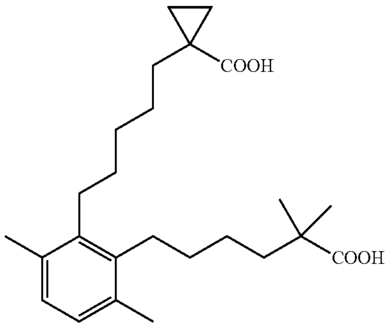 [SMILES: Cc1ccc(C)c(CCCCC(C)(C)C(=O)O)c1CCCCCC1(C(=O)O)CC1] |

TABLE A-7-continued
| Structure | Structure |
| --- | --- |
| 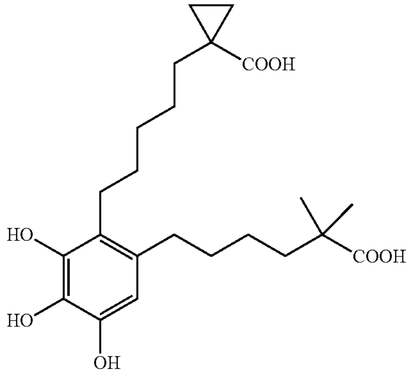 [SMILES: CC(C)(CCCCc1cc(O)c(O)c(O)c1CCCCCC1(C(=O)O)CC1)C(=O)O] | 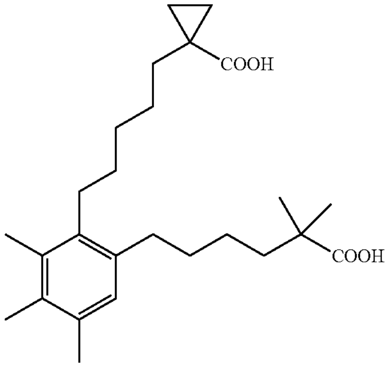 [SMILES: Cc1cc(CCCCC(C)(C)C(=O)O)c(CCCCCC2(C(=O)O)CC2)c(C)c1C] |
| 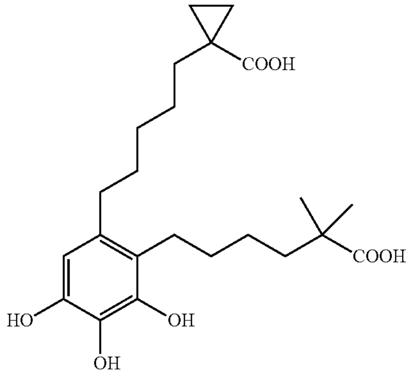 [SMILES: CC(C)(CCCCc1c(CCCCCC2(C(=O)O)CC2)cc(O)c(O)c1O)C(=O)O] | 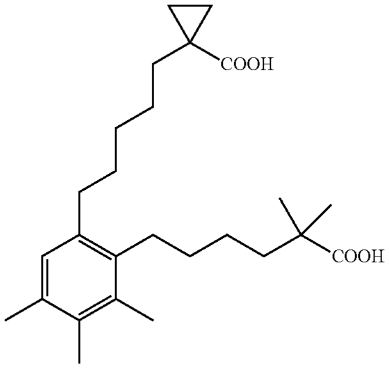 [SMILES: Cc1cc(CCCCCC2(C(=O)O)CC2)c(CCCCC(C)(C)C(=O)O)c(C)c1C] |
| 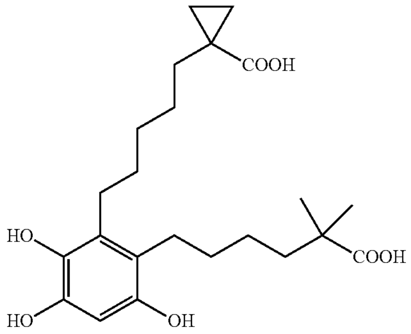 [SMILES: CC(C)(CCCCc1c(O)cc(O)c(O)c1CCCCCC1(C(=O)O)CC1)C(=O)O] | 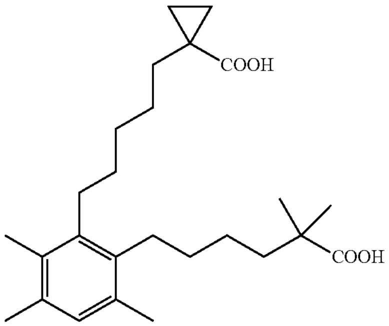 [SMILES: Cc1cc(C)c(CCCCC(C)(C)C(=O)O)c(CCCCCC2(C(=O)O)CC2)c1C] |
| 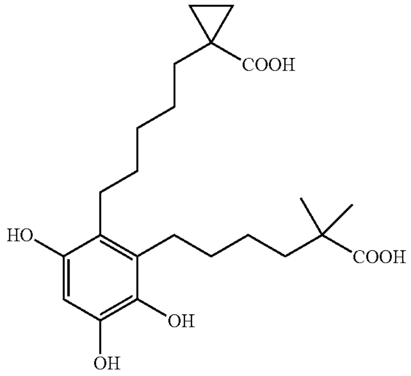 [SMILES: CC(C)(CCCCc1c(O)c(O)cc(O)c1CCCCCC1(C(=O)O)CC1)C(=O)O] | 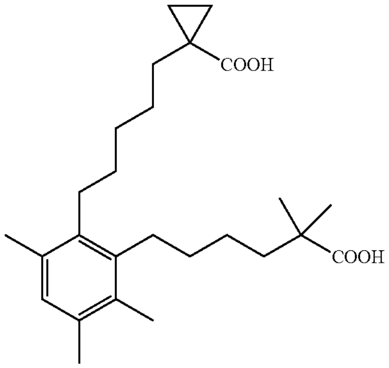 [SMILES: Cc1cc(C)c(CCCCCC2(C(=O)O)CC2)c(CCCCC(C)(C)C(=O)O)c1C] |

TABLE A-7-continued
| Structure | Structure |
| --- | --- |
| 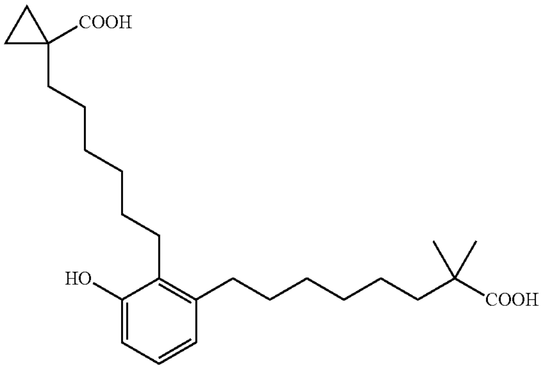 [SMILES: CC(C)(CCCCCCc1cccc(O)c1CCCCCCC1(C(=O)O)CC1)C(=O)O] | 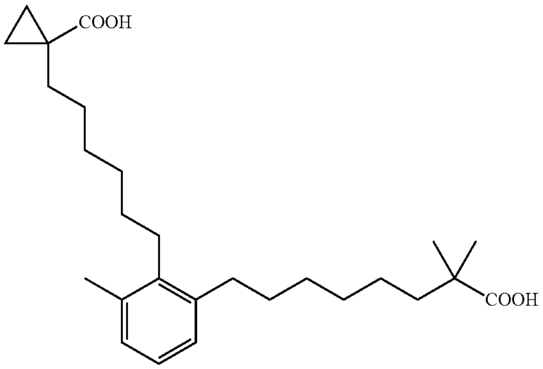 [SMILES: Cc1cccc(CCCCCCC(C)(C)C(=O)O)c1CCCCCCC1(C(=O)O)CC1] |
| 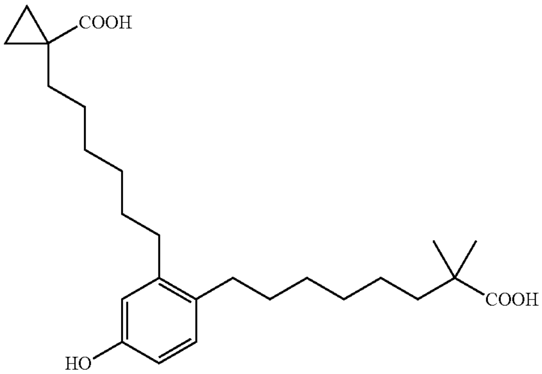 [SMILES: CC(C)(CCCCCCc1ccc(O)cc1CCCCCCC1(C(=O)O)CC1)C(=O)O] | 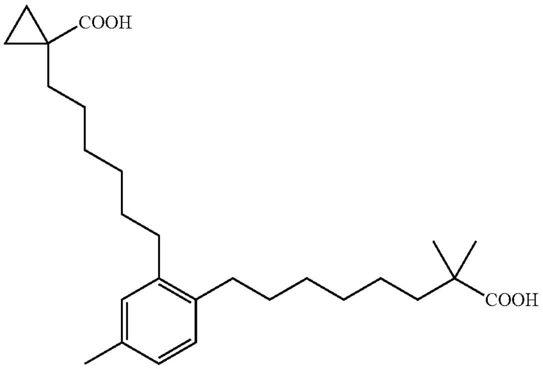 |
| 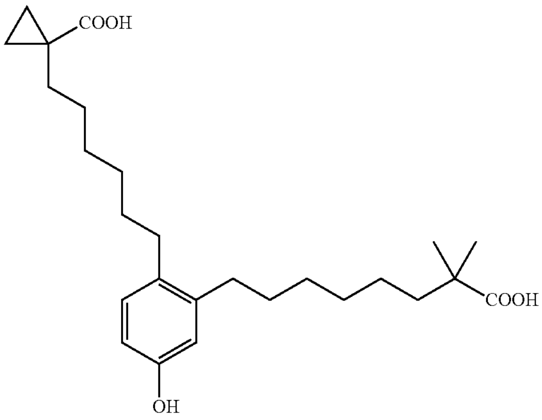 [SMILES: CC(C)(CCCCCCc1cc(O)ccc1CCCCCCC1(C(=O)O)CC1)C(=O)O] | 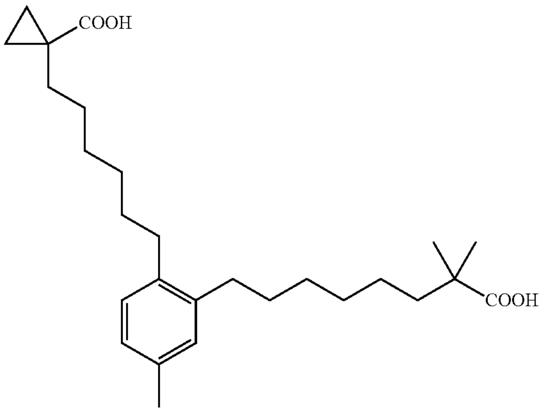 [SMILES: Cc1ccc(CCCCCCC2(C(=O)O)CC2)c(CCCCCCC(C)(C)C(=O)O)c1] |
| 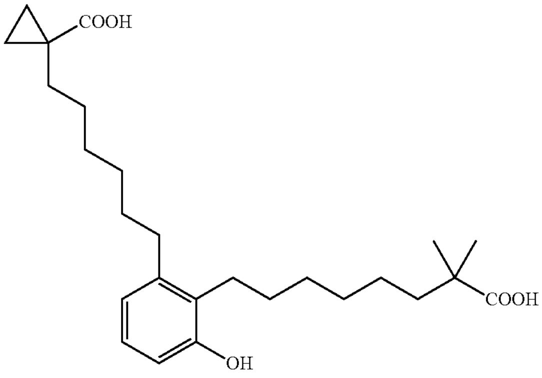 [SMILES: CC(C)(CCCCCCc1c(O)cccc1CCCCCCC1(C(=O)O)CC1)C(=O)O] | 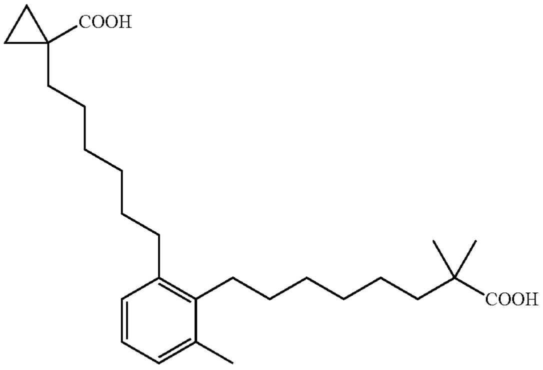 |

TABLE A-7-continued
| Structure | Structure |
| --- | --- |
| 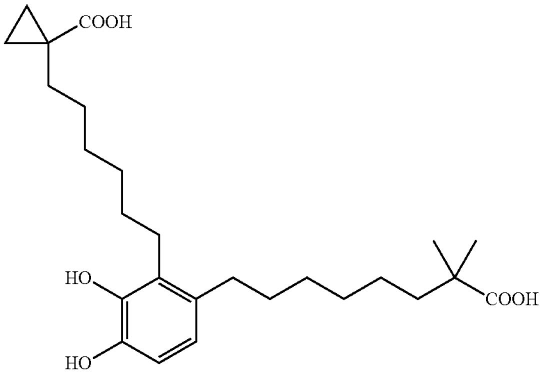 [SMILES: CC(C)(CCCCCCc1ccc(O)c(O)c1CCCCCCC1(C(=O)O)CC1)C(=O)O] | 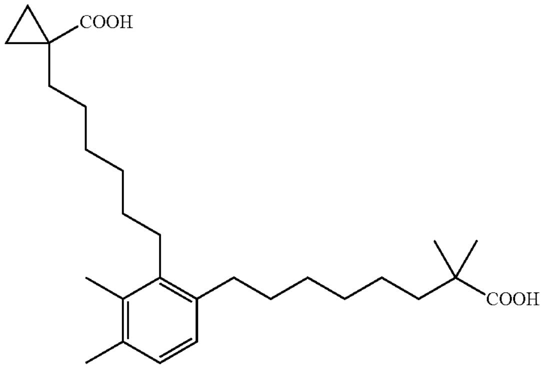 [SMILES: Cc1ccc(CCCCCCC(C)(C)C(=O)O)c(CCCCCCC2(C(=O)O)CC2)c1C] |
| 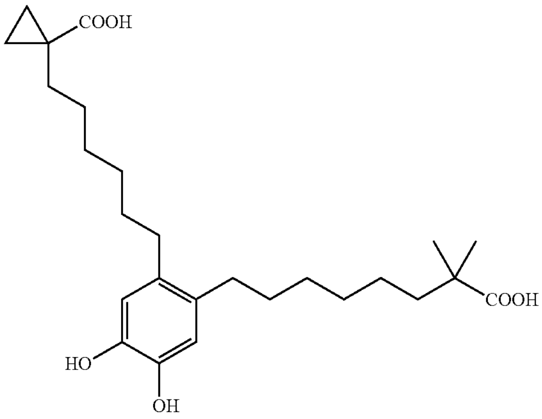 [SMILES: CC(C)(CCCCCCc1cc(O)c(O)cc1CCCCCCC1(C(=O)O)CC1)C(=O)O] | 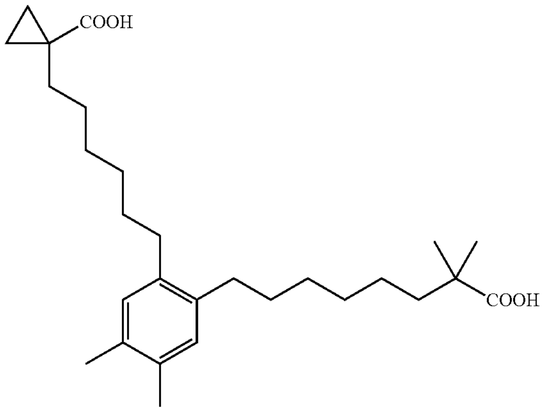 [SMILES: Cc1cc(CCCCCCC(C)(C)C(=O)O)c(CCCCCCC2(C(=O)O)CC2)cc1C] |
| 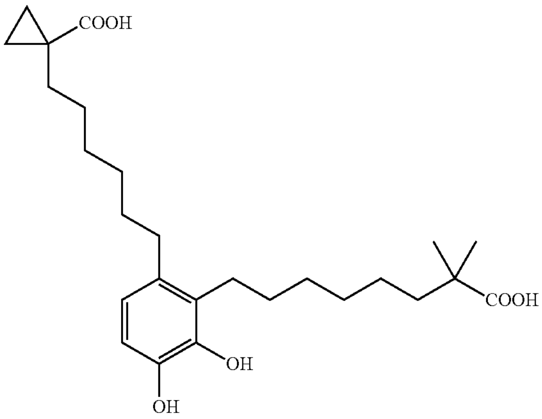 [SMILES: CC(C)(CCCCCCc1c(CCCCCCC2(C(=O)O)CC2)ccc(O)c1O)C(=O)O] | 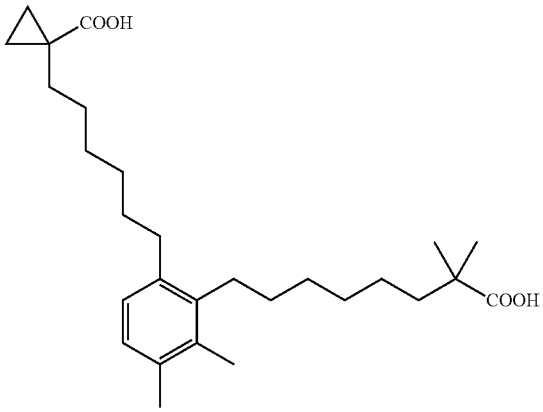 [SMILES: Cc1ccc(CCCCCCC2(C(=O)O)CC2)c(CCCCCCC(C)(C)C(=O)O)c1C] |

TABLE A-7-continued
| Structure | Structure |
| --- | --- |
| 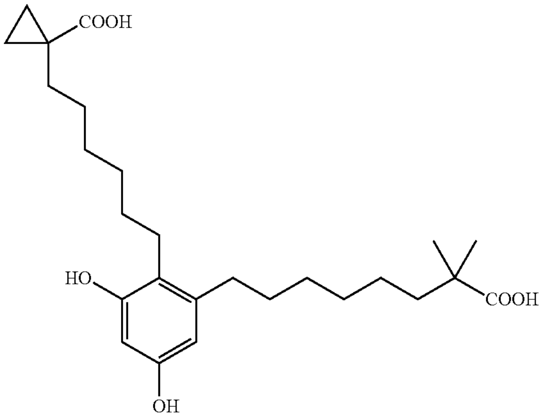 [SMILES: CC(C)(CCCCCCc1cc(O)cc(O)c1CCCCCCC1(C(=O)O)CC1)C(=O)O] | 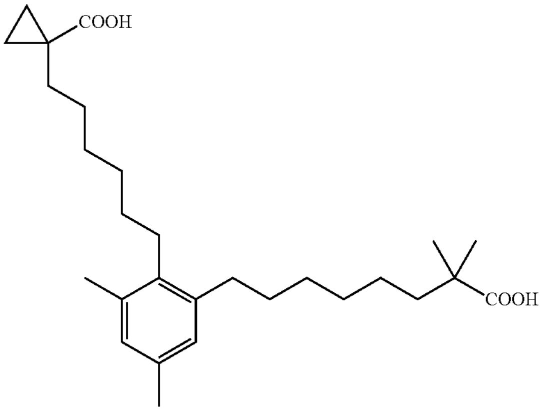 [SMILES: Cc1cc(C)c(CCCCCCC2(C(=O)O)CC2)c(CCCCCCC(C)(C)C(=O)O)c1] |
| 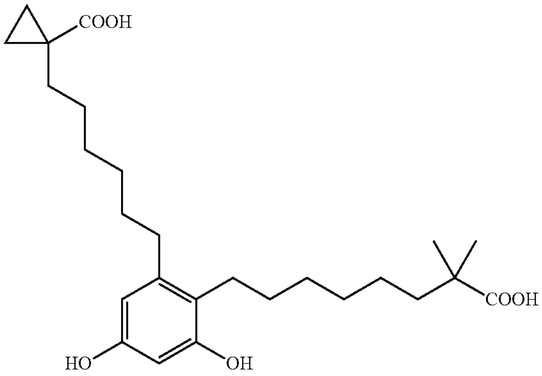 [SMILES: CC(C)(CCCCCCc1c(O)cc(O)cc1CCCCCCC1(C(=O)O)CC1)C(=O)O] | 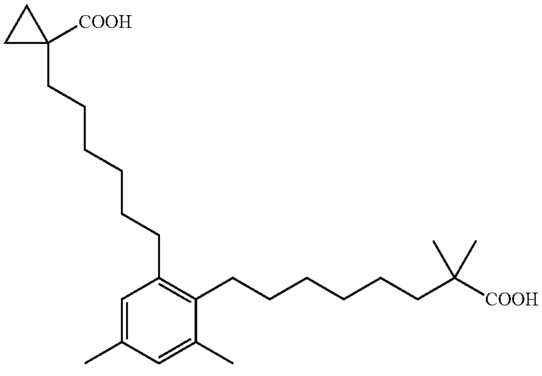 [SMILES: Cc1cc(C)c(CCCCCCC(C)(C)C(=O)O)c(CCCCCCC2(C(=O)O)CC2)c1] |
| 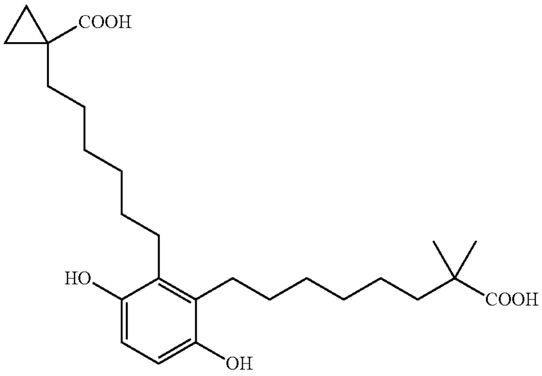 [SMILES: CC(C)(CCCCCCc1c(O)ccc(O)c1CCCCCCC1(C(=O)O)CC1)C(=O)O] | 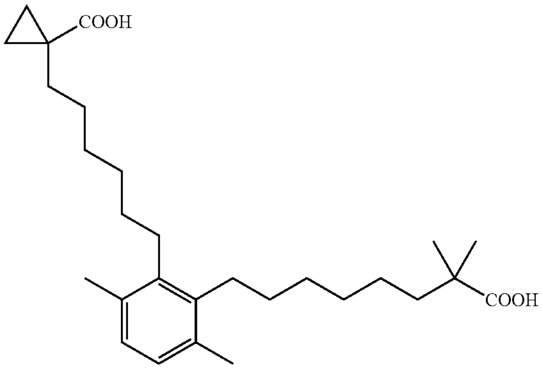 [SMILES: Cc1ccc(C)c(CCCCCCC2(C(=O)O)CC2)c1CCCCCCC(C)(C)C(=O)O] |
| 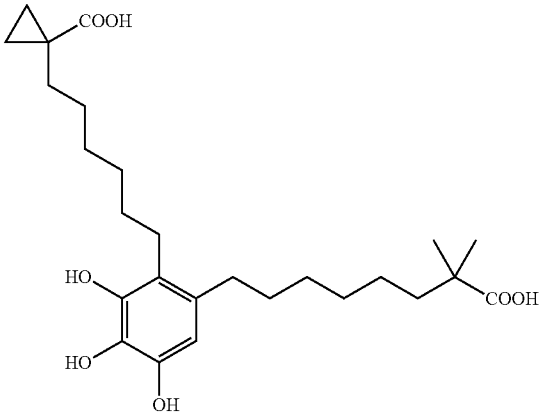 [SMILES: CC(C)(CCCCCCc1cc(O)c(O)c(O)c1CCCCCCC1(C(=O)O)CC1)C(=O)O] | 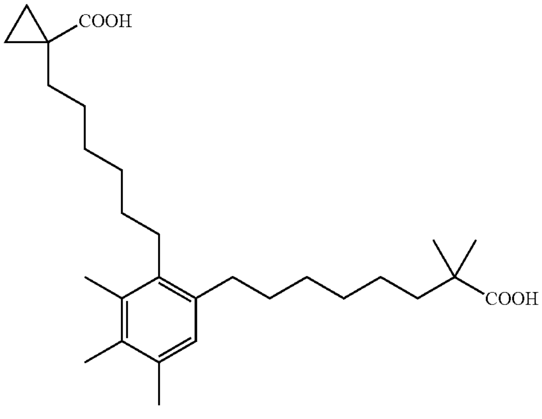 [SMILES: Cc1cc(CCCCCCC(C)(C)C(=O)O)c(CCCCCCC2(C(=O)O)CC2)c(C)c1C] |

TABLE A-7-continued
| Structure | Structure |
| --- | --- |
| 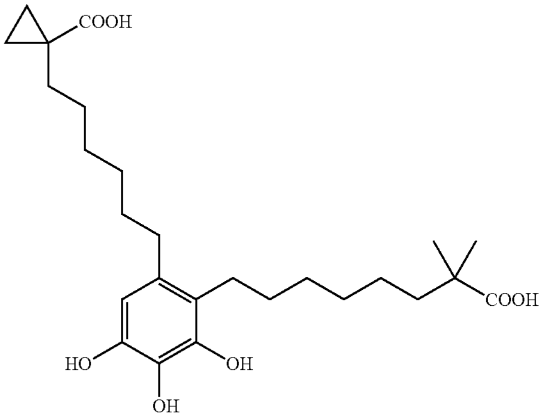 [SMILES: CC(C)(CCCCCCc1c(CCCCCCC2(C(=O)O)CC2)cc(O)c(O)c1O)C(=O)O] | 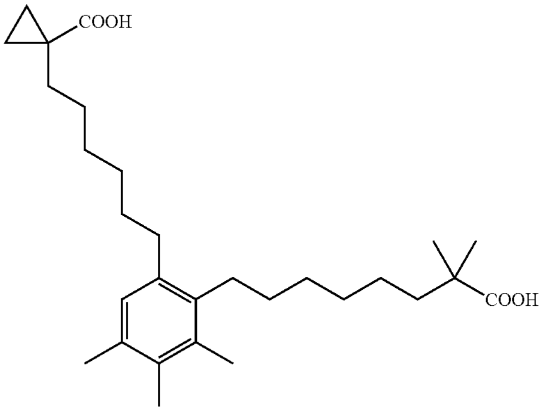 [SMILES: Cc1cc(CCCCCCC2(C(=O)O)CC2)c(CCCCCCC(C)(C)C(=O)O)c(C)c1C] |
| 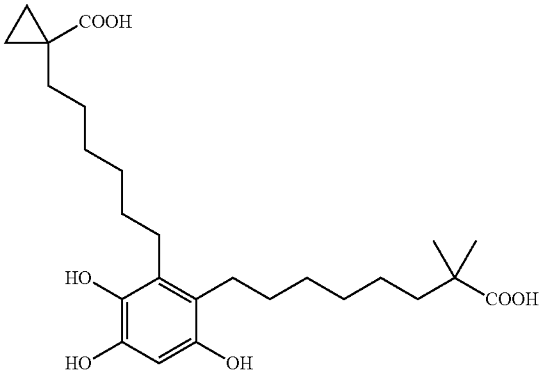 [SMILES: CC(C)(CCCCCCc1c(O)cc(O)c(O)c1CCCCCCC1(C(=O)O)CC1)C(=O)O] | 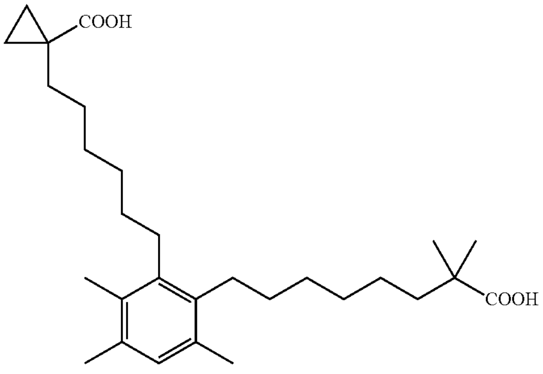 [SMILES: Cc1cc(C)c(CCCCCCC(C)(C)C(=O)O)c(CCCCCCC2(C(=O)O)CC2)c1C] |
| 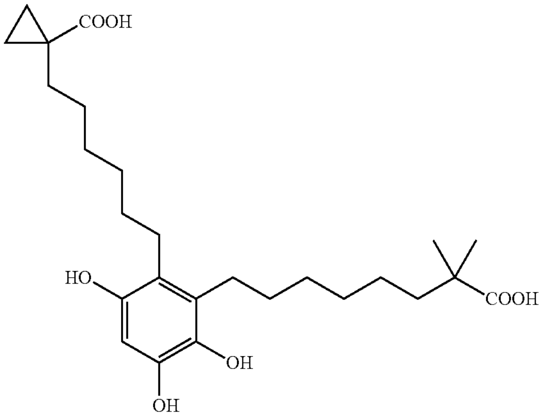 [SMILES: CC(C)(CCCCCCc1c(O)c(O)cc(O)c1CCCCCCC1(C(=O)O)CC1)C(=O)O] | 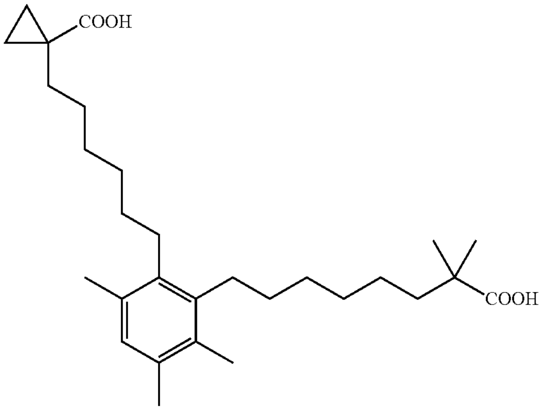 [SMILES: Cc1cc(C)c(CCCCCCC2(C(=O)O)CC2)c(CCCCCCC(C)(C)C(=O)O)c1C] |
| 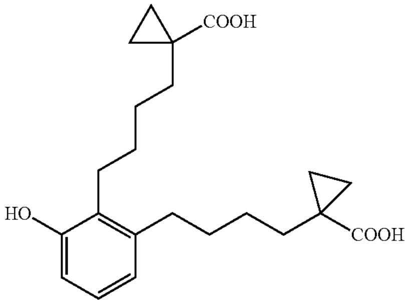 [SMILES: O=C(O)C1(CCCCc2cccc(O)c2CCCCC2(C(=O)O)CC2)CC1] | 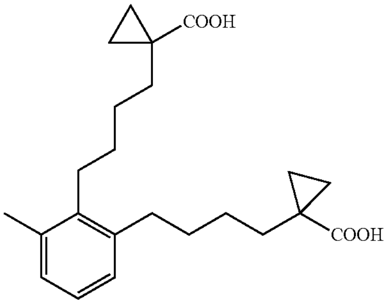 [SMILES: Cc1cccc(CCCCC2(C(=O)O)CC2)c1CCCCC1(C(=O)O)CC1] |

TABLE A-7-continued
| Structure | Structure |
|---|---|
| 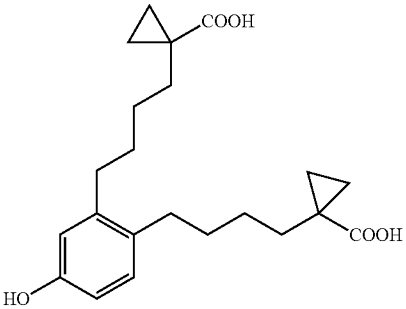 [SMILES: O=C(O)C1(CCCCc2ccc(O)cc2CCCCC2(C(=O)O)CC2)CC1] | 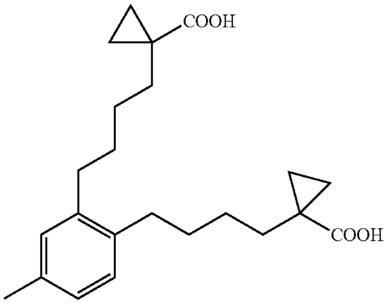 [SMILES: Cc1ccc(CCCCC2(C(=O)O)CC2)c(CCCCC2(C(=O)O)CC2)c1] |
| 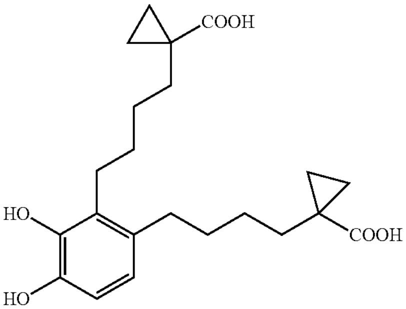 [SMILES: O=C(O)C1(CCCCc2ccc(O)c(O)c2CCCCC2(C(=O)O)CC2)CC1] | 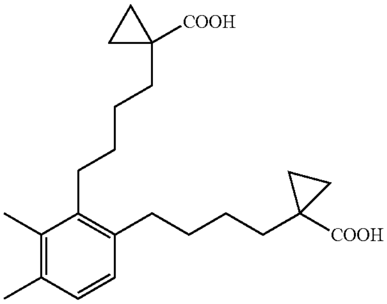 [SMILES: Cc1ccc(CCCCC2(C(=O)O)CC2)c(CCCCC2(C(=O)O)CC2)c1C] |
| 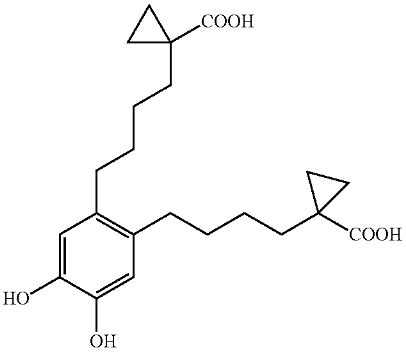 [SMILES: O=C(O)C1(CCCCc2cc(O)c(O)cc2CCCCC2(C(=O)O)CC2)CC1] | 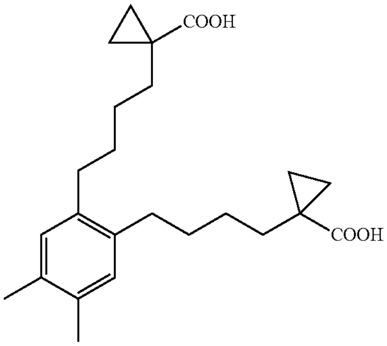 [SMILES: Cc1cc(CCCCC2(C(=O)O)CC2)c(CCCCC2(C(=O)O)CC2)cc1C] |
| 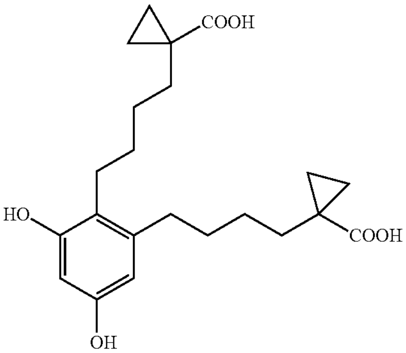 [SMILES: O=C(O)C1(CCCCc2cc(O)cc(O)c2CCCCC2(C(=O)O)CC2)CC1] | 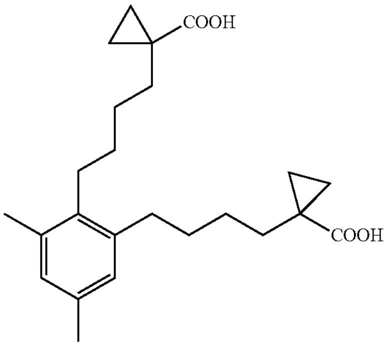 [SMILES: Cc1cc(C)c(CCCCC2(C(=O)O)CC2)c(CCCCC2(C(=O)O)CC2)c1] |

TABLE A-7-continued
| Structure | Structure |
|---|---|
| 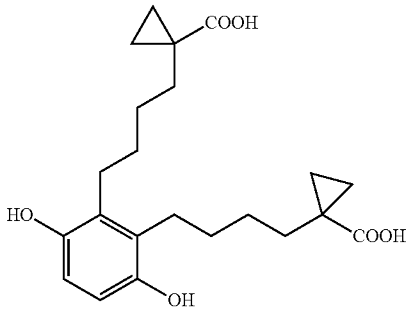 [SMILES: O=C(O)C1(CCCCc2c(O)ccc(O)c2CCCCC2(C(=O)O)CC2)CC1] | 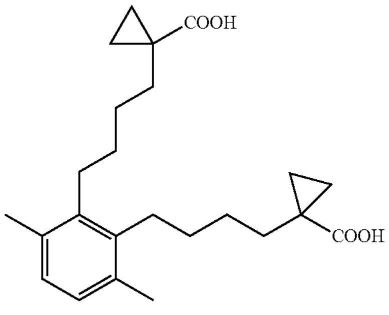 [SMILES: Cc1ccc(C)c(CCCCC2(C(=O)O)CC2)c1CCCCC1(C(=O)O)CC1] |
| 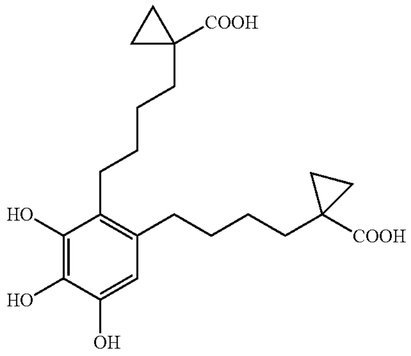 [SMILES: O=C(O)C1(CCCCc2cc(O)c(O)c(O)c2CCCCC2(C(=O)O)CC2)CC1] | 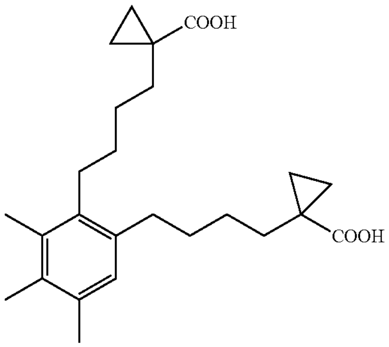 [SMILES: Cc1cc(CCCCC2(C(=O)O)CC2)c(CCCCC2(C(=O)O)CC2)c(C)c1C] |
| 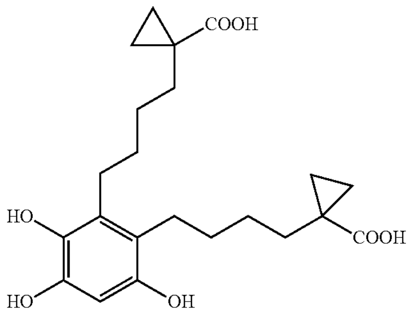 [SMILES: O=C(O)C1(CCCCc2c(O)cc(O)c(O)c2CCCCC2(C(=O)O)CC2)CC1] | 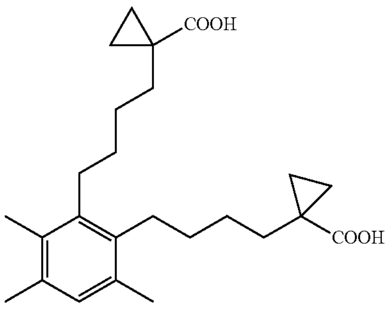 [SMILES: Cc1cc(C)c(CCCCC2(C(=O)O)CC2)c(CCCCC2(C(=O)O)CC2)c1C] |
| 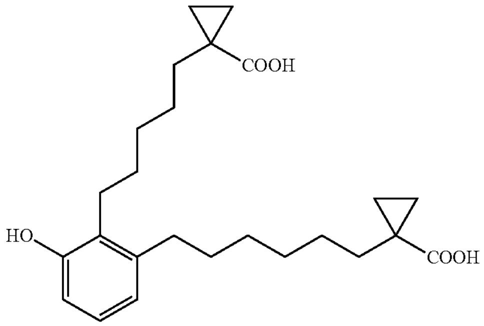 [SMILES: O=C(O)C1(CCCCCCc2cccc(O)c2CCCCCC2(C(=O)O)CC2)CC1] | 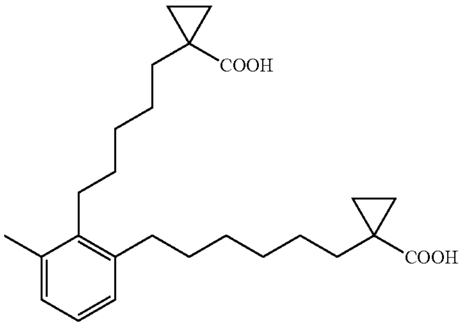 [SMILES: Cc1cccc(CCCCCCC2(C(=O)O)CC2)c1CCCCCC1(C(=O)O)CC1] |

TABLE A-7-continued
| Structure | Structure |
| --- | --- |
| 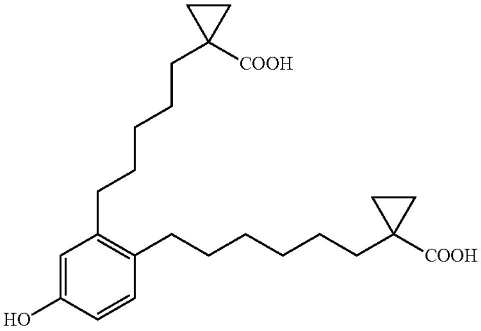 [SMILES: O=C(O)C1(CCCCCCc2ccc(O)cc2CCCCCC2(C(=O)O)CC2)CC1] | 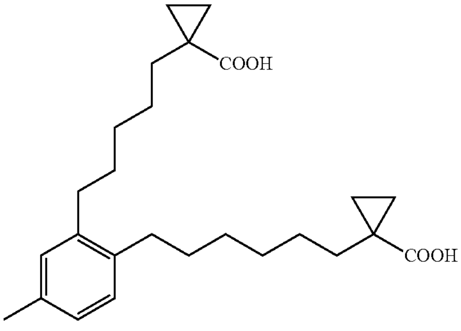 [SMILES: Cc1ccc(CCCCCCC2(C(=O)O)CC2)c(CCCCCC2(C(=O)O)CC2)c1] |
| 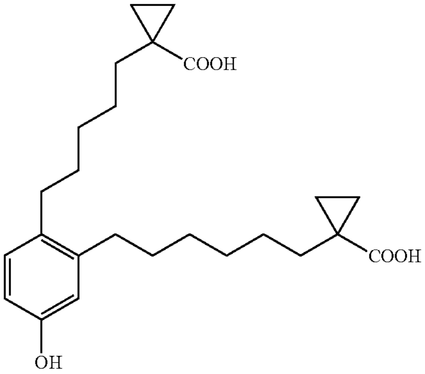 [SMILES: O=C(O)C1(CCCCCCc2cc(O)ccc2CCCCCC2(C(=O)O)CC2)CC1] | 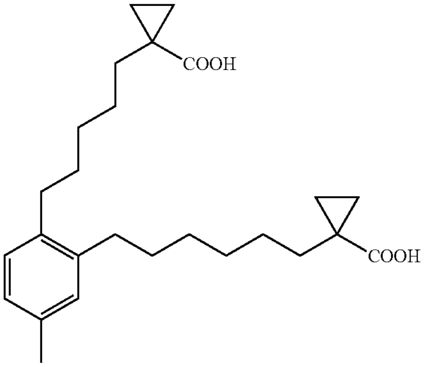 [SMILES: Cc1ccc(CCCCCC2(C(=O)O)CC2)c(CCCCCCC2(C(=O)O)CC2)c1] |
| 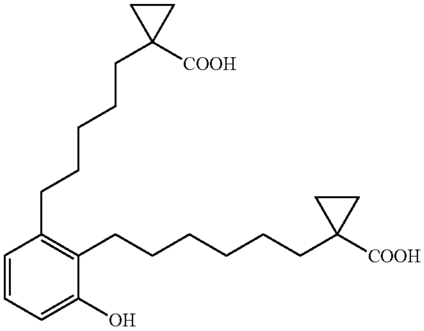 [SMILES: O=C(O)C1(CCCCCCc2c(O)cccc2CCCCCC2(C(=O)O)CC2)CC1] | 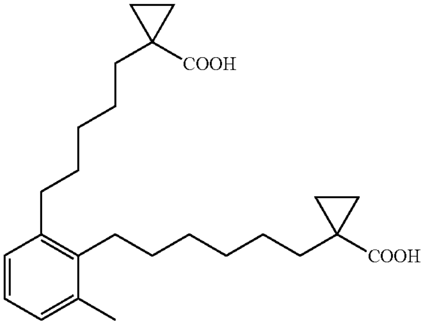 [SMILES: Cc1cccc(CCCCCC2(C(=O)O)CC2)c1CCCCCCC1(C(=O)O)CC1] |
| 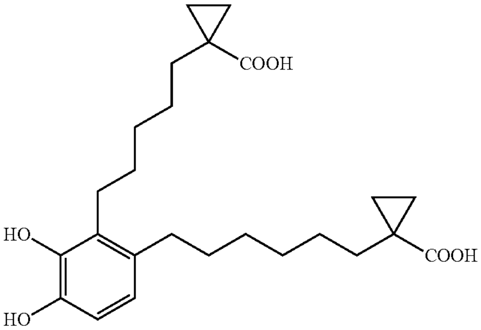 [SMILES: O=C(O)C1(CCCCCCc2ccc(O)c(O)c2CCCCCC2(C(=O)O)CC2)CC1] | 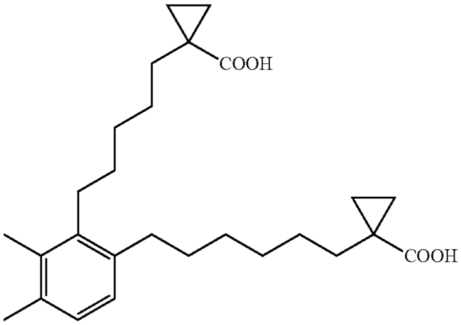 [SMILES: Cc1ccc(CCCCCCC2(C(=O)O)CC2)c(CCCCCC2(C(=O)O)CC2)c1C] |

TABLE A-7-continued
| Structure | Structure |
|---|---|
| 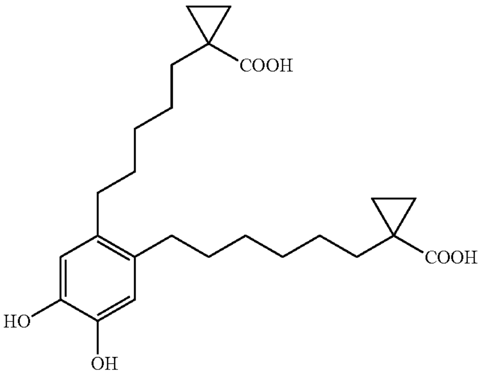 [SMILES: O=C(O)C1(CCCCCCc2cc(O)c(O)cc2CCCCCC2(C(=O)O)CC2)CC1] | 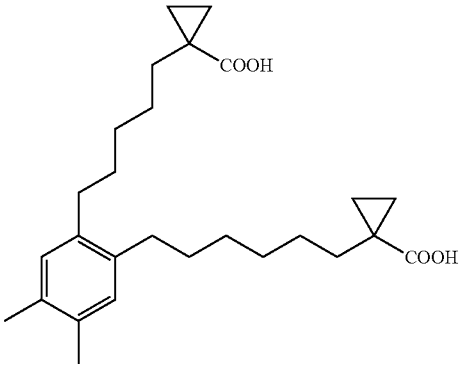 [SMILES: Cc1cc(CCCCCCC2(C(=O)O)CC2)c(CCCCCC2(C(=O)O)CC2)cc1C] |
| 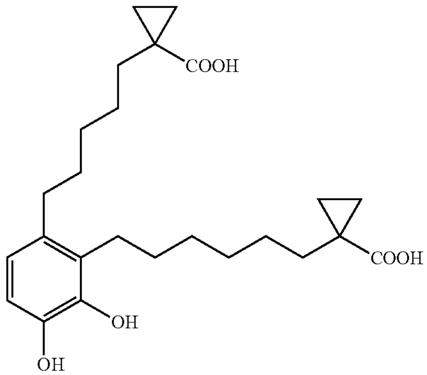 [SMILES: O=C(O)C1(CCCCCCc2c(CCCCCC3(C(=O)O)CC3)ccc(O)c2O)CC1] | 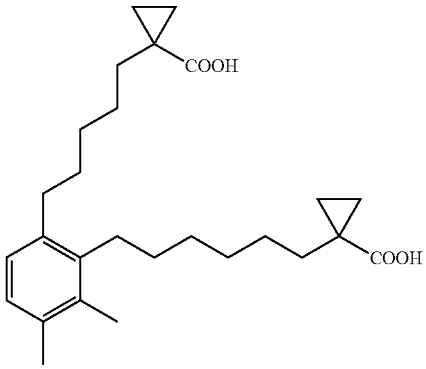 [SMILES: Cc1ccc(CCCCCC2(C(=O)O)CC2)c(CCCCCCC2(C(=O)O)CC2)c1C] |
| 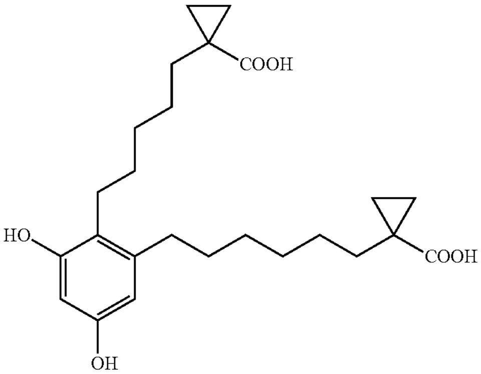 [SMILES: O=C(O)C1(CCCCCCc2cc(O)cc(O)c2CCCCCC2(C(=O)O)CC2)CC1] | 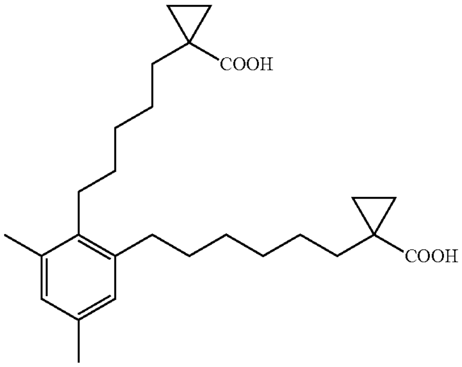 [SMILES: Cc1cc(C)c(CCCCCC2(C(=O)O)CC2)c(CCCCCCC2(C(=O)O)CC2)c1] |
| 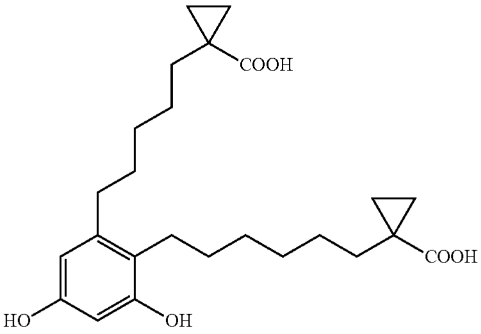 [SMILES: O=C(O)C1(CCCCCCc2c(O)cc(O)cc2CCCCCC2(C(=O)O)CC2)CC1] | 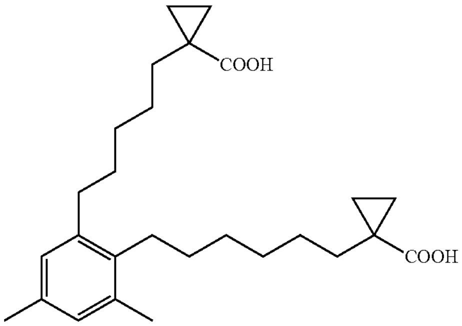 [SMILES: Cc1cc(C)c(CCCCCCC2(C(=O)O)CC2)c(CCCCCC2(C(=O)O)CC2)c1] |

TABLE A-7-continued
| Structure | Structure |
| --- | --- |
| 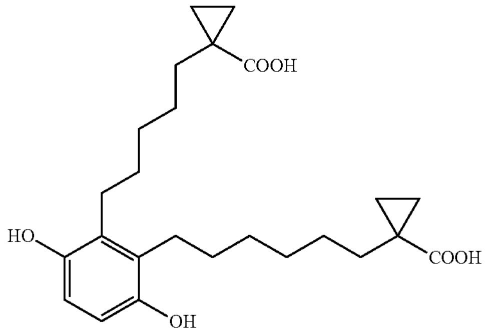 [SMILES: O=C(O)C1(CCCCCCc2c(O)ccc(O)c2CCCCCC2(C(=O)O)CC2)CC1] | 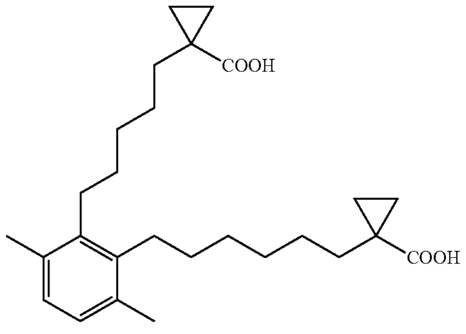 [SMILES: Cc1ccc(C)c(CCCCCC2(C(=O)O)CC2)c1CCCCCCC1(C(=O)O)CC1] |
| 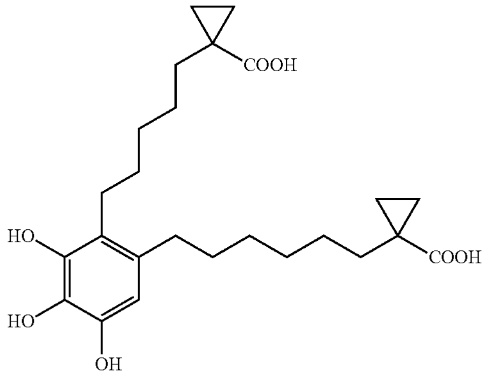 [SMILES: O=C(O)C1(CCCCCCc2cc(O)c(O)c(O)c2CCCCCC2(C(=O)O)CC2)CC1] | 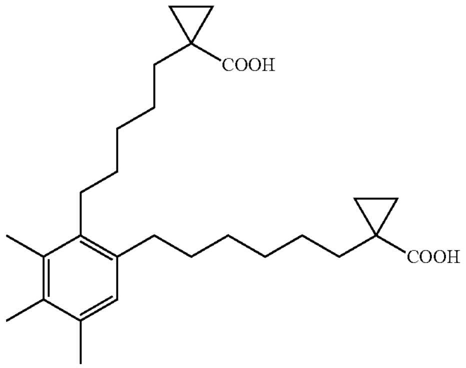 [SMILES: Cc1cc(CCCCCCC2(C(=O)O)CC2)c(CCCCCC2(C(=O)O)CC2)c(C)c1C] |
| 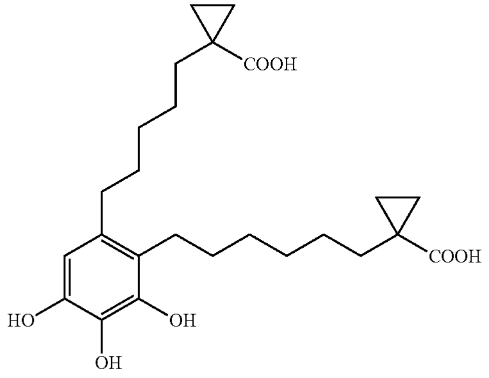 [SMILES: O=C(O)C1(CCCCCCc2c(CCCCCC3(C(=O)O)CC3)cc(O)c(O)c2O)CC1] | 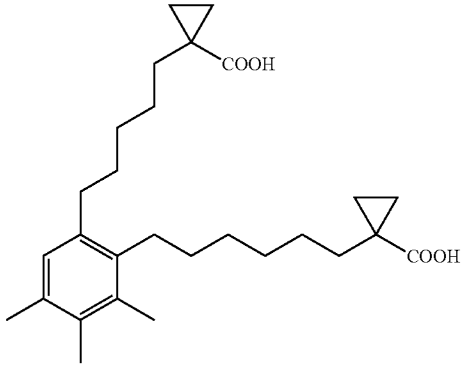 [SMILES: Cc1cc(CCCCCC2(C(=O)O)CC2)c(CCCCCCC2(C(=O)O)CC2)c(C)c1C] |
| 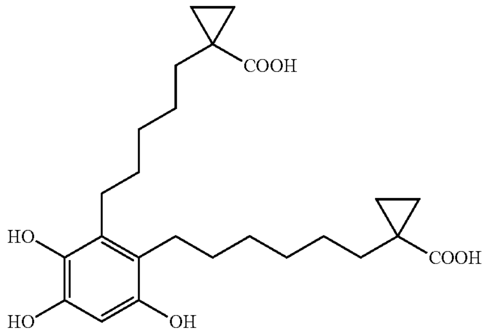 [SMILES: O=C(O)C1(CCCCCCc2c(O)cc(O)c(O)c2CCCCCC2(C(=O)O)CC2)CC1] | 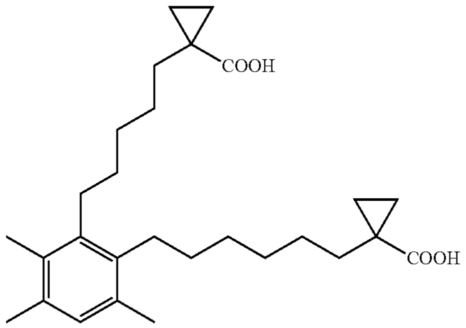 [SMILES: Cc1cc(C)c(CCCCCCC2(C(=O)O)CC2)c(CCCCCC2(C(=O)O)CC2)c1C] |

TABLE A-7-continued
| Structure | Structure |
|---|---|
| 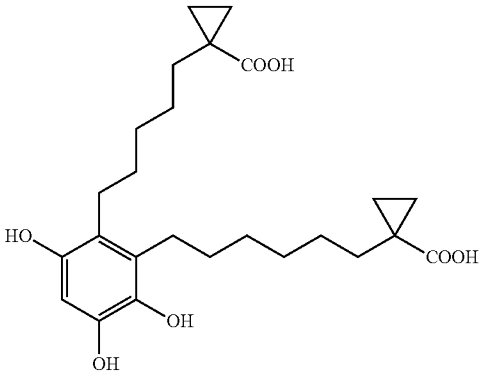 [SMILES: O=C(O)C1(CCCCCCc2c(O)c(O)cc(O)c2CCCCCC2(C(=O)O)CC2)CC1] | 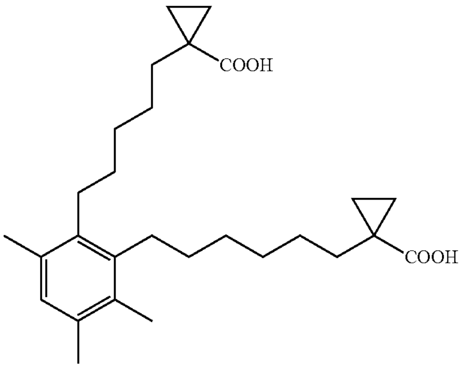 [SMILES: Cc1cc(C)c(CCCCCC2(C(=O)O)CC2)c(CCCCCCC2(C(=O)O)CC2)c1C] |
| 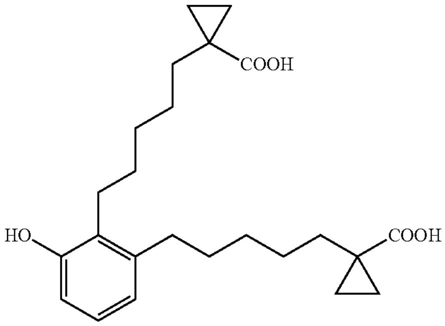 [SMILES: O=C(O)C1(CCCCCc2cccc(O)c2CCCCCC2(C(=O)O)CC2)CC1] | 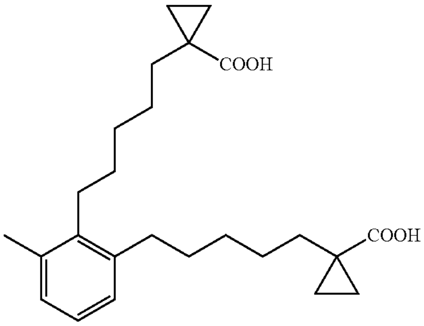 [SMILES: Cc1cccc(CCCCCC2(C(=O)O)CC2)c1CCCCCC1(C(=O)O)CC1] |
| 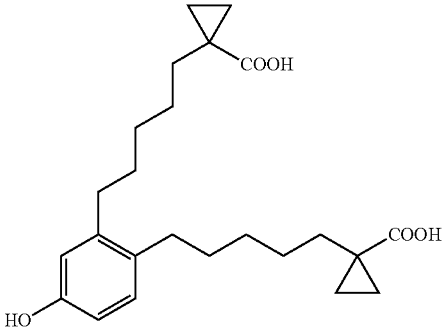 [SMILES: O=C(O)C1(CCCCCc2ccc(O)cc2CCCCCC2(C(=O)O)CC2)CC1] | 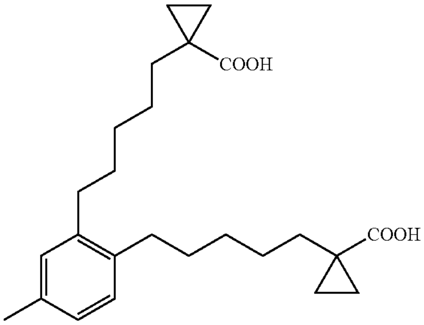 [SMILES: Cc1ccc(CCCCCC2(C(=O)O)CC2)c(CCCCCC2(C(=O)O)CC2)c1] |
| 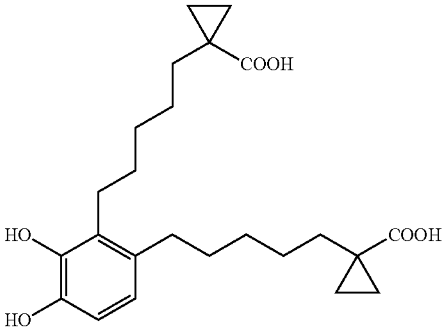 [SMILES: O=C(O)C1(CCCCCc2ccc(O)c(O)c2CCCCCC2(C(=O)O)CC2)CC1] | 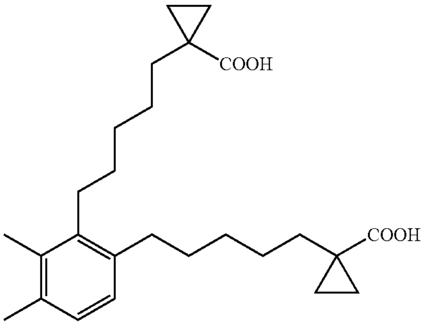 [SMILES: Cc1ccc(CCCCCC2(C(=O)O)CC2)c(CCCCCC2(C(=O)O)CC2)c1C] |

TABLE A-7-continued
| Structure | Structure |
| --- | --- |
| 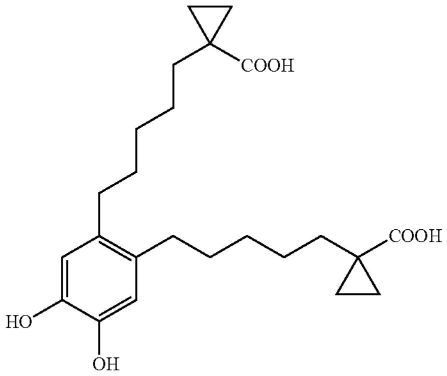 [SMILES: O=C(O)C1(CCCCCc2cc(O)c(O)cc2CCCCCC2(C(=O)O)CC2)CC1] | 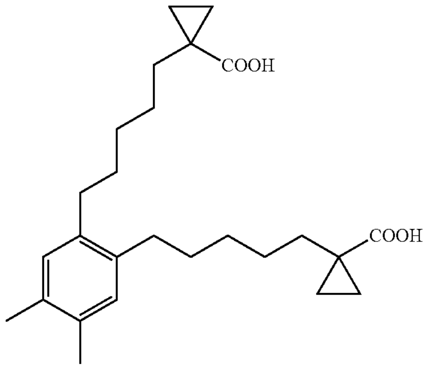 [SMILES: Cc1cc(CCCCCC2(C(=O)O)CC2)c(CCCCCC2(C(=O)O)CC2)cc1C] |
| 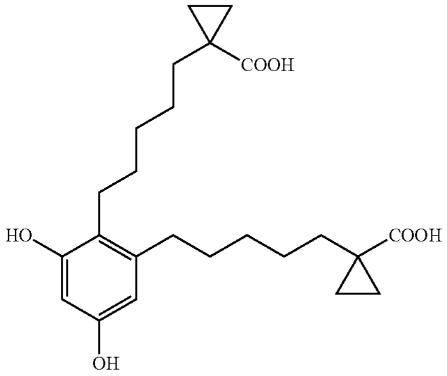 [SMILES: O=C(O)C1(CCCCCc2cc(O)cc(O)c2CCCCCC2(C(=O)O)CC2)CC1] | 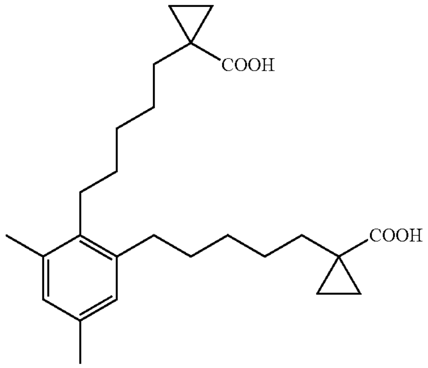 [SMILES: Cc1cc(C)c(CCCCCC2(C(=O)O)CC2)c(CCCCCC2(C(=O)O)CC2)c1] |
| 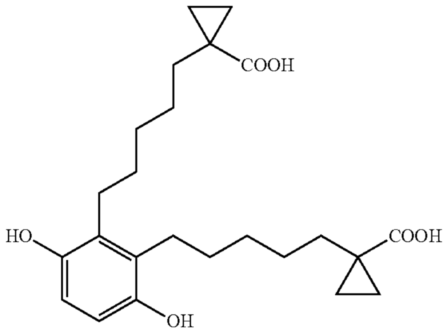 [SMILES: O=C(O)C1(CCCCCc2c(O)ccc(O)c2CCCCCC2(C(=O)O)CC2)CC1] | 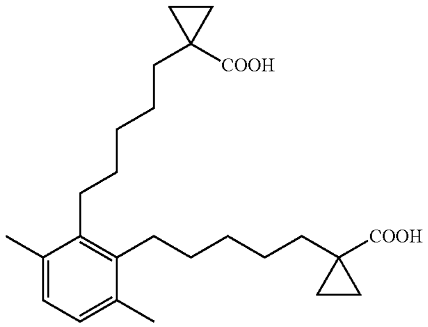 [SMILES: Cc1ccc(C)c(CCCCCC2(C(=O)O)CC2)c1CCCCCC1(C(=O)O)CC1] |
| 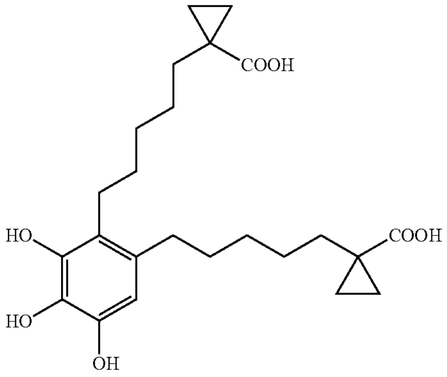 [SMILES: O=C(O)C1(CCCCCc2cc(O)c(O)c(O)c2CCCCCC2(C(=O)O)CC2)CC1] | 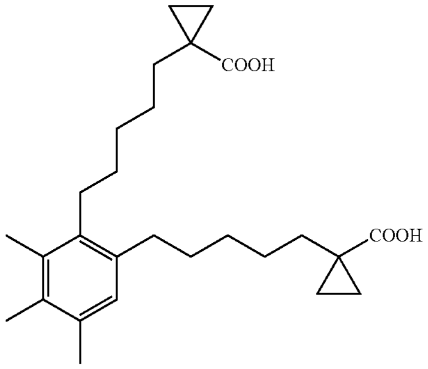 [SMILES: Cc1cc(CCCCCC2(C(=O)O)CC2)c(CCCCCC2(C(=O)O)CC2)c(C)c1C] |

TABLE A-7-continued
| Structure | Structure |
|---|---|
| 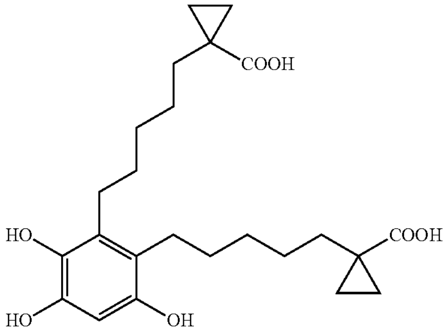 [SMILES: O=C(O)C1(CCCCCc2c(O)cc(O)c(O)c2CCCCCC2(C(=O)O)CC2)CC1] | 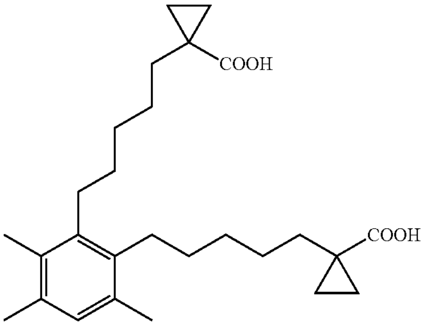 [SMILES: Cc1cc(C)c(CCCCCC2(C(=O)O)CC2)c(CCCCCC2(C(=O)O)CC2)c1C] |
| 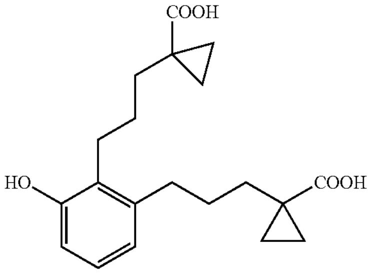 [SMILES: O=C(O)C1(CCCc2cccc(O)c2CCCC2(C(=O)O)CC2)CC1] | 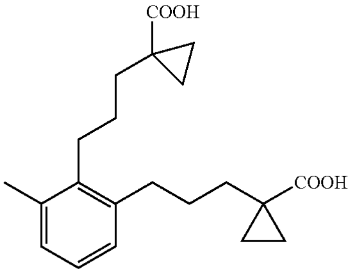 [SMILES: Cc1cccc(CCCC2(C(=O)O)CC2)c1CCCC1(C(=O)O)CC1] |
| 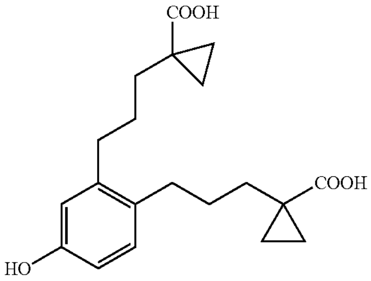 [SMILES: O=C(O)C1(CCCc2ccc(O)cc2CCCC2(C(=O)O)CC2)CC1] | 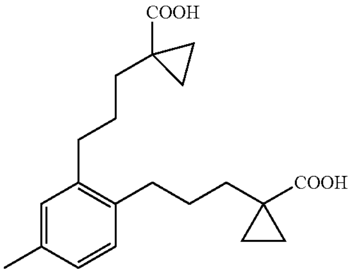 [SMILES: Cc1ccc(CCCC2(C(=O)O)CC2)c(CCCC2(C(=O)O)CC2)c1] |
| 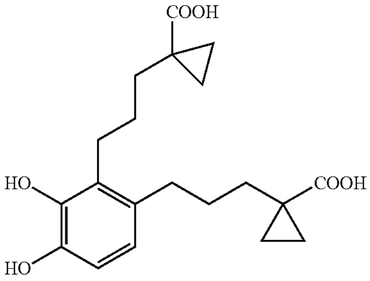 [SMILES: O=C(O)C1(CCCc2ccc(O)c(O)c2CCCC2(C(=O)O)CC2)CC1] | 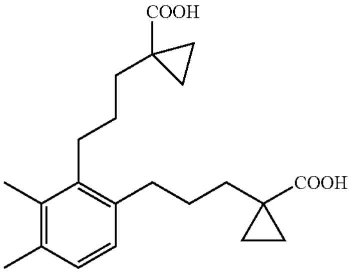 [SMILES: Cc1ccc(CCCC2(C(=O)O)CC2)c(CCCC2(C(=O)O)CC2)c1C] |
| 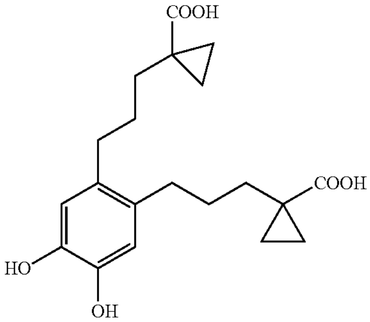 [SMILES: O=C(O)C1(CCCc2cc(O)c(O)cc2CCCC2(C(=O)O)CC2)CC1] | 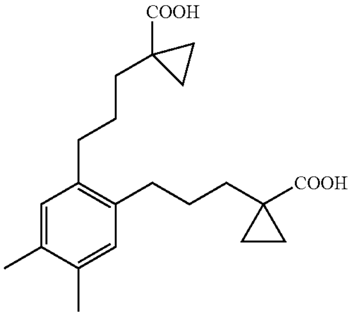 [SMILES: Cc1cc(CCCC2(C(=O)O)CC2)c(CCCC2(C(=O)O)CC2)cc1C] |

TABLE A-7-continued
| Structure | Structure |
|---|---|
| 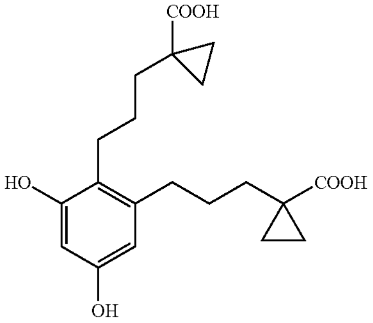 [SMILES: O=C(O)C1(CCCc2cc(O)cc(O)c2CCCC2(C(=O)O)CC2)CC1] | 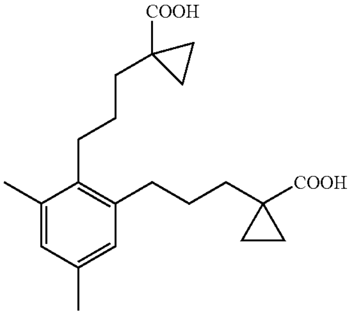 [SMILES: Cc1cc(C)c(CCCC2(C(=O)O)CC2)c(CCCC2(C(=O)O)CC2)c1] |
| 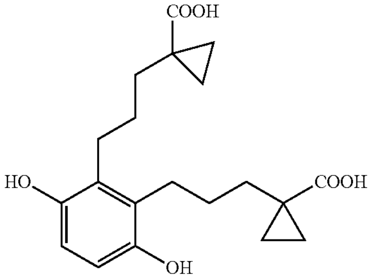 [SMILES: O=C(O)C1(CCCc2c(O)ccc(O)c2CCCC2(C(=O)O)CC2)CC1] | 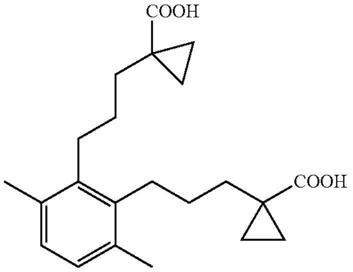 [SMILES: Cc1ccc(C)c(CCCC2(C(=O)O)CC2)c1CCCC1(C(=O)O)CC1] |
| 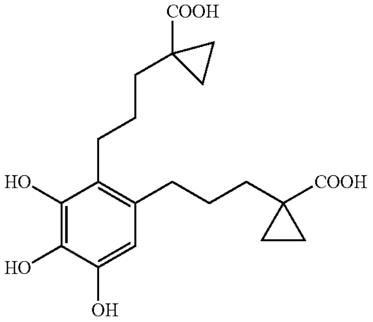 [SMILES: O=C(O)C1(CCCc2cc(O)c(O)c(O)c2CCCC2(C(=O)O)CC2)CC1] | 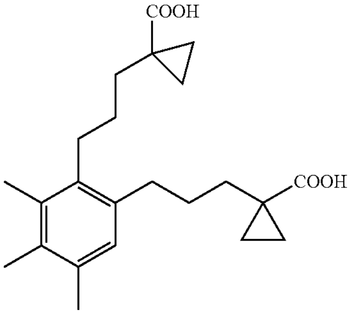 [SMILES: Cc1cc(CCCC2(C(=O)O)CC2)c(CCCC2(C(=O)O)CC2)c(C)c1C] |
| 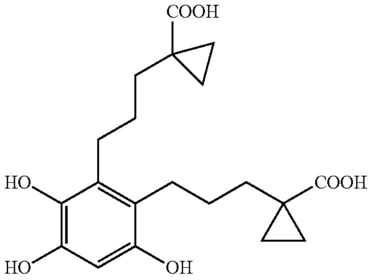 [SMILES: O=C(O)C1(CCCc2c(O)cc(O)c(O)c2CCCC2(C(=O)O)CC2)CC1] | 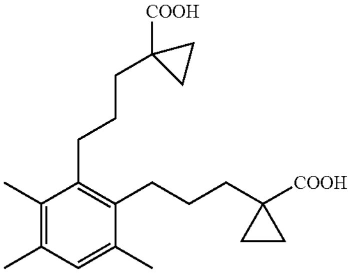 [SMILES: Cc1cc(C)c(CCCC2(C(=O)O)CC2)c(CCCC2(C(=O)O)CC2)c1C] |
| 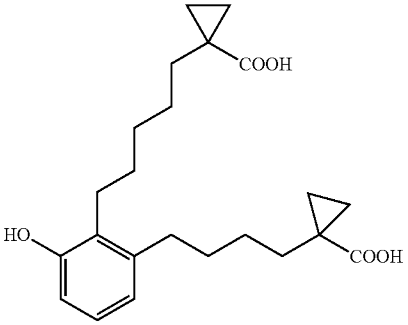 [SMILES: O=C(O)C1(CCCCCc2c(O)cccc2CCCCC2(C(=O)O)CC2)CC1] | 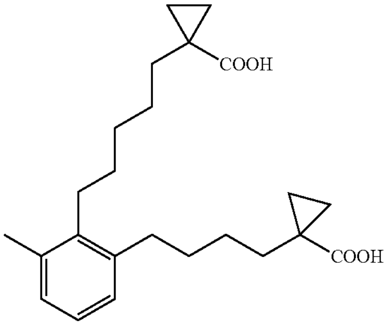 [SMILES: Cc1cccc(CCCCC2(C(=O)O)CC2)c1CCCCCC1(C(=O)O)CC1] |

TABLE A-7-continued
| Structure | Structure |
|---|---|
| 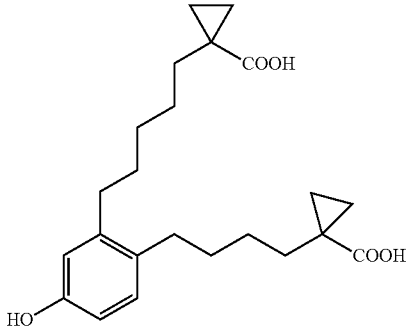 [SMILES: O=C(O)C1(CCCCCc2cc(O)ccc2CCCCC2(C(=O)O)CC2)CC1] | 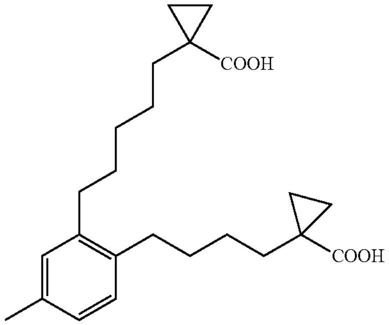 [SMILES: Cc1ccc(CCCCC2(C(=O)O)CC2)c(CCCCCC2(C(=O)O)CC2)c1] |
| 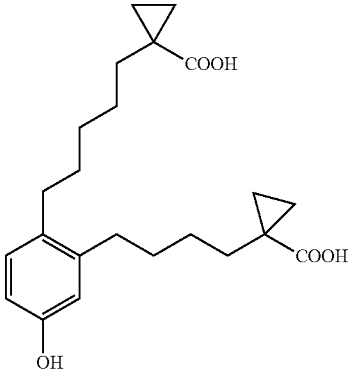 [SMILES: O=C(O)C1(CCCCCc2ccc(O)cc2CCCCC2(C(=O)O)CC2)CC1] | 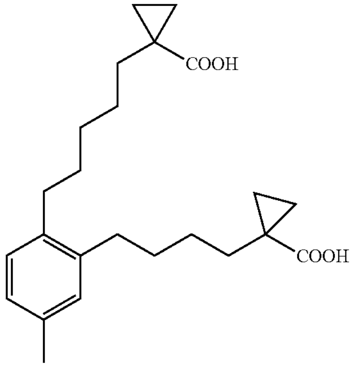 [SMILES: Cc1ccc(CCCCCC2(C(=O)O)CC2)c(CCCCC2(C(=O)O)CC2)c1] |
| 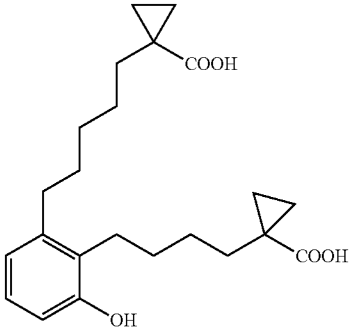 [SMILES: O=C(O)C1(CCCCCc2cccc(O)c2CCCCC2(C(=O)O)CC2)CC1] | 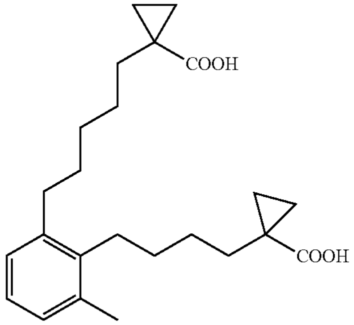 [SMILES: Cc1cccc(CCCCCC2(C(=O)O)CC2)c1CCCCC1(C(=O)O)CC1] |
| 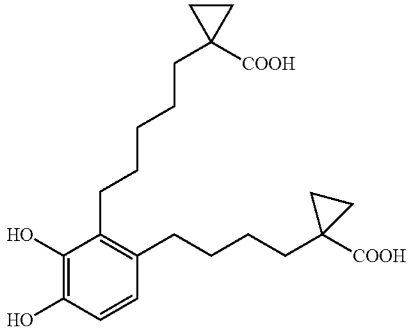 [SMILES: O=C(O)C1(CCCCCc2c(CCCCC3(C(=O)O)CC3)ccc(O)c2O)CC1] | 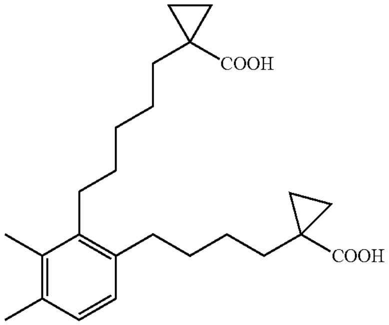 [SMILES: Cc1ccc(CCCCC2(C(=O)O)CC2)c(CCCCCC2(C(=O)O)CC2)c1C] |

TABLE A-7-continued
| Structure | Structure |
| --- | --- |
| 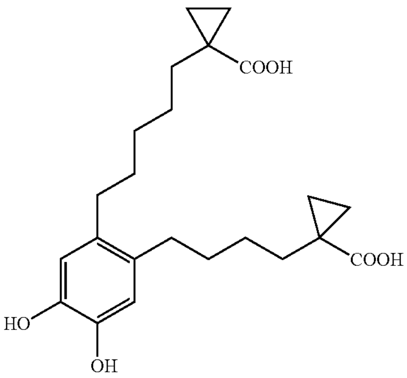 [SMILES: O=C(O)C1(CCCCCc2cc(O)c(O)cc2CCCCC2(C(=O)O)CC2)CC1] | 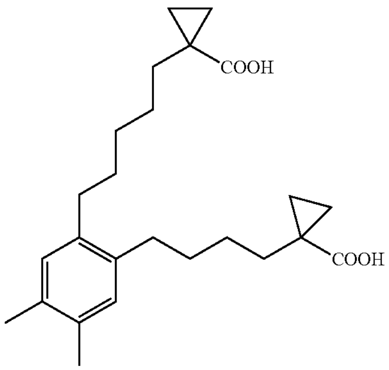 [SMILES: Cc1cc(CCCCCC2(C(=O)O)CC2)c(CCCCC2(C(=O)O)CC2)cc1C] |
| 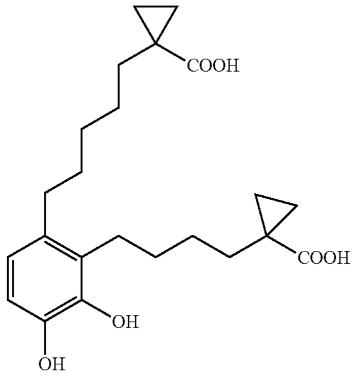 [SMILES: O=C(O)C1(CCCCCc2ccc(O)c(O)c2CCCCC2(C(=O)O)CC2)CC1] | 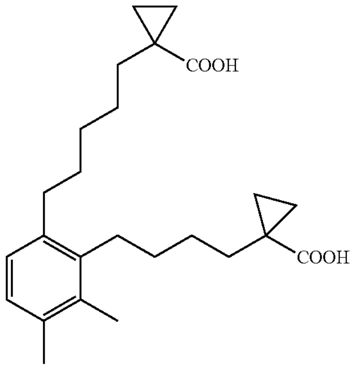 [SMILES: Cc1ccc(CCCCCC2(C(=O)O)CC2)c(CCCCC2(C(=O)O)CC2)c1C] |
| 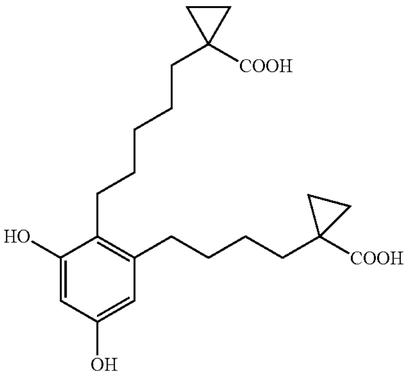 [SMILES: O=C(O)C1(CCCCCc2c(O)cc(O)cc2CCCCC2(C(=O)O)CC2)CC1] | 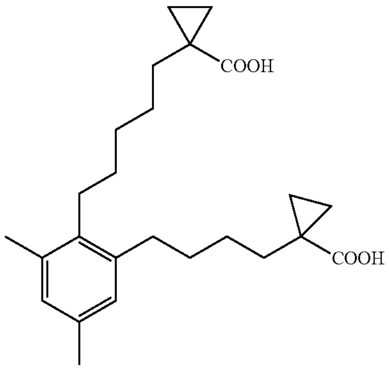 [SMILES: Cc1cc(C)c(CCCCCC2(C(=O)O)CC2)c(CCCCC2(C(=O)O)CC2)c1] |
| 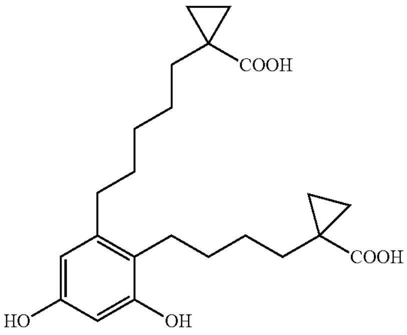 [SMILES: O=C(O)C1(CCCCCc2cc(O)cc(O)c2CCCCC2(C(=O)O)CC2)CC1] | 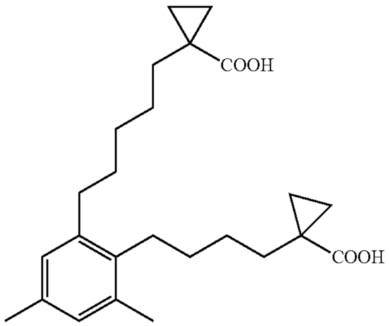 [SMILES: Cc1cc(C)c(CCCCC2(C(=O)O)CC2)c(CCCCCC2(C(=O)O)CC2)c1] |

TABLE A-7-continued
| Structure | Structure |
| --- | --- |
| 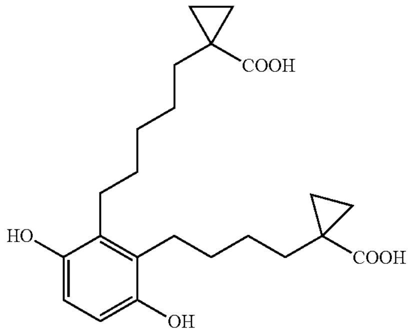 [SMILES: O=C(O)C1(CCCCCc2c(O)ccc(O)c2CCCCC2(C(=O)O)CC2)CC1] | 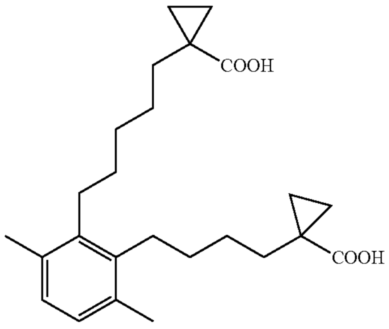 [SMILES: Cc1ccc(C)c(CCCCC2(C(=O)O)CC2)c1CCCCCC1(C(=O)O)CC1] |
| 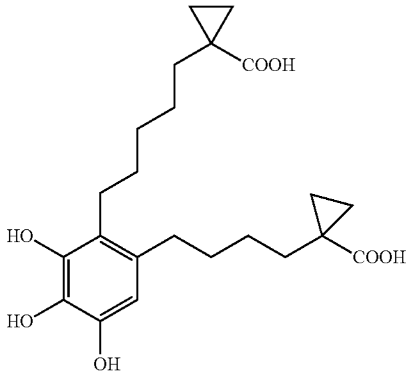 [SMILES: O=C(O)C1(CCCCCc2c(CCCCC3(C(=O)O)CC3)cc(O)c(O)c2O)CC1] | 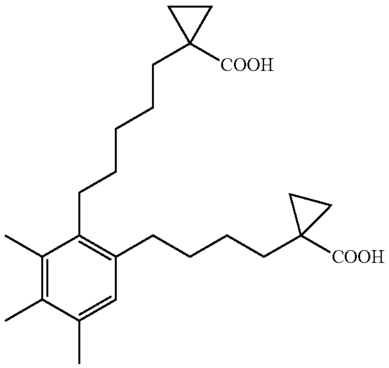 [SMILES: Cc1cc(CCCCC2(C(=O)O)CC2)c(CCCCCC2(C(=O)O)CC2)c(C)c1C] |
| 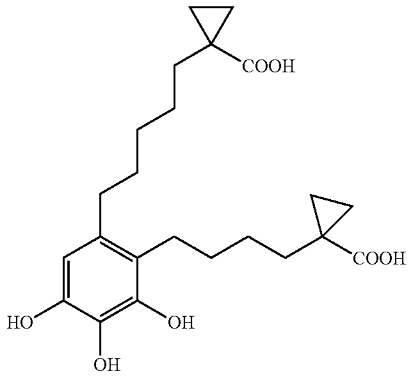 [SMILES: O=C(O)C1(CCCCCc2cc(O)c(O)c(O)c2CCCCC2(C(=O)O)CC2)CC1] | 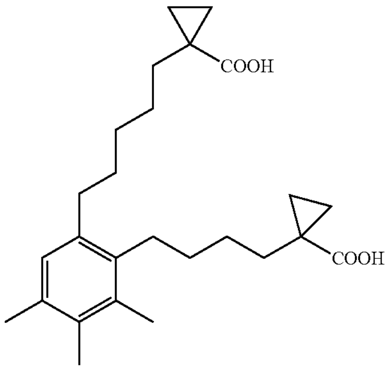 [SMILES: Cc1cc(CCCCCC2(C(=O)O)CC2)c(CCCCC2(C(=O)O)CC2)c(C)c1C] |
| 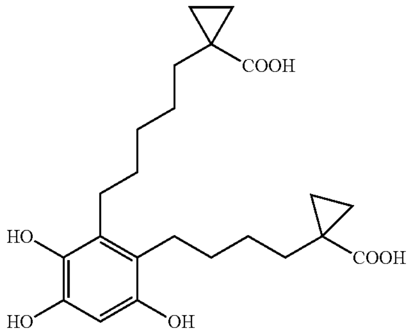 [SMILES: O=C(O)C1(CCCCCc2c(O)c(O)cc(O)c2CCCCC2(C(=O)O)CC2)CC1] | 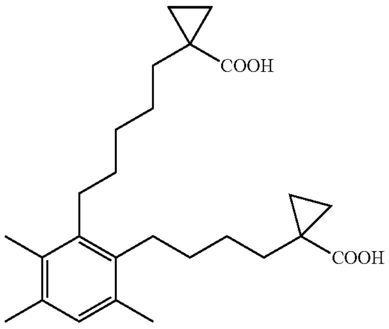 [SMILES: Cc1cc(C)c(CCCCC2(C(=O)O)CC2)c(CCCCCC2(C(=O)O)CC2)c1C] |

TABLE A-7-continued
| Structure | Structure |
|---|---|
| 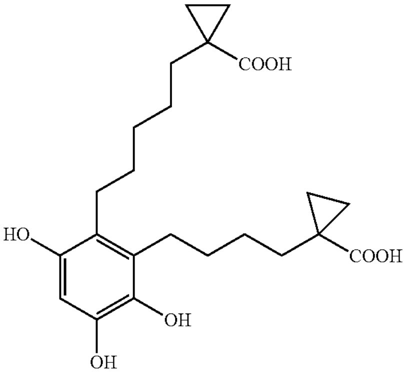 [SMILES: O=C(O)C1(CCCCCc2c(O)cc(O)c(O)c2CCCCC2(C(=O)O)CC2)CC1] | 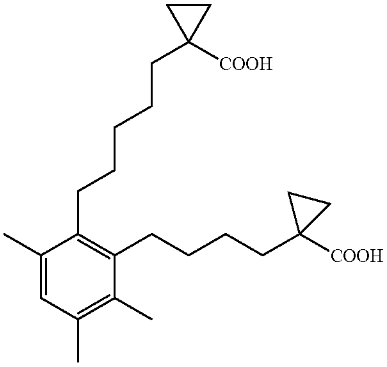 [SMILES: Cc1cc(C)c(CCCCCC2(C(=O)O)CC2)c(CCCCC2(C(=O)O)CC2)c1C] |
| 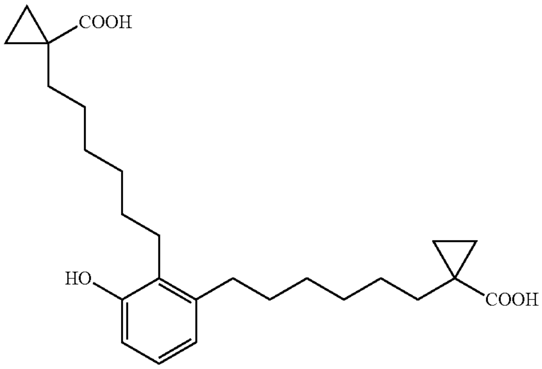 [SMILES: O=C(O)C1(CCCCCCc2cccc(O)c2CCCCCCC2(C(=O)O)CC2)CC1] | 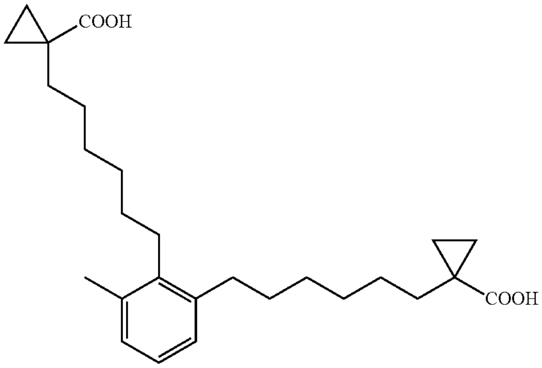 [SMILES: Cc1cccc(CCCCCCC2(C(=O)O)CC2)c1CCCCCCC1(C(=O)O)CC1] |
| 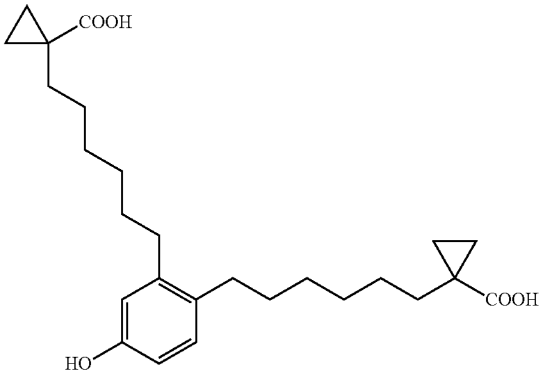 [SMILES: O=C(O)C1(CCCCCCc2ccc(O)cc2CCCCCCC2(C(=O)O)CC2)CC1] | 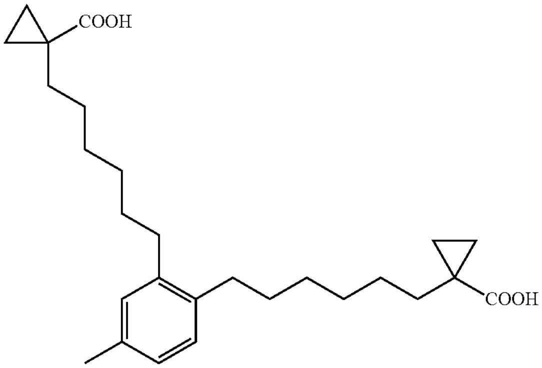 [SMILES: Cc1ccc(CCCCCCC2(C(=O)O)CC2)c(CCCCCCC2(C(=O)O)CC2)c1] |
| 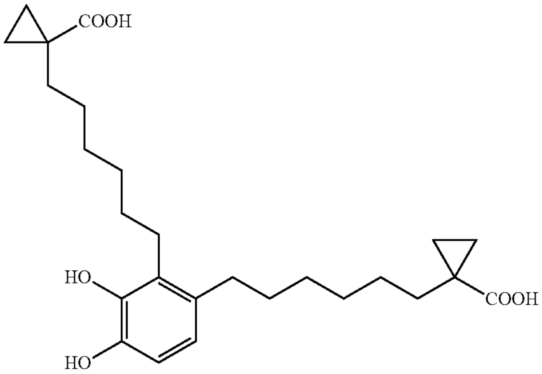 [SMILES: O=C(O)C1(CCCCCCc2ccc(O)c(O)c2CCCCCCC2(C(=O)O)CC2)CC1] | 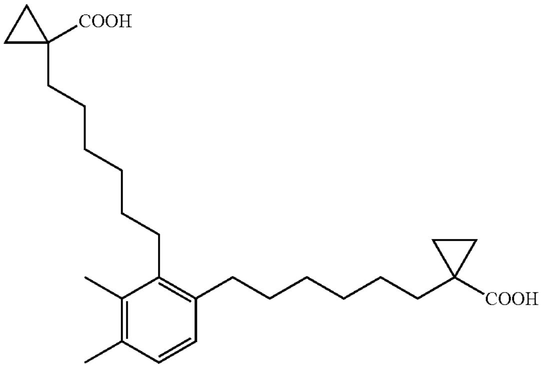 [SMILES: Cc1ccc(CCCCCCC2(C(=O)O)CC2)c(CCCCCCC2(C(=O)O)CC2)c1C] |

TABLE A-7-continued
| Structure | Structure |
| --- | --- |
| 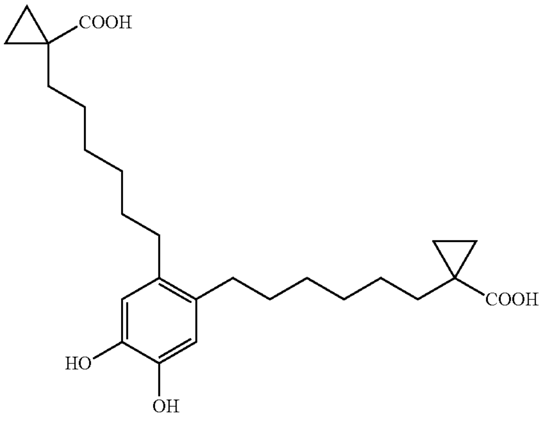 [SMILES: O=C(O)C1(CCCCCCc2cc(O)c(O)cc2CCCCCCC2(C(=O)O)CC2)CC1] | 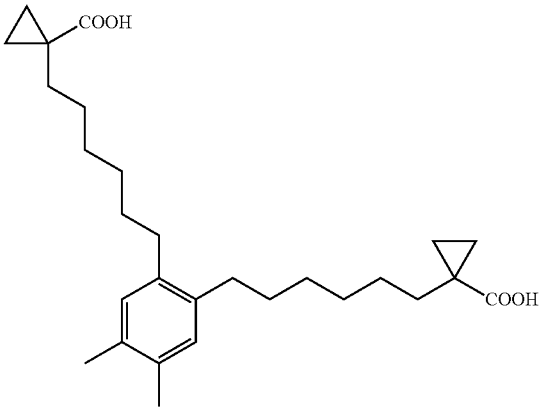 [SMILES: Cc1cc(CCCCCCC2(C(=O)O)CC2)c(CCCCCCC2(C(=O)O)CC2)cc1C] |
| 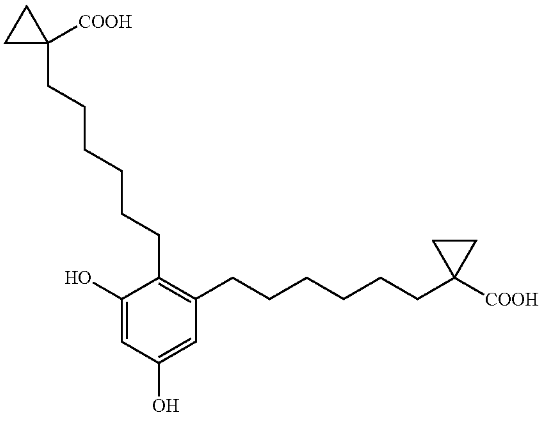 [SMILES: O=C(O)C1(CCCCCCc2cc(O)cc(O)c2CCCCCCC2(C(=O)O)CC2)CC1] | 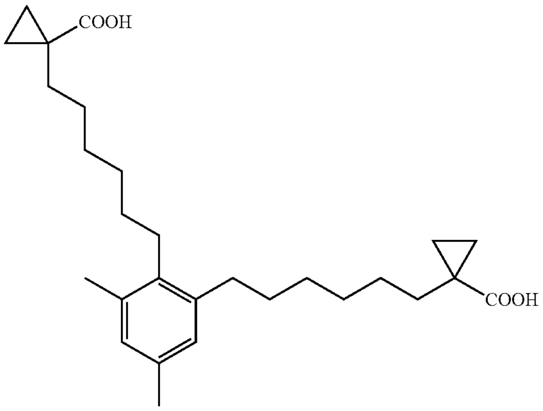 [SMILES: Cc1cc(C)c(CCCCCCC2(C(=O)O)CC2)c(CCCCCCC2(C(=O)O)CC2)c1] |
| 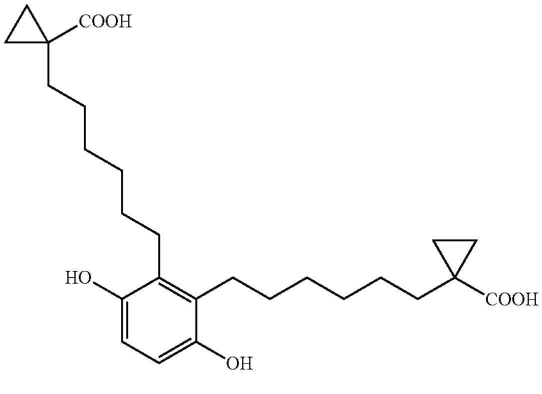 [SMILES: O=C(O)C1(CCCCCCc2c(O)ccc(O)c2CCCCCCC2(C(=O)O)CC2)CC1] | 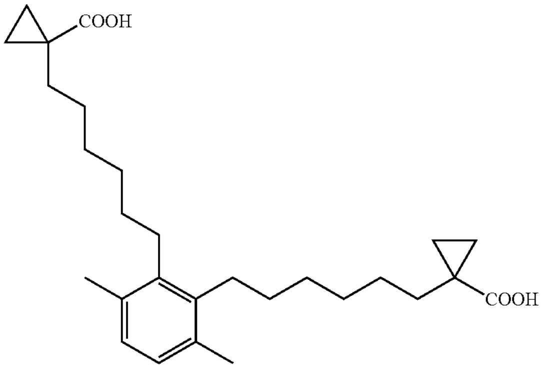 [SMILES: Cc1ccc(C)c(CCCCCCC2(C(=O)O)CC2)c1CCCCCCC1(C(=O)O)CC1] |

TABLE A-7-continued

| Structure | Structure |
|---|---|
| 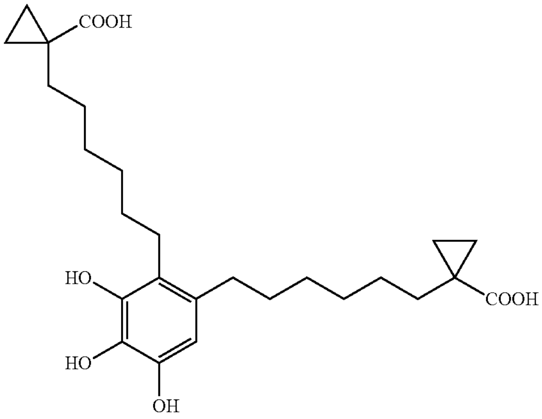 [SMILES: O=C(O)C1(CCCCCCc2cc(O)c(O)c(O)c2CCCCCCC2(C(=O)O)CC2)CC1] | 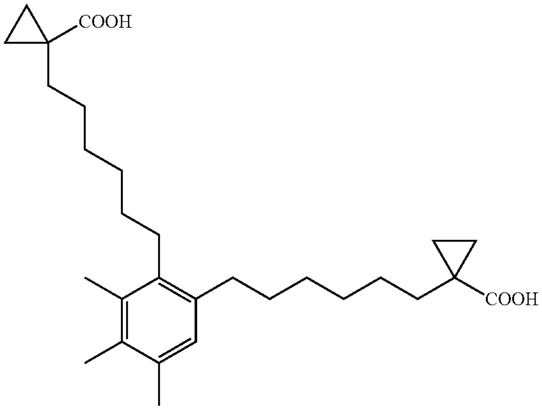 [SMILES: Cc1cc(CCCCCCC2(C(=O)O)CC2)c(CCCCCCC2(C(=O)O)CC2)c(C)c1C] |
| 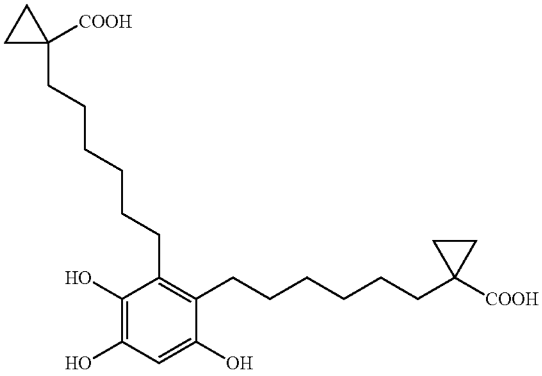 [SMILES: O=C(O)C1(CCCCCCc2c(O)cc(O)c(O)c2CCCCCCC2(C(=O)O)CC2)CC1] | 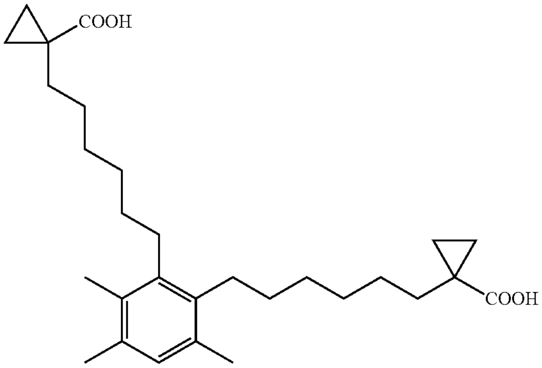 [SMILES: Cc1cc(C)c(CCCCCCC2(C(=O)O)CC2)c(CCCCCCC2(C(=O)O)CC2)c1C] |

Compounds of Formula (II)

In some embodiments, the compound of the invention is a compound of Formula (II):

(II)

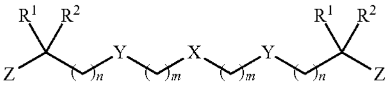

or a pharmaceutically acceptable salt or solvate thereof, wherein:

each $R^1$ and $R^2$ is independently H, $-C_1$-$C_6$ alkyl, $-C_2$-$C_6$ alkenyl, $-C_2$-$C_6$ alkynyl, phenyl or benzyl, or each carbon atom together with the $R^1$ and $R^2$ attached to the carbon atom independently form a $-C_3$-$C_7$ cycloalkyl group;

each n is independently 0, 1, 2, or 3;

each m is independently 1, 2, 3, 4, 5, 6, 7, 8 or 9;

X is $-C(=O)-$, $-CHR^3-$, $-CH-CH_2(OR^3)-$, $-O-$, $-S-$, $-S(=O)-$, $-S(O)_2-$, $-NR_3-$, $-N(OH)-$, $-N(\rightarrow O)-$, or $-Se-$;

$R^3$ is H, $-OH$, $-O(C_1$-$C_6$ alkyl), $-C_1$-$C_6$ alkyl, $-C_2$-$C_6$ alkenyl, $-C_2$-$C_6$ alkynyl, $-C_3$-$C_7$ cycloalkyl, $C_4$-$C_7$ cycloalkenyl, $C_5$-$C_8$ cycloalkynyl, phenyl, or benzyl, each $-C_1$-$C_6$ alkyl, $-C_2$-$C_6$ alkenyl, $-C_2$-$C_6$ alkynyl, $-C_3$-$C_7$ cycloalkyl, $C_4$-$C_7$ cycloalkenyl, $C_5$-$C_8$ cycloalkynyl, phenyl and benzyl being unsubstituted or substituted with one or more halogen, $-CN$, $-NO_2$, or $-CF_3$ groups;

each Y is independently $-O-$, $-NH-$, $-N(OH)-$, $-N(\rightarrow O)-$, $-S-$, $-S(=O)-$, $-S(O)_2-$, or $-Se-$;

each Z is independently $-OH$, $-COOH$, $-COOR^5$, $-SO_3H$, $-SO_3R^5$,

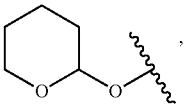 , 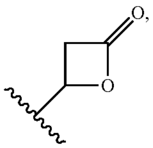 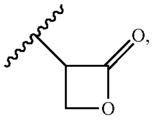

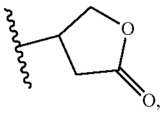 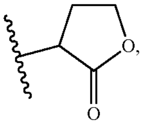 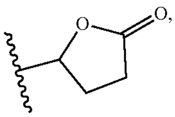

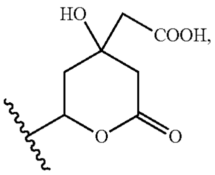 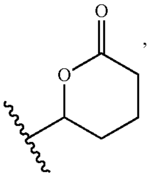 , 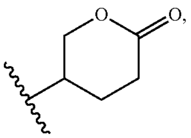

-continued

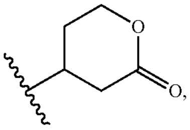 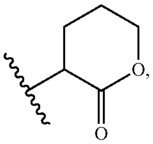

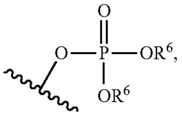 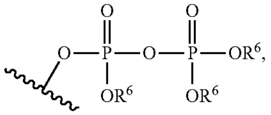

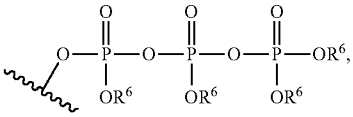 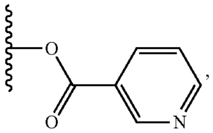

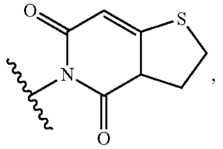

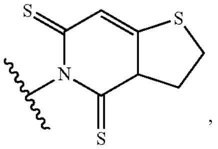 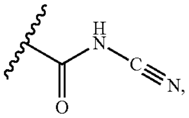

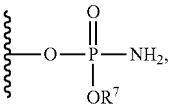 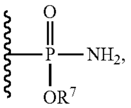 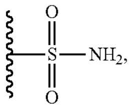 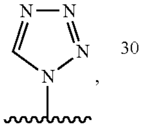

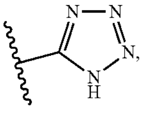 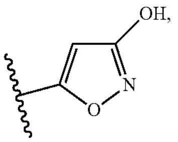 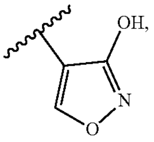

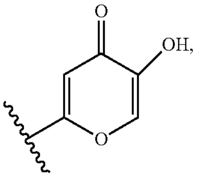 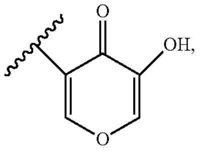

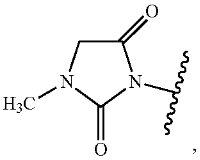 , 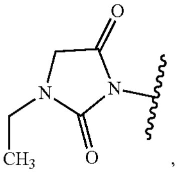 , 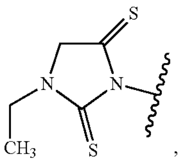 ,

-continued

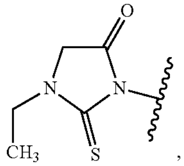 , or 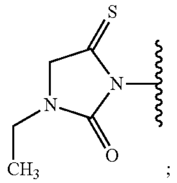 ;

each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups; and each $R^7$ is independently H, —$C_1$-$C_6$ alkyl, —$C_2$-$C_6$ alkenyl, or —$C_2$-$C_6$ alkynyl.

In some embodiments of compounds of Formula (II), X is —C(═O)—, —$CHR^3$—, —O—, —S—, —S(═O)—, or Se. In some embodiments, X is —C(═O)—, —CH(OH)—, —O—, —S—, —S(═O)—, or Se.

In some embodiments of compounds of Formula (II), $R^3$ is H, —OH, —O($C_1$-$C_3$ alkyl), or —$C_1$-$C_3$ alkyl.

In some embodiments of compounds of Formula (II), each Y is independently —O— or —S—.

In some embodiments of compounds of Formula (II), each $R^1$ and $R^2$ is independently H, —$C_1$-$C_3$ alkyl, —$C_2$-$C_3$ alkenyl, or —$C_2$-$C_3$ alkynyl. In some embodiments, each $R^1$ and $R^2$ is independently H or methyl.

In some embodiments of compounds of Formula (II), each Z is independently —COOH or —$COOR^5$. In some embodiments, each Z is —COOH.

In some embodiments of compounds of Formula (II), each $R^5$ is independently —$C_1$-$C_3$ alkyl, —$C_2$-$C_3$ alkenyl, or —$C_2$-$C_3$ alkynyl.

In some embodiments of compounds of Formula (II), each n is independently 0, 1, or 2. In some embodiments, n is 1.

In some embodiments of compounds of Formula (II), each m is independently 3, 4, 5, or 6. In some embodiments, each m is independently 4 or 5.

In some embodiments, the compound of Formula (II) has any one of the structures shown in Table B1, or a pharmaceutically acceptable salt or solvate thereof.

TABLE B1

| Compound No. | Structure and Name |
| --- | --- |
| II-1 | 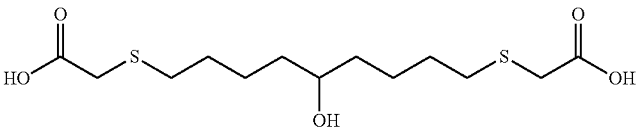 (9-Carboxymethylsulfanyl-5-hydroxy-nonylsulfanyl)-acetic acid |

TABLE B1-continued

| Compound No. | Structure and Name |
|---|---|
| II-2 | 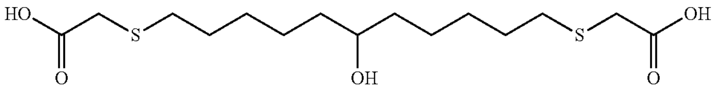 [SMILES: O=C(O)CSCCCCCC(O)CCCCCSCC(=O)O] (11-Carboxymethylsulfanyl-6-hydroxy-undecylsulfanyl)-acetic acid |
| II-3 | 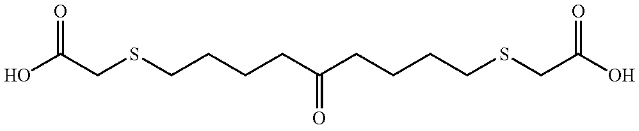 [SMILES: O=C(O)CSCCCCC(=O)CCCCSCC(=O)O] (9-Carboxymethylsulfanyl-5-oxo-nonylsulfanyl)-acetic acid |
| II-4 | 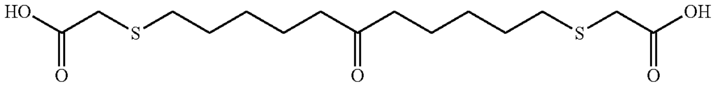 [SMILES: O=C(O)CSCCCCCC(=O)CCCCCSCC(=O)O] (11-Carboxymethylsulfanyl-6-oxo-undecylsulfanyl)-acetic acid |
| II-5 | 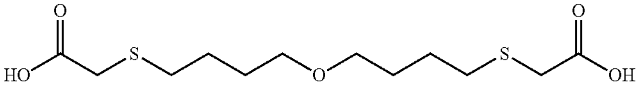 [4-(4-Carboxymethylsulfanyl-butoxy)-butylsulfanyl]-acetic acid |
| II-6 | 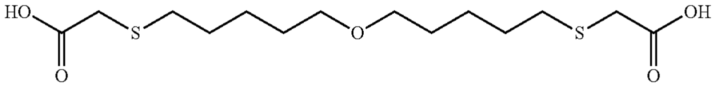 [5-(5-Carboxymethylsulfanyl-pentyloxy)-pentylsulfanyl]-acetic acid |
| II-7 | 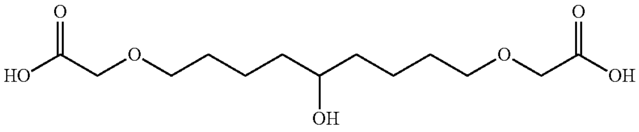 [SMILES: O=C(O)COCCCCC(O)CCCCOCC(=O)O] (9-Carboxymethoxy-5-hydroxy-nonyloxy)-acetic acid |
| II-8 | 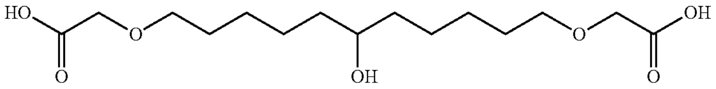 (11-Carboxymethoxy-6-hydroxy-undecyloxy)-acetic acid |
| II-9 | 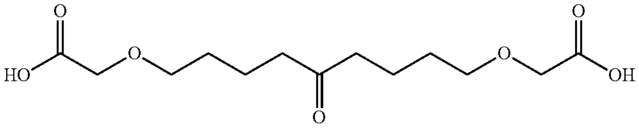 [SMILES: O=C(O)COCCCCC(=O)CCCCOCC(=O)O] (9-Carboxymethoxy-5-oxo-nonyloxy)-acetic acid |
| II-10 | 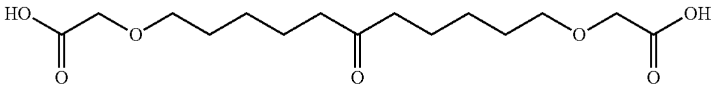 [SMILES: O=C(O)COCCCCCC(=O)CCCCCOCC(=O)O] (11-Carboxymethoxy-6-oxo-undecyloxy)-acetic acid |
| II-11 | 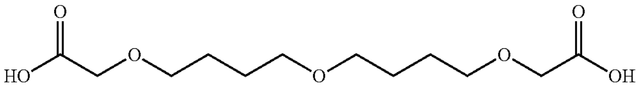 [SMILES: O=C(O)COCCCCOCCCCOCC(=O)O] [4-(4-Carboxymethoxy-butoxy)-butoxy]-acetic acid |

TABLE B1-continued

| Compound No. | Structure and Name |
| --- | --- |
| II-12 | 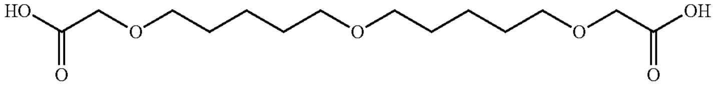 [SMILES: O=C(O)COCCCCCOCCCCCOCC(=O)O]<br>[5-(5-Carboxymethoxy-pentyloxy)-pentyloxy]-acetic acid |
| II-13 | 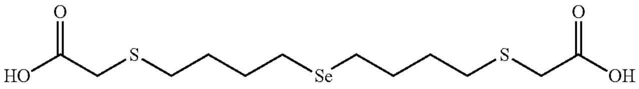<br>[4-(4-Carboxymethylsulfanyl-butylselanyl)-butylsulfanyl]-acetic acid |
| II-14 | 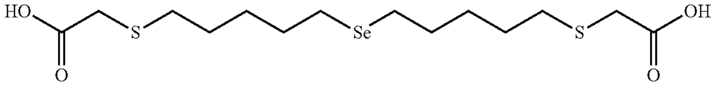<br>[5-(5-Carboxymethylsulfanyl-pentylselanyl)-pentylsulfanyl]-acetic acid |
| II-15 | 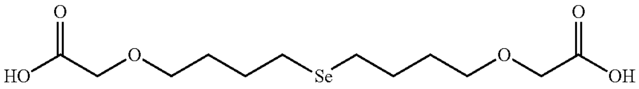 [SMILES: O=C(O)COCCCC[Se]CCCCOCC(=O)O]<br>[4-(4-Carboxymethoxy-butylselanyl)-butoxy]-acetic acid |
| II-16 | 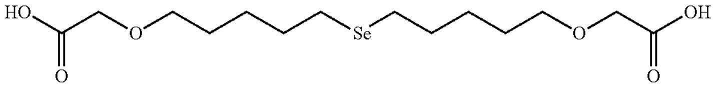 [SMILES: O=C(O)COCCCCC[Se]CCCCCOCC(=O)O]<br>[5-(5-Carboxymethoxy-pentylselanyl)-pentyloxy]-acetic acid |
| II-17 | 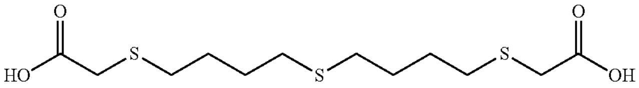<br>[4-(4-Carboxymethylsulfanyl-butylsulfanyl)-butylsulfanyl]-acetic acid |
| II-18 | 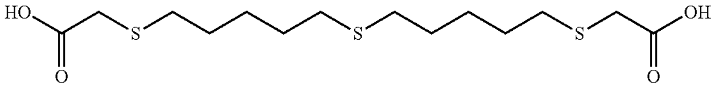<br>[5-(5-Carboxymethylsulfanyl-pentylsulfanyl)-pentylsulfanyl]-acetic acid |
| II-19 | 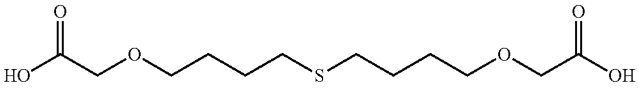<br>[4-(4-Carboxymethoxy-butylsulfanyl)-butoxy]-acetic acid |
| II-20 | 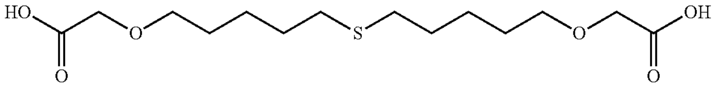<br>[5-(5-Carboxymethoxy-pentylsulfanyl)-pentyloxy]-acetic acid |
| II-21 | 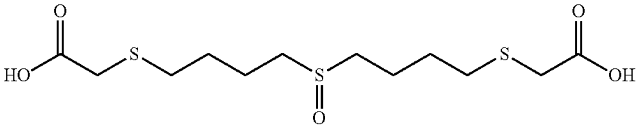<br>[4-(4-Carboxymethylsulfanyl-butane-1-sulfinyl)-butylsulfanyl]-acetic acid |

TABLE B1-continued

| Compound No. | Structure and Name |
|---|---|
| II-22 | 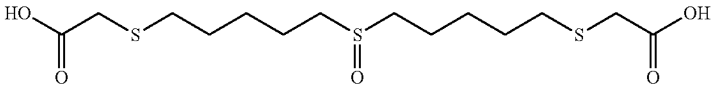 [SMILES: O=C(O)CSCCCCCS(=O)CCCCCSCC(=O)O] [5-(5-Carboxymethylsulfanyl-pentane-1-sulfinyl)-pentylsulfanyl]-acetic acid |
| II-23 | 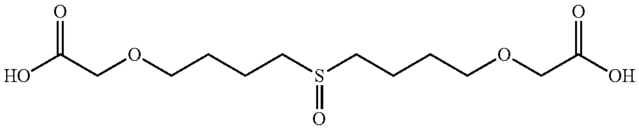 [SMILES: O=C(O)COCCCCS(=O)CCCCOCC(=O)O] [4-(4-Carboxymethoxy-butane-1-sulfinyl)-butoxy]-acetic acid |
| II-24 | 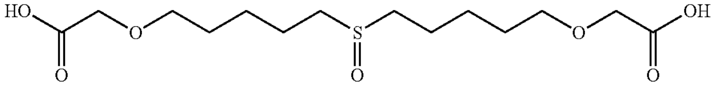 [5-(5-Carboxymethoxy-pentane-1-sulfinyl)-pentyloxy]-acetic acid |

Compounds of Formula (III), (IIIA), and (IIIB)

In some embodiments, the compound of the invention is a compound of Formula (III):

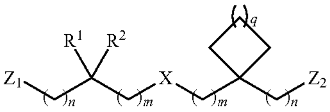

(III)

or a pharmaceutically acceptable salt or solvate thereof, wherein:

$R^1$ and $R^2$ are independently —$C_1$-$C_6$ alkyl, —$C_2$-$C_6$ alkenyl, —$C_2$-$C_6$ alkynyl, phenyl or benzyl, or $R^1$ and $R^2$ together with the attached carbon atom form a —$C_3$-$C_7$ cycloalkyl group;

each m is independently 3, 4, 5, 6, or 7;

each n is independently 0, 1, 2, 3, 4, or 5;

each q is 0, 1, 2, 3, or 4;

X is —O—, —S—, —S(=O)—, —S(O)$_2$—, —NH—, —N(OH)—, —N(→O)—, N(alkyl)-, or —N(aryl)-;

$Z_1$ and $Z_2$ are independently —$C_1$-$C_6$ alkyl, —OH, —COOH, —COOR$^5$, —SO$_3$H, —SO$_3$R$^5$,

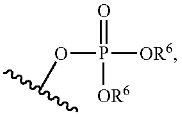 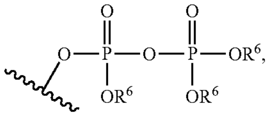

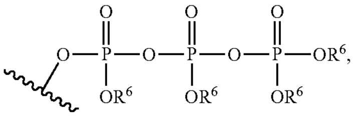 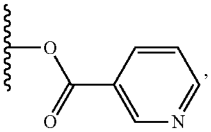,

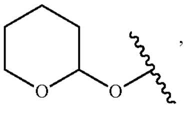, 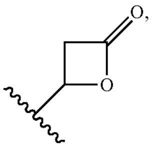 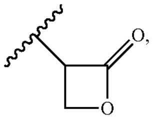

-continued

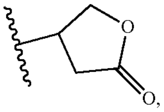 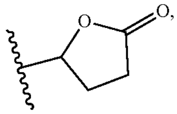 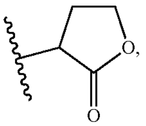

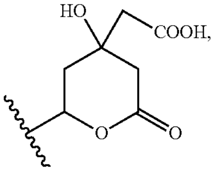, 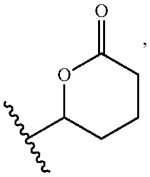 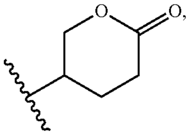

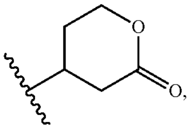 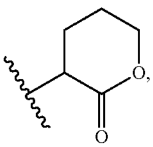 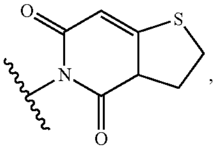,

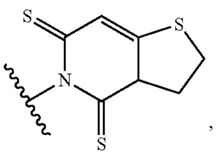, 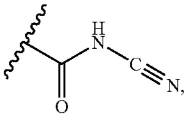

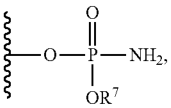 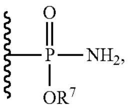 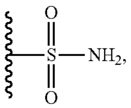 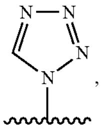,

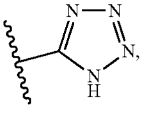 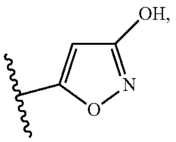 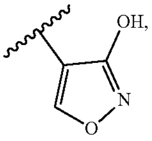

-continued

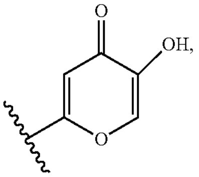 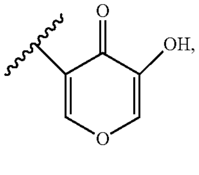

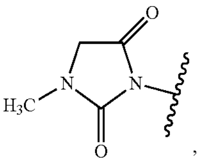 , 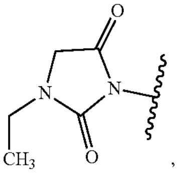 , 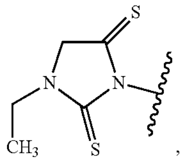 ,

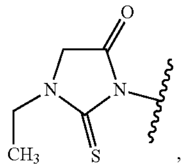 , or 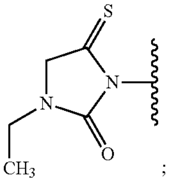 ;

each $R^5$ is independently $—C_1$-$C_6$ alkyl, $—C_2$-$C_6$ alkenyl, $—C_2$-$C_6$ alkynyl, phenyl, or benzyl, each being unsubstituted or substituted with one or more halogen, —OH, $—O(C_1$-$C_6$ alkyl), or phenyl groups;

each $R^6$ is independently H, $—C_1$-$C_6$ alkyl, $—C_2$-$C_6$ alkenyl, or $—C_2$-$C_6$ alkynyl, wherein the $—C_1$-$C_6$ alkyl, $—C_2$-$C_6$ alkenyl, or $—C_2$-$C_6$ alkynyl is unsubstituted or substituted with one or two halogen, —OH, $—O(C_1$-$C_6$ alkyl), or phenyl groups; and each $R^7$ is independently H, $—C_1$-$C_6$ alkyl, $—C_2$-$C_6$ alkenyl, or $—C_2$-$C_6$ alkynyl.

In some embodiments, the compound of the invention is a compound of Formula (IIIA):

(IIIA)

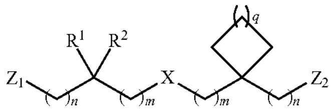

or a pharmaceutically acceptable salt or solvate thereof, wherein:

$R^1$ and $R^2$ are independently $—C_1$-$C_6$ alkyl, $—C_2$-$C_6$ alkenyl, $—C_2$-$C_6$ alkynyl, phenyl or benzyl, or $R^1$ and $R^2$ together with the attached carbon atom form a $—C_3$-$C_7$ cycloalkyl group;

each m is independently 2, 3, 4, 5, 6, or 7;

each n is independently 0, 1, 2, 3, 4, or 5;

each q is 0, 1, 2, 3, or 4;

X is —O—, —S—, —S(═O)—, $—S(O)_2—$, —NH—, —N(OH)—, —N(→O)—, N(alkyl)-, or —N(aryl)-;

$Z_1$ and $Z_2$ are $—C_1$-$C_6$ alkyl, —COOH, $—COOR^5$, $—SO_3R^5$,

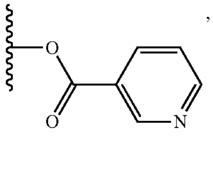 , 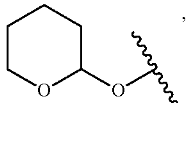 , 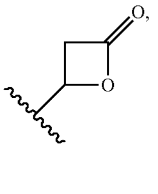

-continued

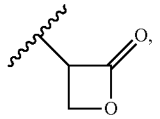 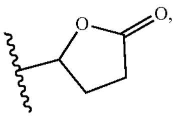 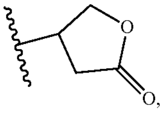

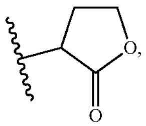 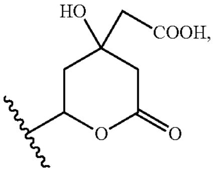 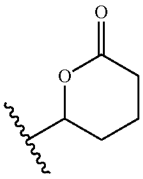 ,

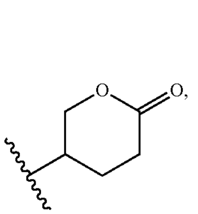 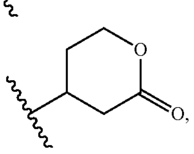 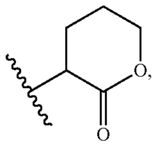

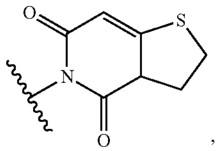 , 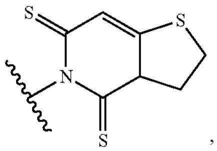 ,

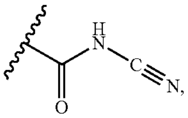 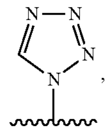 , 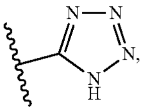

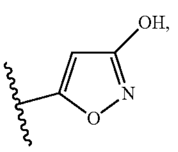 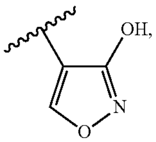 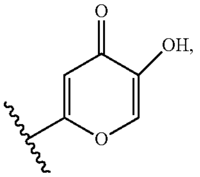

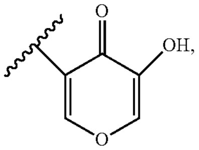 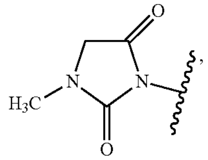

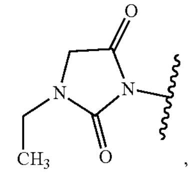 , 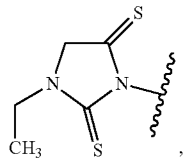 ,

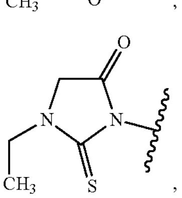 , or 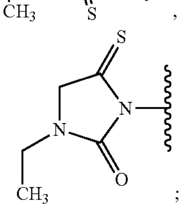 ;

wherein $Z_1$ and $Z_2$ are the same;

each $R^5$ is independently $—C_1$-$C_6$ alkyl, $—C_2$-$C_6$ alkenyl, $—C_2$-$C_6$ alkynyl, phenyl, or benzyl, each being unsubstituted or substituted with one or more halogen, —OH, $—O(C_1$-$C_6$ alkyl), or phenyl groups;

each $R^6$ is independently H, $-C_1$-$C_6$ alkyl, $-C_2$-$C_6$ alkenyl, or $-C_2$-$C_6$ alkynyl, wherein the $-C_1$-$C_6$ alkyl, $-C_2$-$C_6$ alkenyl, or $-C_2$-$C_6$ alkynyl is unsubstituted or substituted with one or two halogen, —OH, $-O(C_1$-$C_6$ alkyl), or phenyl groups; and each $R^7$ is independently H, $-C_1$-$C_6$ alkyl, $-C_2$-$C_6$ alkenyl, or $-C_2$-$C_6$ alkynyl.

In some embodiments, the compound of the invention is a compound of Formula (IIIB):

(IIIB)

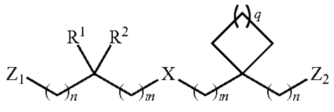

or a pharmaceutically acceptable salt or solvate thereof, wherein:

$R^1$ and $R^2$ are independently $-C_1$-$C_6$ alkyl, $-C_2$-$C_6$ alkenyl, $-C_2$-$C_6$ alkynyl, phenyl or benzyl, or $R^1$ and $R^2$ together with the attached carbon atom form a $-C_3$-$C_7$ cycloalkyl group;

each m is independently 2, 3, 4, 5, 6, or 7;

each n is independently 0, 1, 2, 3, 4, or 5;

each q is 0, 1, 2, 3, or 4;

X is —S—, —S(=O)—, $-S(O)_2-$, —NH—, —N(OH)—, —N(→O)—, N(alkyl)-, or —N(aryl)-;

$Z_1$ and $Z_2$ are independently $-C_1$-$C_6$ alkyl, —OH, —COOH, $-COOR^5$, $-SO_3H$, $-SO_3R^5$,

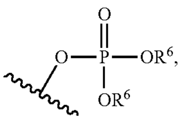 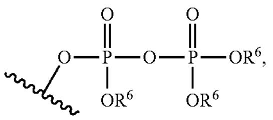

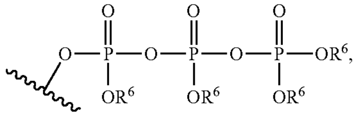 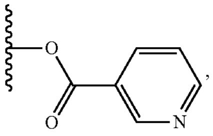

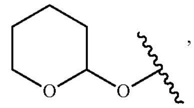 , 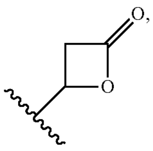 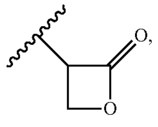

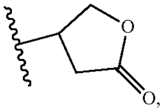 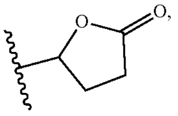 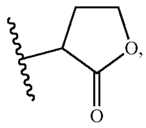

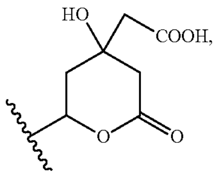 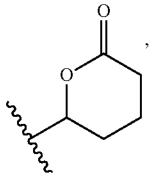 , 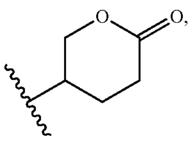

-continued

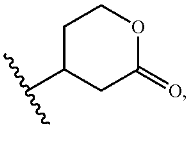 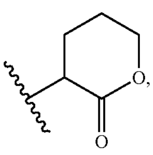 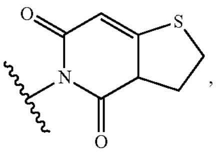 ,

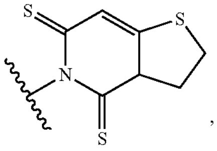 , 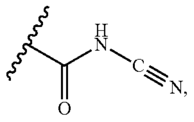

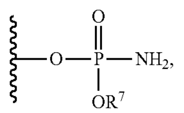 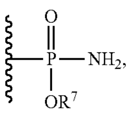 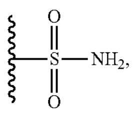 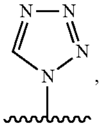 ,

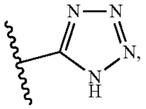 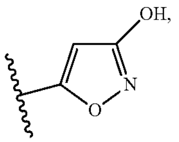 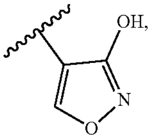

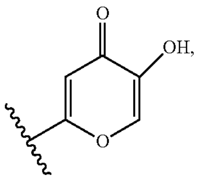 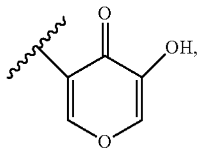

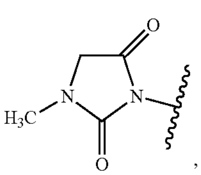 , 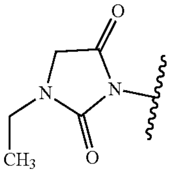 , 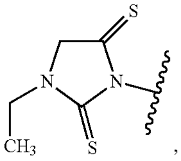 ,

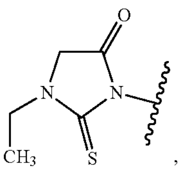 , or 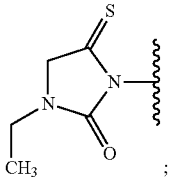 ;

each $R^5$ is independently $-C_1$-$C_6$ alkyl, $-C_2$-$C_6$ alkenyl, $-C_2$-$C_6$ alkynyl, phenyl, or benzyl, each being unsubstituted or substituted with one or more halogen, —OH, $-O(C_1$-$C_6$ alkyl), or phenyl groups;

each $R^6$ is independently H, $-C_1$-$C_6$ alkyl, $-C_2$-$C_6$ alkenyl, or $-C_2$-$C_6$ alkynyl, wherein the $-C_1$-$C_6$ alkyl, $-C_2$-$C_6$ alkenyl, or $-C_2$-$C_6$ alkynyl is unsubstituted or substituted with one or two halogen, —OH, $-O(C_1$-$C_6$ alkyl), or phenyl groups; and each $R^7$ is independently H, $-C_1$-$C_6$ alkyl, $-C_2$-$C_6$ alkenyl, or $-C_2$-$C_6$ alkynyl.

In some embodiments of compounds of Formula (III) and (IIIB), each $Z^1$ and $Z^2$ is independently —OH, —COOH, or $-COOR^5$. In some embodiments, each $Z^1$ and $Z^2$ is independently $-C_1$-$C_6$ alkyl.

In some embodiments of compounds of Formula (III), (IIIA), and (IIIB), $Z^1$ and $Z^2$ are the same group: —OH, —COOH, or $-COOR^5$. In some embodiments, both $Z^1$ and $Z^2$ is $-C_1$-$C_6$ alkyl.

In some embodiments of compounds of Formula (III), X is —S—, —S(=O)—, $-S(O)_2-$, —NH—, —N(OH)—, —N(→O)—, N(alkyl)-, or —N(aryl)-.

In some embodiments of compounds of Formula (III) and (IIIA), X is O. In some embodiments of compounds of Formula (III), when X is O, m is 2, 3, 5, 6, or 7.

In some embodiments of compounds of Formula (III), (IIIA), and (IIIB), each n is independently 0 or 1. In some embodiments, n is 0. In some embodiments, n is 1.

In some embodiments of compounds of Formula (III), (IIIA), and (IIIB), each m is independently 4, 5, or 6. In some embodiments, m is 5 or 6. In some embodiments, m is 4. In some embodiments, m is 5. In some embodiments, m is 6. In some embodiments, m is 2 or 3.

In some embodiments of compounds of Formula (III), (IIIA), and (IIIB), $R^1$ and $R^2$ together with the attached carbon atom form a —$C_3$-$C_7$ cycloalkyl group.

In some embodiments, the compound of Formula (III) or (IIIA) has any one of the structures shown in Table B2, or a pharmaceutically acceptable salt or solvate thereof.

TABLE B2

| Compound No. | Structure and Name |
|---|---|
| III-10 | 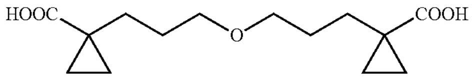 [SMILES: O=C(O)C1(CCCOCCCC2(C(=O)O)CC2)CC1] 1,1'-(oxybis(propane-3,1-diyl))bis(cyclopropane-1-carboxylic acid) |
| III-11 | 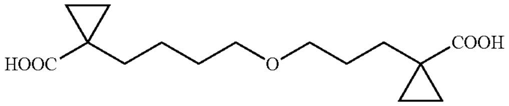 [SMILES: O=C(O)C1(CCCCOCCCC2(C(=O)O)CC2)CC1] 1-(3-(4-(1-carboxycyclopropyl)butoxy)propyl)cyclopropane-1-carboxylic acid |
| III-12 | 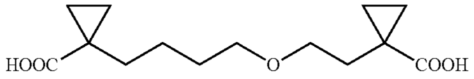 [SMILES: O=C(O)C1(CCCCOCCC2(C(=O)O)CC2)CC1] 1-(2-(4-(1-carboxycyclopropyl)butoxy)ethyl)cyclopropane-1-carboxylic acid |
| III-13 | 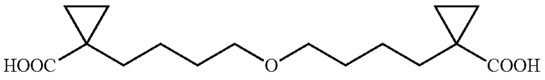 [SMILES: O=C(O)C1(CCCCOCCCCC2(C(=O)O)CC2)CC1] 1,1'-(oxybis(butane-4,1-diyl))bis(cyclopropane-1-carboxylic acid) |
| III-14 | 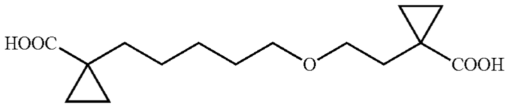 [SMILES: O=C(O)C1(CCCCCOCCC2(C(=O)O)CC2)CC1] 1-(5-(2-(1-carboxycyclopropyl)ethoxy)pentyl)cyclopropane-1-carboxylic acid |
| III-15 | 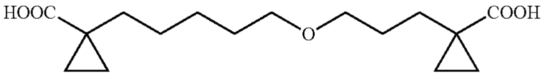 [SMILES: O=C(O)C1(CCCCCOCCCC2(C(=O)O)CC2)CC1] 1-(3-((5-(1-carboxycyclopropyl)pentyl)oxy)propyl)cyclopropane-1-carboxylic acid |
| III-16 | 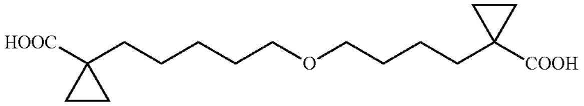 [SMILES: O=C(O)C1(CCCCCOCCCCC2(C(=O)O)CC2)CC1] 1-(5-(4-(1-carboxycyclopropyl)butoxy)pentyl)cyclopropane-1-carboxylic acid |
| III-17 | 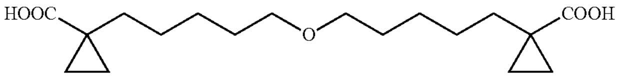 [SMILES: O=C(O)C1(CCCCCOCCCCCC2(C(=O)O)CC2)CC1] 1,1'-(oxybis(pentane-5,1-diyl))bis(cyclopropane-1-carboxylic acid) |
| III-18 | 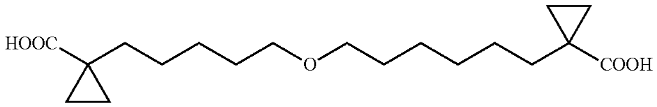 [SMILES: O=C(O)C1(CCCCCCOCCCCCC2(C(=O)O)CC2)CC1] 1-(5-((6-(1-carboxycyclopropyl)hexyl)oxy)pentyl)cyclopropane-1-carboxylic acid |

TABLE B2-continued

| Compound No. | Structure and Name |
| --- | --- |
| III-19 | 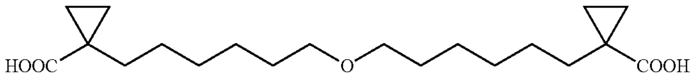 [SMILES: O=C(O)C1(CCCCCCOCCCCCCC2(C(=O)O)CC2)CC1] 1,1'-(oxybis(hexane-6,1-diyl))bis(cyclopropane-1-carboxylic acid) |
| III-20 | 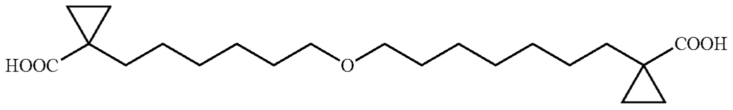 [SMILES: O=C(O)C1(CCCCCCCOCCCCCCC2(C(=O)O)CC2)CC1] 1-(6-((7-(1-carboxycyclopropyl)heptyl)oxy)hexyl)cyclopropane-1-carboxylic acid |
| III-21 | 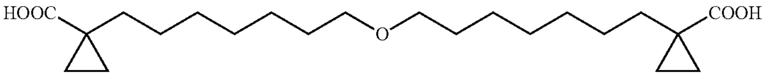 [SMILES: O=C(O)C1(CCCCCCCOCCCCCCCC2(C(=O)O)CC2)CC1] 1,1'-(oxybis(heptane-7,1-diyl))bis(cyclopropane-1-carboxylic acid) |

Compositions of the Invention

In some embodiments, the composition of the invention comprises (i) an effective amount of a compound of the invention and (ii) a pharmaceutically acceptable carrier or vehicle.

In some embodiments, the composition of the invention comprises (i) an effective amount of a compound of Formula (IA):

(IA)

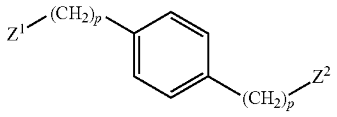

or a pharmaceutically acceptable salt or solvate thereof, wherein:

each p is independently 1, 2, 3, 4, 5, 6, or 7;

$Z^1$ and $Z^2$ is independently $—C(R^1)(R^2)—(CH_2)_c—COOH$ or $—C(R^1)(R^2)—(CH_2)_c—COOR^5$;

each c is independently 0, 1, 2, or 3;

each $R^1$ and $R^2$ is independently $—C_1$-$C_6$ alkyl, $—C_2$-$C_6$ alkenyl, $—C_2$-$C_6$ alkynyl, phenyl or benzyl, or each carbon atom together with the $R^1$ and $R^2$ attached to the carbon atom independently form a $—C_3$-$C_7$ cycloalkyl group;

each $R^5$ is independently $—C_1$-$C_6$ alkyl, $—C_2$-$C_6$ alkenyl, $—C_2$-$C_6$ alkynyl, phenyl, or benzyl, each being unsubstituted or substituted with one or more halogen, —OH, $—O(C_1$-$C_6$ alkyl), or phenyl groups; and (ii) a pharmaceutically acceptable carrier or vehicle.

In some embodiments of the composition comprising a compound of Formula (IA), each $R^1$ and $R^2$ is independently $—C_1$-$C_6$ alkyl, $—C_2$-$C_6$ alkenyl, or $—C_2$-$C_6$ alkynyl. In some embodiments, each $R^1$ and $R^2$ is independently $—C_1$-$C_3$ alkyl, $—C_2$-$C_3$ alkenyl, or $—C_2$-$C_3$ alkynyl. In some embodiments, $R^1$ and $R^2$ are methyl.

In some embodiments of the composition comprising a compound of Formula (IA), c is 0 or 1.

In some embodiments of the composition comprising a compound of Formula (IA), $R^5$ is $—C_1$-$C_6$ alkyl, $—C_2$-$C_6$ alkenyl, or $—C_2$-$C_6$ alkynyl. In some embodiments, $R^5$ is $—C_1$-$C_3$ alkyl, $—C_2$-$C_3$ alkenyl, or $—C_2$-$C_3$ alkynyl.

In some embodiments of the composition comprising a compound of Formula (IA), the compound is Compound I-1, I-2, I-3, I-4, I-5, I-6, I-7, I-8, I-9, or I-10, or a pharmaceutically acceptable salt or solvate thereof, or a compound having the structure

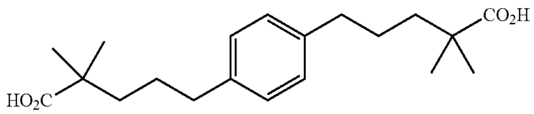

or

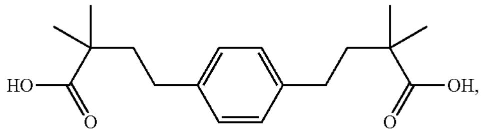

or a pharmaceutically acceptable salt or solvate thereof.

In some embodiments, the composition of the invention comprises an effective amount of a compound having a structure depicted in Tables A-1, A-2, A-3, or A-4, or a pharmaceutically acceptable salt or solvate thereof. In some embodiments, the composition of the invention comprises an effective amount of a compound having a structure depicted in Table B1, or a pharmaceutically acceptable salt or solvate thereof. In some embodiments, the composition of the invention comprises an effective amount of a compound having a structure depicted in Table B2, or a pharmaceutically acceptable salt or solvate thereof. In some embodiments, the composition of the invention comprises an effective amount of a compound having a structure depicted in Table C, or a pharmaceutically acceptable salt or solvate thereof.

TABLE C

| Compound No. | Structure and Name |
|---|---|
| III-1 | 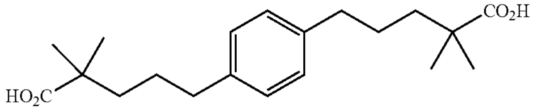 [SMILES: CC(C)(CCCc1ccc(CCCC(C)(C)C(=O)O)cc1)C(=O)O] 5-[4-(4-Carboxy-4-methylpentyl)-phenyl]-2,2-dimethylpentanoic acid |

In some embodiments, the composition of the invention further comprises another pharmaceutically active agent.

In some embodiments, the other pharmaceutically active agent is a statin, a thiazolidinedione or fibrate, a bile-acid-binding-resin, a niacin, an anti-obesity drug, a hormone, a tyrophostine, a sulfonylurea-based drug, a biguanide, an α-glucosidase inhibitor, an apolipoprotein A-I agonist, apolipoprotein E agonist, a phosphodiesterase type-5 inhibitor, a cardiovascular drug, an HDL-raising drug, an HDL enhancer, an agonist of the apolipoprotein A-I gene or protein, an agonist of the apolipoprotein A-IV gene or protein, an agonist of an apolipoprotein gene, an ATP citrate lyase modulator, an ATP citrate lyase allosteric inhibitor, an acetyl-CoA carboxylase modulator, or an acetyl-CoA carboxylase allosteric inhibitor.

In some embodiments, the other pharmaceutically active agent is an antagonist or an inhibitor of a proinflammatory gene or protein or an agonist of an anti-inflammatory gene or protein. In some embodiments, the other pharmaceutically active agent inhibits or reduces a proinflammatory function or increases an anti-inflammatory function of IL-6, CRP, TNF-α, MCP-1, MIP-1β, CCR5, CCR2, NF-κB or TGF-β1.

In some embodiments, the other pharmaceutically active agent affects the expression or function of a fibrosis gene or protein or a mitogenesis gene or protein. In some embodiments, the other pharmaceutically active agent regulates the expression or function of FGF-21, MMP-2, TIMP-1, ASK1 or Collagen type 3.

In some embodiments, the other pharmaceutically active agent is a regulator of lipid metabolism- or -trafficking-related genes, a regulator of PPAR-α target genes such as, but not limited to, HD (ECHS1), PDK4 and Cyp7A1, a regulator of SGLT1, SGL2, ApoC-III, Sulf-2, ANGPTL3, ANGPTL4 and LPL genes.

In some embodiments, the other pharmaceutically active agent is a statin. In some embodiments, the statin is atorvastatin, simvastatin, pravastatin, rosuvastatin, fluvastatin, lovastatin, pitavastatin, mevastatin, dalvastatin, dihydrocompactin, or cerivastatin, or a pharmaceutically acceptable salt thereof. In some embodiments, statin is lovastatin.

In some embodiments, the other pharmaceutically active agent is a fibrate. In some embodiment, the fibrate is fenofibrate, gemfibrozil, or fenofibric acid.

In some embodiments, the other pharmaceutically active agent is sorafenib. In yet some other embodiments, the other pharmaceutically active agent is TAXOL® (paclitaxel). In yet some other embodiments, the other pharmaceutically active agent is carotuximab. In yet some other embodiments, the other pharmaceutically active agent is pembrolizumab. In yet some other embodiments, the other pharmaceutically active agent is lenvatinib. In yet some other embodiments, the other pharmaceutically active agent is avelumab. In some embodiments, the other pharmaceutically active agent is durvalumab. In yet some other embodiments, the other pharmaceutically active agent is tremelimumab. In yet some other embodiments the other pharmaceutically active agent is nivolumab. In yet some other embodiments the other pharmaceutically active agent is tazemetostat, cemiplimab, ABX196, T-cell receptor (TCR) immune cell therapy agent, such as LioCyx™, TBI-302, namodenoson, MM-310, a tumor-injected oncolytic virus or gene-modified oncolytic virus such as, but not limited to, telomelysin and imlygic; or an immunomodulating gene-therapy agent such as MDA-7/IL-24, GLIPR1/RTVP-1, and REIC/Dkk-3.

In yet some other embodiments the other pharmaceutically active agent is cenicriviroc, elafibranor, eicosapentaenoic acid, galunisertib, LY2109761, LDE225, nivolumub, firsocostat, apararenone, metformin, Leucine-Metformin-Sildenafil Combination, IMM-124E, RG-125, Vitamin E, cysteamine, selonsertib, losartan, RO5093151, pradigastat, sitagliptin, vildagliptin, NGM282, pegbelfermin, PF-05231023, obeticholic acid, cilofexo, tropifexor, EDP-305, INT-767, galactoarabino-rhamnogalacturonate, liraglutide, semaglutide, exenatide, ND-L02-s0201/BMS-986263, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, or nalmafene. In some embodiments, the other pharmaceutically active agent is pentamidine, berberine, L-carnitine, EYP001a, silymarin, miricorilant, ursodeoxycholic acid, metadoxine, ezetimibe, cystadane, L-alanine, saroglitazar magnesium, volixibat, firsocostat, cilofexor, elafibranor, nalmefene, solithromycin, 99m Technetium-Mebrofenin, Tropifexor, S-adenosylmethionine, pentoxifylline, olesoxime, AKR-001, seladelpar, fisogatinib, doxorubicin, cabozantinib, deferoxamine, itacitinib, chiauranib, SF1126, anlotinib, P1101, varlitinib, SHR-1210, SHR6390, capmatinib, dabrafenib, trametinib, sapaniserlib, meclizine, enzalutamide, H3B-6527, OBI-3424, brivanib, tepotinib, temsirolimus, epacadostat, RO7119929, guadecitabine, linrodostat, copanlisib, MIV-818, vorolanib, RO7070179, axitinib, sunitinib, zotiraciclib citrate, sintilimab, camrelizumab, spartalizumab, toripalimab, bispecific antibody XmAb20717, mapatumumab, tremelimumab, carotuximab, tocilizumab, ipilimumab, atezolizumab, bevacizumab, ramucirumab, IBI305, ascrinvacumab, sitravatinib, cytokine-based biologic agent IRX-2, bempegaldesleukin, DKN-01, PTX-9908, AK104, PT-112, SRF388, ET1402L1-CART, Glypican 3-specific Chimeric Antigen Receptor Expressing T Cells (CAR-T cells), CD147-targeted CAR-T cells, NKG2D-based CAR T-cells, neoantigen reactive T cells, Pexastimogene Devacirepvec, Talimogene Laherparepvec, GNOS-PV02, INO-9012, ABBV-176, NCI-4650, DNAJB1-PRKACA fusion kinase peptide vaccine, or IMA970A, novantrone, prednisone, pixantrone, losoxantrone, Cytidine-phosphate-guanosine (CpG) DNA, paclitaxel, oraxol, MTL-CEBPA, ribavirin, elbasvir, grazoprevir, lipotecan, ZSP1241, U3-1784, avadomide, INCAGN01949, or CMP-001.

In some embodiments, the other pharmaceutically active agent is an anti-cancer agent, immunotherapeutic agent, oncologic virus, or vaccine.

In some embodiments, the other pharmaceutically active agent is an anti-cancer agent. In some embodiments, the anti-cancer agent is sorafenib, TAXOL® (paclitaxel), lenvatinib, tazemetostat, TBI-302, namodenoson, MM-310, cenicriviroc, elafibranor, eicosapentaenoic acid, galunisertib, LY2109761, LDE225, firsocostat, apararenone, metformin, Leucine-Metformin-Sildenafil Combination, Vitamin E, cysteamine, selonsertib, losartan, RO5093151 pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine, L-carnitine, EYP001a, silymarin, miricorilant, ursodeoxycholic acid, metadoxine, ezetimibe, cystadane, L-alanine, saroglitazar magnesium, volixibat, elafibranor, nalmefene, solithromycin, 99m Technetium-Mebrofenin, S-adenosylmethionine, pentoxifylline, olesoxime, AKR-001, seladelpar, fisogatinib, doxorubicin, cabozantinib, deferoxamine, itacitinib, chiauranib, SF1126, anlotinib, P1101, varlitinib, SHR-1210, SHR6390, capmatinib, dabrafenib, trametinib, sapanisertib, meclizine, enzalutamide, H3B-6527, OBI-3424, brivanib, tepotinib, temsirolimus, epacadostat, RO7119929, guadecitabine, linrodostat, copanlisib, MIV-818, vorolanib, RO7070179, axitinib, sunitinib, or zotiraciclib citrate.

In some embodiments, the composition of the invention further comprises an anti-cancer agent.

In some embodiments, the other pharmaceutically active agent is an immunotherapeutic agent. In some embodiments, the immunotherapeutic agent is pembrolizumab, avelumab, durvalumab, nivolumab, cemiplimab, ABX196, sintilimab, camrelizumab, spartalizumab, toripalimab, bispecific antibody XmAb20717, mapatumumab, tremelimumab, carotuximab, tocilizumab, ipilimumab, atezolizumab, bevacizumab, ramucirumab, IBI305, ascrinvacumab, TCR T-cell therapy agent, sitravatinib, cytokine-based biologic agent IRX-2, bempegaldesleukin, DKN-01, PTX-9908, AK104, PT-112, SRF388, ET1402L1-CART, Glypican 3-specific Chimeric Antigen Receptor Expressing T Cells (CAR-T cells), CD147-targeted CAR-T cells, NKG2D-based CAR T-cells, or neoantigen reactive T cells.

In some embodiments, the composition of the invention further comprises an immunotherapeutic agent.

In some embodiments, the other pharmaceutically active agent is an oncologic virus. In some embodiments, the oncologic virus is Pexastimogene Devacirepvec or Talimogene Laherparepvec. In some embodiments, the composition of the invention further comprises an oncologic virus.

In some embodiments, the other pharmaceutically active agent is a vaccine. In some embodiments, the vaccine is GNOS-PV02, INO-9012, ABBV-176, NCI-4650, DNAJB1-PRKACA fusion kinase peptide vaccine, or IMA970A. In some embodiments, the composition of the invention further comprises a vaccine.

In some embodiments, the other pharmaceutically active agent is novantrone, prednisone, pixantrone, losoxantrone, Cytidine-phosphate-guanosine (CpG) DNA, paclitaxel, oraxol, MTL-CEBPA, ribavirin, elbasvir, grazoprevir, lipotecan, ZSP1241, U3-1784, avadomide, INCAGN01949, or CMP-001.

In some embodiments, the composition of the invention further comprises two or more other pharmaceutically active agents. In some embodiments, the two or more other pharmaceutically active agents are oncolytic agents, such as, but not limited to, nanatinostat and valganciclovir.

In some embodiments, the composition of the invention further comprises a pharmaceutically active agent: sorafenib, TAXOL® (paclitaxel), lenvatinib, tazemetostat, TBI-302, namodenoson, MM-310, cenicriviroc, elafibranor, eicosapentaenoic acid, galunisertib, LY2109761, LDE225, firsocostat, apararenone, metformin, Leucine-Metformin-Sildenafil Combination, Vitamin E, cysteamine, selonsertib, losartan, RO5093151 pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine, L-carnitine, EYP001a, silymarin, miricorilant, ursodeoxycholic acid, metadoxine, ezetimibe, cystadane, L-alanine, saroglitazar magnesium, volixibat, elafibranor, nalmefene, solithromycin, 99m Technetium-Mebrofenin, S-adenosylmethionine, pentoxifylline, olesoxime, AKR-001, seladelpar, fisogatinib, doxorubicin, cabozantinib, deferoxamine, itacitinib, chiauranib, SF1126, anlotinib, P1101, varlitinib, SHR-1210, SHR6390, capmatinib, dabrafenib, trametinib, sapanisertib, meclizine, enzalutamide, H3B-6527, OBI-3424, brivanib, tepotinib, temsirolimus, epacadostat, RO7119929, guadecitabine, linrodostat, copanlisib, MIV-818, vorolanib, RO7070179, axitinib, sunitinib, or zotiraciclib citrate. In some embodiments of the composition of the invention, composition comprises (a) Compound I-1, Compound I-32, Compound I-61, or Compound III-1, or a pharmaceutically acceptable salt or solvate thereof and (b) a pharmaceutically active agent: sorafenib, TAXOL® (paclitaxel), lenvatinib, tazemetostat, TBI-302, namodenoson, MM-310, cenicriviroc, elafibranor, eicosapentaenoic acid, galunisertib, LY2109761, LDE225, firsocostat, apararenone, metformin, Leucine-Metformin-Sildenafil Combination, Vitamin E, cysteamine, selonsertib, losartan, RO5093151 pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine, L-carnitine, EYP001a, silymarin, miricorilant, ursodeoxycholic acid, metadoxine, ezetimibe, cystadane, L-alanine, saroglitazar magnesium, volixibat, elafibranor, nalmefene, solithromycin, 99m Technetium-Mebrofenin, S-adenosylmethionine, pentoxifylline, olesoxime, AKR-001, seladelpar, fisogatinib, doxorubicin, cabozantinib, deferoxamine, itacitinib, chiauranib, SF1126, anlotinib, P1101, varlitinib, SHR-1210, SHR6390, capmatinib, dabrafenib, trametinib, sapanisertib, meclizine, enzalutamide, H3B-6527, OBI-3424, brivanib, tepotinib, temsirolimus, epacadostat, RO7119929, guadecitabine, linrodostat, copanlisib, MIV-818, vorolanib, RO7070179, axitinib, sunitinib, or zotiraciclib citrate.

In some embodiments of the composition of the invention, composition comprises a compound of the invention and a pharmaceutically active agent: sorafenib, TAXOL® (paclitaxel), carotuximab, pembrolizumab, lenvatinib, avelumab, durvalumab, tremelimumab, nivolumab, tazemetostat, cemiplimab, ABX196, T-cell receptor (TCR) immune cell therapy agent, TBI-302, namodenoson, MM-310, tumor-injected oncolytic viruses or gene-modified oncolytic viruses, or immunomodulating gene-therapy agents. In some embodiments, composition comprises (a) Compound I-1, Compound I-32, Compound I-61, or Compound III-1, or a pharmaceutically acceptable salt or solvate thereof and (b) a pharmaceutically active agent is sorafenib, TAXOL® (paclitaxel), carotuximab, pembrolizumab, lenvatinib, avelumab, durvalumab, tremelimumab, nivolumab, tazemetostat, cemiplimab, ABX196, T-cell receptor (TCR) immune cell therapy agent, TBI-302, namodenoson, MM-310, tumor-injected oncolytic viruses or gene-modified oncolytic viruses, or immunomodulating gene-therapy agents.

In some embodiments of the composition of the invention, composition comprises a compound of the invention and sorafenib or lenvatinib. In some embodiments, composition comprises (a) Compound I-1, Compound I-32, Compound I-61, or Compound III-1, or a pharmaceutically acceptable salt or solvate thereof and (b) sorafenib or lenvatinib. In some embodiments, composition comprises (a) Compound I-1 or a pharmaceutically acceptable salt or solvate thereof and (b) sorafenib or lenvatinib. In some embodiments, composition comprises (a) Compound I-32 or a pharmaceutically acceptable salt or solvate thereof and (b) sorafenib or lenvatinib. In some embodiments, composition comprises (a) Compound I-32 or a pharmaceutically acceptable salt or solvate thereof and (b) sorafenib. In some embodiments, composition comprises (a) Compound I-32 or a pharmaceutically acceptable salt or solvate thereof and (b) lenvatinib. In some embodiments, composition comprises (a) Compound I-61 or a pharmaceutically acceptable salt or solvate thereof and (b) sorafenib or lenvatinib. In some embodiments, composition comprises (a) Compound I-61 or a pharmaceutically acceptable salt or solvate thereof and (b) sorafenib. In some embodiments, composition comprises (a) Compound I-61 or a pharmaceutically acceptable salt or solvate thereof and (b) lenvatinib. In some embodiments, composition comprises (a) Compound III-1 or a pharmaceutically acceptable salt or solvate thereof and (b) sorafenib or lenvatinib.

Table D sets forth embodiments A1-A4, B1-B4, C1-C4, D1-D4, E1-E4, F1-F4, G1-G4, H1-H4, I1-I4, J1-J4, K1-K4, L1-L4, M1-M4, N1-N4, O1-O4, P1-P4, Q1-Q4, R1-R4 amd S1-S4. Each embodiment of Table D refers to a particular compound of invention and another pharmaceutically active agent. For example, embodiment A1 refers to Compound I-1 (or a pharmaceutically acceptable salt or solvate thereof) and sorafenib; embodiment A2 refers to Compound I-32 (or a pharmaceutically acceptable salt or solvate thereof and sorafenib; etc. In some embodiments, the compositions of the invention comprise an effective amount of a compound of the invention and another pharmaceutically active agent set forth in an embodiment of Table D.

TABLE D

| | | Embodiments | | | |
|---|---|---|---|---|---|
| | | 1 Compound I-1 or a pharmaceutically acceptable salt or solvate thereof | 2 Compound I-32 or a pharmaceutically acceptable salt or solvate thereof | 3 Compound I-61 or a pharmaceutically acceptable salt or solvate thereof | 4 Compound III-1 or a pharmaceutically acceptable salt or solvate thereof |
| A | sorafenib | A1 | A2 | A3 | A4 |
| B | lenvatinib | B1 | B2 | B3 | B4 |
| C | taxol | C1 | C2 | C3 | C4 |
| D | carotuximab | D1 | D2 | D3 | D4 |
| E | pembrolizumab | E1 | E2 | E3 | E4 |
| F | avelumab | F1 | F2 | F3 | F4 |
| G | durvalumab | G1 | G2 | G3 | G4 |
| H | tremelimumab | H1 | H2 | H3 | H4 |
| I | nivolumab | I1 | I2 | I3 | I4 |
| J | tazemetostat | J1 | J2 | J3 | J4 |
| K | cemiplimab | K1 | K2 | K3 | K4 |
| L | ABX196 | L1 | L2 | L3 | L4 |
| M | T-cell receptor (TCR) immune cell therapy | M1 | M2 | M3 | M4 |
| N | TBI-302 | N1 | N2 | N3 | N4 |
| O | namodenoson | O1 | O2 | O3 | O4 |
| P | MM-310 | P1 | P2 | P3 | P4 |
| Q | tumor-injected oncolytic virus | Q1 | Q2 | Q3 | Q4 |
| R | gene-modified oncolytic virus | R1 | R2 | R3 | R4 |
| S | immunomodulating gene-therapy agent | S1 | S2 | S3 | S4 |

In some embodiments, the pharmaceutically acceptable carrier or vehicle includes, but is not limited to, a binder, filler, diluent, disintegrant, wetting agent, lubricant, glidant, coloring agent, dye-migration inhibitor, sweetening agent or flavoring agent.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, PA); and mixtures thereof.

Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. In some embodiments, the binder is hydroxypropylcellulose.

The binder or filler can be present from about 2% to about 49% by weight of the compositions of the invention provided herein or any range within these values. In some embodiments, the binder or filler is present in the composition of the invention from about 5% to about 15% by weight. In some embodiments, the binder or filler is present in the composition of the invention at about 5%, 6%, 7%, 8%, 9%, 8%, 10%, 11%, 12%, 13%, 14%, or 15% by weight or any range within any of these values.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. In some embodiments, the diluent is lactose monohydrate. In some embodiments, the diluent is lactose monohydrate Fast-Flo 316 NF.

The compositions of the invention can comprise a diluent, e.g., from about 5% to about 49% of a diluent by weight of composition or any range between any of these values. In some embodiments, the diluent is present in the compositions of the invention from about 15% to about 30% by weight. In some embodiments, the diluent is present in the composition of the invention at about 15%, 16%, 17%, 18%, 19%, 18%, 20%, 21%, 22%, 23%, 24%, 25%, 26%, 27%, 28%, 29%, or 30% by weight or any range within any of these values.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the compositions of the invention can vary. In some embodiments, the disintegrant is croscarmellose sodium. In some embodiments, the disintegrant is croscarmellose sodium NF (Ac-Di-Sol).

The compositions of the invention can comprise a disintegrant, e.g., from about 0.5% to about 15% or from about 1% to about 10% by weight of a disintegrant. In some embodiments, the compositions of the invention comprise a disintegrant in an amount of about 5%, 6%, 7%, 8%, 9%, 8%, 10%, 11%, 12%, 13%, 14%, or 15% by weight of the composition or in any range within any of these values.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W. R. Grace Co., Baltimore, MD) and CAB-O-SIL® (Cabot Co. of Boston, MA); and mixtures thereof. In some embodiments, the lubricant is magnesium stearate.

The compositions of the invention can comprise a lubricant, e.g., about 0.1 to about 5% by weight of a lubricant. In some embodiments, the compositions of the invention comprise a lubricant in an amount of about 0.5%, 0.6%, 0.7%, 0.8%, 0.9%, 0.8%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, or 3.0%, by weight of the composition or in any range within any of these values.

Suitable glidants include colloidal silicon dioxide, CAB-O-SIL® (Cabot Co. of Boston, MA), and talc, including asbestos-free talc.

Coloring agents include any of the approved, certified, water soluble FD&C dyes, and water insoluble FD&C dyes suspended on alumina hydrate, and color lakes and mixtures thereof.

Flavoring agents include natural flavors extracted from plants, such as fruits, and synthetic blends of compounds that provide a pleasant taste sensation, such as peppermint and methyl salicylate.

Sweetening agents include sucrose, lactose, mannitol, syrups, glycerin, sucralose, and artificial sweeteners, such as saccharin and aspartame.

Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether.

Solvents include glycerin, sorbitol, ethyl alcohol, and syrup.

Examples of non-aqueous liquids utilized in emulsions include mineral oil and cottonseed oil. Organic acids include citric and tartaric acid. Sources of carbon dioxide include sodium bicarbonate and sodium carbonate.

The compounds of the invention and the compositions of the invention can be formulated for administration by a variety of means including orally, parenterally, by inhalation spray, topically, or rectally in formulations containing pharmaceutically acceptable carriers, adjuvants and vehicles. The term "parenteral" as used here includes subcutaneous, intravenous, intramuscular, and intraarterial injections with a variety of infusion techniques. Intraarterial and intravenous injection as used herein includes administration through catheters.

The compounds of the invention and the compositions of the invention can be formulated in accordance with the routine procedures adapted for desired administration route. Accordingly, the compositions of the invention can take such forms as suspensions, solutions or emulsions in oily or aqueous vehicles, and can contain formulatory agents such as suspending, stabilizing and/or dispersing agents. The compounds of the invention and the compositions of the invention can be formulated as a preparation suitable for implantation or injection. Thus, for example, the compositions of the invention can be formulated with suitable polymeric or hydrophobic materials (e.g., as an emulsion in an acceptable oil) or ion exchange resins, or as sparingly soluble derivatives (e.g., as a sparingly soluble salt). The compounds of the invention and the compositions of the invention can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, PA.

In some embodiments, the compositions of the invention are suitable for oral administration. These compositions can comprise solid, semisolid, gelmatrix or liquid dosage forms suitable for oral administration. As used herein, oral administration includes buccal, lingual, and sublingual administration. Suitable oral dosage forms include, without limitation, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, syrups or any combination thereof. In some embodiments, compositions of the invention suitable for oral administration are in the form of a tablet or a capsule. In some embodiments, the composition of the invention is in a form of a tablet. In some embodiments, the composition of the invention is in a form of a capsule. In some embodiments, the compound of the invention is contained in a capsule.

In some embodiments, capsules are immediate release capsules. Non-limiting example of a capsule is a Coni-snap® hard gelatin capsule.

The compositions of the invention can be in the form of compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which can be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. A film coating can impart the same general characteristics as a sugar coating. Multiple compressed tablets are compressed tablets made by more than one compression cycle, including layered tablets, and press-coated or dry-coated tablets.

In some embodiments, the coating is a film coating. In some embodiments, the film coating comprises Opadry White and simethicone emulsion 30% USP.

In some embodiments, the compound of the invention is contained in a tablet. In some embodiments, the compound of the invention is contained in a compressed tablet. In some embodiments, the compound of the invention is contained in a film-coated compressed tablet. In some embodiments, the compositions of the invention are in the form of film-coated compressed tablets.

In some embodiments, the compositions of the invention is prepared by fluid bed granulation of the compound of the invention with one or more pharmaceutically acceptable carrier, vehicle, or excipients. In some embodiments, the compositions of the invention prepared by fluid bed granulation process can provide tablet formulation with good flowability, good compressibility, fast dissolution, good stability, and/or minimal to no cracking. In some embodiments, the fluid bed granulation process allows preparation of formulations having high drug loading, such as over 70% or over 75% of a compound of the invention.

The compositions of the invention can be in the form of soft or hard capsules, which can be made from gelatin, methylcellulose, starch, or calcium alginate. The hard gelatin capsule, also known as the dry-filled capsule (DFC), can comprise of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells can contain a preservative to prevent the growth of microorganisms. Suitable preservatives are those as described herein, including methyl- and propyl-parabens, and sorbic acid. The liquid, semisolid, and solid dosage forms provided herein can be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules can also be coated as known by those of skill in the art in order to modify or sustain dissolution of the active ingredient.

The compositions of the invention can be in liquid or semisolid dosage forms, including emulsions, solutions, suspensions, elixirs, and syrups. An emulsion can be a two-phase system, in which one liquid is dispersed in the form of small globules throughout another liquid, which can be oil-in-water or water-in-oil. Emulsions can include a pharmaceutically acceptable non-aqueous liquids or solvent, emulsifying agent, and preservative. Suspensions can include a pharmaceutically acceptable suspending agent and preservative. Aqueous alcoholic solutions can include a pharmaceutically acceptable acetal, such as a di-(lower alkyl)acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs can be clear, sweetened, and hydroalcoholic solutions. Syrups can be concentrated aqueous solutions of a sugar, for example, sucrose, and can comprise a preservative. For a liquid dosage form, for example, a solution in a polyethylene glycol can be diluted with a sufficient quantity of a pharmaceutically acceptable liquid carrier, e.g., water, to be measured conveniently for administration.

The compositions of the invention for oral administration can be also provided in the forms of liposomes, micelles, microspheres, or nanosystems. Miccellar dosage forms can be prepared as described in U.S. Pat. No. 6,350,458.

The compositions of the invention can be provided as non-effervescent or effervescent, granules and powders, to be reconstituted into a liquid dosage form. Pharmaceutically acceptable carriers and excipients used in the non-effervescent granules or powders can include diluents, sweeteners, and wetting agents. Pharmaceutically acceptable carriers and excipients used in the effervescent granules or powders can include organic acids and a source of carbon dioxide.

Coloring and flavoring agents can be used in all of the above dosage forms. And, flavoring and sweetening agents are especially useful in the formation of chewable tablets and lozenges.

The compositions of the invention can be formulated as immediate or modified release dosage forms, including delayed-, extended, pulsed-, controlled, targeted-, and programmed-release forms.

In some embodiments, the compositions of the invention comprise a film-coating.

The compositions of the invention can comprise another active ingredient that does not impair the composition's therapeutic or prophylactic efficacy or can comprise a substance that augments or supplements the composition's efficacy.

The tablet dosage forms can comprise the compound of the invention in powdered, crystalline, or granular form, and can further comprise a carrier or vehicle described herein, including binder, disintegrant, controlled-release polymer, lubricant, diluent, or colorant.

In some embodiments, the compositions of the invention can further comprise an excipient such as a diluent, a disintegrant, a wetting agent, a binder, a glidant, a lubricant, or any combination thereof. In some embodiments, a tablet comprises a binder. And, in some embodiments, the binder comprises microcrystalline cellulose, dibasic calcium phosphate, sucrose, corn starch, polyvinylpyrridone, hydroxypropyl cellulose, hydroxymethyl cellulose, or any combination thereof. In other embodiments, the tablet comprises a disintegrant. In other embodiments, the disintegrant comprises sodium croscarmellose, sodium starch glycolate, or any combination thereof. In other embodiments, the tablet comprises a lubricant. And, in some embodiments, the lubricant comprises magnesium stearate stearic acid, hydrogenated oil, sodium stearyl fumarate, or any combination thereof.

In some embodiments, the compositions of the invention are in the form of a tablet that comprises a binder such as any of the binders described herein.

In some embodiments, the compositions of the invention are in the form of a tablet that comprises a disintegrant such as any of the disintegrants described herein.

In some embodiments, the compositions of the invention are in the form of a tablet that comprises a lubricant such as any of the lubricants described herein.

In some embodiments, the compositions of the invention can be in a modified release or a controlled release dosage form. In some embodiments, the compositions of the invention can comprise particles exhibiting a particular release profile. For example, the composition of the invention can comprise a compound of the invention in an immediate release form while also comprising a statin or a pharmaceutically acceptable salt thereof in a modified release form, both compressed into a single tablet. Other combination and modification of release profile can be achieved as understood by one skilled in the art. Examples of modified release dosage forms suited for pharmaceutical compositions of the instant invention are described, without limitation, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

In some embodiments, the compositions of the invention are a matrix-controlled release dosage form. For example, the compositions of the invention can comprise about 300 mg to about 600 mg of a compound of the invention provided as a matrix-controlled release form. In some embodiments, a matrix-controlled release form can further comprise another pharmaceutically active agent. In some embodiments, the release profile of the compound of the invention and of the other pharmaceutically active agent is the same or different. Suitable matrix-controlled release dosage forms are described, for example, in Takada et al in "Encyclopedia of Controlled Drug Delivery," Vol. 2, Mathiowitz ed., Wiley, 1999.

In some embodiments, the compositions of the invention comprise from about 10 mg to about 400 mg of another pharmaceutically active agent and from about 300 mg to about 600 mg of a compound of the invention. In some embodiments, the compositions of the invention comprise from about 10 mg to about 400 mg of the anti-cancer agent and from about 300 mg to about 600 mg of a compound of the invention. In some embodiment, the composition is in a matrix-controlled modified release dosage form.

In some embodiments, the compositions of the invention comprise from about 10 mg to about 40 mg of a statin and from about 300 mg to about 600 mg of a compound of the invention, wherein the composition is in a matrix-controlled modified release dosage form.

In some embodiments, the matrix-controlled release form comprises an erodible matrix comprising water-swellable, erodible, or soluble polymers, including synthetic polymers, and naturally occurring polymers and derivatives, such as polysaccharides and proteins.

In some embodiments, the erodible matrix of the matrix-controlled release form comprises chitin, chitosan, dextran, or pullulan; gum agar, gum arabic, gum karaya, locust bean gum, gum tragacanth, carrageenans, gum ghatti, guar gum, xanthan gum, or scleroglucan; starches, such as dextrin or maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), carrrboxymethyl ethyl cellulose (CMEC,) hydroxyethyl cellulose (HEC), hydroxypropyl cellulose (HPC), cellulose acetate (CA), cellulose propionate (CP), cellulose butyrate (CB), cellulose acetate butyrate (CAB), cellulose acetate phthalate (CAP), cellulose acetate trimellitate (CAT), hydroxypropyl methyl cellulose (HPMC), HPMCP, HPMCAS, hydroxypropyl methyl cellulose acetate trimellitate (HPMCAT), or ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, NJ); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; or other acrylic acid derivatives, such as homopolymers and copolymers of butylmethacrylate, methylmethacrylate, ethylmethacrylate, ethylacrylate, (2-dimethylaminoethyl)methacrylate, or (trimethylaminoethyl)methacrylate chloride; or any combination thereof.

In other embodiments, the compositions of the invention are in a matrix-controlled modified release form comprising a non-erodible matrix. In some embodiments, the statin, the compound of the invention is dissolved or dispersed in an inert matrix and is released primarily by diffusion through the inert matrix once administered. In some embodiments, the non-erodible matrix of the matrix-controlled release form comprises an insoluble polymer, such as polyethylene, polypropylene, polyisoprene, polyisobutylene, polybutadiene, polymethylmethacrylate, polybutylmethacrylate, chlorinated polyethylene, polyvinylchloride, a methyl acrylate-methyl methacrylate copolymer, an ethylene-vinylacetate copolymer, an ethylene/propylene copolymer, an ethylene/ethyl acrylate copolymer, a vinylchloride copolymer with vinyl acetate, a vinylidene chloride, an ethylene or a propylene, an ionomer polyethylene terephthalate, a butyl rubber epichlorohydrin rubber, an ethylene/vinyl alcohol copolymer, an ethylene/vinyl acetate/vinyl alcohol terpolymer, an ethylene/vinyloxyethanol copolymer, a polyvinyl chloride, a plasticized nylon, a plasticized polyethyleneterephthalate, a natural rubber, a silicone rubber, a polydimethylsiloxane, a silicone carbonate copolymer, or a hydrophilic polymer, such as an ethyl cellulose, a cellulose acetate, a crospovidone, or a cross-linked partially hydrolyzed polyvinyl acetate; a fatty compound, such as a carnauba wax, a microcrystalline wax, or a triglyceride; or any combination thereof.

The compositions of the invention that are in a modified release dosage form can be prepared by methods known to those skilled in the art, including direct compression, dry or wet granulation followed by compression, melt-granulation followed by compression.

In some embodiments, the compositions of the invention comprise a tablets-in-capsule system, which can be a multifunctional and multiple unit system comprising versatile mini-tablets in a hard gelatin capsule. The mini-tablets can be rapid-release, extended-release, pulsatile, delayed-onset extended-release minitablets, or any combination thereof. In some embodiments, combinations of mini-tablets or combinations of mini-tablets and minibeads comprising multiple active pharmaceutical agents can each have specific lag times, of release multiplied pulsatile drug delivery system (DDS), site-specific DDS, slow-quick DDS, quick/slow DDS and zero-order DDS.

In some embodiments, the compositions of the invention are in an osmotic-controlled release dosage form.

In some embodiments, the osmotic-controlled release device comprises a one-chamber system, a two-chamber system, asymmetric membrane technology (AMT), an extruding core system (ECS), or any combination thereof. In some embodiments, such devices comprise at least two components: (a) the core which contains the active pharmaceutical agent(s); and (b) a semipermeable membrane with at least one delivery port, which encapsulates the core. The semipermeable membrane controls the influx of water to the core from an aqueous environment of use so as to cause drug release by extrusion through the delivery port(s).

In some embodiments, the core of the osmotic device optionally comprises an osmotic agent, which creates a driving force for transport of water from the environment of use into the core of the device. One class of osmotic agents useful in the compositions of invention comprises water-swellable hydrophilic polymers, which are also referred to as "osmopolymers" or "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly (2-hydroxyethyl methacrylate), poly(acrylic) acid, poly (methacrylic) acid, polyvinylpyrrolidone (PVP), cross-linked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

Another class of osmotic agents useful in the compositions of the invention comprises osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the compound of the invention dissolves following administration. For example, an amorphous sugar, such as Mannogeme EZ (SPI Pharma, Lewes, DE) can be included to provide faster delivery during the first couple of hours (e.g., about 1 to about 5 hrs) to promptly produce prophylactic or therapeutic efficacy, and gradually and continually release of the remaining amount to maintain the desired level of therapeutic or prophylactic effect over an extended period of time. In some embodiments, the compound of the invention is released from the compositions of the invention at such a rate to replace the amount of the compound of the invention metabolized or excreted by the subject.

The core can also include a wide variety of other excipients and carriers as described herein to enhance the performance of the dosage form or to promote stability or processing.

Materials useful for forming the semipermeable membrane include various grades of acrylics, vinyls, ethers, polyamides, polyesters, and cellulosic derivatives that are water-permeable and water-insoluble at physiologically relevant pHs or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

The semipermeable membranes can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the compound of the invention released and the release rate can substantially be modulated via the thickness and porosity of the semipermeable membrane, the composition of the core, and the number, size, and position of the delivery ports.

In some embodiments, the pharmaceutical composition in an osmotic controlled-release dosage form can further comprise additional conventional excipients as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In some embodiments, the pharmaceutical composition provided herein is formulated as asymmetric membrane technology (AMT) controlled-release dosage form that comprises an asymmetric osmotic membrane that coats a core comprising the active ingredient(s) and other pharmaceutically acceptable excipients. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In some embodiments, the pharmaceutical composition provided herein is formulated as ESC controlled-release dosage form that comprises an osmotic membrane that coats a core comprising the compound of the invention, hydroxylethyl cellulose, and other pharmaceutically acceptable excipients.

In some embodiments, the compositions of the invention are a modified release dosage form that is fabricated as a multiparticulate-controlled release dosage form that comprises a plurality of particles, granules, or pellets, microparticulates, beads, microcapsules and microtablets, ranging from about 10 μm to about 3 mm, about 50 μm to about 2.5 mm, or from about 100 μm to 1 mm in diameter.

The multiparticulate-controlled release dosage forms can provide a prolonged release dosage form with an improved bioavailability. Suitable carriers to sustain the release rate of the compound of the invention include, without limitation, ethyl cellulose, HPMC, HPMC-phtalate, colloidal silicondioxide and Eudragit-RSPM.

Compositions of the invention in pellet form can comprise 50-80% (w/w) of a drug and 20-50% (w/w) of microcrystalline cellulose or other polymers. Suitable polymers include, but are not limited to, microcrystalline wax, pregelatinized starch and maltose dextrin.

Beads can be prepared in capsule and tablet dosage forms. Beads in tablet dosage form can demonstrate a slower dissolution profile than microparticles in capsule form. Microparticle fillers suitable for compositions and therapeutic or prophylactic methods of the invention include, without limitation, sorbitan monooleate (Span 80), HPMC, or any combination thereof. Suitable dispersions for controlled release latex include, for example, ethyl-acrylate and methyl-acrylate.

In some embodiments, the compositions of the invention are in the form or microcapsules and/or microtablets. In some embodiments, microcapsules comprise extended release polymer microcapsules containing a statin and a compound of the invention with various solubility characteristics. Extended release polymer microcapsules can be prepared with colloidal polymer dispersion in an aqueous environment. In other embodiments, microcapsules suitable for the compositions and methods provided herein can be prepared using conventional microencapsulating techniques (Bodmeier & Wang, 1993).

Such multiparticulates can be made by the processes known to those skilled in the art, including wet-and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989. Excipients for such technologies are commercially available and described in US Pharmacopeia.

Other excipients as described herein can be blended with the compositions of the invention to aid in processing and forming the multiparticulates. The resulting particles can themselves constitute the multiparticulate dosage form or can be coated by various film-forming materials, such as enteric polymers, water-swellable, or water-soluble polymers. The multiparticulates can be further processed as a capsule or a tablet.

In other embodiments, the compositions of the invention are in a dosage form that has an instant releasing component and at least one delayed releasing component, and is capable of giving a discontinuous release of the compound in the form of at least two consecutive pulses separated in time from about 0.1 hour to about 24 hours.

In some embodiments, the compositions of the invention comprise from about 1 mg to about 1000 mg of a compound of the invention or any amount ranging from and to these values. In some embodiment, the compositions of the invention comprise from about 1 mg to about 500 mg of a compound of the invention or any amount ranging from and to these values. In some embodiment, the compositions of the invention comprise from about 1 mg to about 400 mg of a compound of the invention or any amount ranging from and to these values.

In other embodiments, the compositions of the invention comprise a compound of the invention in an amount that is a molar equivalent to about 1 mg to about 1000 mg of a compound of the invention or any amount ranging from and to these values. In other embodiments, the compositions of the invention comprise a compound of the invention in an amount that is a molar equivalent to about 1 mg to about 500 mg of a compound of the invention or any amount ranging from and to these values. In other embodiments, the compositions of the invention comprise a compound of the invention in an amount that is a molar equivalent to about 1 mg to about 400 mg of a compound of the invention or any amount ranging from and to these values.

In some embodiments, the compositions of the invention comprise a compound of the invention in an amount of about 10 wt % to about 99 wt % of the total weight of the composition of the invention.

Methods of the Invention

The present invention provides methods for treating or preventing a disease, comprising administering to a subject in need thereof an effective amount of the compound of the invention or the composition of the invention, wherein the disease is liver disease or an abnormal liver condition; cancer (such as hepatocellular carcinoma or cholangiocarcinoma); a malignant or benign tumor of the lung, liver, gall bladder, bile duct or digestive tract; an intra- or extra-hepatic bile duct disease; a disorder of lipoprotein; a lipid-and-metabolic disorder; cirrhosis; fibrosis; a disorder of glucose metabolism; a cardiovascular or related vascular disorder; a disease resulting from steatosis, fibrosis, or cirrhosis; a disease resulting from steatosis, fibrosis, and cirrhosis; a disease associated with increased inflammation (such as hepatic inflammation or pulmonary inflammation); hepatocyte ballooning; a peroxisome proliferator activated receptor-associated disorder; an ATP citrate lyase disorder; an acetyl-coenzyme A carboxylase disorder; obesity; pancreatitis; or renal disease.

The present invention provides methods for treating or preventing a disease, comprising administering to a subject in need thereof an effective amount of the compound of the invention or the composition of the invention, wherein the disease is cancer, a lipid-and-metabolic disorder, a liver disorder, cirrhosis, fibrosis, a disorder of glucose metabolism, a peroxisome proliferator activated receptor-associated disorder, a malignant or benign tumor of the lung, liver, bile and digestive tract, an ATP citrate lyase disorder, an acetyl-coenzyme A carboxylase disorder, obesity, pancreatitis, renal disease, hepatocyte ballooning, hepatic inflammation, or pulmonary inflammation.

In some embodiments of the methods as disclosed herein, the disease is cancer. In some embodiments, the cancer is hepatocellular carcinoma (HCC), HCC with cirrhosis, HCC without cirrhosis, cholangiocarcinoma, colorectal cancer, biliary cancer, or pulmonary cancer. In some embodiments, the cancer is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma, multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia (CML), chronic lymphocytic leukemia (CLL), hairy cell leukemia, multiple myeloma, lymphoblastic leukemia, myelogenous leukemia, lymphocytic leukemia, myelocytic leukemias, Hodgkin's disease, non-Hodgkin's lymphoma, multiple myeloma, Waldenstrom's macroglobulinemia, heavy chain disease, gastrointestinal cancer, head-and-neck cancer, hematopoietic cancer, or polycythemia vera.

In some embodiments, gastrointestinal (digestive) cancer is gastrointestinal stromal tumor (GIST), esophagueal cancer, gallbladder cancer, gastrointestinal carcinoid tumor, cholangiocarcinoma, duodenal cancer, gastroesophageal (ge) junction cancer, islet cell cancer, lpancreatic cancer, stomach cancer, colon cancer, rectal cancer, colorectal cancer, anal cancer, liver cancer, biliary cancer, bile duct cancer, cancer of the small intestine, seudomyxoma peritonei, small bowel cancer, or cancer of unknown primary.

In some embodiments, the hematopoietic cancer is non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), or chronic myeloid leukemia (CML).

In some embodiments of the methods as disclosed herein, the cancer is in any stage. In some embodiments, the cancer can be in stage 0, stage I, stage II, stage III, or stage IV. In some embodiments of the methods as disclosed herein, the disease is tumor and the tumor can be in any stage. In some embodiments, the tumor is grade 1, grade 2, grade 3, or grade 4.

In some embodiments of the methods as disclosed herein, the disease is a lipid-and-metabolic disorder. In some embodiments, the lipid-and-metabolic disorder is characterized by high C-reactive protein (CRP), high serum amyloid A (SAA),high alanine aminotransferase (ALT), high aspartate aminotransferase (AST), high alkaline phosphatase (ALP), high gamma-glutamyl transferase (GGT), high low-density lipoprotein (LDL), high very-low-density lipoprotein (VLDL), high apolipoprotein B (ApoB) and ApoB/Lp (a) (lipoprotein(a)) ratio, high total cholesterol, low high-density lipoprotein (HDL), or high non-HDL-cholesterol in the subject's plasma or blood serum; or by high glucose and insulin resistance in a subject with diabetes. In some embodiments, the lipid-and-metabolic disorder is non-alcoholic fatty liver disease (NAFLD), non-alcoholic steatohepatitis (NASH), or alcoholic steatohepatitis (ASH).

In some embodiments of the methods as disclosed herein, the disease is a disorder of glucose metabolism. In some embodiments, the disorder of glucose metabolism is type I diabetes or type II diabetes.

In some embodiments of the methods as disclosed herein, the disease is a disease resulting from steatosis, fibrosis, and cirrhosis. In some embodiment, the disease resulting from steatosis is inflammation. In some embodiment, the disease resulting from steatosis is NAFLD, NASH, or ASH. In some embodiment, the disease resulting from fibrosis is liver cirrhosis or liver failure. In some embodiment, the disease resulting from cirrhosis is, hepatocellular carcinoma, liver damage, or hepatic encephalopathy.

The present invention provides methods for reducing a concentration in a subject's blood plasma or blood serum the subject's C-reactive protein (CRP) concentration, serum amyloid A (SAA) concentration, alanine aminotransferase (ALT) concentration, aspartate aminotransferase (AST) concentration, alkaline phosphatase (ALP) concentration, gamma-glutamyl transferase (GGT) concentration, serum creatinine concentration, 7α-hydroxy-4-cholesten-3-one (C4) concentration, protein:creatinine ratio, creatine kinase concentration, angiopoietin-like protein 3 concentration, angiopoietin-like protein 4 concentration, angiopoietin-like protein 8 concentration, fibrinogen concentration, total cholesterol concentration, low-density lipoprotein cholesterol concentration, low-density lipoprotein concentration, very low-density lipoprotein cholesterol concentration, very low-density lipoprotein concentration, non-HDL cholesterol concentration, non-HDL concentration, apolipoprotein B concentration, lipoprotein(a) concentration, or serum triglyceride concentration, comprising administering to a subject in need thereof an effective amount of the compound of the invention or the composition of the invention.

The present invention provides methods for reducing triglyceride concentration in a subject's liver, comprising administering to a subject in need thereof an effective amount of the compound of the invention or the composition of the invention.

The present invention provides methods for elevating in a subject's blood plasma or blood serum a concentration of high-density lipoprotein cholesterol or high-density lipoprotein, comprising administering to a subject in need thereof an effective amount of a compound of the invention or the composition of the invention.

The present invention provides methods for increasing functionalization of the high-density lipoprotein cholesterol, without increasing its concentration in a subject's blood plasma or blood serum, comprising administering to a subject in need thereof an effective amount of a compound of the invention or the composition of the invention, wherein an amount or rate of excretion of cholesterol and triglycerides increases.

The present invention provides methods for treating a disease, comprising administering to a subject in need thereof an effective amount of the compound of the invention or the composition of the invention, wherein the disease is gastrointestinal disease, irritable bowel syndrome (IBS), inflammatory bowel disease (IBD), or autoimmune disease.

In some embodiments of the methods as disclosed herein, the disease is inflammatory bowel disease. In some embodiments, the inflammatory bowel disease is Crohn's Disease or ulcerative colitis.

In some embodiments of the methods as disclosed herein, the disease is autoimmune disease. In some embodiments, the autoimmune disease is systemic lupus erythematosus.

The present invention provides methods for regressing, reducing the rate of progression or inhibiting progression of fibrosis, hepatocyte ballooning or hepatic inflammation, comprising administering to a subject in need thereof an effective amount of the compound of the invention or the composition of the invention.

The present invention provides methods for inhibiting, reducing, or delaying advancement of a subject's lipid synthesis, liver steatosis, hepatocyte ballooning or inflammation, liver fibrosis, lung fibrosis, or cirrhosis, comprising administering to a subject in need thereof an effective amount of the compound of the invention or the composition of the invention.

The present invention provides methods for reducing a subject's risk of developing or having atherosclerosis, coronary heart disease, peripheral vascular disease, stroke, or restenosis, comprising administering to a subject in need thereof an effective amount of a compound of the invention.

The present invention provides methods for elevating HDL concentration in the subject's blood serum or plasma, comprising administering to a subject in need thereof an effective amount of the compound of the invention or the composition of the invention.

The present invention provides methods for inhibiting NF-kB or stellate cell activation, comprising administering to a subject in need thereof an effective amount of the compound of the invention or the composition of the invention.

The present invention provides methods for activating PPAR (peroxisome proliferator-activated receptor) in a subject, comprising administering to a subject in need thereof an effective amount of the compound of the invention or the composition of the invention.

The present invention provides methods for CCR2/CCR5 gene downregulation, comprising administering to a subject in need thereof an effective amount of a compound of the invention.

The present invention provides methods for inhibiting one or more of NF-kB activation, CCR2 activation, CCR5 activation, and stellate cell activation, comprising administering to a subject in need thereof an effective amount of the compound of the invention or the composition of the invention.

The present invention provides methods for inhibiting an interleukin's activation or concentration, comprising administering to a subject in need thereof an effective amount of a compound of the invention or the composition of the invention. In some embodiments, the interleukin (IL) is IL-2, IL-6, IL-17 or IL-18.

The present invention provides methods for inhibiting fibrin/fibrinogen, gastrin, lactate dehydrogenase, prostatic acid phosphatase (PAP), thyroglobulin, urine catecholamine, urine vanillylmandelic acid (VMA) or urine homovanillic acid (HVA), comprising administering to a subject in need thereof an effective amount of a compound of the invention or the composition of the invention.

The present invention provides methods for inhibiting beta-human chorionic gonadotropin (beta-hCG), beta-2-microglobulin (B2M), B-cell immunoglobulin, comprising administering to a subject in need thereof an effective amount of a compound of the invention or the composition of the invention.

The present invention provides methods for inhibiting alpha-fetoprotein (AFP), comprising administering to a subject in need thereof an effective amount of a compound of the invention or the composition of the invention.

The present invention also provides methods for inhibiting hepatic fatty acid or sterol synthesis, comprising administering to a subject in need thereof an effective amount of the compound of the invention or the composition of the invention.

The present invention also provides methods for treating or preventing a disease or disorder that is capable of being treated or prevented by increasing HDL levels, comprising administering to a subject in need thereof an effective amount of the compound of the invention or the composition of the invention.

The present invention also provides methods for treating or preventing a disease or disorder that is capable of being treated or prevented by lowering LDL levels, which comprises administering to a subject in need thereof an effective amount of the compound of the invention or the composition of the invention.

Without being limited by theory, it is believed that the compounds of the invention favorably alter lipid metabolism at least in part by enhancing oxidation of fatty acids through the ACC/malonyl-CoA/CPT-I regulatory axis. Accordingly, the invention also provides methods for treating or preventing a metabolic syndrome disorder, comprising administering to a subject in need thereof an effective amount of a compound of the invention or composition of the invention.

The present invention further provides methods for modulating, directly inhibiting or allosterically inhibiting ATP citrate lyase in a subject, comprising administering to the subject an effective amount of a compound of the invention or composition of the invention.

The present invention further provides methods for modulating, directly inhibiting or allosterically inhibiting acetyl-CoA carboxylase 1 (ACC1) or acetyl-CoA carboxylase 2 (ACC2) in a subject, comprising administering to the subject an effective amount of a compound of the invention or composition of the invention.

The present invention further provides methods for reducing the fat or cholesterol content of livestock meat or poultry eggs, comprising administering to the livestock or poultry an effective amount of the compound of the invention or the composition of the invention.

In some embodiments of the methods as disclosed herein, the compound of the invention is administered to the subject in need thereof in the range from about 1 mg to about 1000 mg or any amount ranging from and to these values. In some embodiment, the compound of the invention is administered to the subject in need thereof in the rage from about 1 mg to about 900 mg, about 1 mg to about 800 mg, about 1 mg to about 700 mg, about 1 mg to about 600 mg, about 1 mg to about 500 mg, about 1 mg to about 400 mg, or about 1 mg to about 300 mg.

In some embodiments of the methods as disclosed herein, the compound of the invention is administered to the subject in need thereof in a daily dose ranging from about 1 mg to about 1000 mg or any amount ranging from and to these values. In some embodiments, the compound of the invention is administered to the subject in need thereof at a daily dose of about 1000 mg, about 950 mg, about 900 mg, about 850 mg, about 800 mg, about 750 mg, about 700 mg, about 650 mg, about 600 mg, about 550 mg, about 500 mg, about 450 mg, about 400 mg, about 350 mg, about 300 mg, about 250 mg, about 200 mg, about 150 mg, about 100 mg, about 80 mg, about 60 mg, about 40 mg, about 20 mg, about 10 mg, about 5 mg, or about 1 mg.

In some embodiments of the methods as disclosed herein, the compound of the invention is administered to the subject in need thereof once a day at a dose of about 1 mg to about 1000 mg or any amount ranging from and to these values.

In some embodiments of the methods as disclosed herein, the compound of the invention is administered to the subject in need thereof twice a day, each dose comprising the compound of the invention in about 1 mg to about 500 mg or any amount ranging from and to these values. In some embodiment, the compound of the invention is administered to the subject in need thereof twice a day, each dose comprising the compound of the invention in about 500 mg, about 450 mg, about 400 mg, about 350 mg, about 300 mg, about 250 mg, about 200 mg, about 150 mg, about 100 mg, about 80 mg, about 60 mg, about 40 mg, about 20 mg, about 10 mg, about 5 mg, or about 1 mg.

In some embodiments of the methods as disclosed herein, the compound of the invention is administered to the subject in need thereof three times a day, each dose comprising the compound of the invention in about 1 mg to about 400 mg or any amount ranging from and to these values. In some embodiment, the compound of the invention is administered to the subject in need thereof three times a day, each dose comprising the compound of the invention in about 400 mg, about 350 mg, about 300 mg, about 250 mg, about 200 mg, about 150 mg, about 100 mg, about 80 mg, about 60 mg, about 40 mg, about 20 mg, about 10 mg, about 5 mg, or about 1 mg.

In some embodiments of the methods as disclosed herein, the methods further comprise administering an effective amount of another pharmaceutically active agent. In some embodiments, the other pharmaceutically active agent is administered concurrently or sequentially with (prior or subsequent to) the administration of the compound of the invention or the composition of the invention. In some embodiments, the other pharmaceutically active agent is a statin, a thiazolidinedione or fibrate, a bile-acid-binding-resin, a niacin, an anti-obesity drug, a hormone, a tyrophostine, a sulfonylurea-based drug, a biguanide, an α-glucosidase inhibitor, an apolipoprotein A-I agonist, apolipoprotein E agonist; a phosphodiesterase type-5 inhibitor, a cardiovascular drug, an HDL-raising drug, an HDL enhancer, a regulator of the apolipoprotein A-I gene, a regulator of the apolipoprotein A-IV gene, a regulator of the apolipoprotein gene, an ATP citrate lyase modulator, an ATP citrate lyase allosteric inhibitor, an acetyl-CoA carboxylase modulator, or an acetyl-CoA carboxylase allosteric inhibitor. In some embodiments, the other pharmaceutically active agent is lovastatin. In some embodiments, the other pharmaceutically active agent is sorafenib; TAXOL® (paclitaxel); carotuximab; pembrolizumab; lenvatinib; avelumab; durvalumab; tremelimumab; nivolumab; tazemetostat; cemiplimab; ABX196; T-cell receptor (TCR) immune cell therapy agent; TBI-302; namodenoson; MM-310; a tumor-injected oncolytic virus or gene-modified oncolytic virus such as, but not limited to, telomelysin and imlygic; or an immunomodulating gene-therapy agent such as MDA-7/IL-24, GLIPR1/RTVP-1, and REIC/Dkk-3.

In some embodiments of the methods as disclosed herein, the methods further comprises administering two or more other pharmaceutically active agents. In some embodiments, the methods of the invention comprise administering two or more other pharmaceutically active agents, optionally in combination. In some embodiments, the two or more other pharmaceutically active agents are oncolytic agents, such as, but not limited to, nanatinostat and valganciclovir. In other embodiments, the methods of the invention comprise orally administering a compound of the invention and further comprise administering a tumor-injected oncolytic treatment. In some embodiments, the combination is administered orally.

In some embodiments, the other pharmaceutically active agent is cenicriviroc, elafibranor, eicosapentaenoic acid, galunisertib, LY2109761, LDE225, nivolumub, firsocostat, apararenone, metformin, leucine-metformin-sildenafil combination (NS-0200), IMM-124E, RG-125, vitamin E, cysteamine, selonsertib, losartan, RO5093151, pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, ND-L02-s0201/BMS-986263, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine, L-carnitine, EYP001a, silymarin, miricorilant, ursodeoxycholic acid, metadoxine, ezetimibe, cystadane, L-alanine, saroglitazar magnesium, volixibat, solithromycin, 99m technetium-mebrofenin, tropifexor, S-adenosylmethionine, pentoxifylline, olesoxime, AKR-001, or seladelpar.

In some embodiments of the methods as disclosed herein, the methods for treating or preventing a disease comprise administering Compound I-1, Compound I-32, Compound I-61, or Compound III-1, or a pharmaceutically acceptable salt or solvate thereof.

In some embodiments of the methods as disclosed herein, the methods for treating or preventing a disease comprise administering an effective amount of (a) a compound of the invention and (b) another pharmaceutically active agent that is sorafenib, TAXOL® (paclitaxel), lenvatinib, tazemetostat, TBI-302, namodenoson, MM-310, cenicriviroc, elafibranor, eicosapentaenoic acid, galunisertib, LY2109761, LDE225, firsocostat, apararenone, metformin, Leucine-Metformin-Sildenafil Combination, Vitamin E, cysteamine, selonsertib, losartan, RO5093151 pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine, L-carnitine, EYP001a, silymarin, miricorilant, ursodeoxycholic acid, metadoxine, ezetimibe, cystadane, L-alanine, saroglitazar magnesium, volixibat, elafibranor, nalmefene, solithromycin, 99m Technetium-Mebrofenin, S-adenosylmethionine, pentoxifylline, olesoxime, AKR-001, seladelpar, fisogatinib, doxorubicin, cabozantinib, deferoxamine, itacitinib, chiauranib, SF1126, anlotinib, P1101, varlitinib, SHR-1210, SHR6390, capmatinib, dabrafenib, trametinib, sapaniserlib, meclizine, enzalutamide, H3B-6527, OBI-3424, brivanib, tepotinib, temsirolimus, epacadostat, RO7119929, guadecitabine, linrodostat, copanlisib, MIV-818, vorolanib, RO7070179, axitinib, sunitinib, or zotiraciclib citrate. In some embodiments of the methods as disclosed herein, the method for treating or preventing a disease comprise administering an effective amount of (a) Compound I-1, Compound I-32, Compound I-61, or Compound III-1, or a pharmaceutically acceptable salt or solvate thereof and (b) another pharmaceutically active agent that is sorafenib, TAXOL® (paclitaxel), lenvatinib, tazemetostat, TBI-302, namodenoson, MM-310, cenicriviroc, elafibranor, eicosapentaenoic acid, galunisertib, LY2109761, LDE225, firsocostat, apararenone, metformin, Leucine-Metformin-Sildenafil Combination, Vitamin E, cysteamine, selonsertib, losartan, RO5093151 pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine, L-carnitine, EYP001a, silymarin, miricorilant, ursodeoxycholic acid, metadoxine, ezetimibe, cystadane, L-alanine, saroglitazar magnesium, volixibat, elafibranor, nalmefene, solithromycin, 99m Technetium-Mebrofenin, S-adenosylmethionine, pentoxifylline, olesoxime, AKR-001, seladelpar, fisogatinib, doxorubicin, cabozantinib, deferoxamine, itacitinib, chiauranib, SF1126, anlotinib, P1101, varlitinib, SHR-1210, SHR6390, capmatinib, dabrafenib, trametinib, sapanisertib, meclizine, enzalutamide, H3B-6527, OBI-3424, brivanib, tepotinib, temsirolimus, epacadostat, RO7119929, guadecitabine, linrodostat, copanlisib, MIV-818, vorolanib, RO7070179, axitinib, sunitinib, or zotiraciclib citrate.

In some embodiments of the methods as disclosed herein, the methods for treating or preventing a disease comprise administering an effective amount of (a) a compound of the invention and (b) another pharmaceutically active agent that is sorafenib, TAXOL® (paclitaxel), carotuximab, pembrolizumab, lenvatinib, avelumab, durvalumab, tremelimumab, nivolumab, tazemetostat, cemiplimab, ABX196, T-cell receptor (TCR) immune cell therapy agent, TBI-302, namodenoson, MM-310, a tumor-injected oncolytic virus, a gene-modified oncolytic virus, or an immunomodulating gene-therapy agent. In some embodiments of the methods as disclosed herein, the methods for treating or preventing a disease comprise administering an effective amount of (a) Compound I-1, Compound I-32, Compound I-61, or Compound III-1, or a pharmaceutically acceptable salt or solvate thereof and (b) another pharmaceutically active agent that is sorafenib, TAXOL® (paclitaxel), carotuximab, pembrolizumab, lenvatinib, avelumab, durvalumab, tremelimumab, nivolumab, tazemetostat, cemiplimab, ABX196, T-cell receptor (TCR) immune cell therapy agent, TBI-302, namodenoson, MM-310, a tumor-injected oncolytic virus, a gene-modified oncolytic virus, or an immunomodulating gene-therapy agent.

In some embodiments, the methods of the invention comprise administering to a subject in need thereof an effective amount of a compound of the invention and another pharmaceutically active agent set forth of an embodiment of Table D. In some embodiments, the other pharmaceutically active agent is administered concurrently with, prior to or subsequent to the administration of the compound of the invention or the composition of the invention.

In some embodiments of the methods as disclosed herein, the methods further comprise administering radiation therapy to the subject. In some embodiments, the radiation therapy is gamma ray radiation therapy or x-ray radiation therapy. In some embodiments, the radiation therapy is administered via a gamma ray or x-ray radiation apparatus.

In some embodiments, the radiation therapy is administered concurrently with, prior to or subsequent to the administration of the compound of the invention or the composition of the invention. In some embodiments, the radiation therapy is administered prior to or subsequent to the administration of the compound of the invention or the composition of the invention.

Methods for Making the Compounds of the Invention

Synthesis and General Protocols

The compounds of Formulae (IA), (IB), (IC), (ID), (IE), (IF), (IG), (IH), (IJ), (IK), and (IL), (collectively "Formula (I)") can be prepared via the synthetic methodologies illustrated in Schemes 1-7. The starting materials useful for preparing the compounds of the invention and intermediates thereof are commercially available or can be prepared from commercially available materials using known synthetic methods and reagents.

Scheme 1

General Synthesis of Formula (I)

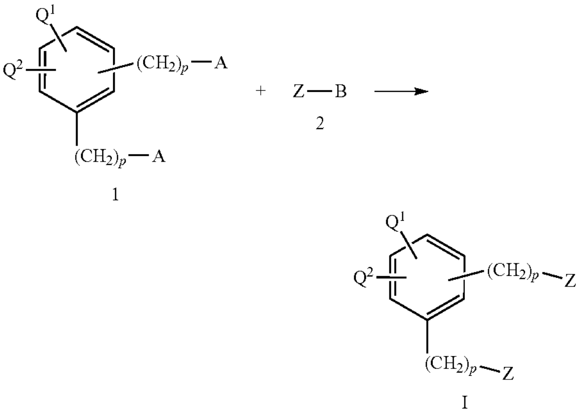

1

2

I

In Scheme 1, A can be halogen, such as Cl, Br, or I. In some embodiments, A is Br. In Scheme 1, B can be carbanions of esters of carboxylic or malonic esters. In Scheme 1, $Q^1$ and $Q^2$ can each independently be —O-alkyl, —S-alkyl, —S-aryl, —$NR^{1A}R^{2A}$ $NHR^{1A}$ phenoxy, aryloxy, benzyl, aryl, cycloalkyl, F, Cl, Br, I, —$CF_3$, —$COR^{1A}$, heteroaryl, or heterocyclyl, or each carbon atom together with the $Q^1$ and $Q^2$ attached to the carbon atom independently form a heterocyclyl or a carbocyclyl group. $R^{1A}$ and $R^{2A}$ are as defined herein for formula (I).

Scheme 2

General Synthesis of Formula (I)

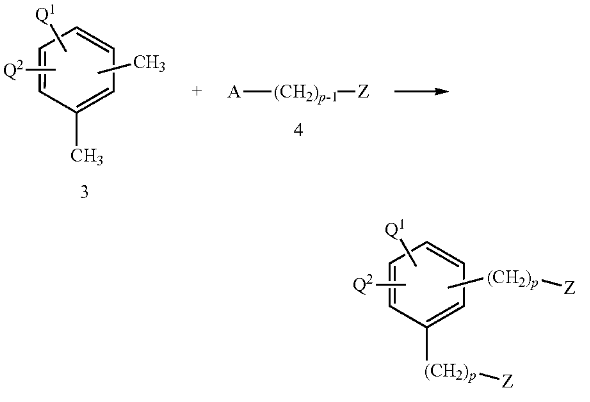

3

4

I

In Scheme 2, $Q^1$ and $Q^2$ can each independently be —O-alkyl, —S-alkyl, —S-aryl, —$NR^{1A}R^{2A}$ $NHR^{1A}$, phenoxy, aryloxy, benzyl, aryl, cycloalkyl, F, Cl, Br, I, —$CF_3$, —$COR^{1A}$, heteroaryl, or heterocyclyl, or each carbon atom together with the $Q^1$ and $Q^2$ attached to the carbon atom independently form a heterocyclyl or a carbocyclyl group. $R^{1A}$ and $R^{2A}$ are as defined herein for formula (I)

Scheme 3

General Synthesis of Formula (I)

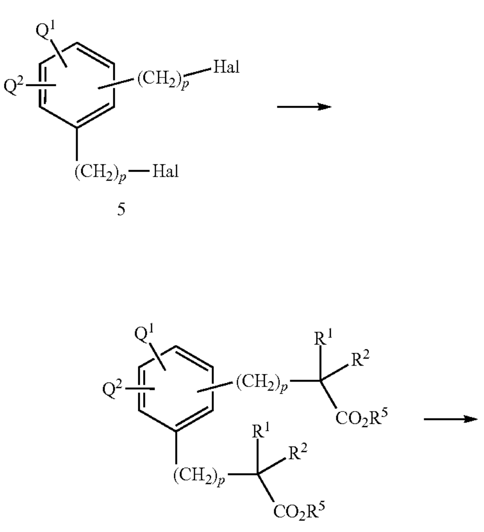

5

6

-continued

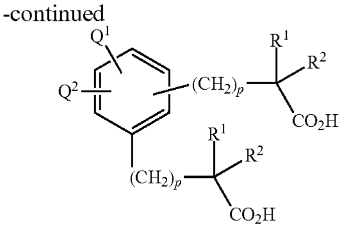

7 where Z is —$C(R^1)(R^2)$—$(CH_2)_c$—X, X is $COOR^5$, or COOH, and c is 0.

In Scheme 3, $Q^1$ and $Q^2$ can each independently be —O-alkyl, —S-alkyl, —S-aryl, —$NR^{1A}R^{2A}$ $NHR^{1A}$, phenoxy, aryloxy, benzyl, aryl, cycloalkyl, F, Cl, Br, I, —$CF_3$, —$COR^{1A}$, heteroaryl, or heterocyclyl, or each carbon atom together with the $Q^1$ and $Q^2$ attached to the carbon atom independently form a heterocyclyl or a carbocyclyl group. $R^{1A}$ and $R^{2A}$ are as defined herein for formula (I).

Scheme 3 illustrates the transformation of ortho, meta, or para ω-haloalkyl substituted arenes of the formula 5, wherein p is an integer in the range of 2-5 and Hal is Cl, Br, or I, to dicarboxylic acids of the formula 7, wherein $R^1$ and $R^2$ are alkyl and/or aryl moieties or are connected in a three- to seven-membered cycle. This transformation can be accomplished by two different, however related pathways. According to the first method, esters of the formula $R^1R^2CHCO_2R^5$, wherein $R^1$ and $R^2$ are alkyl and/or aryl moieties or are connected in a three- to seven-membered cycle and $R^5$ is typically ethyl or methyl, are deprotonated by strong bases, preferably, but not limited to, butyl lithium or lithium diisopropylamide, and then reacted with dihalides of the formula 5 to furnish the corresponding diesters of the formula 6. Generally, the reaction is performed at temperatures from about −78° C. to about 25° C. and the reaction solvent is preferably THF or diethyl ether (see Larock, R. C. *Comprehensive Organic Transformations. A Guide to Functional Group Preparations,* 2$^{nd}$ ed.; Wiley-VCH, New York, 1999, pp 1725-1726 for a discussion of the scope of this method. See, Dasseux et al., U.S. Pat. Nos. 6,646,170 and 6,410,802, Oniciu et al. U.S. Pat. No. 10,227,285 and Ackerley et al., *J. Med. Chem.* 1995, 38, 1608-1628 for specific examples of this method). In the second step, a diester of the formula 6 is saponified (see Larock, R. C. *Comprehensive Organic Transformations. A Guide to Functional Group Preparations,* 2$^{nd}$ ed.; Wiley-VCH, New York, 1999, pp 1959-1968 and Smith, M. B.; March, J. *March's Advanced Organic Chemistry. Reactions, Mechanisms, and Structure,* 5$^{th}$ ed.; John Wiley and Sons, New York, 2001, pp 469-474 for an overview) to a diacid of the formula 7. As an alternative, this transformation of a dihalide of the formula 5 to a diacid of the formula 7 can also be achieved in one step, when a carboxylic acid of the formula $R^1R^2CHCO_2H$, wherein $R^1$ and $R^2$ are alkyl and/or aryl, is deprotonated twice under conditions similar to the alkylation of $R^1R^2CHCO_2R^5$ described above and subsequently reacted with dibromide 5 (for a discussion, see Larock, R. C. *Comprehensive Organic Transformations. A Guide to Functional Group Preparations,* 2$^{nd}$ ed.; Wiley-VCH, New York, 1999, pp 1717-1718). For example, a compound of the formula 5 (ortho, p=3, Hal=Br) is reacted with lithio ethyl isobutyrate (prepared from ethyl isobutyrate with lithium diisopropylamide) in a solvent mixture of THF and DMPU at a temperature ranging from about −78° C. to room temperature, affording the corresponding diester of formula 7 (ortho, p=3). This diester is subsequently hydrolyzed under standard conditions (aqueous ethanol, potassium hydroxide, reflux temperature) to provide, after re-acidification with dilute aqueous hydrochloric acid, the dicarboxylic acid of the formula 7 with ortho substitution pattern, $R^1$═$R^2$=methyl and p=3. In another method, which is described in Gleiter et al., *J. Org. Chem.* 1992, 57, 252-258, isobutyric acid is deprotonated twice with n-butyl lithium and diisopropylamine in THF solution first at about −20° C. and then at about 50° C. After re-cooling to about −20° C., a solution of a compound of the formula 5 (ortho, $R^1$═$R^2$=methyl, p=3, Hal=Br) in THF is then added dropwise, while the temperature is kept below 10° C. The mixture is subsequently stirred first at room temperature and then at about 40° C., and worked up in a typical manner to afford the corresponding diacid 7. Halide derivatives of type 5 can be obtained by several methods, described for instance in Gleiter et al., *J. Org. Chem.* 1992, 57, 252-258.

Scheme 4
General Synthesis of Compound 5-Br

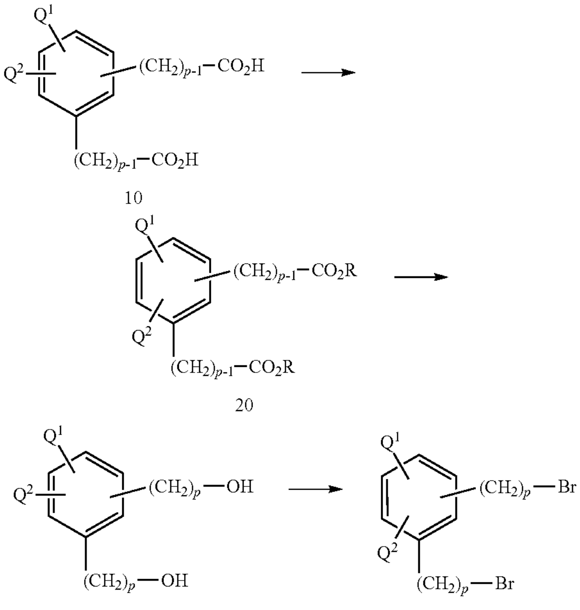

10

20

30

(Compound 5 where Hal = Br)

5-Br

In Scheme 4, $Q^1$ and $Q^2$ can each independently be —O-alkyl, —S-alkyl, —S-aryl, —$NR^{1A}R^{2A}$ $NHR^{1A}$, phenoxy, aryloxy, benzyl, aryl, cycloalkyl, F, Cl, Br, I, —$CF_3$, —$COR^{1A}$, heteroaryl, or heterocyclyl, or each carbon atom together with the $Q^1$ and $Q^2$ attached to the carbon atom independently form a heterocyclyl or a carbocyclyl group. $R^{1A}$ and $R^{2A}$ are as defined herein for formula (I).

Scheme 4 illustrates the synthesis of para, meta, and ortho di-bromoalkyl substituted arene compounds 5-Br from the parent dicarboxylic acids 10 wherein (p−1) is an integer in the range from 1-2. Scheme 4 first outlines the esterification of compounds of the formula 10 to diesters of the formula 20, wherein R is an alkyl moiety such as, but not limited to, methyl, ethyl, or isopropyl using general procedures referenced in Larock, R. C. *Comprehensive Organic Transformations. A Guide to Functional Group Preparations,* $2^{nd}$ ed.; Wiley-VCH, New York, 1999, pp 1932-1941 and Smith, M. B.; March, J. *March's Advanced Organic Chemistry. Reactions, Mechanisms, and Structure,* $5^{th}$ ed.; John Wiley and Sons, New York, 2001, pp 484-486. Diols 30 can be prepared from diesters 20 by well-known synthetic methods (for a discussion of suitable reduction methods, see for example Hudlicky, M. *Reductions in Organic Chemistry,* $2^{nd}$ ed.; ACS Monograph 188, Washington, DC, 1996, pp 212-216). In the next step, transformation of the alcohol functionalities in 30 to the bromo moieties in Compound 5-Br can be accomplished by a variety of standard methods as referenced in Larock, R. C. *Comprehensive Organic Transformations. A Guide to Functional Group Preparations,* $2^{nd}$ ed.; Wiley-VCH, New York, 1999, pp 693-695. For example, a compound of the formula 10 with para substitution pattern and (p−1)=1 (available from Aldrich Chemical Co., Milwaukee, Wisconsin) is treated with an excess of methanol and concentrated sulfuric acid at reflux temperature to give the corresponding dimethyl ester of the formula 2. A procedure that can be used for this transformation is, for example, referenced in Schimelpfenig, C. W. *J. Org. Chem.* 1975, 40, 1493-1494, incorporated by reference herein. In addition, a compound of the formula 20 (para, (p−1)=1) can be transformed to the corresponding compound of the formula 30 by reaction with a complex metal hydride, preferably, but not limited to, lithium aluminum hydride in an aprotic organic solvent, such as THF or diethyl ether, as referenced in Reynolds et al. U.S. Pat. No. 2,789,970, Appl. No. 397,037, filed Dec. 8, 1953. Further, a diol of the formula 30 (para, p=1) can be converted to a bromide of the formula 5-Br (para, p=1) by treatment with sodium bromide and concentrated sulfuric acid at elevated temperature. A useful solvent for this conversion is water, as is described in Schimelpfenig, C. W. *J. Org. Chem.* 1975, 40, 1493-1494.

Scheme 5
General Synthesis of Compound 5A-Br

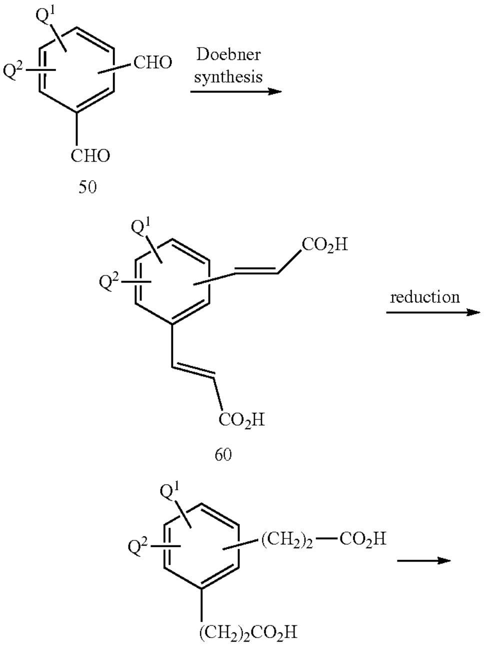

50

60

70

-continued

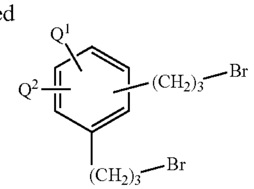

5A-Br

In Scheme 5, $Q^1$ and $Q^2$ can each independently be —O-alkyl, —S-alkyl, —S-aryl, —$NR^{1A}R^{2A}$ $NHR^{1A}$, phenoxy, aryloxy, benzyl, aryl, cycloalkyl, F, Cl, Br, I, —$CF_3$, —$COR^{1A}$, heteroaryl, or heterocyclyl, or each carbon atom together with the $Q^1$ and $Q^2$ attached to the carbon atom independently form a heterocyclyl or a carbocyclyl group. $R^{1A}$ and $R^{2A}$ are as defined herein for formula (I).

Scheme 5 illustrates the preparation of ortho, meta, and para substituted arene compounds with two 3-bromopropyl substituents of the formula 5A-Br. Specific examples for the synthesis of compounds 5A-Br with meta and para substitution are given in Schimelpfenig, C. W. *J. Org. Chem.* 1975, 40, 1493-1494 and Gleiter et al., *J. Org. Chem.* 1992, 57, 252-258, respectively. For example, a compound of the formula 50 is treated with malonic acid and piperidine in pyridine solution at about 90-110° C. to give an α,β-unsaturated carboxylic acid of the formula 60. The end point of this conversion is typically indicated by cessation of the $CO_2$ effervescence. This procedure is known as a Knoevenagel-Doebner reaction and a useful reaction protocol for this conversion is given in *Organikum, Organisch-Chemisches Grundpraktikum*, VEB Verlag Deutscher Wissenschaften, Berlin 1984, pp 572-574. Reduction of compounds of the formula 60 to compounds of the formula 70 can be accomplished by catalytic hydrogenation over colloidal palladium, Raney nickel, or copper chromite as discussed in Hudlicky, M. *Reductions in Organic Chemistry,* 2nd ed.; ACS Monograph 188, Washington, DC, 1996, pp 196-197. Conversion of a compound of the formula 60 with meta substitution to the corresponding compound 70 by treatment with hydrogen gas at pressures from ca. 20-60 psi and palladium on carbon catalyst in aqueous sodium hydroxide solution is reported in Schimelpfenig, C. W. *J. Org. Chem.* 1975, 40, 1493-1494, which is included herein as a reference in its entirety. The further transformation of compounds of the formula 70 to compounds of formula 5A-Br can then be accomplished according to the methodology described in Scheme 4.

Scheme 6

General Synthesis of Compound 5-Br by Chain Elongation

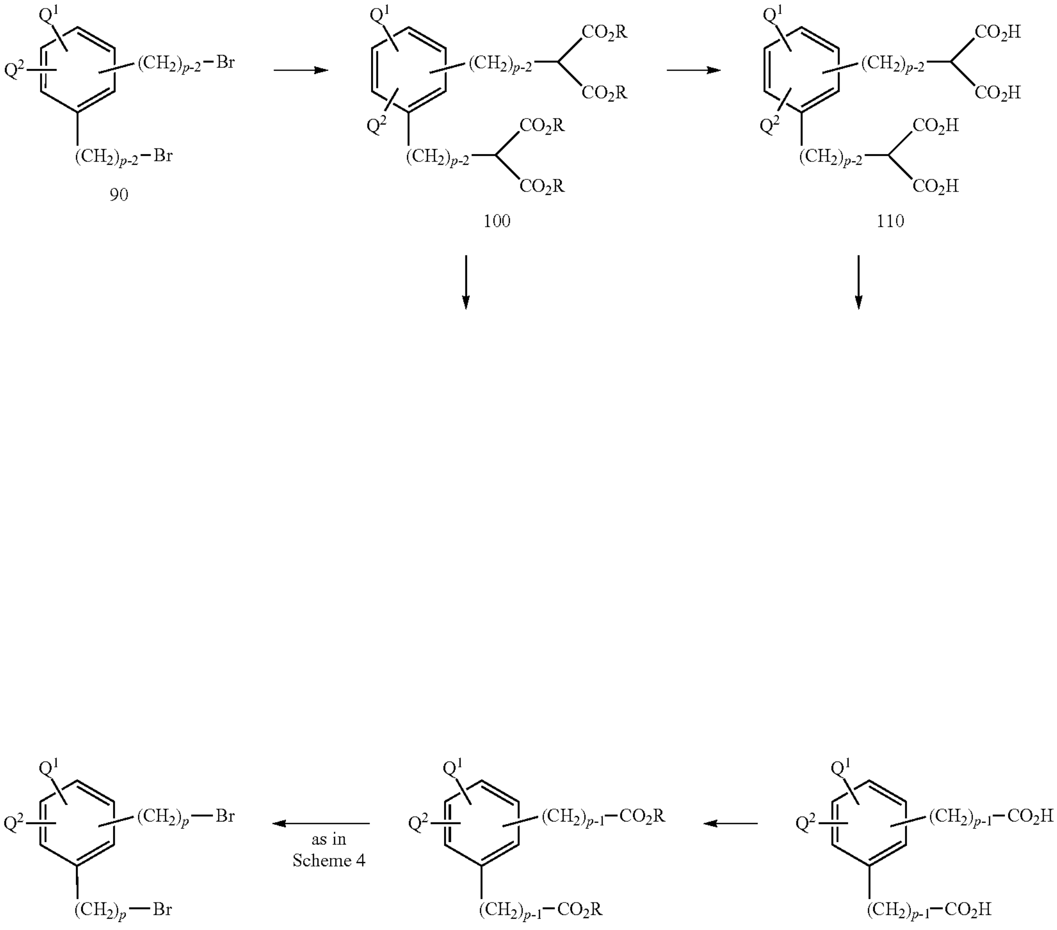

90, 100, 110, 5-Br, 20, 120

In Scheme 6, $Q^1$ and $Q^2$ can each independently be —O-alkyl, —S-alkyl, —S-aryl, —$NR^{1A}R^{2A}$ $NHR^{1A}$, phenoxy, aryloxy, benzyl, aryl, cycloalkyl, F, Cl, Br, I, —$CF_3$, —$COR^{1A}$, heteroaryl, or heterocyclyl, or each carbon atom together with the $Q^1$ and $Q^2$ attached to the carbon atom independently form a heterocyclyl or a carbocyclyl group. $R^{1A}$ and $R^{2A}$ are as defined herein for formula (I).

Scheme 6 illustrates a general method for the chain elongation of bromides of the formula 90 with an alkyl chain consisting of (p−2) methylene groups to bromides of the formula 5-Br with an alkyl chain consisting of p methylene groups. The conversion sequence from alkyl halides (such as 90) to carboxylic acid (such as 120) can be accomplished using a malonic ester synthesis referenced in Smith, M. B.; March, J. *March's Advanced Organic Chemistry. Reactions, Mechanisms, and Structure,* 5th ed.; John Wiley and Sons, New York, 2001, p 549 and Larock, R. C. *Comprehensive Organic Transformations. A Guide to Functional Group Preparations,* 2nd ed.; Wiley-VCH, New York, 1999, p 1765. Generally, the monoalkylation of malonic esters (R is typically ethyl or methyl) employs the base-solvent combination of sodium ethoxide in ethanol, which inhibits the formation of dialkylated side-products (*Organic Reactions, Volume IX,* editor-in-chief: R. Adams; Robert E. Krieger Publishing Company, Malabar, Florida, 1957, p 132) to give compounds of the formula 100. Compounds of the formula 100 are then saponified to give compounds of the formula 110, which can be heated above their melting point for decarboxylation to compounds of the formula 120. The transformation from dicarboxylic acids 120 via diesters 20 to the chain-elongated dibromides 5-Br is then conducted according to the methodologies described in Scheme 4. Alternatively, a direct decarbalkoxylation of geminal diesters 100 to compounds of the formula 20 can be achieved by treatment with water and DMSO with or without the presence of added salts. However, the addition of salts such as KCN, NaCl or LiCl to the water/DMSO solvent can enhance the decarbalkoxylation rates of theses substrates (Fakhri, S. A.; Yousefi, B. H. *Tetrahedron* 2000, 56, 8301-8308). For example, ethyl malonate is reacted with sodium metal in ethanol and a solution of a compound of the formula 90 with (p−2)=2, and ethyl malonate is added to give the corresponding compound of the formula 100. This tetraester is subsequently saponified using, for example, aqueous ethanol and potassium hydroxide, yielding the corresponding tetraacid of the formula 110. The tetraacid is then decarboxylated at a temperature of ca. 200° C. to the diacid of the formula 120. After esterification with methanol and concentrated sulfuric acid (see Scheme 4) to diester 20. Useful methods for the transformation of a tetraester of the formula 100 (ortho, (p−2)=1, R=ethyl) to a diester of the formula 20 are described in Fakhri, S. A.; Yousefi, B. H. *Tetrahedron* 2000, 56, 8301-8308, which is included herein in its entirety as a reference.

Scheme 7

General Synthesis for Compounds of Formula 7

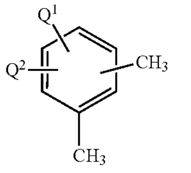

3

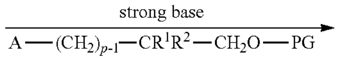

180

-continued

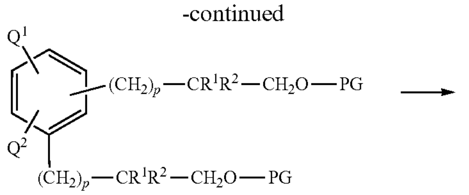

190

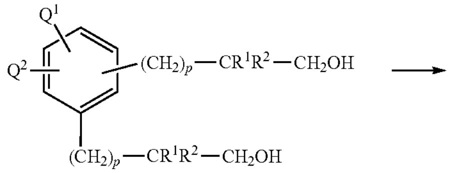

200

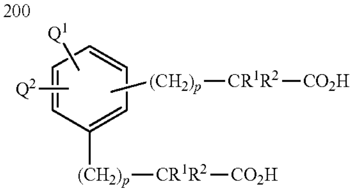

7

In Scheme 7, $Q^1$ and $Q^2$ can each independently be —O-alkyl, —S-alkyl, —S-aryl, —$NR^{1A}R^{2A}$ $NHR^{1A}$, phenoxy, aryloxy, benzyl, aryl, cycloalkyl, F, Cl, Br, I, —$CF_3$, —$COR^{1A}$, heteroaryl, or heterocyclyl, or each carbon atom together with the $Q^1$ and $Q^2$ attached to the carbon atom independently form a heterocyclyl or a carbocyclyl group. $R^{1A}$ and $R^{2A}$ are as defined herein for formula (I).

Scheme 7 illustrates the synthesis of ortho, meta, and para substituted arene compounds of the formula 7 with ω-carboxyalkyl substitution, wherein (p−1) is an integer in the range from 2-12 and $R^1$ and $R^2$ are either alkyl and/or aryl moieties or two alkyl moieties connected in a 3- to 7-membered cycle. The synthesis starts with the twofold deprotonation of ortho-, meta-, or para-xylene 3 with a strong base, such as, but not limited to, a combination of n-butyl lithium and potassium tert-butoxide in an aprotic solvent, such as, but not limited to, hexane and reaction of the formed dianion of 3 with suitable electrophiles A-$(CH_2)_{p-1}$—$CR^1R^2$—$CH_2O$—PG, wherein (p−1), $R^1$, and $R^2$ are defined as above and A is Cl, Br, or I. "PG" is a hydroxyl-protecting group. Examples of hydroxyl-protecting groups are described in Greene, T. W.; Wuts, P. G. M. *Protective groups in organic synthesis,* 3rd ed., John Wiley and Sons, New York, 1999, pp 17-245, which is incorporated herein by reference. Methyl arenes can be alkylated via deprotonation using lithium bases followed by alkylation with suitable electrophiles according to Larock, R. C. *Comprehensive Organic Transformations. A Guide to Functional Group Preparations,* 2nd ed.; Wiley-VCH, New York, 1999, p 88. See, Bates et al., *J. Am. Chem. Soc.* 1981, 103, 5052-5058, for an example for the preparation of xylene dianions. In the following step, the protective groups of 190 are removed to liberate the terminal hydroxylmethyl moieties in 200, which are the oxidized using a suitable oxidizing agent (Larock, R. C. *Comprehensive Organic Transformations. A Guide to Functional Group Preparations,* 2nd ed.; Wiley-VCH, New York, 1999, pp 1646-1648 and Smith, M. B.; March, J. March's Advanced Organic Chemistry. Reactions, Mechanisms, and Structure, 5th ed.; John Wiley and Sons, New York, 2001, p 1537) to give a dicarboxylic acid of the formula 7. For example, m-xylene (meta-3) is reacted with n-butyl lithium and potassium tert-butoxide in hexanes, first at room temperature and then at reflux temperature. After cooling to 0° C., a compound of the formula 180 (A=Br, (p−1)=3, $R^1$=$R^2$=methyl, PG=tetrahydropyranyl, prepared according to Dasseux et al., U.S. Pat. Nos. 6,646,170 and 6,410,802) is added and reaction is continued at reflux temperature, affording, after the usual workup and purification by column chromatography, the corresponding compound of the formula 190. Deprotection of 190 to 200 ($R^1$, $R^2$=methyl, p=3) is then accomplished by heating in methanol and concentrated, aqueous hydrochloric acid (Vogel, A. I. *Vogel's textbook of practical organic chemistry,* 5th ed., Longman Scientific and Technical, 1989, p. 552). This compound 200 is then treated with pyridinium dichromate in N,N'-dimethylformamide according to Vedejs, E.; Dent, W. H., III; Gapinski, D. M.; McClure, C. K. *J. Am. Chem. Soc.* 1987, 109, 5437-5446 to yield the dicarboxylic acid of the formula 7 (meta, p=3; $R^1$,$R^2$=methyl).

Scheme 8 shows illustrative alternate syntheses of compounds I-1 and I-32. Commercially available benzene-dicarboxaldehydes (Sigma-Aldrich, AK Scientific, etc.) are reacted with (5-ethoxy-4,4-dimethyl-5-oxopentyl)triphenylphosphonium bromide (220) (prepared as described in Oniciu, D, C. et al., WO2012/054535 and U.S. Pat. No. 8,349,833 B2) in the presence of base (including but not limited to sodium or potassium hydroxide, potassium or sodium tert-butoxide, potassium or sodium carbonate, and sodium hydride), in the manner described in Le Bigot Y. et al., 1988, Tetrahedron 44(4), pp. 1057-1072, as a mixture of cis and trans isomers. The mixture of cis and trans isomers of formula (230) or (240) can be reduced catalytically by methods for the hydrogenation of olefins known in the art, such as the methods described by H.-U. Blaser, F. Spindler, M. Thommen, The Handbook of Homogeneous Hydrogenation, J. G. De Vries, C. J. Elsevier, Eds. (Wiley-VCH, 2008), chap. 37; Scharnagl, F. K. et al., Sci. Adv. 2018; 4: eaaul248, 21 Sep. 2018; and references cited herein. The esters thus obtained are subjected to hydrolysis after the hydrogenation reaction is deemed substantially complete by using an appropriate analytical methods. The reaction mixtures containing compounds of formula (250) or (260), respectively, are hydrolyzed in the presence of an alkaline earth metal salt or base, or oxide, or alkali metal salt or base. in refluxing alcohols for 2 to 96 hours. Typical examples include, but are not limited to, hydrolysis with $K_2CO_3$ in a refluxing mixture of DMSO and water. Other suitable procedures are referenced in Houben-Weyl, Methoden der Organische Chemie, Georg Thieme Verlag Stuttgart 1964, vol. XII/2, pp. 143-210 and 872-879, or Anderson, N. G., Practical Process Research & Development, Academic Press, London, 2000, pp.93-94 and 181-182.

Scheme 8. Illustrative Synthesis of Compounds I-1 and I-32.

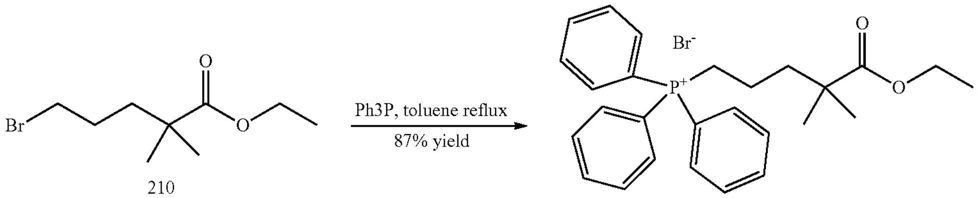

210

220

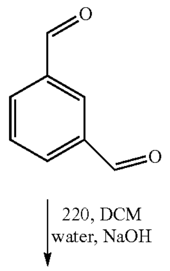

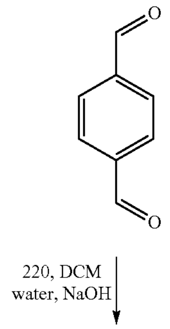

-continued
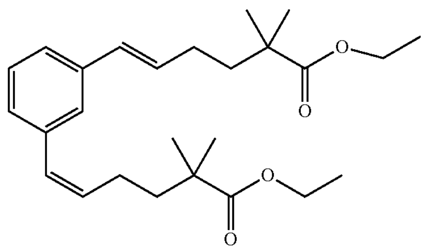
230
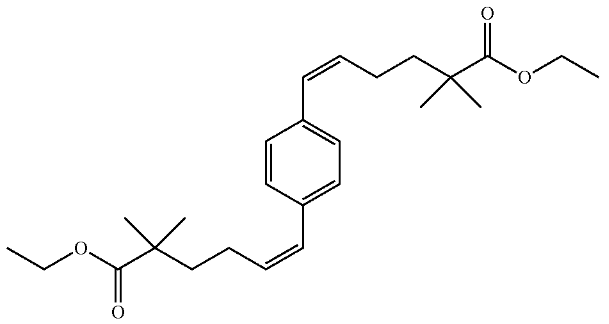
240
$H_2$, 5% Pd/C
EtOH
$H_2$, 5% Pd/C
EtOH
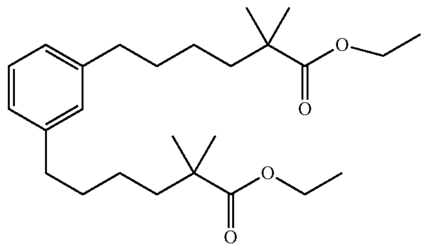
250
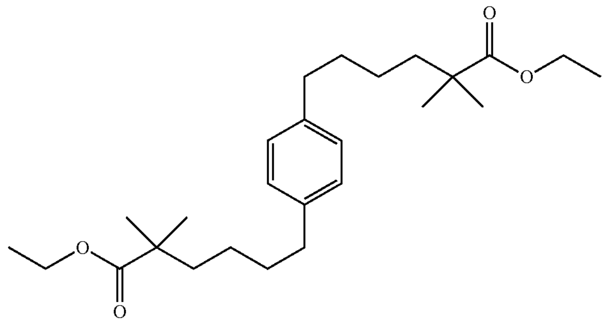
260
EtOH, water
KOH reflux
EtOH, water
KOH reflux
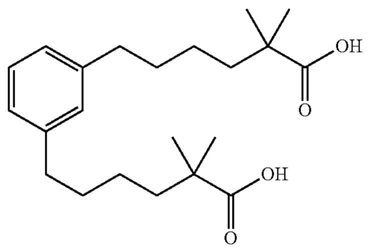
I-32
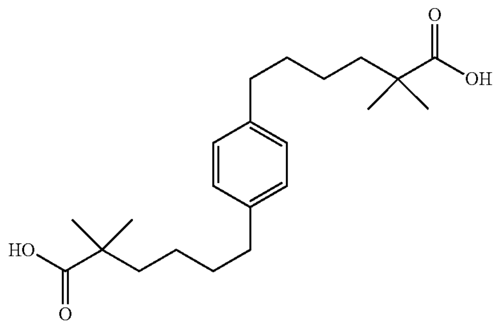
I-1

Scheme 9. General Synthesis of Compounds of Formula (III) or (IIIA) where X = O, $Z^1$, $Z^2$ = COOH, q = 0, and $R^1$ and $R^2$ together form a cyclopropyl ring

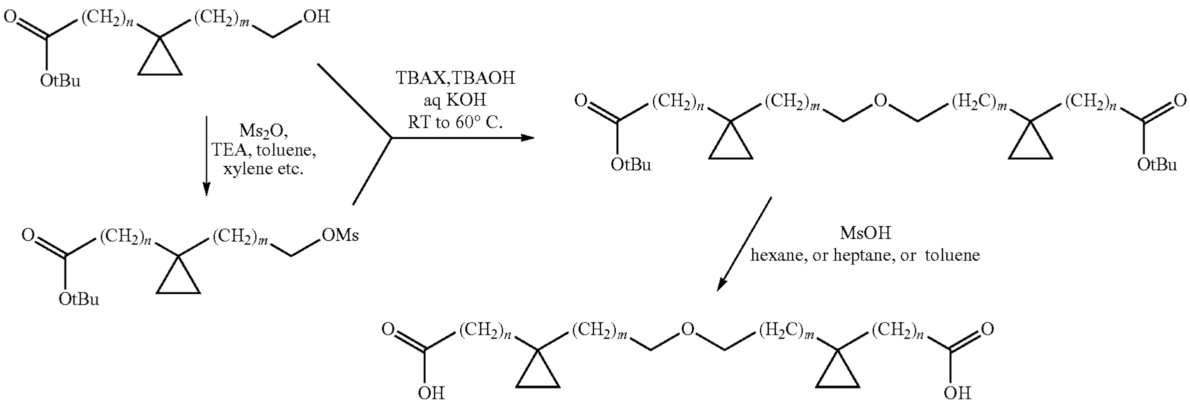

The compound of Formula (III) or (IIIA) where X═O can be prepared by a Williamson synthesis, by reacting an alcohol with a derivative comprising a leaving group such as halide, tolylsulphonate or mesylate. See Scheme 9.

Synthesis Examples

Example 1: Synthesis of (9-Carboxymethylsulfanyl-5-oxo-nonylsulfanyl)-acetic acid (Compound II-3)

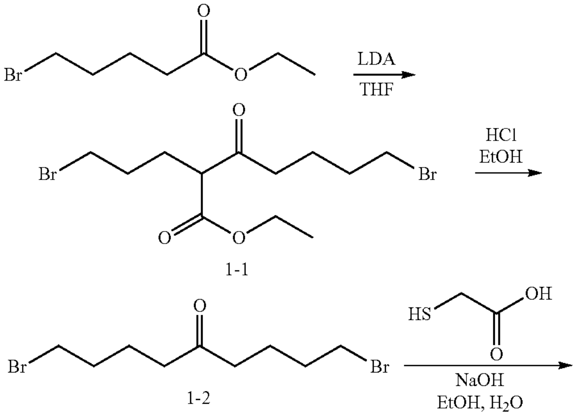

-continued

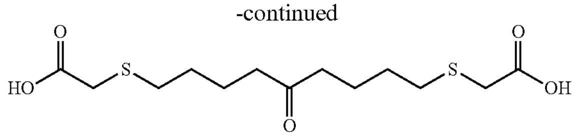

II-3

Reaction of ethyl 5-bromovalerate with lithium diisopropylamide in THF at room temperature produces ketone ester 1-1 (see, e.g., Cooke, M. P. *J. Org. Chem.* 1993, 58, 2910-2912; Stetter, H.; Rauhut, H. *Chem. Ber.* 1958, 91). Decarboxylation of 1-1 by refluxing in HCl/EtOH (Cooke, M. P. *J. Org. Chem.* 1993, 58, 2910-2912) produces crude 1-2, which can be purified by column chromatography using systems such as silica gel and mixtures of ethyl acetate/hexanes in ratios from 1/20 to 1/8. Mercaptoacetic acid dissolved in mixtures of ethanol and water is treated with a solution of sodium hydroxide in water to make sodium mercaptoacetate and is used to treat 1-2 in solvents such as ethanol as described in Agnus, A., Louis, Gissebrecht, J. P., Weiss, R., *J. Am. Chem. Soc.*, 1984, 106, 93 or Riesen, P. C.; Kaden, T. A. *Helv. Chim. Acta.* 1995, 78, 1325-1333, to provide crude compound II-3. The crude compound II-3 can be purified by recrystallization from solvents or mixtures of solvents such as MTBE and heptane.

Example 2: Synthesis of (9-Carboxymethylsulfanyl-5-hydroxy-nonylsulfanyl)-acetic acid (Compound II-1)

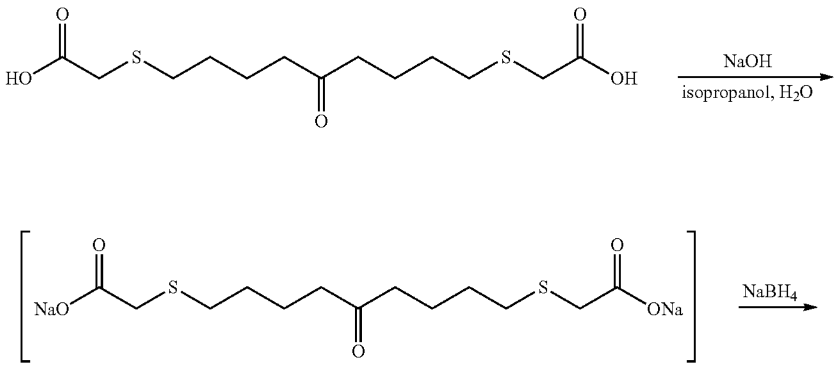

-continued

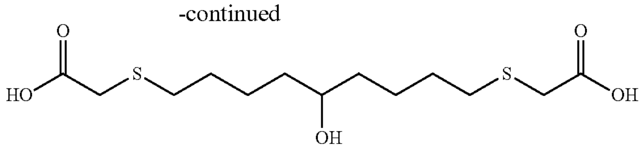

II-1

The reduction of ketodiacid compound II-3 from Example 1 is achieved with sodium borohydride after salt formation with NaOH to yield compound II-1 (see U.S. Pat. No. 7,119,221 for suitable reaction conditions). Compound II-3 (Example 1) is dissolved in NaOH solution (2 to 7 equiv) to form an intermediate disodium salt in water. Isopropanol is then added followed by addition of sodium borohydride (1.05 equiv) in portions. The reaction mixture is heated at about 45° C. for a few hours to yield compound II-1. Such product can be purified by recrystallization from MTBE, heptane or mixtures.

Example 3: Synthesis of [5-(5-Carboxymethoxy-pentyloxy)-pentyloxy]-acetic acid (Compound II-12)

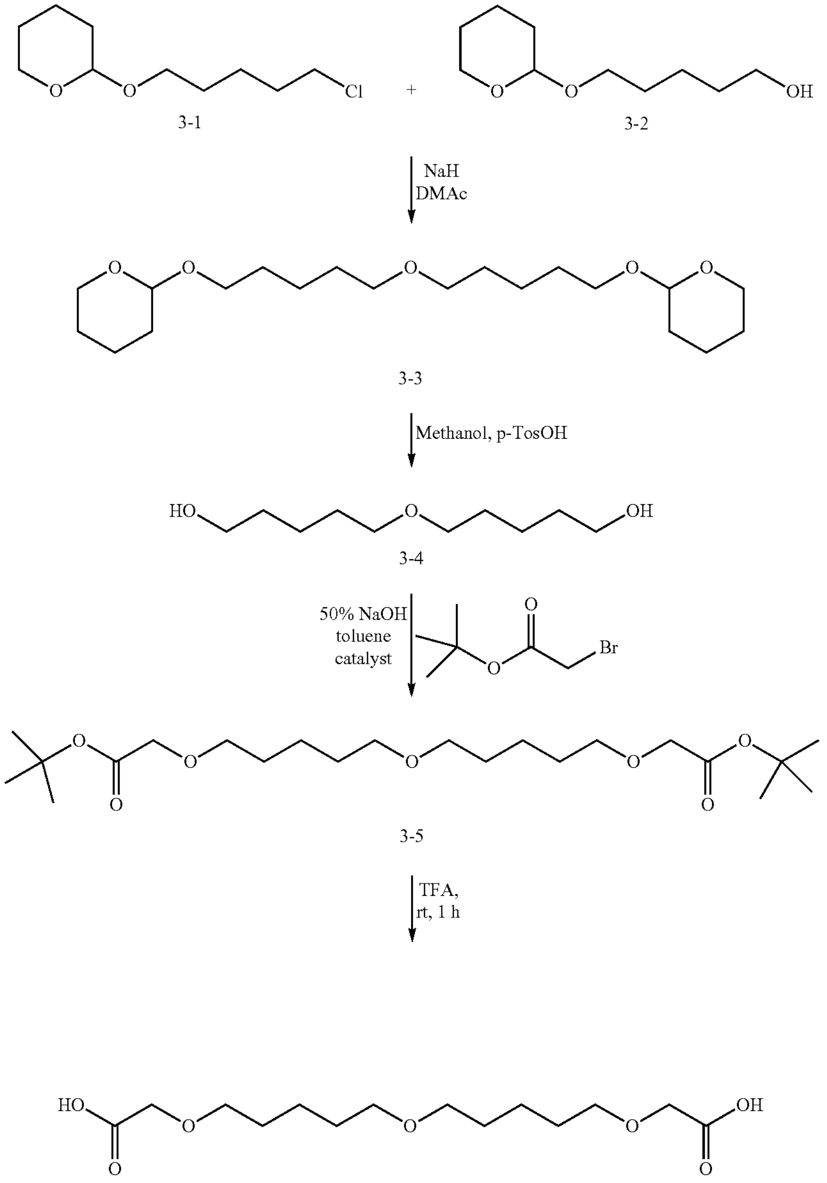

3-1 + 3-2

3-3

3-4

3-5

II-12

Compound II-12 is prepared via a Williamson ether synthesis starting from 3-1 and 3-2 (prepared as described in Dasseux et al. U.S. Pat. No. 6,459,003). The resulting 3-3 is deprotected in methanol in the presence of a catalytic amount of p-toluenesulphonic acid monohydrate to give diol 3-4. This diol is then coupled with tert-butyl bromoacetate in a two-phase system of aqueous NaOH and toluene in the presence of tetrabutylammonium bromide as PTC catalyst, as described in U.S. Pat. No. 10,227,285. Finally, this tert-butyl ester is cleaved under acidic conditions to afford compound II-12.

Example 4: Synthesis of [5-(5-Carboxymethoxy-pentylsulfanyl)-pentyloxy]-acetic acid (Compound II-20)

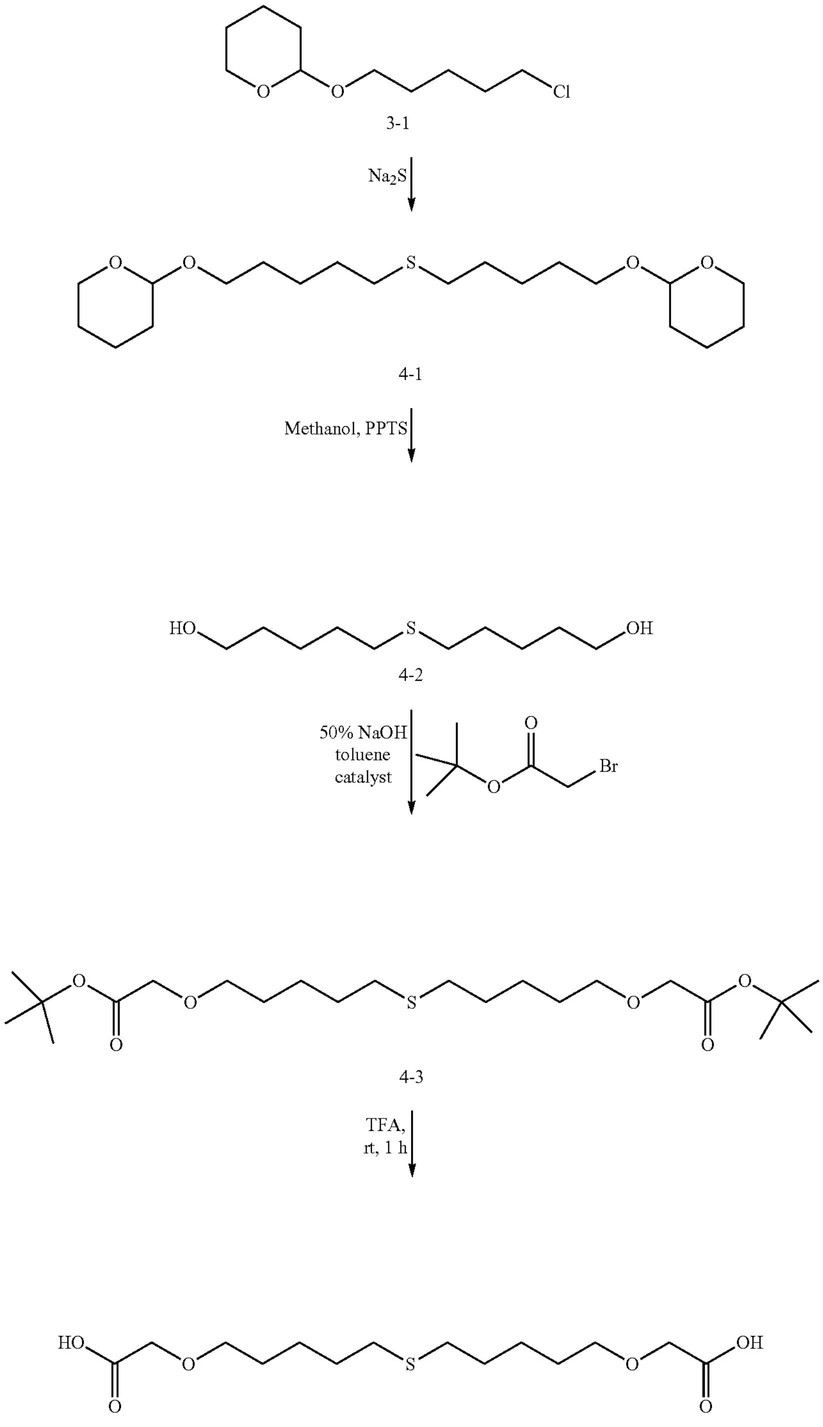

3-1

4-1

4-2

4-3

II-20

Compound 3-1 (prepared as described in U.S. Pat. No. 6,790,953) is treated with sodium sulfide similarly to the method by Edwards, D.; Stenlake, J. B. *J. Pharmacy Pharmacol.* 1955, 7, 852-860, to form thio ether 4-1, which is deprotected in methanol in the presence of a catalytic amount of pyridinium p-toluenesulphonate (PPTS) as described in Miyashita, N.; Yoshikoshi, A.; Grieco, P. A. *J. Org. Chem.* 1977, 42(23), 3772-73. The diol 4-2 thus obtained is reacted with tert-butyl bromoacetate under phase-transfer catalysis conditions using $(Bu_4N)(HSO_4)$ as catalyst, following the method of Nagatsugi, F.; Sasaki, S.; Maeda, M. *J. Fluorine Chem.* 1992, 56, 373-383, to obtain its tert-butyl ester 4-3. Subsequent cleavage of tert-butyl ester by trifluoroacetic acid (TFA) affords free acid compound 11-20 in 90% yield similar to the procedure in Nagatsugi, F.; Sasaki, S.; Maeda, M. *J. Fluorine Chem.* 1992, 56, 373-383.

Example 5: Synthesis of [5-(5-Carboxymethoxy-pentane-1-sulfinyl)-pentyloxy]-acetic acid (Compound II-24)

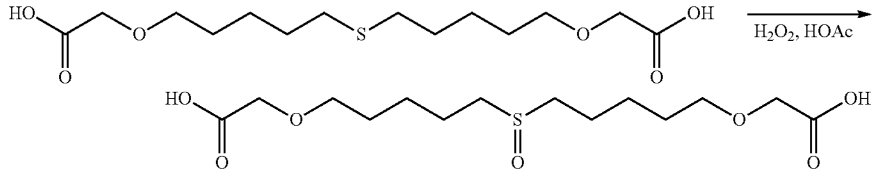

Compound II-24 is prepared starting from compound II-12 (Example 4) using hydrogen peroxide as an oxidizer similarly to the procedure described in U.S. Pat. No. 6,673,780.

Example 6: Synthesis of [5-(5-Carboxymethylsulfanyl-pentyloxy)-pentylsulfanyl]-acetic acid (Compound II-6)

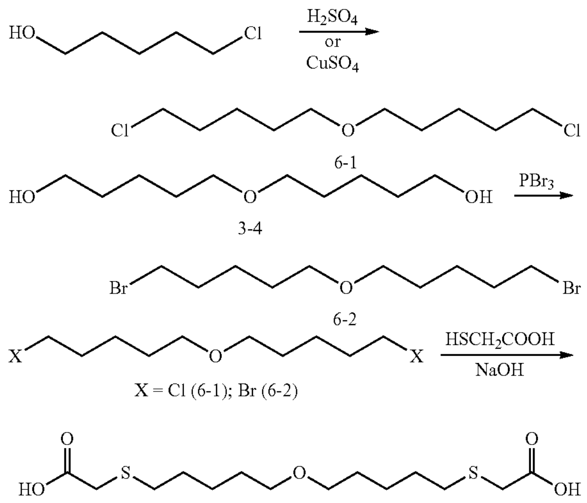

6-1

3-4

6-2

X = Cl (6-1); Br (6-2)

II-6

Compounds 6-1 and 6-2 are obtained according the methods described in Harrison, G. C.; Diehl, H. *Organic Synthesis* 1955 *Coll. Vol* 3, 370, and Francis, G. W.; Berg, J. F. *Acta Chem. Scand.* B 1977, 31, 721-722, respectively. 5-Chloro-pentan-1-ol is commercially available and 3-4 is prepared as described in Example 3, as follows: mercaptoacetic acid (8.1 g, 87.9 mmol) was dissolved in deionized water/ethanol solution (50 mL/40 mL). A solution of sodium hydroxide (7.0 g, 175.5 mmol) in water (50 mL) was added under stirring. To this mixture, bis(4-chlorobutyl ether) (7.0 g, 35.1 mmol) in ethanol (20 mL) was added dropwise over 30 min. This mixture was heated to reflux for 20 h, with subsequent evaporation of ethanol. The residue was diluted with water (20 mL). The aqueous layer was extracted with MTBE (4×20 mL) and the organic layers were discarded. The aqueous layer was acidified with concd HCl to pH 2 (ca. 12 mL) and extracted with MTBE (4×30 mL). The combined organic layers were checked by TLC (silica, CH2Cl2:MeOH=9:1) for presence of starting mercaptoacetic acid ($R_f$=0.7; bright blue spot with phosphomolybdic acid/EtOH). The organic layer was washed with water until the starting acid was completely gone (ca. 700 mL in portions). The solvent was removed under reduced pressure to give a colorless oil (7.7 g), which solidified at rt. This solid was recrystallized from heptane/MTBE (50/60 mL) to give nice white crystals (6.2 g, yield 57%; purity 99%-RI, 91%-UV, mp 43-44° C.). An additional amount of the product was obtained from the mother liquor (0.87 g, mp 38-40° C.).

Example 7: Synthesis of (11-Carboxymethylsulfanyl-6-oxo-undecylsulfanyl)-acetic acid (Compound II-4) and (11-Carboxymethylsulfanyl-6-hydroxy-undecylsulfanyl)-acetic acid (Compound II-2)

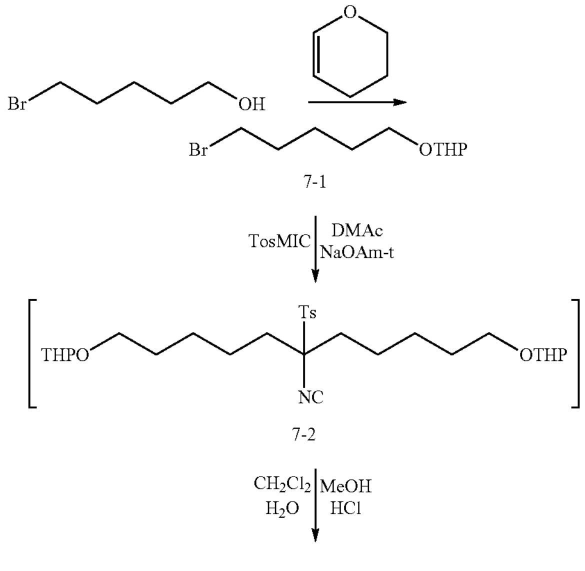

7-1

7-2

-continued

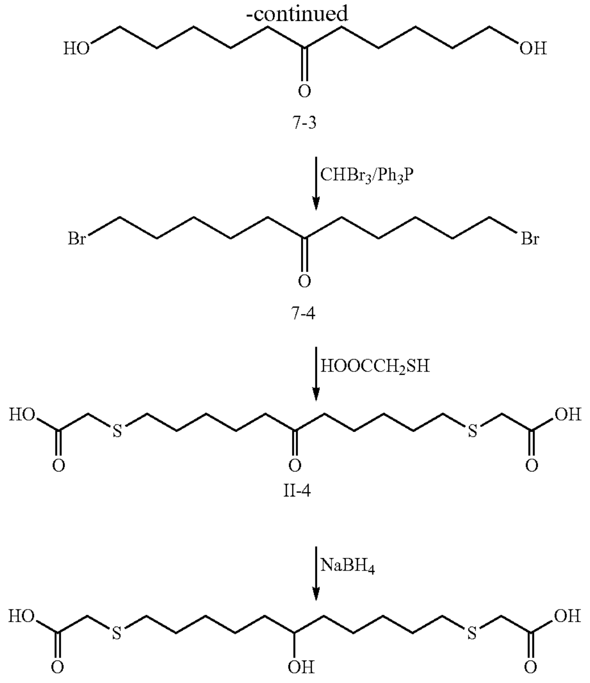

7-3

7-4

II-4

II-2

The synthesis of compounds II-4 and II-2 begins with 1,11-dibromoundecan-6-one (7-4), prepared as shown in above, starting with commercially available 6-bromohexanol. Protection of 6-bromohexanol's hydroxyl group with dihydropyran affords intermediate 7-1 as described in U.S. Pat. Nos. 6,646,170 and 6,410,802. Reaction of 7-1 with TosMIC in dimethyl acetamide (DMAc) in the presence of sodium amylate (NaOAm-t) leads to formation of intermediate 7-2, which is transformed to diol 7-3. The removal of the THP-protective groups and the transformation of the isocyano-tosyl-fragment into the ketone group proceeds simultaneously in mixture of solvents, such as methylene chloride, methanol, in the presence of aqueous HCl in about 12 to 24 hours. Diol 7-3 may be purified by column chromatography on silica gel and mixtures of solvents, such as ethyl acetate and methylene chloride. Compound 7-3 thus obtained is subjected to a Mitsunobu reaction to afford bromide 7-4, which is subsequently treated with the sodium salt of mercaptoacetic acid in an alcohol or a mixture of alcohols (ethanol, isopropanol) to provide diacid compound II-4. Compound II-4 is reduced with sodium borohydride to provide compound II-2 (see Example 2).

Example 8: Synthesis of [4-(4-Carboxymethoxy-butoxy)-butoxy]-acetic acid (Compound II-11)

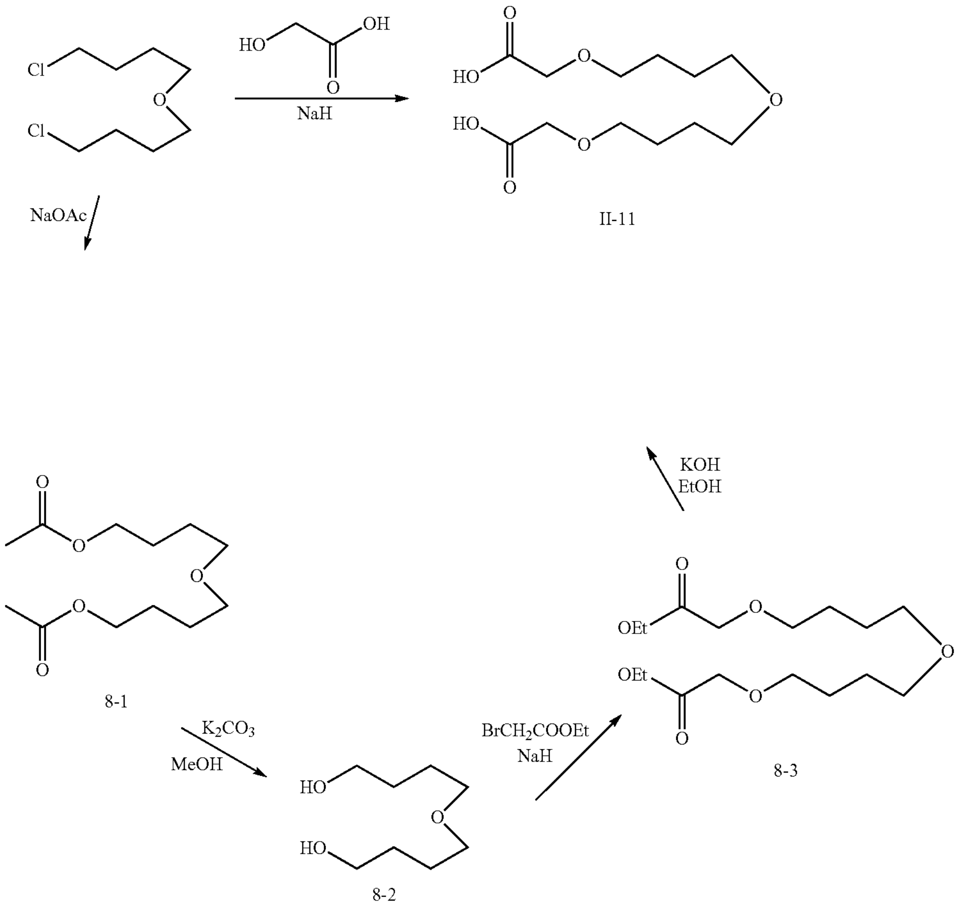

II-11

8-1

8-2

8-3

Commercially available bis(4-chlorobutyl ether) is converted via diacetate 8-1 [Kliem, A., Schniepp, L. E. *J. Am. Chem. Soc,* 1948, 70, 1839] to diol 8-2, which is further reacted with ethyl bromoacetate to provide 8-3. Compound 8-3 is hydrolyzed to provide II-11. Alternatively, bis(4-chlorobutyl ether) is treated with the dianion of hydroxyacetic acid to provide compound II-11 via autoclave or high temperatures.

Specifically, diacetate 8-1 is treated with potassium carbonate in methanol similarly to the method described in Kliem, A., Schniepp, L. E. *J. Am. Chem. Soc,* 1948, 70, 1839, and the crude compound 8-2 is optionally purified by column chromatography. Diol 8-2 is reacted deprotonated with sodium hydride (95% or 60% in mineral oil) in THF for about 2 h to about 4 h and then it is reacted with ethyl bromoacetate to give diester 8-3. The last step, hydrolysis of 8-3, is carried out with KOH in ethyl alcohol for about 2 to about 8 h. The product is then subjected to workup, including acidification with aqueous HCl followed by extraction with methylene chloride, to provide crude compound II-11. Crude compound II-11 is optionally purified by gradient column chromatography on silica gel using solvents such as EtOAc and hexanes and their mixtures.

Example 9: Synthesis of 5,5'-(1,4-Phenylene)bis(2,2-dimethylpentanoic acid) (Compound I-78)

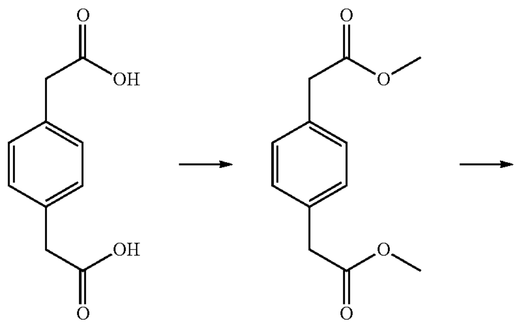

A1 A2

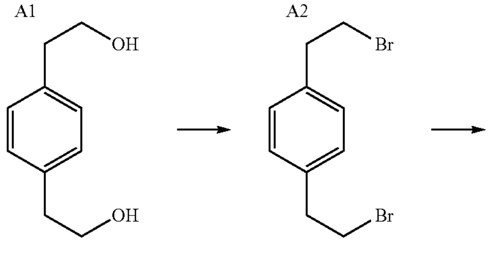

A3 A4

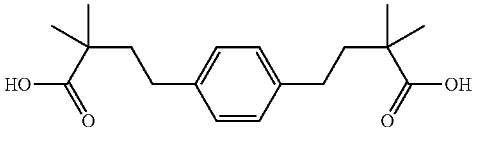

I-78

(4-Methoxycarbonylmethylphenyl)-acetic acid methyl ester (A2)

Concentrated sulfuric acid (40 mL) was added to phenylenediacetic acid (A1) (25.0 g, 0.129 mol) in MeOH (300 mL). The reaction mixture was heated to reflux overnight. Most of the MeOH was evaporated in vacuum. The residue was diluted with EtOAc (300 mL) and water (300 mL). The aqueous solution was separated and extracted with EtOAc (2×100 mL). The combined organic solutions were washed with water (100 mL), saturated $NaHCO_3$ solution (2×100 mL) and brine (100 mL), and dried over $MgSO_4$. The solvent was evaporated to yield (4-methoxycarbonylmethylphenyl)-acetic acid methyl ester (27.1 g, 95%, 92.3% by HPLC) as a white solid. Mp 59-60° C. (51-54° C., Dynamit Nobel, British patent 1495472, Appl. No. 9008/75, filed Mar. 4, 1975). $^1H$ NMR ($CDCl_3$): δ=7.25 (s, 4H), 3.70 (s, 6H), 3.60 (s, 4H). $^{13}C$ NMR ($CDCl_3$): δ=174.0, 132.5, 129.0, 52.0, 40.5.

2-[4-(2-Hydroxyethyl)-phenyl]-ethanol (A3)

(4-Methoxycarbonylmethylphenyl)-acetic acid methyl ester (A2) (26.5 g, 0.12 mol) in THF (100 mL) was added to a solution of $LiAlH_4$ (11.0 g, 0.29 mol) in THF (300 mL) at room temperature with stirring. The reaction mixture was heated to reflux for 2 h. Water (100 mL) was carefully added followed by addition of dilute, aqueous HCl (75 mL concd HCl in 100 mL of water). The aqueous phase was extracted with EtOAc (2×100 mL). The combined organic solutions were washed with water (100 mL), saturated $NaHCO_3$ solution (150 mL) and brine (100 mL), and dried over $MgSO_4$. The solvent was evaporated to yield 2-[4-(2-hydroxyethyl)-phenyl]-ethanol (18.68 g, 94%, 93.5% pure by HPLC) as a white solid. Mp 89-90° C. (87-88° C., Reynolds et al. U.S. Pat. No. 2,789,970, Appl. No. 397,037, filed Dec. 8, 1953). $^1H$ NMR ($CDCl_3$): δ=7.17 (s, 4H), 3.78 (t, J=6.6 Hz, 4H), 2.81 (t, J=6.6 Hz, 4H), 2.30 (br s, 2H). $^{13}C$ NMR ($CDCl_3$): δ=136.9, 129.4, 63.8, 39.0.

1,4-Bis-(2-bromoethyl)-benzene (A4)

Concentrated sulfuric acid (30.0 g) was added dropwise over 1 h into a boiling mixture of 2-[4-(2-hydroxyethyl)-phenyl]-ethanol (A3) (18.29 g, 0.11 mol), NaBr (40.0 g, 0.39 mol) and water (50 mL). The reaction mixture was heated to reflux for 1 h. Additional portions of sulfuric acid (10 mL) and NaBr (16.0 g, 0.16 mol) were added and heating at reflux was continued for 1.5 h. Water (100 mL) was added to the cooled mixture and the product was extracted with methylene chloride (3×100 mL). The combined organic solutions were washed with water (100 mL) and brine (100 mL), and dried over $MgSO_4$. The solvent was evaporated and the residue was purified by column chromatography (silica gel, EtOAc:hexanes, 1:1). The solid product was recrystallized from hexanes to yield 1,4-bis-(2-bromoethyl)-benzene (22.27 g, 69%, 99.8% pure by HPLC) as a white solid. Mp 71-72° C. (70-71° C., Longone, D. T.; Kusefoglu, S. H.; Gladysz, J. A. *J. Org. Chem.* 1977, 42, 2787-2788. $^1H$ NMR ($CDCl_3$): δ=7.18 (s, 4H), 3.57 (t, J=2.2 Hz, 4H), 3.16 (t, J=7.8 Hz, 4H). $^{13}C$ NMR ($CDCl_3$): δ=138.6, 130.0, 40.1, 34.0.

4-[4-(3-Carboxy-3-methylbutyl)-phenyl]-2,2-dimethylbutyric acid

A solution of lithium diisopropylamide (89 mL, 0.16 mol, 1.8 M in heptane/THF/EtPh) was added dropwise to a solution of ethyl isobutyrate (18.0 g, 155 mmol) in THF (100 mL) at −78° C. The reaction mixture was stirred for 1 h and a solution of 1,4-bis-(2-bromoethyl)-benzene (A4) (20.0 g, 68.5 mmol) in THF (50 mL) was added slowly followed by DMPU (10 mL). The reaction mixture was warmed to room temperature over 2 h and stirred for 1 h at 40-50° C. Water (200 mL) was added, the aqueous solution was separated, and extracted with EtOAc (3×80 mL). The combined organic solutions were washed with water (100 mL) and brine (100 mL). After concentration under reduced pressure, the residue was purified by column chromatography (silica gel, EtOAc:heptane, 1:10) to give 4-[4-(3-ethoxycarbonyl-3-methylbutyl)-phenyl]-2,2-dimethylbutyric acid ethyl ester (24.0 g). This intermediate (24.0 g, 66.2 mmol) was dissolved in EtOH (300 mL) and water (50 mL), KOH (85%, 15.0 g, 227 mmol) was added, and the reaction mixture was refluxed for 3 h. The solvent was evaporated, the residue was dissolved in water (150 mL) and extracted with MTBE (2×30 mL). The aqueous solution was acidified with aqueous HCl to pH 1-2. The precipitate was filtered, recrystallized from $CHCl_3$/EtOH (1:1), and dried in vacuum to give 4-[4-(3-carboxy-3-methylbutyl)-phenyl]-2,2-dimethylbutyric acid (13.6 g, 64%, 94.8% pure by HPLC) as white crystals (Compound I-78). Mp 214-215° C. Elemental analysis ($C_{18}H_{26}O_4$): Calcd for C, 70.56; H, 8.55, found: C, 70.78; H, 8.64. $^1$H NMR ($CD_3OD$): δ=7.06 (s, 4H), 4.90 (s, 2H), 2.54-2.48 (m, 4H), 1.80-1.74 (m, 4H), 1.22 (m, 12H). $^{13}$C NMR ($CD_3OD$): δ=181.5, 140.9, 129.2, 44.3, 43.2, 32.3, 25.8. HRMS calcd for $C_{18}H_{26}O_4(M^+)$: 306.1831, found: 306.1831.

Example 10: Synthesis of 6,6'-(1,4-phenylene)bis(2,2-dimethylhexanoic acid) (Compound I-1)

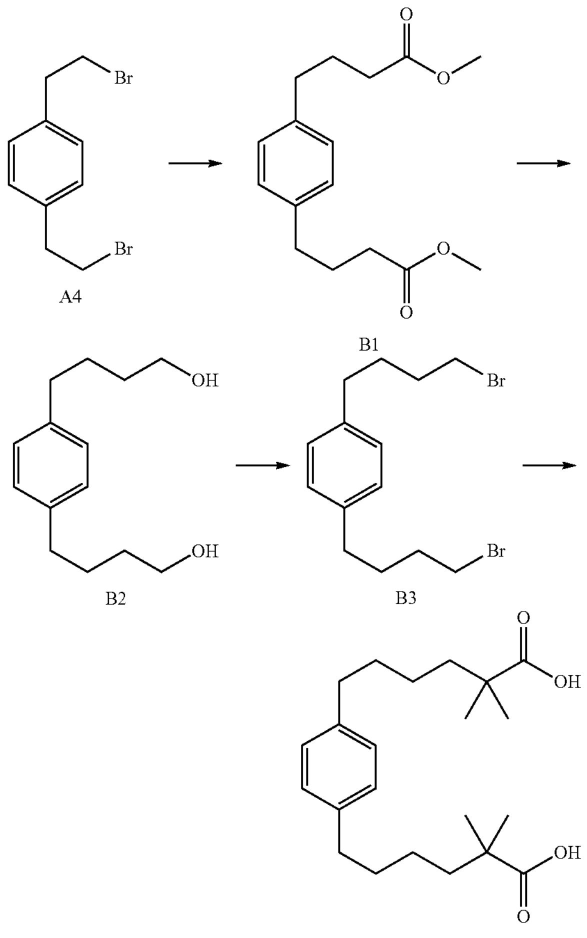

A4

B1

B2

B3

I-1

4-[4-(3-Methoxycarbonylpropyl)-phenyl]-butyric acid methyl ester (B1)

The compound was prepared by a modified method than reported in Cram, D. J.; Allinger, N. L.; Steinberg, H. *J. Amer. Chem. Soc.* 1954, 76, 6132.

Under $N_2$ atmosphere, sodium (3.5 g, 0.152 mol) was dissolved in EtOH (200 mL) and ethyl malonate (50.0 g, 0.31 mol) was added to the warm solution. The reaction mixture was heated to reflux for 5 min and a solution of 1,4-bis-(2-bromoethyl)-benzene (A4) (22.02 g, 75.4 mmol) in ethyl malonate (50 mL) was added dropwise at the room temperature over 5 min. The reaction mixture was heated to reflux for 0.5 h. After the addition of water (150 mL) and EtOAc (200 mL), the solvents were evaporated, and the residue was dissolved in EtOAc (200 mL). The solution was washed with water (100 mL) and brine (100 mL), dried over $MgSO_4$, and concentrated in vacuo. The residue was dried in high vacuum at 80-100° C. (oil bath). The obtained crude 2-{2-[4-(3,3-bis-ethoxycarbonylpropyl)-phenyl]-ethyl}malonic acid diethyl ester was dissolved in aqueous EtOH (80%, 200 mL) and KOH (85%, 35.0 g, 0.53 mol) was added. The reaction mixture was heated to reflux for 2 h. The solvent was partially evaporated and EtOAc (150 mL) was added. The aqueous layer was separated and extracted with EtOAc (2×100 mL). The combined organic solutions were washed with brine (100 mL), dried over $MgSO_4$, and concentrated. The crude 2-{2-[4-(3,3-bis-carboxypropyl)-phenyl]-ethyl}malonic acid (28.0 g) was heated on an oil bath at 200-210° C. for 1.5 h. The obtained, crude 4-[4-(3-carboxypropyl)-phenyl]-butyric acid (16.3 g) was dissolved in MeOH (100 mL) and concentrated sulfuric acid (40 mL) was added. The reaction mixture was refluxed for 5 h, then stirred overnight at room temperature. The MeOH was partially evaporated, the residue was dissolved in EtOAc (150 mL), washed with water (150 mL) and brine (150 mL), and dried over $MgSO_4$. The solvent was evaporated to yield crude 4-[4-(3-methoxycarbonylpropyl)-phenyl]-butyric acid methyl ester (B1) (17.9 g, 85%) as a yellow oil, which was used without purification for the next step. $^1$H NMR ($CDCl_3$): δ=7.10 (s, 4H), 3.67 (s, 6H), 2.59 (t, J=7.4 Hz, 4H), 2.33 (t, J=7.4 Hz, 4H), 1.95-1.90 (m, 4H). $^{13}$C NMR ($CDCl_3$): δ=174.0, 138.9, 128.4, 51.5, 34.6, 33.3, 26.5.

4-[4-(4-Hydroxybutyl)-phenyl]-butan-1-ol (B2)

The compound is prepared according to Cram, D. J.; Allinger, N. L.; Steinberg, H. *J. Am. Chem. Soc.* 1954, 76, 6132-6141). A solution of 4-[4-(3-methoxycarbonylpropyl)-phenyl]-butyric acid methyl ester (17.7 g, 63.6 mmol) in THF (50 mL) was added to a suspension of $LiAlH_4$ (7.2 g, 0.19 mol) in THF (300 mL) with stirring at 0° C. The reaction mixture was heated to reflux for 1 h. Water (100 mL) and aqueous HCl (10%, 200 mL) were added. The aqueous layer was separated and extracted with EtOAc (2×50 mL). The combined organic solutions were washed with brine, dried over $MgSO_4$, and concentrated. The residue was purified by column chromatography (silica gel, ETOAc:hexanes, 1:1) to yield 4-[4-(4-hydroxybutyl)-phenyl]-butan-1-ol (7.5 g, 53%, 96.2% pure by HPLC) as white crystals. Mp 60-62° C. (60.5-62.4° C., Cram, D. J.; Allinger, N. L.; Steinberg, H. *J. Am. Chem. Soc.* 1954, 76, 6132-6141). $^1$H NMR ($CDCl_3$): δ=7.10 (s, 4H), 3.63 (t, J=6.4 Hz, 4H), 2.61 (t, J=7.1 Hz, 4H), 2.12 (br s, 2H), 1.71-1.57 (m, 8H). $^{13}$C NMR ($CDCl_3$): δ=140.7, 129.4, 63.8, 36.3, 33.4, 28.67.

1,4-Bis-(4-bromobutyl)-benzene (B3)

Concentrated sulfuric acid (30 mL) was added dropwise to a boiling mixture of 4-[4-(4-hydroxybutyl)-phenyl]-butan-1-ol (9.4 g, 42.3 mmol), NaBr (17.4 g, 0.169 mol) and water (50 mL) over 1 h. The reaction mixture was refluxed for 1 h. Additional concentrated sulfuric acid (10 mL) was added over 20 min and refluxing was continued for 1.5 h. After the addition of water (300 mL) and methylene chloride (500 mL), the aqueous solution was separated and extracted with methylene chloride (2×50 mL). The combined organic solutions were washed with water (200 mL) and brine (150 mL), and dried over $MgSO_4$. The solvent was evaporated and residue was purified by column chromatography (silica gel, EtOAc:hexanes, 1:20) to yield 1,4-bis-(4-bromobutyl)-benzene (11.8 g, 80%, 96.1% pure by HPLC) as an oil. $^1H$ NMR ($CDCl_3$): δ=7.14 (s, 4H), 3.46 (t, J=6.6 Hz, 4H), 2.65 (t, J=7.5 Hz, 4H), 1.96-1.89 (m, 4H), 1.83-1.75 (m, 4H). $^{13}C$ NMR ($CDCl_3$): δ=139.5, 128.6, 34.7, 34.0, 32.5, 30.1. This procedure is modified from the one described by Cram, D. J.; Allinger, N. L.; Steinberg, H. *J. Am. Chem. Soc.* 1954, 76, 6132-6141.

6-[4-(5-Carboxy-5methylhexyl)-phenyl]-2,2-dimethylhexanoic acid

A solution of lithium diisopropylamide (90 mmol, 1.8 M in heptane/THF/EtPh, 50 mL) was added dropwise to a solution of ethyl isobutyrate (8.97 g, 77.2 mmol) in THF (200 mL) at −78° C. The reaction mixture was stirred for 1 h before a solution of 1,4-bis-(4-bromobutyl)-benzene (11.2 g, 32.2 mmol) in THF (50 mL) was added slowly, followed by addition of DMPU (10 mL). The reaction mixture was warmed to room temperature over 2 h and stirred for 1 h at 40-50° C. Water (200 mL) was added, the aqueous solution was separated, and extracted with EtOAc (3×80 mL). The combined organic solutions were washed with water (100 mL) and brine (100 mL). The solvent was evaporated, and the residue was dissolved in EtOH (100 mL). Water (50 mL) and KOH (85%, 15.0 g, 227 mmol) were added and the reaction mixture was heated to reflux for 3 h. After addition of water (200 mL) and cooling to room temperature, the reaction mixture was acidified with concentrated HCl to pH 1 and stirred for 1 h. The precipitate was filtered, washed with water and dissolved in methylene chloride (400 mL). The solution was dried with $MgSO_4$ and evaporated in vacuum. The residue was dissolved under heating in EtOAc: hexanes (1:30, 200 mL) and cooled in a freezer. The solution was decanted from the oil and evaporated to a volume of 60 mL. The mixture was stirred overnight, the precipitate was filtered, washed with hexanes, and dried in vacuum to yield 6-[4-(5-carboxy-5-methylhexyl)-phenyl]-2,2-dimethylhexanoic acid (8.02 g, 69%, 96.4% pure by HPLC) as a white solid (Compound I-1). Mp 129-131° C. Elemental analysis ($C_{22}H_{34}O_4$): Calcd for C, 72.89; H, 9.45. Found: C, 72.90; H, 9.49. $^1H$ NMR ($CDCl_3$): δ=7.05 (s, 4H), 2.66-2.62 (m, 4H), 1.68-1.56 (m, 4H), 1.53-1.47 (m, 4H), 1.17 (s, 12H), 1.08-0.98 (m, 4H). $^{13}C$ NMR ($CDCl_3$): δ=185.3, 138.6, 128.5, 42.3, 41.5, 34.5, 30.6, 25.0, 23.2. HRMS calcd for $C_{22}H_{34}O_4(M^+)$: 362.2457, found: 362.2453.

Example 11: Synthesis of 1,4-Bis(4-carboxy-4-methylpentyl)benzene (Compound III-1)

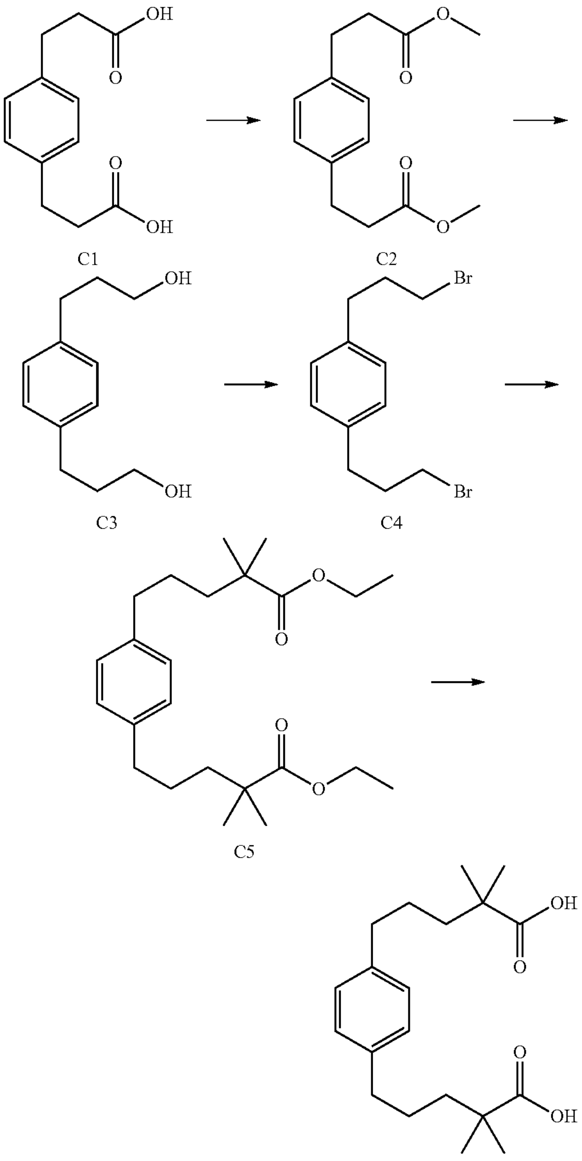

C1 C2 C3 C4 C5 III-1

1,4-Bis(2-methoxycarbonylethyl)benzene (C2)

Under Ar-atmosphere, a solution of 1,4-bis(2-carboxyethyl)benzene (C1) (10.0 g, 45.0 mmol) in anhydrous methanol (75 mL) and concentrated sulfuric acid (5.0 g) was heated to reflux for 5 h. The reaction mixture was cooled to room temperature, the crystals were filtered, washed with MeOH (30 mL), and dried in vacuum to yield 1,4-bis(2-methoxycarbonylethyl)-benzene (11.0 g, 99%) as white crystals. Mp 116-117° C. (116-118° C., Matsuoka, T.; Negi, T.; Otsubo, T.; Sakata, Y.; Misumi, S. *Bull. Chem. Soc. Japan* 1972, 45, 1825-1833). $^1H$ NMR ($CDCl_3$): δ=7.11 (s, 4H), 3.69 (s, 6H), 2.94 (t, J=8.1 Hz, 4H), 2.62 (t, J=8.2 Hz, 4H). $^{13}C$ NMR ($CDCl_3$): δ=173.3, 138.4, 128.4, 51.6, 35.6, 30.5. This known compound was prepared by a method different from the one described in Matsuoka, T.; Negi, T.; Otsubo, T.; Sakata, Y.; Misumi, S. *Bull. Chem. Soc. Japan* 1972, 45, 1825-1833.

1,4-Bis(3-hydroxypropyl)benzene (C3)

C3 was prepared according to Matsuoka, T.; Negi, T.; Otsubo, T.; Sakata, Y.; Misumi, S. *Bull. Chem. Soc. Japan* 1972, 45, 1825-1833. Under Ar-atmosphere, lithium aluminum hydride (5.2 g, 13.7 mmol) was added in portions to anhydrous THF (300 mL). A solution of 1,4-bis(2-methoxycarbonylethyl)benzene (11.5 g, 45.9 mmol) in THF (50 mL) was added dropwise over 1 h, resulting in an exothermic reaction. The reaction mixture was refluxed for 5 min and stirred at room temperature for 3 h. It was then hydrolyzed with water (100 mL) and a 10% aqueous solution of $NH_4Cl$ (50 mL). The organic layer was separated and the water solution was extracted with EtOAc (100 mL). The organic phases were combined, washed with brine (50 mL), dried over $MgSO_4$, and concentrated to afford 1,4-bis(3-hydroxypropyl)benzene (9.0 g, quantitative) as an oil, which was used without further purification for the next step. $^1H$ NMR (DMSO-$d_6$): δ=7.10 (s, 4H), 4.43 (br s, 2H), 3.41 (t, J=8.1 Hz, 4H), 2.59 (t, J=8.2 Hz, 4H), 1.71 (m, 2H). $^{13}C$ NMR (DMSO-$d_6$): δ=139.0, 127.0, 60.0, 34.5, 31.2.

1,4-Bis(3-bromopropyl)benzene (C4)

An emulsion of 1,4-bis(3-hydroxypropyl)benzene (9.0 g, 46.3 mmol) and sodium bromide (24.0 g, 0.23 mol) in deionized water (25 mL) was heated to reflux, while concentrated sulfuric acid (17 mL) was added dropwise over 1 h. After the addition, heating under reflux was continued for additional 3.5 h. The solution was cooled to room temperature, diluted with water (40 mL), and extracted with $CH_2Cl_2$ (2×150 mL). The combined organic layers were washed with saturated solution of $NaHCO_3$ (100 mL), saturated NaCl solution (100 mL) and dried over $MgSO_4$. The solvent was evaporated and the residue was purified by column chromatography (silica gel, EtOAc:hexanes, 1:40) to yield 1,4-bis(3-bromopropyl)benzene (11.6 g, 78%) as a colorless oil. $^1H$ NMR ($CDCl_3$): δ=7.15 (s, 4H), 3.41 (t, J=6.6 Hz, 4H), 2.77 (t, J=7.1 Hz, 4H), 2.18 (m, 4H). $^{13}C$ NMR ($CDCl_3$): δ=138.3, 128.7, 34.2, 33.4, 33.3. This known compound was prepared by a method different from the one described in Matsuoka, T., Negi, T., Otsubo, T., Sakata, Y., Misumi, S. *Bull. Chem. Soc.*, Japan, 1972, 45, 1825-1833 and Ruzicka, L.; Buijs, J. B.; Stoll, M. *Helv. Chim. Acta* 1932, 15, 1220.

1,4-Bis(4-ethoxycarboxy-4-methylpentyl)benzene (C5)

Under $N_2$-atmosphere, to a solution of ethyl isobutyrate (9.0 g, 77.5 mmol) in anhydrous THF (300 mL) was added dropwise lithium diisopropylamide (1.8 M solution in heptane/THF/EtPh, 46.7 mL, 84.0 mmol) at −78° C. After 1 h, a solution of 1,4-bis(3-bromopropyl)benzene (11.6 g, 36.3 mmol) in anhydrous THF (70 mL) was added dropwise, followed by the addition of DMPU (20 mL). The reaction mixture was allowed to warm to room temperature overnight, then cooled with an ice-bath, and hydrolyzed with saturated $NH_4Cl$ solution (100 mL). Water (100 mL) was added and the layers were separated. The aqueous layer was extracted with ethyl acetate (2×50 mL). The combined organic layers were washed with saturated NaCl solution (100 mL), dried with $MgSO_4$, and concentrated in vacuum. The residue was purified by column chromatography on silica gel (EtOAc:hexanes, 1:10) to give 1,4-bis(4-ethoxycarboxy-4-methylpentyl)benzene (13.3 g, 94%) as a colorless oil. $^1H$ NMR ($CDCl_3$): δ=7.09 (s, 4H), 4.11 (q, J=7.1 Hz, 4H), 2.57 (m, 4H), 1.57 (m, 8H), 1.24 (t, J=7.1 Hz, 6H), 1.47 (s, 12H). $^{13}C$ NMR ($CDCl_3$): δ=177.9, 139.6, 128.2, 60.1, 42.0, 40.2, 35.8, 26.8, 25.1, 14.2. HRMS calcd for $C_{24}H_{39}O_4(MH^+)$: 391.2838, found: 391.2836.

1,4-Bis(4-carboxy-4-methylpentyl)benzene

A solution of 1,4-bis(4-ethoxycarboxy-4-methylpentyl)benzene (13.0 g, 33.3 mmol) and potassium hydroxide (85%, 7.0 g, 106 mmol) in ethanol (25 mL) and water (15 mL) was heated to reflux for 3.5 h. The reaction mixture was cooled to room temperature, diluted with water (100 mL) and acidified with HCl (2 M solution in water) to pH 1. A precipitate formed immediately. The mixture was stirred for 1 h, the precipitate was filtered and washed with water (2×50 mL). The crude precipitate was dissolved in methylene chloride (700 mL) and the solution was dried over $MgSO_4$ overnight. The solvent was evaporated and the residue was recrystallized (methylene chloride:hexanes, 1:1) to give 1,4-bis(4-carboxy-4-methylpentyl)benzene (9.5 g, 85%, 100% pure by HPLC) as white crystals (Compound III-1). Mp 131° C. (125-126° C., Gleiter, R.; Krämer, R.; Irngartinger, H.; Bissinger, C. *Synthesis and Properties of* 4,4,9,9-*Tetramethyl*[12]*paracyclophane*-5,6,7,8-*tetrone. J. Org. Chem.* 1992, 57, 252-258). Elemental analysis ($C_{20}H_{30}O_4$): Calcd for C, 71.82; H, 9.04; found: C, 71.10; H, 9.00. $^1H$ NMR ($CDCl_3$): δ=7.07 (br s, 4H), 2.55 (m, 4H), 1.59 (m, 8H), 1.18 (s, 12H). $^{13}C$ NMR ($CDCl_3$): δ=184.9, 139.6, 128.1, 42.1, 40.3, 35.8, 26.8, 24.9. This known compound was prepared by a method modified to the one described in Gleiter, R.; Krämer, R.; Irngartinger, H.; Bissinger, *C. Synthesis and Properties of* 4,4,9,9-*Tetramethyl* [12]*paracyclophane*-5,6,7,8-*tetrone. J. Org. Chem.* 1992, 57, 252-258.

Example 12: Synthesis of 5,5'-(1,3-Phenylene)bis(2,2-dimethylpentanoic acid) (Compound I-31)

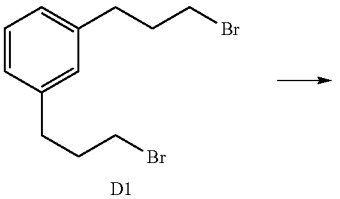

D1

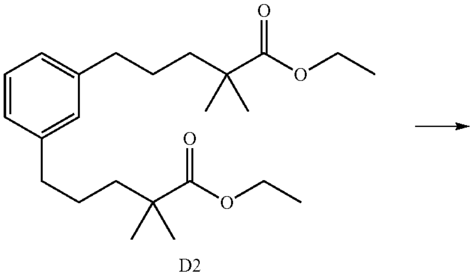

D2

-continued

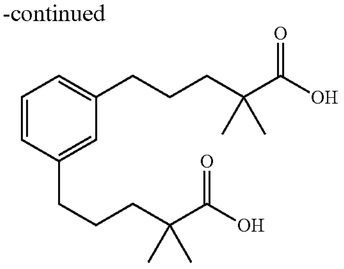

I-31

Dimethyl m-benzene-bis(2,2-dimethyl)pentanoate (D2)

Under Ar-atmosphere, to a solution of ethyl isobutyrate (21.2 g, 24.4 mL, 183 mmol) in anhydrous THF (200 mL) was added dropwise lithium diisopropylamide (2.0 M in heptane/THF/ethylbenzene, 91.5 mL, 183 mmol) at −78° C. After 1 h, a solution of m-bis(3-bromopropyl)benzene (D1) (prepared according to Schimelpfenig, C. W. *J. Org. Chem.* 1975, 40, 1493-1494 and Effenberger, F.; Kurtz, W. *Chem. Ber.* 1973, 106, 511-524; 26.6 g, 83.1 mmol) in anhydrous THF (50 mL) was added dropwise, followed by the addition of DMPU (25 mL). The reaction mixture was allowed to warm to room temperature overnight, then cooled with an ice-bath, and hydrolyzed with saturated $NH_4Cl$ solution (100 mL). Deionized water (100 mL) was added and the layers were separated. The aqueous layer was extracted with ethyl acetate (3×100 mL). The combined organic layers were washed with saturated NaCl solution (100 mL), 1 N hydrochloric acid (2×100 mL), saturated $NaHCO_3$ solution (100 mL), and saturated NaCl solution (100 mL). The combined organic phases were dried over $MgSO_4$, concentrated in vacuo, and dried in high vacuo. The residue was purified by flash chromatography on silica (hexanes/ethyl acetate=95/5) to give diethyl 5,5'-(1,3-phenylene)bis(2,2-dimethylpentanoate) (15.7 g, 48%) as a yellowish oil. $^1H$ NMR ($CDCl_3$): δ=7.17 (t, 1H, J=7.0 Hz), 6.97 (m, 3H), 4.09 (q, 4H, J=7.3 Hz), 2.55 (m, 4H), 1.56 (m, 8H), 1.22 (t, 6H, J=7.3 Hz), 1.15 (s, 12H). $^{13}C$ NMR ($CDCl_3$): δ=178.02, 142.37, 128.58, 128.32, 125.86, 60.31, 42.25, 40.52, 36.48, 27.03, 25.30, 14.39.

5,5'-(1,3-Phenylene)bis(2,2-dimethylpentanoic acid)

A solution of diethyl 5,5'-(1,3-phenylene)bis(2,2-dimethylpentanoate) (D2) (10.6 g, 27.14 mmol) and potassium hydroxide (85%, 6.3 g, 95.00 mmol) in ethanol (20 mL) and water (10 mL) was heated to reflux for 4 h. The reaction mixture was cooled to room temperature, diluted with water (50 mL), and the ethanol was removed under reduced pressure. The remaining aqueous solution was extracted with dichloromethane (2×50 mL). The aqueous layer was acidified with concd hydrochloric acid (10 mL) to pH 1 and extracted with dichloromethane (3×50 mL). The combined organic layers were washed with saturated NaCl solution (50 mL), dried over $MgSO_4$, concentrated in vacuo, and dried in high vacuo to give a viscous oil (9.3 g). This oil was crystallized from pentane/dichloromethane (75 mL/5 mL) at −5° C. to afford 5,5'-(1,3-phenylene)bis(2,2-dimethylpentanoic acid) (4.78 g, 49%, 93.2% pure by HPLC) as a white powder (Compound I-31). Mp 79° C. Elemental analysis ($C_{20}H_{30}O_4$): Calcd for C, 71.82; H, 9.04; found: C, 71.71; H, 9.22. $^1H$ NMR (DMSO-$d_6$): δ=12.2-11.7 (m br, 2H), 7.17 (m, 1H), 6.98 (m, 3H), 2.52 (m, 4H), 1.49 (m, 8H), 1.07 (s, 12H). $^{13}C$ NMR (DMSO-$d_6$): δ=178.86, 141.96, 128.26, 125.69, 41.21, 39.91, 35.68, 26.62, 25.06. HRMS calcd for $C_{30}H_{31}O_3(MH^+)$: 335.2222, found: 335.2232.

Example 13: Synthesis of 6-[3-(5-Carboxy-5-methylhexyl)-phenyl]-2,2-dimethylhexanoic acid (Compound I-32)

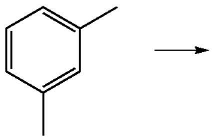

E1

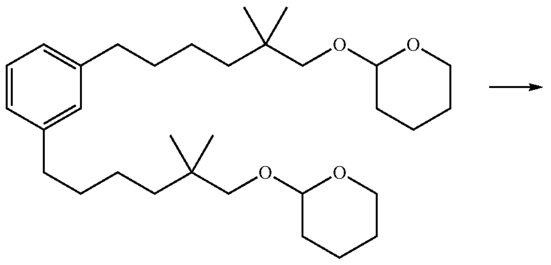

E2

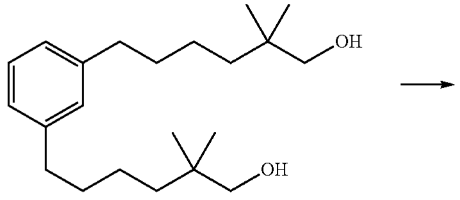

E3

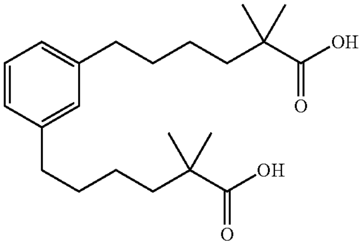

I-32

[1,3-Bis(5,5-dimethyl-6-(tetrahydropyran-2-yloxy)-hexyl]-phenylene (E2)

A solution of n-butyl lithium (38.8 mL, 2.5 M in hexanes/THF/EtPh, 96.9 mmol) was added to a mixture of m-xylene (E1) (5.0 g, 47.1 mmol) and potassium tert-butoxide (5.4 g, 48.1 mmol) in hexanes (100 mL) at room temperature. The reaction mixture was heated to reflux for 1 h. A yellow precipitate was formed. The reaction mixture was cooled to 0° C. and 2-(5-bromo-2,2-dimethylpentyloxy)-tetrahydropyran (prepared according to Dasseux et al., U.S. Pat. Nos. 6,646,170 and 6,410,802, 30.0 g, 107.5 mmol) was added dropwise. The reaction mixture was heated to reflux for 20 h. Water (150 mL) was added and the organic phase was separated. The aqueous solution was extracted with EtOAc (2×100 mL). The organic phases were combined, washed with brine (50 mL), and dried over $MgSO_4$. The solvent was evaporated and the residue was purified by column chromatography (silica gel, EtOAc:hexanes, 1:30) to give [1,3-bis(5,5-dimethyl-6-(tetrahydropyran-2-yloxy)-hexyl]-phenylene (14.8 g, 62%, 96.1% pure by HPLC) as an oil. $^1$H NMR ($CDCl_3$): δ=7.17-7.14 (m, 1H), 7.00-6.98 (m, 3H), 4.54 (t, J=3.0 Hz, 2H), 3.78-3.86 (m, 2H), 3.50-3.45 (m, 2H), 3.47 (d, J=9.1 Hz, 2H) 2.98 (d, J=9.1 Hz, 2H), 2.59 (t, J=7.6 Hz, 4H), 1.90-1.28 (m, 24H), 0.89 (s, 12H). $^{13}$C NMR ($CDCl_3$): δ=142.8, 128.5, 128.1, 125.6, 99.1, 77.5, 61.8, 39.2, 36.0, 34.2, 32.5, 30.7, 25.6, 24.6, 23.7, 19.4. HRMS calcd for $C_{32}H_{54}O_4(M^+)$: 501.3943, found: 501.3943.

6-[3-(6-Hydroxy-5,5-dimethylhexyl)-phenyl]-2,2-dimethylhexan-1-ol (E3)

Concentrated, aqueous HCl (20 mL) was added to 1,3-bis(5,5-dimethyl-6-(tetrahydropyran-2-yloxy)-hexyl]-phenylene (18.0 g, 35.7 mmol) in MeOH (200 mL). The reaction mixture was heated to reflux for 2 h and stirred overnight at room temperature. MeOH was evaporated in vacuum and the residue was dissolved in methylene chloride (200 mL). The solution was washed with water (100 mL), saturated $NaHCO_3$ solution (100 mL) and brine (100 mL), and dried over $MgSO_4$. The solvent was evaporated and the residue was purified by column chromatography (silica gel, EtOAc:hexanes, 1:1) to give 6-[3-(6-hydroxy-5,5-dimethylhexyl)-phenyl]-2,2-dimethylhexan-1-ol (10.41 g, 87%, 86.4% by HPLC) as an oil. $^1$H NMR ($CDCl_3$): δ=7.21-7.19 (m, 1H), 7.02-6.99 (3H), 3.32 (s, 4H), 2.62 (t, J=7.8 Hz, 4H), 1.64-1.26 (m, 12H), 0.89 (s, 12H). $^{13}$C NMR ($CDCl_3$): δ=142.6, 128.5, 128.1, 125.6, 71.9, 38.4, 35.8, 35.0, 32.4, 23.7, 23.5. HRMS calcd for $C_{22}H_{38}O_4(M^+)$: 335.2950, found: 335.2950.

6-[3-(5-Carboxy-5-methylhexyl)-phenyl]-2,2-dimethylhexanoic acid

Pyridinium dichromate (74.85 g, 199 mmol) was added to a solution of 6-[3-(6-hydroxy-5,5-dimethylhexyl)-phenyl]-2,2-dimethylhexan-1-ol (8.5 g, 25.4 mmol) in DMF (200 mL) at room temperature. The reaction mixture was stirred for 30 h, then heated to 40° C. for 10 h. Ethyl acetate (100 mL) was added, followed by the addition of water (200 mL) and concd $H_2SO_4$ (20 mL) under stirring. The organic layer was separated, and the aqueous layer was extracted with EtOAc (3×100 mL). The combined organic solutions were washed with water (100 mL), saturated $NaHCO_3$ solution (100 mL) and brine (2×100 mL) and dried over $MgSO_4$. The solvent was evaporated and the residue was purified by column chromatography (silica gel, EtOAc:hexanes, 1:1). The obtained oil was stirred in $Et_2O$:hexanes (1:10, 50 mL) for 3 h and the precipitated solid product was filtered (7.2 g, 78%, 96.1% by HPLC) (Compound I-32). Mp 99-101° C. Elemental analysis ($C_{22}H_{34}O_4$): Calcd for C, 72.89; H, 9.45; found: C, 73.02; H, 9.57. $^1$H NMR ($CDCl_3$): δ=7.19-7.16 (m, 1H), 6.99-6.94 (m, 3H), 2.58 (t, J=7.1 Hz, 4H), 1.63-1.56 (m, 8H), 1.32-1.22 (m, 4H), 1.18 (s, 12H). $^{13}$C NMR ($CDCl_3$): δ=185.5, 142.2, 128.6, 128.3, 126.0, 42.0, 40.8, 35.7, 31.0, 25.1, 24.4. HRMS calcd for $C_{22}H_{35}O_4(MH^+)$: 363.2535, found: 363.2530.

Example 14: Synthesis of 5,5'-(1,2-Phenylene)bis(2,2-dimethylpentanoic acid) (Compound I-61)

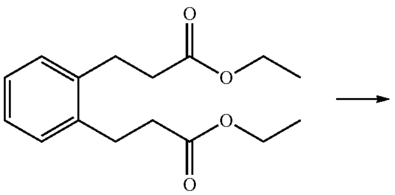

F1

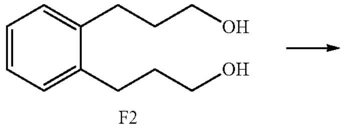

F2

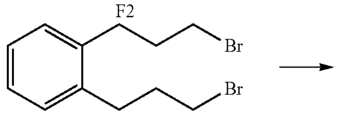

F3

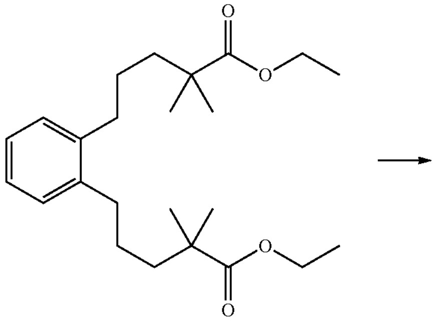

F4

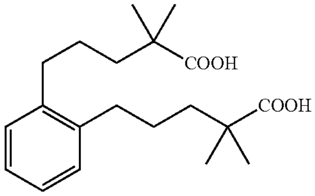

I-61

3-[2-(3-Hydroxypropyl)-phenyl]-propanol (F2)

Under Ar-atmosphere, to a stirred suspension of lithium aluminum hydride (3.0 g, 78.2 mmol) in anhydrous THF (100 mL) was added dropwise a solution of 3-[2-(2-ethoxycarbonylethyl)-phenyl]-propionic acid ethyl ester (prepared according to Fakhri, S. A.; Behrooz, Y. H. *Tetrahedron* 2000, 56, 8301-8308; 14.5 g, 52.1 mmol) in THF (100 mL) over 50 min at room temperature. The mixture was stirred for 2 h, then cooled with an ice bath, and carefully hydrolyzed by dropwise addition of deionized water (100 mL). The hydrolysis was completed by dropwise addition of 10% sulfuric acid at room temperature and stirring overnight. The mixture was extracted with dichloromethane (200 mL, 2×100 mL). The combined organic layers were washed with saturated sodium chloride solution (100 mL), dried over $MgSO_4$, concentrated in vacuo, and dried in high vacuo to give 3-[2-(3-hydroxypropyl)-phenyl]-propanol (8.6 g, 85%, 87.9% pure by GC) as a turbid oil, which was used without further purification for the next step. $^1$H NMR ($CDCl_3$):

δ=7.20-7.05 (m, 4H), 3.67 (t, 4H, J=6.1 Hz), 3.50-3.20 (m br., 2H), 2.72 (m, 4H), 1.82 (m, 4H). $^{13}$C NMR ($CDCl_3$): δ=139.98, 129.43, 126.24, 62.35, 34.36, 29.01. HRMS calcd for $C_{12}H_{19}O_2$ ($MH^+$): 195.1385, found: 195.1388. This known compound was prepared by a method different than the one described in Uenaka, M.; Kubota, B. *Bull. Chem. Soc. Jpn.* 1936, 11, 19-26.

1,2-Bis-(3-bromopropyl)-benzene (F3)

A mixture of 3-[2-(3-hydroxypropyl)-phenyl]-propanol (8.6 g, 44.27 mmol), sodium bromide (18.6 g, 180.62 mmol) and water (16 mL) was heated at reflux while concentrated sulfuric acid (13.3 mL) was added dropwise over 20 min. The solution was heated for additional 75 min at reflux, then cooled to room temperature, and diluted with deionized water (200 mL). The mixture was extracted with dichloromethane (3×100 mL) and the combined organic layers were successively washed with water (100 mL), saturated sodium bicarbonate solution (100 mL), 10% aqueous sodium thiosulfate solution (200 mL), and saturated sodium chloride solution (100 mL). The organic layer was dried over $MgSO_4$, concentrated in vacuo, and dried in high vacuo to give the crude product (11.2 g) as a brown oil. The crude material was purified by flash chromatography (silica, hexanes, then hexanes/ethyl acetate=90/10), affording 1,2-bis-(3-bromopropyl)-benzene (8.25 g, 58%, 95.9% pure by GC) as a viscous, yellow oil. $^1$H NMR ($CDCl_3$): 06=7.16 (s, 4H), 3.33 (t, 4H, J=6.3 Hz), 2.79 (m, 4H), 2.12 (m, 4H). $^{13}$C NMR ($CDCl_3$): δ=138.69, 129.69, 126.66, 34.14, 33.62, 30.99. HRMS calcd for $C_{12}H_{16}Br_2$ ($M^+$): 317.9619, found: 317.9624. This known compound was prepared by a method different than the one described in Uenaka, M.; Kubota, B. *Bull. Chem. Soc. Jpn.* 1936, 11, 19-26.

5-[2-(4-Ethoxycarbonyl-4-methylpentyl)-phenyl]-2,2-dimethylpentanoic acid ethyl ester (F4)

Under Ar-atmosphere, to a solution of ethyl isobutyrate (8.7 g, 10.0 mL, 74.98 mmol) in anhydrous THF (100 mL) was added dropwise over 15 min a solution of lithium diisopropylamide (2.0 M in heptane/THF/ethyl benzene, 41.2 mL, 82.48 mmol) at −78° C. After 85 min, a solution of 1,2-bis-(3-bromopropyl)-benzene (8.0 g, 74.98 mmol) in anhydrous THF (25 mL) was added dropwise over 10 min, followed by dropwise addition of DMPU (15 mL). The mixture was stirred at −78° C. for an additional hour, then allowed to slowly warm to room temperature over the next 2 h and stirred overnight. The reaction mixture was cooled with an ice-bath and hydrolyzed by addition of saturated $NH_4Cl$ solution (100 mL) and deionized water (100 mL). The layers were separated, and the aqueous layer was extracted with ethyl acetate (3×100 mL). The combined organic layers were washed with water (100 mL), 1 N hydrochloric acid (100 mL), water (100 mL), and saturated sodium chloride solution (100 mL). The organic phase was then dried over $MgSO_4$ and concentrated in vacuo to yield the crude product (14.0 g) as a reddish oil. Purification by flash chromatography (silica, hexane/ethyl acetate=95/5) afforded 5-[2-(4-ethoxycarbonyl-4-methylpentyl)-phenyl]-2,2-dimethylpentanoic acid ethyl ester (8.2 g, 84%, 79% pure by GC) as a slightly yellowish oil. $^1$H NMR ($CDCl_3$): δ=7.11 (s, 4H), 4.10 (q, 4H, J=7.0 Hz), 2.56 (t, 4H, J=7.6 Hz), 1.68-1.42 (m, 8H), 1.23 (t, 6H, J=7.0 Hz), 1.16 (s, 16H). $^{13}$C NMR ($CDCl_3$): δ=177.95, 140.01, 129.12, 126.04, 60.34, 42.26, 40.79, 33.11, 26.75, 25.29, 14.41. HRMS caled for $C_{24}H_{39}O_4$ ($MH^+$): 391.2848, found: 391.2846.

5,5'-(1,2-phenylene)bis(2,2-dimethylpentanoic acid) (or 5-[2-(4-carboxy-4-methylpentyl)-phenyl]-2,2-dimethylpentanoic acid)

A solution of 5-[2-(4-ethoxycarbonyl-4-methylpentyl)-phenyl]-2,2-dimethylpentanoic acid ethyl ester (8.3 g, 21.25 mmol) and potassium hydroxide (>85%, 4.91 g, 74.38 mmol) in ethanol (20 mL) and water (10 mL) was heated at reflux for 4 h. After cooling to room temperature, the mixture was diluted with water (50 mL) and concentrated in vacuo to ca. 60 mL volume. This aqueous solution was extracted with dichloromethane (2×30 mL) and then acidified with 1 N hydrochloric acid (8 mL) to pH 1. The aqueous layer was extracted with dichloromethane (3×30 mL). The combined organic extracts were washed with saturated NaCl solution (30 mL), dried over $MgSO_4$, and concentrated in vacuo to furnish the crude product (5.50 g) as a white solid/viscous oil. The crude material was crystallized from heptane/dichloromethane at −5° C. to afford tiny white crystals that were washed with cold heptane (10 mL) and dried in high vacuo (5.05 g, 71%, 98.3% pure by HPLC) (Compound I-61). Mp 108-109° C. Elemental analysis ($C_{20}H_{30}O_4$): Calcd for C, 71.82; H, 9.04; found: C, 71.14; H, 9.06. $^1$H NMR (DMSO-$d_6$): δ=12.7-11.5 (m br, 2H), 7.11 (s, 4H), 2.55 (t, 4H, J=7.3 Hz), 1.62-1.38 (m, 8H), 1.09 (s, 12H). $^{13}$C NMR (DMSO-$d_6$): δ=178.83, 139.69, 128.98, 125.89, 41.25, 40.20, 32.49, 26.57, 25.04. HRMS calcd for $C_{20}H_{31}O_4$ (MH): 335.2222, found: 335.2232.

Biological Assays

Example 15: Anti-Proliferative Effects of Compounds I-32, I-61, I-1, and III-1 in Hep3B and Hepa1-6 Liver Cancer Cells Human liver cancer cells Hep3B and murine liver cancer cells Hepa1-6, respectively, were seeded at a cell density of 3000 cells/well in 96-well plates using either Eagle's Minimum Essential Medium (Corning) for Hep3B or Dulbecco's Modified Eagle's Medium (DMEM) High Glucose (Gibco) for Hepa1-6 cells, supplemented with 10% fetal bovine serum (FBS, Gibco) and 1% Antibiotic-Antimycotic solution (Thermo-Fisher Scientific). The next day, the cells were treated with 0 (vehicle control), 0.1, 0.5, 1, 5, 10, 30, 50 or 100 μM Compound I-32, I-61, I-1, or III-1 (final concentration of DMSO 0.1%) and were allowed to grow for 72 hours at 37° C. On day 5, 10 μl of PrestoBlue™ Cell Viability Reagent (Invitrogen) was added to each well and the plate was incubated at 37° C. for an additional 1-2 hours. After incubation, fluorescence signal was measured with an excitation/emission wavelength of 560/590 nm using a SpectraMax M5 Microplate Reader (Molecular Devices).

The effects of Compounds I-32, I-61, I-1, and III-1 on cell proliferation in Hepa1-6 cells as a percent of vehicle control (DMSO, 0.1% final concentration) are shown in FIGS. 2A-2D, respectively (n=4 replicates, single experiment, error bar represents the standard deviation). The effects of the Compounds I-32, I-61, I-1, and III-1 on Hep3B cell proliferation as a percent of vehicle control (DMSO, 0.1% final concentration) are shown in FIGS. 3A-3D, respectively (n=5, single experiment, error bar represents the standard deviation).

Example 16: Anti-Clonogenic Effects of Compounds I-32, I-61, I-1, and III-1 in Hep3B and Hep1-6 Liver Cancer Cells Liver cancer cell lines Hep3B (human) and Hepa1-6 (murine) were maintained in either Eagle's Minimum Essential Medium (Corning) for Hep3B cells or High Glucose DMEM (Gibco) for Hepa1-6 cells, supplemented with 10% FBS (Gibco) and 1% Antibiotic-Antimycotic (Thermo-Fisher Scientific). Each cell line was seeded at 1000 cells/well in 12-well plates. The next day, the media were replaced, and cells were treated with 0 (vehicle control, 0.1% DMSO), 1, 5, 10, 30, 50, or 100 μM Compound I-32, I-61, I-1, or III-1 (final concentration of DMSO 0.1%) for 7 days. On day 9, the media were removed, and cells were fixed with 10% formalin (500 μl) for 10 minutes at room temperature, washed with 1×PBS and stained with crystal violet. After 10 minutes the excess stain was removed by rinsing three times with tap water. The plates were allowed to dry overnight, then the number of colonies (>50 cells) in each well were counted using light microscopy as described previously by Villiani L. A., et al.

The effects of Compounds I-32, I-61, I-1, and III-1 on clonogenicity in Hepa1-6 cells as a percent of vehicle control (DMSO, 0.1% final concentration) are shown in FIGS. 4A-4D, respectively (n=2, error bars represent the standard deviation). The effects of Compounds I-32, I-61, I-1, and III-1 on clonogenicity in Hep3B cells as a percent of vehicle control (DMSO, 0.1% final concentration) are shown in FIGS. 5A-5D, respectively (n=2, error bars represent the standard deviation).

Table 1 summarizes the biology results from Examples 15-17. ND=not determined.

TABLE 1

Effects on de Novo Lipogenesis (DNL), Clonogenicity and Cancer Cell Proliferation of Illustrative Compounds of the Invention in Human (h) and Murine (m) cells ($IC_{50}$ or % Proliferation Reduction, respectively).

| Assay | Cell Line | Compound I-1 | Compound I-32 | Compound I-61 | Compound III-1 |
|---|---|---|---|---|---|
| | | $IC_{50}$ (μM) | | | |
| DNL | primary hepatocytes (m) | 12.1 | 8.3 | ND | ND |
| Clonogenicity | Hepa1-6 (m) | 55.6 | 52.3 | 73.4 | 61.0 |
| Clonogenicity | Hep3B (h) | 53.9 | 41.7 | 57.3 | 55.6 |
| | | % reduction vs control at 100 μM Mean (Standard Deviation) | | | |
| Cancer Cell Proliferation | Hepa1-6 (m) | 25.9 (5.7) | 18.6 (3.1) | 21.8 (8.9) | 15.7 (6.7) |
| Cancer Cell Proliferation | Hep3B (h) | 41.8 (8.4) | 30.8 (2.6) | 35.7 (5.8) | 29.7 (6.2) |

Example 17: Synergistic Effect of Illustrative Compounds of the Invention with Sorafenib or Lenvatinib Combination studies were undertaken with the compounds of the invention to determine potential synergy of sorafenib or lenvatinib in the presence of compound 1-32 or compound 1-61. In a separate experiment, the $IC_{50}$ for inhibition of proliferation by sorafenib in the absence of a compound of the invention and lenvatinib in the absence of a compound of the invention was determined to be 3 μM and 0.5 μM, respectively, in Hep3B cells and 5 μM and 30 μM, respectively, in Hepa1-6 cells (data not shown).

Figure 6A:
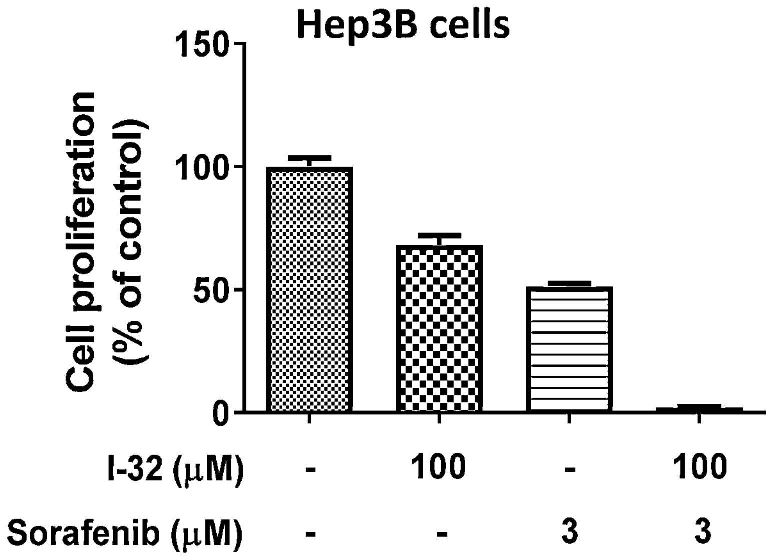
FIG. 6A shows anti-proliferation effects of Compound I-32 and sorafenib, in the absence or presence of the other, in Hep3B cells.
Figure 6B:
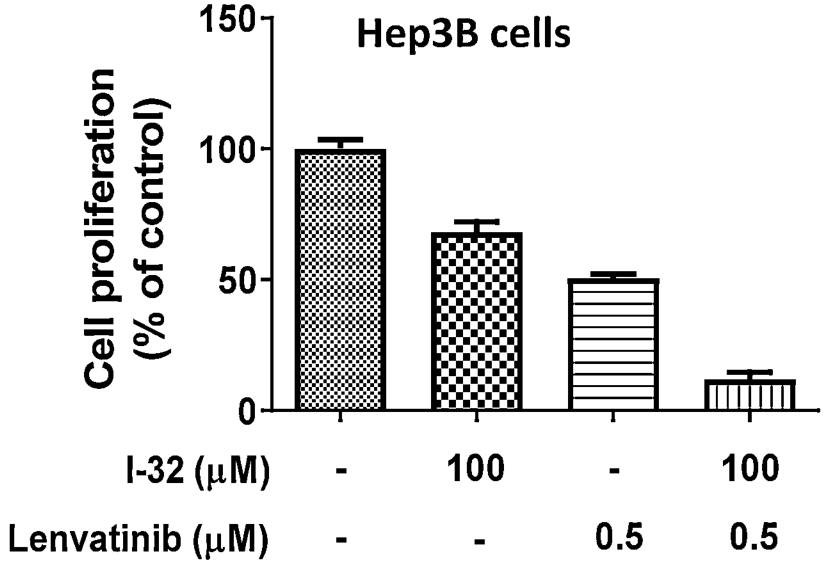
FIG. 6B shows anti-proliferation effects of Compound I-32 and lenvatinib, in the absence or presence of the other, in Hep3B cells.
Figure 6C:
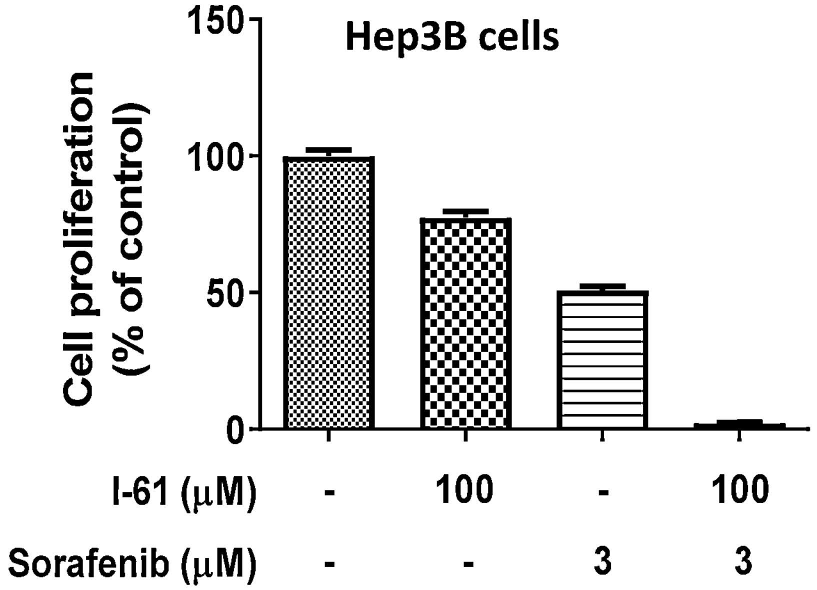
FIG. 6C shows anti-proliferation effects of Compound I-61 and sorafenib, in the absence or presence of the other, in Hep3B cells.
Figure 6D:
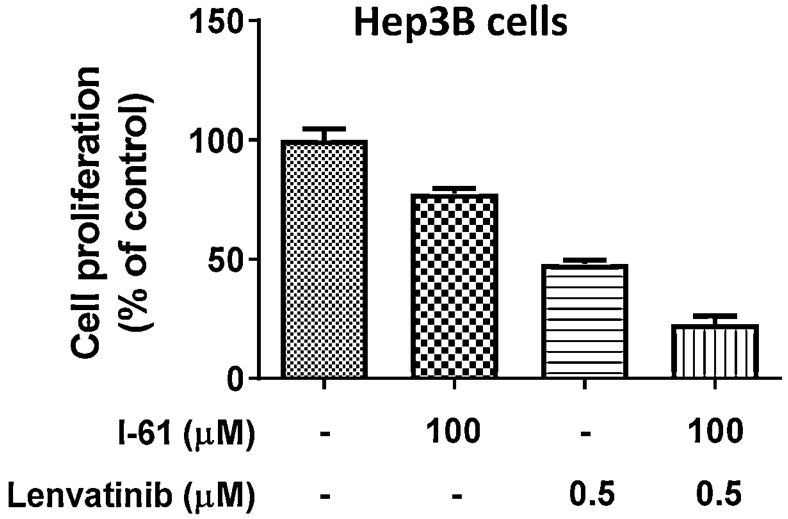
FIG. 6D shows anti-proliferation effects of Compound I-61 and lenvatinib, in the absence or presence of the other, in Hep3B cells.
Figure 7A:
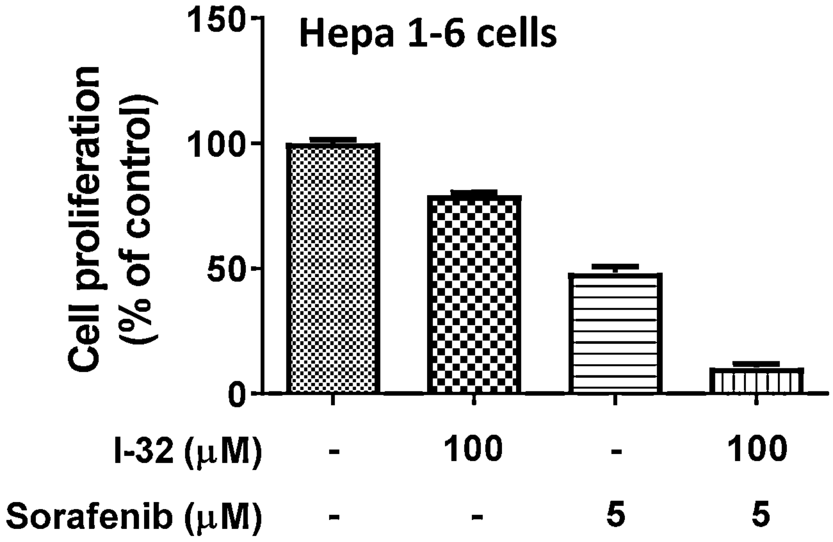
FIG. 7A shows anti-proliferation effects of Compound I-32 and sorafenib, in the absence or presence of the other, in Hepa1-6 cells.
Figure 7B:
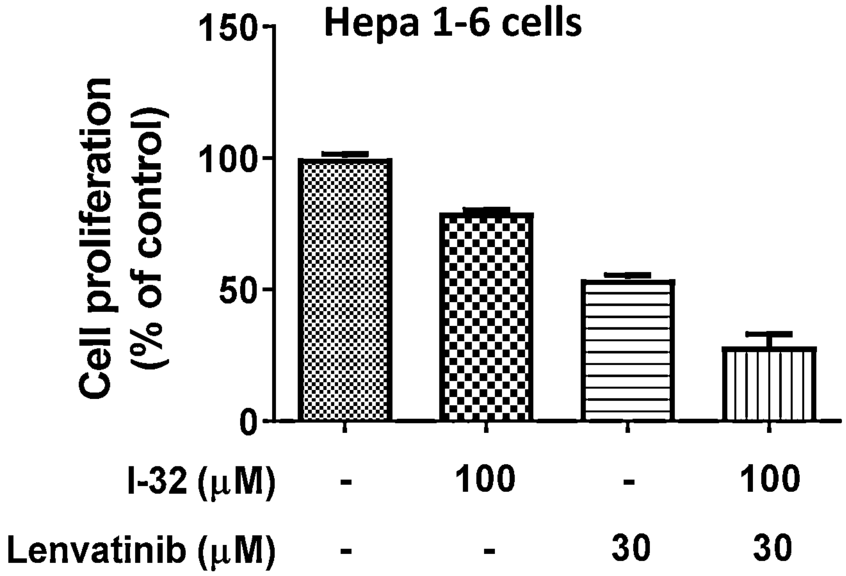
FIG. 7B shows anti-proliferation effects of Compound I-32 and lenvatinib, in the absence or presence of the other, in Hepa1-6 cells.
Figure 7C:
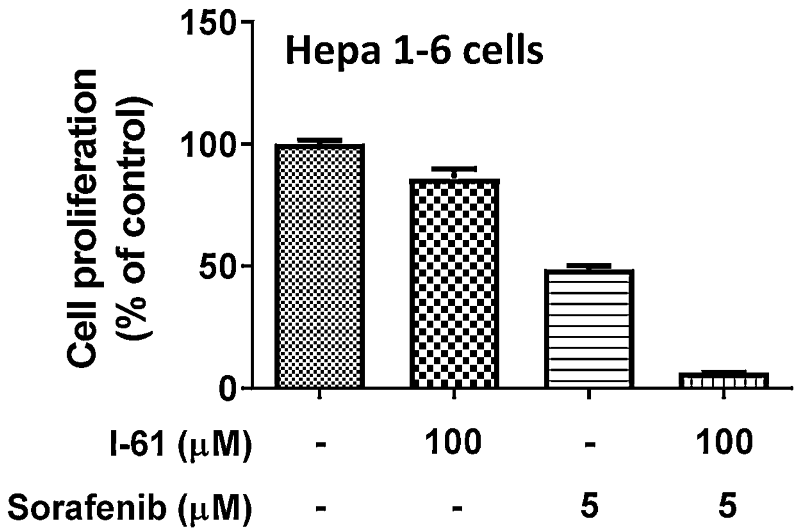
FIG. 7C shows anti-proliferation effects of Compound I-61 and sorafenib, in the absence or presence of the other, in Hepa1-6 cells.
Figure 7D:
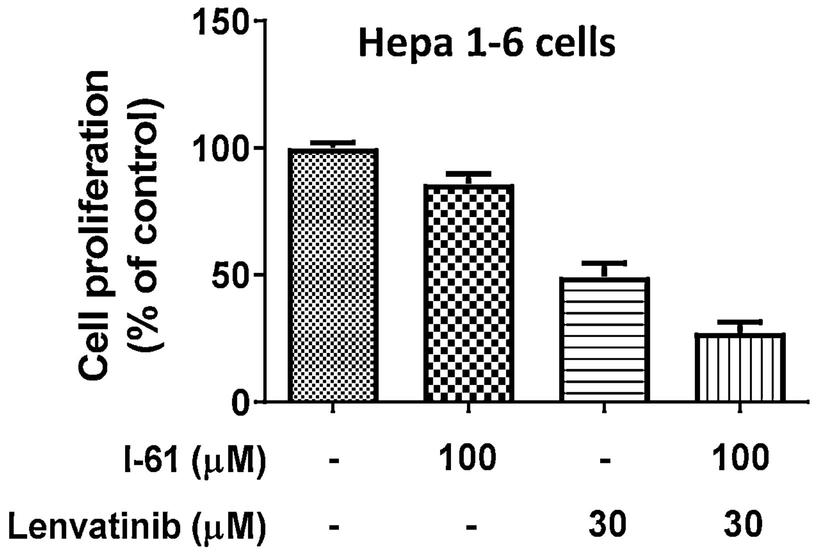
FIG. 7D shows anti-proliferation effects of Compound I-61 and lenvatinib, in the absence or presence of the other, in Hepa1-6 cells.
Figure 8A:
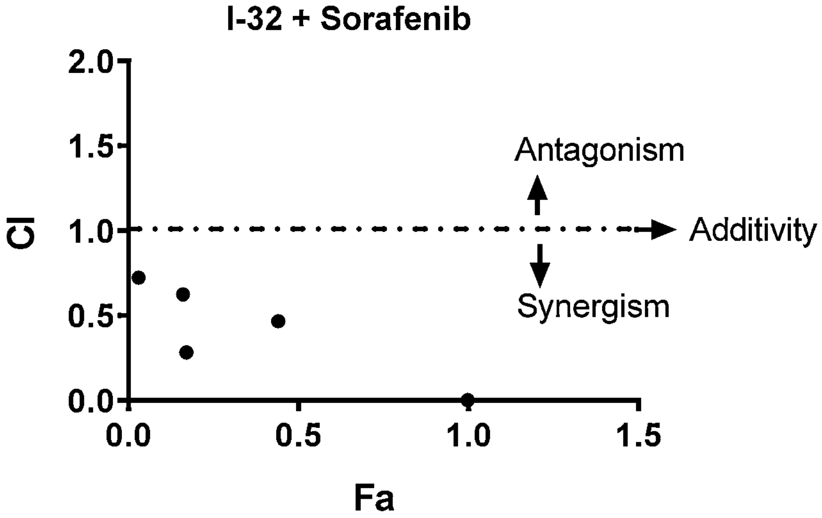
FIG. 8A shows synergistic anti-proliferation effect of Compound I-32 and sorafenib in Hep3B cells.
Figure 8B:
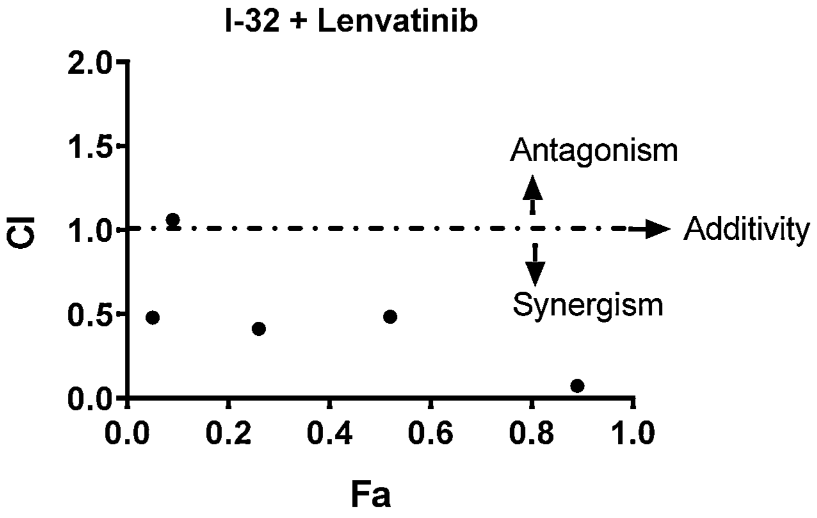
FIG. 8B shows synergistic anti-proliferation effect of Compound I-32 and lenvatinib in Hep3B cells.
Figure 8C:
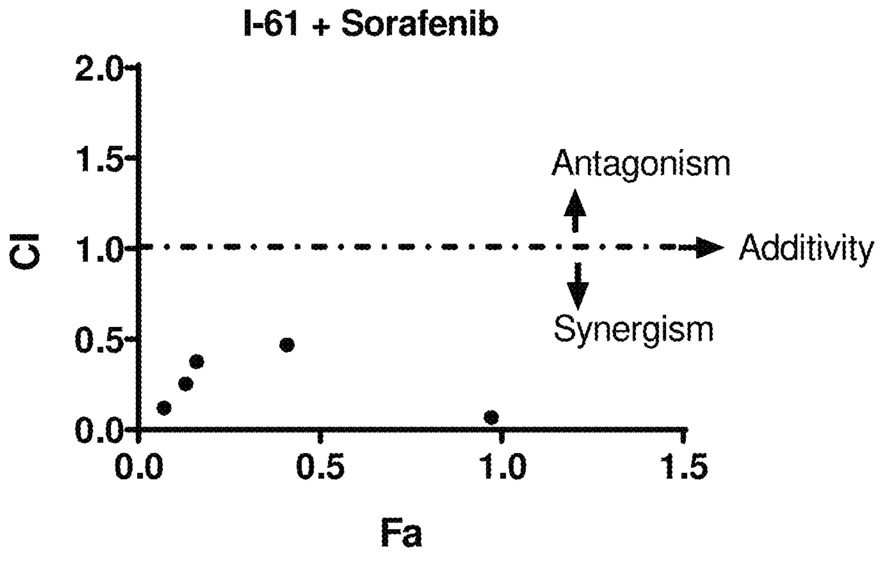
FIG. 8C shows synergistic anti-proliferation effect of Compound I-61 and sorafenib in Hep3B cells.
Figure 8D:
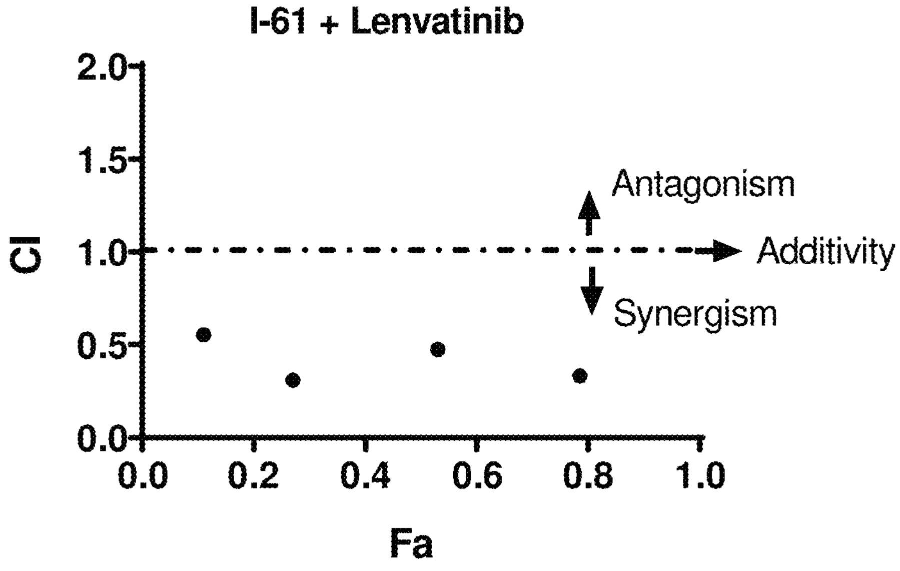
FIG. 8D shows synergistic anti-proliferation effect of Compound I-61 and lenvatinib in Hep3B cells.

Hep3B (supplied by ATCC) or Hepa1-6 (supplied by ATCC) cells were seeded in 96-well plates at a density of 500 cells/well with complete media. On day 2, media in each well was aspirated and replaced with 100 μl of fresh complete media and cells were treated with sorafenib or lenvatinib in the presence of or without the compounds of the invention, in a concentration dependent manner (Compound I-32 (100 μM) or Compound I-61 (100 μM) either alone or in combination with sorafenib (3 μM) or lenvatinib (0.5 μM)). Then, cells were incubated in an incubator for 72 h. On day 5, 10 μl of presto blue (Invitrogen, cat #A13261) cell viability reagent was added in each 96-well plate and incubated at 37° C. for 1-2 h. After incubation, fluorescence was measured with an excitation/emission wavelength of 560/590 nm. Results were indicated as mean±standard deviation (SD). All bar diagrams and line graphs were prepared using Graph Pad Prism 8 software. Proliferation $IC_{50}$ values were calculated using a non-linear regression model in Graph pad Prism 8. For each cell type, combination treatment showed a decrease in cell proliferation when compared to sorafenib or lenvatinib alone. Results in Hep3B cells are presented in FIGS. 6A-6B and results in Hepa1-6 cells are presented in FIGS. 7A-7B.

Sorafenib and lenvatinib have the following structure:

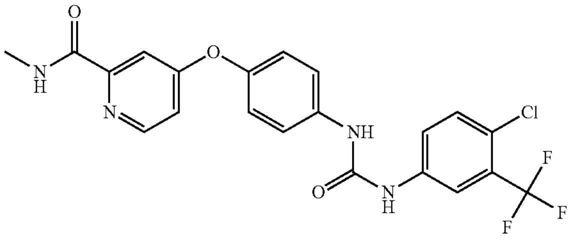

(sorafenib)

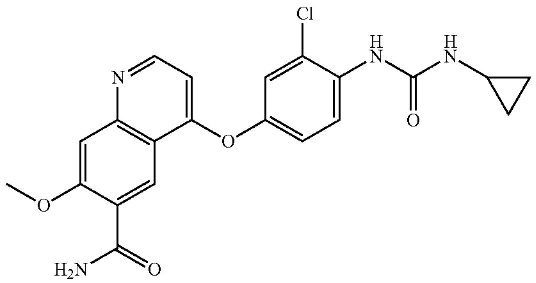

(lenvatinib)

Since additional inhibition of cell proliferation was observed in the combination studies, the results were analyzed using CompuSyn software (provided by ComboSyn Inc.) to examine if there was a synergistic or additive effect on the antiproliferative activity. FIGS. 8A-8D demonstrate that both Compounds I-32 and I-61 showed synergistic inhibition in the presence of sorafenib or lenvatinib.

What is claimed is:

1. A compound having the structure

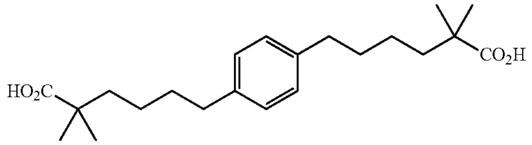 [SMILES: CC(C)(CCCCc1ccc(CCCCC(C)(C)C(=O)O)cc1)C(=O)O]

or

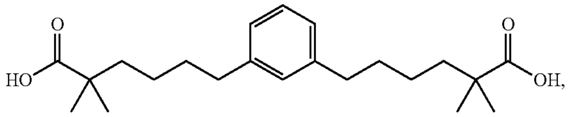 [SMILES: CC(C)(CCCCc1cccc(CCCCC(C)(C)C(=O)O)c1)C(=O)O]

or a pharmaceutically acceptable salt or solvate thereof.

2. The compound of claim 1, having the structure

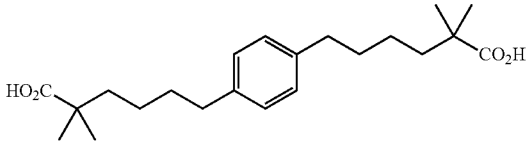 [SMILES: CC(C)(CCCCc1ccc(CCCCC(C)(C)C(=O)O)cc1)C(=O)O]

or a pharmaceutically acceptable salt or solvate thereof.

3. The compound of claim 1, having the structure

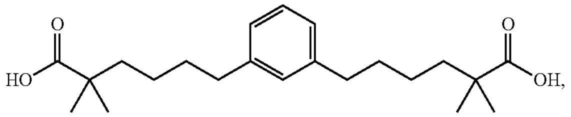

or a pharmaceutically acceptable salt or solvate thereof.

4. A composition comprising:

(a) a compound having the structure

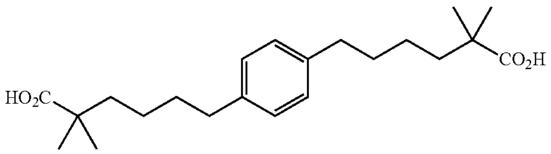

or

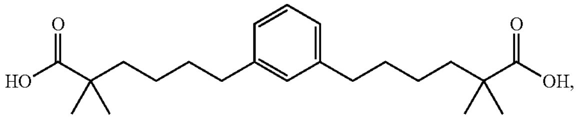

or a pharmaceutically acceptable salt or solvate thereof; and (b) a pharmaceutically acceptable carrier or vehicle.

5. The composition of claim 4, wherein the compound has the structure

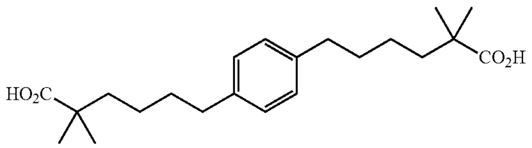

or a pharmaceutically acceptable salt or solvate thereof.

6. The composition of claim 4, wherein the compound has the structure

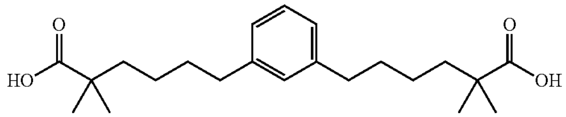 [SMILES: CC(C)(CCCCc1cccc(CCCCC(C)(C)C(=O)O)c1)C(=O)O]

or a pharmaceutically acceptable salt or solvate thereof.

7. A method for treating cirrhosis, non-alcoholic fatty liver disease (NAFLD) or non-alcoholic steatohepatitis (NASH), comprising administering to a subject in need thereof an effective amount of a compound having the structure

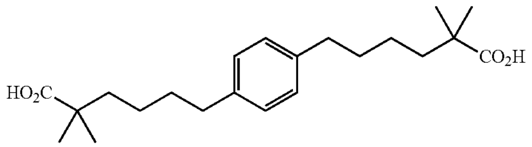

or

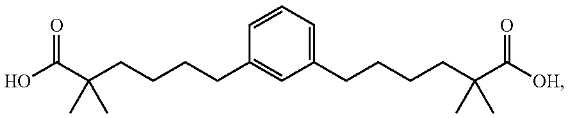

or a pharmaceutically acceptable salt or solvate thereof.

8. The method of claim 7, wherein the method is for treating NAFLD or NASH.

9. The method of claim 8, wherein the compound has the structure

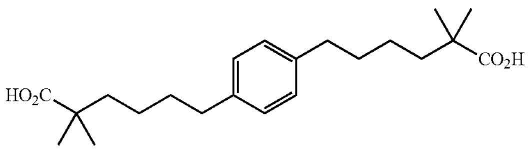 [SMILES: CC(C)(CCCCc1ccc(CCCCC(C)(C)C(=O)O)cc1)C(=O)O]

or a pharmaceutically acceptable salt or solvate thereof.

10. The method of claim 8, wherein the compound has the structure

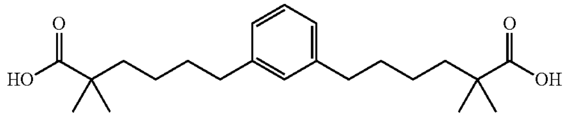 [SMILES: CC(C)(CCCCc1cccc(CCCCC(C)(C)C(=O)O)c1)C(=O)O]

or a pharmaceutically acceptable salt or solvate thereof.

11. The method of claim 7, wherein the method is for treating cirrhosis.

12. The method of claim 11, wherein the compound has the structure

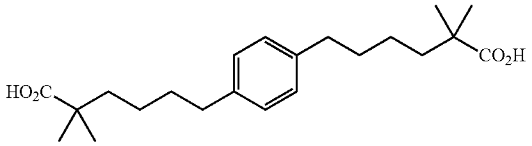 [SMILES: CC(C)(CCCCc1ccc(CCCCC(C)(C)C(=O)O)cc1)C(=O)O]

or a pharmaceutically acceptable salt or solvate thereof.

13. The method of claim 11, wherein the compound has the structure

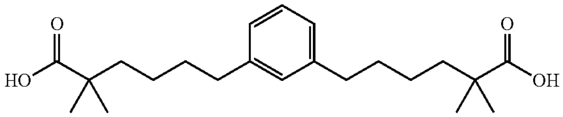 [SMILES: CC(C)(CCCCc1cccc(CCCCC(C)(C)C(=O)O)c1)C(=O)O]

or a pharmaceutically acceptable salt or solvate thereof.

14. A method for inhibiting, reducing, or delaying advancement of a subject's liver fibrosis, comprising administering to the subject an effective amount of a compound having the structure

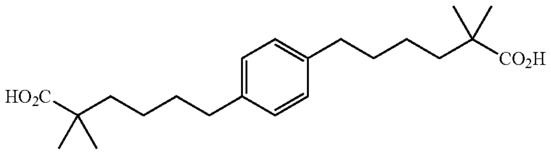

or

-continued

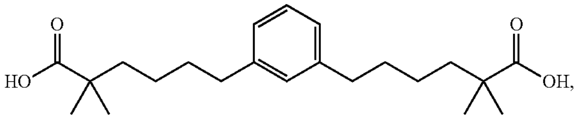

, or a pharmaceutically acceptable salt or solvate thereof.

15. The method of claim 14, wherein the compound has the structure

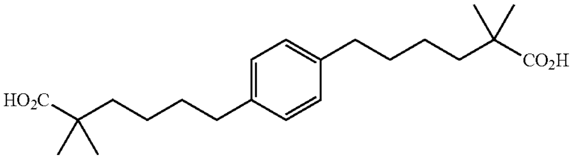 [SMILES: CC(C)(CCCCc1ccc(CCCCC(C)(C)C(=O)O)cc1)C(=O)O]

or a pharmaceutically acceptable salt or solvate thereof.

16. The method of claim 14, wherein the compound has the structure

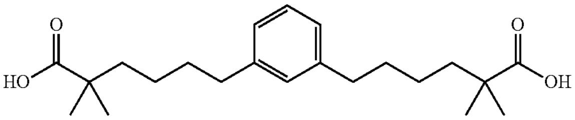 [SMILES: CC(C)(CCCCc1cccc(CCCCC(C)(C)C(=O)O)c1)C(=O)O]

or a pharmaceutically acceptable salt or solvate thereof.

* * * * *